(12) United States Patent
Shimizu et al.

(10) Patent No.: US 11,707,610 B2
(45) Date of Patent: *Jul. 25, 2023

(54) INGESTIBLE DEVICE FOR DELIVERY OF THERAPEUTIC AGENT TO THE GASTROINTESTINAL TRACT

(71) Applicant: BIORA THERAPEUTICS, INC., San Diego, CA (US)

(72) Inventors: Jeffrey A. Shimizu, Poway, CA (US); Mitchell Lawrence Jones, La Jolla, CA (US); Mark Sasha Drlik, Victoria (CA); Iman Niknia, Victoria (CA); Nathan John Muller, Victoria (CA); Tuyen Nguyen, Victoria (CA); Christopher Loren Wahl, San Diego, CA (US); Edward Mudge, Cambridgeshire (GB); Nicholas Mark Salt, Cambridgeshire (GB); Nia Eleri Stevens, Cambridgeshire (GB); Stuart Robert Abercrombie, Cambridgeshire (GB); Christopher Ian Bunce, Cambridgeshire (GB); Ryan Elliott Jones, Turks and Caicos Island (CA); Kevin Howe, London (GB); Pejman Rahimian, Colleyville, TX (US); Nelson Quintana, Temecula, CA (US)

(73) Assignee: BIORA THERAPEUTICS, INC., San Diego, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/784,453

(22) PCT Filed: Dec. 11, 2020

(86) PCT No.: PCT/US2020/064590
§ 371 (c)(1),
(2) Date: Jun. 10, 2022

(87) PCT Pub. No.: WO2021/119482
PCT Pub. Date: Jun. 17, 2021

(65) Prior Publication Data
US 2023/0149315 A1 May 18, 2023

Related U.S. Application Data

(60) Provisional application No. 62/948,082, filed on Dec. 13, 2019, provisional application No. 63/027,427, filed on May 20, 2020, provisional application No. 63/086,630, filed on Oct. 2, 2020.

(51) Int. Cl.
*A61J 3/07* (2006.01)
*A61K 9/48* (2006.01)
*A61M 31/00* (2006.01)
*A61M 37/00* (2006.01)

(52) U.S. Cl.
CPC ......... *A61K 9/4808* (2013.01); *A61M 31/002* (2013.01); *A61M 37/0015* (2013.01); *A61M 2037/0061* (2013.01); *A61M 2210/1042* (2013.01)

(58) Field of Classification Search
None
See application file for complete search history.

(56) References Cited

U.S. PATENT DOCUMENTS

| | | |
|---|---|---|
| 3,057,344 A | 10/1962 | Alberto |
| 3,118,439 A | 1/1964 | Barana |
| 3,315,660 A | 4/1967 | Abella |
| 3,485,235 A | 12/1969 | Felson |
| 4,036,214 A | 7/1977 | Bucalo |
| 4,172,446 A | 10/1979 | Bucalo |
| 4,239,040 A | 12/1980 | Hosoya |
| 4,425,117 A | 1/1984 | Hugeman |
| 4,481,952 A | 11/1984 | Pawelec |
| 4,507,115 A | 3/1985 | Kambara |
| 4,522,625 A | 6/1985 | Edgren |
| 5,167,626 A | 12/1992 | Casper et al. |
| 5,170,801 A | 12/1992 | Casper |
| 5,217,449 A | 6/1993 | Yuda et al. |
| 5,279,607 A | 1/1994 | Schentag |
| 5,316,015 A | 5/1994 | Sinaiko |
| 5,318,557 A | 6/1994 | Gross |

(Continued)

FOREIGN PATENT DOCUMENTS

| CN | 1856290 B | 11/2006 |
|---|---|---|
| CN | 108784634 | 11/2018 |

(Continued)

OTHER PUBLICATIONS

Written Opinion of the International Search Authority for International Application No. PCT/US2020/064590; dated Apr. 7, 2021; 9 pages.

(Continued)

*Primary Examiner* — Susan T Tran
(74) *Attorney, Agent, or Firm* — Perkins Coie LLP

(57) ABSTRACT

Ingestible devices can directly deliver therapeutic agents to desired tissue(s) of the GI tract of a subject, such as the submucosa, the mucosa, and/or the mucus layer of the GI tract, and methods of using the same. The ingestible devices can deliver therapeutic agents in a safe, effective, and reliable manner. The disclosure also provides pharmaceutical compositions for use in methods of treating a disease or condition in a subject in need thereof.

19 Claims, 37 Drawing Sheets

(56) References Cited

U.S. PATENT DOCUMENTS

| | | |
|---|---|---|
| 5,395,366 A | 3/1995 | D'Andrea et al. |
| 5,604,531 A | 2/1997 | Iddan et al. |
| 5,738,110 A | 4/1998 | Beal et al. |
| 5,858,001 A | 1/1999 | Tsals et al. |
| 5,951,538 A | 9/1999 | Joshi |
| 5,971,942 A | 10/1999 | Gu et al. |
| 6,632,216 B2 | 10/2003 | Houzego |
| 6,884,239 B2 | 4/2005 | Houzego et al. |
| 6,950,690 B1 | 9/2005 | Meron et al. |
| 7,144,366 B2 | 12/2006 | Takizawa et al. |
| 7,160,258 B2 | 1/2007 | Imran et al. |
| 7,611,480 B2 | 11/2009 | Levy |
| 7,662,093 B2 | 2/2010 | Gilad et al. |
| 7,717,862 B2 | 5/2010 | Stoltz |
| 7,763,014 B2 | 7/2010 | Houzeao et al. |
| 7,946,979 B2 | 5/2011 | Gilad et al. |
| 8,005,536 B2 | 8/2011 | Imran |
| 8,216,130 B2 | 6/2012 | Glukhovsky et al. |
| 8,360,976 B2 | 1/2013 | Imran |
| 8,597,279 B2 | 12/2013 | Dijksman et al. |
| 8,626,268 B2 | 1/2014 | Adler |
| 8,696,602 B2 | 4/2014 | Semler et al. |
| 8,740,774 B2 | 6/2014 | Takizawa et al. |
| 8,809,271 B2 | 8/2014 | Imran |
| 8,926,526 B2 | 1/2015 | Shuck |
| 9,072,834 B2 | 7/2015 | Vogt |
| 9,456,737 B2 | 10/2016 | Pascal |
| 9,511,121 B2 | 12/2016 | Imran |
| 10,172,598 B2 | 1/2019 | Amoako-Tuffour et al. |
| 10,588,608 B2 | 3/2020 | Jones et al. |
| 10,765,360 B2 | 9/2020 | Euliano et al. |
| 10,835,152 B2 | 11/2020 | Jones et al. |
| 11,439,802 B2 | 9/2022 | Shimizu et al. |
| 2002/0198470 A1 | 12/2002 | Imran et al. |
| 2004/0162469 A1 | 8/2004 | Imran |
| 2004/0199054 A1 | 10/2004 | Wakefield et al. |
| 2004/0253304 A1 | 12/2004 | Gross et al. |
| 2005/0158246 A1 | 7/2005 | Takizawa |
| 2007/0043320 A1 | 2/2007 | Kenany |
| 2008/0051635 A1 | 2/2008 | Tanaka et al. |
| 2009/0275923 A1 | 11/2009 | Shimizu et al. |
| 2010/0063486 A1 | 3/2010 | Diiksman et al. |
| 2010/0324381 A1 | 12/2010 | Glukhovskv et al. |
| 2011/0046458 A1 | 2/2011 | Pinedo |
| 2011/0092959 A1 | 4/2011 | Zou et al. |
| 2011/0106063 A1 | 5/2011 | Diiksman et al. |
| 2012/0136209 A1 | 5/2012 | Kostenich et al. |
| 2015/0011874 A1 | 1/2015 | Amoaka-Tuffour et al. |
| 2015/0051589 A1 | 2/2015 | Sako et al. |
| 2015/0065926 A1 | 3/2015 | Nakamura et al. |
| 2016/0213234 A1 | 7/2016 | Poon |
| 2016/0235663 A1 | 8/2016 | Zou et al. |
| 2017/0050006 A1 | 2/2017 | Imran et al. |
| 2017/0106099 A1 | 4/2017 | Bellinger et al. |
| 2017/0296092 A1 | 10/2017 | Jones et al. |
| 2018/0049725 A1 | 2/2018 | Jones et al. |
| 2018/0052084 A1 | 2/2018 | Jones et al. |
| 2018/0070857 A1 | 3/2018 | Jones et al. |
| 2018/0160950 A1 | 6/2018 | Rabinovitz et al. |
| 2018/0279908 A1 | 10/2018 | Jones et al. |
| 2018/0318496 A1 | 11/2018 | Zou et al. |
| 2019/0083073 A1 | 3/2019 | Amoaka-Tuffour et al. |
| 2020/0094031 A1 | 3/2020 | Jones et al. |
| 2020/0245897 A1 | 8/2020 | Jones et al. |
| 2020/0038268 A1 | 10/2020 | Imran |
| 2020/0316352 A1 | 10/2020 | Aran et al. |
| 2021/0015398 A1 | 1/2021 | Jones et al. |
| 2021/0038872 A1* | 2/2021 | Shimizu ............... C07K 16/241 |
| 2021/0093248 A1 | 4/2021 | Euliano et al. |
| 2021/0161805 A1 | 6/2021 | Zou et al. |
| 2021/0283385 A1* | 9/2021 | Shimizu ............... C07K 16/241 |
| 2022/0072286 A1 | 3/2022 | Bonner et al. |

FOREIGN PATENT DOCUMENTS

| | | |
|---|---|---|
| CN | 108784634 A | 11/2018 |
| DE | 19801573 A1 | 7/1999 |
| EP | 1530950 A1 | 5/2005 |
| EP | 2515992 B1 | 10/2012 |
| JP | 2005073888 A | 3/2005 |
| WO | 92/21307 | 12/1992 |
| WO | 9221307 A1 | 12/1992 |
| WO | WO2008014439 A2 | 1/2008 |
| WO | WO2009104110 A1 | 8/2009 |
| WO | 2011/018753 | 2/2011 |
| WO | 2011018753 A1 | 2/2011 |
| WO | WO2013003824 A1 | 1/2013 |
| WO | 2018/049133 | 3/2018 |
| WO | 2018049133 A1 | 3/2018 |
| WO | 2018/183934 | 10/2018 |
| WO | 2018183934 A1 | 10/2018 |
| WO | WO2018213588 A1 | 11/2018 |
| WO | WO2020041774 A1 | 2/2020 |
| WO | 2020/106754 | 5/2020 |
| WO | 2020106754 A1 | 5/2020 |
| WO | WO2020157324 A1 | 8/2020 |
| WO | WO2020160399 A1 | 8/2020 |

OTHER PUBLICATIONS

International Search Report and Written Opinion for PCT/US2020/064590, dated Apr. 7, 2021, 15 pages.

Examination Report for European Application No. 20834101.6; dated Nov. 28, 2022; 4 pages.

* cited by examiner

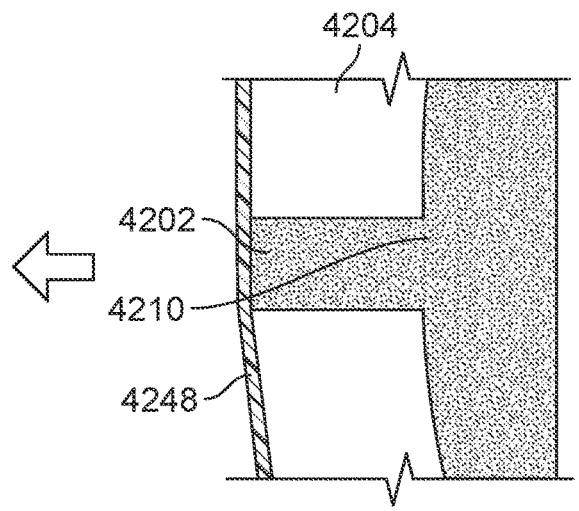
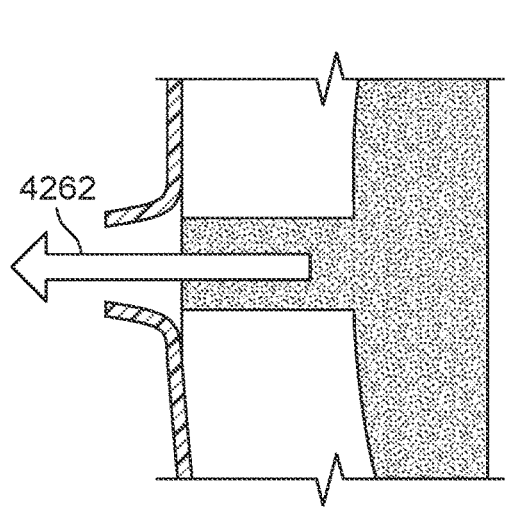
FIG. 42B  FIG. 42A
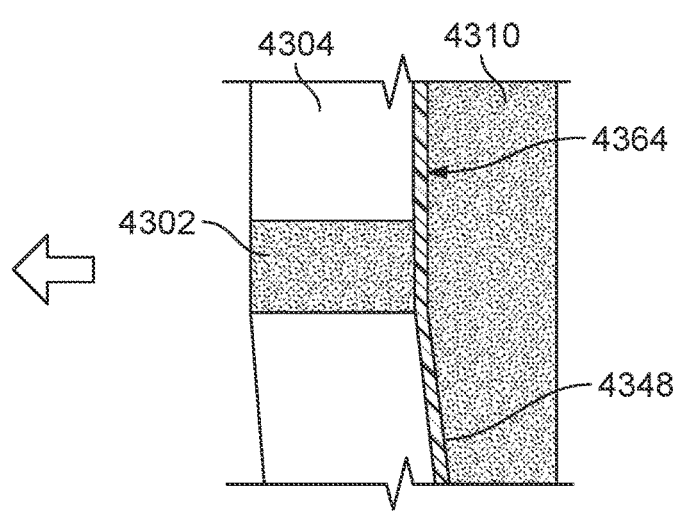
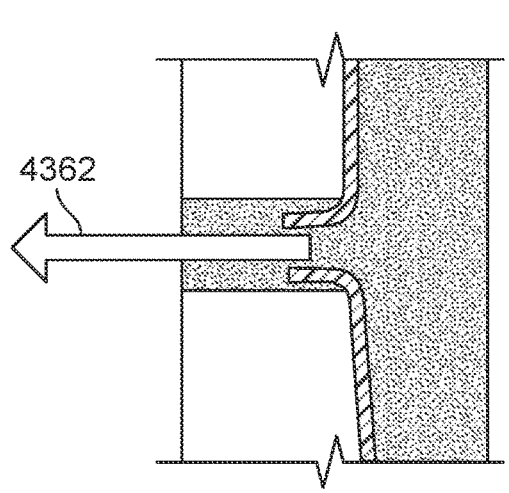
FIG. 43B  FIG. 43A

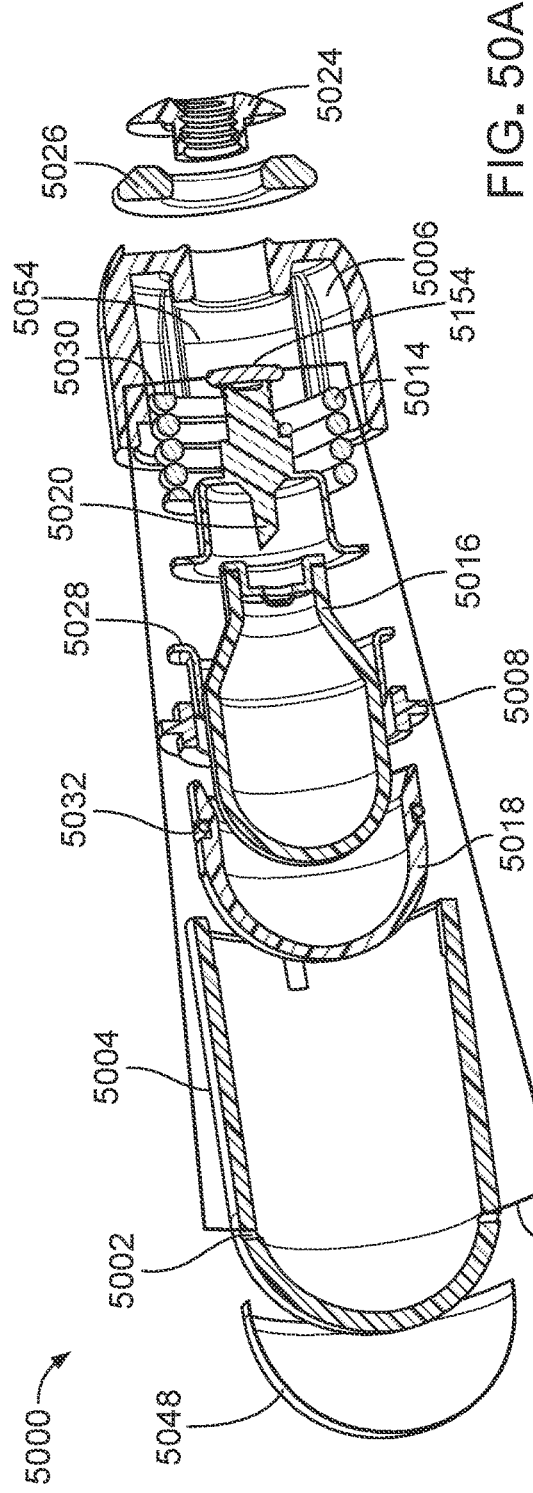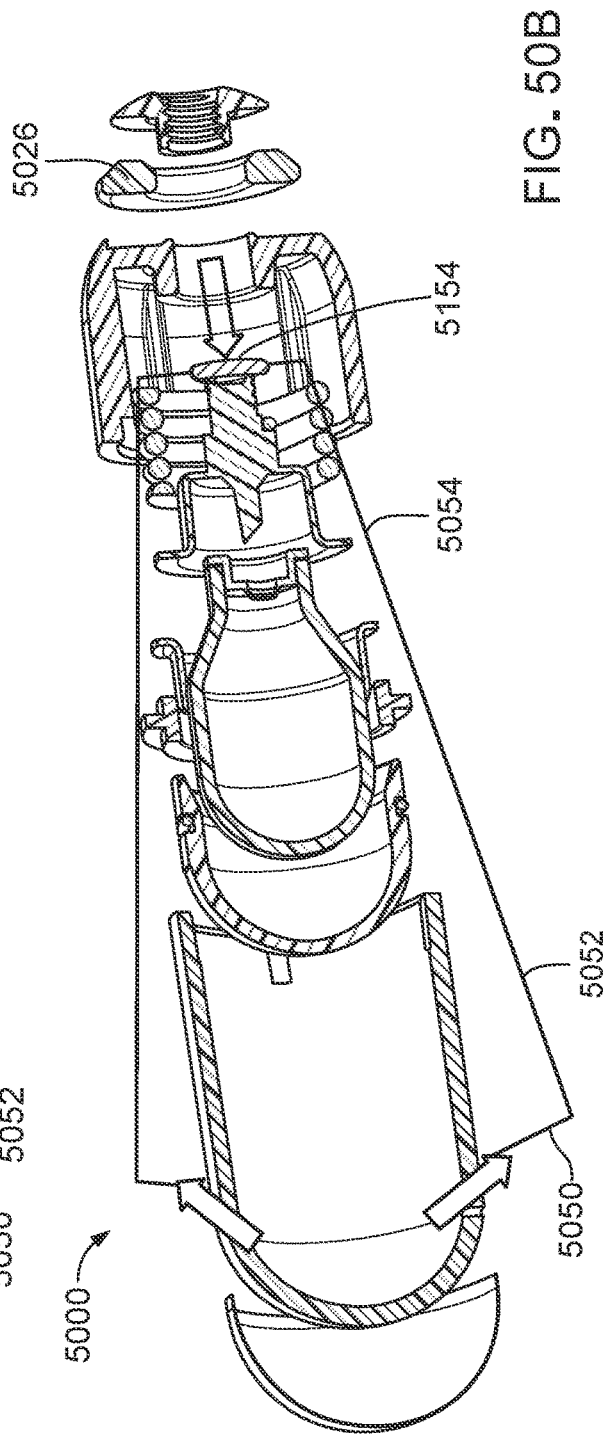

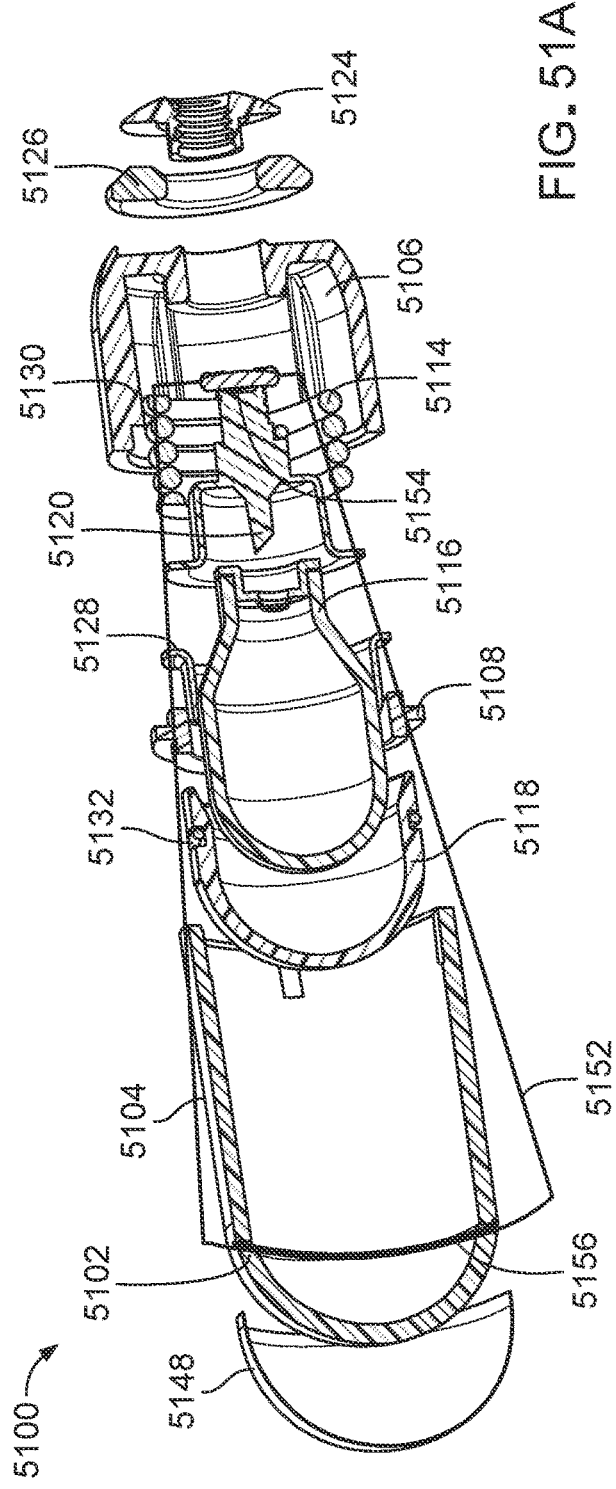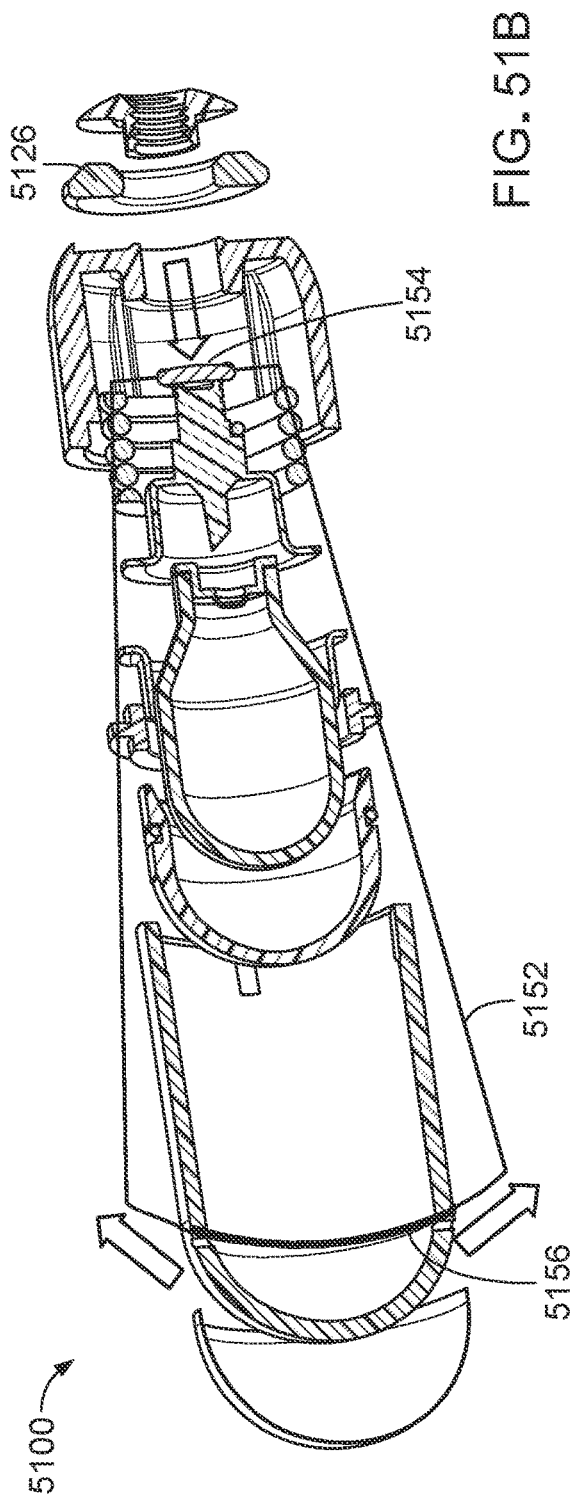

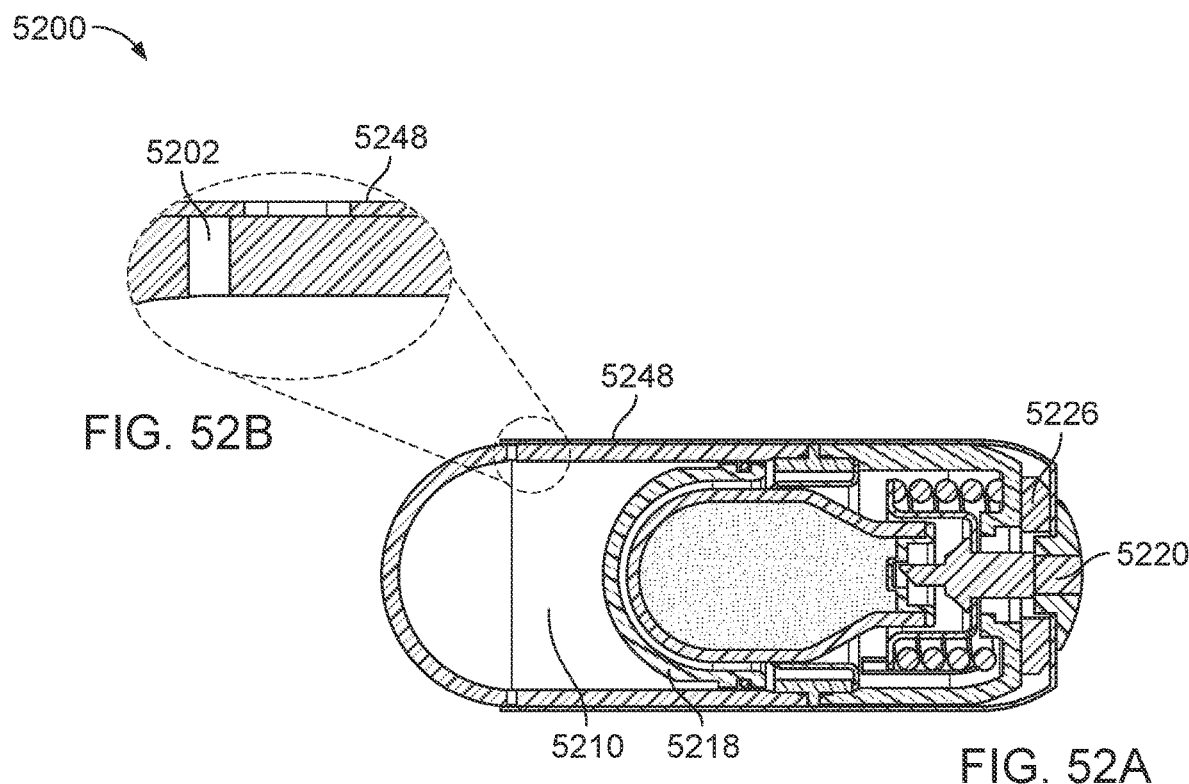
FIG. 52B
FIG. 52A
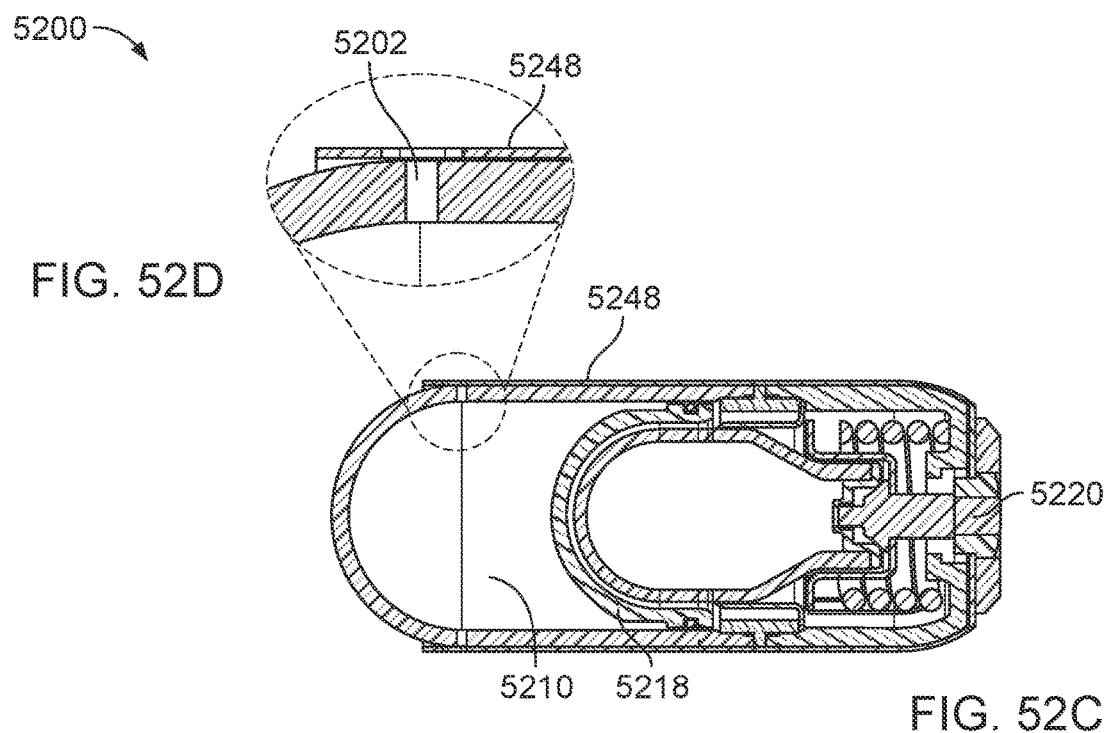
FIG. 52D
FIG. 52C

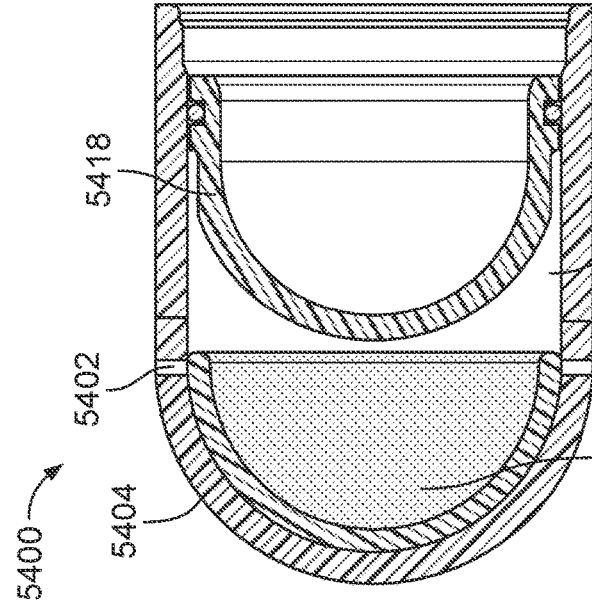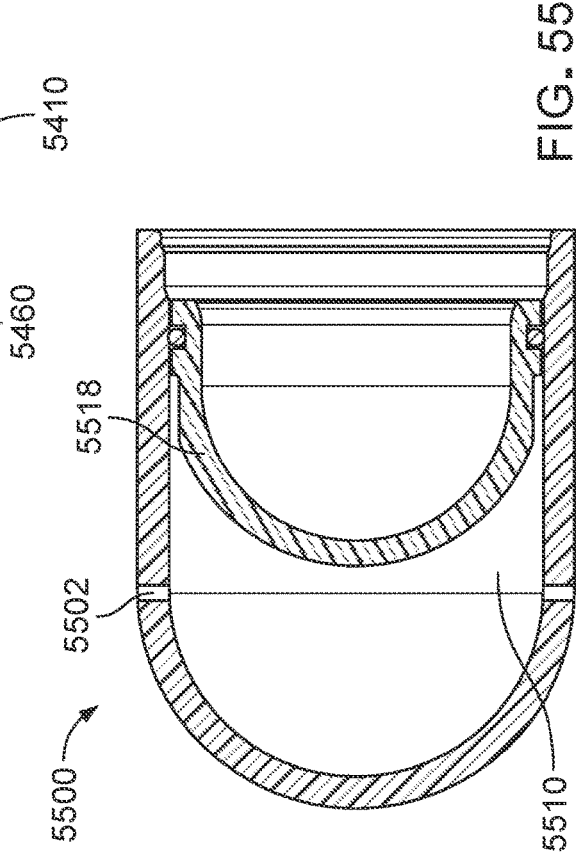

INGESTIBLE DEVICE FOR DELIVERY OF THERAPEUTIC AGENT TO THE GASTROINTESTINAL TRACT

CROSS-REFERENCE TO RELATED APPLICATIONS

This application claims priority under 35 U.S.C. § 119 to: U.S. Ser. No. 62/948,082, filed Dec. 13, 2019, and entitled "Ingestible Device for Delivery of Therapeutic Agent to the Gastrointestinal Tract"; U.S. Ser. No. 63/027,427, filed May 20, 2020, and entitled "Ingestible Device for Delivery of Therapeutic Agent to the Gastrointestinal Tract"; and U.S. Ser. No. 63/086,630, filed Oct. 2, 2020, and entitled "Ingestible Device for Delivery of Therapeutic Agent to the Gastrointestinal Tract." The entire disclosure of each of these applications is incorporated by reference herein.

FIELD

The disclosure generally relates to ingestible devices capable of delivering a dispensable substance, such as a therapeutic agent, as well as related components, systems and methods.

BACKGROUND

The gastrointestinal (GI) tract generally provides a therapeutic medium for an individual's body. At times, it is desirable to dispense therapeutic agents to the GI tract to treat a medical condition.

SUMMARY

The disclosure provides ingestible devices that can directly deliver therapeutic agents to desired tissue(s) of the GI tract of a subject, such as the submucosa, the mucosa, and/or the mucus layer of the GI tract, and methods of using the same. The ingestible devices can deliver therapeutic agents in a safe, effective, and reliable manner. The disclosure also provides pharmaceutical compositions for use in methods of treating a disease or condition in a subject in need thereof.

Ingestible devices of the present disclosure are configured to provide at least three different modes of direct delivery of therapeutic agents to the GI tract of a subject, referred to herein as trans-epithelial, epithelial, and topical delivery. Direct delivery, as used herein, refers to a force-driven delivery mechanism.

Thus, in one aspect, this disclosure relates to trans-epithelial delivery of a therapeutic agent to the GI tract of a subject. Accordingly, the disclosure provides an ingestible device that can directly deliver a therapeutic agent past the epithelial cell layer of the mucosa of the GI tract of a subject to yield systemic exposure of the therapeutic agent to the subject. In such embodiments, the ingestible device is configured to directly deliver the therapeutic agent past the epithelial cell layer of the mucosa and into the submucosa and/or into a region of the mucosa beneath the epithelial layer (e.g., into the lamina propria) of the GI tract, where it is available for systemic uptake. This can be particularly relevant when the oral bioavailability of the therapeutic agent is otherwise low. In some embodiments, systemic exposure of the therapeutic agent is achieved by trans-epithelial delivery of the therapeutic agent into the submucosa and/or into a region of the mucosa beneath the epithelial layer (e.g., into the lamina propria) of the small intestine, for example, in the duodenum, the jejunum, and/or the ileum. In further embodiments, the trans-epithelial delivery directly delivers the therapeutic agent into the submucosa submucosa and/or into a region of the mucosa beneath the epithelial layer (e.g., into the lamina propria) of the GI tract such that the percent systemic uptake of the trans-epithelial delivery relative to intravenous or subcutaneous administration is at least about 10% (e.g., at least about 15%, at least about 20%, at least about 25% or more).

Without wishing to be bound by theory, it is believed that trans-epithelial delivery to the submucosa and/or into a region of the mucosa beneath the epithelial layer (e.g., into the lamina propria) of the GI tract is achieved by using an appropriate value for one or more performance parameters associated with the ingestible device configured for such use. Such performance parameters include, for example, internal pressure of the ingestible device, peak fluid pressure of the ingestible device, nozzle pressure of the ingestible device, peak jet power of the dispensable substance (e.g., a pharmaceutical formulation containing the therapeutic agent) delivered from the ingestible device, peak jet velocity of the dispensable substance (e.g., a pharmaceutical formulation containing the therapeutic agent) delivered from the ingestible device, peak jet pressure of the dispensable substance (e.g., a pharmaceutical formulation containing the therapeutic agent) delivered from the ingestible device, peak jet force of the dispensable substance (e.g., a pharmaceutical formulation containing the therapeutic agent) delivered from the ingestible device, peak jet stable length of the dispensable substance (e.g., a pharmaceutical formulation containing the therapeutic agent) delivered from the ingestible device, nozzle shape, nozzle length and nozzle diameter.

In another aspect, this disclosure relates to epithelial delivery of a therapeutic agent to the GI tract of a subject. Accordingly, the disclosure provides an ingestible device configured to directly deliver the therapeutic agent into the mucus and/or onto the epithelial layer, but not past the epithelial layer of the mucosa, of the small or large intestine, from which it can act locally, and in some cases away from the site of direct delivery. In some embodiments, the device is configured so that the therapeutic agent is delivered from the device with sufficient force to provide the epithelial delivery, the force being lower than that required for trans-epithelial delivery.

In yet another aspect, this disclosure relates to topical delivery of a therapeutic agent to the GI tract of a subject. Accordingly, the disclosure provides an ingestible device configured to deliver the therapeutic agent into the lumen and/or onto the mucus or other surface of the GI tract facing the lumen of the small or large intestine, from which it can act locally, and in some cases away from the site of delivery. In some embodiments, the device is configured so that the therapeutic agent is delivered from the device with sufficient force so that the therapeutic agent is delivered topically, the force being lower than that required for the epithelial or the trans-epithelial delivery.

The ingestible device, whether configured for trans-epithelial, epithelial or topical delivery, can have a streamlined and/or relatively simple mechanical design, be relatively small, and/or be inexpensive to manufacture. In general, the device protects a dispensable substance (e.g., a therapeutic agent, or a pharmaceutical formulation comprising the therapeutic agent) until the device reaches a desired location of the subject. As an example, the device can be designed to deliver dispensable substance to a desired location in the GI tract of a subject, and the device can be designed so that the dispensable substance is not subject to constituents of the GI tract (e.g., acids, enzymes) prior to reaching the desired location in the GI tract. As another example, the device can be designed to deliver dispensable substance such that the therapeutic properties of the dispensable substance are not altered during delivery (e.g., the dispensable substance is a therapeutic agent that binds its therapeutic target after delivery).

The present disclosure provides ingestible devices that can directly deliver therapeutic agents to desired tissue(s) of the GI tract of a subject (such as the submucosa, the mucosa, and/or the mucus layer of the GI tract), e.g., to treat a particular class of disease, or a specific disease. Relatedly, methods of using the device to deliver the therapeutic agents to desired tissue(s) of the GI tract, e.g., to treat a particular class of disease, or a specific disease, are disclosed. These disclosures also inherently provide disclosures of corresponding medical uses—that is, disclosures of the recited therapeutic agents for use in a method of treating the recited class of disease, or specific disease, by using the device to deliver the recited agents to desired tissue(s) of the GI tract of a subject.

In an aspect, the disclosure provides an ingestible device that includes: a housing comprising an interior and an opening; a gas cylinder in the interior of the housing, the gas cylinder having a breakable seal; a spring in the interior of the housing; a piston in the interior of the housing; a piercer in the interior of the housing; a retainer; and a trigger exposed to an environment external to the housing. In a first state of the ingestible device: the trigger holds the retainer in a first position; the retainer holds the piercer in a first position in which the piercer does not break the breakable seal of the gas cylinder; and the interior of the ingestible device is configured to contain a dispensable substance without the dispensable substance being delivered from the ingestible device via the opening in the housing.

In some embodiments, in a second state of the ingestible device: the trigger is at least partially dissolved, degraded and/or eroded so that the trigger is unable to hold the retainer in its first position; and the retainer is unable to hold piercer in its first position.

In some embodiments, in the second state of the ingestible device: the spring applies a force to the piercer to move the piercer so that the piercer breaks the breakable seal of the gas cylinder; a gas is released from the gas cylinder; the gas applies a force to the piston so that the piston applies a force to the dispensable substance; and the dispensable substance is delivered out of the ingestible device via the opening in the housing.

The ingestible device can further include a seal between the piston and the housing, and/or a seal between the piercer and the housing.

In an aspect, the disclosure provides an ingestible device that includes: a housing configured to contain a dispensable substance comprising a therapeutic agent in an interior of the housing; a gas cylinder in the interior of the housing; a spring in the interior of the housing; a piston in the interior of the housing; a seal between the piston and the housing; a piercer in the interior of the housing; a retainer; and a trigger exposed to an environment external to the housing.

In an aspect, the disclosure provides an ingestible device that includes: a housing configured to contain a dispensable substance comprising a therapeutic agent in an interior of the housing; a gas cylinder in the interior of the housing; a spring in the interior of the housing; a piston in the interior of the housing; a piercer in the interior of the housing; a retainer; a seal between the retainer and the housing; and a trigger exposed to an environment external to the housing.

In an aspect, the disclosure provides an ingestible device that includes: a housing configured to contain a dispensable substance comprising a therapeutic agent in an interior of the housing; a gas cylinder in the interior of the housing; a spring in the interior of the housing; a piston in the interior of the housing; a first seal between the piston and the housing; a piercer in the interior of the housing; a retainer; a second seal between the retainer and the housing; and a trigger exposed to an environment external to the housing.

An ingestible device can be 00 sized device.

The trigger can include an enteric material.

The housing can include first and second housing parts, with the piston and the dispensable substance inside the first housing part, and the spring and the retainer inside the second housing part.

The opening of an ingestible device can be a nozzle, e.g., having a diameter of from about 325 µm to 375 µm.

In some embodiments, at least one of the following holds: the ingestible device is configured for trans-epithelial delivery of the dispensable subject to the GI tract of a subject; the ingestible device is configured for epithelial delivery of the dispensable subject to the GI tract of a subject; and the ingestible device is configured for topical delivery of the dispensable subject to the GI tract of a subject.

An ingestible device can further include the dispensable substance. In some embodiments, the dispensable substance is a solution or a suspension.

In some embodiments, at least one of the following holds: the ingestible device is configured to deliver the dispensable substance to tissue of the GI tract of a subject as a jet with a peak jet power of from about one Watt to about three Watts; the ingestible device is configured to deliver the dispensable substance at a peak jet velocity of from about 25 meters per second to about 45 meters per second; the ingestible device is configured to deliver the dispensable substance to tissue of the GI tract of a subject at a peak jet pressure of from about 100 psig to about 250 psig; the ingestible device is configured to deliver the dispensable substance to tissue of the GI tract of a subject at a peak jet force of from about 0.09 N to about 0.15 N; the ingestible device is configured to deliver the dispensable substance as a jet having jet stable length of at least about 0.5 millimeter; the ingestible device is configured to provide an internal pressure of from about 225 psig to about 425 psig; and the ingestible device is configured to contain the dispensable substance at a peak fluid pressure of from about 200 psig to about 400 psig.

In some embodiments, at least one component of an ingestible device includes a cylic olefin polymer.

In some embodiments, the breakable seal is scored.

In some embodiments, the breakable seal has a varying thickness.

In some embodiments, the gas cylinder has a burst pressure of from about 2,800 psig to about 4,500 psig.

In some embodiments, the gas cylinder contains at least one gas selected from the group consisting of air, nitrogen, oxygen, carbon dioxide, hydrofluorocarbon gases and noble gases.

In some embodiments, an ingestible device further includes an element having a first state in which the element at least partially covers the opening in the housing and a second state in which the element does not cover the opening in the housing, wherein the ingestible device is configured so that, when the piston moves, the element moves from its first state to its second state. The element can move synchronously with the piston. When the piston moves a distance, the element can move the same distance. The ingestible device can further include a seal mechanically coupled with the piston and element. The seal can be configured to cause the movement of the piston to result in the movement of the element. The element can conform to an inner radius of the housing.

In some embodiments, the ingestible device further includes a covering over the opening in the housing. The covering can be removable from the ingestible device. The covering can be configured to be removed from the housing due to pressure applied by the dispensable substance. The covering can include an enteric material. The covering can be a film, a foil, a band, a plug, or a patch. The covering has a burst pressure of at most 420 psig.

In some embodiments, the ingestible device further includes a second piston configured so that, when the first piston applies the force on the dispensable substance, the dispensable substance applies a force on the second piston to slide the second piston to expose the openings and the dispensable substance is forced out of the ingestible device via the openings.

In some embodiments, the ingestible device further includes a removable cap affixed to the ingestible device and configured so that, when the piston moves to apply the force on the dispensable substance, the dispensable substance applies a force on the cap to slide the cap to expose the opening in the housing.

In some embodiments, the ingestible device further includes an inflated membrane volume covering the opening and configured so that, when the piston moves to apply force on the dispensable substance, the dispensable substance applies force on the inflated membrane volume and the inflated membrane volume is compressed to expose the opening in the housing.

In an aspect, the disclosure provides a method that includes using an ingestible device according to the disclosure to deliver a dispensable substance to the GI tract of a subject.

The details of one or more embodiments of the device and methods are set forth in the accompanying drawings and the description below. Other features and advantages will be apparent from the description and drawings, and from the claims.

BRIEF DESCRIPTION OF THE DRAWINGS

FIGS. 42A-47C show aspects of an ingestible device.

FIGS. 50A and 50B show exploded views of an ingestible device.

FIGS. 51A and 51B show exploded views of an ingestible device.

FIGS. 52A-52D show views of an ingestible device.

FIGS. 54a and 54B show views of a portion of an ingestible device.

FIG. 55 shows a view of a portion of an ingestible device.

DETAILED DESCRIPTION

Incorporation by Reference

Figure 1A:
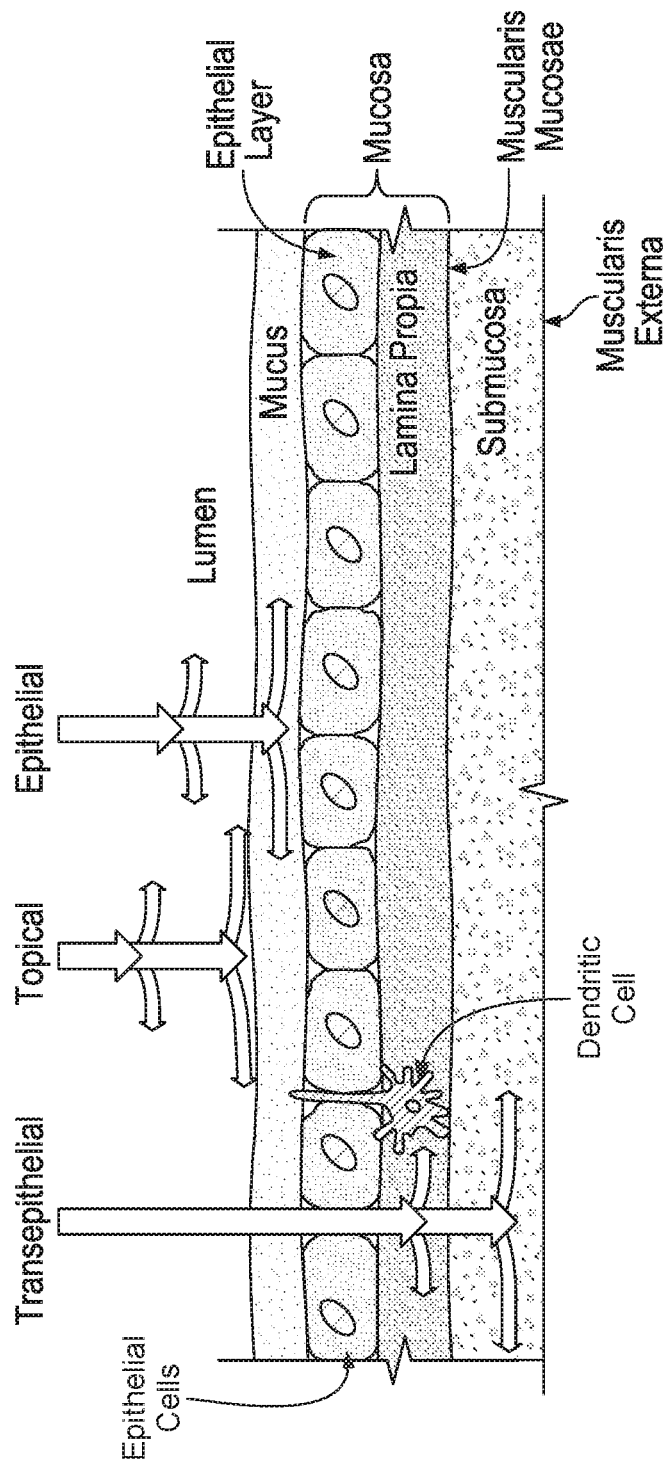
FIG. 1A is a schematic cross section of the different regions of healthy intestinal tissue.

This application incorporates by reference the following patent applications in their entirety: U.S. Ser. No. 62/769,496, filed Nov. 19, 2018, and entitled "Ingestible Device With High Pressure Substance Delivery to the Gastrointestinal Tract"; U.S. Ser. No. 62/818,731, filed Mar. 14, 2019, and entitled "Ingestible Device With High Pressure Substance Delivery to the Gastrointestinal Tract"; U.S. Ser. No. 62/819,513, filed Mar. 15, 2019, and entitled "Ingestible Device With High Pressure Substance Delivery to the Gastrointestinal Tract"; and U.S. Ser. No. 62/932,459, filed Nov. 7, 2019, and entitled "Ingestible Device and Method of Use to Deliver Therapeutic Agent to the Gastrointestinal Tract."

Definitions

"Ingestible," as used herein in reference to the device, means that the device can be swallowed whole.

"Dispensable" as used herein with reference to any substance, refers to any substance that may be released from an ingestible device as disclosed herein, or from a component of the device such as a reservoir. For example, a dispensable substance may be a therapeutic agent as disclosed herein, and/or a formulation that includes a therapeutic agent as disclosed herein. A dispensable substance may be a fluid, such as a liquid, a suspension or a semi-solid. For example, a dispensable substance can be a liquid in the form of a solution, such as an aqueous solution. In some embodiments, when disposed in an ingestible device, a substance is a non-fluid, such as a solid. In such embodiments, the substance may be converted to a fluid prior to being delivered from the ingestible device. In some embodiments, the therapeutic agent is a small molecule. In other embodiments, the therapeutic agent is a large molecule, such as a biologic drug. Nonlimiting examples of biologic drugs include antibodies (including monoclonal antibodies), proteins (including fusion proteins), peptides (including cyclic peptides), cells (including stem cells), and nucleic acids (including inhibitory nucleic acids, antisense nucleic acids, siRNA, ribozymes). In some embodiments, the dispensable substance is a pharmaceutical formulation comprising a therapeutic agent and a liquid carrier. In some embodiments, the pharmaceutical formulation comprising the therapeutic agent and the liquid carrier is a solution formulation. In other embodiments, the pharmaceutical formulation comprising the therapeutic agent and the liquid carrier is a suspension formulation, or an emulsion formulation. In some embodiments, a dispensable substance delivered as described herein is particularly well-suited for treatment of diseases and conditions of the endoderm, for example, it may be more efficacious in gut-associated lymphoid tissue (GALT) or the hepatic system as compared to subcutaneous or intravenous administration. In general, the viscosity of a dispensable substance can be selected as appropriate. In some embodiments, the dispensable substance has a viscosity of at least about 0.5 centiPoise (cP) (e.g., at least about 0.8 cP, at least about 1 cP, at least about 2 cP, at least about 3 cP, at least about 4 cP, at least about 5 cP, at least about 10 cP, at least about 15 cP, at least about 25 cP, at least about 50 cP) and/or at most about 100 cP (e.g., at most about 75 cP, at most about 65 cP, at most about 50 cP, at most about 25 cP, at most about 20 cP, at most about 10 cP at most about 9 cP, at most about 8 cP, at most about 7 cP). In certain embodiments the dispensable substance has a viscosity of from about 0.5 cP to about 10 cP (e.g., from about 0.8 cP to about 9 cP, from about 0.8 cP to about 8 cP). In some embodiments, the dispensable substance has a viscosity of from about 0.5 cP to about 100 cP (e.g., from about 1 cP to about 100 cP, from about 1 cP to about 50 cP, from about 1 cP to about 25 cP, from about 1 cP to about 20 cP, from about 1 cP to about 15 cP, from about 1 cP to about 10 cP, from about 5 cP to about 100 cP, from about 10 cP to about 100 cP, from about 25 cP to about 100 cP, from about 25 cP to about 75 cP, from about 25 cP to about 50 cP).

As used herein, the term "enteric" refers a material that permits transition to a desired location in the GI tract (e.g., through the stomach to the intestine) before being dissolved/degraded/eroded due to exposure of certain conditions (e.g., pH, temperature, enzymes) of the GI tract. An enteric material may prevent a drug from degradation by gastric fluid and enzymes. In some embodiments, an enteric composition (e.g., when formed as a coating on the housing of an ingestible device) is selected from mixtures of fats and fatty acids; shellac and shellac derivatives; and cellulose acetate phthalates. An enteric material can be an enteric polymer. In some embodiments, an enteric polymer can remain insoluble in the stomach, but dissolve at the higher pH of the intestine (e.g., small intestine or large intestine), and are used to deliver drugs to the intestine. Examples include Colorcon's Opadry Enteric 91 series Polyvinyl Acetate Phthalate, Opadry Enteric 94 series Methacrylic Acid, Opadry Enteric 95 series Methacrylic Acid, Sureteric PVAP (Polyvinyl Acetate Phthalate), Nutrateric Ethylcellulose Evonik Acryl-EZE (Colorcon & Evonik collaboration—Eudragit L 100-55 Mixture Methacrylic copolymers); Evonik's Eudragit L 100-55 Methacrylic copolymers, Eudragit L 30 D-55 Methacrylic copolymers (30%), EudragitL 100 Methacrylic copolymers, EudragitL 12,5 Methacrylic copolymers (12.5%), Eudragit S 100 Methacrylic copolymers, Eudragit S 12,5 Methacrylic copolymers (12.5%), Eudragit FS 30 D Methacrylic copolymers (30%); Kerry's SheffCoat ENT Cellulose Acetate Phthalate, Acrylate copolymer, HPMC-P; Eastman's C-A-P NF Cellulose Acetate Phthalate; Sensient's PROTECT™ ENTERIC Shellac & Sodium Alginate. In certain embodiments, an enteric material dissolves in the small intestine and is suitable for small intestine release. Examples of such enteric materials include, but are not limited to, cellulose derivatives, e.g., cellulose acetate phthalate, hydroxypropylmethylcellulose phthalate (HPMCP), hydroxypropylmethylcellulose acetate succinate (HPMCAS) and RL100 (e.g., HP-55), malic acid-propane 1,2-diol, polyvinyl acetate phthalate, anionic polymers of methacrylic acid and methyl methacrylate, hydroxypropylcellulose acetate phthalate, polyvinyl acetate phthalate, methacrylate-methacrylic acid copolymers, styrol, maleic acid copolymers, shellac, and others. Another suitable enteric material is a water emulsion of ethylacrylate methylacrylic acid copolymer, or hydroxypropyl methyl cellulose acetate succinate (HPMAS). (See, e.g., U.S. Pat. No. 5,591,433). In some embodiments, an enteric material dissolves in the large intestine and is suitable for colonic release. Enteric materials suitable for large intestine (e.g., colonic) release are known to one of skill in the art. In some embodiments, degradation of the coating is microbially triggered, e.g., the bacteria in the colon enzymatically trigger degradation of the coating (see, e.g., Archana et al., Int. J. Pharm. Sci. Res. 1(5):40-47 (2016); and Sethi et al., Int. J. Pharm. Sci. Res. 3(9):2989-3000 (2012)). In some embodiments, the coating is a pH-dependent polymer that is insoluble at low pH but becomes increasingly soluble as pH increases. In some embodiments, the coating is a polymethacrylates with a pH-dependent dissolution threshold of about pH 6.0 to about 7.0. Examples of suitable enteric materials include, but are not limited to, chitosan, alginates (e.g., as calcium salts), Eudragit® L (e.g., Eudragit® 100), Eudragit® S (e.g., Eudragit® S 100), Eudragit® L (e.g., Eudragit® L-30D), Eudragit® FS (e.g., Eudragit® FS 30D), hydroxypropylmethylcellulose phthalate 50, hydroxypropylmethylcellulose phthalate 55, and cellulose acetate trimellate. In some embodiments, an enteric material is a material described in U.S. Pat. No. 10,226,430; Sethi et al., Int. J. Pharm. Sci. Res. 3(9):2989-3000 (2012); or Archana et al., Int. J. Pharm. Sci. Res. 1(5):40-47 (2016), each of which are herein incorporated by reference in their entireties. In some embodiments, the colon-specific degradation of an enteric material can be based on the presence of microorganisms that reside only in the colon, more particularly, biodegradable enzymes produced by these microorganisms. In general, such microorganisms are anaerobic bacteria, e.g., *Bacteroides*, Bifidobacteria, Enterobacteria, Eubacteria, Clostridia, Enterococci, and Ruminococcus, etc. These micro floras fulfill their energy needs by fermenting various types of substrates that have been left undigested in the small intestine, e.g., polysaccharides, di- and tri-saccharides, etc. These polymers are stable in the environments of the stomach and small intestine. On reaching the colon, the polymers undergo degradation by the enzyme or break down of the polymer backbone leads to a subsequent reduction in their molecular weight and thereby loss of the mechanical strength.

The term "jet," as used herein, refers to a collimated stream of fluid, e.g., liquid or suspension, that is stable without breaking up into a spray. A jet may be formed by forcing the fluid, e.g., liquid or suspension, through an opening in an ingestible device. Generally, a jet maintains a stable form and is capable of achieving its intended purpose by maintaining appropriate properties (e.g., to penetrate a surface), such as its diameter and/or velocity.

As used herein, "jet diameter" is the cross-sectional diameter of a jet at a given location.

As used herein, "average jet diameter" refers to the average cross-sectional diameter of a jet between the location where the jet is formed (e.g., a nozzle opening through which the dispensable substance is delivered from the ingestible device) and the location where the jet impacts the GI tissue of the subject.

"Jet stable length," as used herein, refers to the distance from an opening (e.g., nozzle opening) of an ingestible device that a dispensable substance delivered through the opening remains in the form of a jet.

"Jet velocity," as used herein is the average fluid velocity across the cross-section of a jet at a given point in time.

As used herein, "peak jet velocity," refers to the maximum jet velocity of a jet at the interface of the lumen and the surface of the GI tract facing the lumen. In general, the peak jet velocity is achieved at the time of initial delivery of the dispensable substance from the ingestible device.

As used herein, "minimum jet velocity," refers to the minimum velocity of a jet at the interface of the lumen and the surface of the GI tract facing the lumen. In general, the minimum jet velocity is achieved at the end of delivery of the dispensable substance from the ingestible device.

"Mean jet velocity" and "average jet velocity," as used herein, refer to the average velocity of a jet at the interface of the lumen and the surface of the GI tract facing the lumen as determined over the time that the ingestible device delivers the dispensable substance.

As used herein, "peak jet power" refers to the maximum power of a jet at the interface of the lumen and the surface of the GI tract facing the lumen. In general, the peak jet power is achieved at the time of initial delivery of the dispensable substance from the ingestible device.

As used herein, "minimum jet power," refers to the minimum power of a jet at the interface of the lumen and the surface of the GI tract facing the lumen. In general, the minimum jet power is achieved at the end of delivery of the dispensable substance from the ingestible device.

"Mean jet power" and "average jet power," as used herein, refer to the average power of a jet at the interface of the lumen and the surface of the GI tract facing the lumen as determined over the time that the ingestible device delivers the dispensable substance.

"Jet power during delivery," as used herein, refers to the power of a jet at the interface of the lumen and the mucosa of the GI tract of a subject.

"Jet pressure," as used herein, refers to the pressure of a jet at the interface of the lumen and the surface of the GI tract facing the lumen. As an example, the jet pressure can be the pressure by the jet measured at the intestinal wall. In some embodiments, jet pressure is referred to herein as "impact pressure."

"Peak jet pressure," as used herein, refers to the maximum pressure of a jet at the interface of the lumen and the surface of the GI tract facing the lumen. In general, the peak jet pressure is achieved at the time of initial delivery of the dispensable substance from the ingestible device.

As used herein, "minimum jet pressure," refers to the minimum pressure of a jet at the interface of the lumen and the surface of the GI tract facing the lumen. In general, the minimum jet pressure is achieved at the end of delivery of the dispensable substance from the ingestible device.

"Mean jet pressure" and "average jet pressure," as used herein, refer to the average pressure of a jet at the interface of the lumen and the surface of the GI tract facing the lumen as determined over the time that the ingestible device delivers the dispensable sub stance.

"Jet force," as used herein, refers to the force of a jet at the interface of the lumen and the surface of the GI tract facing the lumen. In some embodiments, jet force is referred to herein as "impact force."

"Peak jet force," as used herein, refers to the maximum force of a jet at the interface of the lumen and the surface of the GI tract facing the lumen. In general, the peak jet force is achieved at the time of initial delivery of the dispensable substance from the ingestible device. In some embodiments, peak jet force is referred to herein as "impact force."

As used herein, "minimum jet force," refers to the minimum force of a jet at the interface of the lumen and the mucosa of the GI tract of a subject. In general, the minimum jet force is achieved at the end of delivery of the dispensable substance from the ingestible device.

"Mean jet force" and "average jet force," as used herein, refer to the average pressure of a jet at the interface of the lumen and the surface of the GI tract facing the lumen as determined over the time that the ingestible device delivers the dispensable sub stance.

As used herein, "fluid volume" refers to the volume of the dispensable substance contained in the ingestible device.

"Initial fluid volume," as used herein, refers to the volume of the dispensable substance contained in the ingestible device just prior to delivery of the dispensable substance from the ingestible device.

"Final fluid volume," as used herein, refers to the volume of the dispensable substance contained in the ingestible device just after delivery of the dispensable substance from the ingestible device has ended.

As herein, "delivered fluid volume" refers to the volume of dispensable substance delivered from the ingestible device. In some embodiments, the delivered fluid volume is less than the fluid volume.

"End round" as used herein is the radius on the curve at the end of the housing of the ingestible device.

"Fluid pressure" as used herein refers to the pressure in the fluid volume.

As used herein, "peak fluid pressure" refers to maximum pressure generated in the fluid volume. Generally, the peak fluid pressure is achieved at initial delivery of the dispensable substance from the ingestible device. In some embodiments, peak fluid pressure is referred to herein as "internal pressure on the pharmaceutical formulation in the device, prior to release from the device."

As used herein, "minimum fluid pressure" refers to minimum pressure generated in the fluid volume. Generally, the minimum fluid pressure is achieved at the end of delivery of the dispensable substance from the ingestible device.

"Fluid pressure during delivery," as used herein, refers to the pressure in the fluid volume as it decreases during the delivery process.

As used herein, "nozzle" refers to a channel between a fluid reservoir space and an external environment. Generally, in embodiments in which a nozzle is used, pressure in the fluid volume generates a high speed flow of fluid through the nozzle to produce a fluid jet at the opening of the nozzle through which the dispensable substance leaves the ingestible device and enters an environment exterior to the ingestible device.

"Nozzle diameter," as used herein, refers to the diameter of the opening of the nozzle at the opening of the nozzle through which the dispensable substance leaves the ingestible device and enters an environment exterior to the ingestible device.

As used herein, "nozzle length" refers to the length of the opening of the nozzle.

"Nozzle stand-off distance," as used herein, refers to the distance between: 1) the opening of the nozzle through which the dispensable substance leaves the ingestible device and enters an environment exterior to the ingestible device; and 2) the interface of the lumen and the surface of the GI tract facing the lumen.

As used herein, the "internal pressure" of an ingestible device refers to the pressure applied to a dispensable substance, such as a therapeutic agent, or a formulation containing a therapeutic agent, contained in the ingestible device prior to delivery of the dispensable substance from the ingestible device. In some embodiments, the internal pressure is provided by the drive force generator of the ingestible device. In certain embodiments, the internal pressure is greater than the fluid pressure. This may be due, for example, to friction, such as O-ring friction, acting on the drive coupling of the ingestible device. This friction is referred to herein as the "piston friction."

"Nozzle pressure" as used herein refers to the pressure of a dispensable substance at a nozzle opening as measured at the surface facing the interior of the nozzle as the dispensable substance is delivered from the ingestible device. In general, for a given ingestible device at a given point in time, the nozzle pressure is approximately the same as the fluid pressure.

"Topical delivery" or "topical administration," as used herein, refers to a route of administration of a dispensable substance (for example, a therapeutic agent or a pharmaceutical formulation containing a therapeutic agent) where the dispensable substance is delivered to a localized area of the body or to the surface of a body part, regardless of the location of the effect; more particularly, the topical administration of the dispensable substance comprises releasing the dispensable substance to the lumen of the GI tract, a surface of the GI tract facing the lumen, a mucous membrane and/or a lining of the gastrointestinal tract of a subject, including, but not limited to, a surface, mucous membrane or lining containing one or more disease sites, such as gastrointestinal mucosal lesions. The effect of the topical delivery or topical administration of the dispensable substance may be local to, or away from (e.g., distal to), the site of the topical administration.

"Epithelial delivery" or "epithelial administration," as used herein, refers to a route of administration of a dispensable substance (for example, a therapeutic agent or a pharmaceutical formulation containing a therapeutic agent) where the dispensable substance is directly delivered into the mucus or onto the epithelium, but not past the epithelial layer, of the GI tract of a subject, such as the small or large intestine, from which the dispensable substance can act locally or peripherally. In some embodiments of epithelial delivery or epithelial administration, the therapeutic agent can move deeper into the GI tissue (i.e., past the epithelial layer) away from the site of direct delivery, such as, for example, via diffusion or active transport.

"Trans-epithelial delivery" or "trans-epithelial administration," as used herein, refers to a route of administration of a dispensable substance (for example, a therapeutic agent or a pharmaceutical formulation containing a therapeutic agent) where the dispensable substance is directly delivered through the epithelial layer of the mucosa of the GI tract to the submucosa of the GI tract of a subject; optionally, at least a portion of the dispensable substance is directly delivered past the epithelial layer to a region of the mucosa beneath the epithelial layer. In embodiments of trans-epithelial delivery in which a portion of the dispensable substance is directly delivered to a region of the mucosa beneath the epithelial layer, at least some (e.g., all) of the portion of the dispensable substance is directly delivered to the lamina propria. Once the therapeutic agent or a pharmaceutical formulation containing a therapeutic agent is directly delivered past the epithelial layer of the GI tract, it is available for systemic exposure of the therapeutic agent to the subject.

General Introduction

Figure 1B:
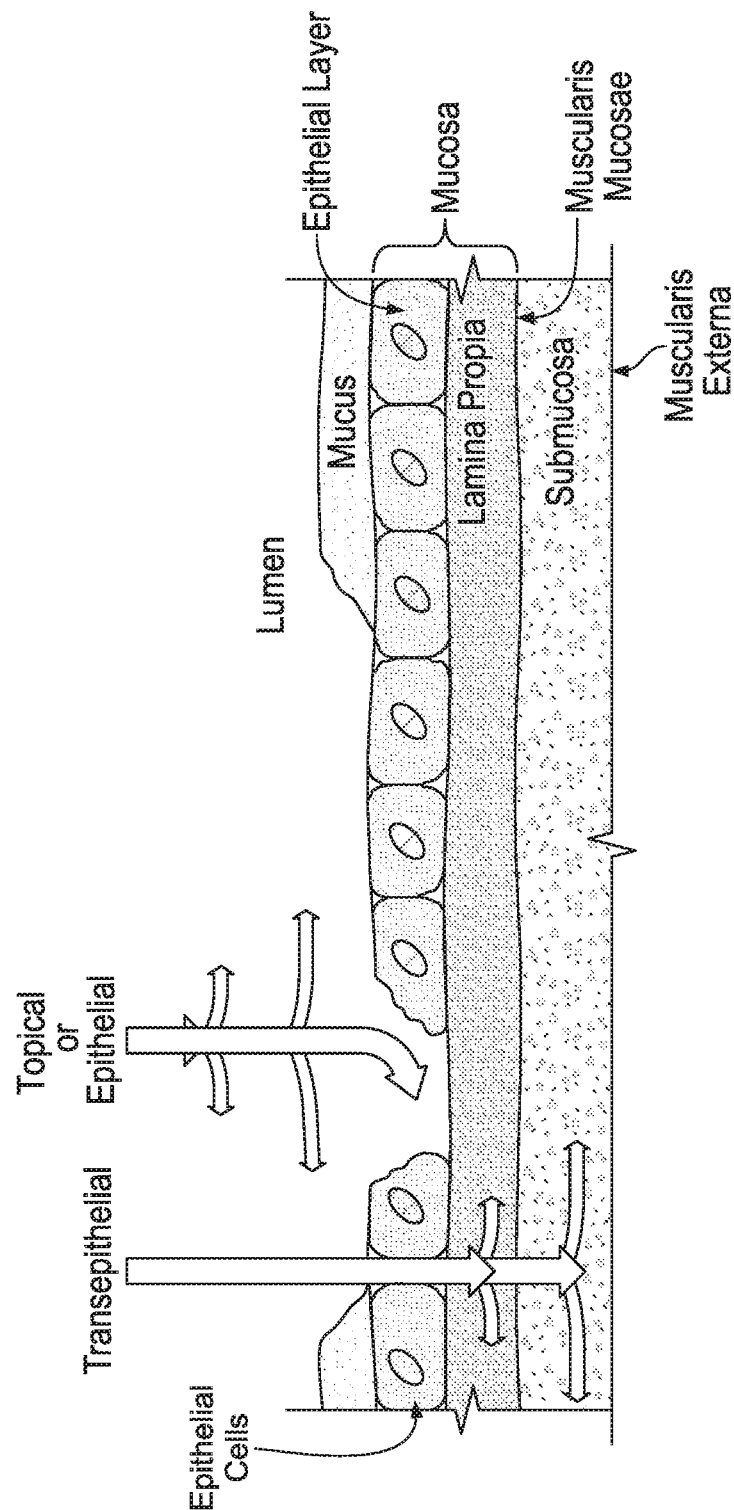
FIG. 1B is a schematic cross section corresponding to FIG. 1A but for diseased intestinal tissue.

FIG. 1A schematically describes the different regions of healthy intestinal tissue, presented in a cross section. The regions include the lumen of the GI tract, the mucus of the GI tissue, the mucosa of the GI tissue and the submucosa of the GI tissue. The mucosa of the GI tissue includes the epithelial layer and the lamina propria. The muscularis mucosae separates the mucosa from the submucosa. The muscularis extrema is below the submucosa. FIG. 1B schematically describes corresponding regions of diseased intestinal tissue, presented in a cross section.

An ingestible device described herein can deliver a therapeutic agent via topical delivery (without being directly delivered to the mucus, mucosa or submucosa), epithelial delivery (directly delivered to the mucus or epithelium without being directly delivered past the epithelial layer to the mucosa or submucosa) or trans-epithelial delivery (directly delivered to the submucosa and/or into a region of the mucosa beneath the epithelial layer, such as the lamina propria.

In general, the form of delivery may depend on the design of the ingestible device and parameters used with the device (e.g., internal pressure, fluid pressure, number of nozzles, design of nozzles). Holding other parameters constant, at relatively low fluid pressures and/or internal pressures, the therapeutic agent may be topically delivered, while higher fluid pressures and/or internal pressures may result in epithelial delivery, and still higher fluid pressures and/or internal pressure may result in trans-epithelial delivery. During trans-epithelial delivery, a bolus of the therapeutic agent initially contained in the dispensable substance may form within the submucosa and/or into a region of the mucosa beneath the epithelial layer, such as the lamina propria.

In some embodiments, the following holds. The ingestible device is designed to deliver a dispensable substance, for example, a therapeutic agent or a pharmaceutical formulation containing a therapeutic agent through the epithelial layer of the mucosa of the GI tract. In some embodiments, the dispensable substance is a solution formulation; optionally, a suspension. In some embodiments, the dispensable substance enters the submucosa and/or into a region of the mucosa beneath the epithelial layer, such as the lamina propria, of the small intestine, where it can be absorbed systemically. After the patient swallows the device, it passes through the GI tract and eventually reaches the small intestine. The device includes a restraining mechanism, an optionally a triggering mechanism (e.g., a degradable and/or erodible coating, such as an enteric coating, that partially or completely degrades and/or erodes when the device reaches the desired location in the GI tract). The desired location can be the small intestine or the large intestine. When the device is configured for trans-epithelial GI tract delivery to the submucosa submucosa and/or into a region of the mucosa beneath the epithelial layer, such as the lamina propria, the preferred location can be the small intestine. With the restraining element is removed, relative movement between certain components (e.g., sliding of a component) occurs such that one or more openings in the ingestible device (e.g., in a compartment containing the dispensable substance, such as a reservoir, sometimes referred to herein as the "drug reservoir," "storage reservoir" or "substance reservoir") become aligned with one or more additional openings (e.g., one or more nozzles) in the ingestible device (e.g., in the housing). With the ingestible device now in this open position, a force (e.g., generated by a force generator and/or transferred by a drive coupling, such as a membrane or a piston) forces the dispensable substance from the drug reservoir out of the device via the one or more openings (e.g., the one or more nozzles). The dispensable substance is delivered as a jet of fluid (e.g., liquid) through the epithelial layer of the mucosa and directly into the submucosa and/or into a region of the mucosa beneath the epithelial layer, such as the lamina propria, of the GI tract in the form of single or multiple boluses. After swallowing the device, the device travels through the GI tract (mouth, esophagus, stomach, duodenum, jejunum, ileum, cecum and colon), ultimately exiting the GI tract via the anus.

Thus, in general, the ingestible devices disclosed herein provide delivery of therapeutic agent to the GI tract of a subject. In one aspect, the disclosure relates to trans-epithelial delivery of a dispensable substance (e.g., a therapeutic agent or a formulation comprising a therapeutic agent) to the GI tract of a subject. Accordingly, the disclosure provides an ingestible device that can directly deliver a dispensable substance (e.g., a therapeutic agent or a formulation comprising a therapeutic agent) to the submucosa and/or into a region of the mucosa beneath the epithelial layer, such as the lamina propria, of the GI tract of a subject, which may result in systemic exposure of the therapeutic agent to the subject. In such embodiments, the ingestible device is configured to directly deliver the dispensable substance past the epithelial cell layer of the mucosa and into the submucosa and/or into a region of the mucosa beneath the epithelial layer, such as the lamina propria, of the GI tract, where the therapeutic agent so delivered is available for systemic uptake. In some embodiments, systemic exposure of the therapeutic agent is achieved by trans-epithelial delivery of the dispensable substance into the submucosa and/or into a region of the mucosa beneath the epithelial layer, such as the lamina propria, of the small intestine, for example, in the duodenum, the jejunum, and/or the ileum. In some further embodiments, the trans-epithelial delivery directly delivers the dispensable substance into the submucosa and/or into a region of the mucosa beneath the epithelial layer, such as the lamina propria, of the GI tract such that the percent systemic uptake of the therapeutic agent via the trans-epithelial delivery relative to intravenous or subcutaneous administration is at least about 10% (e.g., at least about 15%, at least about 20%, at least about 25% or more).

In some embodiments, the direct delivery of the therapeutic agent to the submucosa and/or into a region of the mucosa beneath the epithelial layer, such as the lamina propria, via trans-epithelial delivery may also or alternatively provide therapeutic effects locally and/or away from (e.g., distal to) the site of the direct delivery.

In some embodiments, the trans-epithelial delivery may directly deliver a first portion of the dispensable substance to the submucosa of the GI tract, and a second portion of the dispensable substance to the mucosa, all or a further portion of which may be directly delivered to the lamina propria. In some embodiments, the second portion of the dispensable substance delivered to the mucosa, such as the lamina propria, of the GI tract via the trans-epithelial delivery may provide therapeutic effects locally and/or away from (e.g., distal to) the site of the direct delivery.

In another aspect, the disclosure relates to epithelial delivery of a dispensable substance (e.g., a therapeutic agent or a formulation comprising a therapeutic agent) to the GI tract of a subject. Accordingly, the disclosure provides an ingestible device configured to directly deliver a dispensable substance (e.g., a therapeutic agent or a formulation comprising a therapeutic agent) into the mucus, but not past the epithelial layer of the mucosa, of the small or large intestine, from which it may provide therapeutic effects locally and/or away from (e.g., distal to) the site of the direct delivery. In some further embodiments, the ingestible device directly delivers the dispensable substance such that it contacts the surface of the epithelial cell layer of the mucosa facing the lumen, but as previously noted, the epithelial delivery does not directly delivery the dispensable substance past the epithelial layer of the mucosa. In some embodiments, the device is configured so that the dispensable substance is delivered from the device with sufficient force to provide the epithelial delivery, the force being lower than that required for trans-epithelial delivery to the GI tract. In some further embodiments, the epithelial delivery directly delivers the dispensable substance into the mucus of the GI tract such that the percent systemic uptake of the therapeutic agent via the epithelial delivery relative to intravenous or subcutaneous administration is greater than that for topical delivery, but less than for trans-epithelial delivery. In other embodiments, the epithelial delivery directly delivers the dispensable substance into the mucus of the GI tract such that the percent systemic uptake of the therapeutic agent via the epithelial delivery relative to intravenous or subcutaneous administration is about 0.5% to about 10% or more (e.g., about 0.5%, about 2%, about 3%, about 4%, about 5%, about 6%, about 7%, about 8%, about 9%, about 10%, or more).

In some embodiments of epithelial delivery, the therapeutic agent directly delivered into the mucus of the GI tract via the epithelial delivery may undergo active or passive transport or diffusion past the epithelial layer. Once past the epithelial layer, the therapeutic agent may provide therapeutic effects locally and/or away from (e.g., distal to) the site of the direct delivery. In some embodiments, the therapeutic agent binds to a therapeutic target present in the GI epithelial layer or elicits other pharmacodynamic effects locally or away from the site of delivery via immune cells or tissue in the GI tract (e.g., dendritic cells, lymphocytes, mucosa-associated lymphoid tissue).

In yet another aspect, this disclosure relates to topical delivery of a dispensable substance (e.g., a therapeutic agent or a formulation comprising a therapeutic agent) to the GI tract of a subject. Accordingly, the disclosure provides an ingestible device configured to deliver the dispensable substance (e.g., a therapeutic agent or a formulation comprising a therapeutic agent) into the lumen and/or onto the mucus or other surface (e.g., a diseased surface) of the GI tract facing the lumen of the small or large intestine, from which it may provide therapeutic effects locally and/or away from (e.g., distal to) the site of delivery. In some embodiments, the device is configured so that the dispensable substance is delivered from the device with sufficient force so that the dispensable substance is delivered topically, the force being lower than that required for the epithelial or the trans-epithelial delivery to the GI tract. In some embodiments, the topical delivery to the GI tract results in reduced systemic uptake of the therapeutic agent compared to trans-epithelial delivery to the GI tract, intravenous or subcutaneous delivery.

In some further embodiments, topical delivery delivers the dispensable substance into the lumen and/or onto the mucus or the other surface facing the lumen of the GI tract such that the percent systemic uptake of the therapeutic agent via the topical delivery relative to intravenous or subcutaneous administration is less than about 20%, less than about 10%, less than about 5%, less than about 4%, less than about 3%, less than about 2% or less than about 1%. In some embodiments, the topical delivery to the GI tract results in negligible or no systemic uptake of the therapeutic agent compared to trans-epithelial delivery to the GI tract, intravenous or subcutaneous delivery.

In some embodiments, the topically delivered dispensable substance may spread over the mucus or other surface facing the lumen of the GI tract, thereby coating the surface of the GI tract at or away from (e.g., distal to) the site of delivery. In some embodiments, upon or after the dispensable substance has been topically delivered, the therapeutic agent may undergo transport (e.g., diffusion) from the surface of the mucus into the mucus, and optionally, active or passive transport or diffusion past the epithelial layer of the mucosa.

In some embodiments, the mucus and/or epithelial layer of the mucosa may be disrupted or even absent, such as in a patient having a disease or condition of the GI tract. In such embodiments, the topical delivery of the dispensable substance to the GI tract of the patient may provide direct delivery of the dispensable substance to the surface of the GI tract facing the lumen, such as mucosal tissue exposed by said disruption and/or absence (e.g., both the mucus layer and/or epithelial layer are completely or partially absent or compromised in portions of the GI tract due to a disease or condition). For example, in some embodiments, the topical delivery of the dispensable substance to the GI tract of the patient may provide topical delivery to one or more lesions of the GI tract. In some embodiments, the disease or condition is an inflammatory bowel disease. In some further embodiments, the inflammatory bowel disease is ulcerative colitis. In some other embodiments, the inflammatory bowel disease is Crohn's disease.

Accordingly, provided herein are new systemic delivery devices and methods that deliver therapeutic agents into the small intestinal mucosa and/or submucosa by jet injection. Current methods of administration for most large molecule therapeutic agents are subcutaneous (SC), intramuscular (IM), or bolus intravenous (IV) injection targeting the systemic circulation. The devices and methods described herein provide an alternative route of administration to current injectable medications, which can lead to greater convenience and compliance since they minimize or avoid the logistical challenges, patient compliance and adherence challenges, pain, and discomfort associated with traditional routes of administration.

Also, by providing a higher concentration of therapeutic in GI tissue, the devices and methods described herein are particularly well-suited for treatment of diseases and conditions of the endoderm, including the liver.

Device Description
General

In general, the ingestible device is suitable for swallowing by a patient and for safely and effectively passing through the GI tract of the patient. Generally, the device can be in the shape of a capsule, a pill or any other swallowable form that may be orally consumed by the subject. In some embodiments, the ingestible device can be swallowed voluntarily under medical supervision or in a home use environment with instruction provided ahead of subsequent ingestion. Generally, ingestible devices are intended for single subject, single use. The ingestible device can have a density high enough to cause the ingestible device to sink within human stomach fluid, e.g., the unfilled ingestible device can have a density of greater than 1.01 g/cm$^3$. The ingestible device can have maximum dimensions that allow the ingestible device to pass through an average human GI tract. In some embodiments, the ingestible device is configured to prevent tumbling in the small intestine of a human. For example, the ingestible device is of sufficient length whereby it will not tumble in the small intestine of a human before, during, or after the dispensable substance is released. Generally, the ingestible device is configured to deliver a sufficient amount of therapeutic agent contained in the dispensable substance to be effective for its intended purpose. In general, the ingestible device's patient-contacting portions (e.g., exterior surface) and dispensable substance-contacting portions are biocompatible. Preferably, the device can withstand an indirect bite force without damaging the housing damage or resulting in leakage. As an example, when containing the dispensable substance, the ingestible device can withstand a bite force of at least about 60 Newtons (N). Generally, unless otherwise intended (see discussion below) components of the ingestible device can withstand exposure to a pH range expected in the human GI tract without substantial loss of functionality, substantial structural damage, or substantial leakage. As an example, in some embodiments, the ingestible device can withstand submersion in a pH 1.5±0.5 fluid environment for at least about 24 hours without substantial loss of functionality, substantial structural damage, or substantial leakage. In general, the ingestible device can maintain an external fluid barrier between the inside of the ingestible device and the GI tract of the subject during transit therethrough. Generally, the ingestible device can withstand external fluid pressures to which it is exposed during use without substantial loss of functionality, substantial structural damage, or substantial leakage. As an example, in some embodiments, the ingestible device undergoes no substantial loss of functionality, substantial structural damage, or substantial leakage when exposed to a sustained pressure of at least about 2 psig for at least about 24 hours and/or when exposed to a momentary pressure of at least about 5 psig momentary pressure for at least about 1 minute.

In general, an ingestible device disclosed herein includes the following features.

Housing

In some embodiments, the ingestible device comprises a housing configured to maintain its mechanical integrity during use of the ingestible device. In some embodiments, the housing has a first portion and a second portion. In some further embodiments, the housing has a first actuation component on the housing, and a second actuation component within the housing. In some embodiments, a storage reservoir is located within the housing, wherein the storage reservoir is configured to store a dispensable substance. In some embodiments, the housing has an opening in fluid communication with the storage reservoir. In some embodiments, the ingestible device employs an electrolytic mechanism for creating one or more openings in the ingestible device, wherein a substance can be dispensed through said opening as described in PCT Application Number PCT/US2019/021814, which published as WO2019178071, and which is incorporated by reference herein. For example, the housing may comprise an external electrolytic circuit (electrolytically erodible surface being on the exterior of the device), whereby the surrounding gastric fluids are the electrolyte that completes an electrolytic circuit between anode and cathode. With sufficient bias voltage (e.g., 1.5-15 volts, such as 3-5 volts), the anode will dissolve or erode electrolytically and thus create an opening in the housing within a desired time interval. In some embodiments, the one or more openings created by an electrolytic mechanism are coupled to one or more nozzles, thereby allowing for trans-epithelial, epithelial, or topical delivery as described herein. In some embodiments an ingestible device includes an enteric coating on the housing. In certain embodiments, the enteric coating covers only certain regions of the housing. The housing may be designed to withstand the chemical and mechanical environment of the GI tract (e.g., effects of muscle contractile forces and concentrated hydrochloric acid in the stomach). A broad range of materials that may be used for the housing. Examples of these materials include, but are not limited to, thermoplastics, fluoropolymers, elastomers, stainless steel, and glass complying with ISO 10993 and USP Class VI specifications for biocompatibility; and any other suitable materials and combinations thereof. In certain embodiments, these materials may further include liquid silicone rubber material with a hardness level of 10 to 90 as determined using a durometer (e.g., MED-4942™ manufactured by NuSil™), a soft biocompatible polymer material such as, but not limited to, polyvinyl chloride (PVC), polyethersulfone (PES), polyethylene (PE), polyurethane (PU) or polytetrafluoroethylene (PTFE), and a rigid polymer material coated with a biocompatible material that is soft or pliable (e.g., a poly(methyl methacrylate) (PMMA) material coated with silicone polymer). Use of different materials for different components may enable functionalization of certain surfaces for interaction with proteins, antibodies, and other biomarkers. For example, Teflon® may be used as a material in the ingestible device for movable components in order to reduce friction between these components. Other example materials may include other materials commonly used in micro-fabrication, such as polydimethylsiloxane (PDMS), borosilicate glass, and/or silicon. Although specific materials may be referred to herein as being used to construct the device for illustrative purposes, the materials recited are not intended to be limiting, and one skilled in the art may easily adapt the device to use any number of different materials without affecting the overall operation or functionality of the device. In some embodiments, the housing of the ingestible device may be manufactured from a type of plastic, such as a photosensitive acrylic polymer material or an inert polycarbonate material. The housing may also be formed using material that can be sterilized by chemicals. In some embodiments, the wall of the housing may have a thickness of, for example, from about 0.5 millimeter to about 1 millimeter. In some embodiments, in addition to being biocompatible, the material from which the housing is made is non-ferric and non-magnetic. Such materials include various plastics (e.g., PVC, or polycarbonate). Optionally, the housing can include a metal-based material, such as an alloy, stainless steel or a substantially pure metal. Such materials can be sterilized without affecting the mechanical workings of the ingestible device or the exterior surface of the ingestible device. In some embodiments, the metal-based material is compatible with the dispensable substance over long duration of storage. A wide variety of stainless steel alloys satisfy these criteria, including SAE grades 303, 304, 304L, 316, 316L, 440. In consideration of nickel content, purity, and/or traceability, in some embodiments, the stainless steel grade is approved for use as a surgical implant material, such as ASTM grades F138, F1314, F1586, F2229, or F2581. The walls of the housing of the ingestible device generally are sufficiently thick to withstand internal and external pressures to which they are exposed without substantial loss of functionality, substantial structural damage, or substantial leakage. In general, the walls of the housing are desirably as thin as possible to enhance the volume available for containing dispensable substance. As an example, in some embodiments, the walls are from about 0.05 mm to about 0.5 mm thick (e.g., if made of metal-based material, such as stainless steel) or from about 0.1 to about 1 mm thick (e.g., if made of plastic, such as polycarbonate). In general, the housing is made of material with a thermal expansion coefficient low enough that the device does not substantially deform at temperatures encountered during shipping and storage, or within the GI tract. In some embodiments, the walls of the housing are made of an electrolytically erodible surface as described in PCT/US2019/021814, which published as WO2019178071. For example, in some embodiments, the housing includes an electrolytically erodible valve coupled to a nozzle for exposing the liquid volume to its surrounding environment. The exposed metal anode material acting as valve can include a metal alloy or substantially pure metal that is acceptable for human ingestion from consideration of its biocompatibility in the amounts electrolyzed during opening of the valve. It can be desirable to have the thickness of metal in the valve area be small (e.g., to reduce the time and amount of current used to open the valve). For example, the metal portion of the drug container can be 0.025 mm thick across a diameter that matches or slightly exceeds the diameter of the coupled nozzle (e.g., 0.60 mm). In general, the thickness of the metal in the valve area can be in the range 0.002 mm to 0.200 mm.

In some embodiments, the housing of an ingestible device is assembled from multiple modules. For example, in some embodiments, the housing is assembled from two modules. In such embodiments, one of the modules can contain the dispensable substance ("drug module"), and the other module can contain the drive force generator and the drive coupling ("drive module"). Typically, the drug module includes a housing part of appropriate size, shape and material(s) as discussed herein. Usually, the housing part is sterilized, and dispensable substance is subsequently disposed within the housing under aseptic conditions. Optionally a sterile seal (e.g., a sterile foil seal) is incorporated into the drug module. The components of the drug module (e.g., a housing part, a drive force generator, a drive coupling) are assembled in a clean environment. The drug module and the drive module are subsequently combined to form the ingestible device. Representative examples of modules, their separate assembly, and their combination to form an ingestible device, are provide elsewhere herein.

Generally, an ingestible device is sized and shaped for relatively safe and effective movement and intended use within the GI tract of the subject. In certain embodiments, an ingestible device is a capsule having an industry standard size. For example, in some embodiments, an ingestible device is configured as a 00 capsule or a 000 capsule.

In certain embodiments, the housing of an ingestible device has a length of at least about 20 mm (e.g., at least about 21 mm, at least about 22 mm, at least about 23 mm) and/or at most about 28 mm (e.g., at most about 27 mm, at most about 26 mm).

In some embodiments, the housing of an ingestible device has a diameter of at least about 7 mm (e.g., at least about 7.5 mm, at least about 8 mm, at least about 8.5 mm, at least about 9 mm, at least about 9.5 mm) and/or at most about 12 mm (e.g., at most about 11.5 mm, at most about 11 mm, at most about 10.5 mm, at most about 10 mm, at most about 9.5 mm, at most about 9 mm).

In certain embodiments, the housing of an ingestible device has an aspect ratio (ratio of length to width) of at least about 0.75 (e.g. at least about 1) and/or at most about 4 (e.g., at most about 3, at most about 2). In some embodiments, the housing of an ingestible device has an aspect ratio of from about 0.75 to 4 (e.g., from about 1 to about 3, from about 1 to about 2). For example, in some embodiments, the housing aspect ratio is about 1.5:1 (length:diameter). In some other embodiments, the housing aspect ratio is about 2:1 (length:diameter).

In certain embodiments, the housing of an ingestible device has a wall thickness of at least about 0.05 mm (e.g., at least about 0.5 mm, at least about 0.6 mm, at least about 0.7 mm) and/or at most about 1 mm (e.g., at most about 0.9 mm, at most about 0.8 mm).

In certain embodiments, an ingestible device has a wall thickness of from about 0.05 mm to about 0.5 mm. In some embodiments, an ingestible device has a wall thickness of from about 0.1 mm to about 1 mm. In certain embodiments, one region of the housing of an ingestible device may have a wall thickness that is different from that of a different region of the housing of the ingestible device.

In some embodiments, the housing of an ingestible device has an end round that is spline-shaped or that is spherical. In certain embodiments, an ingestible device has an end round that is from about 1 mm to about 2 mm (e.g., about 1.5 mm). In some embodiments, an ingestible device has an end round that is from about 4 mm to about 4.5 mm (e.g., about 4.25 mm). In certain embodiments, an ingestible device has an end round that is from about 4.9 to about 5 mm (e.g., about 4.95 mm). In some embodiments, an ingestible device has an end round that is from about 5.4 mm to about 5.6 mm (e.g., about 5.5 mm).

In certain embodiments, the housing of an ingestible device has an internal volume of at least about 700 µL (e.g., at least about 750 µL, at least about 800 µL, at least about 850 µL) and/or most about 1700 µL (e.g., at most about 1650 µL, at most about 1600 µL, at most about 1500 µL, at most about 1400 µL, at most about 1300 µL, at most about 1200 µL).

In an exemplary embodiment, the housing of an ingestible device has a diameter of about 11 mm, a length of about 26 mm, a wall thickness of about 0.8 mm, an end round of about 1.5 mm, and an internal volume of about 1685 µL.

In another exemplary embodiment, the housing of an ingestible device has a diameter of about 11 mm, a length of about 26 mm, a wall thickness of about 0.8 mm, an end round of about 5.5 mm (spherical), and an internal volume of about 1475 µL.

In a further exemplary embodiment, the housing of an ingestible device has a diameter of about 9.9 mm, a length of about 26 mm, a wall thickness of about 0.8 mm, an end round of about 1.5 mm, and an internal volume of about 1315 µL.

In yet another exemplary embodiment, the housing of an ingestible device has a diameter of about 9.9 mm, a length of about 26 mm, a wall thickness of about 0.8 mm, an end round of about 4.95 mm (spherical), and an internal volume of about 1177 µL.

In a further exemplary embodiment, the housing of an ingestible device has a diameter of about 8.5 mm, a length of about 23.3 mm, a wall thickness of about 0.7 mm, an end round of about 1.5 mm, and an internal volume of about 861 µL.

In still a further exemplary embodiment, the housing of an ingestible device has a diameter of about 8.5 mm, a length of about 23.3 mm, a wall thickness of about 0.7 mm, an end round of about 4.25 mm (spherical), and an internal volume of about 773 µL.

In yet a further exemplary embodiment, the housing of an ingestible device has a diameter of about 8.5 mm, a length of about 23.3 mm, a wall thickness of about 0.7 mm, an end round that is spline-shaped, and an internal volume of about 820 µL.

Fluid Volume

The ingestible device includes a fluid volume to contain a dispensable substance (e.g., a liquid, a suspension). In some embodiments, the fluid volume is completely disposed within the housing. Optionally, the fluid volume can be defined by a storage reservoir. Such a storage reservoir can be a component that can be prepared separately from the housing. In such a storage reservoir, the dispensable substance can be disposed in the storage reservoir before the storage reservoir is associated with the ingestible device.

Dispensable Substance

The device may include one or more dispensable substances, with each dispensable substance including one or more therapeutic agents and/or one or more pharmaceutical formulations including one or more therapeutic agents.

Nozzles

In some embodiments, an ingestible device includes one or more nozzles in fluid communication with the one or more openings in the ingestible device. The nozzle(s) is(are) configured so that the dispensable substance through the nozzle(s) when the dispensable substance is delivered from the ingestible device. In general, a nozzle can have any desired size and shape appropriate for the desired type of delivery of a dispensable substance from the ingestible device. In certain embodiments, a nozzle has a shape and/or size appropriate for trans-epithelial delivery, epithelial delivery or topical delivery. In some embodiments, an ingestible device includes more than one nozzle. For example, an ingestible device can include, for example, up to 50 nozzles (e.g., up to 40 nozzles, up to nozzles, up to 30 nozzles, up to 25 nozzles, up to 20 nozzles, up to 15 nozzles, 10 nozzles). In some embodiments, an ingestible device includes from 2 nozzles to 50 nozzles. In certain embodiments, an ingestible device includes 2 nozzles, three nozzles, four nozzles, five nozzles, six nozzles, seven nozzles, eight nozzles, 10 nozzles, 20 nozzles, 30 nozzles, 36 nozzles, 40 nozzles, 50 nozzles). In some embodiments, the nozzles are arranged at even intervals (optionally pairwise if an even number of nozzles are used) around the circumference of the device.

Restraining Mechanism

In some embodiments, the ingestible device comprises a restraining mechanism. Generally, a restraining mechanism has a first state in which it is configured to prevent the dispensable substance from exiting the ingestible device via the opening(s), and a second state in which it is configured so that it does not prevent the dispensable substance from exiting the ingestible device via the opening(s). The restraining mechanism can be configured to transition from its first state to its second state when it is exposed to a triggering condition. The restraining mechanism may be provided by one or more restraining elements. The restraining elements can have a first state in which they are configured to prevent the dispensable substance from exiting the ingestible device via the openings, and a second state in which they are configured to allow the dispensable substance to exit the ingestible device via the openings. The restraining elements can be configured to transition from the first state to the second state when the restraining elements are exposed to a triggering condition. In some embodiments, the restraining elements comprise a first type of restraining element and a second type of restraining element different from the first type of restraining element. The first type of restraining element can be configured to transition to its second state before the second type of restraining element transitions to its second state. In some embodiments, a restraining elements comprises a lid, a pin, a band, a plug, a dowel, a clasp, a clamp, a flange, a rivet, an annulus, a torus, a ring, a wafer, a cylinder, an asymmetric shape such as a partial annulus, partial torus, a partial ring, a partial wafer, a partial cylinder, or any combination thereof (e.g., two partial tori). Optionally, a restraining element can have a filled interior (e.g., no hole). Optionally, a restraining element can have a varying thickness (e.g., a center region that is thinner than the edges). In some embodiments, the restraining elements comprise a plasticizer such as triethyl citrate (TEC). In some embodiments, the restraining elements comprise a degradable and/or erodible material, such as, for example, an enteric material. The enteric material may be degradable and/or erodible in the small intestine of the GI tract, or may be degradable and/or erodible in the large intestine of the GI tract, for example, the colon. In some embodiments, a restraining mechanism can be a mechanism that prevents the dispensable substance from being delivered from the ingestible device even when the drive force generator (or optionally the drive coupling) applies an internal force. For example, such a restraining can be an element (e.g., a pin, a band, a plug) in the opening (e.g., nozzle opening) through which the dispensable substance can be delivered from the ingestible device. Such a restraining element can be formed, for example, of a material that degrades and/or erodes as discussed above.

In general, a restraining mechanism includes a material that will lose a sufficient degree of its mechanical strength at the desired location to cause the ingestible device to deliver the dispensable substance. The material may undergo loss of mechanical strength to any appropriate mechanism or combination of mechanisms, including, for example, moisture ingress, solubility, swelling, leaching, eroding and/or the like.

In some embodiments, a restraining mechanism includes a degradable and/or erodible material such as a water soluble material, optionally with one or more coatings of one or more enteric materials. The degradable and/or erodible material is designed to lose its mechanical strength in the presence of moisture (e.g., liquid present in the GI tract).

Generally, an enteric material erodes after being swallowed, e.g., in the small intestine or in the large intestine. In some embodiments, the degradable and/or erodible material is coated with an enteric material that limits the amount of moisture or fluid reaching the degradable and/or erodible material, whereby the degradable and/or erodible material is able to resist a trigger load, for example, for at least two hours at a pH of 1.1. In certain embodiments, the enteric material breaks down to release a trigger load after being exposed to a pH of 1.1 for two hours followed by exposure to a pH of 6.8 for 10, 20, 30, 40, 50, 60 or more minutes.

An enteric material can be in the form of one or more coatings at varying coating weights (e.g., one or more spray coatings and/or one or more dip coatings) on a degradable and/or erodible material such as a water soluble material. For example, in some embodiments, compared to the weight of the degradable and/or erodible material, the coating weight can be 5%, 10%, 15%, 20%, 25%, 30%, 35%, 40%, 45%, 50%, 55% or more. In general, the coating weight can be selected as desired, e.g., based on the intended use of the ingestible device. For example, the coating weight can be selected to select a desired location and/or time for the degradable and/or erodible material to degrade and/or erode to a sufficient extent to trigger delivery of the dispensable substance from the ingestible device.

Desirably, the degradable and/or erodible material is sufficiently strong enough to resist the trigger load when dry, but also capable of sufficiently weakening to release the trigger load when the degradable and/or erodible material is exposed to an aqueous environment for a desired period of time, such as, for example, at least two minutes, e.g., at least 5, at least 10, at least 20, at least 30, at least 40, at least 50, at least 60, at least 70, at least 80, at least 90, at least 100, at least 110, at least 120, at least 130, at least 140, at least 150, or at least 160 minutes.

In some embodiments, a triggering mechanism has a density of from about one $g/cm^3$ to about 3 grams/$cm^3$ (e.g., from about 1.3 $g/cm^3$ to about 2 $g/cm^3$).

In certain embodiments, a triggering mechanism is from about 1 mm to about 5 mm thick (e.g., from about 1 mm to about 2 mm thick).

In some embodiments, a coating of enteric material has a density of from about 0.5 $mg/cm^2$ to 20 $mg/cm^2$ (e.g., from about 2 $mg/cm^2$ to about 6 $mg/cm^2$).

Examples of degradable and/or erodible materials include polyethylene glycol (PEG) and Isolmalt. In some embodiments, a degradable and/or erodible material includes one or more diluents/fillers, one or more binders, and/or or more disintegrants. Examples of diluents/fillers include lactose, starch, mannitol, microcrystalline cellulose, carboxymethyl cellulose, and dicalcium phosphate. Examples of binders include povidone, hypromellose, hydroxypropyl cellulose, copovidone, and microcrystalline cellulose. Examples of disintegrants include crospovidone, croscarmellose sodium (SD-711), sodium starch glycolate, and low-substituted hydroxypropyl cellulose. Optionally, a degradable and/or erodible material can include a lubricant, such as, for example, magnesium stearate.

As an example, a degradable and/or erodible material includes starch (e.g., StarTab grade from Colorcon, Starch 1500 grad from Colorcon), microcrystalline cellulose (e.g., Vivapur 102 grade from JRS Pharma), croscarmellose sodium (e.g., Ac-di-sol SD-711 grade from FMC Biopolymer), and magnesium stearate (e.g., Ligamed MF-2-V grade from Giusto Faravelli), and optionally further includes talc (e.g., PSD<75 μm grade from Acros), enteric methacrylate polymer (e.g., FL30 D-55 grade from Evonik), and HPMC polymer sub coat (e.g, Opadry 03K19229 grade from Colorcon). As an example, a degradable and/or erodible material can include Starch 1500 (e.g., 49.6% w/w), microcrystalline cellulose 102 Starch (e.g., 49.6% w/w); and croscarmellose sodium SD-711 (e.g., 0.5% w/w); and magnesium stearate (e.g., 0.26% w/w). As a further example, a degradable and/or erodible material can include Startab (e.g., 49.6% w/w), microcrystalline cellulose 102 Starch (e.g., 49.6% w/w); and croscarmellose sodium SD-711 (e.g., 0.5% w/w); and magnesium stearate (e.g., 0.26% w/w). As another example, a degradable and/or erodible material can include Starch 1500 (e.g., 48.9% w/w), microcrystalline cellulose 102 Starch (e.g., 48.9% w/w); croscarmellose sodium SD-711 (e.g., 2% w/w); and magnesium stearate (e.g., 0.26% w/w). As further example, a degradable and/or erodible material can include Startab (e.g., 49.6% w/w), microcrystalline cellulose 102 Starch (e.g., 49.6% w/w); croscarmellose sodium SD-711 (e.g., 2% w/w); and magnesium stearate (e.g., 0.26% w/w). As another example, a degradable and/or erodible material can include dicalcium phosphate (e.g., 48.9% w/w), microcrystalline cellulose 102 Starch (e.g., 48.9% w/w); croscarmellose sodium SD-711 (e.g., 2% w/w); and magnesium stearate (e.g., 0.25% w/w). As a further example, a degradable and/or erodible material can include dicalcium phosphate (e.g., 33.25% w/w), microcrystalline cellulose 102 Starch (e.g., 33.25% w/w); mannitol (e.g., 33.25% w/w); and magnesium stearate (e.g., 0.25% w/w).

Examples of enteric materials coated on a degradable and/or erodible material include: spray coated Eudragit FL 30 D-55 (e.g., 12 $mg/cm^2$ direct spray coated Eudragit FL 30 D-55 on a water soluble material); dip coated Eudragit L 100 D-55 (e.g., 4 $mg/cm^2$ Eudragit L 100 D-55 dip coated onto an HPMC capsule cap); and spray coated Eudragit FL 30 D-55 (e.g., 9 $mg/cm^2$ Eudragit FL 30 D-55 direct spray coated on a water soluble material; 6 mg/cm² Eudragit FL 30 D-55 direct spray coated on a water soluble material).

Triggering Mechanism

In some embodiments, the ingestible device comprises a triggering mechanism. In some embodiments, a triggering mechanism is configured to cause the dispensable substance within the fluid volume to be released under one or more triggering conditions. In some embodiments, a triggering mechanism initiates a drive force generator. In some embodiments, a triggering mechanism incorporates a mechanical feature like a restraining mechanism. As an example, one or more restraining elements degrade and/or erode in the presence of certain GI tract conditions (e.g., pH greater than 5), thereby triggering a drive force generator, such as a compressed spring. As another example, a spring may have a piercing element that pierces a cylinder with compressed gas, whereby the released gas acts as a force applied to a dispensable substance. In certain embodiments, a triggering mechanism incorporates an electrical feature. For example, an enteric coating degrades and/or erodes in the presence of certain GI tract conditions (e.g., pH greater than 5), thereby exposing conductors to intestinal fluid, which acts as a liquid conductor to triggering the drive force generator. In some embodiments, a triggering condition relates to a condition of the GI tract. In some embodiments, the condition of the GI tract comprises at least one condition selected from the group consisting of temperature, pH, presence of one or more enzymes, and time. In some more particular embodiments, the condition of the GI tract is a pH of greater than 5. In certain embodiments, the triggering mechanism is configured so that the release mechanism is autonomously triggered (e.g., due to degradation, dissolution and/or erosion of the restraining mechanism due to conditions in the GI tract).

In some embodiments, a restraining element can include one or more small molecule therapeutic agents, e.g., one or more small molecule therapeutic agents as disclosed herein. In certain embodiments, a small molecule therapeutic agent contained in the restraining mechanism can be the same as a therapeutic agent contained in the dispensable substance. In some embodiments, a small molecule therapeutic agent contained in the restraining mechanism can different from a therapeutic agent contained in the dispensable substance. In certain embodiments, the restraining mechanism includes multiple small molecule therapeutic agents, and the dispensable substance contains the same therapeutic agents. In some embodiments, the restraining mechanism includes multiple small molecule therapeutic agents, and the dispensable substance contains one or more different therapeutic agents. In certain embodiments, the dispensable substance includes a therapeutic agent that is capable of treating a certain condition, and a small molecule therapeutic agent included in the restraining element is capable of treating the same condition. In some embodiments, the dispensable substance includes a therapeutic agent that is capable of treating a certain condition, and a small molecule therapeutic agent included in the restraining element is capable of treating a different condition. In certain embodiments, the dispensable substance includes a therapeutic agent that is capable of treating a certain condition, and the small molecule therapeutic agent included in the restraining element is capable of treating the same condition and at least one different condition. In some embodiments, a small molecule therapeutic agent included in the restraining element is capable of treating a certain condition, and the dispensable substance includes a therapeutic agent that is capable of treating at least one different condition. Other combinations are possible.

In general, the initial gas pressure within the gas cylinder (gas pressure before the gas cylinder is implemented as a force generator) is appropriate to provide the desired internal pressure. Typically, the initial gas pressure in the cylinder is at least about 500 psig (e.g., at least about 600 psig, at least about 700 psig, at least about 750 psig, at least about 800 psig, at least about 850 psig, at least about 900 psig) and/or at most about 1,200 psig (e.g., at most about 1,100 psig, at most about 1,000 psig, at most about 950 psig, at most about 900 psig). In some embodiments, the initial gas pressure within the gas cylinder is from about 500 psig to about 1,200 psig (e.g., from about 600 psig to about 1,100 psig, from about 700 psig to about 1,000 psig, from about 750 psig to about 950 psig, from about 800 psig to about 950 psig, from about 850 psig to about 950 psig).

The burst pressure of the gas cylinder (the minimum pressure at which the gas cylinder bursts) is usually based on the desired initial gas pressure within the gas cylinder. For initial gas pressures noted in the preceding paragraph, the burst pressure of the gas cylinder can be at least about 2,800 psig (e.g., at least about 2,900 psig, at least about 3,000 psig, at least about 3,100 psig, at least about 3,200 psig, at least about 3,300 psig, at least about 3,400 psig, at least about 3,500 psig, at least about 3,600 psig) and/or at most about 4,500 psig (e.g., at most about 4,400 psig, at most about 4,300 psig, at most about 4,200 psig, at most about 4,100 psig, at most about 4,000 psig, at most about 3,900 psig, at most about 3,800 psig). In some embodiments, the burst pressure of the gas cylinder is from about 2,800 psig to about 4,500 psig (e.g., from about 2,900 psig to about 4,400 psig, from about 3,000 psig to about 4,300 psig, from about 3,100 psig to about 4,200 psig, from about 3,200 psig to about 4,100 psig, from about 3,100 psig to about 4,000 psig, from about 3,200 psig to about 3,900 psig, from about 3,300 psig to about 3,800 psig, from about 3,400 psig to about 3,800 psig, from about 3,500 psig to about 3,800 psig, from about 3,600 psig to about 3,800 psig, from about 3,700 psig to about 3,800 psig).

Generally, the gas within the gas cylinder can be a single gas or a mixture of two or more gases. Exemplary gases include air, nitrogen, oxygen, carbon dioxide, hydrofluorocarbon gases, and noble gases (e.g., helium, neon, argon, krypton, xenon). In some embodiments, the gas within the gas cylinder is a mixture of gases that include helium (e.g., nitrogen/helium mixture, argon/helium mixture). Optionally, such gas mixtures include at most about 5% helium. The presence of helium in a gas mixture can allow for leak checking the gas cylinder based on the presence of helium gas adjacent the exterior of the gas cylinder.

In general, the gas cylinder may be made of any appropriate and/or desired material. Examples include metal, plastic, and/or composite materials. In some embodiments, the gas cylinder is made of stainless steel or galvanized steel. In certain embodiments, the gas cylinder may be made from a material which is itself prepared by a process that includes drawing, stamping, machining, casting, molding, and/or the like (e.g., deep drawing from sheet metal). In some embodiments, the gas cylinder may be made of a ceramic, an alloy, aluminum and/or titanium.

In some embodiments the gas cylinder includes a breakable seal (e.g., a membrane) which is broken via an element (e.g., a piercer) when the gas cylinder is being used as a force generator, as described in more detail below. Typically, the breakable seal is part of an end cap of the gas cylinder.

The end cap and/or the breakable seal can be formed of one or more of the materials noted in the preceding paragraph. Breaking the breakable seal may involve, for example, tearing a portion of the breakable seal and/or puncturing a portion of the breakable seal. More generally, breaking the breakable seal means to modify the seal in a manner such that the breakable seal is no longer able to confine the gas within the gas cylinder. In general, the breakable seal is made of a material that has at least a region that is relatively thin and/or that is configured (e.g., scored) to break. Optionally, the entire barrier is relatively thin. As an example, the barrier may have a relatively thin perimeter with a relatively thick portion within the perimeter (e.g., central portion) so that, when the element (e.g., piercer) applies an appropriate force, the relatively thin portion of the breakable seal breaks. As another example, the barrier may have an inner (e.g., central) portion surrounded by a portion that is scored so that, when the element (e.g., piercer) applies an appropriate force, the scored portion of the breakable seal breaks. In some embodiments, the breakable seal has a substantial constant thickness and has a portion that is configured (e.g., scored) to break when the element (e.g., piercer) applies an appropriate force. In general, such scoring can be configured as desired. As an example, scoring can be configured as a series of parallel lines. As another example, scoring can be configured as a grid (cross-hatched). As a further example, scoring can be configured as a plurality of dots (e.g., equally spaced dots).

In some embodiments, the element (e.g., piercer) has a contact point on the breakable seal. Optionally, the contact point is concentrated in a relatively small local area. For example, the piercer may be a needle or a thin rod element that is cut at an angle to initially generate a single point contact. Relative to the breakable seal, the point of initial contact may be on-center or off-center. Having the point of initial contact off-center relative to the breakable seal can result in a reduced force applied by the element (e.g., piercer). In embodiments where the modified (e.g., scored) region of the breakable seal is off-center, placing the element (e.g., piercer) off-center means that the contact point is closer to the modified (e.g., thinner scored region) of the breakable seal at the contact point of the element (e.g., piercer) with the breakable seal. In certain embodiments where the modified (e.g., scored) region of the breakable seal is a circle, the element (e.g., piercer) can be configures to that its contact point with the breakable seal is near one point on the circle. In general, the closer this contact point is to the modified region of the breakable seal, the lower the force of the element (e.g., piercer) used to break the breakable seal. To create a relatively fast release, the modified (e.g., score) portion of the breakable seal desirably fails over substantially most of the modified region, e.g., the diameter of the circle when the modified region is a scored region shaped as a circle. In some embodiments, the closer the contact point is to the center of the scored circle, the more likely that the seal fails on the entire circumference of the scored circle. In such embodiments, it is typically desirable to have the contact point of the element (e.g., piercer) be near the circle but not on it. Optionally, the contact point can be move inwards to get fast release properties. Optionally, a wider footprint for the initial contact of the element (e.g., piercer) may be implemented in some embodiments. For example, the contact point can be a sector of an arc placed near a circular score of the breakable seal. This can encourage failure of the breakable seal over a larger sector of the score region, which can yield faster gas escape.

In some embodiments, before the gas cylinder is used as a force generator, the element (e.g., piercer) is not in contact with the breakable seal. In certain embodiments, before the gas cylinder is used as a force generator, the element (e.g., piercer) may be in contact with the breakable seal such that the element (e.g., piercer) applies a relatively low pressure to the breakable seal. This pressure may be, for example, at least about one Newton (e.g., at least about two Newtons, at least about three Newtons, at least about four Newtons, at least about five Newtons) and/or at most about 15 Newtons (e.g., at most about 14 Newtons, at most about 13 Newtons, at most about 12 Newtons, at most about 11 Newtons, at most about 10 Newtons). In some embodiments, this pressure is from about one Newton to about 15 Newtons.

Generally, to cause the gas in the gas cylinder to be released from the gas cylinder, the element (e.g., piercer) applies a relatively high pressure to the breakable seal. This relatively high pressure may be, for example, at least about five Newtons (e.g., at least eight Newtons, at least about 10 Newtons, at least about 15 Newtons) and/or at most about Newtons (e.g., at most about 35 Newtons, at most about 30 Newtons, at most about 25 Newtons). In some embodiments, the relatively high pressure may be from about five Newtons about 35 Newtons.

Examples of gas cylinders, including those with an end cap and/or breakable seal, are disclosed, for example, in US 2017/0258583, the entire disclosure of which is incorporated by reference herein.

In some embodiments, the element (e.g., the piercer) is coupled to an actuator in an actuator assembly. In some embodiments, the actuator assembly has a total length of less than about 10 mm (e.g., less than about 9 mm, less than about 8 mm, less than about 7 mm, less than about 6 mm, less than about 5 mm, less than about 4 mm, less than about 3 mm, less than about 2 mm). In some embodiments, the actuator is a spring (e.g., a wave spring). In some embodiments, the spring has a compressed length of less than about 5 mm, less than about 4 mm, less than about 3.5 mm, less than about 3 mm, less than about 2.5 mm). In some embodiments, the spring has a stroke length of less than about 0.8 mm (e.g., less than about 0.7 mm, less than about 0.6 mm, less than about 0.5 mm, less than about 0.4 mm, less than about 0.3 mm).

In some embodiments, the element (e.g., the piercer) is moved relatively quickly when applying the relatively high force to the breakable seal. In certain embodiments, the element (e.g., the piercer) is moved relatively slowly when applying the relatively high force to the breakable seal. In some embodiments, to break the breakable seal, using a lower speed for moving the element (e.g., piercer) allows for use of a lower force compared to the force used to break the breakable seal when the element (e.g., piercer) moves at a higher speed.

In some embodiments, the element (e.g., piercer) moves relative to the gas cylinder. In certain embodiments, the gas cylinder moves relative to the element (e.g., piercer). For example, the gas cylinder can be coupled to an actuator which causes the gas cylinder to move.

In some embodiments of any of the devices or methods described herein, the releasing of the therapeutic is triggered by one or more of: a pH in the jejunum of about 6.1 to about 7.2, a pH in the mid small bowel of about 7.0 to about 7.8, a pH in the ileum of about 7.0 to about 8.0, a pH in the right colon of about 5.7 to about 7.0, a pH in the mid colon of about 5.7 to about 7.4, or a pH in the left colon of about 6.3 to about 7.7, such as about 7.0.

Drive Force Generator

The drive force generator is configured to provide the requisite force to the dispensable substance such that, when the restraining mechanism is removed, the dispensable substance is delivered from the ingestible device as desired. The drive force generator can apply force using different mechanisms, including, for example, a compressed gas, a gas generated by chemical reaction, a spring, a liquid-gas mixture, an impact ram, a sudden expansion caused by a controlled exothermic reaction, or the like. When the drive force generator is a spring, the spring can have one or more of the following properties: the outer diameter of the spring is smaller than the inner diameter of the ingestible device; the compressed length of the spring is minimized to leave more space for dispensable substance; the spring is of a conical shape, potentially with a reduction in the solid length of the spring; the free length of the spring is maximized and larger than the free length of the inner cavity of the ingestible device to ensure an acceptable driving pressure is provided throughout the entire time step of delivery; and the spring rate is large enough to provide acceptable pressure from the beginning until the end of delivery of the dispensable substance. Examples of springs include parallel springs, wave springs and conical springs. Examples of chemical reactants include an airbag inflator, a hydrogen cell (e.g., a Varta hydrogen cell), sodium bicarbonate and acid (e.g., alka seltzer and water on board the ingestible device, alka seltzer and GI tract fluid). Examples of compressed gas include a gas charged within the ingestible device, and a container (e.g., cylinder) of compressed gas. In some embodiments, the compressed gas is a gas cylinder from Picocyl. Exemplary gas cylinders are disclosed, for example, in US 2017-0258583, which is incorporated by reference herein. An example of a liquid-gas mixture is liquid nitrogen/HFA (hexafluoroacetone)/propane. An example of an impact ram is a two-phase spring/ram. Other examples of drive force generators include a wax actuator, heat generated by electric power (Peltier effect-based mechanism), and a mechanical puncture of tissue followed by delivery.

Drive Coupling

In general, the drive force coupling transfers a force from the drive force generator to the dispensable substance. Examples of a drive coupling include a piston and a membrane. Examples of membranes include balloons and elastomeric materials. An example of a piston is an O-ring sealed piston. In some embodiments, a piston is provided by a gas cylinder, e.g., with added O-rings or a custom housing. In some embodiments, a drive coupling is a vein, such as a rotating vein. In certain embodiments, a drive coupling is a double piston configured to counteract cap impact. In certain embodiments, a drive coupling is a collapsing bag, such as a collapsing foil bag. In some embodiments, a drive coupling is a collapsing bellows.

Storage Reservoir

In some embodiments, an ingestible device includes a storage reservoir configured to store a dispensable substance. In some embodiments, the storage reservoir stores the dispensible substance. In some embodiments, the storage reservoir is completely disposed within the housing.

Figure 2:
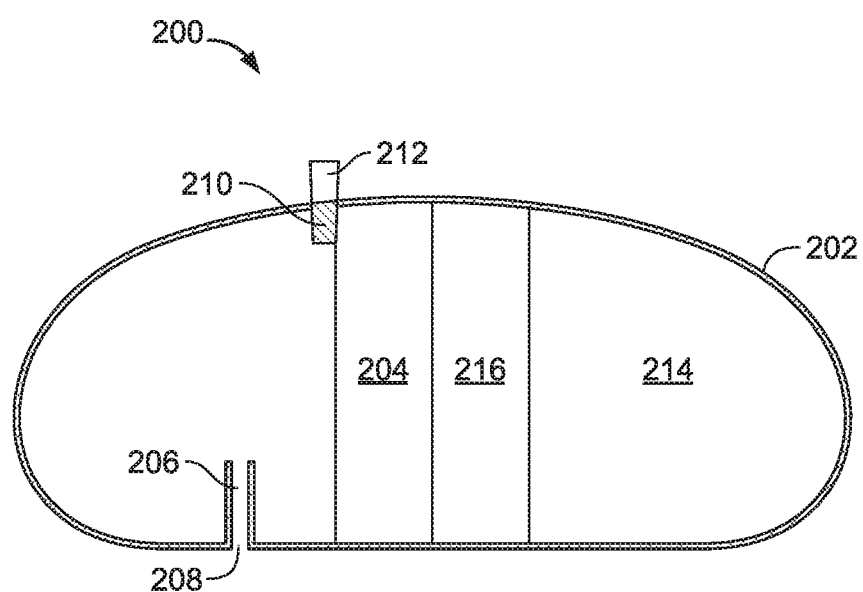
FIG. 2 is a cross section of an ingestible device.

FIG. 2 is a schematic representation of an ingestible device 200 which includes a housing 202, a fluid volume 204 containing a dispensable substance, a nozzle 206 with a nozzle opening 208, a restraining mechanism 210, a triggering mechanism 212, a drive force generator 214 and drive coupling 216. During use, ingestible device 200 is swallowed by a subject and traverses the GI tract. At an appropriate location, the triggering mechanism 212 is triggered, allowing the drive force generator to apply pressure to the drive coupling 216, which then applies pressure to the fluid volume such that at least some of the dispensable substance is delivered out of fluid volume 204, through the nozzle 206, and out of the device 200 via the nozzle opening 208. In some embodiments, the internal pressure is applied, even before the triggering mechanism 212 is triggered. As an example, at an appropriate location, the triggering mechanism 212 is triggered, allowing the drive coupling 216 to apply pressure to the fluid volume 204. In certain embodiments, the internal pressure is not applied until the triggering mechanism 212 is triggered.

Device for Trans-Epithelial Delivery

Generally, trans-epithelial delivery can be achieved at any desired location within the GI tract of a subject. In some embodiments, trans-epithelial delivery is achieved in the small intestine of the subject, such as, for example, in the duodenum, the jejunum and/or the ileum. In certain embodiments, trans-epithelial delivery is achieved in the large intestine of the subject, such as, for example, the cecum or the colon.

In general, an ingestible device for trans-epithelial delivery is configured to deliver a jet of the dispensable substance having a peak jet power of from at least about 1 Watt (e.g., at least about 1.1 Watts, at least about 1.2 Watts, at least about 1.3 Watts, at least about 1.4 Watts, at least about 1.5 Watts, at least about 1.6 Watts, at least about 1.7 Watts, at least about 1.8 Watts) and/or at most about 3 Watts (e.g., at most about 2.9 Watts, at most about 2.8 Watts, at most about 2.7 Watts, at most about 2.6 Watts, at most about 2.5 Watts, at most about 2.4 Watts, at most about 2.3 Watts, at most about 2.2 Watts, at most about 2.1 Watts). In some embodiments, an ingestible device for trans-epithelial delivery is configured to deliver a jet of the dispensable substance having a peak jet power of from about 1 Watt to about 3 Watts (e.g., of from about 1.3 Watts to about 2.8 Watts, of from about 1.5 Watts to about 2.5 Watts).

In general, an ingestible device for trans-epithelial delivery is configured to deliver a jet of the dispensable substance having a minimum jet power of at least about 0.1 W (e.g., at least about 0.2 W, at least about 0.3 W) and/or at most about 0.6 W (e.g., at most about 0.5 W, at most about 0.4 W). In some embodiments, a device for trans-epithelial delivery is configured to deliver a jet of the dispensable substance having a minimum jet power of from about 0.1 W to about 0.6 W (e.g., from about 0.2 W to about 0.5 W, from about 0.3 W to about 0.4 W).

In general, an ingestible device for trans-epithelial delivery is configured to deliver a jet of the dispensable substance having an average jet power of at least about 0.5 W (e.g., about 0.8 W, about 1 W) and/or at most about 2 W (e.g., at most about 1.7 W, at most about 1.5 W). In some embodiments, a device for trans-epithelial delivery is configured to deliver a jet of the dispensable substance having an average jet power of from about 0.5 W to about 2 W (e.g., from about 0.8 W to about 1.7 W, from about 1 W to about 1.5 W). Generally, an ingestible device for trans-epithelial delivery is configured to deliver a jet of the dispensable substance having a peak jet pressure of at least about 100 psig (e.g., at least about 110 psig, at least about 120 psig, at least about 130 psig, at least about 140 psig, at least about 150 psig, at least about 160 psig, at least about 170 psig, at least about 180 psig, at least about 190 psig) and/or at most about 250 psig (e.g., at most about 240 psig, at most about 230 psig, at most about 220 psig, at most about 210 psig). In certain embodiments, an ingestible device for trans-epithelial delivery is configured to deliver a jet of the dispensable substance having a peak jet pressure of from about 100 psig to about 250 psig (e.g., from about 140 psig to about 225 psig, from about 180 psig to about 205 psig).

In general, an ingestible device for trans-epithelial delivery is configured to deliver a jet of the dispensable substance having a minimum jet pressure of at least about 30 psig (e.g., at least about 40 psig, at least about 50 psig) and/or at most about 80 psig (e.g., at most about 70 psig, at most about 60 psig. In some embodiments, an ingestible device for trans-epithelial delivery is configured to deliver a jet of the dispensable substance having a minimum jet pressure of from about 30 psig to about 80 psig (e.g., from about 40 psig to about 70 psig, from about 50 psig to about 60 psig).

In general, an ingestible device for trans-epithelial delivery is configured to deliver a jet of the dispensable substance having an average jet pressure of 60 psig (e.g., at least about 80 psig, at least about 100 psig) and/or at most about 160 psig (e.g., at most about 140 psig, at most about 120 psig). In some embodiments, an ingestible device for trans-epithelial delivery is configured to deliver a jet of the dispensable substance having an average jet pressure of from about 60 psig to about 160 psig (e.g., from about 80 psig to about 140 psig, from about 100 psig to about 120 psig).

In general, an ingestible device for trans-epithelial delivery is configured to deliver a jet of the dispensable substance having a peak jet force of at least about 0.09 Newton (N) (e.g., at least about 0.1 N, at least about 0.11 N, at least about 0.12 N, at least about 0.13N) and/or at most about 0.15 N (e.g., at most about 0.14 N). In some embodiments, an ingestible device for trans-epithelial delivery is configured to deliver a jet of the dispensable substance having a peak jet force of from about 0.09 N to about 0.15 N (e.g., from about 0.1 N to about 0.14 N, from about 0.11 N to about 0.14 N).

In general, an ingestible device for trans-epithelial delivery is configured to deliver a jet of the dispensable substance having a minimum jet force of at least about 0.01 N (e.g., at least about 0.02 N, at least about 0.03 N) and/or at most about 0.06 N (e.g., at most about 0.05 N at most about 0.04 N). In some embodiments, an ingestible device for trans-epithelial delivery is configured to deliver a jet of the dispensable substance having a minimum jet force of from about 0.01 N to about 0.06 N (e.g., from about 0.02 N to about 0.05 N, from about 0.03 N to about 0.04 N).

In general, an ingestible device for trans-epithelial delivery is configured to deliver a jet of the dispensable substance having an average jet force of at least about 0.05 N (e.g., at least about 0.06 N, at least about 0.07 N) and/or at most about 0.1 N (e.g., at most about 0.09 N, at most about 0.08 N). In some embodiments, an ingestible device for trans-epithelial delivery is configured to deliver a jet of the dispensable substance having an average jet force of from about 0.05 N to about 0.1 N (e.g., from about 0.06 N to about 0.09 N, from about 0.07 N to about 0.08 N).

Generally, an ingestible device for trans-epithelial delivery is configured to deliver a jet of the dispensable substance having a peak jet velocity of at least about 25 meters per second (m/s) (e.g., at least about 26 m/s, at least about 27 m/s, at least about 28 m/s, at least about 29 m/s, at least about 30 m/s, at least about 31 m/s, at least about 32 m/s, at least about 34 m/s, at least about 35 m/s, at least about 36 m/s) and/or at most about 45 m/s (e.g., at most about 44 m/s, at most about 43 m/s, at most about 42 m/s, at most about 41 m/s, at most about 40 m/s, at most about 39 m/s, at most about 38 m/s, at most about 37 m/s). In some embodiments, an ingestible device for trans-epithelial delivery is configured to deliver a jet of the dispensable substance having a peak jet velocity of from about 25 m/s to about 45 m/s (e.g., from about 30 m/s to about 42 m/s, from about 34 m/s to about 39 m/s, about 36.5 m/s).

In general, an ingestible device for trans-epithelial delivery is configured to deliver a jet of the dispensable substance having a minimum jet velocity of at least about 15 m/s (e.g., at least about 16 m/s, at leat about 17 m/s) and/or at most about 22 m/s (e.g., at most about 21 m/s, at most about 20 m/s). In some embodiments, an ingestible device for trans-epithelial delivery is configured to deliver a jet of the dispensable substance having a minimum jet velocity of from about 15 m/s to about 22 m/s (e.g., from about 16 m/s to about 21 m/s, from about 17 m/s to about 20 m/s).

In general, an ingestible device for trans-epithelial delivery is configured to deliver a jet of the dispensable substance having an average jet velocity of at least about 20 m/s (e.g., at least about 25 m/s) and/or at most about 35 m/s (e.g., at most about 30 m/s). In some embodiments, an ingestible device for trans-epithelial delivery is configured to deliver a jet of dispensable substance having an average jet velocity of from about 20 m/s to about 30 m/s (e.g., about 20 m/s, about 21 m/s, about 22 m/s, about 23 m/s, about 24 m/s, about 25 m/s, about 26 m/s, about 27 m/s, about 28 m/s about 29 m/s, about 30 m/s). In certain embodiments, an ingestible device for trans-epithelial delivery is configured to deliver a jet of dispensable substance having an average jet velocity of from about 25 m/s to about 35 m/s (e.g., about 25 m/s, about 26 m/s, about 27 m/s, about 28 m/s, about 29 m/s, about 30 m/s, about 31 m/s, about 32 m/s, about 33 m/s about 34 m/s, about 35 m/s).

In general, an ingestible device for trans-epithelial delivery is configured to deliver a jet of a dispensable substance having a jet stable length of at least about 0.5 millimeter (mm) (e.g., at least about 1 mm, at least about 1.5 mm, at least about 2 mm, at least about 2.5 mm, at least about 3 mm, at least about 3.5 mm, at least about 4 mm, at least about 4.5 mm, at least about 5 mm) and/or at most about 20 mm (e.g., at most about 15 mm, at most about 10 mm). In certain embodiments, an ingestible device for trans-epithelial delivery is configured to deliver a jet of a dispensable substance having a jet stable length of from about 0.5 mm to about 20 mm (e.g., from about 2 mm to about 20 mm, from about 5 mm to about 20 mm).

In some embodiments, an ingestible device for trans-epithelial delivery is configured to deliver a jet of a dispensable substance having a jet diameter of at least about 0.1 mm (e.g., at least about 0.2 mm, at least about 0.3 mm, at least about 0.4 mm) and/or at most about 2 mm (e.g., at most about 1.5 mm, at most about 1 mm, at most about 0.9 mm, at most about 0.8 mm, at most 0.7 mm, at most about 0.6 mm, at most about 0.5 mm). For example, such an ingestible device for trans-epithelial delivery is configured to deliver a jet of a dispensable substance having a jet diameter of from about 0.1 mm to about 2 mm (e.g., from about 0.2 mm to about 0.5 mm, from about 0.3 mm to about 0.4 mm, from about 0.3 mm to about 0.5 mm, about 0.35 mm).

In general, an ingestible device for trans-epithelial delivery is configured to provide an internal pressure of at least about 225 psig (e.g., at least about 235 psig, at least about 245 psig, at least about 255 psig, at least about 265 psig, at least about 275 psig, at least about 285 psig, at least about 295 psig, at least about 305 psig, at least about 315 psig) and/or at most about 425 psig (e.g., at most about 400 psig, at most about 390 psig, at most about 380 psig, at most about 375 psig, at most about 370 psig, at most about 360 psig, at most about 350 psig, at most about 340 psig, at most about 330 psig). In certain embodiments, an ingestible device for trans-epithelial delivery is configured to provide an internal pressure of from about 225 psig to about 400 psig (e.g., from about 250 psig to about 375 psig, from about 300 psig to about 340 psig).

In general, an ingestible device for trans-epithelial delivery is configured to have a nozzle pressure at least about 150 psig (e.g., at least about 175 psig, at least about 200 psig, at least about 210 psig, at least about 220 psig, at least about 225 psig, at least about 230 psig, at least about 240 psig, at least about 250 psig, at least about 260 psig, at least about 270 psig, at least about 275 psig, at least about 280 psig, at least about 290 psig, at least about 300 psig, at least about 325 psig) and/or at most about 400 psig (e.g., at most about 375 psig, at most about 365 psig, at most about 355 psig, at most about 350 psig, at most about 345 psig, at most about 335 psig, at most about 325 psig, at most about 315 psig, at most about 305 psig). In certain embodiments, an ingestible device for trans-epithelial delivery is configured to have a nozzle pressure encompassed by any of the endpoints noted in the preceding sentence (e.g., of from about 150 psig to about 400 psig).

Generally, an ingestible device for trans-epithelial delivery is configured to contain a dispensable substance at a peak fluid pressure of at least about 150 psig (e.g., at least about 175 psig, at least about 200 psig, at least about 210 psig, at least about 220 psig, at least about 225 psig, at least about 230 psig, at least about 240 psig, at least about 250 psig, at least about 260 psig, at least about 270 psig, at least about 275 psig, at least about 280 psig, at least about 290 psig, at least about 300 psig, at least about 325 psig) and/or at most about 400 psig (e.g., at most about 375 psig, at most about 365 psig, at most about 355 psig, at most about 350 psig, at most about 345 psig, at most about 335 psig, at most about 325 psig, at most about 315 psig, at most about 305 psig). In certain embodiments, an ingestible device for trans-epithelial delivery is configured to contain a dispensable substance at a peak fluid pressure having any of the endpoints noted in the preceding sentence (e.g., from about 150 psig to about 400 psig).

Generally, an ingestible device for trans-epithelial delivery is configured to contain a dispensable substance at a minimum fluid pressure of at least about 50 psig (e.g., at least about 60 psig, at least about 70 psig) and/or at most about 100 psig (e.g., at most about 90 psig, at most about 80 psig). In some embodiments, an ingestible device for trans-epithelial delivery is configured to contain a dispensable substance at a minimum fluid pressure from about 50 psig to about 100 psig (e.g., from about 60 psig to about 90 psig, from about 70 psig to about 80 psig).

In general, an ingestible device for trans-epithelial delivery is configured to have a piston friction of at least about 1 N (e.g., at least about 2 N, at least about 3 N) and/or at most about 20 N (e.g., at most about 15 N, at most about 12 N). In certain embodiments, an ingestible device for trans-epithelial delivery is configured to have a piston friction of from 1 N to 20 N (e.g., from 2 N to 15 N, from about 3N to about 12N).

In general, an ingestible device for trans-epithelial delivery contains the dispensable substance at an initial fluid volume of at least about 50 microliters (μL) (e.g., at least about 100 μL, at least about 150 μL, at least about 200 μL, at least about 250 μL) and/or at most about 800 μL (e.g., at most about 700 μL, at most about 600 μL, at most about 500 μL, at most about 400 μL). In some embodiments, an ingestible device for trans-epithelial delivery contains the dispensable substance at an initial fluid volume of from about 50 μL to about 800 μL (e.g., from about 100 μL to about 600 μL, from about 200 μL to about 400 μL).

Generally, an ingestible device for trans-epithelial delivery is configured to provide a delivered fluid volume of dispensable substance of at least about 50 microliters (μL) (e.g., at least about 100 μL, at least about 150 μL, at least about 200 μL, at least about 250 μL) and/or at most about 800 μL (e.g., at most about 700 μL, at most about 600 μL, at most about 500 μL, at most about 400 μL). In some embodiments, an ingestible device for trans-epithelial delivery has a fluid volume of dispensable substance of from about 50 μL to about 800 μL, (e.g., from about 50 μL to about 500 μL, from about 100 μL to about 450 μL, from about 100 μL, to about 600 μL, from about 200 μL to about 400 μL, from about 250 μL to about 400 μL, from about 300 μL, to about 400 μL).

In general, an ingestible device for trans-epithelial delivery contains the dispensable substance at a final fluid volume of at most about 100 microliters (μL) (e.g., at least about 90 μL, at least about 80 μL, at least about 70 μL, at least about 60 μL) and/or at most least 5 μL (e.g., at most about 10 μL, at most about 20 μL, at most about 30 μL, at most about 40 μL). In some embodiments, an ingestible device for trans-epithelial delivery contains the dispensable substance at a fluid volume of from about 30 μL, to about 70 μL (e.g., from about 40 μL, to about 60 μL, from about 45 μL, to about 55 μL). In general, an ingestible device for trans-epithelial delivery is configured to directly deliver at least about 50% (e.g., at least about 60%, at least about 70%, at least about 80%, at least about 90%, at least about 95%, at least about 97%) of the dispensable substance from the ingestible device to the submucosa and/or the mucosa (e.g., into the lamina propria).

In general, an ingestible device for trans-epithelial delivery has at least 1 opening for delivery of dispensable substance (e.g. at least 2 openings for delivery of dispensable substance, at least 3 openings for delivery of dispensable substance, at least 4 openings for delivery of dispensable substance) and/or most about 8 openings for delivery of dispensable substance (e.g., at most 7 openings for delivery of dispensable substance, at most 6 openings for delivery of dispensable substance, at most 5 openings for delivery of dispensable substance, at most 4 openings for delivery of dispensable substance). In certain embodiments, an ingestible device for trans-epithelial delivery has from 1 to 8 openings for delivery of dispensable substance (e.g., from 2 to 4 openings for delivery of dispensable substance, 2 opening for delivery of dispensable substance). In some embodiments, an ingestible device for trans-epithelial delivery has one or more nozzles, with each nozzle having a nozzle opening for delivering dispensable substance. In such embodiments, the ingestible device can have at least 1 nozzle (e.g., at least 2 nozzles, at least 3 nozzles, at least 4 nozzles) and/or at most 8 nozzles (e.g., at most 7 nozzles, at most 6 nozzles, at most nozzles, at most 4 nozzles). For example, the ingestible device can have from 1 to 8 nozzles (e.g., from 1 to 5 nozzles, from 2 to 4 nozzles, 2 nozzles). In embodiments in which an ingestible device for trans-epithelial delivery includes one or more nozzles, each nozzle can have a nozzle length of at least about 0.2 mm (e.g., at least about 0.5 mm, at least about 0.7 mm, at least about 1 mm, at least about 2 mm, at least about 3 mm) and/or at most about 5 mm (e.g., at most about 4 mm). In some embodiments, each nozzle can have a nozzle length of from about 0.2 mm to about 5 mm. In embodiments in which an ingestible device for trans-epithelial delivery includes one or more nozzles, each nozzle can have a nozzle diameter of at least about 0.1 mm (e.g., at least about 0.2 mm, at least about 0.3 mm) and/or at most about 2 mm (e.g., at most about 1 mm, at most about 0.8 mm, at most bout 0.5 mm, at most about 0.4 mm). In some embodiments, each nozzle can have a nozzle diameter of from about 0.1 mm to about 2 mm (e.g., from about 0.1 mm to about 1 mm, from about 0.15 mm to about 0.5 mm, from about 0.2 mm to about 0.8 mm, from about 0.25 mm to about 0.45 mm, from about 0.3 mm to about 0.4 mm, from about 0.3 mm to about 0.5 mm, from about 0.34 mm to about 0.36 mm, about 0.35 mm).

In general, an ingestible device for trans-epithelial delivery is configured to provide a delivered fluid volume per opening for delivery of dispensable substance (e.g., per nozzle) of at least about 20 microliters (µL) (e.g., at least about 25 µL, at least about µL, at least about 50 µL, at least about 75 µL, at least about 100 µL) and/or at most about 800 µL (e.g., at most about 700 µL, at most about 600 µL, at most about 500 µL, at most about 400 µL, at most about 300 µL). In some embodiments, an ingestible device for trans-epithelial delivery is configured to provide a delivered fluid volume per opening for delivery of dispensable substance (e.g., per nozzle) of from about 25 µL to about 400 µL (e.g., from about 25 µL, to about 300 µL, from about 100 µL to about 300 µL).

In one example, an ingestible device with a nozzle having a nozzle diameter of 0.35 mm diameter and containing a dispensable substance at a peak fluid pressure of 150 psig can deliver a jet of the dispensable substance at an average jet velocity of about 20 m/s and at an average jet impact pressure of about 29 psig.

In another example, an ingestible device having a nozzle pressure of 300 psig can deliver a dispensable substance at an average jet velocity of about 27 m/s and an average jet impact pressure of about 58 psig. In some embodiments, such an arrangement results in piercing of the intestinal wall.

In another example, an ingestible device having a nozzle with a nozzle diameter of 0.35 mm diameter and containing a dispensable substance at a peak fluid pressure of 320 psig can deliver a jet of the dispensable substance having an average jet velocity of about 28 m/s and an average jet impact pressure of about 62.4 psig.

Figure 3:
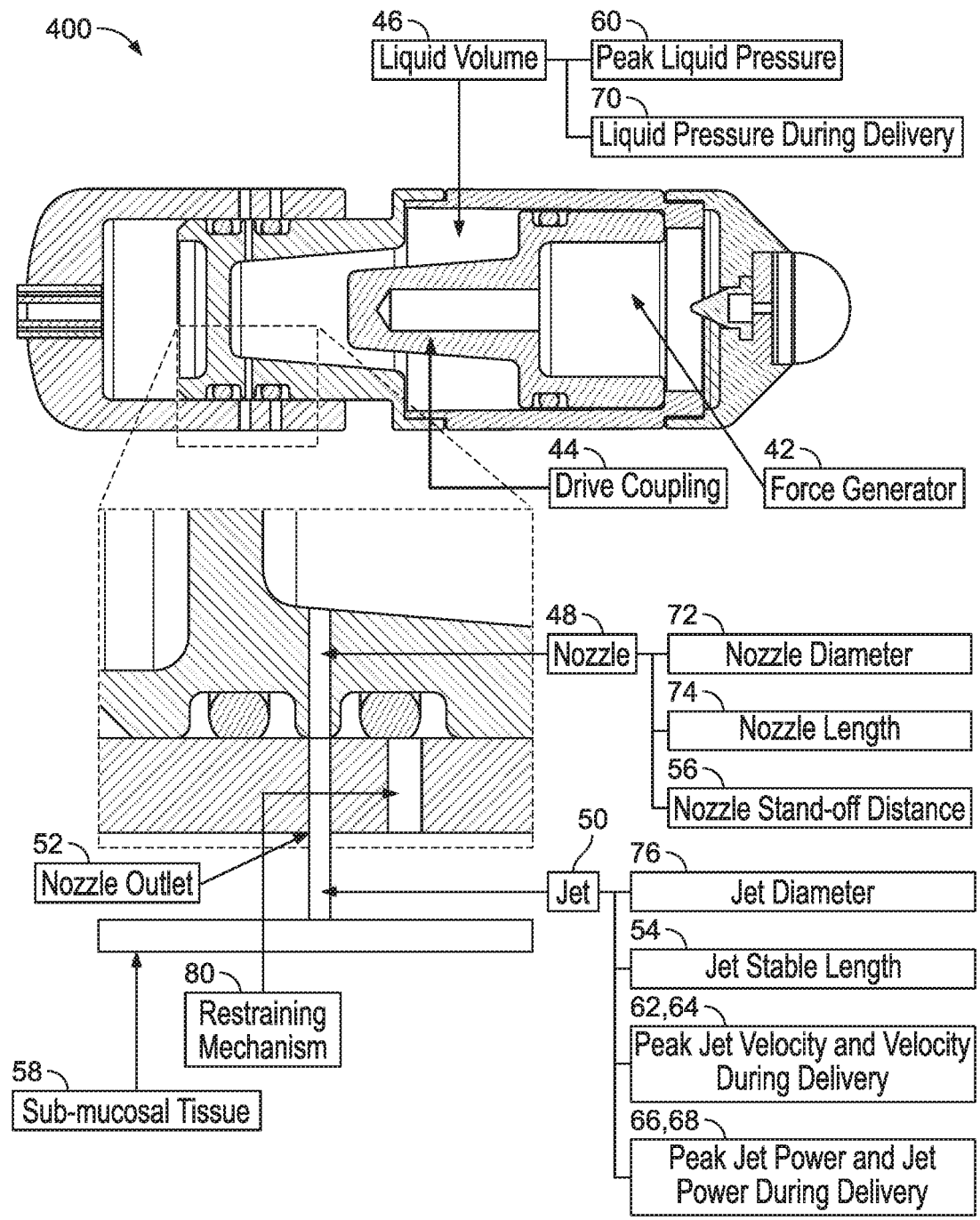
FIG. 3 is a cross section of an ingestible device.

FIG. 3 shows cross sectional views of a representative ingestible device 400 for trans-epithelial delivery, schematically illustrating certain parameters and components of action for the device 400. These include a drive force generator 42 which applies a force (resulting in an internal pressure) to a drive coupling 44. The drive coupling 44 transfers force from the force generator 42 to a fluid volume 46 containing a dispensable substance (e.g., a liquid, a suspension). The force applied to the fluid volume 46 by the drive coupling 44 generates pressure in the fluid volume 46 (fluid pressure). The pressure in the fluid volume 46 generates high-speed flow through an open nozzle 48 to produce a jet 50 of fluid at the nozzle outlet 52 that has a nozzle diameter 72 and the nozzle has a nozzle length 74.

During trans-epithelial delivery, the fluid jet 50 has a jet stable length 54 that is sufficient for the fluid jet 50 to travel across a nozzle stand-off distance 56 to reach the interface of the lumen of the GI tract and the surface of the GI tract facing the lumen. Ultimately, the fluid (e.g., liquid, suspension) impacts the mucosal layer of the GI tract (e.g., the epithelial layer and any mucus that may be present on the epithelial layer) as a stable stream of fluid with little breakup into a spray and is deposited in the submucosal and/or the mucosal tissue 58. That is, between the nozzle outlet 52 and the site of impact at the mucosa, the jet 50 has a jet diameter 76 that can vary in the manner discussed above with respect to the average jet diameter.

The fluid volume 46 experiences a peak fluid pressure 60 that generates the fluid jet 50 that exits the device 40 with a peak jet velocity, and impacts the interface of the lumen of the GI tract and the surface of the GI tract facing the lumen with a peak jet power, peak jet pressure and peak jet force. One of ordinary skill in the art recognizes that these three parameters are interconnected.

The pressure in the fluid volume 46 decreases during delivery so that the fluid pressure during delivery 70 varies, as does the jet power, jet force, and jet pressure. The fluid pressure during delivery 70 maintains the fluid jet 50 at sufficient jet impact force during delivery to continue fluid (dispensable substance including one or more therapeutic agents) delivery from the fluid volume 46 into the submucosal and/or mucosal tissue 58. The surrounding tissue can then absorb the delivered therapeutic agents for systemic delivery of the therapeutic agent.

Even prior to when the subject swallows the ingestible device, the drive coupling 44 transmits force from the force generator 42 to the fluid volume 46. The drive coupling 44 is prevented from moving by a restraining mechanism 80 (e.g., a pin or plug that selectively degrades and/or selectively erodes) until movement of the drive coupling is triggered by a triggering mechanism, and/or an opening becomes open.

Figure 4:
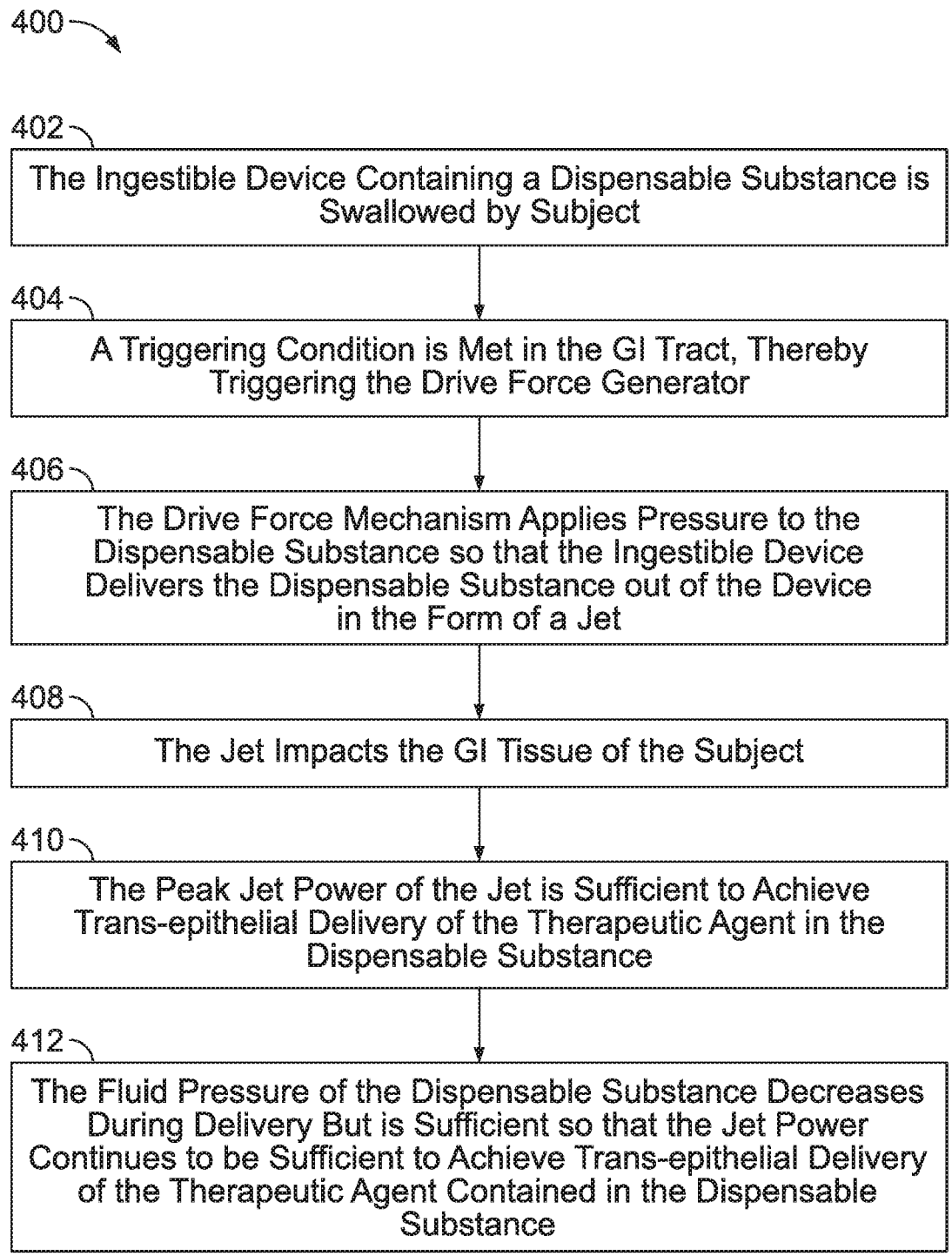
FIG. 4 shows an exemplary process flow chart for use of an ingestible device in which pressure is not applied to the dispensable substance before the subject swallows the ingestible device.

FIG. 4 shows an exemplary process flow chart 400 for use of an ingestible device in which pressure is not applied to the dispensable substance before the subject swallows the ingestible device. The process beings at step 402, when the patient swallows the ingestible device. In step 404, a triggering condition (e.g., pH, change in pH, presence of certain enzyme, concentration of certain enzyme) is met in the GI tract, thereby triggering the drive force generator. In step 406, the drive force mechanism applies pressure to the dispensable substance, resulting delivery of a jet of the dispensable substance from the ingestible device for each opening. In step 408, the jet has a sufficient jet stable length for the jet to impact the GI tissue of the subject. In step 410, the peak jet power of the jet is sufficient to achieve transepithelial delivery of the therapeutic agent contained in the dispensable substance. In step 412, the fluid pressure of the dispensable substance decreases during delivery but is sufficiently so that the peak jet power continues to be sufficient to achieve trans-epithelial delivery of the therapeutic agent contained in the dispensable substance.

Figure 5A:
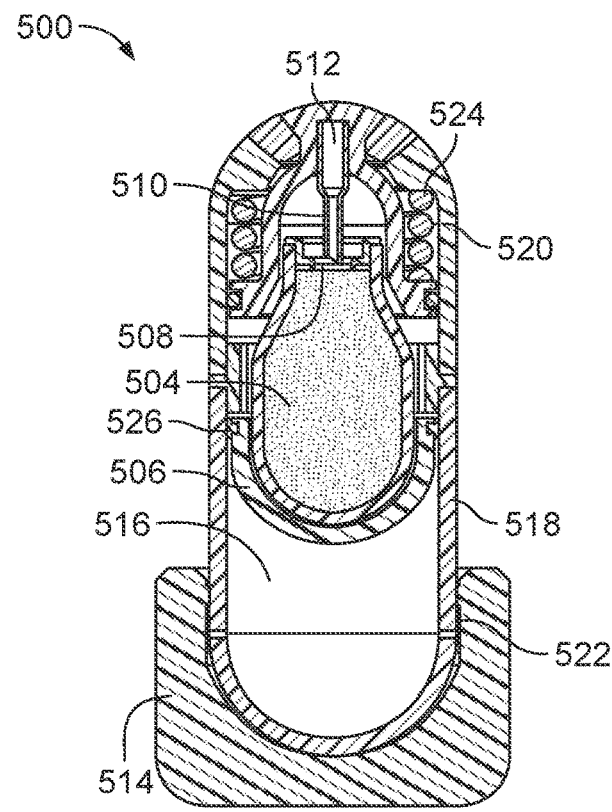
FIGS. 5A-5C show an ingestible device with aspects similar to those shown in FIG. 4.
Figure 5B:
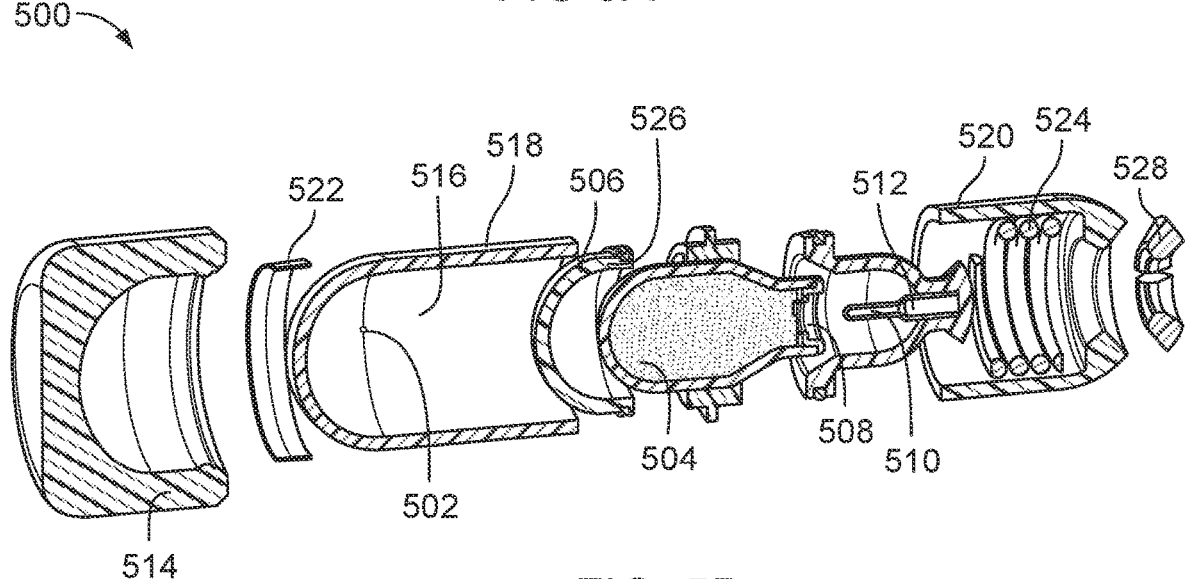
Figure 5C:
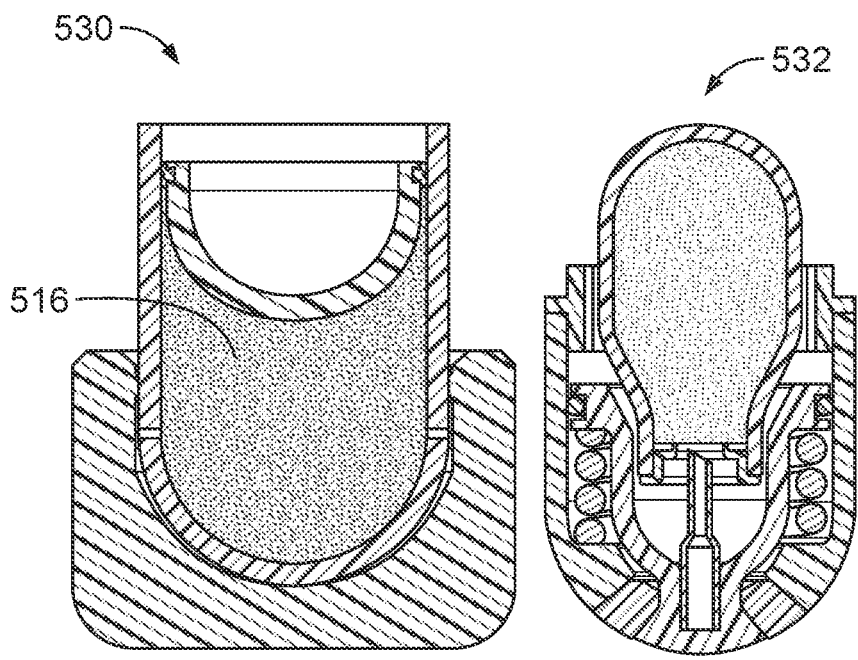

FIGS. 5A-5C show, respectively, a view of an ingestible device 500 as assembled, an exploded of the ingestible device, and aspects of a process of assembly for the ingestible device. Ingestible device 500 includes, a nozzle 502, gas cylinder 504, piston 506, seal 508, pierce pin 510, and piercer 512. A removable cap 514 can be secured over a portion of the ingestible device 500 and removed prior to swallowing. The ingestible device 500 may be used for trans-epithelial delivery. The ingestible device 500 is configured so that a dispensable substance 516 retained within the device that is not under pressure when the subject swallows the ingestible device 500. The ingestible device has two housing parts, a primary container 518 and a secondary container 520. The primary container 518, which includes a fluid volume containing the dispensable substance, can be formed of a cyclic olefin copolymer (COC), such as a molded COC. The primary container 518 includes nozzles 502 with nozzle openings. In some embodiments, the nozzle lengths are about equal to the primary container wall thickness. Exemplary nozzle lengths include about 0.2 mm, about 0.3 mm, about 0.4 mm, about 0.5 mm, about 0.6 mm, about 0.7 mm, about 0.8 mm, about 0.9 mm, and about 1.0 mm. In some embodiments, the nozzle lengths are about 0.7 mm. The ingestible device also includes coverings 522 over the nozzle openings, a spring 524, a gas cylinder 504 having a breakable seal, a piston 506 (e.g., made of a COC), a piercer 512, and an O-ring 526. Nozzle covering 522 can be an integral nozzle cover for gastric protection and can be softened after the ingestible device 500 is ingested, e.g., by gastric fluids, such that the coverings 522 dissolve/degrade and expose the nozzles 502. In some embodiments, O-ring 526 may be lubricated. Similarly, any O-ring disclosed elsewhere herein can optionally be lubricated.

The ingestible device 500 also includes a collar-shaped trigger element 528 which is the triggering mechanism. Although FIG. 5B depicts the trigger element 528 as being collar-shaped, other shapes may be used. In general, the trigger element 528 can have any appropriate shape. Examples of shapes for the trigger element include a complete annulus, an annulus partitioned into two pieces. In some embodiments, the trigger element includes two or more sectors of an annulus with gaps between the sectors. In some embodiments, such a design can increase surface exposure to the environment (e.g., water environment) to promote degradation. For example, FIG. 5C shows a split two-piece collar, e.g., separate assembly modules 530 and 532 which are assembled to form ingestible device 500.

Figure 6A:
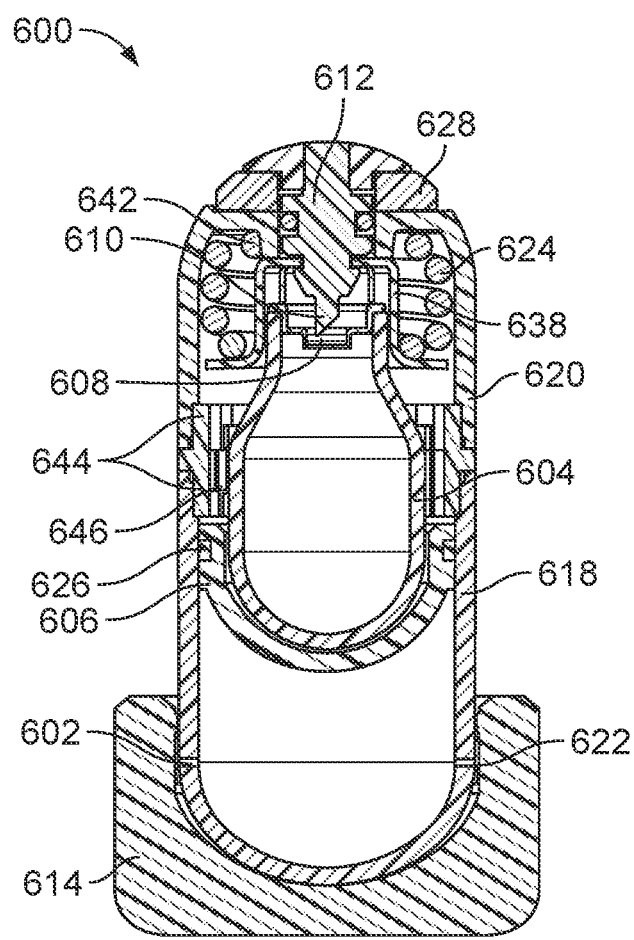
FIGS. 6A-6C shows an ingestible device with aspects similar to those shown in FIGS. 4 and 5.
Figure 6B:
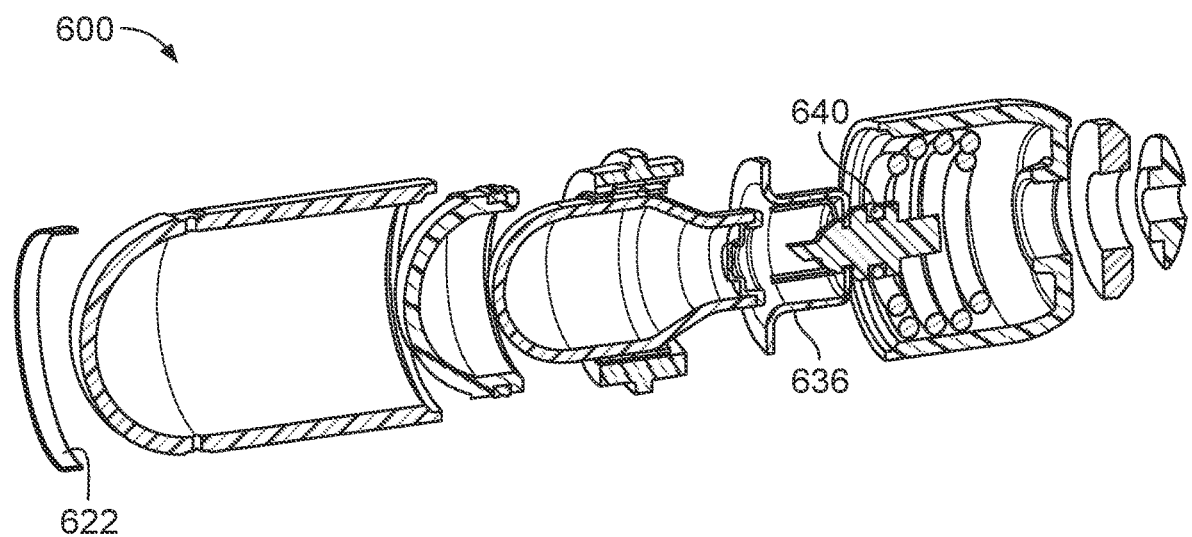
Figure 6C:
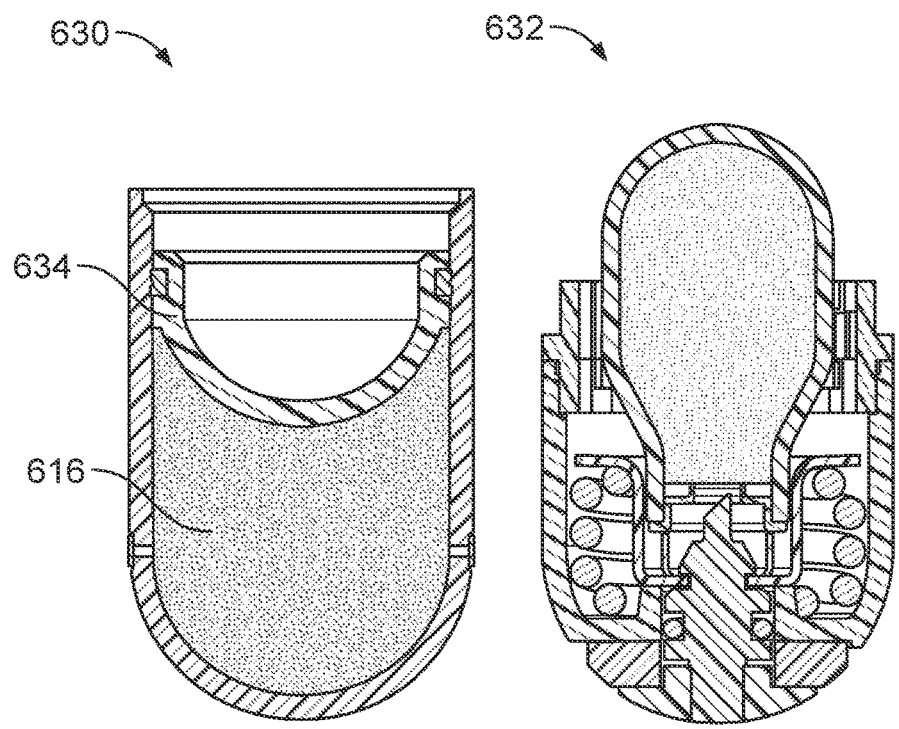
Figure 8:
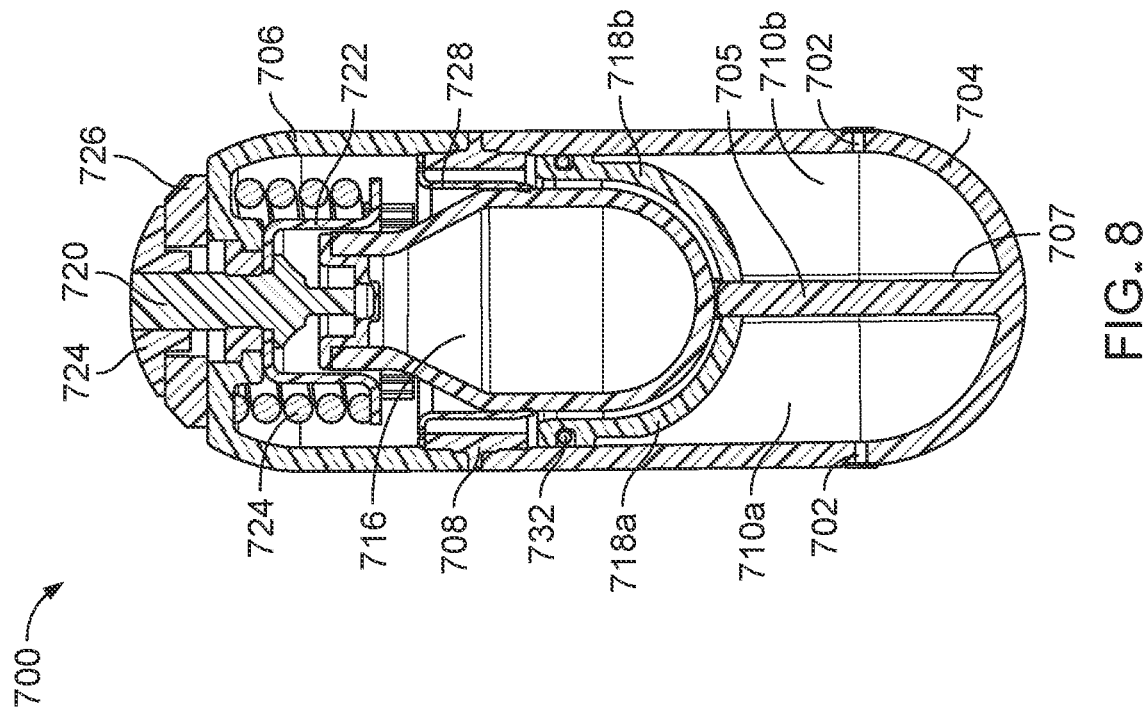
FIGS. 7-13 show an ingestible device having multiple chambers for one or more dispensable substances.
Figure 7:
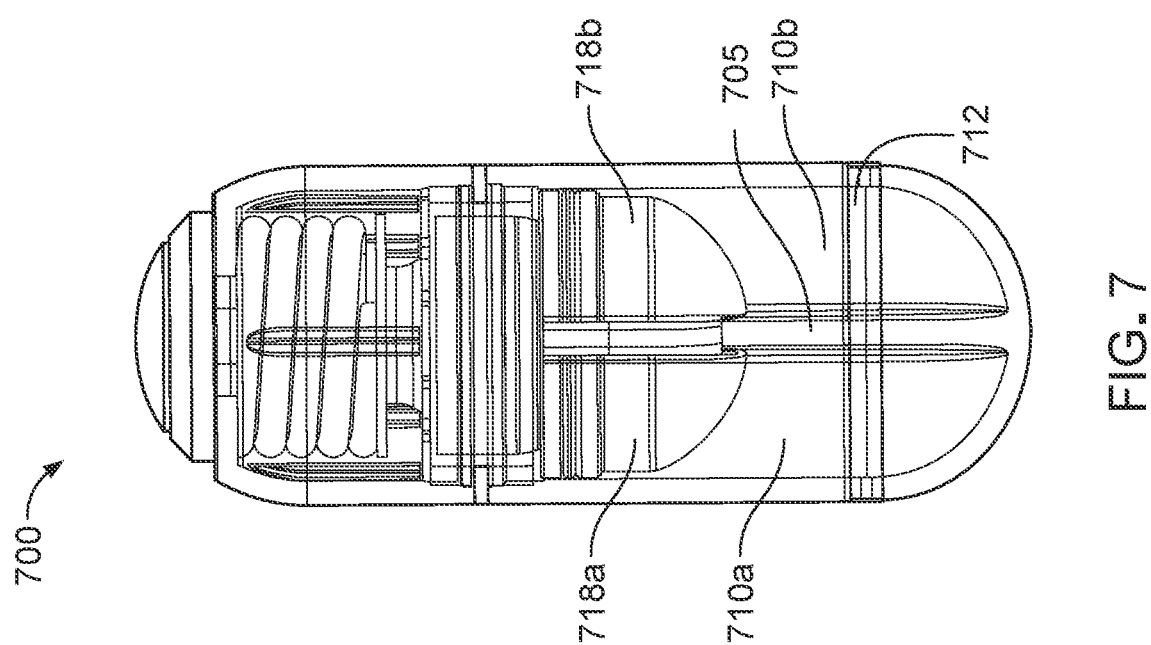
Figure 9:
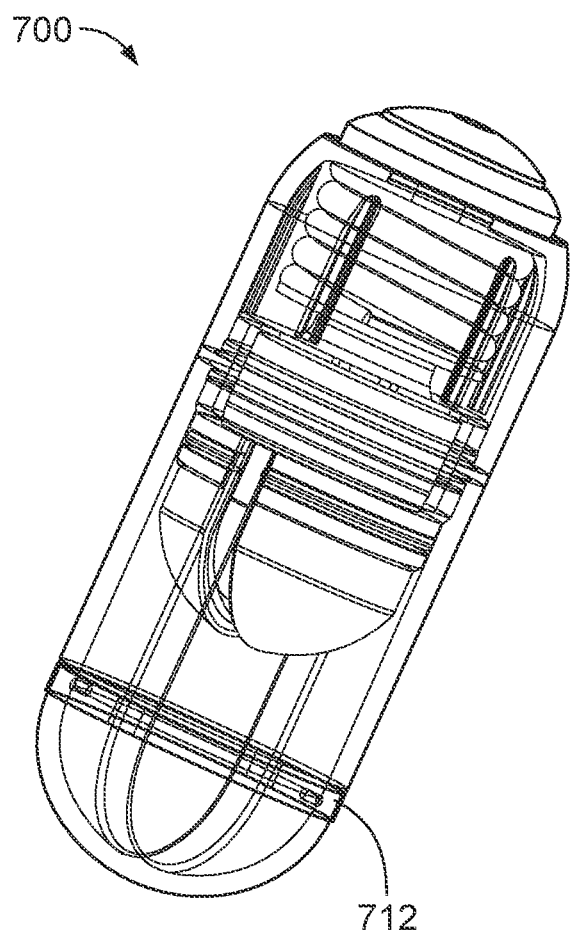
Figure 10:
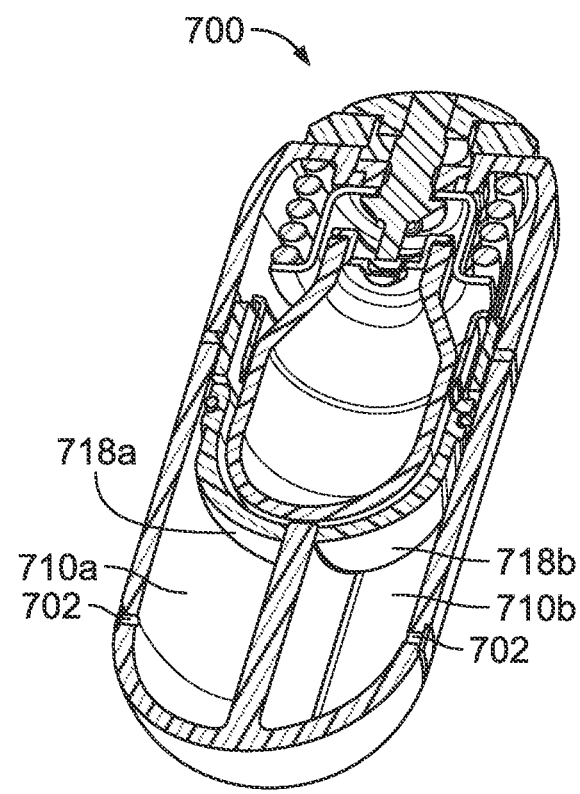
Figure 11:
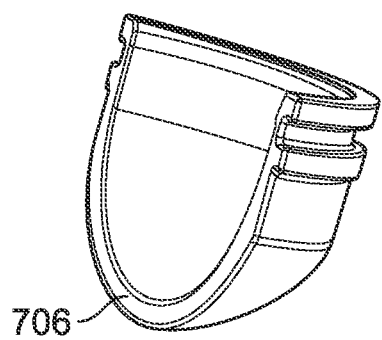
Figure 13:
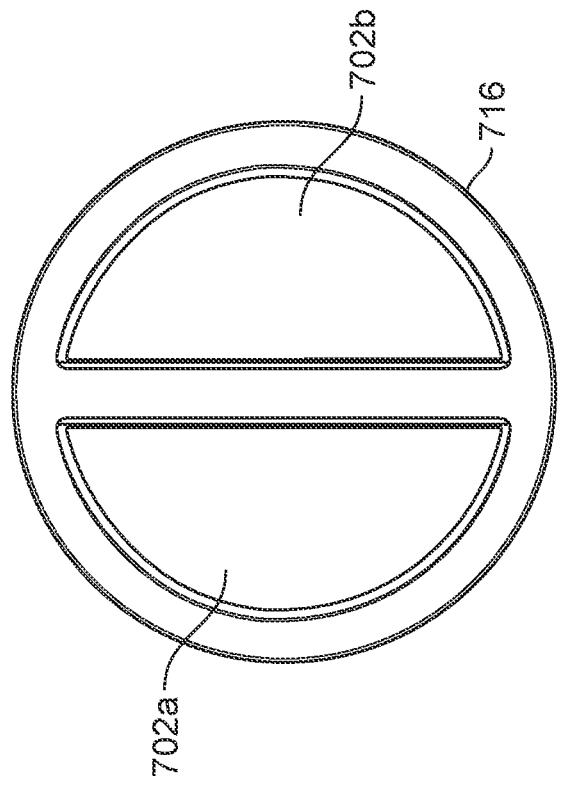
Figure 12:
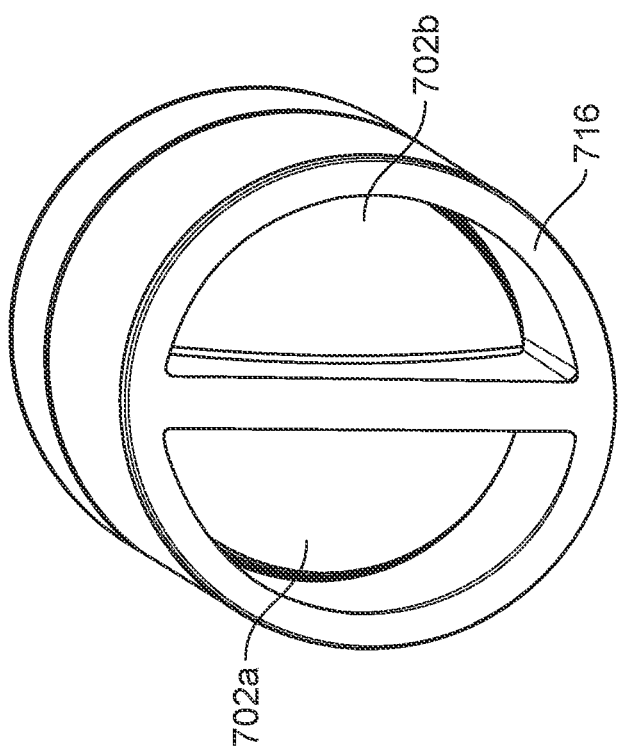

FIGS. 6A-6C, respectively, show view of an ingestible device 600 as assembled, an exploded of the ingestible device 600, and aspects of a process of assembly for the ingestible device 600. The ingestible device 600 may be used for trans-epithelial delivery or for other forms of delivery as appropriate as discussed elsewhere herein. Ingestible device 600 includes, a nozzle 602, gas cylinder 604, piston 606 seal 608, pierce pin 610, and piercer 612. A removable cap 614 can be secured over a portion of the ingestible device 600 and removed prior to swallowing. The ingestible device is configured so that the dispensable substance 616 in the device is not under pressure when the subject swallows the ingestible device. The ingestible device has two housing parts, a primary container 618 and a secondary container 620. The primary container 618, which includes a fluid volume containing the dispensable substance, can be formed of a cyclic olefin copolymer (COC), such as a molded COC, or any other appropriate material as disclosed elsewhere herein. The primary container 618 includes nozzles 602 with nozzle openings. In some embodiments, the nozzle lengths are about equal to the primary container wall thickness. Exemplary nozzle lengths include about 0.3 mm, about 0.4 mm, about 0.5 mm, about 0.6 mm, about 0.7 mm, about 0.8 mm, about 0.9 mm, and about 1.0 mm. In some embodiments, the nozzle lengths are about 0.7 mm. The ingestible device 600 also includes coverings 622 over the nozzle openings, a spring 624, a gas cylinder 604 having a breakable seal 608, a piston 606 (e.g., made of a COC, or another appropriate material), a two-part piercer, and an O-ring 626. The ingestible device also includes a collar-shaped trigger element 628 which is the triggering mechanism, which can be made of any appropriate material as discussed elsewhere herein. Although FIGS. 6A-6C depict the trigger element 628 as being collar-shaped, other shapes may be used, as disclosed elsewhere herein.

The device shown in FIGS. 6A-6C has an enhanced piston stabilization length 634 (e.g., about 2 millimeters). The device shown in FIGS. 6A-6C has a metal spring slider 636, which can enhance space efficiency. The device shown in FIGS. 6A-6C has a piercer slider 638 (e.g., a metal piercer slider) that bottoms out on the spring housing during assembly. This can enhance space efficiency. In the device shown in FIGS. 6A-6C, the two part piercer reduces (e.g., removes) tolerances when manufacturing the trigger element from the piercer clearance with the gas cylinder. In the device shown in FIGS. 6A-6C, the piercer seal 640 (e.g., O-ring) has a relatively small diameter, which can enhance stability and/or reduce resistive pressure build up along its stroke length. In the device shown in FIGS. 6A-6C, the spring 624 has a tapered end coil 642, which can enhance the maximum force potential. In some embodiments, a wave spring may be used. FIGS. 6A-6C shows a gas tight seal 644 (e.g., an ultranonic weld). FIGS. 6A-6C also shows a gas cylinder retention feature 646.

In addition, the ingestible device includes a removable cap 614 which is removed (e.g., by the user) before the ingestible device is swallowed. When the device 600 is swallowed by the subject, the trigger element 628 prevents the dispensable substance 616 in the fluid volume from being under pressure by holding the spring 624 and the piercer 612 in place. When the device reaches the appropriate location in the GI tract, the trigger element 628 at least partially erodes, degrades and/or dissolves (e.g., due to pH, change in pH, presence of certain enzyme, and/or concentration of certain enzyme), and the trigger element 628 is no longer sufficient to hold back the pressure from the spring 624. In some embodiments, the trigger element 628 at least partially erodes, degrades and/or dissolves in the presence of water. In such embodiments, the trigger element may include a covering of a thin film of material that preferentially degrades due to, for example, a change in pH and/or presence of enzyme. The spring 624 forces the pierce pin 610 of piercer 612 into the breakable seal 608, causing the breakable seal to break. This causes gas at elevated pressure to leave the cylinder 604, causing an elevated pressure to bear against the piston 606 and apply pressure to the fluid volume 616. This causes the coverings 622 of the nozzle openings, which are made of a relatively low mechanical strength material (e.g., a foil or a film), to break so that the dispensable substance is delivered out of the nozzle openings in the form of a jet. In certain embodiments, the covering 622 of the nozzle openings are made of a material that erodes, degrades and/or dissolves in the presence of, for example water or elevated pH (e.g., an enteric band or band of water soluble polymer material). The coverings may be partially or completely displaced from the capsule at the time the trigger element actuates. This results in in trans-epithelial delivery of the therapeutic agent contained in the dispensable substance.

FIG. 6C shows aspects of a process for the assembly of the ingestible device, e.g., separate assembly modules 630 and 632 which are assembled to form ingestible device 600. FIG. 6C depicts that the primary container, combined with the cap and nozzle coverings, has the dispensable substance added thereto, followed by adding the piston. This may be done in aseptic environment or other environment appropriate for drug filling and separate from the environment where the mechanical drive assembly is constructed. The other housing part and its components are assembled in a clean environment with the piercer held in place by the trigger element. The gas cylinder 604 is held in place by components of this assembly, including the assembly housing which includes features for locating the gas cylinder in its proper position in the assembled ingestible device. Locating and mounting of the gas cylinder may be aided by the formation of a mounting feature integral to the gas cylinder component such as a flange.

FIGS. 7-13 show various views of an ingestible device 700 and/or aspects of the ingestible device 700. As is apparent, the delivery mechanism of the ingestible device 700 is shown as having a design substantially similar to the device shown in FIG. 5, although, more generally, the ingestible device 700 depicted in FIGS. 7-13 can have a delivery mechanism as described elsewhere herein.

Ingestible device 700 includes a gas cylinder 716, a union ring 708, an o-ring 732, an enteric trigger 726, a piercer 720, a spring 724, a spring retention cup 722, a retention element 728, a drug housing 704, a drive housing 706, and a piercer retainer 724.

The ingestible device 700 has two chambers 710*a*, 710*b*, each containing a dispensable substance. The chambers are separated by a separator 705, such as a rib, which prevents the dispensable substance in one chamber from entering another chamber, e.g., from 710*a* to 710*b* and vice versa. In addition, the ingestible device 700 includes a face seal 707 that seals the separator. The ingestible device also has two pistons 718*a*, 718*h*, one for each chamber. Each chamber 710*a*, 710*b* has at least nozzle 702 for delivering the dispensable substance from the chamber to an exterior of the ingestible device 700. In general, the dispensable substance in one chamber, e.g., chamber 710*a* can be the same as or different from the dispensable substance in the other chamber, e.g., chamber 710*b*. While shown as having two chambers 710*a*, 710*b*, the disclosure is not limited in this sense. More generally, the ingestible device 700 can have as many chambers as desired (e.g., two chambers, three chambers, four chambers, five chambers, six chambers, seven chambers, eight chambers, nine chambers, 10 chambers, more than 10 chambers). In general, each chamber 710*a*, 710*b* will have a corresponding piston 718*a*, 718*b*, and there will be a separator 705 between adjacent chambers. In some embodiments, each chamber has the same internal volume. In certain embodiments, different chambers can have different volumes. Combinations of such embodiments are also possible.

In some embodiments the disclosure provides an ingestible device that includes an element 712 (e.g., covering) having a first state in which the element 712 at least partially covers the nozzle opening of nozzle 702 in the housing 704 and a second state in which the element 712 does not cover the nozzle opening in the housing 704, where the ingestible device 700 is configured so that, when the drive force coupling (e.g., piston 718*a*, 718*b*) moves, the element 712 moves from its first state to its second state. In certain embodiments, the element 712 conforms to an inner radius of the housing 704, is flexible and/or includes a cylindrical portion. In some embodiments, the element 712 is removable from the ingestible device 700 (e.g., when the element 712 is in its second state, the element 712 is removed from the ingestible device). Such a removable element 712 can be, for example, a cap. Optionally, the element 712 moves can move synchronously with the drive force coupling, e.g., pistons 718*a*, 718*b*. In some embodiments, when the drive force coupling moves a distance, the element 712 moves the same distance. The ingestible device can include a seal 718 (e.g., an O-ring) that mechanically coupled (e.g., sealed) with the drive force coupling and element 712. With this arrangement, the seal 718 can be configured to cause the movement of the drive force coupling to result in the movement of the element 712.

Figure 14:
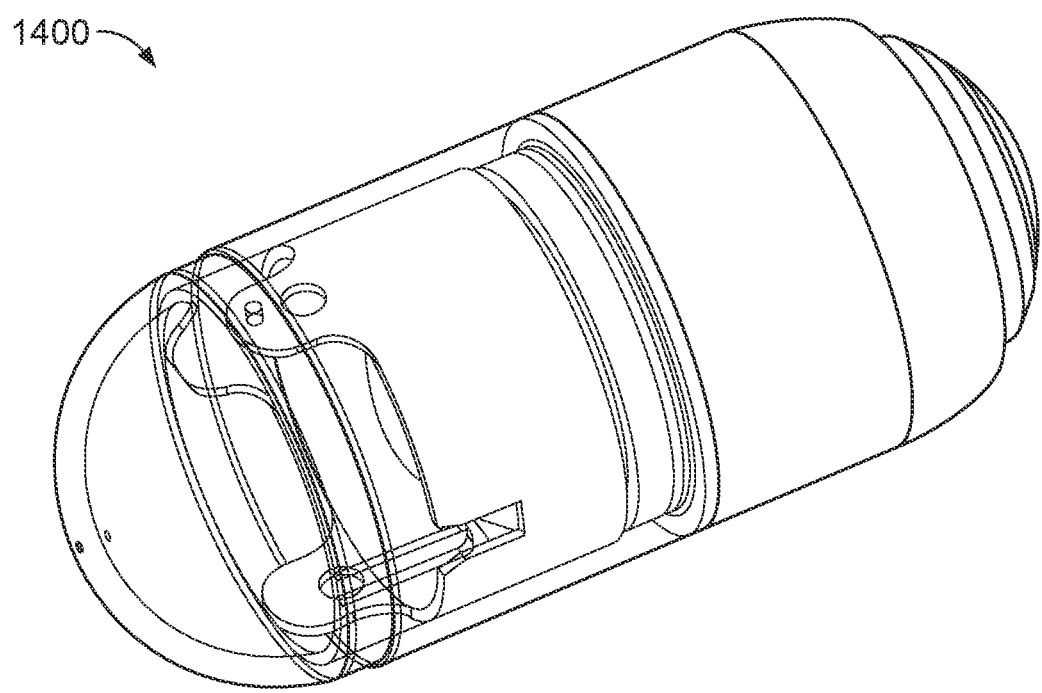
FIGS. 14-17 show an ingestible device.
Figure 15:
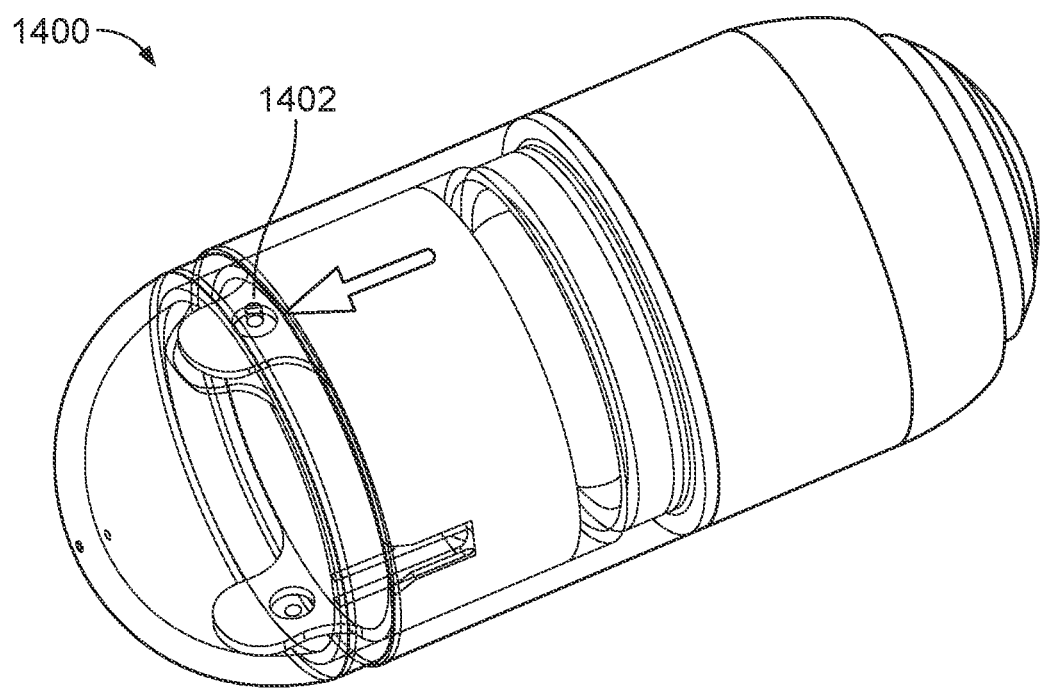

FIGS. 14-18 show an ingestible device 1400 which contains a dispensable substance that is not under pressure when the subject swallows the ingestible device. In FIG. 14, the jet opening 1402 is depicted is covered, and in FIG. 15 the jet opening 1402 is uncovered.

Figure 16:
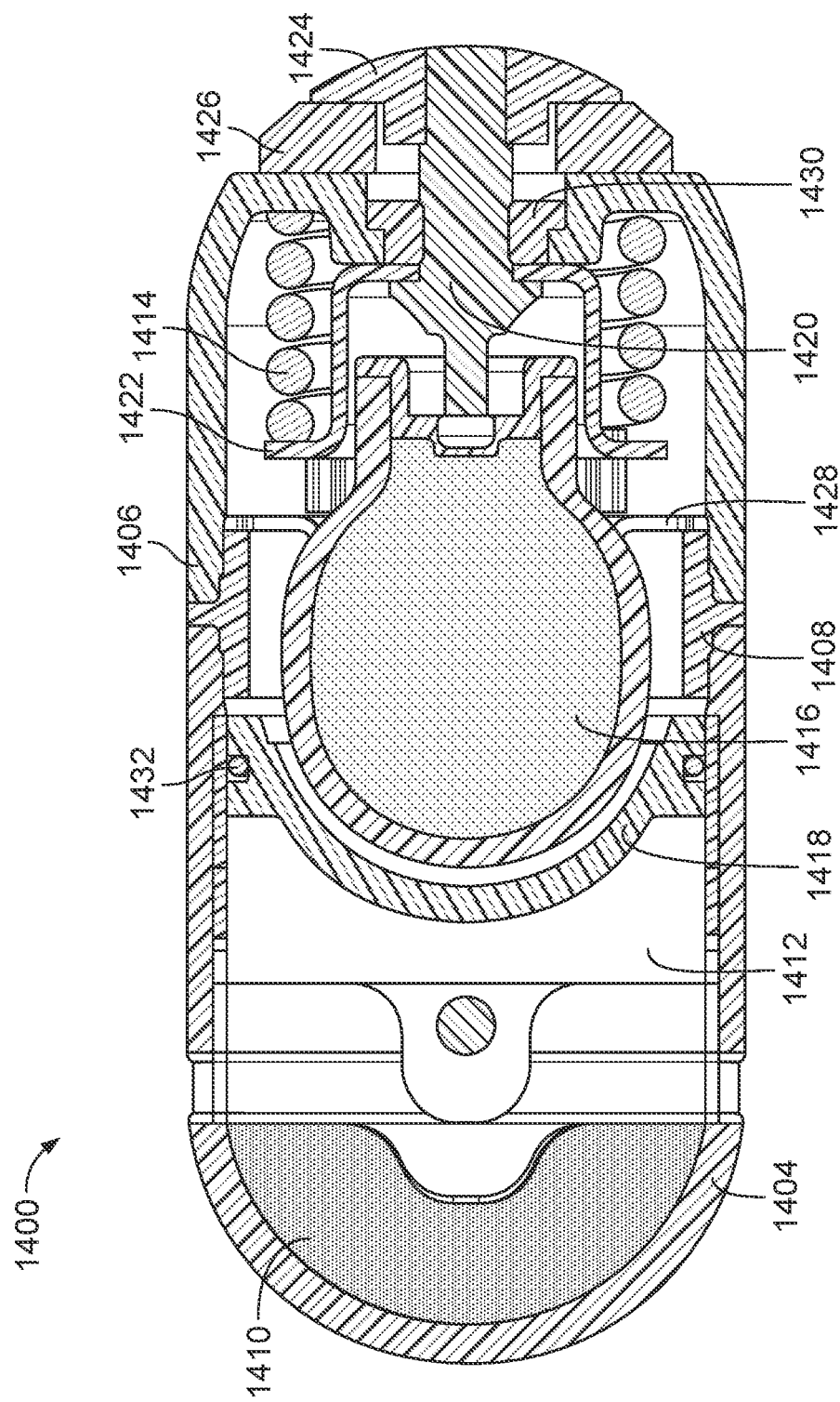
Figure 17:
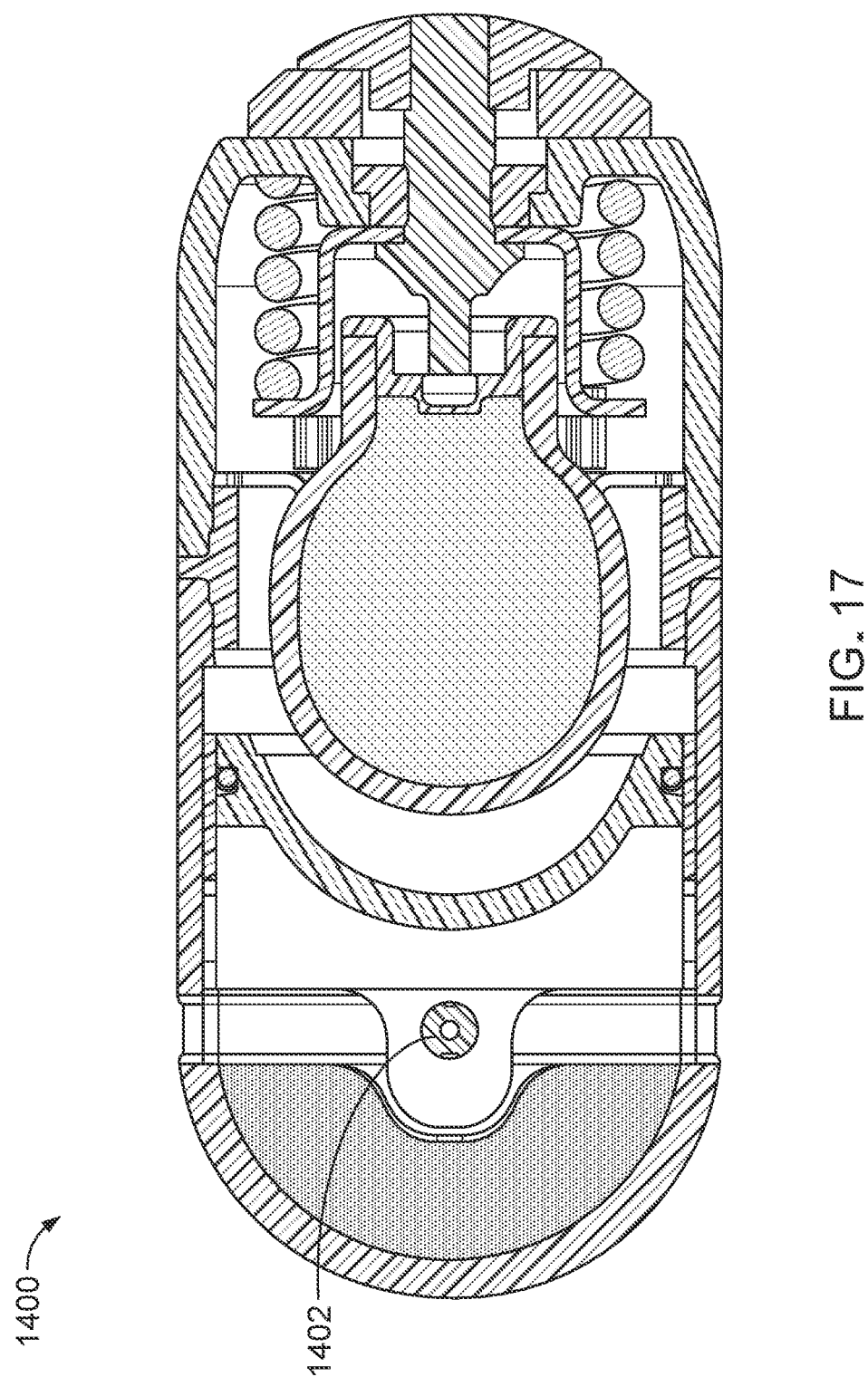

FIGS. 16 and 17 show the ingestible device 1400 in more detail. The ingestible device 1400 has housing parts 1404 and 1406 connected by a union ring 1408 and with a fluid volume 1410 containing a dispensable substance, opening 1402, and a jet covering 1412, e.g., a cylindrical sleeve made of a flexible material which is able to conform to an inside radius of the housing 1406 which slides to open or seal the opening 1402, a spring 1414, a gas cylinder 1416, a piston 1418, a piercer 1420, and an O-ring 1432. Gas cylinder 1416 is retained by retention element 1428. A seal 1430 forms a gas seal between the piercer 1420 and the housing 1404. A spring retention cup 1422 retains the spring-loaded piercer 1420. A piercer retainer 1424 holds the piercer 1420 in place with an enteric trigger 1426 that retains the piercer retainer in place until it dissolves and used as the triggering mechanism. When the device 1400 is swallowed by the subject, the enteric trigger 1426 prevents the dispensable substance in fluid volume 1410 from being under pressure by holding the spring 1414 and the piercer 1420 in place. When the device 1400 reaches the appropriate location in the GI tract, the enteric trigger 1426 degrades and/or dissolves (e.g., due to pH, change in pH, presence of certain enzyme, and/or concentration of certain enzyme) that the pierce pin retainer 1424 is no longer sufficient to hold back the pressure from the spring 1414. The spring 1414 forces the piercer 1420 into the gas cylinder 1416, puncturing the gas cylinder 1416 and causing gas at elevated pressure to leave the cylinder 1416. This causes the gas cylinder 1416 to press against the piston 1418 and apply pressure to the fluid volume 1410. The piston provides friction to slide the jet covering 1412 open exposing the jet openings 1402 such that the dispensable substance is delivered out of the jet opening 1402 in the form of a jet. This results in trans-epithelial delivery of the therapeutic agent contained in the dispensable substance. FIG. 17 shows the embodiment of the ingestible device 1400 in which the jet covering 1412 is slide open to expose the jet openings 1402.

Typically, the ingestible device 1400 is used in trans-epithelial delivery. However, the ingestible device 1400 may be used for either epithelial delivery or topical delivery. Appropriate parameters for the different types of delivery are provided elsewhere herein.

Figure 18:
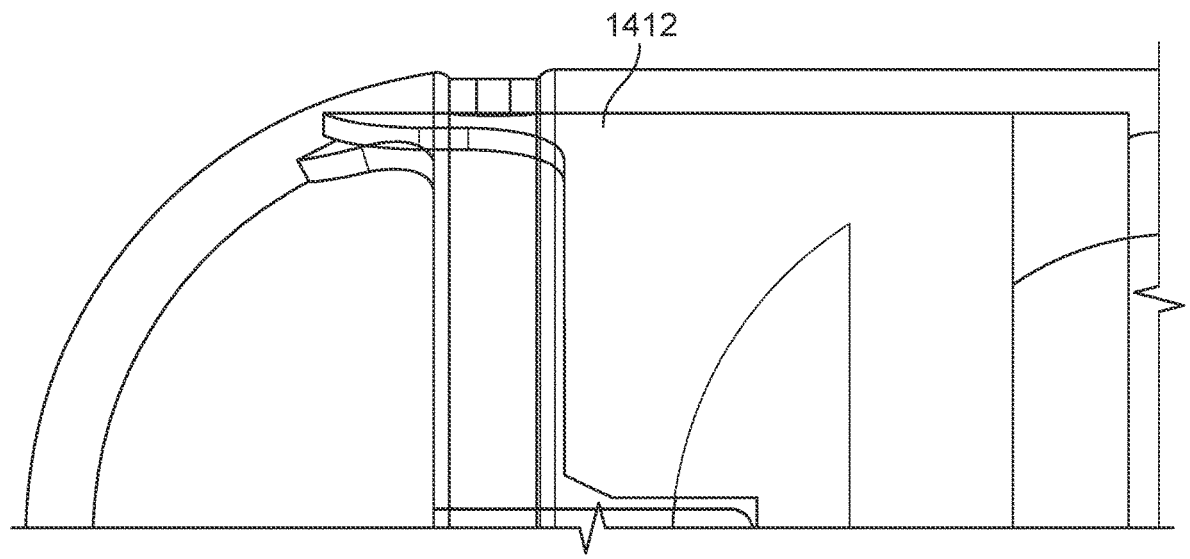
FIG. 18 shows certain elements of an ingestible device of FIG. 19V.

In some embodiments, the housing of the ingestible device 1400 has a diameter from about 9.5 mm to about 10.5 mm (e.g., from about 9.8 mm to about 10 mm), a length from about 23 mm to about 26.5 mm (e.g., from about 23.3 mm to about 26.1 mm), a wall thickness from about 0.4 mm to about 0.6 mm (e.g., about 0.5 mm), a fluid volume from about 425 μL to about 600 μL (e.g., from about 450 μL to about 585 μL), and/or a gas volume in the gas cylinder 1416 from about 150 μL to about 175 μL (e.g., about 160 μL). FIG. 18 shows the ingestible device 1400 where the jet covering 1412 conforms along a radius of the ingestible device 1400.

Figure 19:
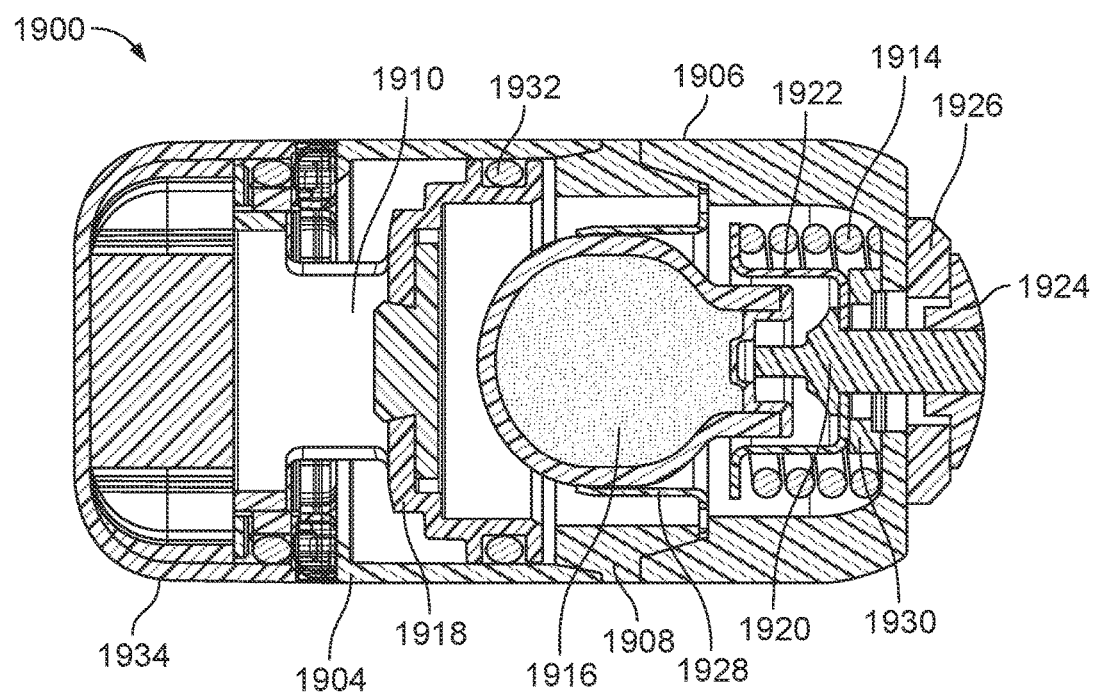
FIGS. 19 and 20 show states of an ingestible device.
Figure 20:
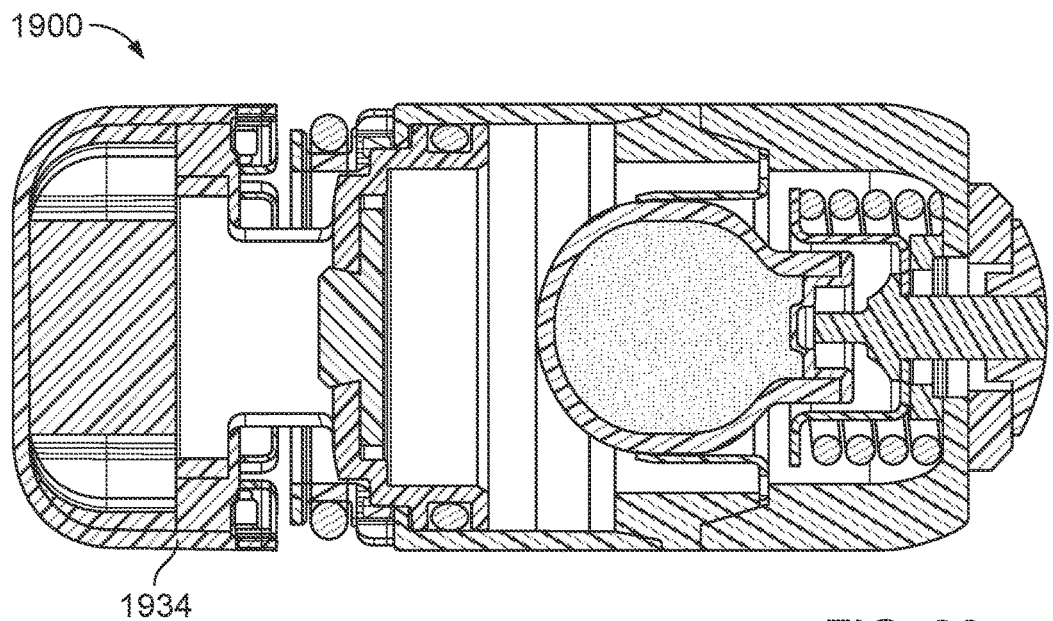

FIGS. 19 and 20 show an ingestible device 1900 in its closed and open states, respectively. The ingestible device 1900 contains a dispensable substance that is not under pressure when the subject swallows the ingestible device. The ingestible device 1900 has housing parts 1904 and 1906 connected by a union ring 1908 and with a fluid volume 1910 containing a dispensable substance, a spring 1914, a gas cylinder 1916, a piston 1918, a piercer 1920, and an O-ring 1932. Gas cylinder 1916 is retained by retention element 1928. A seal 1930 forms a gas seal between the piercer 1920 and the housing 1906. A spring retention cup 1922 retains the spring-loaded piercer 1920. A piercer retainer 1924 holds the piercer 1920 in place with an enteric trigger 1926 that retains the piercer retainer in place until it dissolves and used as the triggering mechanism. When the device 1900 is swallowed by the subject, the enteric trigger 1926 prevents the dispensable substance in fluid volume 1910 from being under pressure by holding the spring 1914 and the piercer 1920 in place. When the device 1900 reaches the appropriate location in the GI tract, the enteric trigger 1926 degrades and/or dissolves (e.g., due to pH, change in pH, presence of certain enzyme, and/or concentration of certain enzyme) that the piercer retainer 1924 is no longer sufficient to hold back the pressure from the spring 1914. The spring 1914 forces the piercer 1920 into the gas cylinder 1916, puncturing the gas cylinder 1916 and causing gas at elevated pressure to leave the cylinder 1916. This causes the gas cylinder 1916 to press against the piston 1918 and apply pressure to the fluid volume 1910. The piston provides friction to cause the cap 1934 to open/deploy such that the dispensable substance is delivered out of the volume 1910. This results in release of the therapeutic agent into the GI tract of the subject.

In some embodiments, the housing of the ingestible device 1900 has a diameter from about 10 mm to about 12 mm (e.g., from about 11.3 mm to about 11.5 mm), a length from about 23 mm to about 26.5 mm (e.g., from about 23.3 mm to about 26.3 mm), a wall thickness from about 0.4 mm to about 0.6 mm (e.g., about 0.5 mm), a fluid volume from about 565 μL to about 630 μL (e.g., from about 574 μL to about 623 μL), and/or a gas volume in the gas cylinder 1916 from about 150 μL to about 175 μL (e.g., about 160 μL).

In general, the ingestible device 1900 is used in topical delivery.

Figure 21:
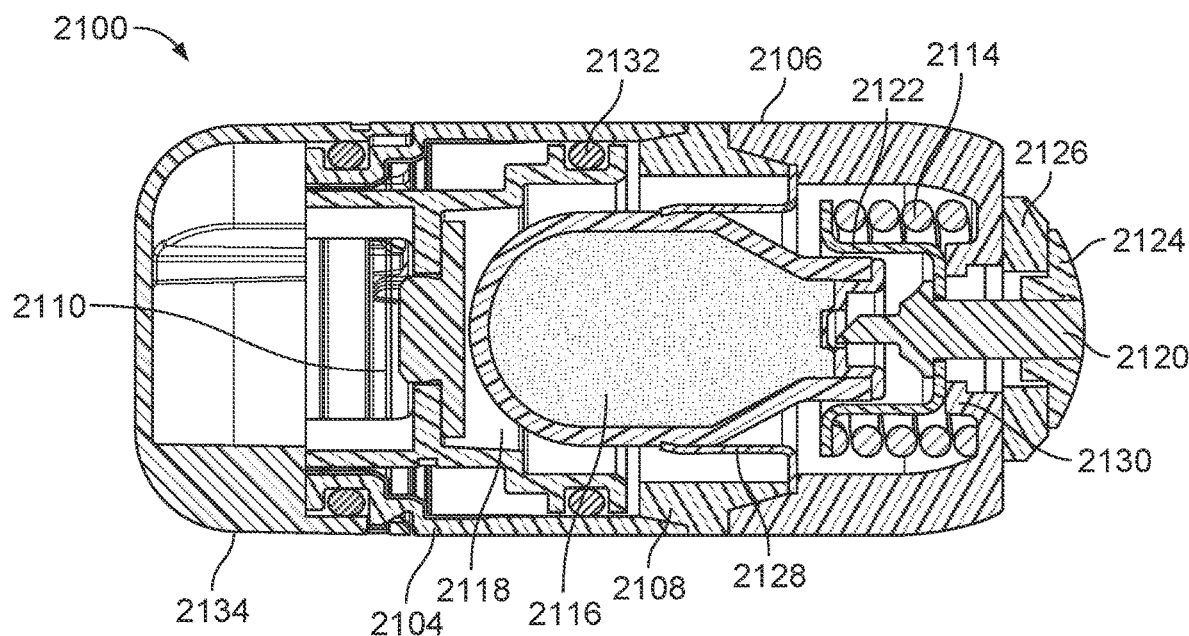
FIGS. 21 and 22 show states of an ingestible device.
Figure 22:
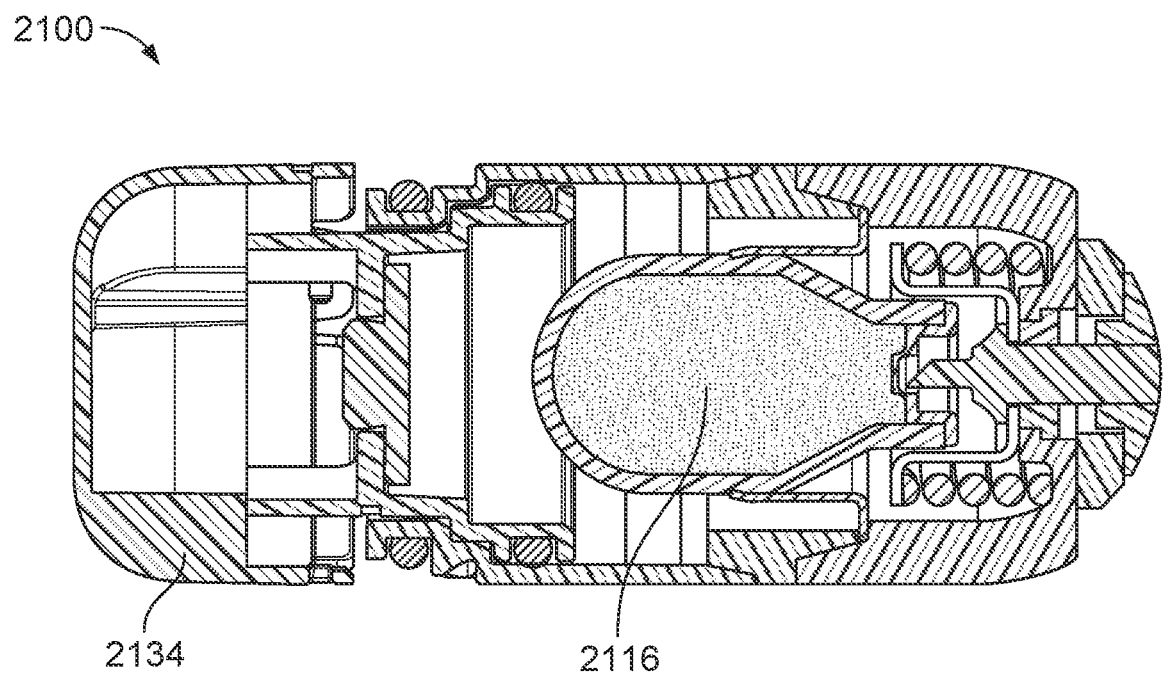

FIGS. 21 and 22 show an ingestible device 2100 in its closed and open states, respectively. The ingestible device 2100 contains a dispensable substance that is not under pressure when the subject swallows the ingestible device. The ingestible device 2100 has housing parts 2104 and 2106 connected by a union ring 2108 and with a fluid volume 2110 containing a dispensable substance, a spring 2114, a gas cylinder 2116, a piston 2118, a piercer 2120, and an O-ring 2132. Gas cylinder 2116 is retained by retention element 2128. A seal 2130 forms a gas seal between the piercer 2120 and the housing 2106. A spring retention cup 2122 retains the spring-loaded piercer 2120. A piercer retainer 2124 holds the piercer 2120 in place with an enteric trigger 2126 that retains the piercer retainer in place until it dissolves and used as the triggering mechanism. When the device 2100 is swallowed by the subject, the enteric trigger 2126 prevents the dispensable substance in fluid volume 2110 from being under pressure by holding the spring 2114 and the piercer 2120 in place. When the device 2100 reaches the appropriate location in the GI tract, the enteric trigger 2126 degrades and/or dissolves (e.g., due to pH, change in pH, presence of certain enzyme, and/or concentration of certain enzyme) that the piercer retainer 2124 is no longer sufficient to hold back the pressure from the spring 2114. The spring 2114 forces the piercer 2120 into the gas cylinder 2116, puncturing the gas cylinder 2116 and causing gas at elevated pressure to leave the cylinder 2116. This causes the gas cylinder 2116 to press against the piston 2118 and apply pressure to the fluid volume 2110. The piston provides friction to cause the cap 2134 to open/deploy such that the dispensable substance is delivered out of the volume 2110. This results in delivery (e.g., topical delivery) of the therapeutic agent contained in the dispensable substance.

In some embodiments, the housing of the ingestible device 2100 has a diameter from about 10 mm to about 12 mm (e.g., from about 11.3 mm to about 11.5 mm), a length from about 23 mm to about 26.5 mm (e.g., from about 23.3 mm to about 26.3 mm), a wall thickness from about 0.4 mm to about 0.6 mm (e.g., about 0.5 mm), a fluid volume from about 565 μL to about 630 μL (e.g., from about 574 μL to about 623 μL), and/or a gas volume in the gas cylinder 2116 from about 150 μL to about 175 μL (e.g., about 160 μL).

Figure 23:
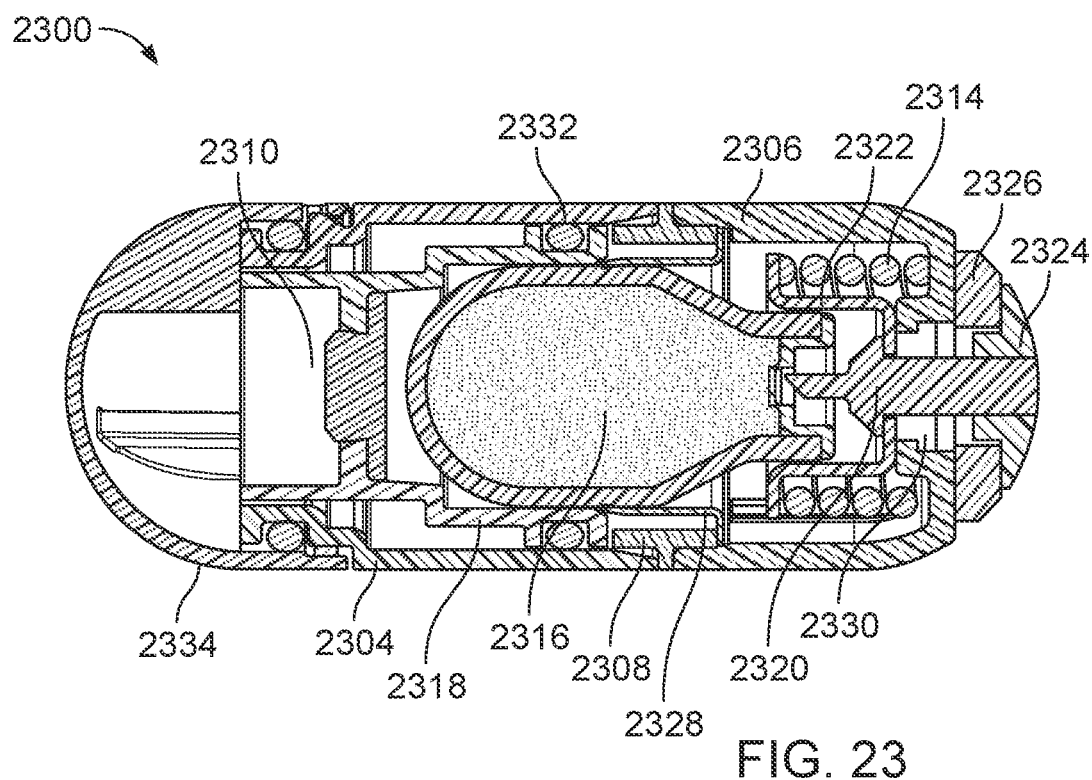
FIGS. 23 and 24 show states of an ingestible device.
Figure 24:
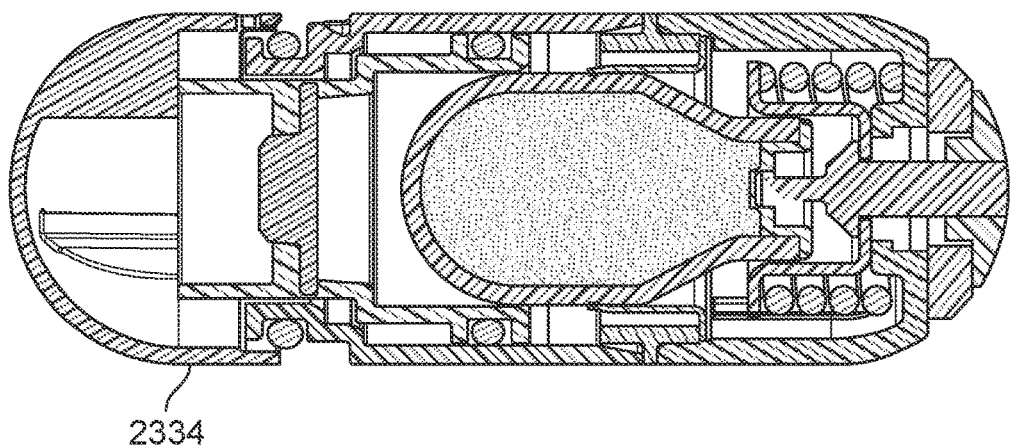

FIGS. 23 and 24 show an ingestible device 2300 in its closed and open states, respectively. The ingestible device 2300 contains a dispensable substance that is not under pressure when the subject swallows the ingestible device. The ingestible device 2300 has housing parts 2304 and 2306 connected by a union ring 2308 and with a fluid volume 2310 containing a dispensable substance, a spring 2314, a gas cylinder 2316, a piston 2318, a piercer 2320, and an O-ring 2332. Gas cylinder 2316 is retained by retention element 2328. A seal 2330 forms a gas seal between the piercer 2320 and the housing 2306. A spring retention cup 2322 retains the spring-loaded piercer 2320. A piercer retainer 2324 holds the piercer 2320 in place with an enteric trigger 2326 that retains the piercer retainer in place until it dissolves and used as the triggering mechanism. When the device 2300 is swallowed by the subject, the enteric trigger 2326 prevents the dispensable substance in fluid volume 2310 from being under pressure by holding the spring 2314 and the piercer 2320 in place. When the device 2300 reaches the appropriate location in the GI tract, the enteric trigger 2326 degrades and/or dissolves (e.g., due to pH, change in pH, presence of certain enzyme, and/or concentration of certain enzyme) that the piercer retainer 2324 is no longer sufficient to hold back the pressure from the spring 2314. The spring 2314 forces the piercer 2320 into the gas cylinder 2316, puncturing the gas cylinder 2316 and causing gas at elevated pressure to leave the cylinder 2316. This causes the gas cylinder 2316 to press against the piston 2318 and apply pressure to the fluid volume 2310. The piston provides friction to cause the cap 2334 to open/deploy such that the dispensable substance is delivered out of the volume 2310. This results in delivery (e.g., topical delivery) of the therapeutic agent contained in the dispensable substance.

In some embodiments, the housing of the ingestible device 2300 has a diameter from about 8 mm to about 11 mm (e.g., from about 9.8 mm to about 10 mm), a length from about 23 mm to about 26.5 mm (e.g., from about 23.3 mm to about 26.3 mm), a wall thickness from about 0.4 mm to about 0.6 mm (e.g., about 0.5 mm), a fluid volume from about 230 μL to about 355 μL (e.g., from about 235 μL to about 349 μL), and/or a gas volume in the gas cylinder 2316 from about 150 μL to about 175 μL (e.g., about 160 μL).

Figure 25:
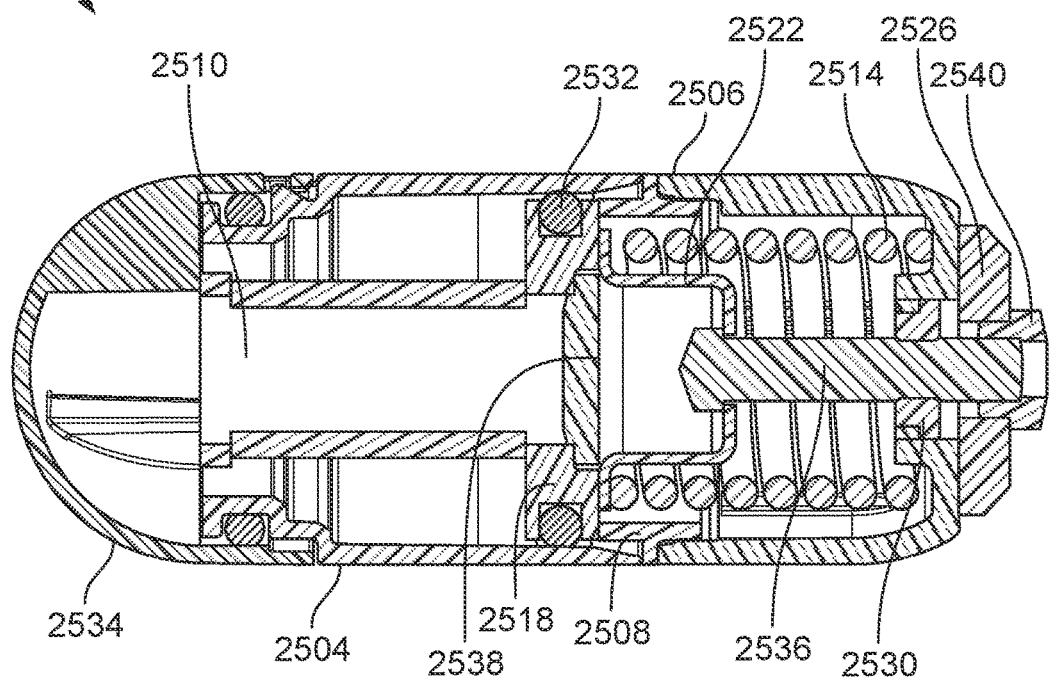
FIGS. 25-27 show ingestible devices.

FIG. 25 shows an embodiment of an ingestible device 2500, which contains a dispensable substance that is not under pressure when the subject swallows the ingestible device. The ingestible device 2500 has housing parts 2504 and 2506 connected by a union ring 2508 and with a fluid volume 2510 containing a dispensable substance, a spring 2514, a piston 2518, a spring retention pin 2536, and an O-ring 2532. A dispensable substance-containing cap 2538 seals in the dispensable substance (e.g., drug-containing liquid) after the housing part 2504 is filled with the dispensable substance (e.g., drug-containing liquid). A seal 2530 forms a gas seal between the spring retention pin 2536 and the housing part 2506. A spring retention cup 2522 retains the spring retention pin 2536. A pin retainer 2540 holds the spring retention pin 2536 in place with an enteric trigger 2526 that retains the pin retainer in place until it dissolves and used as the triggering mechanism. When the device 2500 is swallowed by the subject, the enteric trigger 2526 prevents the dispensable substance in fluid volume 2510 from being under pressure by holding the spring 2514 and the spring retention pin 2536 in place. When the device 2500 reaches the appropriate location in the GI tract, the enteric trigger 2526 degrades and/or dissolves (e.g., due to pH, change in pH, presence of certain enzyme, and/or concentration of certain enzyme) that the pin retainer 2540 is no longer sufficient to hold back the spring retention pin 2536, releasing spring 2514. The spring 2514 pushes against the piston 2518 such that the piston 2518 applies pressure to the fluid volume 2510. The piston provides friction to cause the cap 2534 to open/deploy such that the dispensable substance is delivered out of the volume 2510. This results in delivery (e.g., topical delivery) of the therapeutic agent out of the dispensable substance.

In some embodiments, the housing of the ingestible device 2500 has a diameter from about 8 mm to about 11 mm (e.g., from about 9.8 mm to about 10 mm), a length from about 23 mm to about 26.5 mm (e.g., from about 23.3 mm to about 26.1 mm), a wall thickness from about 0.4 mm to about 0.6 mm (e.g., about 0.5 mm), a fluid volume from about 395 μL to about 570 μL (e.g., from about 403 μL to about 559 μL).

Figure 26:
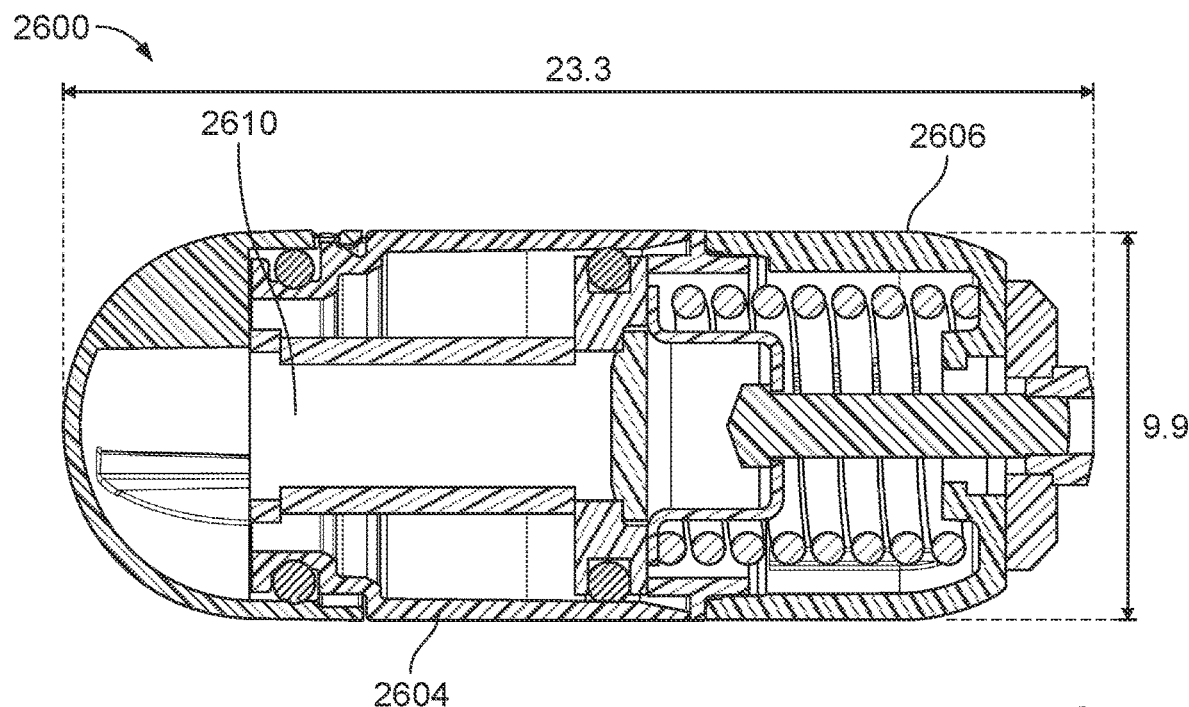
Figure 27:
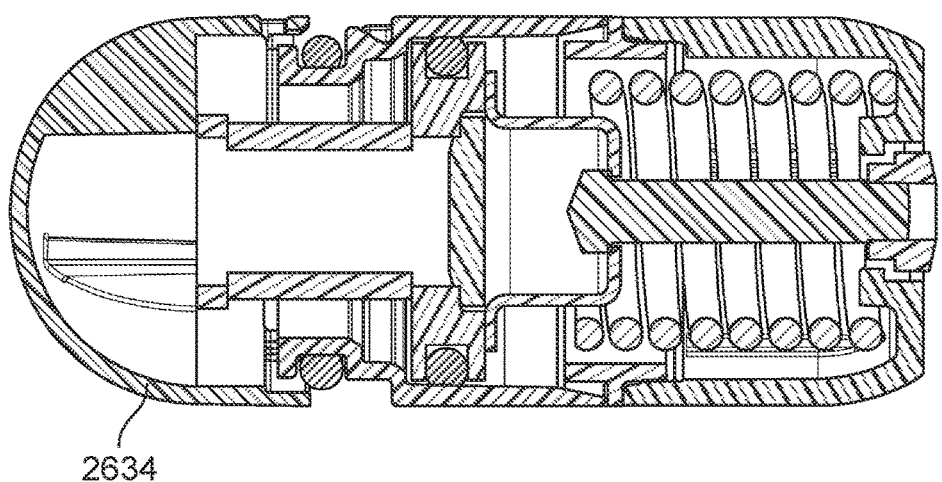

FIGS. 26 and 27 show an ingestible device 2600 in its closed and open states, respectively. The ingestible device 2600 is configured similarly to ingestible device 2500 and having housing components 2604 and 2606 with a smaller profile than the housing component of ingestible device 2500. Fluid volume 2610 of ingestible device 2600 can have a smaller capacity than fluid volume 2510 of ingestible device 2500.

In some embodiments, the housing of the ingestible device 2600 has a diameter from about 8 mm to about 11 mm (e.g., from about 9.8 mm to about 10 mm), a length from about 23 mm to about 26.5 mm (e.g., from about 23.3 mm to about 26.1 mm), a wall thickness from about 0.4 mm to about 0.6 mm (e.g., about 0.5 mm), a fluid volume from about 395 μL to about 570 μL (e.g., from about 403 μL to about 559 μL).

Figure 28:
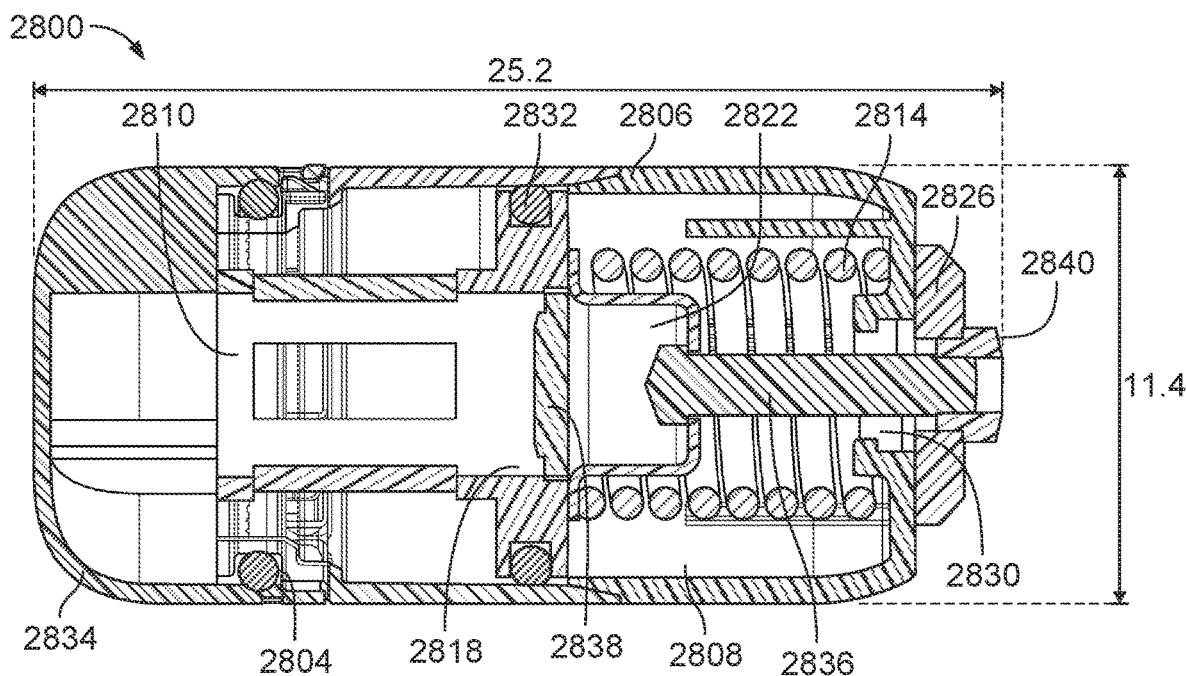
FIGS. 28-30 show states of an ingestible device.

FIG. 28 shows an embodiment of an ingestible device 2800, which contains a dispensable substance that is not under pressure when the subject swallows the ingestible device. The ingestible device 2800 has housing parts 2804 and 2806 connected by a union ring 2808 and with a fluid volume 2810 containing a dispensable substance, a spring 2814, a piston 2818, a spring retention pin 2836, and an O-ring 2832. A dispensable substance-containing cap 2838 seals in the dispensable substance (e.g., drug-containing liquid) after the housing part 2804 is filled with the dispensable substance (e.g., drug-containing liquid). A seal 2830 forms a gas seal between the spring retention pin 2836 and the housing 2806. A spring retention cup 2822 retains the spring retention pin 2836. A pin retainer 2840 holds the spring retention pin 2836 in place with an enteric trigger 2826 that retains the pin retainer in place until it dissolves and used as the triggering mechanism. When the device 2800 is swallowed by the subject, the enteric trigger 2826 prevents the dispensable substance in fluid volume 2810 from being under pressure by holding the spring 2814 and the spring retention pin 2836 in place. When the device 2800 reaches the appropriate location in the GI tract, the enteric trigger 2826 degrades and/or dissolves (e.g., due to pH, change in pH, presence of certain enzyme, and/or concentration of certain enzyme) that the pin retainer 2840 is no longer sufficient to hold back the spring retention pin 2836, releasing spring 2814. The spring 2814 pushes against the piston 2818 such that the piston 2818 applies pressure to the fluid volume 2810. The piston provides friction to cause the cap 2834 to open/deploy such that the dispensable substance is delivered out of the volume 2810. This results in delivery (e.g., topical delivery) of the therapeutic agent contained in the dispensable sub stance.

In some embodiments, the housing of the ingestible device 2800 has a diameter from about 10 mm to about 12 mm (e.g., from about 11.3 mm to about 11.5 mm), a length from about 23 mm to about 26.5 mm (e.g., from about 25.2 mm to about 26.2 mm), a wall thickness from about 0.4 mm to about 0.6 mm (e.g., about 0.5 mm), a fluid volume from about 790 μL to about 870 μL (e.g., from about 802 μL to about 855 μL).

Figure 29A:
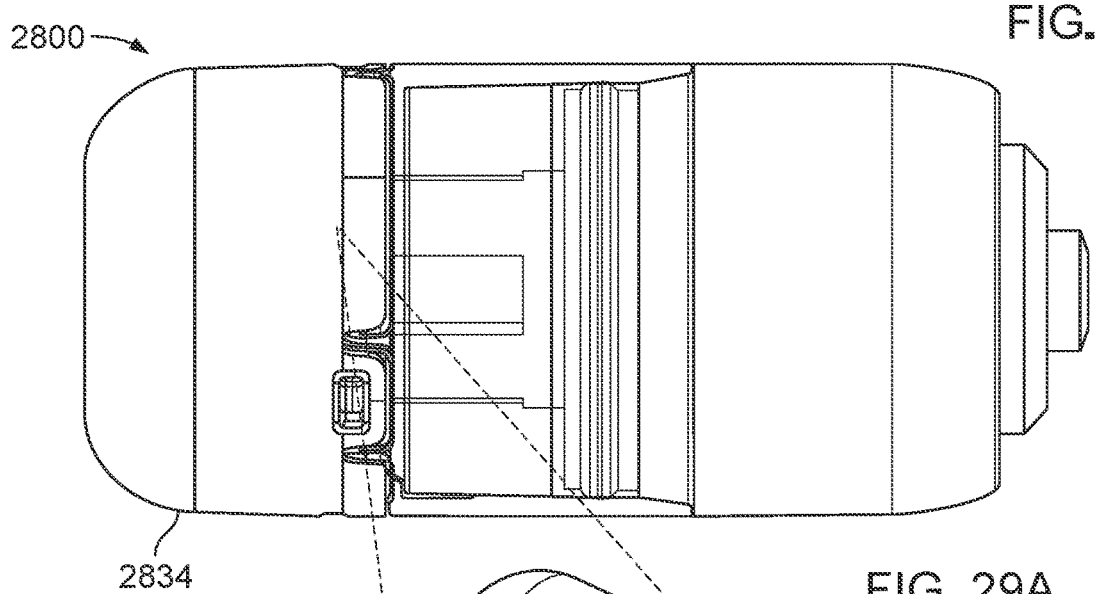
Figure 29B:
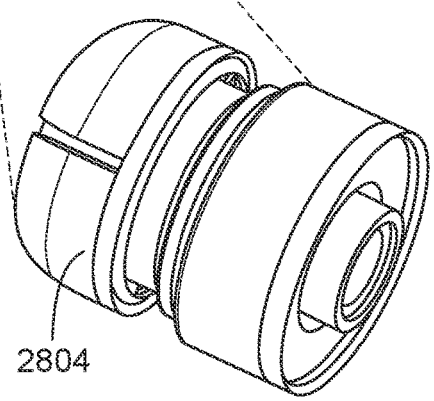

FIG. 29A shows an outer view of the embodiment of ingestible device 2800, and FIG. 29B shows and an outer view of the housing component 2804 that retains a fluid volume 2810.

Figure 30:
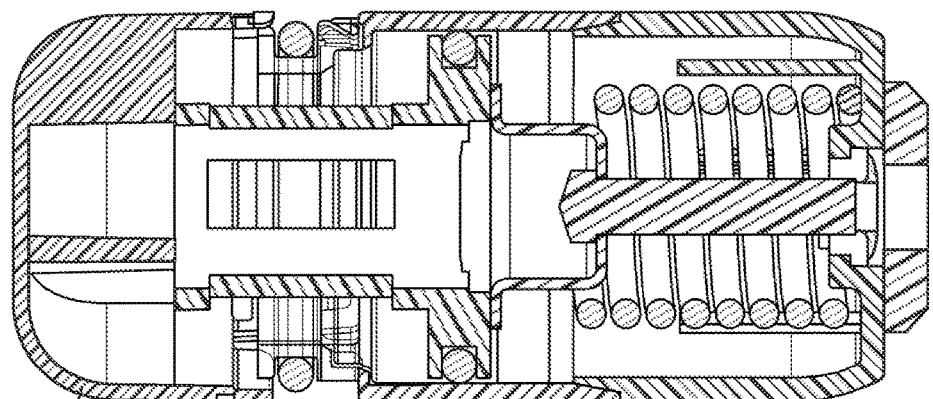

FIG. 30 shows the embodiment of the ingestible device 2800 in which the cap 2834 is opened/deployed.

Figure 31:
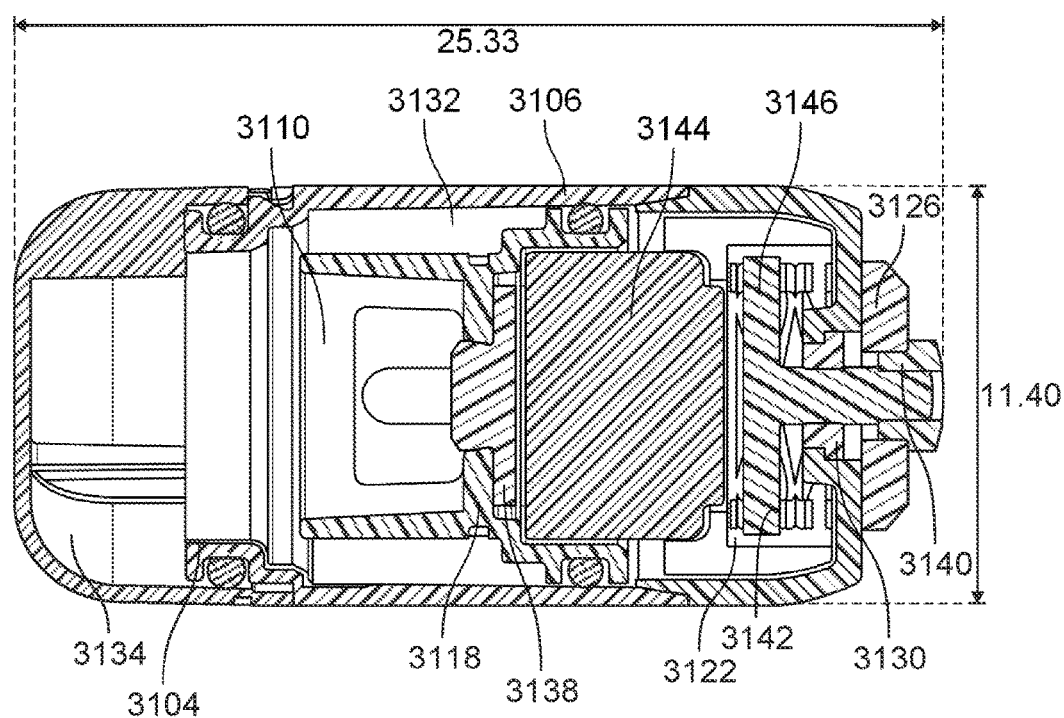
FIGS. 31-34 show states of an ingestible device.

FIG. 31 shows an embodiment of an ingestible device 3100, which contains a dispensable substance that is not under pressure when the subject swallows the ingestible device. The ingestible device 3100 has housing parts 3104 and 3106 and a fluid volume 3110 containing a dispensable substance, a piston 3118, a wave spring 3142, and an O-ring 3132. A dispensable substance-containing cap 3138 seals in the dispensable substance (e.g., drug-containing liquid) after the housing part 3104 is filled with the dispensable substance (e.g., the drug-containing liquid). A seal 3130 forms a gas seal between the switch 3146 and the housing 3106. A spring retention cup 3122 retains the wave spring 3142. A pin retainer 3140 holds the switch 3146 in place with an enteric trigger 3126 that retains the pin retainer in place until it dissolves and is used as the triggering mechanism. When the device 3100 is swallowed by the subject, the enteric trigger 3126 prevents the dispensable substance in fluid volume 3110 from being under pressure by holding the wave spring 3142 and the switch 3146 in place. When the device 3100 reaches the appropriate location in the GI tract, the enteric trigger 3126 degrades and/or dissolves (e.g., due to pH, change in pH, presence of certain enzyme, and/or concentration of certain enzyme) that the pin retainer 3140 is no longer sufficient to hold back the wave spring 3142 and releasing switch 3146. The switch 3146 completes a circuit with the gas cell 3144, which begins gas production. As pressure builds, piston 3118 slides along a trace and closes the circuit via a conductive O-ring 3132. The circuit opens when the trace ends at a defined travel distance to halt gas production by the gas cell 3144. The piston 3118 applies pressure to the fluid volume 3110 and provides friction to cause the cap 3134 to open/deploy such that the dispensable substance is delivered out of the volume 3110. This results in delivery (e.g., topical delivery) of the therapeutic agent contained in the dispensable substance.

In some embodiments, the housing of the ingestible device 3100 has a diameter from about 10 mm to about 12 mm (e.g., from about 11 mm to about 11.5 mm), a length from about 23 mm to about 26.5 mm (e.g., from about 25.2 mm to about 26.2 mm), a wall thickness from about 0.4 mm to about 0.6 mm (e.g., about 0.5 mm), a fluid volume from about 880 μL to about 940 μL (e.g., from about 890 μL to about 930 μL).

Figures 32A, 32B:
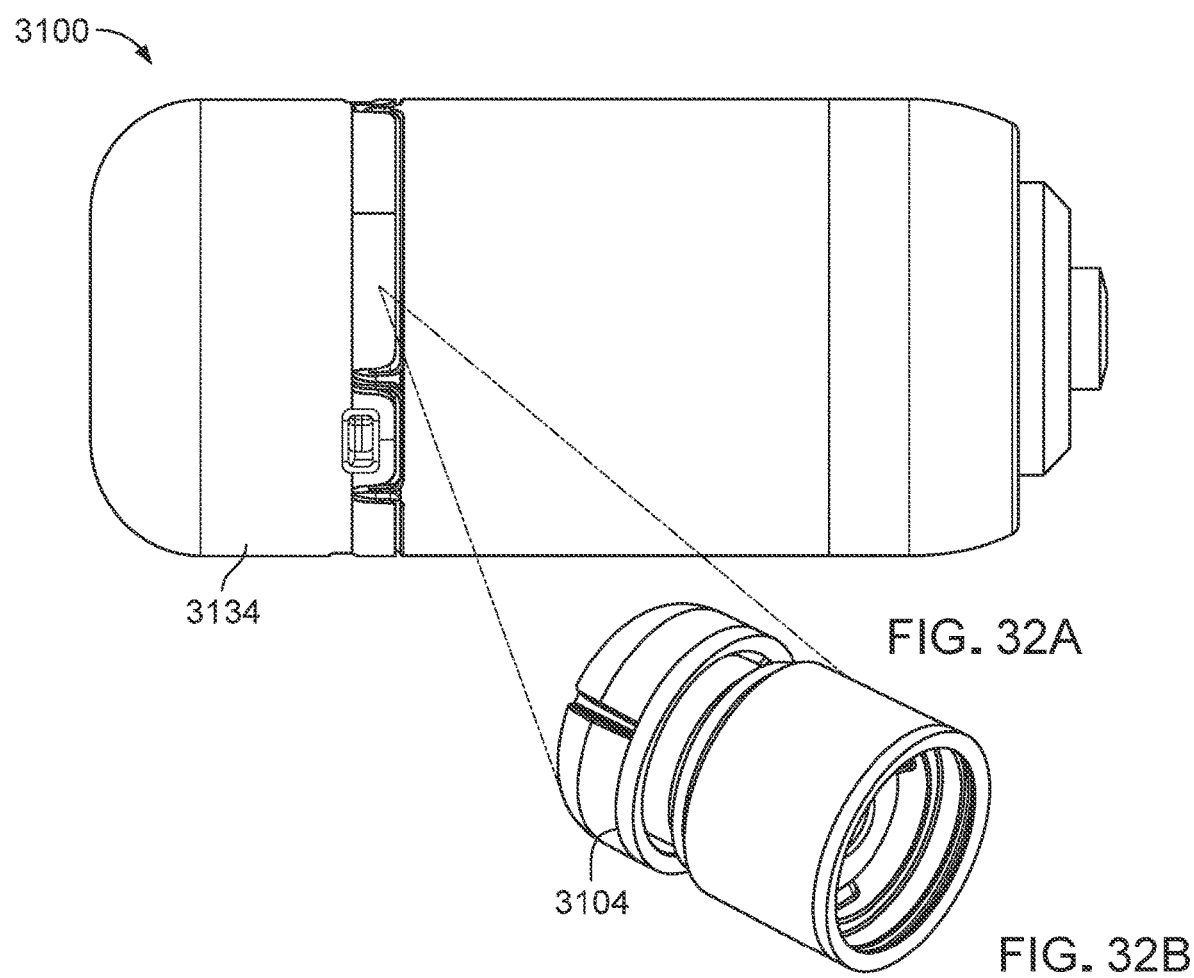

FIG. 32A shows an outer view of the embodiment of ingestible device 3100, and FIG. 32B shows an outer view of the housing component 3104 that retains a fluid volume 3110.

Figure 33:
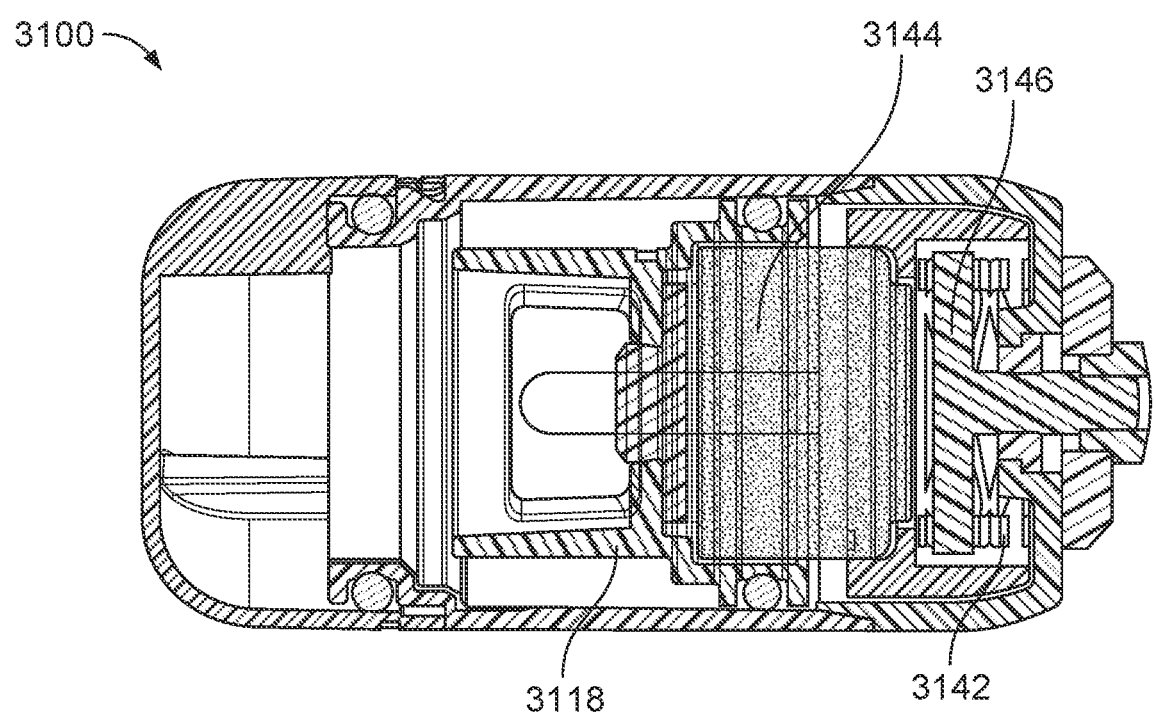

FIG. 33 shows another view of the embodiment of the ingestible device 3100.

Figure 34:
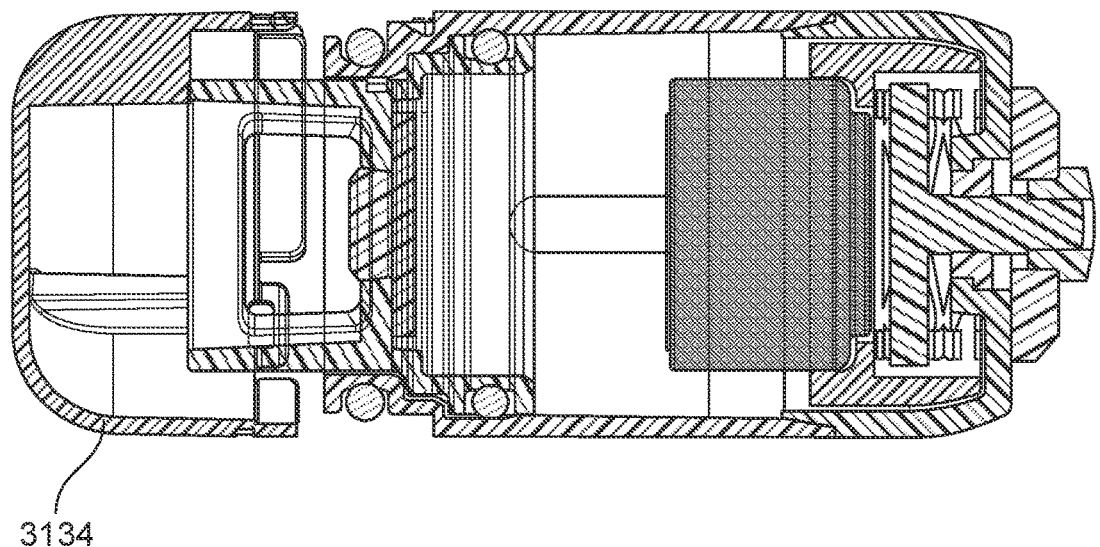

FIG. 34 shows the embodiment of the ingestible device 3100 in which the cap 3134 is opened/deployed.

In some embodiments, a length of an ingestible device can be reduced to achieve a modified 00 standardized length, e.g., approximately 23.3 mm in length, while maintaining a same diameter as a standard size 000. A reduced length of the ingestible device may result in a reduced volume available for the dispensable substance. Adjusting one or more dimensions of a gas cylinder within the ingestible device and/or altering a position of a piston may be utilized to increase an available volume for the dispensable substance, while maintaining a threshold dispensable substance volume and/or pressure provided by the gas cylinder for the ingestible device. Example embodiments are described with reference to FIGS. 35-40 herein.

Figure 35:
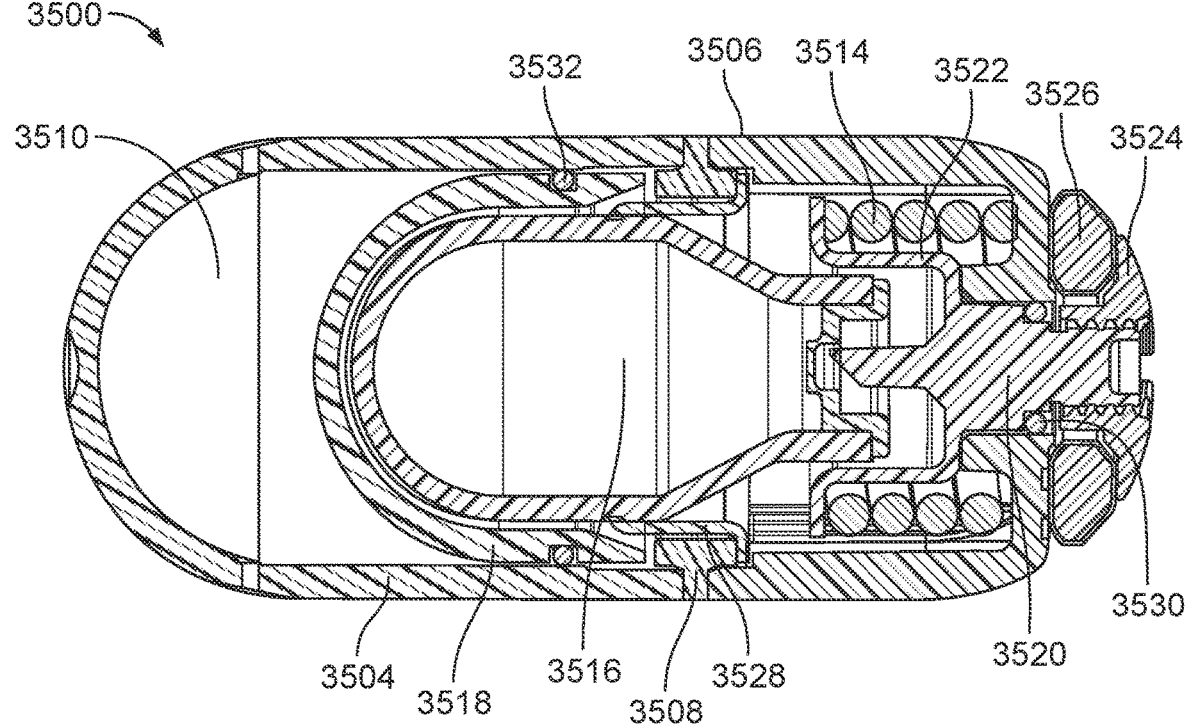
FIGS. 35-40 show ingestible devices.

FIG. 35 shows an embodiment of an ingestible device 3500 for epithelial delivery in which a length of the ingestible device is reduced to achieve a modified size 00 submucosal device, and which contains a dispensable substance that is not under pressure when the subject swallows the ingestible device. The ingestible device 3500 has housing parts 3504 and 3506 connected by a union ring 3508 and with a fluid volume 3510 containing a dispensable substance, a spring 3514, a gas cylinder 3516, a piston 3518, a piercer 3520, and an O-ring 3532. Gas cylinder 3516 is retained by retention element 3528. A seal 3530 forms a gas seal between the piercer 3520 and the housing 3506. A spring retention cup 3522 retains the spring-loaded piercer 3520. A piercer retainer 3524 holds the piercer 3520 in place with an enteric trigger 3526 that retains the piercer retainer in place until it dissolves and used as the triggering mechanism. When the device 3500 is swallowed by the subject, the enteric trigger 3526 prevents the dispensable substance in fluid volume 3510 from being under pressure by holding the spring 3514 and the piercer 3520 in place. When the device 3500 reaches the appropriate location in the GI tract, the enteric trigger 3526 degrades and/or dissolves (e.g., due to pH, change in pH, presence of certain enzyme, and/or concentration of certain enzyme) that the piercer retainer 3524 is no longer sufficient to hold back the pressure from the spring 3514. The spring 3514 forces the piercer 3520 into the gas cylinder 3516, puncturing the gas cylinder 3516 and causing gas at elevated pressure to 3534 leave the cylinder 3516. This causes the gas cylinder 3516 to press against the piston 3518 and apply pressure to the fluid volume 3510. The piston provides friction to cause the cap 3534 to open/deploy such that the dispensable substance is delivered out of the volume 3510. This results in epithelial delivery of the therapeutic agent contained in the dispensable substance.

In some embodiments, the ingestible device 3500 can retain a dispensable substance volume from about 250 µL to about 350 µL (e.g., about 267 µL), can have an expansion volume from about 230 µL to about 260 µL (e.g., about 243 µL), and can have a gas cylinder fill volume from about 140 µL to about 150 µL (e.g., about 160 µL).

In some embodiments, one or more adjustments to a piston length and/or gas cylinder dimensions can be modified for the ingestible device, e.g., ingestible device 3500. FIGS. 36-40 depict various modifications to piston length and/or gas cylinder dimensions of the ingestible device structure described with reference to FIG. 35.

Figure 36:
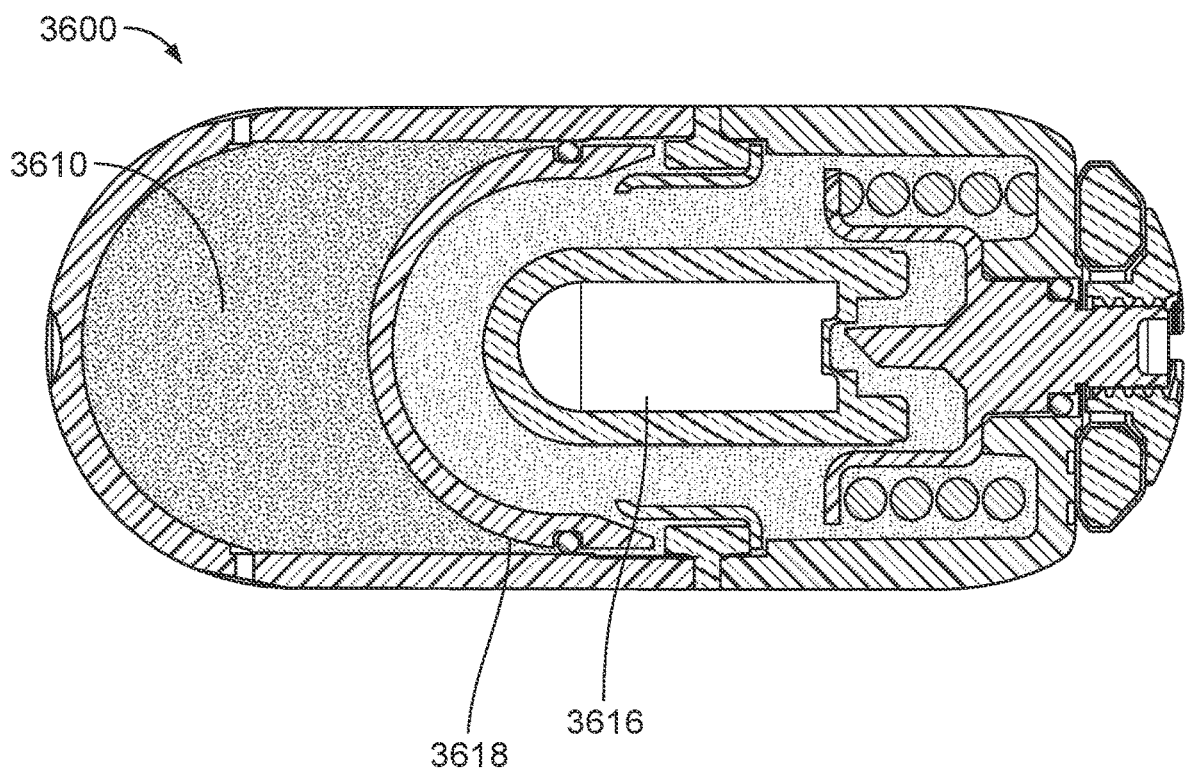

FIG. 36 shows an embodiment of an ingestible device 3600 in which a length of the ingestible device is reduced to achieve a modified size 00 submucosal device and a piston length is reduced. As depicted in FIG. 36, ingestible device 3600 includes a piston 3618, a gas cylinder 3616, and a fluid volume 3610. In some embodiments, the ingestible device 3600 can retain a dispensable substance volume from 300 µL to about 350 µL (e.g., about 322 µL), can have an expansion volume from about 350 µL to about 380 µL (e.g., about 372 µL), and can have a gas cylinder fill volume from about 35 µL to about 45 µL (e.g., about 40 µL). In some embodiments, a 280 PSIG fill pressure of the gas cylinder corresponds to a drive pressure volume from about 70-80 µL (e.g., about 75 µL). In some embodiments, a 240 PSIG fill pressure of the gas cylinder corresponds to a drive pressure volume from about 90-100 µL (e.g., about 95 µL).

Figure 37:
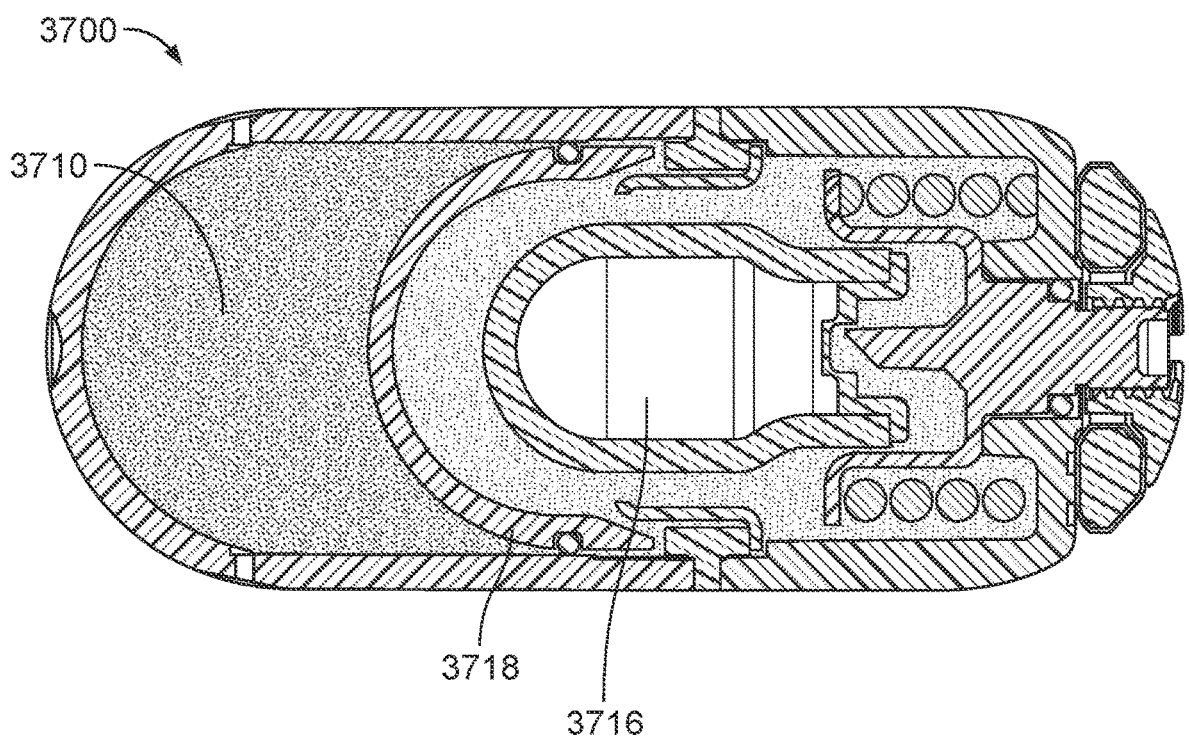

FIG. 37 shows an embodiment of an ingestible device 3700 in which a length of the ingestible device is reduced to achieve a modified size 00 submucosal device and a piston length is reduced. As depicted in FIG. 37, ingestible device 3700 includes a piston 3718, a gas cylinder 3716, and a fluid volume 3710. In some embodiments, the ingestible device 3700 can retain a dispensable substance volume from 300 µL to about 350 µL, (e.g., about 332 µL), can have an expansion volume from about 320 µL to about 380 µL, (e.g., about 336 µL), and can have a gas cylinder fill volume from about 65 µL to about 85 µL (e.g., about 75 µL). In some embodiments, a 280 PSIG fill pressure of the gas cylinder corresponds to a drive pressure volume from about 140-150 µL (e.g., about 145 µL). In some embodiments, a 240 PSIG fill pressure of the gas cylinder corresponds to a drive pressure volume from about 170-190 µL (e.g., about 180 µL).

Figure 38:
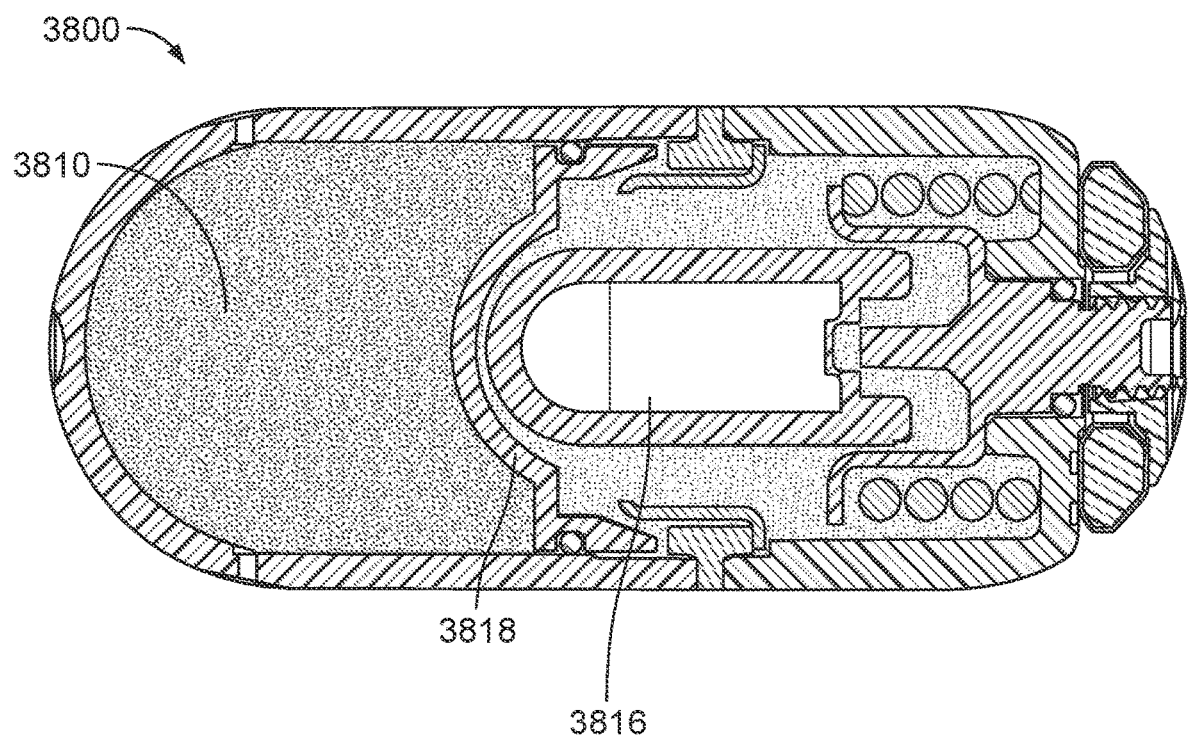

FIG. 38 shows an embodiment of an ingestible device 3800 in which a length of the ingestible device is reduced to achieve a modified size 00 submucosal device and a piston length is reduced. As depicted in FIG. 38, ingestible device 3800 includes a piston 3818, a gas cylinder 3816, and a fluid volume 3810. In some embodiments, the ingestible device 3800 can retain a dispensable substance volume from 300 µL to about 350 µL, (e.g., about 335 µL), can have an expansion volume from about 300 µL to about 320 µL (e.g., about 306 µL), and can have a gas cylinder fill volume from about 35 µL to about 45 µL (e.g., about 40 µL). Piston shape of piston 3818 may result in residual dispensable substance volume of about 80 µL (of a total of 335 µL delivered) within the dispensable substance housing after delivery.

Figure 39:
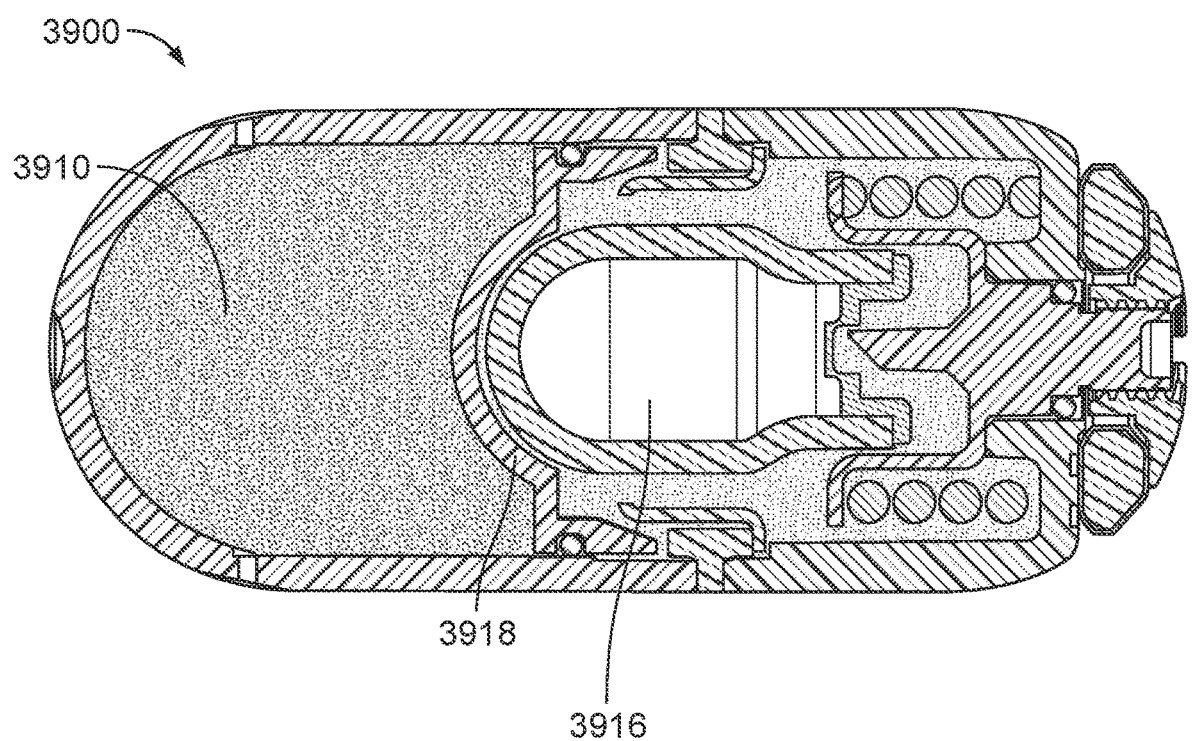

FIG. 39 shows an embodiment of an ingestible device 3900 in which a length of the ingestible device is reduced to achieve a modified size 00 submucosal device and a gas cylinder diameter is modified. As depicted in FIG. 39, ingestible device 3900 includes a piston 3918, a gas cylinder 3916, and a fluid volume 3910. In some embodiments, the ingestible device 3900 can retain a dispensable substance volume from 300 µL to about 350 µL (e.g., about 335 µL), can have an expansion volume from about 250 µL to about 290 µL (e.g., about 271 µL), and can have a gas cylinder fill volume from about 70 µL to about 80 µL (e.g., about 75 µL). Piston shape of piston 19166 may result in residual dispensable substance volume from about 70-90 µL (e.g., about 80 µL) of a total amount of dispensable substance volume delivered within the housing after delivery.

Figure 40:
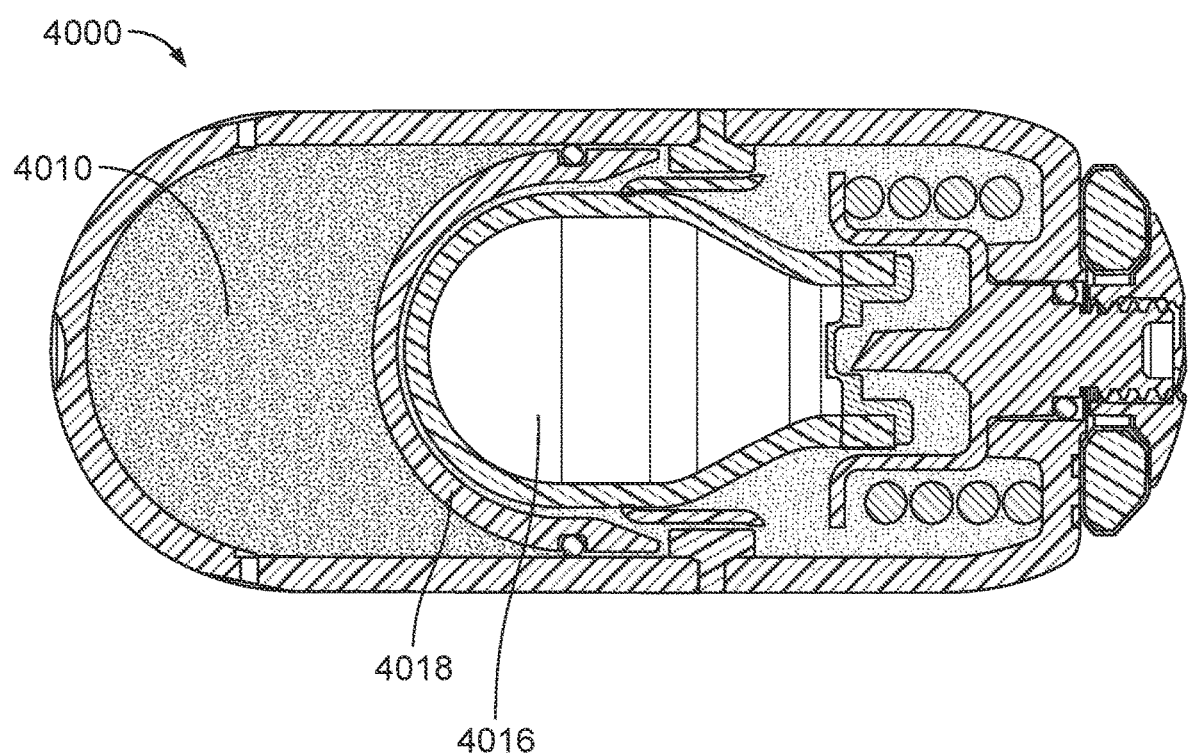

FIG. 40 shows an embodiment of an ingestible device 4000 in which a length of the ingestible device is reduced to achieve a modified size 00 submucosal device and a gas cylinder diameter is modified. As depicted in FIG. 40, ingestible device 4000 includes a piston 4018, a gas cylinder 4016, and a fluid volume 4010. In some embodiments, the ingestible device 4000 can retain a dispensable substance volume from 300 µL to about 350 µL (e.g., about 332 µL), can have an expansion volume from about 220 µL to about 270 µL (e.g., about 240 µL), and can have a gas cylinder fill volume from about 125 µL to about 145 µL (e.g., about 138

μL). In some embodiments, a 240 PSIG drive pressure of the gas cylinder corresponds to a fill pressure from about 780-800 PSIG (e.g., 792.7 PSIG). In some embodiments, 280 PSIG fill pressure of the gas cylinder corresponds to a drive pressure from about 910-930 PSIG (e.g., about 925 PSIG). In some embodiments, a 320 PSIG drive pressure of the gas cylinder corresponds to a fill pressure from about 1040-1060 PSIG (e.g., 1057 PSIG).

In some embodiments, a puncture force required to puncture a gas cylinder can be reduced such that a shorter/lower force spring can be utilized and/or a shorter/stiffer spring can be utilized.

Figure 41C:
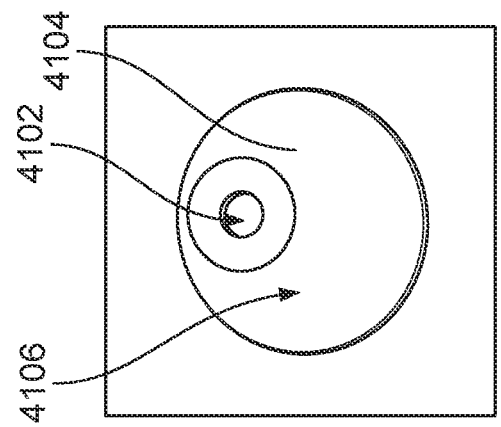
FIGS. 41A-41C show aspects of an ingestible device.
Figure 41B:
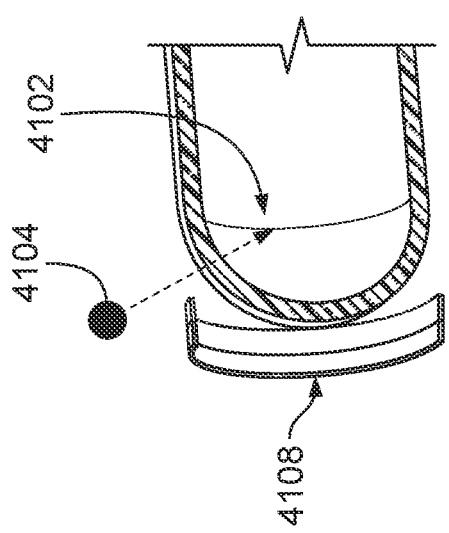
Figure 41A:
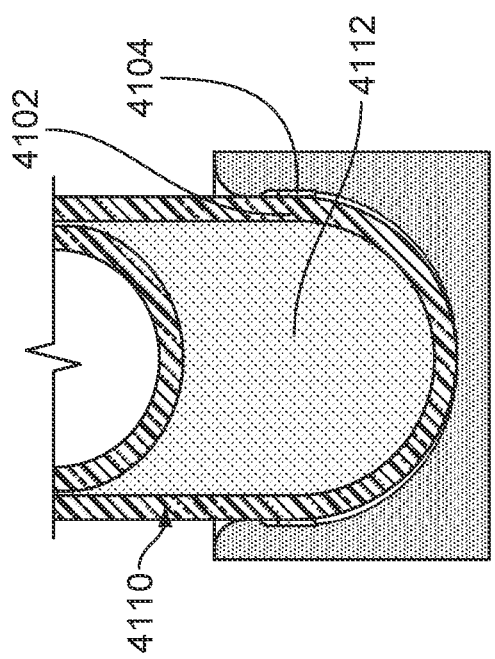

In some embodiments, as depicted in FIGS. 41A-41C, a nozzle opening 4102 can be covered by a covering including a member, e.g., a patch 4104, that forms a barrier between a dispensable substance 4112 retained within the housing 4110 and an environment external to the ingestible device. A patch 4104 can be formed of a materials that is a degradable material, an erodible material and a dissolvable material. A patch can be a barrier film composed of various materials, for example, polyethylene (PE), polypropylene, cyclic olefin copolymer (COC), cyclo-olefin-polymer (COP), polycarbonate, polyvinyl chloride (PVC), polyurethane, or the like. A patch may be a mutli-layer film, e.g., two or more layers of a same or different material, for enhanced barrier properties. Multi-layer construction of a patch 4104 can include, for example, PE/ethylene-vinyl alcohol copolymer (EVOH), ethylene-vinyl acetate (EVA)/EVOH/EVA, EVA/polyvinylidene chloride (PVDC)/EV, or the like. In some embodiments, multi-layer construction of a patch can include a metal layer.

A patch 4104 can have various shape profiles, for example, circular, rectangular, polygonal, or asymmetric profile. In some embodiments, as depicted in FIG. 41, a patch may be affixed off-center 4106 over the nozzle opening 4102 on an outside surface of the ingestible device such that a force of a jet expelled through the nozzle opening 4102, e.g., by pressurized release of the dispensable substance, may preferentially move the patch away from a direction of the formed jet.

A patch 4104 may be affixed loosely over a nozzle opening, e.g., using adhesive or another pressure sensitive method, or using static attraction. Adhesive to affix the patch may be utilized on a surface surrounding the nozzle but not directly on the nozzle.

In some embodiments, a film, a coating, a foil, a band, or the like may be placed over the patch that is affixed over the nozzle opening, and may be composed on a dissolvable material, e.g., enteric material, such that the film, coating, foil, or band holds the patch in place over the nozzle opening during handling, storage, and ingestion of the ingestible device. In one example, a band 4108 is composed of a material that can dissolve upon entry into a body. The film or band may be composed of a material that is water soluble, e.g., hydroxypropyl methyl cellulose (HPMC), hydroxypropylmethylcellulose acetate succinate (HPMCAS), or gelatin. The film or band 4108 may be composed of a material that includes a pH-dependent solubility, e.g., composed of or including polymethacrylate, such that the material is more stable under acidic conditions, e.g., pH 1-4, and where a rate of dissolution increases when the material is exposed to higher pH, e.g., pH 5-7.

In some embodiments, a band covering a nozzle opening can be composed of a heat shrink material that is heat shrunk to the housing such that it provides a nozzle covering. An example of a heat shrink material is polyethylene terephthalate (PET). Additional examples of heat shrink materials include polyolefin, polyethylene, LDPE, PTFE, FEP and COC. In general, such a heat shrink material does not operate by being dissolved. Instead, it is broken (e.g., punctured) by the pressure of the dispensable material applied to the heat shrink material. Such a heat shrunk band can have a thickness of, for example, from about 5 μm to about 100 μm (e.g., from about 5 μm to about 50 μm, about 10 μm, about 12 μm, about 15 μm, about 50 μm). Specific examples include heat shrunk PET (e.g., medical film) having a thickness of about 12 μm, heat shrunk polylefin (e.g., transit packing film) having a thickness of about 15 μm, and heat shrunk polyethylene (e.g., transit packing film) having a thickness of about 50 μm.

In general, a covering (e.g., a film, a coating, a foil, a band) of a nozzle opening can be scored, e.g., to make it easier for the seal to be broken when desired. Generally, such scoring can be configured as desired. As an example, scoring can be configured as a series of parallel lines. As another example, scoring can be configured as a grid (cross-hatched). As a further example, scoring can be configured as a plurality of dots (e.g., equally spaced dots). In some embodiments of a scored seal, the seal is composed of LDPE, for example of having a thickness of from 20 μm to 75 μm (e.g., 25 μm, 50 μm). For example, a seal composed of LDPE can be scored with stripes or a grid or a plurality of dots, with the LDPE having a thickness of 25 μm or 50 μm.

In some embodiments, covering (e.g., a coating, a film, a band, or a patch has a minimal burst pressure. In some embodiments, for example, the minimal burst pressure is less than 420 psig, 410 psig, 400 psig, 390 psig, 380 psig, 370 psig, 360 psig, 350 psig, 340 psig, 330 psig, 320 psig, 310 psig, 300 psig, 290 psig, 280 psig, 270 psig, 260 psig, 250 psig, 240 psig, 230 psig, 220 psig, 210 psig, 200 psig, 190 psig, 180 psig, 170 psig, 160 psig, 150 psig, 140 psig, 130 psig, 120 psig, 110 psig, 100 psig, 90 psig, 80 psig, 70 psig, 60 psig, 50 psig, 40 psig, 30 psig, or 20 psig. Generally, the minimal burst pressure is more than 5 psig (e.g., more than 10 psig, more than 25 psig, more than 50 psig more than 80 psig). For example, in certain embodiments, the burst pressure can be in a range of from 5 psig to any one of the minimal burst pressures noted earlier in this paragraph.

In some embodiments, a coating or film can be applied over a nozzle opening 4102 that may dissolve/degrade or otherwise become unstable after the ingestion of the ingestible device. In some embodiments, the coating or film is hydrophobic. The coating or film can be structurally weakened by drilling/scoring, e.g., using laser drilling, and/or can be composed of a material that weakens based on an environment surrounding the material, e.g., an enteric material within the body. In one example, laser microtoming can be utilized to thin a coating or film, e.g., a sanding/polishing process, to reduce the coating or film thickness. In some embodiments, a coating or film of an enteric material can be applied over a nozzle opening 4102 and a portion of an outer surface of the ingestible device. A machining/polishing processes can be utilized to control a final thickness of the applied coating or film, e.g., centerless lapping or grinding. The coating or film can be further processed using a laser to drill, score, and/or perforate a portion of the coating or film to mechanically weaken the coating or film.

FIGS. 42A-47C depict embodiments of a patch, coating, film, foil and/or band that can be affixed to or in contact with the nozzle opening. While such embodiments are depicted in these figures, the disclosure is not limited in this sense. In some embodiments, a combination of more than one (e.g., more than two, more than three) such approaches to covering a nozzle opening may be used in a given ingestible device. Further, variations on the approaches disclosed herein are available so long as they generally comport with the relevant function(s), such as, for example, providing a barrier between a dispensable substance (e.g., drug-containing liquid) retained within the drug housing and an environment external to the ingestible device.

In some embodiments, as depicted in FIGS. 42A and 42B, a nozzle opening 4202 can be covered by a covering including a member 4248, e.g., a patch, film, foil, band, or the like, that forms a barrier between a fluid volume 4210 including a dispensable substance (e.g., drug-containing liquid) retained within the housing and an environment external to the ingestible device. Certain embodiments including a nozzle covering member 4202 formed of a film, foil, patch, band, or the like are discussed, for example, with reference to FIGS. 17, 18, 19A-N of U.S. Ser. No. 62/932,459, and optionally applicable to FIGS. 42A and 42B.

Internal pressure from a pressurized dispensable substance, e.g., during pressurized dispensable substance release, can cause the dispensable substance to puncture the covering member or partially peel/detach the covering member from the outer surface of the ingestible device to allow dispensable substance-containing jets 4262 to form. The covering member 4248 can be composed of various materials, e.g., PE, PP, PVC, cellulose acetate, hot blocking film, and the like. In some embodiments, the covering member can be composed of material that is intended to be insoluble in gastric media but may break down in the small intestine based on pH (e.g., enteric materials) or one or more enzymes, such as, for example, one or more pancreatic enzymes (e.g., lipid-based materials). The covering member 4248 can be composed of material that can hydrate and/or soften when exposed to gastric media without substantially dissolving. The covering member 4248 in this embodiment and others described herein can be composed on a gas-permeable membrane, e.g., which may help with de-gassing during a process of filing the ingestible device. The covering member can be applied, for example, in a post-molding operation, e.g., from a reel.

In some embodiments, the covering member 4248 can be a thin shrink-fit film or adhesive label component applied to an external surface of the ingestible device to cover the nozzle openings. In certain embodiments, the thin film or adhesive label can be a thin barrier, e.g., having a thickness from 20 μm to 40 μm (e.g., from 25 μm to 35 μm, 30 μm).

In some embodiments, the covering member 4248 can be an external band that is applied to cover the nozzle openings 4202. In certain embodiments, the band can be, for example, from 100 μm to 200 μm (e.g., from 125 μm to 175 μm, e.g., 150 μm) thick. Optionally, the band can be composed of materials such as gelatin, HPMC, or other materials that are soluble in gastric media, or can be composed of enteric material.

In some embodiments, the covering member 4248 can be a partial film or covering, e.g., an external cap, that is applied to an outside of the ingestible device to cover the nozzle openings 4202. The cap can be, for example, from 100 μm to 200 μm (e.g., from 125 μm to 175 μm, e.g., 150 μm) thick and/or cover less than the full exterior of the ingestible device.

In some embodiments, as depicted in FIGS. 43A and 43B, a covering member 4348, e.g., patch, film, foil, band, coating, or the like, that forms a barrier between a fluid volume 4310 including a dispensable substance (e.g., a drug-containing liquid) retained within the housing 4304 and an environment external to the ingestible device can be applied and/or affixed to an interior surface 4364 of the ingestible device. In some embodiments, the covering member 4348 is a thin film that is applied to an internal surface of a primary container 4304 of the ingestible device, e.g., during a molding process, to cover the nozzle openings 4302. Internal pressure from a pressurized dispensable substance, e.g., during pressurized dispensable substance release, can cause the dispensable substance to puncture the covering member or partially peel/detach the covering member from the outer surface of the ingestible device to allow dispensable substance-containing jets 4362 to form. The covering member 4348 can be composed of various materials, e.g., COC-based films such as COC+LLDPE laminate, and the like. In some embodiments, the covering member 4348 can be composed of material that is intended to be insoluble in gastric media but may break down in the small intestine based on pH (e.g., enteric materials) and/or or one or more enzymes, such as, for example, one or more pancreatic enzymes (e.g., lipid-based materials). The covering member 4348 can be composed of material that can hydrate and/or soften when exposed to gastric media without substantially dissolving. The covering member 4348 in this embodiment and others described herein can be composed on a gas-permeable membrane, e.g., which may help with de-gassing during a process of filing the ingestible device. The covering member 4348 can be applied, for example, using a molding process, e.g., based on an in-molded label or blow molded onto an interior surface 4364 of the ingestible device. The covering member can be, for example, from 20 μm to 40 μm (e.g., from 25 μm to 35 μm, 30 μm) thick. In some embodiments, the covering member can be applied/affixed without an adhesive, e.g., molded bond.

Figure 44A:
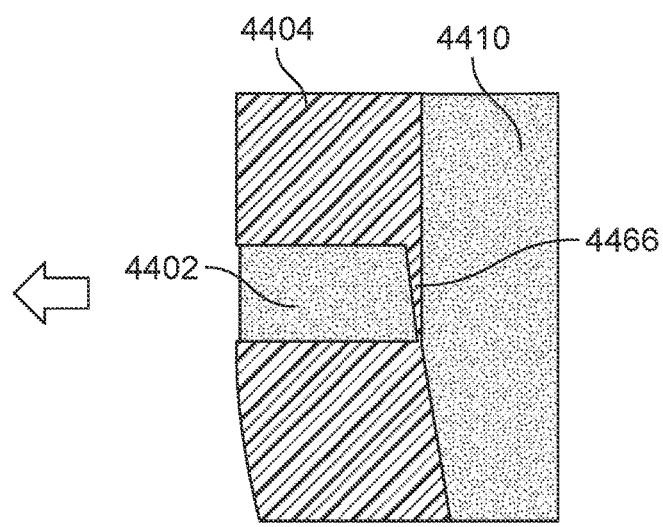
Figure 44B:
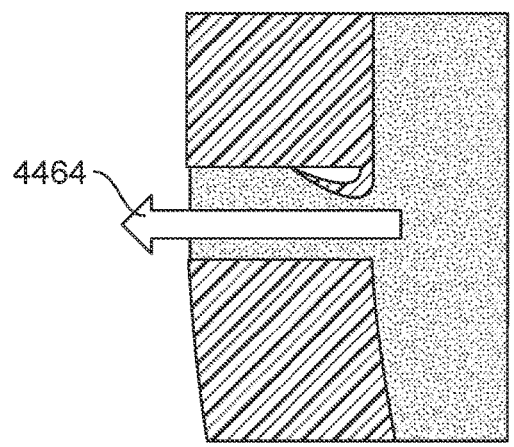

In some embodiments, as depicted in FIGS. 44A and 44B, a covering member can be a feature, such as, for example, a molded feature 4466 formed on (or adjacent to) an interior end of a nozzle opening 4402 and which forms a barrier between a fluid volume 4410 including a dispensable substance (e.g., drug-containing liquid) retained within the housing 4404 and an environment external to the ingestible device. Internal pressure from a pressurized dispensable substance, e.g., during pressurized dispensable substance release, can cause the dispensable substance to puncture the covering member 4466 fully or partially peel/detach the covering member from the outer surface of the ingestible device to allow dispensable substance-containing jets 4464 to form. The covering member can be composed of various materials, e.g., COC-based films such as COC+LLDPE laminate, and the like. In some embodiments, the covering member 4466 can be composed of material that is intended to be insoluble in gastric media but may break down in the small intestine based on pH (e.g., enteric materials) and/or one or more enzymes, such as, for example, one or more pancreatic enzymes (e.g., lipid-based materials). The covering member 4466 can be composed of material that can hydrate and/or soften when exposed to gastric media without substantially dissolving.

Figure 45A:
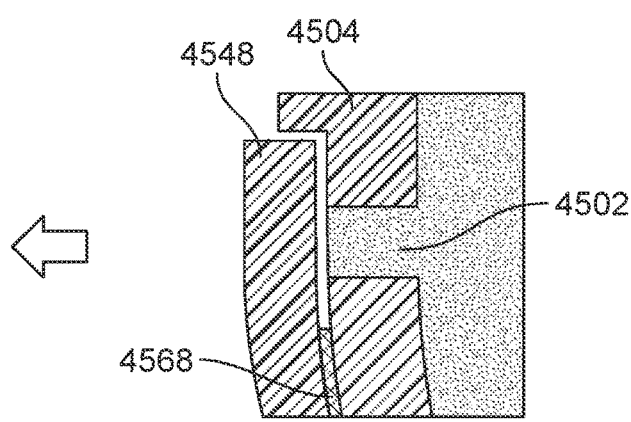
Figure 45B:
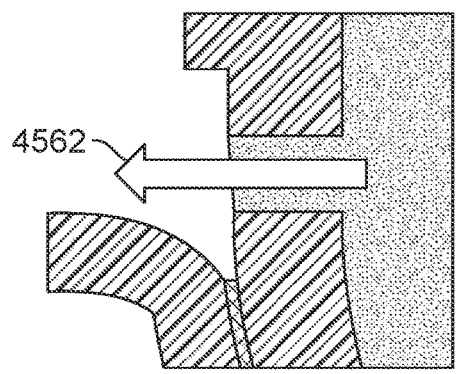

In some embodiments, as depicted in FIGS. 45A and 45B, a covering member 4548 can be a covering member that is tethered 4568 to the ingestible device, e.g., tethered to an outer portion of the housing 4504. The covering member 4548 can be formed of a flexible material, e.g., an elastomer material. Internal pressure from a pressurized dispensable substance, e.g., during pressurized dispensable substance release, can cause the dispensable substance to detach/displace a portion or all of the covering member from the nozzle opening 4502 of the ingestible device to allow dispensable substance-containing jets 4562 to form.

Figures 46A, 46B:
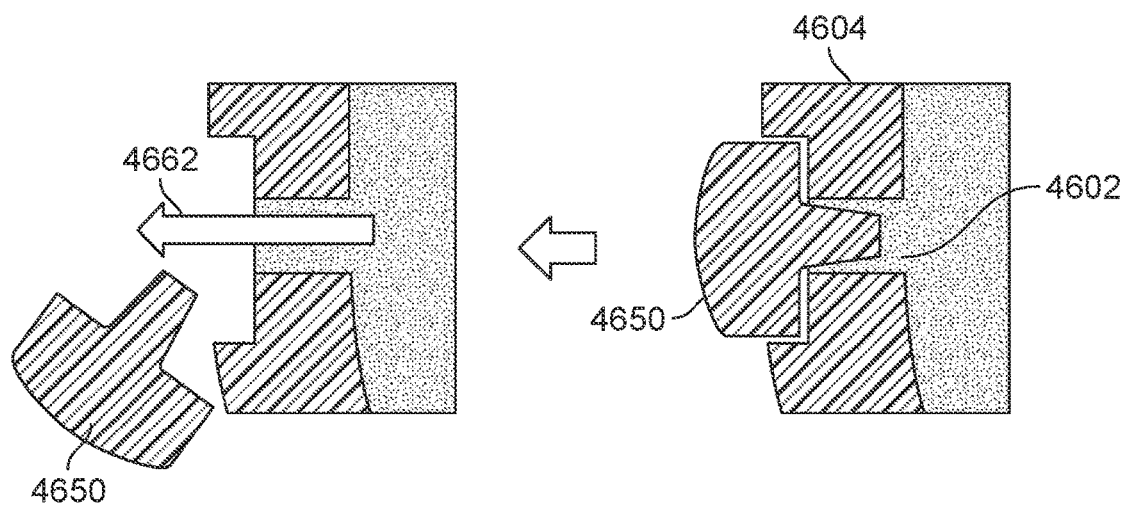

In some embodiments, as depicted in FIGS. 46A and 46B, a covering member can be a plug 4650, e.g., an elastomer plug, that can block the nozzle opening 4602 from an outside surface of the ingestible device. The plug can be tethered to a housing component 4604 of the ingestible device to prevent dispersion of the released plug into the body. The plug 4650 can be formed of biodegradable materials such that the plug can be processed by the body. Internal pressure from a pressurized dispensable substance, e.g., during pressurized dispensable substance release, can cause the dispensable substance to detach/displace the plug 4650 from the nozzle opening of the ingestible device to allow dispensable substance-containing jets 4662 to form.

Figures 47A, 47B, 47C:
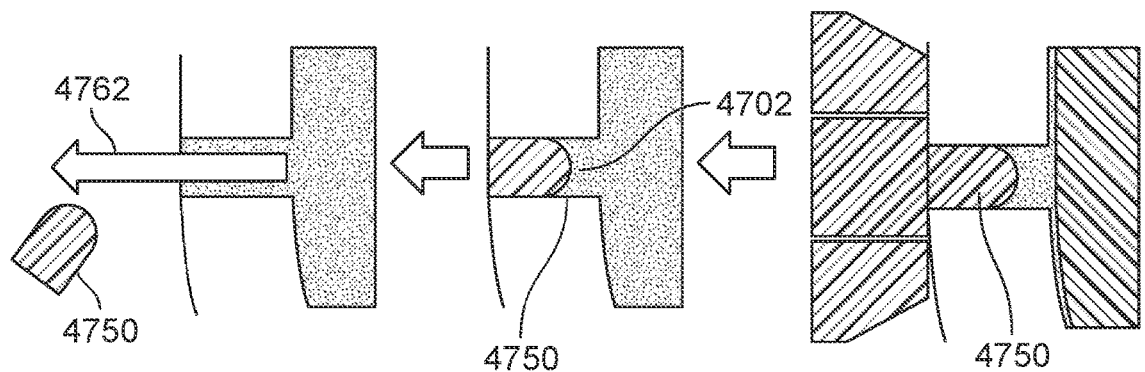

In some embodiments, as depicted in FIGS. 47A-47C, a nozzle opening 4702 can be blocked by a plug 4750 that is formed by applying a liquid-fil gel from an outside apparatus 4770 of the ingestible device, e.g., via a nozzle or rotating mandrel. The liquid-fill gel can harden before a dispensable substance filling process to provide a plug 4750. The gel can be composed of a material that is substantially insoluble in gastric media/dispensable substance, but can break down in small intestine-based pH (e.g., an enteric material) and/or one or more enzymes, such as for example, one or more pancreatic enzymes (e.g., lipid-based material). Internal pressure from a pressurized dispensable substance, e.g., during pressurized dispensable substance release, can cause the dispensable substance to displace the gel from the nozzle opening 4702 of the ingestible device to allow dispensable substance-containing jets 4762 to form.

Figure 48:
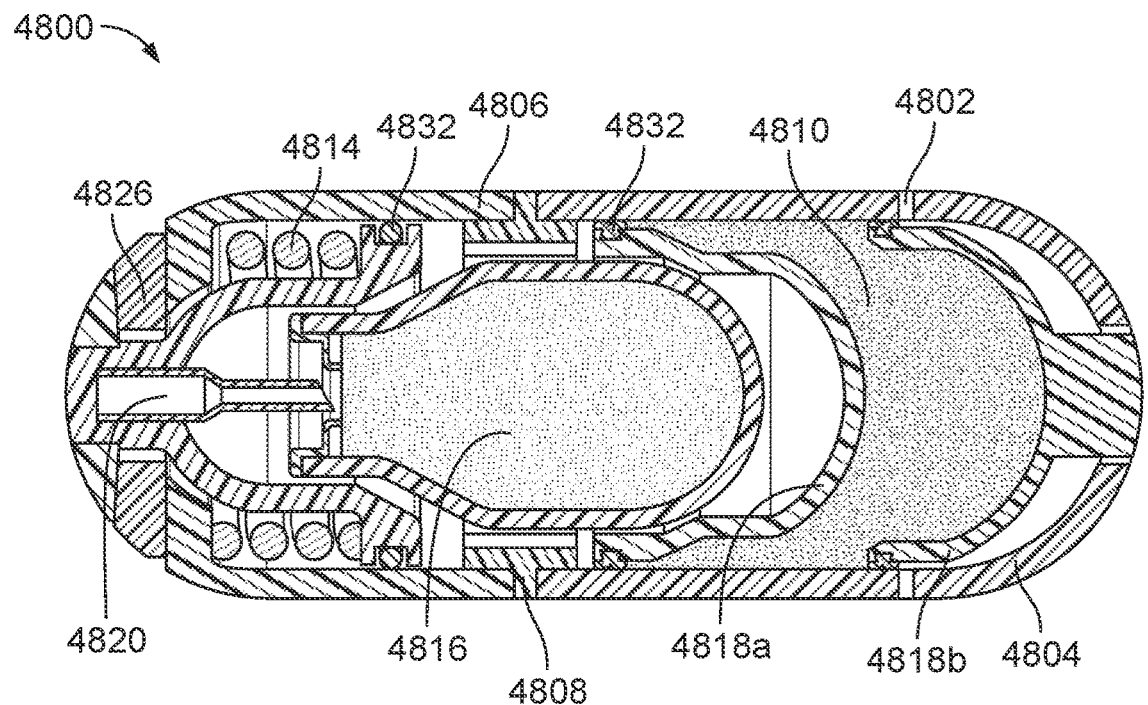
FIGS. 48 and 49 show states of an ingestible device.
Figure 49:
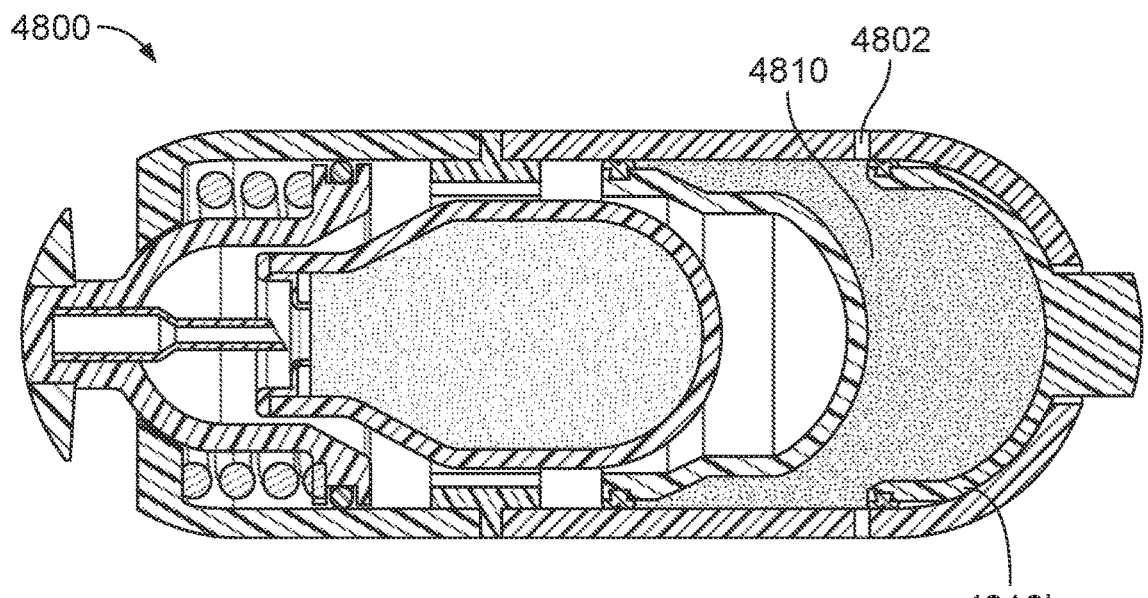

FIGS. 48 and 49 depict an embodiment of an ingestible device 4800 utilizing an internal piston. Ingestible device 4800 contains a dispensable substance that is not under pressure when the subject swallows the ingestible device. In FIG. 48, the nozzles 4802 are depicted as covered, and in FIG. 49 the nozzles 4802 are uncovered. The ingestible device 4800 has housing parts 4804 and 4806 connected by a union ring 4808 and with a fluid volume 4810 containing a dispensable substance, a spring 4814, a gas cylinder 4816, a first piston 4818a and a second piston 4818b, a piercer 4820, and an O-ring 4832. The piercer 4820 is held in place with an enteric trigger 4826 that dissolves and used as the triggering mechanism. When the device 4800 is swallowed by the subject, the enteric trigger 4826 prevents the dispensable substance in fluid volume 4810 from being under pressure by holding the spring 4814 and the piercer 4820 in place. When the device 4800 reaches the appropriate location in the GI tract, the enteric trigger 4826 degrades and/or dissolves (e.g., due to pH, change in pH, presence of certain enzyme, and/or concentration of certain enzyme) such that the spring 4814 forces the piercer 4820 into the gas cylinder 4816, puncturing the gas cylinder 4816 and causing gas at elevated pressure to leave the cylinder 4816. This causes the gas cylinder 4816 to press against the first piston 4818a and apply pressure to the fluid volume 4810. The pressurized fluid volume 4810 applies pressure to the second piston 4818b cause the second piston 4818b to slide and expose the nozzles 4802 such that the dispensable substance is delivered out of the nozzles 4802 in the form of a jet. This can result in trans-epithelial and/or epithelial delivery of the therapeutic agent contained in the dispensable substance.

In some embodiments, a plug/cover can be affixed over a nozzle opening, where the plug/cover is further connected to a piercer component of the ingestible device via connectors and a ring component. FIGS. 50A and 50B depict an embodiment of an ingestible device 5000 including a plug/cover assembly. Ingestible device 5000 includes nozzle opening(s) 5002, a drug container 5004, a drive housing 5006, an o-ring 5032, a retention element 5028, a piercer 5020, a gas seal 5030, a trigger element 5026, a trigger support 5024, a spring 5014, a gas cylinder 5016, a union ring 5008, and a piston 5018. The ingestible device 5000 optionally includes a nozzle cover 5048.

A plug/cover assembly can be a single formed piece, e.g., composed of a plastic material, and fitted externally to the ingestible device such that the plug(s) 5050 cover the nozzle opening(s) 5002 on the ingestible device 5000. The plug/cover assembly can further include connectors 5052 that connect the plug/cover assembly to a ring 5054 component that can be attached to a top of the piercer 5020 and external to a trigger element 5026, such that the ring component 5054 is pulled down by the piercer 5020 when the piercer is released, e.g., after the trigger element 5026 dissolves/degrades, and the plug/cover 5050 are pulled away from the nozzle opening 5002 by the movement of the ring 5054. In some embodiments, the plug/cover 5050 are pulled away from the nozzle opening 5002 by the movement of the ring 5054 in a direction parallel to a length of the ingestible device 5000, e.g., along the outer surface of the ingestible device. In some embodiments, the plug/cover 5050 are pulled away from the nozzle opening 5002 by the movement of the ring 5054 in a direction outwards, e.g., normal, or angled-away, from an outer surface of the ingestible device 5000.

In some embodiments, a band can be affixed over one or more nozzle openings, where the band is further connected to a piercer component of the ingestible device via connectors and a ring component. FIGS. 51A and 51B depicts an embodiment of an ingestible device 5100 including a band assembly. Ingestible device 5100 includes nozzle opening(s) 5102, a drug container 5104, a drive housing 5106, an o-ring 5132, a retention element 5128, a piercer 5120, a gas seal 5130, a trigger element 5126, a trigger support 5124, a spring 5114, a gas cylinder 5116, a union ring 5108, and a piston 5118. The ingestible device 5100 optionally includes a nozzle cover 5148.

A band assembly can be a single formed piece, e.g., composed of a plastic material, including a band 5156, connectors 5152, and a ring component 5154. A band assembly can be instead multi-piece assembly composed of a band 5156 that is placed around the ingestible device 5100 during a filling process and a connector/ring assembly that are affixed to the band 5156 and piercer component 5120. The band assembly can be connected to the piercer 5120 by a ring component 5154 that can be attached to a top of the piercer component and external to a trigger element 5126, such that the ring component 5154 is pulled down by the piercer 5120 when the piercer is released, e.g., after the trigger element 5126 dissolves/degrades, and the band 5156 is pulled away from the nozzle opening(s) 5102, e.g., along a length of the ingestible device 5100, to expose the nozzle opening(s) 5102 by the movement of the ring 5154 prior or simultaneously to the delivery of the dispensable substance via the nozzle openings 5102.

In some embodiments, as depicted in FIGS. 52A-52D, an ingestible device 5200 includes a sliding cover 5248. The sliding cover 5248 can be a single formed piece, e.g., a sleeve composed of a plastic material, and fitted externally to the ingestible device 5200 such that a portion of the sliding cover covers the nozzle opening(s) 5202 on the ingestible device 5200. The sliding cover 5248 can be attached to a top of the piercer component 5220 and external to a trigger element 5226, such that the sliding cover 5248 is pulled down by the piercer 5220 when the piercer is released, e.g., after the trigger element 5226 dissolves/ degrades, and the sliding cover 5248 is pulled away from the nozzle opening 5202 by the movement of the piercer 5220. The sliding cover 5248 can be pulled away from the nozzle openings 5202 by the movement of the sliding cover in a direction parallel to a length of the ingestible device 5200, e.g., along the outer surface of the ingestible device, prior or simultaneously to the delivery of the dispensable substance within fluid volume 5210 via the nozzle openings 5202.

Figure 53A:
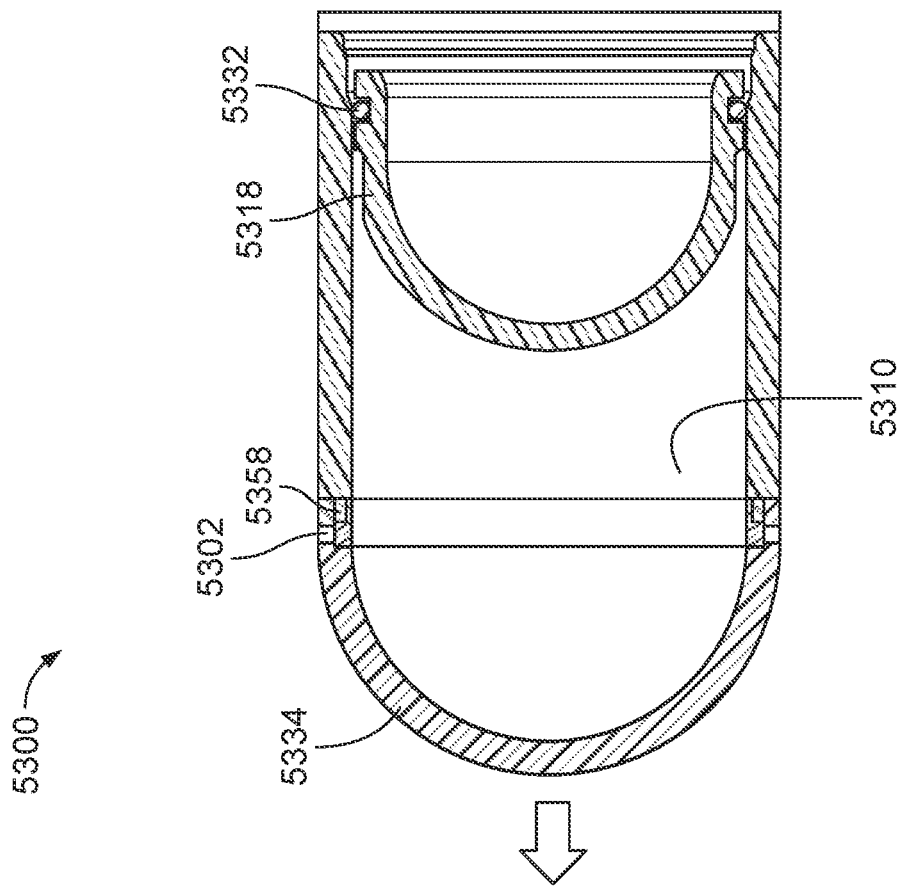
FIGS. 53A and 53B show views of a portion of an ingestible device.
Figure 53B:
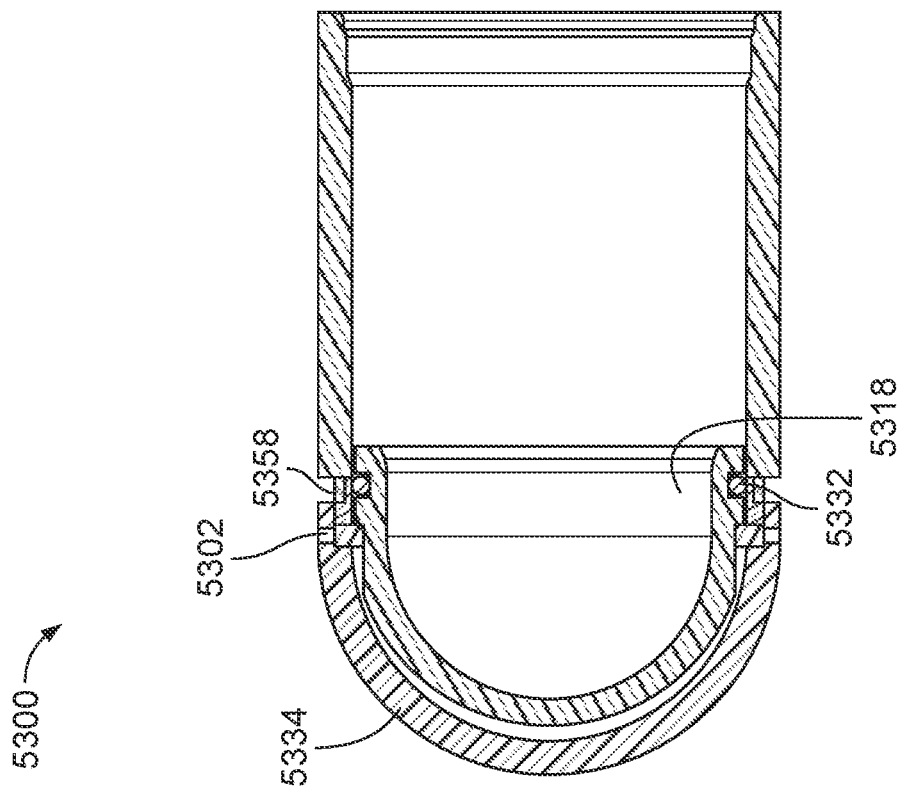

In some embodiments, as depicted in a partial rendering of an ingestible device 5300 in FIGS. 53A and 53B, ingestible device 5300 includes a cap 5334 affixed over one end of an ingestible device 5300 and partially enclosing a volume 5310. A seal 5358, e.g., an over-molded elastomer based seal, can be utilized to seal a dispensable substance within the volume 5310 and prevent the dispensing of the dispensable substance while the cap 5334 is affixed over the end of the ingestible device 5300. The seal 5358 can additionally prevent movement of the cap 5334 prior to a delivery of the dispensable substance. When the device 5300 is swallowed by the subject, the enteric trigger prevents the dispensable substance in the fluid volume from being under pressure by holding the spring and the piercer in place. When the device reaches the appropriate location in the GI tract, the enteric trigger degrades and/or dissolves (e.g., due to pH, change in pH, presence of certain enzyme, and/or concentration of certain enzyme) such that the spring forces the piercer into the gas cylinder, puncturing the gas cylinder and causing gas at elevated pressure to leave the cylinder. This causes the gas cylinder to press against the piston and apply pressure to the fluid volume. The pressurized fluid volume applies pressure to the cap and causes the cap to slide open and expose the nozzles such that the dispensable substance is delivered out of the nozzles in the form of a jet. This can result in trans-epithelial and/or epithelial delivery of the therapeutic agent contained in the dispensable substance.

In some embodiments, as depicted in a partial rendering of an ingestible device in FIGS. 54A and 54B, an ingestible device 5400 includes an inflated membrane volume 5460, e.g., a gas balloon or similar, located within the volume 5410 including a dispensable substance and arranged to seal the nozzle openings 5402 while the inflated volume 5460 is inflated. In some embodiments, the inflated membrane volume 5460 may conform to one or more contours, e.g., an inner curvature, of the ingestible device housing 5404. The inflated membrane volume 5460 can be composed of a balloon and/or soft material, e.g., a low durometer elastomer. When the device 5400 is swallowed by the subject, the enteric trigger prevents the dispensable substance in the fluid volume from being under pressure by holding the spring and the piercer in place. When the device reaches the appropriate location in the GI tract, the enteric trigger degrades and/or dissolves (e.g., due to pH, change in pH, presence of certain enzyme, and/or concentration of certain enzyme) such that the spring forces the piercer into the gas cylinder, puncturing the gas cylinder and causing gas at elevated pressure to leave the cylinder. This causes the gas cylinder to press against the piston and apply pressure to the fluid volume. The pressurized fluid volume applies pressure to the inflated membrane volume 5460 and causes the inflated membrane volume to deflate or otherwise reposition to expose the nozzles openings 5402 such that the dispensable substance is delivered out of the nozzles in the form of a jet. This can result in trans-epithelial and/or epithelial delivery of the therapeutic agent contained in the dispensable substance.

In some embodiments, as depicted in a partial rendering of an ingestible device in FIG. 55, the ingestible device 5500 does not include a covering member. For example, the nozzle openings 5502 may be exposed such that when the ingestible device 5500 is swallowed/inserted, an air gap in the nozzle openings 5502 and/or surface tension effects may prevent or deter gastric media from damaging the internal components or dispensable substance (e.g., drug-containing liquid) within the ingestible device. In other words, a differential force may be generated by the movement of the ingestible device within the gastric region between external intestinal forces/pressure and internal forces of the dispensable substance within the volume of the ingestible device. For example, a surface tension of the dispensable substance within a volume 5510 of the ingestible device can be higher than a surrounding environment, e.g., external intestinal forces/pressure within a gastric region in the body, such that a substantial percentage of the dispensable substance is retained within the volume of the ingestible device until a point of delivery of the dispensable substance, e.g., until piston 5518 applies pressure to the volume 5510 to force the dispensable substance retained within the volume 5510 out of the nozzle opening(s) 5502. In one example, at least 75% of the dispensable substance (e.g., at least 85%, at least 95% of the dispensable substance) is retained within the volume of the ingestible device until a point of delivery of the dispensable substance within a gastric region in the body.

Device for Epithelial Delivery

Generally, epithelial delivery can be achieved at any desired location within the GI tract of a subject. In some embodiments, epithelial delivery is achieved in the small intestine of the subject, such as, for example, in the duodenum, the jejunum and/or the ileum. In certain embodiments, epithelial delivery is achieved in the large intestine of the subject, such as, for example, the cecum or the colon.

In some embodiments, epithelial delivery can be achieved using any one of the ingestible devices described above with respect to epithelial delivery. In such embodiments, the relevant parameters are usually modified accordingly. Typically, this modification involves modifying the values for the relevant parameters. Examples are provided in the following paragraphs.

In general, an ingestible device for epithelial delivery is configured to deliver a jet of the dispensable substance having a peak jet power of at least about 1 mW (e.g., at least about 1.5 mW, at least about 2 mW, at least about 2.5 mW) and/or at most about 4 mW (e.g., at most about 3.5 mW, at most about 3 mW). In some embodiments, an ingestible device for epithelial delivery is configured to deliver a jet of the dispensable substance having a peak jet power of from about 1 mW to about 4 mW (e.g., from about 1 mW to about 3.5 mW, from about 2 mW to about 3 mW).

Generally, an ingestible device for epithelial delivery is configured to deliver a jet of the dispensable substance having a peak jet pressure of about 2 psig (e.g., about 2.5 psig, about 3 psig, about 3.5 psig, about 4 psig) and/or at most about 10 psig (e.g., at most about 8 psig, at most about 6 psig, at most about 5 psig). In some embodiments, an ingestible device for epithelial delivery is configured to deliver a jet of the dispensable substance having a peak jet pressure of from about 2 psig to about 10 psig (e.g., from about 2.5 psig to about 8 psig, from about 3 psig to about 6 psig, from about 3.5 psig to about 5 psig, from about 4 psig to about 5 psig).

In general, an ingestible device for epithelial delivery is configured to deliver a jet of the dispensable substance having a peak jet force of at least about 0.5 mN (e.g., at least about 0.6 mN, at least about 0.7 mN, at least about 0.8 mN, at least about 0.9 mN) and/or at most about 2 mN (e.g., at most about 1.8 mN, at most about 1.6 mN, at most about 1.4 mN, at most about 1.2 mN). In some embodiments, an ingestible device for epithelial delivery is configured to deliver a jet of the dispensable substance having a peak jet force of from about 0.5 mN to about 2 mN (e.g., from about 0.6 mN to about 1.8 mN, from about 0.7 mN to about 1.6 mN, from about 0.8 mN to about 1.4 mN, from about 0.9 mN to about 1.2 mN).

In general, an ingestible device for epithelial delivery is configured to deliver a jet of the dispensable substance having a minimum jet velocity of from at least about 2 m/s (e.g., at least about 3 m/s, at least about 4 m/s, at least about 5 m/s) and/or at most about m/s (e.g., at most about 15 m/s, at most about 10 m/s, at most about 8 m/s). In some embodiments, an ingestible device for epithelial delivery is configured to deliver a jet of the dispensable substance having a peak jet velocity of from about 2 m/s to about 20 m/s (e.g., from about 3 m/s to about 15 m/s, from about 4 m/s to about 10 m/s, from about 5 m/s to about 8 m/s).

In general, an ingestible device for epithelial delivery is configured to provide an internal pressure of from about 3.62 psig to about 21.76 psig (e.g., from about 3.62 psig to about 18.13 psig, from about 3.62 psig to about 14.50 psig, from about 3.62 psig to about 10.88 psig, from about 3.62 psig to about 7.25 psig, from about 4.35 psig to about 7.25 psig, about 4.35 psig).

In general, an ingestible device for epithelial delivery is configured to provide a nozzle pressure of from about 3.62 psig to about 21.76 psig (e.g., from about 3.62 psig to about 18.13 psig, from about 3.62 psig to about 14.50 psig, from about 3.62 psig to about 10.88 psig, from about 3.62 psig to about 7.25 psig, from about 4.35 psig to about 7.25 psig, about 4.35 psig).

Generally, an ingestible device for epithelial delivery is configured to contain a dispensable substance at a peak fluid pressure from 3.62 psig to about 21.76 psig (e.g., from about 3.62 psig to about 18.13 psig, from about 3.62 psig to about 14.50 psig, from about 3.62 psig to about 10.88 psig, from about 3.62 psig to about 7.25 psig, from about 4.35 psig to about 7.25 psig, about 4.35 psig).

In general, an ingestible device for epithelial delivery contains the dispensable substance at an initial fluid volume of at least about 50 microliters (μL) (e.g., at least about 100 μL, at least about 150 μL, at least about 200 μL, at least about 250 μL) and/or at most about 800 μL, (e.g., at most about 700 μL, at most about 600 μL, at most about 500 μL, at most about 400 μL). In some embodiments, an ingestible device for epithelial delivery contains the dispensable substance at an initial fluid volume of from about 50 μL to about 800 μL (e.g., from about 100 μL to about 600 μL, from about 200 μL to about 400 μL). Generally, an ingestible device for epithelial delivery is configured to provide a delivered fluid volume of dispensable substance of at least about 50 microliters (μL) (e.g., at least about 100 μL, at least about 150 μL, at least about 200 μL, at least about 250 μL) and/or at most about 800 μL (e.g., at most about 700 μL, at most about 600 μL, at most about 500 μL, at most about 400 μL). In some embodiments, an ingestible device for epithelial delivery has a fluid volume of dispensable substance of from about 50 μL to about 800 μL (e.g., from about 100 μL to about 600 μL, from about 200 μL to about 400 μL).

In general, an ingestible device for epithelial delivery contains the dispensable substance at a final fluid volume of at most about 100 microliters (μL) (e.g., at least about 90 μL, at least about 80 μL, at least about 70 μL, at least about 60 μL) and/or at most least 5 μL (e.g., at most about 10 μL, at most about 20 μL, at most about 30 μL, at most about 40 μL). In some embodiments, an ingestible device for epithelial delivery contains the dispensable substance at a fluid volume of from about 30 μL, to about 70 μL (e.g., from about 40 μL to about 60 μL, from about 45 μL to about 55 μL).

In general, an ingestible device for epithelial delivery is configured to directly deliver at least about 50% (e.g., at least about 60%, at least about 70%, at least about 80%, at least about 90%, at least about 95%, at least about 97%) of the dispensable substance from the ingestible device to the mucus.

In general, an ingestible device for epithelial delivery is configured to provide a delivered fluid volume per opening for delivery of dispensable substance (e.g., per nozzle) of at least about 20 microliters (μL) (e.g., at least about 25 μL, at least about μL, at least about 50 μL, at least about 75 μL, at least about 100 μL) and/or at most about 800 μL (e.g., at most about 700 μL, at most about 600 μL, at most about 500 μL, at most about 400 μL, at most about 300 μL). In some embodiments, an ingestible device for epithelial delivery is configured to provide a delivered fluid volume per opening for delivery of dispensable substance (e.g., per nozzle) of from about 25 μL to about 400 μL (e.g., from about 25 μL to about 300 μL, from about 100 μL to about 300 μL).

In certain embodiments, an ingestible device for epithelial delivery is configured as disclosed in the above-discussion regarding trans-epithelial delivery, but with a relatively large number of nozzles and a relatively large nozzle diameter such that performance properties for epithelial delivery (discussed above) can be achieved. As an example, in some embodiments, an ingestible device for epithelial delivery has at least 25 nozzles (e.g., at least 30 nozzles, at least 40 nozzles, 50 nozzles). In some embodiments, such an ingestible device for epithelial delivery has 30 nozzles, 31 nozzles, 32 nozzles, 33 nozzles, 34 nozzles, 35 nozzles, 36 nozzles, 37 nozzles, 38 nozzles or 40 nozzles. Each nozzle can have a diameter, for example, of at least about 1 mm (e.g., at least about 1.5 mm, at least about 2 mm) and/or at most about 3 mm (e.g., at most about 2.5 mm). For example, in such an ingestible device, each nozzle can have a diameter of from about 1 mm to about 3 mm (e.g., from about 1 mm to about 2.5 mm, from about 2 to about 2.5 mm).

Device for Topical Delivery

Generally, topical delivery can be achieved at any desired location within the GI tract of a subject. In some embodiments, topical delivery is achieved in the small intestine of the subject, such as, for example, in the duodenum, the jejunum and/or the ileum. In certain embodiments, topical delivery is achieved in the large intestine of the subject, such as, for example, the cecum or the colon.

In general, an ingestible device for topical delivery is configured to provide an internal pressure of at least about 5 psig (e.g., at least about 8 psig, at least about 10 psig) and/or at most about 50 psig (e.g., at most about 40 psig, at most about 30 psig, at most about 20 psig, at most about 15 psig). In certain embodiments, an ingestible device for topical delivery is configured to provide an internal pressure of from about 5 psig to about 50 psig (e.g., from about 5 psig to about 30 psig, from about 5 psig to about 20 psig, from about 8 psig to about 20 psig, from about 10 psig to about 15 psig).

Generally, an ingestible device for topical delivery is configured to contain a dispensable substance at a peak fluid pressure of at least about 5 psig (e.g., at least about 8 psig, at least about 10 psig) and/or at most about 50 psig (e.g., at most about 40 psig, at most about 30 psig, at most about 20 psig, at most about 15 psig). In certain embodiments, an ingestible device for topical delivery is configured to deliver a jet of the dispensable substance having a peak fluid pressure of from about 5 psig to about 50 psig (e.g., from about 5 psig to about 30 psig, from about 5 psig to about 20 psig, from about 8 psig to about 20 psig, from about 10 psig to about 15 psig).

In general, an ingestible device for topical delivery is configured to deliver at least about 50% (e.g., at least about 60%, at least about 70%, at least about 80%, at least about 90%, at least about 95%, at least about 97%) of the dispensable substance from the ingestible device into the lumen of the GI tract.

In general, an ingestible device for topical delivery contains the dispensable substance at an initial fluid volume of at least about 50 microliters (µL) (e.g., at least about 100 µL, at least about 150 µL, at least about 200 µL, at least about 250 µL) and/or at most about 800 µL, (e.g., at most about 700 µL, at most about 600 µL, at most about 500 µL, at most about 400 µL). In some embodiments, an ingestible device for topical delivery contains the dispensable substance at an initial fluid volume of from about 50 µL to about 800 µL, (e.g., from about 100 µL to about 600 µL, from about 200 µL to about 400 µL).

In general, an ingestible device for topical delivery contains the dispensable substance at a final fluid volume of at most about 100 microliters (µL) (e.g., at least about 90 µL, at least about 80 µL, at least about 70 µL, at least about 60 µL) and/or at most least 5 µL (e.g., at most about 10 µL, at most about 20 µL, at most about 30 µL, at most about 40 µL). In some embodiments, an ingestible device for topical delivery contains the dispensable substance at a fluid volume of from about 30 µL, to about 70 µL (e.g., from about 40 µL to about 60 µL, from about 45 µL to about 55 µL).

In certain embodiments, an ingestible device for topical delivery is configured as disclosed in the above-discussion regarding trans-epithelial delivery, but with a relatively large number of nozzles and a relatively large nozzle diameter such that performance properties for topical delivery (discussed above) can be achieved. As an example, in some embodiments, an ingestible device for topical delivery has at least 25 nozzles (e.g., at least nozzles, at least 40 nozzles, 50 nozzles). In some embodiments, such an ingestible device for topical delivery has 30 nozzles, 31 nozzles, 32 nozzles, 33 nozzles, 34 nozzles, nozzles, 36 nozzles, 37 nozzles, 38 nozzles or 40 nozzles. Each nozzle can have a diameter, for example, of at least about 1 mm (e.g., at least about 1.5 mm, at least about 2 mm) and/or at most about 3 mm (e.g., at most about 2.5 mm). For example, in such an ingestible device, each nozzle can have a diameter of from about 1 mm to about 3 mm (e.g., from about 1 mm to about 2.5 mm, from about 2 to 2.5 mm).

Delivery of Therapeutics

Provided herein are ingestible devices and methods that deliver therapeutic agents into the intestinal lumen, mucus, mucosa and/or submucosa by topical, epithelial or trans-epithelial administration to the GI tract of a subject. Current methods of administration for most large molecule therapeutic agents or small molecule therapeutic agents with poor oral bioavailability are subcutaneous (SC), intramuscular (IM), or bolus intravenous (IV) injection targeting the systemic circulation. The devices and methods described herein provide an alternative route of administration to current injectable medications, which can lead to greater convenience and compliance since they minimize or avoid the logistical challenges, patient compliance and adherence challenges, pain, and discomfort associated with traditional routes of administration.

In some embodiments of the devices or methods described herein, the therapeutic is released at a location in the small intestine of the subject. In some embodiments of any of the devices or methods described herein, the location is in the proximal portion of the small intestine (e.g., duodenum or jejunum). In some embodiments of any of the devices or methods described herein, the location is in the distal portion of the small intestine (e.g., jejunum or ileum). In some embodiments of the devices or methods described herein, the therapeutic is released at a location in the large intestine of the subject. In some embodiments of any of the devices or methods described herein, the location is in the proximal portion of the large intestine (e.g., cecum, ascending colon, or transverse colon). In some embodiments of any of the devices or methods described herein, the location is in the distal portion of the large intestine (e.g., transverse colon or descending colon).

Also, by providing a higher concentration of therapeutic in GI tissue, the devices and methods described herein are particularly well-suited for treatment of diseases and conditions of the endoderm, including the liver.

In some embodiments of any of the devices or methods described herein, the releasing of the therapeutic is triggered by one or more of: a pH in the jejunum of about 6.1 to about 7.2, a pH in the mid small bowel of about 7.0 to about 7.8, a pH in the ileum of about 7.0 to about 8.0, a pH in the right colon of about 5.7 to about 7.0, a pH in the mid colon of about 5.7 to about 7.4, or a pH in the left colon of about 6.3 to about 7.7, such as about 7.0.

In some embodiments of any of the devices or methods described herein, the releasing of the therapeutic is triggered by degradation of a release component located in the device. In some embodiments of any of the devices or methods described herein, the releasing of the therapeutic is dependent on enzymatic activity at or in the vicinity of the location. In some embodiments of any of the devices or methods described herein, the composition includes a plurality of electrodes including a coating, and releasing the therapeutic is triggered by an electric signal by the electrodes resulting from the interaction of the coating with an intended site of release of the therapeutic. In some embodiments of any of the devices or methods described herein, the release of the therapeutic is triggered by a remote electromagnetic signal. In some embodiments of any of the devices or methods described herein, the release of the therapeutic is triggered by generation in the composition of a gas in an amount sufficient to expel the therapeutic. In some embodiments of any of the devices or methods described herein, the release of the therapeutic is triggered by an electromagnetic signal generated within the device according to a predetermined drug release profile.

Therapeutics for Delivery

Therapeutics suitable for use with the devices and methods described herein include both small molecules and large molecules. In some embodiments, the therapeutic agent is a large molecule. Examples of large molecules include, but are not limited to, biologic drugs, proteins including fusion proteins, peptides including cyclic peptides, protein-drug conjugates, cells including stem cells, and nucleic acids such as inhibitory nucleic acids, antisense nucleic acids, siRNA, ribozymes, and the like. In some embodiments, the therapeutic agent is a large molecule with a molecular weight of at least about 60 kilodaltons (kDa), or about 60 kDa to about 200 kDa, about 60 kDa to about 175 kDa, or about 60 kDa to about 150 kDa.

In some other embodiments, the therapeutic agent has a molecular weight of at least about 20 kDa, at least about 30 kDa, at least about 40 kDa, or at least about 50 kDa, or from about 20 kDa to about 200 kDa, about 20 kDa to about 175 kDa or about 20 kDa to about 150 kDa.

In some embodiments, the therapeutic agent is a molecule, e.g., a protein or peptide, with a molecular weight of greater than about 1.5 kDa and less than about 20 kDa, less than about 30 kDa, less than about 40 kDa, less than about 50 kDa or less than about 60 kDa.

In some other embodiments, the therapeutic agent has a molecular weight of from about 5 kDa to about 10 kDa, 20 kDa, 30 kDa, 40 kDa or 50 kDa. In some embodiments, the therapeutic agent is a molecule with a molecular weight of about 5 kDa to about 10 kDa, such as about 6 kDa. In some embodiments, the therapeutic agent is a protein or peptide. In some embodiments, the therapeutic agent is a protein-drug conjugate. In some embodiments, the therapeutic agent is insulin.

In some embodiments, the therapeutic agent is a small molecule. A "small molecule," as used herein, is a compound, typically an organic compound, having a molecular weight of about 50 Da to about 1500 Da, about 60 Da to about 1500 Da, about 500 Da to about 1000 Da, or no more than about 1500 Da, such as about 1000 Da, about 750 Da, or about 500 Da. In some embodiments, the therapeutic agent is a small molecule with a molecular weight of about 50 Da to about 1500 Da. In some embodiments, the therapeutic agent is a small molecule with a molecular weight of about 150 Da to about 1500 Da.

In some embodiments, the therapeutic agent is a non-small molecule. Exemplary non-small molecule therapeutic agents for use in the devices and methods provided herein include, but are not limited to, abatacept, teriparatide, eculizumab, emicizumab, pegfilgrastim, semaglutide, dulaglutide, sargramostim, ustekinumab, secukinumab, tocilizumab, vedolizumab, natalizumab, interferon beta-1a, denosumab, alirocumab, evolocumab, adalimumab, etanercept, golimumab, trastuzumab, pembrolizumab, pertuzumab, ARO-HBV, glatiramer acetate Copaxone®, LY-3321367, cetuximab (Erbitux®), ipilimumab (Yervoy®), daratumumab (Darzalex®), albumin-bound paclitaxel (Abraxane®), tanezumab, LY-2510924, LCAR-B38M, PF-004518600, TAK-079, PF-06730512, LY-3076226, NOV-13, FAZ-053, LY-3375880, PF-06823859, CNGB3 gene therapy, mosunetuzumab, RG-6147, scAAV/JeT-GAN-based gene therapy, ranibizumab, cofetuzumab pelidotin, SHR-A1201, TAK-671, A-004 (AAV2/5-hRKp.RPGR) gene therapy, NG-HER2 antibody drug conjugate, TAK-164, RG-7861, JNJ-61186372, PF-05206388, NJH-395, PF-05230907, BIM-059, PF-06688992, ianalumab, TAK-573. PF-06755347, CD200R mAb agonist, cetrelimab, ligelizumab, PF-06801591, JNJ-64407564, polatuzumab vedotin, PF-06817024, NOV-12, BIIB-054, CTL-119, JNJ-61178104, spartalizumab, RNA CART123, LY-3300054, PD-1 mAb agonist, CART-EGFRvIII, NOV-10, TQJ-230, PF-06863135, PCA-062, JNJ-64041757, CNTO-2476, tiragolumab, PF-06946860, elgemtumab, LY-3415244, LKA-651, RG-6109, ECF-843, JNJ-61610588, AAV8-RLBP1 gene therapy, LAG-525, MOR-106, BTLA agonist mAb, AMV-564, JNJ-64041809, MBG-453, CGF-166, brolucizumab, NOV-9, CJM-112, tesidolumab, NIZ-985, MCS-110, BHQ-880, NOV-8, CLR-325, XmAb-13676, huMeso-CART, NZV-930, CGM-097, NOV-7, and certolizumab pegol; and biosimilars thereof; and glycosylation variants thereof. Additional exemplary drugs for delivery using any of the devices or methods described herein include those listed in Table 2.

TABLE 2

| Brand Name (Drug) | Potential Dose | Drug concentration | Drug Volume and # capsules needed per equivalent dose[a] | Storage temperature |
|---|---|---|---|---|
| Humira® (adalimumab) | 40, 80, 160 mg | ~40 mg/ 0.4 mL | 0.8-3.2 mL 2-8 Capsules | 2-8° C. 25° C. for up to 14 days |
| Remicade® (infliximab) | 400 mg | Diluted to ~4 mg/mL | NA | 2-8° C. 30° C. for up to 12 months |
| Cimzia® (certolizumab-pegol) | 400 mg | ~200 mg/mL | 4 mL 10 Capsules | 2-8° C. 2 hrs at room temp |
| Embrel® (etanerecpt) | 50 mg | ~50 mg/mL | 2 mL 5 Capsules | 2-8° C. 25° C. for 14 days |
| Lantis® (insulin), Novalog® (insulin) | sq | 1 unit~0.0347 mg, density of crystal is close to 1 g/cm³ | | 2-8° C. 30° C. for up to 28 days |
| Victoza® (liraglutide) | 1.2 mg | ~6 mg/mL | 0.4 mL 1 Capsules | 2-8° C. 30° C. for up to 30 days |
| Bydureon® (exenatide) | 2 mg | ~2 mg/ 0.6 mL | 1.2 mL 3 Capsules | 2-8° C. 30° C. for up to 28 days |
| (GHIH) (somatostatin) | 0.48-2 mg | | | |
| Sandosatin® (Octreotide) | 100-500 mcg | ~500 mcg/mL | 0.4-2 mL 1-5 Capsules | 2-8° C. 30° C. for up to 14 days |
| Avonex® (interferon beta-1a) | 30 mcg | ~30 mcg/ 0.5 mL | 1 mL 2.5 Capsules | 2-8° C. 30° C. for up to 30 days |
| Tysabri® (natalizumab) | 300 mg | ~2.69 mg/mL | NA | 2-8° C. |
| Avastin® (bevacizumab) | 5 mg | IFU: Do not administer as bolus, IV | NA | 2-8° C. |
| Entyvio® (Vedolizumab) | 300 mg | IFU: Do not administer as bolus, IV | NA | |
| Fragmin® (Dalteparin) | 2500-18000 IU | 5000 IU | 0.6 mL 1.5 Capsules | Room Temp |
| Rocephin® (Ceftriaxone) (or other antimicrobials) | 1 g | ~350 mg/mL | | |
| Interferon alfa-2b | 3-30 million IU | ~50 million 1 U/mL | 0.12-1.2 mL < 1-3 Capsules | 2-8° C., up to seven days at room temp |
| Natpara® (Parathyroid Hormone) (PTH) | 50-100 mcg | ~1 mg/mL | <<1 Capsules | 2-8° C. |
| Genotropin® Human Growth Hormone (HGH) | 0.2-2 mg | ~5.3 mg/mL | <1 Capsule | 2-8° C. 4 weeks after reconstitution |

[a]Number of capsules assumes a drug reservoir of about 400 microliters
sq: subcutaneous
IFU: Instructions for use
IU: International Unit In some embodiments, the therapeutic agent is a small molecule. Exemplary small molecule therapeutic agents for use in the devices and methods provided herein include, but are not limited to, glasdegib maleate, ibuprofen+paracetamol combination, PF-06873600, LY-3200882, PF-06952229, PF-06821497, LY-3405105, LY-3372689, LY-3023414, enzastaurin, SY-008, taladegib, crenigacestat, merestinib, LY-3214996, ralimetinib, galunisertib, TBA-7371, LY-3381916, LY-2874455, erdafitinib, pimodivir, aprocitentan, JNJ-56136379, BMS-986177, lazertinib, JNJ-64619178, JNJ-55308942, AL-034, JNJ-67670187, JNJ-64264681, JNJ-64417184, JNJ-3534, JNJ-64991524, JNJ-64140284, pimodivir+oseltamivir combination, JNJ-61803534, ipatasertib dihydrochloride, fenebrutinib, RG-6171, belvarafenib, RG-6174, alpelisib, asciminib, leniolisib, clofazimine, siremadlin, capmatinib, PBF-509, LNP-023, UNR-844, ganaplacide, cipargamin, adriforant, LYS-006, QCC-374, MAK-683, LCL-161, BLZ-945, LOU-064, VPM-087, WNT-974, totrombopag, hydroxychloroquine+trametinib combination, LTT-462, NOV-11, LSZ-102, allosteric inhibitors of SHP2 phosphatase, mocravimod dihydrochloride, BCL-201, mivavotinib, DSM-265, sapanisertib, TAK-931, TAK-906, alisertib, TAK-580, pediatric formulation of azilsartan, TAK-418, and vonoprazan fumarate+aspirin combination.

In some embodiments, the therapeutic agent is a monoclonal antibody (mAb). In some embodiments, the mAb is an anti-interleukin-17A (anti-IL-17A) mAb. In some embodiments, the mAb is an anti-interleukin-17A (anti-IL-17A) mAb that can be used to treat inflammatory conditions and/or autoimmune diseases, including, but not limited to, rheumatoid arthritis, plaque psoriasis, active psoriatic arthritis, and ankylosing spondylitis. An exemplary anti-IL-17A mAb is ixekizumab (Taltz®). See, e.g., Genovese et al., Arthritis & Rheumatology, 66.7:1693-1704 (2014). In some embodiments, the mAb is a selective mAb against antiopoietin 2 (Ang2). An exemplary mAb selective against Ang2 is LY3127804.

Therapeutics for Growth Disorders

In some embodiments, the therapeutic suitable for use with the devices and methods described herein is a therapeutic for treating a growth disorder. In some embodiments, the growth disorder is a growth hormone deficiency or disorder (GHD). In some embodiments, the GHD is acquired, congenital or idiopathic; or a combination thereof. In some embodiments, the GHD is a result of trauma, infection, radiation therapy or tumor growth. In some embodiments, the GHD is adult-onset GHD.

Exemplary therapeutics for treating growth disorders include, but are not limited to, growth hormones, including, but not limited to, somatropin, lonapegsomatropin, YPEG-somatropin, efpegsomatropin, a human growth hormone (HGH), a recombinant HGH (rHGH), a PEGylated rHGH, somapacitan, somatrogon, genotropin, humatrope, norditropin, nutropin, omnitrope, serostim, TJ-101, ALT-P1, and JR-142; and biosimilars and follow-on biologics thereof. In some embodiments, the growth hormone is an rHGH. Examples of suitable rHGHs include, but are not limited to, recombinant somatropin, e.g., genotropin, humatrope, norditropin, nutropin, omnitrope, serostim, Zomacton®, and Saizen®.

In some embodiments, the therapeutic suitable use with the devices and methods described herein for treating a growth disorder is somatropin or biosimilar or follow-on biologic thereof.

In some embodiments, the therapeutic suitable use with the devices and methods described herein for treating a growth disorder is somapacitan or biosimilar or follow-on biologic thereof.

Therapeutics for Fibrosis

In some embodiments, the therapeutic suitable for use with the devices and methods described herein is a therapeutic for treating fibrosis. In some embodiments, the therapeutic is a biological therapeutic. In some embodiments, the therapeutic is a small molecule. In some embodiments, the therapeutic is a non-oral therapeutic.

In some embodiments, the fibrosis is idiopathic pulmonary fibrosis. In some embodiments, the fibrosis is cystic fibrosis.

Exemplary therapeutics for treating fibrosis for delivery using any of the devices or methods described herein include those listed in Table 3.

TABLE 3

Therapeutics adaptable for delivery via ingestible device for the treatment of fibrosis

| Drug Name/ Class | Existing Formulation Technologies, Methods of Administration | Exemplary Patent Literature |
| --- | --- | --- |
| Rituximab/Biological therapeutic; Chimeric monoclonal antibody; Recombinant protein | Infusion; Intravenous; Subcutaneous | CN-101041907; CN-108676875; WO-08804936; WO-09411026 |
| Abatacept (Orencia)/ Biological therapeutic; Antibody fragment | Formulation powder; Freeze drying; Infusion; Intravenous; Solution; Subcutaneous | WO-09300431 |
| Tocilizumab (Actemra)/ Biological therapeutic; Monoclonal antibody humanized; Protein recombinant | Immunoglobulin-G; Infusion; Intravenous; Solution | WO-09219759 |
| Rilonacept (Arcalyst)/ Biological therapeutic | Formulation powder; Freeze drying; Subcutaneous | WO-00018932; WO-2004039951 |
| Pirfenidone/Small molecule therapeutic | Aerosol formulation inhalant; Inhalant formulation | WO-2012106382 |
| BB-3/Small molecule therapeutic | Infusion; Intravenous | |
| Ensifentrine/Small molecule therapeutic | Aerosol; Inhalant formulation; Nasal formulation; Suspension; Sustained release | WO-00058308 |
| GSK-3008348/Small molecule therapeutic | Inhalant formulation | |
| PLN-74809/Small molecule therapeutic | Systemic | |
| AVID-200/Small molecule therapeutic | Systemic | WO-2017037634 |
| RES-529 (Restorgenex)/Small molecule therapeutic | Ophthalmic (intravitreal/ subconjunctival) | WO-2007101247 |
| Fulvestrant/Small molecule therapeutic | Intramuscular; Sustained release | EP-00138504 |
| Sodium pyruvate/ Small molecule therapeutic | Inhalant | WO-09710818 |
| Glutathione/ascorbic acid/bicarbonate combination/Small molecule therapeutic | Aerosol formulation inhalant | WO-2014070769 |
| CHF-6333/Small molecule therapeutic | Inhalant; Powder inhalant | |
| Fluticasone propionate/ Small molecule therapeutic | Aerosol formulation inhalant | US-04335121; WO-00212265 |
| Beclometasone dipropionate/ Formoterol fumarate combination/Small molecule therapeutic | Aerosol formulation inhalant; Modulite ® | WO-00189480 |
| Dexamethasone sodium phosphate (erythrocyte encapsulated)/Small molecule therapeutic | Infusion; Intravenous | EP-00882448 |

TABLE 3-continued

Therapeutics adaptable for delivery via ingestible device for the treatment of fibrosis

| Drug Name/ Class | Existing Formulation Technologies, Methods of Administration | Exemplary Patent Literature |
|---|---|---|
| TD-139/Small molecule therapeutic | Inhalant | WO-2014067986 |
| N-6022/Small molecule therapeutic | Infusion; Intravenous | WO-2010019903 |
| BG-00011 | Subcutaneous | |
| Lucinactant/Small molecule therapeutic | Aerosol formulation inhalant | WO-2005115520 |
| PRI-724/Small molecule therapeutic | Infusion; Intravenous | WO-2009148192 |
| BLD-2660/Small molecule therapeutic | Systemic, parenteral | |
| DWP-17011/Small molecule therapeutic | Systemic, parenteral | |
| SM-04646/Small molecule therapeutic | Solution; Inhalant | |
| BIIB-110/Biological therapeutic | Systemic, parenteral | |
| QBW-251 | Oral capsule | |

Therapeutics for Asthma

In some embodiments, the therapeutic suitable for use with the devices and methods described herein is a drug for treating asthma. Asthma is a chornic inflammatory condition of the airways of the lungs that results in difficulty in breathing. In some embodiments, the drug for treating asthma is a small molecule. In some embodiments, the small molecule drug or drug combination used to treat asthma is selected from RG-6151, mometasone+indacaterol, indacaterol+glycopyrronium bromide+mometasone furoate, and fevipiprant. In some embodiments, the drug for treating asthma is an antibody or a fragment thereof. In some embodiments, the antibody drug used to treat asthma is selected from omalizumab, tezepelumab, benralizumab, afasevikumab, RG-6149, dectrekumab+VAK-694, NOV-14, CSJ-117, or a biosimilar thereof. In some embodiments, the drug for treating asthma is a combination of small molecules and/or antibodies or fragments thereof.

Therapeutics for Neurological and/or Psychiatric Disorders or Conditions

In some embodiments, the therapeutic agent suitable for use with the devices and methods described herein is a drug for treating a neurological or psychiatric disorder or condition. Examples of neurological or psychiatric diseases or conditions include, but are not limited to, Alzheimer's disease, anxiety disorder, Parkinson's disease, multiple sclerosis, panic disorder, schizophrenia, chronic pain, neuropathic pain, migraine, Amyotrophic Lateral Sclerosis (ALS), epilepsy, seizures, cerebral aneurysm, muscular dystrophy, obsessive-compulsive disorders, eating disorders, bipolar disorders, depression, narcolepsy, and insomnia.

In some embodiments, the drug for treating a neurological or psychiatric disorder and associated symptoms is an antibody and biosimilars thereof. In some embodiments, the drug for treating a neurological or psychiatric disorder and associated symptoms is an antibody-drug conjugate. In some embodiments, the drug for treating a neurological or psychiatric disorder and associated symptoms is a small molecule. In some embodiments, the drug for treating a neurological or psychiatric disorder and associated symptoms is an inhibitory nucleic acid such as an antisense nucleic acid. In some embodiments, the therapeutic suitable for use with the devices and methods described herein is an imaging agent for diagnosing a neurological or psychiatric disorder. In some embodiments, the imaging agent is a radiolabeled protein or peptide. In some embodiments, the imaging agent is a radiolabeled small molecule.

In some embodiments, the neurological disorder is Alzheimer's disease. In some embodiments, the drug for treating Alzheimer's disease is selected from solanezumab, donanemab, LY-3303560, LY-3372993, liraglutide, MEDI-1814, MC-1, LY-3002815, LY-3154207, ACI-35, JNJ-63733657, BAN-2401, gosuranemab, IONIS-MAPTRx, BIIB-076, elenbecestat, RG-6100, crenezumab, amilomotide, and umibecestat.

In some embodiments, the neurological disorder is Parkinson's disease. In some embodiments, the drug for treating Parkinson's disease is selected from PF-06412562, LY-3154207 and MEDI-1341.

In some embodiments, the neurological disorder is pain. In some embodiments, the pain is chronic pain. In some embodiments, the pain is neuropathic pain. In some embodiments, the pain is migraine. In some embodiments, the drug used to treat pain is selected from fentanyl, PACAP38 mAb, BIIB-095, vixotrigine, lasmiditan, and olodanrigan.

In some embodiments, the psychiatric disorder is schizophrenia. In some embodiments, the drug for treating schizophrenia is selected from paliperidone palmitate, TAK-831, BIIB-104, TAK-041 and erteberel.

In some embodiments, the psychiatric disorder is depression. In some embodiments, the drug for treating depression includes aticaprant, esketamine, PF-04995274, JNJ-39393406, TAK-653, seltorexant, NR2B negative allosteric modulator, and MIJ-821.

Other therapeutic and imaging agents for the treatment or diagnosis of a neurological or psychiatric disorder suitable for use with the devices and methods described herein include, but are not limited to, glibenclamide, IONIS-C9Rx, [18F]MNI-968, 11C-PF-06809247, opicinumab, 18F-JNJ-64511070, PF-3463275, ADX-71149, JNJ-18038683, GDC-0134, tau-protein PET tracer (18F-JNJ-067), diroximel fumarate, 18F-GTP1 (RO-6880276), tofersen sodium, florbetapir (18F) (18F-MNI-798), JNJ-61393215, JNJ-54175446, siponimod, branaplam, LML-134, mavoglurant, JNJ-48816274, SAF-312, JNJ-55375515, 18F-MNI-792, TAK-935, and TAK-925.

Therapeutics for Metabolic and/or Endocrine Diseases or Conditions

In some embodiments, the therapeutic suitable for use with the devices and methods described herein is a therapeutic for treating a metabolic or endocrine disease or condition. Examples of metabolic or endocrine diseases or conditions include, but are not limited to, diabetes, insulin resistance, hyperglycemia, hyperlipidemia, obesity, hepatic steatosis, hyperinsulinemia, obstructive sleep apnea, non-alcoholic fatty liver disease (NAFLD), non-alcoholic steatohepatitis (NASH), liver fibrosis, liver cirrhosis, hypertension, cardiovascular disease (CVD), pulmonary artery hypertension, primary sclerosing cholangitis, high blood triglycerides, hypertriglyceridemia, dyslipidemia, lipid disorder, hyperlipoproteinemia type I, familial hypercholesterolemia, hypercholesterolemia, lipodystrophy, acromegaly, myocardial infarction, and thromboembolism; and combinations thereof. In some embodiments, the metabolic or endocrine disease or condition is obesity.

Therapeutics suitable for treating a metabolic or endocrine disease or condition include, but are not limited to, abatacept, aldesleukin, allogeneic human islets of langerhans, alogliptin, alpha-1 antitrypsin, anagliptin, atorvastatin, benaglutide, berberine, bermekimab, bimagrumab, cibinetide, cotadutide, diabecell, diamyd, dutogliptin ebenatide, efpeglenatide, evogliptin, fluvastatin, FSI-965, gemigliptin, glutazumab, gosogliptin, hinsbet, iscalimab, LAI-287, linagliptin, lovastatin, mecasermin, omarigliptin, osilodrostat, otelixizumab, pegapamodutide, PEG-loxenatide, pitavastatin, pramlintide acetate, prolastin, protrans, pravastatin, rexmyelocel-t, rosuvastatin, saxagliptin, simvastatin, sitagliptin, somatostatin, teneligliptin, teplizumab, tirzepatide, trelagliptin, vildagliptin, and combinations thereof. In some embodiments, the therapeutic suitable for treating a metabolic or endocrine disease or condition is STT-5058 (also called ARGX-116), an antibody-based inhibitor of apolipoprotein C III (apoC-III), which regulates blood triglyceride levels. Antibody-based inhibitors of apolipoprotein C III (apoC-III) are described in WO 2004/081046, WO 2014/131008, WO 2018/193427, WO 2019/087115, and WO 2020/070678, which are each hereby incorporated by reference. In some embodiments, the therapeutic suitable for treating a metabolic or endocrine disease or condition is selected from bortezomib, fulvestrant, bendamustine, itolizumab, golimumab, canakinumab, trichuris suis ova, NNC-0385-0434, NGM-282, BMS-986036, DACRA-089, RG-7992, cetilistat, and remestemcel-L; and biosimilars thereof. In some embodiments, the therapeutic suitable for treating a metabolic or endocrine disease or condition is a bile acid sequestrant. Bile acid sequestrants are a group of hypolipidemic agents used to bind certain components of bile in the GI tract, thereby disrupting the reabsorption of bile acids from the gut and resulting in the overall reduction of LDL cholesterol (LDL-c) in blood. In some embodiments, the bile acid sequestrant is colesevelam. In some embodiments, the bile acid sequestrant is cholestyramine. In some embodiments, the bile acid sequestrant is colestipol. In some embodiments, the therapeutic suitable for treating a metabolic or endocrine disease or condition is a proprotein convertase subtilisin/kexin type 9 (PCSK9) inhibitor. In some embodiments, the PCSK9 inhibitor is alirocumab or evolocumab. Other exemplary PCSK9 inhibitors for treating a metabolic or endocrine disease or disorder include those listed in Table 10.

Therapeutics for Diabetes

In some embodiments, the metabolic or endocrine disease or condition is diabetes. In some embodiments, the diabetes is type I or type II diabetes. In some embodiments, the diabetes is an insulin dependent diabetes. In some embodiments, the diabetes is a non-insulin dependent diabetes. In some embodiments, the diabetes is gestational diabetes.

In some embodiments, the metabolic or endocrine disease or condition is diabetes in combination with another disease or condition, including, but not limited to, diabetes with Alzheimer's disease, diabetes with dementia, diabetes with Alzheimer's disease and dementia, diabetes with obesity, diabetes with NAFLD, diabetes with NASH, diabetes with NAFLD and NASH, and diabetes with a cardiovascular disease. In some embodiments, the diabetes is diabetes with obesity.

Therapeutics suitable for treating a metabolic or endocrine disease or condition include, but are not limited to, an insulin, a glucagon receptor agonist or a glucagon-like peptide-1 (GLP-1) receptor agonist, a dipeptidyl peptidase 4 (DPP-4) inhibitor, a biguanide, a sodium-glucose cotransporter-2 (SGLT-2) inhibitors, a sulfonylurea, an α-glucosidase inhibitor, a maglitinides, a thiazolidinedione, a dopamine-2-agonist, a bile-acid sequestrant, a peptide YY ligand, and an amylin analog.

In some embodiments, the therapeutic suitable for use with the devices and methods described herein is a peptide YY ligand. The gut hormone peptide YY (PYY), also known as peptide tyrosine tyrosine, is a 36-amino acid peptide that is synthesized and released from specialized enteroendocrine cells called L-cells found predominantly within the distal GI tract (see, e.g., Karra et al., J. Physiol. 587(Pt 1):19-25 (2009)). In some embodiments, the peptide YY ligand is NN-9747, NN-9748, NN-9775 or any peptide YY ligand disclosed in WO 2016/198682, which is incorporated by reference herein in its entirety. In some embodiments, the peptide YY ligand is NN-9747 (PYY 1562, NNC0165-1562, NN-9748), an analogue of the appetite-regulating hormone, PYY, which can be used for mono- or combination treatment with the GLP-1 analogue semaglutide. In some embodiments, NN-9747 or NN-9748 is administered subcutaneously qd. In some embodiments, NN-9747 is indicated for obesity. In October 2015, a phase I trial was initiated and completed in February 2017; N=93 (Clinical Trials identifier: NCT02568306; source: Novo Nordisk Annual Report 2018). In some embodiments, NN-9748 is indicated for diabetes. In some embodiments, the peptide YY ligand is NN-9775 (NNC0165-1875), a peptide tyrosine 1875 analog (PYY 1875 analog), for the potential sc treatment of obesity and overweight. NN-9748 is an analogue of the appetite-regulating hormone, PYY, intended for mono- or combination treatment with the GLP-1 analogue semaglutide. In October 2018, a first-human dose, phase I study of NNC0165-1875 as monotherapy and in combination with semaglutide was initiated; N=88 (clinical trials identifier: NCT03707990; source: Novo Nordisk Annual Report 2018). In some embodiments, NN-9747 is the same drug substance as NN-9748.

In some embodiments, the therapeutic suitable for use with the devices and methods described herein is an amylin analog. In some embodiments, the amylin analog is AM-833. In some embodiments, the metabolic or endocrine disease or condition is obesity or diabetes with obesity.

In some embodiments, the therapeutic is NNC0247-0829. In some embodiments, the metabolic or endocrine disease or condition is obesity or diabetes with obesity.

In some embodiments, the therapeutic suitable for use with the devices and methods described herein is a glucagon receptor agonist or a glucagon-like peptide-1 (GLP-1) receptor agonist. In some embodiments, the glucagon receptor agonist or the GLP-1 receptor agonist is glucagon. In some embodiments, the glucagon receptor agonist or the GLP-1 receptor agonist is NN-9277 (see, e.g., Brandt et al., J. Endocrinol. 283(2):R109-R119 (2018)). In some embodiments, the glucagon receptor agonist or the GLP-1 receptor agonist is NN-9423, a triple agonist of the human glucagon-like peptide 1 (GLP-1), gastric inhibitory peptide (GIP) and glucagon receptor (GCG). In some embodiments, the glucagon receptor agonist or the GLP-1 receptor agonist is semaglutide; or a biosimilar thereof, or a reformulation thereof such as Rybelsus®. In some embodiments, the glucagon receptor agonist or the GLP-1 receptor agonist is dulaglutide; or a biosimilar thereof. In some embodiments, the glucagon receptor agonist or the GLP-1 receptor agonist is albiglutide; or a biosimilar thereof. In some embodiments, the glucagon receptor agonist or the GLP-1 receptor agonist is exenatide; or a biosimilar thereof. In some embodiments, the glucagon receptor agonist or the GLP-1 receptor agonist is liraglutide; or a biosimilar thereof. In some embodiments, the glucagon receptor agonist or the GLP-1 receptor agonist is lixisenatide; or a biosimilar thereof. In some embodiments, the glucagon receptor agonist or the GLP-1 receptor agonist is NNC-0090-2746.

In some embodiments, the therapeutic suitable for use with the devices and methods described herein is a dual GIP and GLP-1 receptor agonist. In some embodiments, the dual GIP and GLP-1 receptor agonist is LY3298176, a fatty acid modified peptide with dual GIP and GLP-1 receptor agonist activity that can be used for the treatment of type 2 diabetes mellitus. See, e.g., Coskun et al., Mol. Metab., 18:3-14 (2018).

In some embodiments, the therapeutic suitable for use with the devices and methods described herein is a therapeutic for treating diabetes.

In some embodiments, the therapeutic for treating diabetes that is suitable for use with the devices and methods described herein is an insulin. In some embodiments, the insulin is selected from human insulin, insulin aspart, ultra-fast acting insulin aspart, insulin degludec, insulin detemir, insulin glargine, insulin glulisine, insulin lispro, and insulin tregopil.

In some embodiments, the therapeutic for treating diabetes that is suitable for use with the devices and methods described herein is a dipeptidyl peptidase-4 inhibitor (DPP-4). DPP-4 inhibitors are oral hypoglycemics which can be used to treat diabetes mellitus type-2. Examples of DPP-4 inhibitors include, but are not limited to, sitagliptin, vildagliptin, saxagliptin, linagliptin, gemigliptin, anagliptin, teneligliptin, alogliptin, trelagliptin, omarigliptin, evogliptin, gosogliptin, dutogliptin, and berberine.

In some embodiments, the therapeutic for treating diabetes that is suitable for use with the devices and methods described herein is an SGLT-2 inhibitor. SGLT-2 inhibitors are oral hypoglycemics that inhibit the reabsorption of glucose in the kidney and can be used to treat diabetes mellitus type-2. Examples of SGLT-2 inhibitors include, but are not limited to, canagliflorzin, dapagliflozin, empagliflozin, ertugliflozin, ipragliflozin, luseogliflozin, remogliflozin etabonate, sergliflozin etabonate, sotagliflozin, and tofogliflozin.

In some embodiments, the therapeutic for treating diabetes that is suitable for use with the devices and methods described herein is an α-glucosidase inhibitor. α-Glucosidase inhibitors (AGIs) are oral hypoglycemics that can inhibit the digestion of carbohydrates into monosaccharides by α-glucosidase in the intestine, thereby reducing the blood glucose levels. Examples of α-glucosidase inhibitors include, but are not limited to, acarbose, miglitol, and voglibose.

Exemplary therapeutics for treating diabetes for delivery using any of the devices or methods described herein include those listed in Table 4, and any combination thereof.

TABLE 4

Therapeutics adaptable for delivery via ingestible device for the treatment of diabetes

| Drug Name/ Company | Existing Formulation Technologies, Methods of Administration | Exemplary Patent Literature |
|---|---|---|
| Dulaglutide | Biological therapeutic; Immunoglobulin-G; Protein fusion; Solution; Subcutaneous | WO2004110472 |
| Semaglutide/ Novo Nordisk | Biological therapeutic; Peptide; Subcutaneous; Oral sustained release; Tablet | WO2006097537; WO2012080471 |
| Exenatide/ Astrazeneca; Intarcia/ Servier; Peptron | Biological therapeutic; Intravenous Subcutaneous, Injectable controlled release; Suspension; Sustained release; Subcutaneous drug implant; Drug combination | WO09830231 US05424286; WO2004035754; WO00066629; WO2006083761; WO2008133908; WO2017200943; WO2017200944; WO2018075901 |
| Insulin degludec | Biological therapeutic; Cloning technology; Peptide; Solution; Subcutaneous; Sustained release | WO-2005012347 |
| Liraglutide | Biological therapeutic; Peptide; Protein recombinant; Solution; Subcutaneous | WO-09727866; WO09808871; WO09832825; WO09943341; WO09943705; WO09943708; WO09947160 |
| Insulin lispro/ Sanofi; Gan & Lee Pharmaceuticals; Eli Lilly; Wanbang Biopharma; Adocia/ Tonghua; Diasome Pharmaceuticals | Biological therapeutic; Biosimilar product; Follow on biologic; Protein recombinant; DNA technology; Infusion; Intravenous; Peptide; Quick release; Solution; Subcutaneous; Suspension | EP00383472; WO2004078239; CN104587455; WO2014076422 |
| Insulin glargine/ Sanofi; Biocon/ Mylan/pisa/ Fujifilm/GC Pharma; Eli Lilly/ Boehringer; Wockhardt; Gan & Lee Pharmaceuticals/ LG; Life Sciences; Incepta; Getz Pharma; Tonghua Dongbao; Jiangsu Wanbang Biochemical Pharmaceutical | Biological therapeutic; Biosimilar product; Follow on biologic; Protein recombinant; Solution; Subcutaneous; Sustained release | WO2004078239; EP00368187; WO2011018745; WO00210411; WO2004050672; WO2012152175; CN103439512; CN104587455 |
| Insulin aspart/ Novo Nordisk; Gan & Lee Pharmaceuticals; Sanofi; Zhunhai United Laboratories; Dongbao Group; | Biological therapeutic; Biosimilar product; Infusion; Intravenous; Intramuscular; Protein recombinant; Subcutaneous; Quick release; Solution; Suspension; Ultra-fast acting | WO2010149772; EP00214826; WO09426778; CN103060335 |

TABLE 4-continued

Therapeutics adaptable for delivery via ingestible device for the treatment of diabetes

| Drug Name/ Company | Existing Formulation Technologies, Methods of Administration | Exemplary Patent Literature |
|---|---|---|
| Biocon/ Mylan; Zhejiang Hisun Pharmaceutical | | |
| Insulin glargine + lixisenatide/ Sanofi/ Zealand Pharma | Biological therapeutic; Drug combination; Protein recombinant; Subcutaneous | WO00104156 |
| Insulin degludec + insulin aspart | Biological therapeutic; Drug combination; Peptide; Solution; Subcutaneous | WO2005012347; WO2012080320 |
| Insulin degludec + liraglutide/ Novo Nordisk | Biological therapeutic; Drug combination; Peptide; Subcutaneous; Sustained release | WO09727866; WO09808871; WO09832825; WO09943341; WO09943705; WO09943708; WO09947160; WO2005012347; WO2009063072 |
| Insulin glulisine | Biological therapeutic; Infusion; Intravenous; Peptide; Solution; Subcutaneous | EP-00885961 |
| Insulin detemir | Biological therapeutic; Injectable controlled release; Peptide; Protein recombinant; Solution; Subcutaneous | AU-00745983; WO-09507931 |
| Alpha-1 antitrypsin/ Kamada/Shire | Biological therapeutic; Intravenous; Liquid | WO09856821 |
| Insulin human/ Eli Lilly | Biological therapeutic; Protein recombinant; Solution; Subcutaneous; Suspension | EP00037256 |
| Pramlintide acetate | Biological therapeutic; Peptide; Solution; Subcutaneous | WO09215317; WO09310146 |
| Albiglutide | Biological therapeutic; Powder; Freeze drying; Liquid; Protein fusion; Protein recombinant; Subcutaneous; Sustained release | US20080167238; WO03059934 |
| Insulin/ Generex | Biological therapeutic; Buccal formulation systemic; Formulation aerosol unspecified; Protein recombinant | WO00037053 |
| Lixisenatide | Biological therapeutic; Peptide; Subcutaneous | CN103467365; CN106167528; WO00104156 |
| Prolastin | Biological therapeutic; Powder; Freeze drying; Infusion; Intravenous; Peptide; | EP-00097274 |
| Benaglutide | Biological therapeutic; Protein recombinant; Subcutaneous | WO-03016349 |
| Insulin Technosphere/ Sanofi | Biological therapeutic; Inhalant; Microparticle; Powder Protein recombinant | WO-09636314 |
| Human insulin/ Novo Nordisk A/S; Sanofi-Aventis; Bioton/Scigen/ Actavis; Tonghua Dongbao; Wockhardt; Geropharm; Horizon; Pharma/IBA Tech; | Biological therapeutic; DNA technology, Follow on biologic; Peptide; Subcutaneous; Suspension; Yeast recombinant; Cloning technology; Drug implant; Intravenous; Intramuscular; Protein recombinant; Solution | EP-00427296; US-04029642; WO-2013119132; CN-103439512; WO-2004024862; WO-00204515; WO-09965941 |
| SEDICO; United Laboratories International Holdings; Square Pharmaceuticals; Rechon Life Sciences | | |
| Isophane insulin/Biocon | Biological therapeutic; Follow on biologic; Protein recombinant; Subcutaneous; Sustained release | WO-2010016069 |
| Insulin/ Biocon; MJ Bioton Life Science/MJ Biopharm/ Medipolis/ Marvel Life Sciences/ Pharmstandard; Shenzhen Kexing Biotech; Hefei Tianmai Biotechnology; Valin Technologies | Biological therapeutic; Biosimilar product; Follow on biologic; Protein recombinant; Quick release; Subcutaneous | WO-09426778; CN-202530010; CN-202983284 |
| Glucagon/ Lilly | Biological therapeutic; DNA technology; Injectable; Parenteral formulation unspecified; Protein recombinant | US-04033941 |
| Mecasermin/ Fujisawa | Biological therapeutic; Intravenous ; Protein recombinant | WO-09103253 |
| Short acting insulin/ Popular Pharmaceuticals | Biological therapeutic; Follow on biologic; Protein recombinant; Solution; Subcutaneous: Suspension | |
| Recombinant human insulin/Scigen | Biological therapeutic; Protein recombinant; Transdermal; Transdermal high velocity particle formulation | |
| Rosinsulin | Biological therapeutic; Subcutaneous; Suspension | |
| Somatostatin/ Lunan Pharmaceutical | Biological therapeutic; Follow on biologic; Intravenous; Peptide | |
| Insulin isophane/ Wanbang Biopharma; Shenzhen Kexing Biotech | Biological therapeutic; Follow on biologic; Protein recombinant; Solution; Subcutaneous | CN-101173006 |
| Diabecell | Biological therapeutic; Cell therapy; Intraperitoneal; Microparticle; Xenogeneic transplant | WO-00152871 |
| Bermekimab | Biological therapeutic; Immunoglobulin-G; Infusion; Intravenous; Monoclonal antibody human; Subcutaneous | WO-2009148575 |
| UNI-RE-4 | Biological therapeutic; Powder; Liquid; Parenteral formulation unspecified; Protein recombinant | CN-102370624 |

TABLE 4-continued

Therapeutics adaptable for delivery via ingestible device for the treatment of diabetes

| Drug Name/ Company | Existing Formulation Technologies, Methods of Administration | Exemplary Patent Literature |
|---|---|---|
| PEG-loxenatide | Biological therapeutic; PEGylated formulation; Peptide; Subcutaneous; Sustained release | WO-2012155780 |
| Tirzepatide | Biological therapeutic; PEGylated formulation; Peptide; Subcutaneous | WO-2016111971 |
| Efpeglenatide | Antibody fragment; Biological therapeutic; Protein conjugated; Subcutaneous; Sustained release | WO-2008082274 |
| Teplizumab | Biological therapeutic; Infusion; Intravenous; Monoclonal antibody humanized; Subcutaneous | WO-09428027 |
| Insulin tregopil | Biological therapeutic; Oral; Protein conjugated | WO-2004083234 |
| Insulin/ Alkermes/ Eli Lilly | Biological therapeutic; Infusion; Peptide; Subcutaneous | |
| Rexmyelocel-T | Biological therapeutic; Cell therapy; Infusion; Intra-arterial; Leukocyte cell therapy | WO-2018037134 |
| RE-4 | Biological therapeutic; Protein recombinant; Subcutaneous; Systemic formulation unspecified | |
| Allogeneic human islets of Langerhans/ University of Illinois | Biological therapeutic; Cell therapy; Systemic formulation unspecified | WO-2009006600 |
| Pega-pamodutide | Biological therapeutic; Injectable controlled release; PEGylated formulation; Peptide; Subcutaneous; Sustained release | WO-2011087672 |
| LAI-287 | Biological therapeutic; Peptide; Subcutaneous; Sustained release; | |
| CLBS-03 | Biological therapeutic; Parenteral formulation unspecified; T-lymphocyte | WO-2006031926 |
| Insulin/ Diabetology | Biological therapeutic; Capsule; Enteric coated; Oral absorption enhancer; Oral; Peptide | WO-2007093806 |
| IONIS-gcgrrx | Biological therapeutic; Infusion; Intravenous; Oligonucleotide antisense; RNA antisense; Subcutaneous | WO-2008017081 |
| Bimagrumab | Biological therapeutic; Infusion; Intravenous; Monoclonal antibody human; Protein recombinant | WO-2010125003 |
| IONIS-ANGPTL3-lrx | Biological therapeutic; Oligonucleotide antisense; Subcutaneous | WO-2015100394 |
| Aldesleukin/ ILTOO Pharma | Biological therapeutic; Protein recombinant; Subcutaneous | |
| HM-12525a | Antibody conjugated; Biological therapeutic; Parenteral formulation unspecified; Peptide; Protein conjugated; Subcutaneous; Sustained release | WO-2012173422 |
| ORMD-0901 | Biological therapeutic; Capsule; Oral; Peptide | WO-2009136392 |
| Diamyd/ Diamyd Medical | Antigen; Biological therapeutic; Parenteral formulation unspecified; Protein recombinant | |
| Pec-direct | Biological therapeutic; Cell therapy; Drug implant; Pluripotent stem cell therapy | WO-2018089011 |
| GNBAC-1 | Biological therapeutic; Immunoglobulin-G; Infusion; Intravenous; Monoclonal antibody humanized; Protein recombinant | WO-2010003977 |
| Insulin/ Oramed | Biological therapeutic; Capsule; Oral; Protein recombinant | WO-2007029238 |
| TOL-3021 | Biological therapeutic; Intramuscular | WO-2007044394 |
| MPC-300-iv | Allogenic stem cell therapy; Biological therapeutic; Infusion; Intravenous; Mesenchymal stem cell therapy | WO-2012000064 |
| Glutazumab | Biological therapeutic; Monoclonal antibody; Protein fusion; Subcutaneous | |
| Cotadutide | Biological therapeutic; Peptide; Solution; Subcutaneous | WO-2015086686 |
| REMD-477 | Biological therapeutic; Monoclonal antibody human; Subcutaneous | WO-2015189698 |
| PEC-encap | Biological therapeutic; Cell therapy; Pluripotent stem cell therapy; Subcutaneous drug implant | WO-2005063971 |
| Cibinetide/ Araim | Biological therapeutic; Infusion; Intravenous; Peptide; Subcutaneous | WO-2007019545; WO-2009094172 |
| LY-3209590 | Biological therapeutic; Peptide; Subcutaneous | |
| Otelixizumab | Biological therapeutic; Infusion; Intravenous; Monoclonal antibody humanized; Subcutaneous | WO-09319196 |
| AG-019 | Bacteria recombinant; Biological therapeutic; Capsule; Oral; Peptide | WO-2007063075 |
| GABA + antigen based therapy/ Diamyd | Antigen; Biological therapeutic; Drug combination; Oral; Tablet | WO-2017058074 |
| Allogeneic human mesenchymal stem cells/ Longeveron | Allogenic stem cell therapy; Biological therapeutic; Infusion; Intravenous; Local formulation unspecified; Mesenchymal stem cell therapy | WO-2018089752 |
| Cell therapy/ Sernova | Biological therapeutic; Cell therapy; Subcutaneous | WO-09528167 |
| Insulin Diabetology | Biological therapeutic; Capsule; Enteric coated; Oral absorption enhancer; Oral; Peptide | WO-2007093806 |
| PB-119 | Biological therapeutic; PEGylated formulation; Peptide; Subcutaneous | WO-2010121559 |
| Ionis-DGAT2Rx | Biological therapeutic; Oligonucleotide antisense; Subcutaneous | WO-2017011276 |
| Abatacept/ NIDDK | Biological therapeutic; Immunoglobulin-G; Intravenous; Protein fusion | WO-2013177505 |
| Ebenatide | Biological therapeutic; Protein conjugated; Subcutaneous; Sustained release | WO-2007053946 |
| Protrans | Allogenic stem cell therapy; Biological therapeutic; Infusion; Intravenous; Mesenchymal stem cell therapy; Umbilical cord stem cell therapy | |
| Hinsbet | Biological therapeutic; Injectable; Parenteral formulation unspecified; Peptide; Protein recombinant; Quick release | WO-2010122385 |
| Glucagon-like peptide-1 analog/ Radboud University | Imaging; Infusion; Peptide; Radiolabeling; Systemic formulation unspecified | |

TABLE 4-continued

Therapeutics adaptable for delivery via ingestible device for the treatment of diabetes

| Drug Name/Company | Existing Formulation Technologies, Methods of Administration | Exemplary Patent Literature |
|---|---|---|
| Insulin (long-acting iv, hepatic directed vesicles (HDV))/Diasome Pharmaceuticals | Biological therapeutic; Nanoparticle formulation injectable; Parenteral formulation unspecified; Protein recombinant | WO-2011022396 |
| Human insulin/Dance/Harmony/Dongbao | Aerosol formulation inhalant; Biological therapeutic; Inhalant; Protein recombinant | WO-2011088070 |
| Anti-IL-21 + liraglutide/Novo Nordisk | Biological therapeutic; Intravenous; Monoclonal antibody human; Subcutaneous | WO-2012098113 |
| NNC-0090-2746 | Biological therapeutic; PEGylated formulation; Peptide; Subcutaneous | WO-2010096052 |
| BIOD-531 | Biological therapeutic; Parenteral formulation unspecified; Protein recombinant; Subcutaneous | |
| Allogenic umbilical cord-derived mesenchymal stem cell therapy/Nanjing University | Allogenic stem cell therapy; Biological therapeutic; Intravenous; Mesenchymal stem cell therapy | |
| Insulin/Diasome Pharmaceuticals | Biological therapeutic; Nanoparticle formulation injectable; Intravenous; Capsule; Oral; Nanoparticle formulation oral; Protein recombinant | |
| Insulin 287 + semaglutide/Novo Nordisk | Biological therapeutic; fixed-dose combination; Peptide; Subcutaneous | |
| NNC0113-2023/Novo Nordisk | Small molecule therapeutic; tablet formulation; Oral | |
| LY-3305677/Eli Lilly & Co. | Biological therapeutic; Peptide; Long acting; Subcutaneous | |
| GDF15 agonist/Eli Lilly & Co. | Biological therapeutic; Parenteral | |
| LY-3374849/Eli Lilly & Co. | Biological therapeutic; Peptide; Subcutaneous | |
| Canagliflozin + Metformin XR/Janssen Pharmaceutica | Drug combination; Small molecule therapeutic; Sustained release formulation | |
| Empagliflozin + Linagliptin + Metformin/Boehringer/Eli Lilly & Co. | Small molecule therapeutic; tablet formulation; Drug combination; Oral | |
| Namacizumab (JNJ-2463)/Bird Rock Bio Inc/Janssen Pharmaceuticals Inc. | Biological therapeutic; Intravenous; Monoclonal antibody; | |
| LEZ-763/Novartis AG | Small molecule therapeutic; oral formulation | |

Therapeutics for NASH/NAFLD

In some embodiments, the disease or condition is NASH and/or NAFLD. In some embodiments, the therapeutic suitable for use with the devices and methods described herein is a therapeutic for treating non-alcoholic steatohepatitis (NASH) and/or non-alcoholic fatty liver disease (NAFLD). NASH (non-alcoholic steatohepatitis) is a fatty liver disease affecting as many as 12% of the U.S. adults. There are many potential drugs to treat this disease illustrated by: selonsertib, cenicriviroc, elafibranor, ocaliva, tropifexor, firocostat, cilofexor, aramchol, obeticholic acid, ARX618, BI 1467335, DS102, EDP-305, emricasan, gemcabene, belapectin (GR-MD-02), GRI-0621, firsocostat (GS-0976), GS-9674, IMM-124E, IONIS-DGAT2Rx, lanifibranor (IVA-337), lipaglyn, tropifexor (LJN452), nidufexor (LMB-763), licogliflozin bis(prolinate), resmetirom (MGL-3196), tipelukast (MN-001), MSDC-0602K, NC101, aldafermin (NGM282), NGM313, NS-0200, ozempic, PF-05221304, PF-06835919, PF-07055341, remogliflozin etabonate, volixibat (SHP626), TVB-2640, VK2809, butanoic acid, CER209, evogliptin, DUR928, MK-4074, OPRX-106, PF-06865571, PF-06882961, PXS-5382A, RG-125 (AZD4076), RYI-018, seladelpar, SGM-1019 and TVB-2640. In some embodiments, the therapeutic suitable for use with the devices and methods described herein is selected from the therapeutic agent is selected from the group consisting of selonsertib, cenicriviroc, elafibinor, ocaliva, tropifexor, firocostat and cilofexor. These represent several biological mechanisms. A combination of multiple drugs may be required. In some embodiments, the drug is selected from selonsertib, cenicriviroc, elafibinor, ocaliva, tropifexor, firocostat and cilofexor.

Exemplary therapeutics for treating NASH and/or NAFLD for delivery using any of the devices or methods described herein include those listed in Table 5.

TABLE 5

Therapeutics adaptable for delivery via ingestible device for the treatment of NASH/NAFLD

| Drug Name | Existing Formulation Technologies and Methods of Administration | Exemplary Patent Literature |
|---|---|---|
| NGM282 (aldafermin) | Biological therapeutic; Protein recombinant; Subcutaneous | WO-2013006486 |
| IONIS-ANGPTL3-LRx | Biological therapeutic; Oligonucleotide antisense; Subcutaneous | WO-2015100394 |
| Insulin/Oramed | Biological therapeutic; Capsule; Oral; Protein recombinant | WO-2007029238 |
| BMS-986036 (pegbelfermin) | Biological therapeutic; PEGylated formulation; Protein recombinant; Subcutaneous | WO-2008121563 |

TABLE 5-continued

Therapeutics adaptable for delivery via ingestible device for the treatment of NASH/NAFLD

| Drug Name | Existing Formulation Technologies and Methods of Administration | Exemplary Patent Literature |
|---|---|---|
| IMM-124E | Antibody polyclonal; Biological therapeutic; Powder; Immunoglobulin-G; Oral | WO-2010125565 |
| Semaglutide/ Novo Nordisk | Biological therapeutic; Peptide; Subcutaneous; Sustained release | |
| IONIS-DGAT2Rx | Biological therapeutic; Oligonucleotide antisense; Subcutaneous | WO-2017011276 |

Therapeutics for Rheumatoid Arthritis

In some embodiments, the therapeutic suitable for use with the devices and methods described herein is a therapeutic for treating rheumatoid arthritis. Exemplary therapeutics for treating rheumatoid arthritis for delivery using any of the devices or methods described herein include those listed in Table 6.

TABLE 6

Therapeutics adaptable for delivery via ingestible device for the treatment of rheumatoid arthritis

| Drug Name/ Company | Existing Formulation Technologies, Methods of Administration | Exemplary Patent Literature |
|---|---|---|
| Certolizumab pegol | Antibody fragment; Biological therapeutic; Powder; Freeze drying; Monoclonal antibody humanized; PEGylated formulation; Protein conjugated; Protein recombinant; Solution; Subcutaneous | WO-00194585 |
| Corticotropin/ Mallinckrodt | Biological therapeutic; Gel; Injectable controlled release; Intramuscular; Peptide; Subcutaneous; Sustained release | WO-2011143152 |
| Ciclosporin/ Novartis; Chong Kun Dang | Biological therapeutic; Capsule; Emulsion; Infusion; Intravenous; Oral; Oral gel; Peptide; Solution | GB-01491509; US-06306825; WO-09522982 |
| Etanercept/ Sandoz/Hexal; Zhejiang Hisun Pharmaceutical; Shanghai Citic Pacific Guojian Pharmaceutical; Samsung Bioepis; Shanghai Celgen Biopharmaceutical; LG Chem/Mochida; Viropro; Aryogen; AXXO; Amega; Pfizer; Hanwha; Lupin; Coherus Biosciences; Qilu Pharmaceutical | Biological therapeutic; Biosimilar product; Cell culture; Powder; Freeze drying; Immunoglobulin-G; Liquid; Protein fusion; Solution; Subcutaneous | EP-00417563; EP-00835939; WO-09013575; WO-09103553; WO-2014060551; WO-00036092; WO-2014102814; WO-2012165917; WO-2010099153; WO-2014064637; WO-2013059405 |
| Abatacept | Biological therapeutic; Powder; Freeze drying; Immunoglobulin-G; Infusion; Intravenous; Protein conjugated; Protein fusion; Solution; Subcutaneous | WO-09300431 |
| Adalimumab/ Actavis/Amgen/ Daiichi Sankyo/ Orion; Samsung Bioepis; Sandoz; Zydus Cadilla/ Glenmark Pharmaceuticals; Fujifilm Kyowa Kirin Biologics/ Mylan; Hetero; Reliance Life Sciences, AXXO; Boehringer Ingelheim; Zhejiang Hisun Pharmaceutical; Pfizer; Innovent Biologies; Fresenius; Shanghai Henlius Biotech; Bio-Thera Solutions; Celltrion; Momenta/Shire; LG Life Sciences | Biological therapeutic; Biosimilar product; Immunoglobulin-G; DNA technology; Monoclonal antibody human; Protein recombinant; Solution; Subcutaneous | US-07517963; US-20130122018; WO-09102078; WO-09729131; WO-2016019726; WO-2018119142; WO-2016000813; WO-2015007912; WO-2014207763; WO-2013021148; WO-2013186230; WO-2014099636; WO-2019024783; WO-2013181577; WO-2018169348 |
| Tocilizumab/ Roche/Chugai; Bio-Thera Solutions | Biological therapeutic; Biosimilar; Monoclonal antibody humanized; Protein recombinant; Subcutaneous; Infusion; Intravenous; Solution | WO-00117542; WO-09219759; WO-2016103093 |
| Itolizumab | Biological therapeutic; Intravenous; Monoclonal antibody humanized; Subcutaneous | WO-0973142; WO-2009113083 |
| Infliximab/ Pfizer/Sandoz; Samsung Bioepis/ Merck & Co; Celltrion/ Nippon Kayaku/ Hospira/ Orion/EGIS Gyogyszergyar; Bionovis/ Fiocruz/IVB; Aprogen/ Nichi-Iko Pharm/Sanofi; | Biological therapeutic; Biosimilar product; Cell culture technique; Chimeric monoclonal antibody; Protein recombinant; Powder; Freeze drying; Immunoglobulin-G; Infusion; Intra-articular; Intravenous | US-07517963; US-20050255104; WO-09102078; WO-09216553; WO-03045400; WO-2006122187; WO-2006093397; WO-2009026122; WO-2011103700; WO-2017120614 |

TABLE 6-continued

Therapeutics adaptable for delivery via ingestible device for the treatment of rheumatoid arthritis

| Drug Name/ Company | Existing Formulation Technologies, Methods of Administration | Exemplary Patent Literature |
|---|---|---|
| Celltrion Healthcare; Amgen; Biomab Pharmaceuticals; Mabtech/ Sorrento; Biocad; Genor | | |
| Sarilumab | Biological therapeutic; Monoclonal antibody human; Solution; Subcutaneous | WO-2007143168 |
| Rituximab/ Celltrion/ Mundipharm/ Teva/Nippon Kayaku; Sandoz; Aryogen; Reliance Life Sciences, AXXO; Biocad; Hetero; Dr Reddy's/ CFR Pharmaceuticals/ Cinnagen; Intas Biopharmaceuticals; Shanghai Henlius; Mabion; Allergan/ Amgen | Biological therapeutic; Biosimilar product; Chimeric monoclonal antibody; Immunoglobulin-G; Infusion; Intravenous; Protein recombinant; Subcutaneous | CN-101041907; WO-09411026; WO-08804936; CN-108676875; WO-2006093397; WO-00027428; WO-2009007993; WO-2013126813 |
| Golimumab/ Johnson & Johnson | Biological therapeutic; Immunoglobulin-G; Monoclonal antibody human; Solution; Subcutaneous; Infusion; Intravenous | US-07691378; WO-00212502; WO-2018140121 |
| Canakinumab | Biological therapeutic; DNA technology;Powder; Freeze drying; Immunoglobulin-G; Infusion; Intra-articular; Liquid; Monoclonal antibody human; Protein recombinant; Subcutaneous | WO-00216436 |
| Opinercept | Biological therapeutic; Freeze drying; Protein fusion; Solution; Subcutaneous | |
| Trichuris suis ova, ovamed/Dr Falk/Fortress Biotech | Biological therapeutic; Cell therapy; Oral; Oral suspension | WO-09933479 |
| Anakinra/ AXXO | Biological therapeutic; Follow on biologic; Intramuscular; Intravenous; Peptide; Protein recombinant; Subcutaneous | WO-08911540 |
| Interleukin-2/ Changchun Institute of Biological Products; Changchun changsheng Gene Pharmaceutical; Guangdong Weilun Biological Products; | Biological therapeutic; Follow on biologic; Injectable; Parenteral formulation unspecified; Protein recombinant; Subcutaneous; Freeze drying; Intratumoral; Intravenous | WO-2011106991 |
| Beijing SL Pharmaceutical; Shandong Quangang Pharmaceutical; Shenzhen Neptunus Cartistem | Biological therapeutic; Mesenchymal stem cell therapy; Parenteral formulation unspecified | WO-2010131917 |
| Interferon gamma/Livzon Pharmaceutical Group; Shanghai Chemo Wanbang Biopharma | Biological therapeutic; Follow on biologic; Freeze drying; Intramuscular; Protein recombinant; Subcutaneous | CN-01799626 |
| Ka shu ning | Biological therapeutic; Intramuscular; Oligosaccharide; Solution | |
| VAY-736 | Biological therapeutic; Immunoglobulin-G; Infusion; Monoclonal antibody human; Subcutaneous | WO-2010007082 |
| Tadekinig alfa/ AB2 Bio | Biological therapeutic; Protein recombinant; Subcutaneous | WO-2015032932 |
| Olokizumab | Biological therapeutic; Intravenous; Monoclonal antibody humanized; Subcutaneous | WO-2007066082 |
| Recombinant human CD22 monoclonal antibody, Lonn Ryonn Pharma/ sinomab Bioscience | Biological therapeutic; Infusion; Intravenous; Monoclonal antibody | WO-2013188864 |
| RCT-18 | Biological therapeutic; Monoclonal antibody humanized; Protein fusion; Protein recombinant; Subcutaneous | |
| Ocaratuzumab | Biological therapeutic; Immunoglobulin-G; Infusion; Intravenous; Monoclonal antibody humanized; Protein recombinant | WO-2004103404 |
| Otilimab | Biological therapeutic; Immunoglobulin-G; Infusion; Intravenous; Monoclonal antibody human; Protein recombinant; Subcutaneous | WO-2006122797 |
| E-6011/EA Pharma | Biological therapeutic; Monoclonal antibody humanized; Subcutaneous | EP-03159007 |
| MPC-300-iv | Allogenic stem cell therapy; Biological therapeutic; Infusion; Intravenous; Mesenchymal stem cell therapy | WO-2012000064 |
| ASP-5094 | Biological therapeutic; Intravenous; Monoclonal antibody human; Systemic formulation unspecified | |
| Cibinetide/ Araim | Biological therapeutic; Infusion; Intravenous; Peptide; Subcutaneous | WO-2007019545; WO-2009094172 |
| Pf-06687234 | Biological therapeutic; Intravenous; Protein fusion; Subcutaneous | WO-2009056268 |

TABLE 6-continued

Therapeutics adaptable for delivery via ingestible device for the treatment of rheumatoid arthritis

| Drug Name/ Company | Existing Formulation Technologies, Methods of Administration | Exemplary Patent Literature |
|---|---|---|
| $^{99m}$Tc labelled annexin V-128/ Advanced Accelerator Applications | Imaging; Intravenous; Protein recombinant; Radiolabeling | WO-2018069409 |
| Cx-611 | Adipose stem cell therapy; Allogenic stem cell therapy; Biological therapeutic; Intravenous; Mesenchymal stem cell therapy | WO-2006037649 |
| CreaVax-RA | Autoantigen; Biological therapeutic; Cell therapy; Parenteral formulation unspecified; Subcutaneous | WO-2008102937 |
| AMG-592 | Biological therapeutic; Protein fusion; Protein recombinant; Subcutaneous | WO-2014153063 |
| Ozoralizumab | Biological therapeutic; Intravenous; Monoclonal antibody humanized; Subcutaneous | WO-2006122786; WO-2010077422 |
| NI-0101 | Biological therapeutic; Immunoglobulin-G; Infusion; Intravenous; Monoclonal antibody humanized | WO-2009101479 |
| PRTX-100 | Biological therapeutic; Infusion; Intravenous | WO-03086317 |
| Vobarilizumab/ Ablynx | Biological therapeutic; Multivalent antibody; Subcutaneous | WO-2008020079 |
| BCD-089 | Biological therapeutic; Monoclonal antibody human; Subcutaneous | WO-2018034597 |
| Theralizumab | Biological therapeutic; Immunoglobulin-G; Infusion; Intravenous; Monoclonal antibody humanized | WO-09854225 |
| AT-132 | Biological therapeutic; Monoclonal antibody humanized; Subcutaneous | WO-2012116595 |
| Oralgam | Biological therapeutic; Immunoglobulin; Oral | WO-03028668 |
| INV-103 | Biological therapeutic; Intravenous; Protein recombinant; Subcutaneous | WO-2004041300 |
| Umbilical cord-derived mesenchymal stem cells/ Alliancells/ Zhongyuan Union | Biological therapeutic; Intravenous Mesenchymal stem cell therapy | |
| PF-06650833/ Pfizer | Small molecule therapeutic; Capsule formulation; Oral controlled release formulation; Oral solution formulation; Oral suspension formulation | |
| Tibulizumab/ Eli Lilly | Biological therapeutic; Bispecifc humanized monoclonal antibody; Subcutaneous | |
| DEN-181/ Janssen | Biological therapeutic; Drug combination; Liposome formulation; Nanoparticle formulation injectable; Peptide; Subcutaneous formulation | |
| Ianalumab/ Novartis | Biological therapeutic; Infusion; Monoclonal antibody human; Subcutaneous formulation | |

Therapeutics for IBD

In some embodiments, the therapeutic suitable for use with the devices and methods described herein is a therapeutic for treating inflammatory bowel disease (IBD). Exemplary therapeutics for treating IBD for delivery using any of the devices or methods described herein include those listed in Table 7.

TABLE 7

Therapeutics adaptable for delivery via ingestible device for the treatment of IBD

| Drug Name/ Company | Existing Formulation Technologies and Methods of Administration | Exemplary Patent Literature |
|---|---|---|
| Certolizumab pegol | Biological therapeutic; Powder; Freeze drying; Monoclonal antibody humanized; PEGylated formulation; Protein conjugated; Protein recombinant; Solution; Subcutaneous | WO-00194585 |
| Ustekinumab | Biological therapeutic; Cell culture; Immunoglobulin-G; Infusion; Intravenous; Monoclonal antibody human; Subcutaneous | WO-00212500 |
| Adalimumab/ Actavis/ Amgen/ Daiichi Sankyo/ Orion; Samsung Bioepis; Sandoz; Fujifilm Kyowa Kirin Biologics/ Mylan; CinnaGen; Reliance Life Sciences; Boehringer Ingelheim; Fresenius; Bio-Thera Solutions | Biological therapeutic; DNA technology; Biosimilar product; Immunoglobulin-G; Monoclonal antibody human; Protein recombinant; Solution; Subcutaneous | US-07517963; US-20130122018; WO-09102078; WO-09729131; WO-2016019726; WO-2018119142; WO-2016000813; WO-2015007912; WO-2013021148; WO-2013186230; WO-2014099636; WO-2019024783 |
| Vedolizumab | Biological therapeutic; Powder; Freeze drying; Immunoglobulin-G; Infusion; Intravenous; Monoclonal antibody humanized; Subcutaneous | WO-09806248 |
| Infliximab/ Celltrion/ Nippon Kayaku/ Hospira/ Orion/EGIS Gyogyszergyar/ Pfizer/ Sandoz; Bionovis/ Fiocruz/IVB Samsung Bioepis/ Merck & Co; Aprogen/ Nichi-Iko Pharm/ Sanofi; AXXO | Biological therapeutic; Cell culture technique; Biosimilar product; Protein recombinant; Chimeric monoclonal antibody; Powder; Freeze drying; Immunoglobulin-G; Infusion; Intra-articular; Intravenous | US-07517963; US-20050255104; WO-09102078; WO-09216553; WO-2006093397; WO-03045400; WO-2006122187 |
| Natalizumab | Biological therapeutic; Cell culture technique; Immunoglobulin-G; Infusion; Intravenous; Monoclonal antibody humanized; Solution; Subcutaneous | WO-09519790 |

TABLE 7-continued

Therapeutics adaptable for delivery via ingestible device for the treatment of IBD

| Drug Name/Company | Existing Formulation Technologies and Methods of Administration | Exemplary Patent Literature |
|---|---|---|
| Guselkumab | Biological therapeutic; Monoclonal antibody human; Subcutaneous | WO-2007005955; WO-2007076524 |
| Golimumab | Biological therapeutic; Immunoglobulin-G; Monoclonal antibody human; Monthly dosing; Solution; Subcutaneous | US-07691378; WO-00212502 |
| Adipose-derived stem cell therapy (Celution System), Cytori | Adipose stem cell therapy; Aerosol formulation dermatological; Autologous stem cell therapy; Biological therapeutic; Dermatological; Infusion; Intravenous; Subcutaneous | US-07887795; WO-03053346 |
| Remestemcel-L | Allogenic stem cell therapy; Biological therapeutic; Haematopoietic stem cell therapy; Intravenous; Mesenchymal stem cell therapy | WO-09623058 |
| Anakinra | Biological therapeutic; Intramuscular; Intravenous; Peptide; Protein recombinant; Subcutaneous | WO-08911540 |
| Clostridium butyricum/Qingdao Eastsea Pharmaceuticals | Biological therapeutic; Capsule; Oral | US-08092793 |
| Bacillus Licheniformis, Northeast Pharmaceutical Group Shenyang No. 1 Pharmaceutical Co. | Biological therapeutic; Capsule; Oral | |
| Risankizumab | Biological therapeutic; Immunoglobulin-G; Infusion; Intravenous; Monoclonal antibody humanized; Subcutaneous | WO-2012061448 |
| Alicaforsen | Biological therapeutic; Oligonucleotide antisense; Rectal formulation; Rectal formulation local | WO-09405333 |
| Bimekizumab | Biological therapeutic; Immunoglobulin-G; Infusion; Intravenous; Monoclonal antibody humanized; Subcutaneous | WO-2008047134 |
| Mirikizumab | Biological therapeutic; Humanized antibody; Immunoglobulin-G; Intravenous; Subcutaneous | WO-2014137962 |
| BI-655130 | Biological therapeutic; Immunoglobulin-G; Infusion; Intravenous; Monoclonal antibody humanized | WO-2013074569 |
| Brazikumab | Biological therapeutic; Infusion; Intravenous; Monoclonal antibody human; Subcutaneous | WO-2011056600 |
| SHP-647 | Biological therapeutic; Immunoglobulin-G; Intravenous; Monoclonal antibody human; Subcutaneous | WO-203 500572 |
| Cobitolimod | Biological therapeutic; Oligonucleotide; Rectal; Rectal formulation local | WO-09535032; WO-2010053430 |
| Umbilical cord blood-derived stem cell therapy, Kang Stem Biotech/Daewoong | Biological therapeutic; Parenteral formulation unspecified; Umbilical cord stem cell therapy | WO-2016048107 |
| Etrolizumab | Biological therapeutic; Immunoglobulin-G; Intravenous; Monoclonal antibody humanized; Protein recombinant; Subcutaneous | WO-2006026759 |
| BBT-401 | Biological therapeutic; Capsule; Oral; Peptide | |
| SER-287 | Bacterium novel; Biological therapeutic; Capsule; Cell therapy; Oral | WO-2017008026 |
| KHK-4083 | Biological therapeutic; Intravenous; Monoclonal antibody human; Subcutaneous | WO-2007062245 |
| AbGn-168H | Biological therapeutic; Infusion; Intravenous; Monoclonal antibody humanized | EP-01663290; WO-03013603 |
| RG-7880 | Biological therapeutic; Immunoglobulin; Infusion; Intravenous; Protein fusion; Protein recombinant; Subcutaneous | WO-2005009238 |
| SB-012 | Biological therapeutic; DNA technology; Oligonucleotide antisense; Rectal formulation; Rectal formulation local | |
| Olamkicept | Biological therapeutic; Intravenous; Protein fusion | WO-2007071449 |
| Bertilimumab | Biological therapeutic; Immunoglobulin-G; Infusion; Intravenous; Monoclonal antibody human; Parenteral formulation unspecified; Subcutaneous | WO-00166754 |
| PF-06480605 | Biological therapeutic; Intravenous; Subcutaneous | |
| PF-06687234 | Antibody fragment; Biological therapeutic; Intravenous; Protein fusion; Subcutaneous | WO-2009056268 |
| IBP-9414 | Biological therapeutic; Natural product; Oral | WO-2016113363 |
| Molgramostim + fosfomycin + carbapenem)/Reponex | Antibiotic; Biological therapeutic; Capsule; Follow on biological product; Local formulation unspecified; Oral; Peptide; Protein recombinant; Rectal formulation; Rectal formulation local | |
| STNM-01 | Biological therapeutic; Injectable; Local formulation unspecified; Oligonucleotide; Parenteral formulation unspecified; Transmucosal | WO-2008020489 |
| Adrenomedullin/University of Miyazaki | Biological therapeutic; Intravenous; Parenteral formulation unspecified; Peptide | |
| Tulinercept | Antibody fragment; Biological therapeutic; Immunoglobulin-G; Oral; Protein fusion | WO-2014136113 |
| E-6011, EA Pharma | Biological therapeutic; Intravenous; Monoclonal antibody | EP-03211007 |

TABLE 7-continued

Therapeutics adaptable for delivery via ingestible device for the treatment of IBD

| Drug Name/ Company | Existing Formulation Technologies and Methods of Administration | Exemplary Patent Literature |
|---|---|---|
| STP-206 | Biological therapeutic; Natural product; Parenteral formulation unspecified | WO-2005032567 |
| FFP-104 | Biological therapeutic; Monoclonal antibody; Parenteral formulation unspecified | WO-09858678 |
| Ciclosporin/ Sublimity Therapeutics/ Dr Falk Pharma | Biological therapeutic; Capsule; Oral controlled release ; Oral; Peptide | WO-2004084870 |
| AEVI-002 | Biological therapeutic; Monoclonal antibody human; Parenteral formulation unspecified; Subcutaneous | WO-2013148350 |
| Midismase | Biological therapeutic; Controlled release; Infusion; Intravenous; Protein conjugated | EP-00406804 |
| V-565 | Antibody; Biological therapeutic; Oral; Protein recombinant; Tablet | WO-2016156465; WO-2016156468; WO-2016156474; WO-2016156475 |
| PF-06835375 | Biological therapeutic; Intravenous; Subcutaneous | |
| EB-8018 | Small molecule therapeutic; oral formulation | |
| PF-06826647 | Small molecule therapeutic; oral formulation | |
| JNJ-4447 | Biological therapeutic; Capsule formulation; Oral formulation | |
| IONIS-JBI1-2.5Rx | Biological therapeutic; Local formulation unspecified; Oligonucleotide antisense; Oral formulation; RNA antisense | |

Therapeutics for Short Bowel Syndrome

Short bowel syndrome (SBS) is a malabsorption disorder caused by a lack of functional small intestine. The primary symptom is diarrhea, which can result in dehydration, malnutrition, and weight loss. An exemplary therapeutic for treating SBS for delivery using any of the devices or methods described herein includes teduglutide, which is a GLP-2 receptor agonist. Teduglutide is described in the U.S. Pat. Nos. 5,789,379 and 7,056,886, both of which are hereby incorporated by reference.

Therapeutics for Blood Disorders

In some embodiments, the therapeutic suitable for use with the devices and methods described herein is a therapeutic for treating blood disorders. In some embodiments, the blood disorder is anemia. In some embodiments, the therapeutic for treating anemia is a recombinant human erythropoietin. In some embodiments, the therapeutic for treating anemia is a human erythropoietin analog. In some embodiments, the therapeutic for treating anemia is selected from darbepoetin alpha/alfa and epoetin alfa; and biosimilars thereof.

Ziltivekimab (COR-001), a human IgG1k anti-inflammatory IL-6 monoclonal antibody, is being developed for the potential treatment of anemia, chronic kidney disease, and/or cardiovascular disease. Ziltivekimab is an exemplary therapeutic for treating any one or more of these conditions via delivery using any of the devices or methods described herein. Ziltivekimab is described is PCT Publication No. WO-2019136312, which is hereby incorporated by reference.

In some embodiments, the blood disorder is a sickle cell disease. In some embodiments, the blood disorder is thalassemia. In some embodiments, the therapeutic for treating sickle cell disease or thalassemia is selected from PF-04447943, crizanlizumab, EPI-01 and rivipansel sodium.

In some embodiments, the blood disorder is hemophilia. In some embodiments, the hemophilia is hemophilia A, hemophilia B, or Von Willebrand disease.

In some embodiments, the therapeutic for treating hemophilia is an alternative coagulation promotor (ACP). In some embodiments, the ACP is an anti-tissue factor pathway inhibitor (anti-TFPI). Exemplary anti-TFPIs include, but are not limited to, concizumab, MG-1113A (GC Pharma, Gyeonggi-do, South Korea), marstacimab (PF-6741086) or BAY-1093884; or biosimilars thereof. In some embodiments, the anti-TFPI is concizumab or a biosimilar thereof.

In some embodiments, the therapeutic for treating hemophilia is a factor VIII mimetic. In some embodiments, the factor VIII mimetic is emicizumab or a biosimilar thereof. In some embodiments, the factor VIII mimetic is a bi-specific antibody such as NNC0365-3769 A (Mim8) described in WO 2019/096874, which is herein incorporated by reference in its entirety.

In some embodiments, the therapeutic for treating hemophilia is selected from albutrepenonacog alfa, AMT-061, beroctocog alpha, betafact, BIVV-001, BS027125, byclot, catridecacog, clotnine, dalcinonacog alfa, damoctocog alfa pegol, DTX-201, eftrenonacog alfa, eptacog alfa, Factor VIII, Factor IX, Factor X, fidanacogene elaparvovec, fitusiran, FLT-180a, hemoleven, lonoctocog alfa, LR-769, marzeptacog alfa, monofix, moroctocog alfa, NIBX-2101, nonacog alfa, nonacog beta pegol, octocog alfa, OPK-88005, recolyl, recombinate, rurioctocog alfa pegol, simoctocog alfa, SHP-654, SB-525, SPK-8011, SPK-8016, SCT-800, AAV2/8-HLP-FVIII-v3, susoctocog alfa, trenonacog alfa and valoctocogene roxaparvovec; and biosimilars thereof.

In some embodiments, the therapeutic for treating hemophilia is a recombinant factor VIIa. Exemplary recombinant factor VIIa include OPK-88005 (OPKO Health, Miami, Fla.) and LR-769 (see, e.g., Chevreux et al., Haemophilia 23(4):e324-e334 (2017)). Additional exemplary therapeutics for treating hemophilia for delivery using any of the devices or methods described herein include those listed in Table 8.

TABLE 8

Therapeutics adaptable for delivery via ingestible device for the treatment of hemophilia

| Drug Name/ Class/Company | Existing Formulation Technologies and Methods of Administration | Exemplary Patent Literature |
|---|---|---|
| Damoctocog alfa pegol | Biological therapeutic; Infusion; Intravenous; PEGylated formulation; Protein recombinant; Sustained release | WO-2010083536 |

TABLE 8-continued

Therapeutics adaptable for delivery via ingestible device for the treatment of hemophilia

| Drug Name/ Class/Company | Existing Formulation Technologies and Methods of Administration | Exemplary Patent Literature |
|---|---|---|
| Efmoroctocog alfa | Antibody fragment; Biological therapeutic; Cell culture technique; Powder; Freeze drying; Immunoglobulin-G; Injectable controlled release; Protein fusion; Protein recombinant | WO-2011069164 |
| Octocog alfa/Bayer; Baxalta; Genentech/ Bayer/Aventis | Biological therapeutic; Plasma-free, sucrose-formulated; Intravenous; Peptide; Protein recombinant; Powder; Freeze drying; Glycoprotein; Infusion | EP-00160457; EP-00818204; EP-00152746; EP-00160457; EP-00818204 |
| Rurioctocog alfa pegol | Biological therapeutic; Formulation powder; Freeze drying; Intravenous; PEGylated formulation; Protein recombinant; Sustained release | US-07884075; WO-2004075923; WO-2006071801 |
| Albutrepenonacog alfa | Biological therapeutic; Infusion; Intravenous; Protein fusion; Protein recombinant; Sustained release | WO-00177137; WO-2007144173 |
| Lonoctocog alfa | Biological therapeutic; Infusion; Parenteral formulation unspecified; Protein recombinant | WO-2004067566 |
| Trenonacog alfa | Biological therapeutic; Freeze drying; Infusion; Intravenous; Protein recombinant | WO-2009082648 |
| Nonacog gamma | Biological therapeutic; Cloning technology; Powder; Freeze drying; Infusion; Intravenous; Protein recombinant; Solution | WO-2011135071 |
| Turoctocog alfa/Novo Nordisk | Biological therapeutic; Powder; Freeze drying; Intravenous; Protein recombinant | WO-2007055789; WO-2009108806 |
| Turoctocog alfa pegol/ Novo Nordisk | Biological therapeutic; Lyophilized powder; Intravenous PEGylated; long-acting; Protein recombinant | |
| Von Willebrand/Factor VIII therapy/Alpha Therapeutic | Biological therapeutic; Intravenous; Peptide | EP-00144709 |
| Emicizumab | Biological therapeutic; Immunoglobulin-G; Monoclonal antibody humanized; Multivalent monoclonal antibody; Protein recombinant; Subcutaneous | WO-2005035753; WO-2012067176 |
| Nonacog alfa/IBC Generium/CJSC Generium/Stragen | Biological therapeutic; Biosimilar product; Powder; Freeze drying; Infusion; Intravenous; Peptide; Protein recombinant | EP-00430930 |
| Nonacog beta pegol | Biological therapeutic; Powder; Freeze drying; Glycoprotein; Infusion; Intravenous; PEGylated formulation; Protein recombinant; Sustained release | WO-03031464; WO-03045980; WO-03046150; WO-2004099231; WO-2006127896; WO-2008060780 |
| Eptacog alfa (activated)/ Aryogen; IBC Generium/CJSC Generium/Stragen; Revo Biologics/LFB | Biological therapeutic; Biosimilar product; Powder; Freeze drying; Intravenous; Protein recombinant; Solution; Transgenic animal | EP-00200421; WO-2008155509; |
| Factor VIII concentrate (albumin-free), CSL | Biological therapeutic; Blood constituents; Infusion; Intravenous | |
| Simoctocog alfa | Biological therapeutic; Infusion; Intravenous; Protein recombinant | WO-00170968 |
| Eftrenonacog alfa | Antibody fragment; Biological therapeutic; Powder; Freeze drying; Immunoglobulin-G; Injectable controlled release; Intravenous; Protein fusion | WO-2004101740; WO-2007112005 |
| Susoctocog alfa | Biological therapeutic; Formulation powder; Freeze drying; Infusion; Intravenous; Protein recombinant | WO-09749725 |
| Factor VIII follow-on biologic, AXXO | Biological therapeutic; Follow on biological product; Intravenous; Protein recombinant | |
| Moroctocog alfa | Biological therapeutic; Injectable; Parenteral formulation unspecified; Protein recombinant | WO-08606101 |
| Factor VIII (plasma-derived)/Octapharma/ Shire | Biological therapeutic; Intravenous; Peptide; Blood constituents; Freeze drying; Infusion | WO-09110439; US-03631018 |
| Factor XIII concentrate, CSL | Biological therapeutic; Intravenous; Peptide | WO-2005079839 |
| Monofix | Biological therapeutic; Intravenous; Peptide | EP-00118256 |
| Hemoleven | Biological therapeutic; Blood constituents; Parenteral formulation unspecified; Peptide; Systemic formulation unspecified | |

TABLE 8-continued

Therapeutics adaptable for delivery via ingestible device for the treatment of hemophilia

| Drug Name/ Class/Company | Existing Formulation Technologies and Methods of Administration | Exemplary Patent Literature |
| --- | --- | --- |
| Catridecacog | Biological therapeutic; Formulation powder; Freeze drying; Intravenous; Protein recombinant | EP-00268772 |
| Byclot | Biological therapeutic; Drug combination; Freeze drying; Intravenous; Peptide | JP-04046377 |
| Factor VIII/von Willebrand Factor complex, CSL | Biological therapeutic; Infusion; Intravenous; Peptide | WO-2008151817 |
| Recombinant moroctocog alfa (plasma/albumin-free), Wyeth | Biological therapeutic; Powder; Freeze drying; Glycoprotein; Infusion; Intravenous; Protein recombinant | WO-08606101 |
| Beroctocog alpha (albumin-free)/GC Pharma | Biological therapeutic; Infusion; Intravenous; Protein recombinant | EP-01712223 |
| Moroctocog alfa biosimilar, IBC Generium/CJSC Generium/Stragen | Biological therapeutic; Biosimilar product; Intravenous; Protein recombinant | |
| Beroctocog alfa | Biological therapeutic; Infusion; Intravenous; Protein recombinant | KR-00251286 |
| Factor VIII concentracte, Kedrion Biopharma | Blood constituents; Infusion; Intravenous; Small molecule therapeutic | |
| Factor XI concentrate, CSL Behring | Blood constituents; Parenteral formulation unspecified; Small molecule therapeutic; Systemic formulation unspecified | |
| Factor VIII/Tonrol Biopharmaceutical; Novo Nordisk | Biological therapeutic; Blood constituents; Intravenous; Peptide | WO-08403628 |
| Recombinate | Biological therapeutic; Powder; Freeze drying; Glycoprotein; Intravenous; Protein recombinant | WO-08501961 |
| Factor XP/Behring | Biological therapeutic; Freeze drying; Intravenous; Peptide | |
| Human coagulation factor VIII, Hemarus | Biological therapeutic; Blood constituents; Intravenous; Protein recombinant | WO-2015114664 |
| Clotnine | Biological therapeutic; Blood constituents; Intravenous; Protein recombinant | WO-2015114664 |
| Betafact | Biological therapeutic; Peptide; Systemic formulation unspecified | EP-00317376 |
| Factor VIII follow-on biologic, Shandong Taibang Biological Products | Biological therapeutic; Follow on biological product; Parenteral formulation unspecified; Protein recombinant | CN-102295696 |
| Moroctocog alfa follow-on biologic, Amega | Biological therapeutic; Follow on biological product; Parenteral formulation unspecified; Protein recombinant | |
| Plasma derived factor VIII (pegylated liposomal (neclip), Recoly | Biological therapeutic; Liposome; PEGylated formulation; Protein conjugated | WO-09955306 |
| Human prothrombin complex concentrate (plasma-derived), Nanyue Biopharming; Shanxi Kangbao Biological Products | Biological therapeutic; Blood constituents; Infusion; Intravenous; Peptide | |
| Factor IX, Shandong Taibang Biological Products | Biological therapeutic; Intravenous; Peptide | |
| Factor VIII biosimilar, Shanxi Kangbao Biological Products | Biological therapeutic; Biosimilar product; Intravenous | |
| Factor VIII (plasma-derived), Beijing Tiantan Biological Products | Biological therapeutic; Blood constituents; Parenteral formulation unspecified | |
| FLT-180a | Biological therapeutic; Infusion; Virus recombinant | |
| SPK-8011 | Biological therapeutic; Infusion; Intravenous; Nanoparticle formulation injectable; Virus recombinant | WO-2018017956 |
| Fitusiran | Biological therapeutic; Oligonucleotide; Subcutaneous | WO-2004015107 |
| Valoctocogene roxaparvovec | Biological therapeutic; Infusion; Intravenous; Virus recombinant | WO-2013186563 |

TABLE 8-continued

Therapeutics adaptable for delivery via ingestible device for the treatment of hemophilia

| Drug Name/Class/Company | Existing Formulation Technologies and Methods of Administration | Exemplary Patent Literature |
|---|---|---|
| AMT-061 | Biological therapeutic; Infusion; Intravenous; Virus recombinant | WO-2009014445 |
| Fidanacogene elaparvovec | Biological therapeutic; Infusion; Intravenous; Virus recombinant | WO-02063025; WO-08400560; WO-09841240 |
| Plasma-derived Factor VIII, CSL/Zhong Yuan Rui De Biological Products | Biological therapeutic; Blood constituents; Parenteral formulation unspecified | |
| SCT-800 | Biological therapeutic; Intravenous; Protein recombinant | |
| Moroctocog alfa/Chia Tai Tianqing Pharmaceutical Group | Biological therapeutic; Biosimilar product; Intravenous; Peptide; Protein recombinant | |
| Factor IX/Sichuan Yuanda Shuyang Pharmaceutical | Biological therapeutic; Powder; Infusion; Intravenous; Peptide | |
| Factor VIII/Guangdong Danxia Biopharm | Biological therapeutic; Biosimilar product; Blood constituents; Intravenous | |
| Dalcinonacog alfa/Catalyst Biosciences | Biological therapeutic; Intravenous; Protein recombinant; Subcutaneous | WO-2012061654 |
| Marzeptacog alfa (activated) | Biological therapeutic; Infusion; Intravenous; Protein recombinant; Subcutaneous; Sustained release | WO-2008127702; WO-2009126307 |
| DTX-201 | Biological therapeutic; Infusion; Intravenous; Virus recombinant | |
| Factor IX gene therapy, Sangamo | Biological therapeutic; Intravenous; Virus recombinant | WO-2010021692; WO-2012051343 |
| BIVV-001 | Biological therapeutic; Intravenous; Protein fusion; Protein recombinant; Subcutaneous | WO-2013122617 |
| SHP-654 | Biological therapeutic; Infusion; Intravenous; Nanoparticle formulation injectable; Protein recombinant; Virus recombinant | WO-2018128688; WO-2018128689 |
| Marstacimab | Biological therapeutic; Immunoglobulin-G; Infusion; Intravenous; Monoclonal antibody humanized; Subcutaneous | WO-2017029583 |
| SPK-8016 | Biological therapeutic; Infusion; Intravenous; Virus recombinant | |
| BAY-1093884 | Biological therapeutic; Immunoglobulin-G; Intravenous; Monoclonal antibody human; Subcutaneous | |
| AAV2/8-HLP-FVIII-v3 | Biological therapeutic; Infusion; Intravenous; Virus recombinant | |
| SB-525 | Biological therapeutic; Gene transfer system non-viral; Infusion; Intravenous; Virus recombinant | WO-2015089046 |
| Concizumab | Biological therapeutic; Immunoglobulin-G; Monoclonal antibody humanized; Subcutaneous | WO-2010072691 |
| Factor VIIa-CTP | Biological therapeutic; Intravenous; Protein fusion; Subcutaneous; Sustained release | WO-2011004361; WO-2013121416 |

Therapeutics for Hepatocellular Carcinoma

In some embodiments, the therapeutic suitable for use with the devices and methods described herein is a hepatocellular carcinoma drug. Hepatocellular carcinoma is the most common type of primary liver cancer and the most common cause of death in people with cirrhosis. Drugs to treat hepatocellular carcinoma include but are not limited to nivolumab, lenvatinib, sorafenib, regorafenib, PF-04518600, emibetuzumab, and carbozantinib.

Target-Based Therapeutics

GLP-1 Receptor Agonists

In some embodiments, the therapeutic suitable for use with the devices and methods described herein is a glucagon-like peptide 1 (GLP-1) receptor agonist. The GLP-1 pathway has been indicated in the treatment of type 2 diabetes mellitus (T2DM). In some embodiments, the GLP-1 receptor agonist is a peptide. In some embodiments, the GLP-1 receptor agonist is a small molecule. In some embodiments, the GLP-1 receptor agonist is formulated with a carrier, or delivery agent. In some embodiments, the carrier or delivery agent is a salt of a medium chain fatty acid derivative. In some embodiments, the carrier or delivery agent is the sodium salt of N-[8-(2-hydroxybenzoyl)amino] caprylate (SNAC). In some embodiments, the carrier or delivery agent is biotin.

In some embodiments, the GLP-1 receptor agonist is exanatide (synthetic exendin-4), a 39-residue peptide which shares 53% sequence identity with GLP-1, having the sequence: HGEGTFTSDLSKQMEEEAVRLFIEW-LKNGGPSSGAPPPS-NH$_2$ (SEQ ID NO:1).

In some embodiments, the GLP-1 receptor agonist is a compound with a structure selected from:

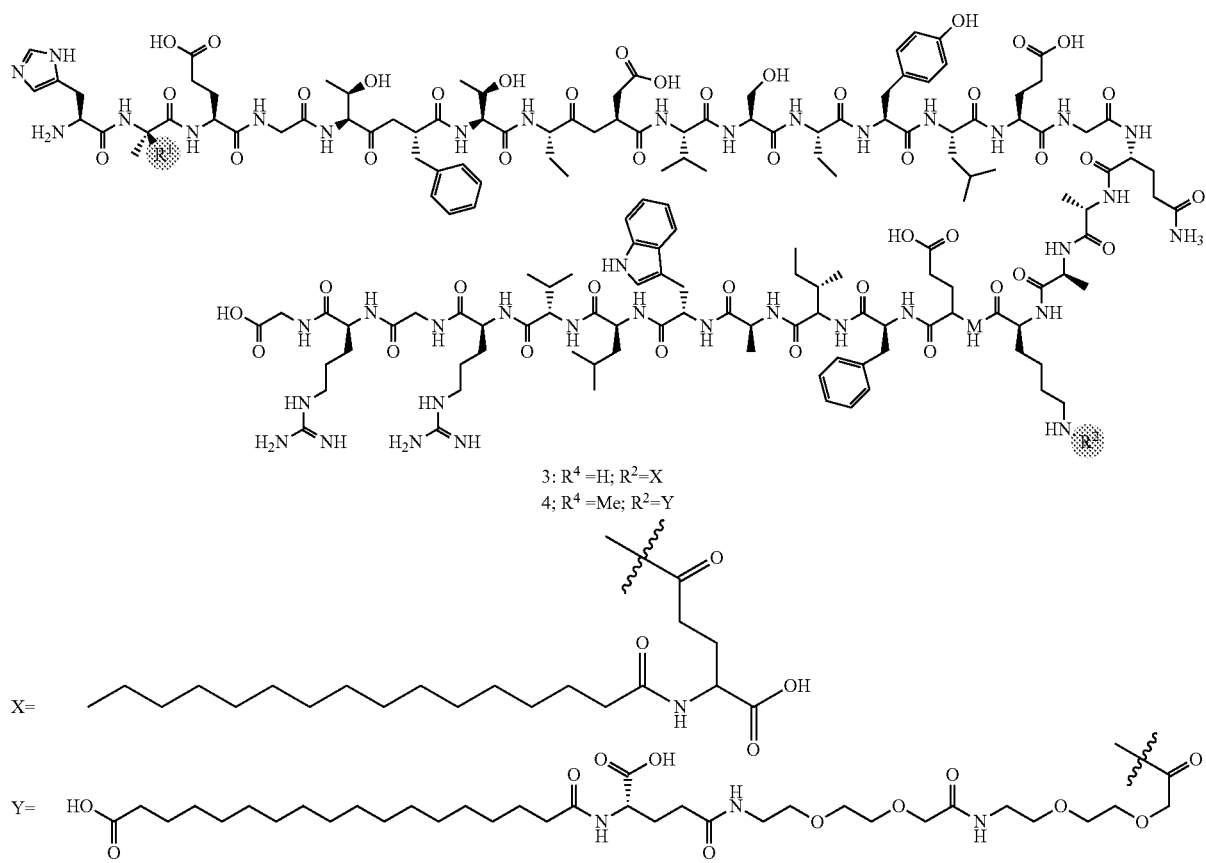

3: R⁴ =H; R²=X
4; R⁴ =Me; R²=Y or any pharmaceutically acceptable salt thereof. In some embodiments, the GLP-1 receptor agonist is liraglutide (compound 3) or a pharmaceutically acceptable salt thereof. In some embodiments, the GLP-1 receptor agonist is semaglutide (compound 4) or a pharmaceutically acceptable salt thereof.

In some embodiments, the GLP-1 receptor agonist is a compound having the structure:

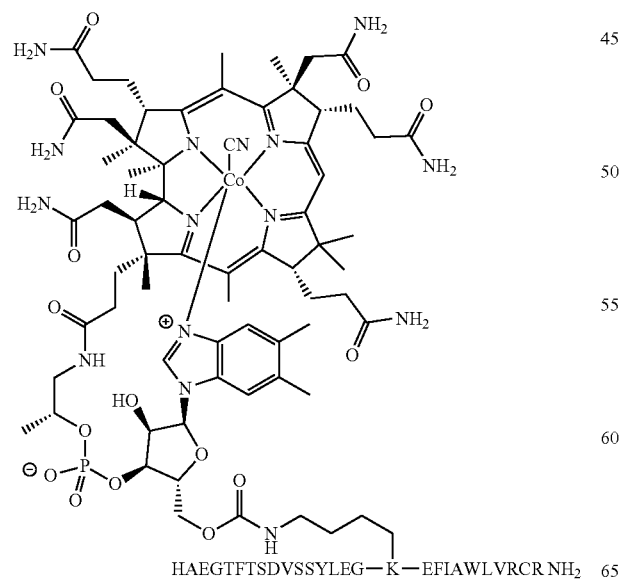

HAEGTFTSDVSSYLEG—K—EFIAWLVRCR NH₂ or a pharmaceutically acceptable salt thereof.

In some embodiments, the GLP-1 receptor agonist is an 11-mer GLP-1 receptor agonist. Exemplary 11-mer GLP-1 receptor agonists are represented by the structures and the table below.

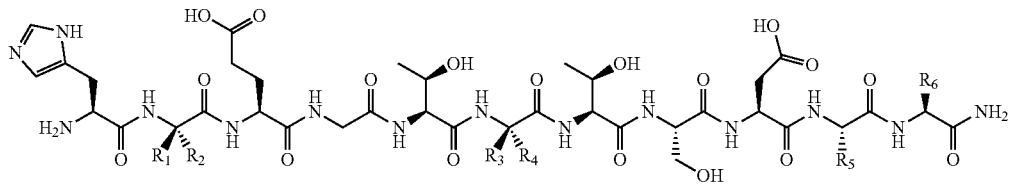

| Cpd | R¹ | R² | R³ | R⁴ | R⁵ | R⁶ | hGLP-1R cAMP EC$_{50}$ (nM) |
|---|---|---|---|---|---|---|---|
| 8 | H | Me | H | Bn | BIP | BIP | 545 |
| 9 | H | Me | H | Bn | BIP(2'-Et,4'-OMe) | BIP(2'-Me) | 7.0 |
| 10 | Me | Me | Me | 2-F-Bn | BIP(2'-Et,4'-OMe) | BIP(2'-Me) | 0.087 |

In some embodiments, the GLP-1 receptor agonist is a compound having the structure:

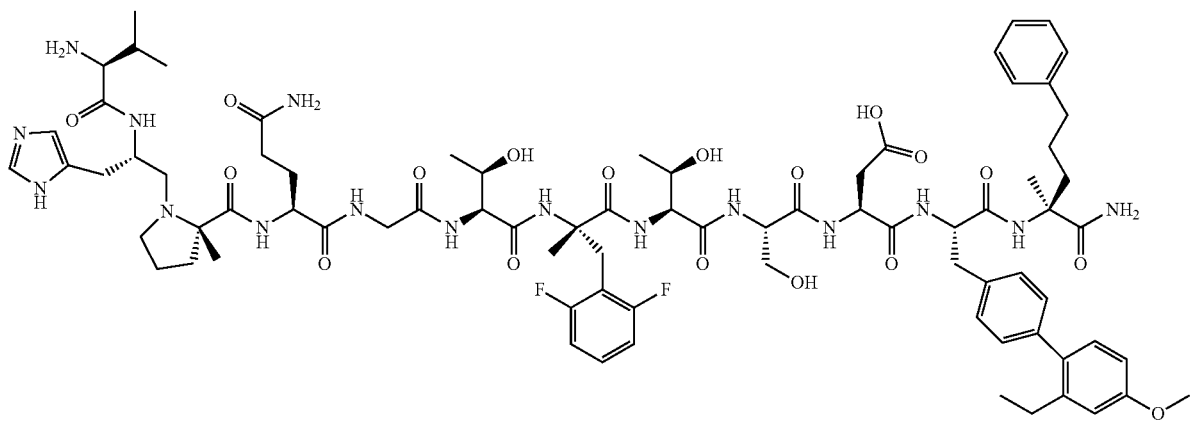 [SMILES: CCc1cc(OC)ccc1-c1ccc(C[C@H](NC(=O)[C@H](CC(=O)O)NC(=O)[C@H](CO)NC(=O)[C@@H](NC(=O)[C@](C)(Cc2c(F)cccc2F)NC(=O)[C@@H](NC(=O)CNC(=O)[C@H](CCC(N)=O)NC(=O)[C@]2(C)CCCN2C[C@H](Cc2cnc[nH]2)NC(=O)[C@@H](N)C(C)C)[C@@H](C)O)[C@@H](C)O)C(=O)N[C@@](C)(CCCc2ccccc2)C(N)=O)cc1]

or a pharmaceutically acceptable salt thereof.

In some embodiments, the GLP-1 receptor agonist is a compound with a structure selected from:

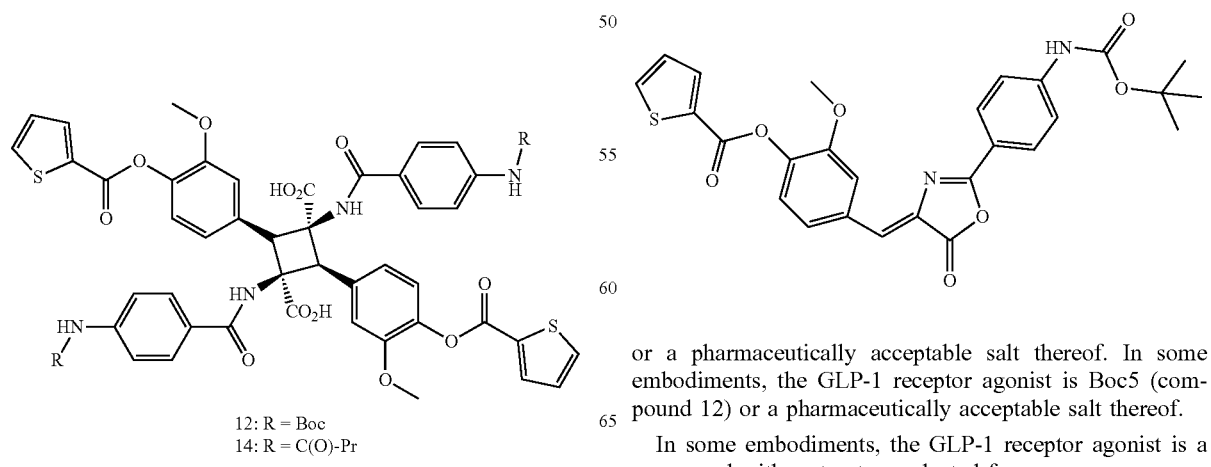

12: R = Boc
14: R = C(O)-Pr

13 or a pharmaceutically acceptable salt thereof. In some embodiments, the GLP-1 receptor agonist is Boc5 (compound 12) or a pharmaceutically acceptable salt thereof.

In some embodiments, the GLP-1 receptor agonist is a compound with a structure selected from:

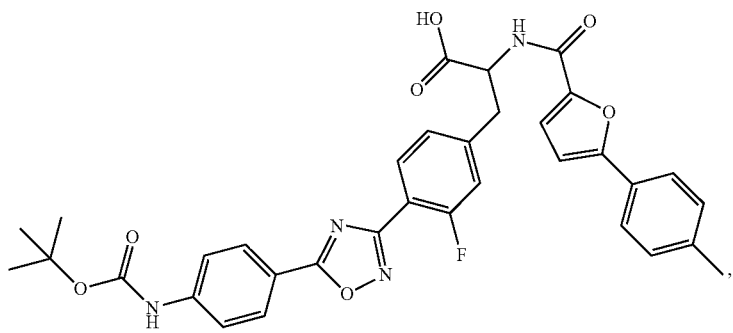

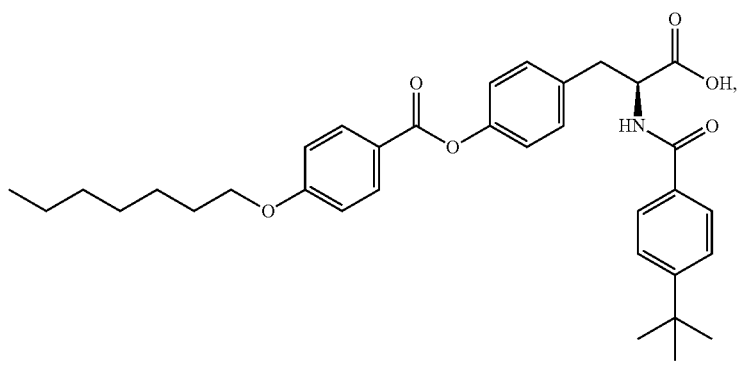

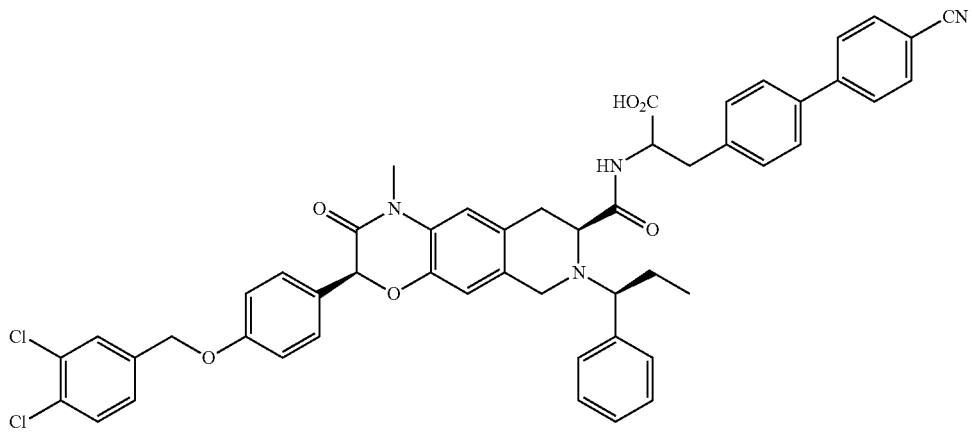

or pharmaceutically acceptable salts thereof. In some embodiments, the GLP-1 receptor agonist is TTP-054 or a pharmaceutically acceptable salt thereof, such as described in Edmonds et al., Annu. Rep. Med. Chem. (2013) 48:119-130, which is herein incorporated by reference in its entirety.

In some embodiments, the GLP-1 receptor agonist is TTP273 or a pharmaceutically acceptable salt thereof, such as described in Freeman et al., Diabetol. Conf. 53rd Annu. Meet. Eur. Assoc. study diabetes, EASD 2017. Port. Vol. 60. No. 1 Supplement 1. 2017, which is herein incorporated by reference in its entirety.

In some embodiments, the GLP-1 receptor agonist is OWL883, such as described in Kawai et al., Diabetes (2018) 67(Supplement 1):1118-P, which is herein incorporated by reference in its entirety.

In some embodiments, the GLP-1 receptor agonist is a compound described in Edmonds and Price, "Chapter Nine: Oral GLP-1 Modulators for the Treatment of Diabetes," Ann. Rep. Med. Chem. (2013) 48:119-130, which is herein incorporated by reference in its entirety.

Other exemplary GLP-1 receptor agonists for delivery using any of the devices or methods described herein include those listed in Table 9.

TABLE 9

GLP-1 receptor agonists adaptable for delivery via ingestible
device for the treatment of the listed diseases and conditions

| GLP-1 Agonist (Company) | Tradename | Dosage and Administration | Comments |
|---|---|---|---|
| Albiglutide (GSK) | Tanzeum EU: Eperzan | 30 mg/dose (0.82 μmol); up to 50 mg/dose; Once weekly, subcutaneus injection | GLP-1 (7-36) dimer fused to recombinant human albumin. MWt ~73 kDa. |
| Dulaglutide (Eli Lilly) | Trulicity | 0.75 mg/dose (0.024 μmol); up to 1.5 mg/dose; Once weekly, subcutaneus injection | GLP-1(7-37) covalently linked to an Fc fragment of human IgG4. MWt ~63 kDa |
| Exenatide (Astra Zeneca) | Byetta | 5 μg/dose (1.2 nmol); up to 10 μg/dose; Twice daily, subcutaneus injection | Synthetic form of exendin-4, a peptide isolated from *H. suspectum* venom MWt ~4 KDa |
| | Bydureon, Bydureon Bcise | 2 mg/dose (0.48 μmole), Once weekly, subcutaneus injection | Extended release microsphere formulations. |
| Liraglutide (Novo Nordisk) | Victoza | 0.6 mg/dose (0.16 μmol); up to 1.8 mg/dose; Once daily, subcutaneus injection | Fatty acylated GLP-1 analog. MWt ~4 KDa. |
| | Saxenda | 0.6 mg/dose (0.16 μmol); up to 3 mg/dose; Once daily, subcutaneus injection | |
| Lixisenatide (Sanofi-Aventis) | Adlyxin EU: Lyxumia | 10 μg/dose (2.06 nmol); up to 20 μg/dose; Once daily, subcutaneus injection | Recombinant DNA-produced GLP-1 analog. MWt ~5 KDa. |
| Semaglutide (Novo Nordisk) | Ozempic | 0.25 mg/dose (0.061 μmol); up to 1 mg/dose; Once weekly, subcutaneus injection | GLP-1-like peptide-1 analog. MWt ~4 KDa. Longer acting alternative to liraglutide. |
| Semaglutide (Novo Nordisk) | Rybelsus | 3 mg oral tablet once daily for first 30 days; followed by 7 mg oral tablet once a day | GLP-1-like peptide-1 analog; oral formulation with Emisphere Technologies' Eligen SNAC Carrier Technology |

PCSK9 Inhibitors

In some embodiments, the therapeutic suitable for use with the devices and methods described herein is a proprotein convertase subtilisin/kexin type 9 (PCSK9) inhibitor. In some embodiments, the PCSK9 inhibitor treats one or more of endocrine and/or metabolic diseases or conditions, cardiovascular diseases, and infection. In some embodiments, the endocrine and/or metabolic disease or condition is familial hypercholesterolemia, hypercholesterolemia, or hyperlipidemia.

In some embodiments, the PCSK9 inhibitor is alirocumab. In some embodiments, the PCSK9 inhibitor is evolocumab. Other exemplary PCSK9 inhibitors for delivery using any of the devices or methods described herein include those listed in Table 10.

TABLE 10

PCSK9 inhibitors adaptable for delivery via ingestible device
for the treatment of the listed diseases and conditions

| Drug Name | Existing Formulation Technologies and Methods of Administration | Therapy Area | Active Indications | Exemplary Patent Literature & Other |
|---|---|---|---|---|
| alirocumab | Biological therapeutic; Cell culture technique; Immunoglobulin-G; Monoclonal antibody human; Solution; Subcutaneous formulation | Endocrine/Metabolic; Cardiovascular; Infection | Atherosclerosis; Familial hypercholesterolemia; Hypercholesterolemia; Lipid metabolism disorder; Sepsis; Septic shock | WO2010077854 Tavori, Hagai, Michelle Melone, and Shirya Rashid. "Alirocumab: PCSK9 inhibitor for LDL cholesterol reduction." Expert review of cardiovascular therapy 12.10 (2014): 1137-1144. |
| evolocumab | Biological therapeutic; Cell culture technique; Immunoglobulin- | Endocrine/Metabolic | Familial hypercholesterolemia; Hypercholesterolemia; Hyperlipidemia; Lipid metabolism | WO2009026558 Kasichayanula, Sreeneeranj, et al. "Clinical pharmacokinetics |

TABLE 10-continued

PCSK9 inhibitors adaptable for delivery via ingestible device
for the treatment of the listed diseases and conditions

| Drug Name | Existing Formulation Technologies and Methods of Administration | Therapy Area | Active Indications | Exemplary Patent Literature & Other |
|---|---|---|---|---|
| | G; Monoclonal antibody human; Solution; Subcutaneous formulation | | disorder | and pharmacodynamics of evolocumab, a PCSK9 inhibitor." Clinical pharmacokinetics 57.7 (2018): 769-779. |
| bococizumab | Biological therapeutic; Humanized monoclonal antibody | Endocrine/Metabolic | Hypercholesterolemia; Hyperlipidemia | Ridker, Paul M., et al. "Cardio vascular efficacy and safety of bococizumab in high-risk patients." New England Journal of Medicine 376.16 (2017): 1527-1539. |
| frovocimab | Biological therapeutic; humanized immunoglobulin G4 (IgG4) monoclonal antibody | Endocrine/Metabolic | Hypercholesterolemia; Hyperlipidemia | Kastelein, John JP, et al. "Safety and efficacy of LY3015014, a monoclonal antibody to proprotein convertase subtilisin/kexin type 9 (PCSK9): a randomized, placebo-controlled Phase 2 study." European heart journal 37.17 (2016): 1360-1369. |
| 1D05-IgG2 | Biological therapeutic; fully humanized monoclonal antibody | Endocrine/Metabolic | Hypercholesterolemia; Hyperlipidemia | Ni, Yan G., et al. "A PCSK9-binding antibody that structurally mimics the EGF (A) domain of LDL-receptor reduces LDL cholesterol in vivo." Journal of lipid research 52.1 (2011): 78-86. |
| evinacumab | Biological therapeutic; a fully human monoclonal antibody to ANGPTL3 | Endocrine/Metabolic | Hypercholesterolemia; Hyperlipidemia | US-9018356 Gaudet, Daniel, et al. "Safety and efficacy of evinacumab, a monoclonal antibody to ANGPTL3, in patients with homozygous familial hypercholesterolemia: A single-arm, open-label, proof-of-concept study." Atherosclerosis 263 (2017): e9. |
| Lodelcizumab | Biological therapeutic; monoclonal antibody | Endocrine/Metabolic; Cardiovascular; Infection | Hypercholesterolemia; Lipid metabolism disorder; Sepsis; Septic shock | WO2011072263 |
| SHR-1209 | Antibody; Biological therapeutic; Freeze drying; Subcutaneous formulation | Endocrine/Metabolic | Hypercholesterolemia; Hyperlipidemia | WO2017114230 |
| IBI-306 | Biological therapeutic; Intravenous formulation; | Endocrine/Metabolic | Hypercholesterolemia; Hyperlipidemia | WO2018113781 |

TABLE 10-continued

PCSK9 inhibitors adaptable for delivery via ingestible device
for the treatment of the listed diseases and conditions

| Drug Name | Existing Formulation Technologies and Methods of Administration | Therapy Area | Active Indications | Exemplary Patent Literature & Other |
|---|---|---|---|---|
| LIB-003 | Monoclonal antibody human; Protein recombinant; Subcutaneous formulation | Endocrine/Metabolic | Familial hypercholesterolemia; Hypercholesterolemia | WO2011130354 |
| JS-002 | Biological therapeutic; Infusion; Intravenous formulation; Protein fusion; Protein recombinant; Subcutaneous formulation | Endocrine/Metabolic | Hypercholesterolemia; Lipid metabolism disorder | WO2017088782 |
| AK-102 | Biological therapeutic; Infusion; Intravenous formulation; Monoclonal antibody humanized; Protein recombinant; Subcutaneous formulation | Endocrine/Metabolic | Familial hypercholesterolemia | WO2016127912 |
| ATH-06 | Biological therapeutic; Humanized antibody; Subcutaneous formulation | Cardiovascular; Endocrine/Metabolic | Hypercholesterolemia | WO2015128287 |
| ATH-04 | Biological therapeutic; Peptide; Subcutaneous formulation | Cardiovascular; Endocrine/Metabolic | Hypercholesterolemia | WO2015128287 |
| C-8304 | Biological therapeutic; Peptide; Subcutaneous formulation | Endocrine/Metabolic | Hyperlipidemia | WO2010075469 |
| | Oral formulation; Small molecule therapeutic; Tablet formulation | | | |

TNFα Inhibitors

In some embodiments, the therapeutic suitable for use with the devices and methods described herein is a TNFα inhibitor. The terms "TNFα inhibitor" or "TNF-alpha inhibitor" refer to an agent which directly or indirectly inhibits, impairs, reduces, down-regulates, or blocks TNFα activity and/or expression. In some embodiments, a TNFα inhibitor is an inhibitory nucleic acid, an antibody or an antigen-binding fragment thereof, a fusion protein, a soluble TNFα receptor (a soluble TNFR1 or a soluble TNFR2), or a small molecule TNFα antagonist. In some embodiments, the inhibitory nucleic acid is a ribozyme, small hairpin RNA, a small interfering RNA, an antisense nucleic acid, or an aptamer.

In other examples, such indirect TNFα inhibitors can be a small molecule inhibitor of a signaling component downstream of a TNFα receptor (e.g., any of the signaling components downstream of a TNFα receptor described herein or known in the art), a small molecule inhibitor of a protein encoded by a TNFα-induced gene (e.g., any protein encoded by a TNFα-induced gene known in the art), and a small molecule inhibitor of a transcription factor selected from the group of NF-κB, c-Jun, and ATF2.

Inhibitory Nucleic Acids of TNFα

Exemplary TNFα inhibitors that are inhibitory nucleic acids targeting TNFα include, e.g., antisense DNA (e.g., Myers et al., J Pharmacol Exp Ther. 304(1):411-424, 2003; Wasmuth et al., Invest. Opthalmol. Vis. Sci, 2003; Dong et al., J. Orthop. Res. 26(8):1114-1120, 2008; U.S. Patent Application Serial Nos. 2003/0083275, 2003/0022848, and 2004/0770970; ISIS 104838; U.S. Pat. Nos. 6,180,403, 6,080,580, and 6,228,642; Kobzik et al., Inhibition of TNF Synthesis by Antisense Oligonucleotides, in Manual of Antisense Methodology, Kluwer Academic Publishers, Vol. 4, pp. 107-123, 1999; Taylor et al., *Antisense Nucleic Acid Drug Develop.* 8(3):199-205, 1998; Mayne et al., *Stroke* 32:240-248, 2001; Mochizuki et al., *J Controlled Release* 151(2):155-161, 2011; Dong et al., *J Orthopaedic Res.* 26(8):1114-1120, 2008; Dong et al., *Pharm. Res.* 28(6): 1349-1356, 2011; and Pampfer et al., *Biol. Reproduction* 52(6):1316-1326, 1995), antisense RNA, short interfering RNA (siRNA) (e.g., Taishi et al., *Brain Research* 1156:125-132, 2007; Presumey et al., *Eur. J Pharm. Biopharm.* 82(3):457-467, 2012; Laroui et al., *J. Controlled Release* 186:41-53, 2014; D'Amore et al., *Int. J. Immunopathology Pharmacol.* 21:1045-1047, 2008; Choi et al., *J. Dermatol. Sci.* 52:87-97, 2008; Qin et al., *Artificial Organs* 35:706-714, 2011; McCarthy et al., *J. Controlled Release* 168: 28-34, 2013; Khoury et al., *Current Opin. Mol. Therapeutics* 9(5):483-489, 2007; Lu et al., *RNA Interference Technology From Basic Science to Drug Development* 303, 2005; Xie et al., *PharmaGenomics* 4(6):28-34, 2004; Aldawsari et al., *Current Pharmaceutical Design* 21(31):4594-4605, 2015; Zheng et al., *Arch. Med. Sci.* 11:1296-1302, 2015; Peng et al., *Chinese J. Surgery* 47(5):377-380, 2009; Aldayel et al., *Molecular Therapy. Nucleic Acids* 5(7):e340, 2016; Bai et al., *Current Drug Targets* 16:1531-1539, 2015; U.S. Patent Application Publications Nos. 2008/0097091, 2009/0306356, and 2005/0227935; and WO 14/168264), short hairpin RNA (shRNA) (e.g., Jakobsen et al., *Mol. Ther.* 17(10): 1743-1753, 2009; Ogawa et al., *PLoS One* 9(3): e92073, 2014; Ding et al., *Bone Joint* 94-6(Suppl. 11):44, 2014; and Hernandez-Alejandro et al., *J. Surgical Res.* 176(2):614-620, 2012), and microRNAs (see, e.g., WO 15/26249). In some embodiments, the inhibitory nucleic acid blocks pre-mRNA splicing of TNFα (e.g., Chiu et al., *Mol. Pharmacol.* 71(6): 1640-1645, 2007).

In some embodiments, the inhibitory nucleic acid, e.g., an aptamer (e.g., Orava et al., *ACS Chem Biol.* 2013; 8(1): 170-178, 2013), can block the binding of a TNFα protein with its receptor (TNFR1 and/or TNFR2).

In some embodiments, the inhibitory nucleic acid can down-regulate the expression of a TNFα-induced downstream mediator (e.g., TRADD, TRAF2, MEKK1/4, MEKK4/7, JNK, AP-1, ASK1, RIP, MEKK 3/6, MAPK, NIK, IKK, NF-κB, p38, JNK, IκB-α, or CCL2). Further teachings of downstream TNFα-induced mediators can be found in, e.g., Schwamborn et al., *BMC Genomics* 4:46, 2003; and Zhou et al., *Oncogene* 22: 2034-2044, 2003, incorporated by reference herein. Additional aspects of inhibitory nucleic acids are described in Aagaard et al., *Adv. Drug Delivery Rev.* 59(2):75-86, 2007, and Burnett et al., *Biotechnol. J.* 6(9):1130-1146, 2011.

TNFα Inhibitor Antibodies

In some embodiments, the TNFα inhibitor is an antibody or an antigen-binding fragment thereof (e.g., a Fab or a scFv). In some embodiments, an antibody or antigen-binding fragment described herein binds specifically to any one of TNFα, TNFR1, or TNFR2. In some embodiments, an antibody or antigen-binding fragment of an antibody described herein can bind specifically to TNFα. In some embodiments, an antibody or antigen-binding fragment of an antibody described herein can bind specifically to an TNFα receptor (TNFR1 or TNFR2).

Non-limiting examples of TNF inhibitors that are antibodies that specifically bind to TNFα are described in Elliott et al., *Lancet* 1994; 344: 1125-1127, 1994; Rankin et al., *Br. J Rheumatol.* 2:334-342, 1995; Butler et al., *Eur. Cytokine Network* 6(4):225-230, 1994; Lorenz et al., *J. Immunol.* 156(4):1646-1653, 1996; Hinshaw et al., *Circulatory Shock* 30(3):279-292, 1990; Wanner et al., *Shock* 11(6):391-395, 1999; Bongartz et al., *JAMA* 295(19):2275-2285, 2006; Knight et al., *Molecular Immunol.* 30(16):1443-1453, 1993; Feldman, *Nature Reviews Immunol.* 2(5):364-371, 2002; Taylor et al., *Nature Reviews Rheumatol.* 5(10):578-582, 2009; Garces et al., *Annals Rheumatic Dis.* 72(12):1947-1955, 2013; Palladino et al., *Nature Rev. Drug Discovery* 2(9):736-746, 2003; Sandborn et al., *Inflammatory Bowel Diseases* 5(2):119-133, 1999; Atzeni et al., *Autoimmunity Reviews* 12(7):703-708, 2013; Maini et al., *Immunol. Rev.* 144(1):195-223, 1995; Ordas et al., *Clin. Pharmacol. Therapeutics* 91(4):635-646, 2012; Cohen et al., *Canadian J Gastroenterol. Hepatol.* 15(6):376-384, 2001; Feldmann et al., *Ann. Rev. Immunol.* 19(1):163-196, 2001; Ben-Horin et al., *Autoimmunity Rev.* 13(1):24-30, 2014; and U.S. Pat. Nos. 6,090,382; 6,258,562; and 6,509,015).

In certain embodiments, the TNFα inhibitor can include or is infliximab (Remicade™), CDP571, CDP 870, golimumab (Golimumab™), adalimumab (Humira™) or certolizumab pegol (Cimzia™). In certain embodiments, the TNFα inhibitor can be a TNFα inhibitor biosimilar. Examples of approved and late-phase TNFα inhibitor biosimilars include, but are not limited to, infliximab biosimilars such as Remsima™ and Inflectra® (CT-P13) from Celltrion/Pfizer, GS071 from Aprogen, Flixabi™ (SB2) from Samsung Bioepis, PF-06438179 from Pfizer/Sandoz, NI-071 from Nichi-Iko Pharmaceutical Co., and ABP 710 from Amgen; adalimumab biosimilars such as Exemptia™ (ZRC3197) from Zydus Cadila, India, Solymbic® and Amgevita® (ABP 501) from Amgen, Imraldi (SB5) from Samsung Bioepis, GP-2017 from Sandoz, Switzerland, ONS-3010 from Oncobiologics/Viropro, U.S.A., M923 from Momenta Pharmaceuticals/Baxalta (Baxter spinoff USA), PF-06410293 from Pfizer, BMO-2 or MYL-1401-A from Biocon/Mylan, CHS-1420 from Coherus, FKB327 from Fujifilm/Kyowa Hakko Kirin (Fujifilm Kyowa Kirin Biologics), Cyltezo (BI 695501) from Boehringer Ingelheim, CT-P17 from Celltrion, BAX 923 from Baxalta (now a part of Shire), MSB11022 from Fresenius Kabi (bought from Merck kGaA (Merck Group) in 2017), LBAL from LG Life Sciences/Mochida Pharmaceutical, South Korea/Japan, PBP1502 from Prestige Biopharma, Adfrar from Torrent Pharmaceuticals, India, a biosimilar of adalimumab in development by Adello Biologics, a biosimilar of adalimumab in development by AET Biotech/BioXpress Therapeutics, Germany/Switzerland, a biosimilar of adalimumab from mAbxience, Spain, a biosimilar of adalimumab in development by PlantForm, Canada; and etanercept biosimilars such as Erelzi™ from Sandoz/Novartis, Brenzys™ (SB4) from Samsung Bioepis, GP2015 from Sandoz, TuNEX® from Mycenax, LBEC0101 from LG Life, PF-688, a biosimilar of certolizumab pegol from Pfenex, and CHS-0214 from Coherus.

In some embodiments, the TNFα inhibitor can be SAR252067 (e.g., a monoclonal antibody that specifically binds to TNFSF14, described in U.S. Patent Application Publication No. 2013/0315913) or MDGN-002 (described in U.S. Patent Application Publication No. 2015/0337046). In some embodiments, the TNFα inhibitor can be PF-06480605, which binds specifically to TNFSF15 (e.g., described in U.S. Patent Application Publication No. 2015/0132311). Additional examples of TNFα inhibitors include DLCX105 (described in Tsianakas et al., *Exp. Dermatol.* 25:428-433, 2016) and PF-06480605, which binds specifically to TNFSF15 (described in U.S. Patent Application Publication No. 2015/0132311). Further examples of TNFα inhibitors that are antibodies or antigen-binding antibody fragments are described in, e.g., WO 17/158097, EP 3219727, WO 16/156465, and WO 17/167997.

In some embodiments, the TNFα inhibitor is DLX-105, e.g., the gel formulation.

In some embodiments, the TNFα inhibitor is adalimumab. Adalimumab is a recombinant human IgG1 monoclonal antibody specific for human tumor necrosis factor and is indicated for the treatment of various inflammatory diseases such as rheumatoid arthritis, Crohn's disease, and ulcerative colitis.

Adalimumab is currently delivered as an SC injection of 40 mg in 0.4-0.8 mL once every 1-2 weeks. It is sold in prefilled pen injectors for self-administration. The bioavailability is approximately 64% by SC injection, the half-life is approximately 2 weeks, and intracellular catabolism is the primary mode of elimination. Adalimumab must be refrigerated but can be temporarily stored at room temperature before use.

Adalimumab is a suitable therapeutic for delivery via ingestible device as described herein. It is currently available as a liquid, administered by self-injection, and, because adverse injection site reactions are not uncommon, patients may readily adopt an alternative dosage form. Lastly, the probability of acute reactions to overdose is low which, theoretically, could allow an increase in dose to compensate for lower bioavailability than SC injection.

TNFα Inhibitor Fusion Proteins

In some embodiments, the TNFα inhibitory agent is a fusion protein (e.g., an extracellular domain of a TNFR fused to a partner peptide, e.g., an Fc region of an immunoglobulin, e.g., human IgG) (see, e.g., Peppel et al., *J Exp. Med.* 174(6):1483-1489, 1991; Deeg et al., *Leukemia* 16(2): 162, 2002) or a soluble TNFR (e.g., TNFR1 or TNFR2) that binds specifically to TNFα. In some embodiments, the TNFα inhibitor includes or is etanercept (Enbrel™) (see, e.g., WO 91/03553 and WO 09/406,476, incorporated by reference herein). In some embodiments, the TNFα inhibitor includes or is r-TBP-I (e.g., Gradstein et al., *J Acquir. Immune Defic. Syndr.* 26(2): 111-117, 2001). In some embodiments, the TNFα inhibitor includes or is a soluble TNFα receptor (e.g., Watt et al., *J Leukoc Biol.* 66(6):1005-1013, 1999; Tsao et al., *Eur Respir J* 14(3):490-495, 1999; Kozak et al., *Am. J Physiol. Reg. Integrative Comparative Physiol.* 269(1):R23-R29, 1995; Mohler et al., *J. Immunol.* 151(3):1548-1561, 1993; Nophar et al., *EMBO J* 9(10): 3269, 1990; Bjornberg et al., *Lymphokine Cytokine Res.* 13(3):203-211, 1994; Piguet et al., *Eur. Respiratory J.* 7(3):515-518, 1994; and Gray et al., *Proc. Natl. Acad. Sci. U.S.A.* 87(19):7380-7384, 1990).

In some embodiments, the TNFα inhibitor is tulinercept.

TNFα Inhibitor Small Molecules

In some embodiments, the TNFα inhibitor is a small molecule. In some embodiments, the TNFα inhibitor is C87 (Ma et al., *J. Biol. Chem.* 289(18):12457-66, 2014). In some embodiments, the small molecule is LMP-420 (e.g., Haraguchi et al., *AIDS Res. Ther.* 3:8, 2006). In some embodiments, the small molecule is a tumor necrosis factor-converting enzyme (TACE) inhibitor (e.g., Moss et al., *Nature Clinical Practice Rheumatology* 4: 300-309, 2008). In some embodiments, the TACE inhibitor is TMI-005 and BMS-561392. Additional examples of small molecule inhibitors are described in, e.g., He et al., *Science* 310(5750):1022-1025, 2005.

In some examples, the TNFα inhibitor is a small molecule that inhibits the activity of one of TRADD, TRAF2, MEKK1/4, MEKK4/7, JNK, AP-1, ASK1, RIP, MEKK 3/6, MAPK, NIK, IKK, and NF-κB, in a mammalian cell.

In some examples, the TNFα inhibitor is a small molecule that inhibits the activity of one of CD14, MyD88 (see, e.g., Olson et al., *Scientific Reports* 5:14246, 2015), IRAK (Chaudhary et al., *J. Med. Chem.* 58(1):96-110, 2015), lipopolysaccharide binding protein (LBP) (see, e.g., U.S. Pat. No. 5,705,398), TRAF6 (e.g., 3-[(2,5-Dimethylphenyl) amino]-1-phenyl-2-propen-1-one), ras (e.g., Baker et al., *Nature* 497:577-578, 2013), raf (e.g., vemurafenib (PLX4032, RG7204), sorafenib tosylate, PLX-4720, dabrafenib (GSK2118436), GDC-0879, RAF265 (CHIR-265), AZ 628, NVP-BHG712, SB590885, ZM 336372, sorafenib, GW5074, TAK-632, CEP-32496, encorafenib (LGX818), CCT196969, LY3009120, R05126766 (CH5126766), PLX7904, and MLN2480), MEK1/2 (e.g., Facciorusso et al., *Expert Review Gastroentrol. Hepatol.* 9:993-1003, 2015), ERK1/2 (e.g., Mandal et al., *Oncogene* 35:2547-2561, 2016), NIK (e.g., Mortier et al., *Bioorg. Med. Chem. Lett.* 20:4515-4520, 2010), IKK (e.g., Reilly et al., *Nature Med.* 19:313-321, 2013), IκB (e.g., Suzuki et al., *Expert. Opin. Invest. Drugs* 20:395-405, 2011), NF-κB (e.g., Gupta et al., *Biochim. Biophys. Acta* 1799(10-12):775-787, 2010), rac (e.g., U.S. Pat. No. 9,278,956), MEK4/7, JNK (e.g., AEG 3482, BI 78D3, CEP 1347, c-JUN peptide, IQ 1S, JIP-1 (153-163), SP600125, SU 3327, and TCS JNK6o), c-jun (e.g., AEG 3482, BI 78D3, CEP 1347, c-JUN peptide, IQ 1S, JIP-1 (153-163), SP600125, SU 3327, and TCS JNK6o), MEK3/6 (e.g., Akinleye et al., *J. Hematol. Oncol.* 6:27, 2013), p38 (e.g., AL 8697, AMG 548, BIRB 796, CMPD-1, DBM 1285 dihydrochloride, EO 1428, JX 401, ML 3403, Org 48762-0, PH 797804, RWJ 67657, SB 202190, SB 203580, SB 239063, SB 706504, SCIO 469, SKF 86002, SX 011, TA 01, TA 02, TAK 715, VX 702, and VX 745), PKR (e.g., 2-aminopurine or CAS 608512-97-6), TTP (e.g., CAS 329907-28-0), and MK2 (PF 3644022 and PHA 767491).

IL-1 Inhibitors

In some embodiments, the therapeutic suitable for use with the devices and methods described herein is an IL-1 inhibitor. The term "IL-1 inhibitor" refers to an agent that decreases the expression of an IL-1 cytokine or an IL-1 receptor and/or decreases the ability of an IL-1 cytokine to bind specifically to an IL-1 receptor. Non-limiting examples of IL-1 cytokines include IL-1α, IL-1β, IL-18, IL-36α, IL-36β, IL-36γ, IL-38, and IL-33. In some examples, an IL-1 cytokine is IL-1α. In some examples, an IL-1 cytokine is IL-1β.

In some embodiments, an IL-1 inhibitory agent is an inhibitory nucleic acid, an antibody or fragment thereof, or a fusion protein. In some embodiments, the inhibitory nucleic acid is an antisense nucleic acid, a ribozyme, or a small interfering RNA.

Inhibitory Nucleic Acids of IL-1

Inhibitory nucleic acids that can decrease the expression of IL-1α, IL-1β, IL-18, IL-36α, IL-36β, IL-36γ, IL-38, IL-33, IL-1R1, IL1RAP, IL-18Rα, IL-1RL2, or IL1RL1 mRNA expression in a mammalian cell include antisense nucleic acid molecules, i.e., nucleic acid molecules whose nucleotide sequence is complementary to all or part of an IL-1α, IL-1β, IL-18, IL-36α, IL-36β, IL-36γ, IL-38, IL-33, IL-1R1, IL1RAP, IL-18Rα, IL-1RL2, or IL1RL1 mRNA.

Examples of modified nucleotides which can be used to generate an antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, b eta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an anti sense orientation (i.e., RNA transcribed from the inserted nucleic acid will be of an antisense orientation to a target nucleic acid of interest).

Inhibitory nucleic acids preferentially bind (e.g., hybridize) to a nucleic acid encoding IL-1α, IL-1β, IL-18, IL-36α, IL-36β, IL-36γ, IL-38, IL-33, IL-1R1, IL1RAP, IL-18Rα, IL-1RL2, or IL1RL1 protein to treat allergic diseases (e.g., asthma (Corren et al., *N. Engl. J. Med.* 365: 1088-1098, 2011)), radiation lung injury (Chung et al., *Sci. Rep.* 6: 39714, 2016), ulcerative colitis (Hua et al., *Br. J. Clin. Pharmacol.* 80:101-109, 2015), dermatitis (Guttman-Yassky et al., *Exp. Opin. Biol. Ther.* 13(4):1517, 2013), and chronic obstructive pulmonary disease (COPD) (Walsh et al. (2010) *Curr. Opin. Investig Drugs.* 11(11):1305-1312, 2010).

Exemplary IL-1 inhibitors that are antisense nucleic acids are described in Yilmaz-Elis et al., *Mol. Ther. Nucleic Acids* 2(1): e66, 2013; Lu et al., *J. Immunol.* 190(12): 6570-6578, 2013), small interfering RNA (siRNA) (e.g., Ma et al., *Ann. Hepatol.* 15(2): 260-270, 2016), or combinations thereof. In certain embodiments, a therapeutically effective amount of an inhibitory nucleic acid targeting a nucleic acid encoding IL-1α, IL-1β, IL-18, IL-36α, IL-36β, IL-36γ, IL-38, IL-33, IL-1R1, IL1RAP, IL-18Rα, IL-1RL2, or IL1RL1 protein can be administered to a subject (e.g., a human subject) in need thereof.

IL-1 Inhibitor Antibodies

In some embodiments, the IL-1 inhibitor is an antibody or an antigen-binding fragment thereof (e.g., a Fab or a scFv). In some embodiments, the IL-1 inhibitor is canakinumab (ACZ885, Ilaris® (Dhimolea, *MAbs* 2(1): 3-13, 2010; Yokota et al., *Clin. Exp. Rheumatol.* 2016; Torene et al., *Ann. Rheum. Dis.* 76(1):303-309, 2017; Gram, *Curr. Opin. Chem. Biol.* 32:1-9, 2016; Kontzias et al., *Semin. Arthritis Rheum* 42(2):201-205, 2012). In some embodiments, the IL-1 inhibitor is anakinra (Kineret®; Beynon et al., *J. Clin. Rheumatol.* 23 (3): 181-183, 2017; Stanam et al., *Oncotarget* 7(46):76087-76100, 2016; Nayki et al., *J. Obstet Gynaecol. Res.* 42(11):1525-1533, 2016; Greenhalgh et al., *Dis. Model Mech.* 5(6):823-833, 2012), or a variant thereof. In some embodiments, the IL-1 inhibitor is gevokizumab (XOMA 052; Knicklebein et al., *Am. J. Ophthalmol.* 172:104-110, 2016; Roubille et al., *Atherosclerosis* 236(2):277-285, 2014; Issafras et al., *J. Pharmacol. Exp. Ther* 348(1):202-215, 2014; Handa et al., *Obesity* 21(2):306-309, 2013; Geiler et al., *Curr. Opin. Mol. Ther.* 12(6):755-769, 2010), LY2189102 (Bihorel et al., *AAPS J.* 16(5):1009-1117, 2014; Sloan-Lancaster et al., *Diabetes Care* 36(8):2239-2246, 2013), MABp1 (Hickish et al., *Lancey Oncol.* 18(2):192-201, 2017; Timper et al., *J. Diabetes Complications* 29(7): 955-960, 2015), CDP-484 (Braddock et al., *Drug Discov.* 3:330-339, 2004), or a variant thereof (Dinarello et al., *Nat. Rev. Drug Discov.* 11(8): 633-652, 2012).

Further teachings of IL-1 inhibitors that are antibodies or antigen-binding fragments thereof are described in U.S. Pat. Nos. 5,075,222; 7,446,175; 7,531,166; 7,744,865; 7,829,093; and 8,273,350; US 2016/0326243; US 2016/0194392, and US 2009/019167, each of which is incorporated by reference in its entirety.

IL-1 Inhibitor Fusion Proteins or Soluble Receptors

In some embodiments, the IL-1 inhibitor is a fusion protein or a soluble receptor. For example, a fusion can include an extracellular domain of any one of IL-1R1, IL1RAP, IL-18Rα, IL-1RL2, and IL1RL1 fused to a partner amino acid sequence (e.g., a stabilizing domain, e.g., an IgG Fc region, e.g., a human IgG Fc region). In some embodiments, the IL-1 inhibitor is a soluble version of one or both of IL-1RL1 and IL1RAP. In some embodiments, the IL-1 inhibitor is a soluble version of IL-18Rα. In some embodiments, the IL-1 inhibitor is a soluble version of one or both of IL-1RL2 and IL-1RAP.

In some embodiments, the IL-1 inhibitor is a fusion protein comprising or consisting of rilonacept (IL-1 Trap, Arcalyst®) (see, e.g., Kapur & Bonk, *P.T.* 34(3):138-141, 2009; Church et al., *Biologics* 2(4):733-742, 2008; McDermott, Drugs Today (Banc) 45(6):423-430, 2009). In some embodiments, the IL-1 inhibitor is a fusion protein that is chimeric (e.g., EBI-005 (Isunakinra®) (Furfine et al., *Invest. Ophthalmol. Vis. Sci.* 53(14):2340-2340, 2012; Goldstein et al., *Eye Contact Lens* 41(3):145-155, 2015; Goldstein et al., *Eye Contact Lens*, 2016)).

In some embodiments, the IL-1 inhibitor is a soluble receptor that comprises or consists of sIL-1RI and/or sIL-1RII (Svenson et al., *Eur. J. Immunol.* 25(10): 2842-2850, 1995).

IL-1 Inhibitor Endogenous Peptides

In some embodiments, the IL-1 inhibitor can be an endogenous ligand or an active fragment thereof, e.g., IL-1Rα or IL-36Rα. IL-1Rα is an endogenous soluble protein that decreases the ability of IL-1α and IL-1β to bind to their receptor (e.g., a complex of IL-1R1 and IL1RAP proteins). IL-36Rα is an endogenous soluble protein that decreases the ability of IL-36α, IL-36β, and IL-36γ to bind to their receptor (e.g., a complex of IL-1RL2 and IL-1RAP proteins). Exemplary sequences for IL-1Rα and IL-36Rα are shown below.

In some embodiments, the IL-1 inhibitor is K(D)PT.

IL-6 Receptor Inhibitors

In some embodiments, the therapeutic suitable for use with the devices and methods described herein is an IL-6 receptor inhibitor. The term "IL-6 receptor inhibitor" refers to an agent which decreases IL-6 receptor expression and/or the ability of IL-6 to bind to an IL-6 receptor. In some embodiments, the IL-6 receptor inhibitor targets the IL-6 receptor β-subunit, glycoprotein 130 (sIL6gp130). In other embodiments, the IL-6 receptor inhibitor targets the IL-6 receptor subunit (IL6R). In other embodiments, the IL-6 receptor inhibitor targets the complex consisting of both the IL-6 receptor subunit (IL6R) and the IL-6 receptor β-subunit, glycoprotein 130 (sIL6gp130). In some embodiments, the IL-6 receptor inhibitor targets IL-6.

In some embodiments, an IL-6 receptor inhibitor is an inhibitory nucleic acid, an antibody or an antigen-binding fragment thereof, a fusion protein, a IL-6 receptor antagonist, or a small molecule. In some embodiments, the inhibitory nucleic acid is a small interfering RNA, an antisense nucleic acid, an aptamer, or a microRNA. Exemplary IL-6 receptor inhibitors are described herein. Additional examples of IL-6 receptor inhibitors are known in the art.

Inhibitory Nucleic Acids of IL-6

An antisense nucleic acid molecule can be complementary to all or part of a non-coding region of the coding strand of a nucleotide sequence encoding an IL6R, sIL6gp130, or IL-6 protein. Non-coding regions (5' and 3' untranslated regions) are the 5' and 3' sequences that flank the coding region in a gene and are not translated into amino acids.

Exemplary antisense nucleic acids that are IL-6 receptor inhibitors are described in Keller et al., *J. Immunol.* 154(8): 4091-4098, 1995; and Jiang et al., *Anticancer Res.* 31(9): 2899-2906, 2011.

Non-limiting examples of short interfering RNA (siRNA) that are IL-6 receptor inhibitors are described in Yi et al., *Int. J. Oncol.* 41(1):310-316, 2012; and Shinriki et al., *Clin. Can. Res.* 15(17):5426-5434, 2009). Non-limiting examples of microRNAs that are IL-6 receptor inhibitors are described in miR34a (Li et al., *Int. J. Clin. Exp. Pathol.* 8(2):1364-1373, 2015) and miR-451 (Liu et al., *Cancer Epidemiol.* 38(1): 85-92, 2014).

Non-limiting examples of aptamers that are IL-6 receptor inhibitors are described in Meyer et al., *RNA Biol.* 11(1): 57-65, 2014; Meyer et al., *RNA Biol.* 9(1):67-80, 2012; and Mittelberger et al., *RNA Biol.* 12(9):1043-1053, 2015. Additional examples of inhibitory nucleic acids that are IL-6 receptor inhibitors are described in, e.g., WO 96/040157.

IL-6 Inhibitor Antibodies

In some embodiments, the IL-6 receptor inhibitor is an antibody or an antigen-binding fragment thereof (e.g., a Fab or a scFv). In some embodiments, an antibody or antigen-binding fragment described herein binds specifically to IL-6. In some embodiments, an antibody or antigen-binding fragment described herein binds specifically to IL-6 receptor (e.g., one or both of IL6R and sIL6gp130).

In certain embodiments, the antibody comprises or consists of an antigen-binding fragment or portion of tocilizumab (artlizumab, Actemra®; Sebba, *Am. J. Health Syst. Pharm.* 65(15):1413-1418, 2008; Tanaka et al., *FEBS Letters* 585(23):3699-3709, 2011; Nishimoto et al., *Arthritis Rheum.* 50:1761-1769, 2004; Yokota et al., *Lancet* 371 (9617):998-1006, 2008; Emery et al., *Ann. Rheum. Dis.* 67(11):1516-1523, 2008; Roll et al., *Arthritis Rheum.* 63(5): 1255-1264, 2011); lazakizumab (BMS945429; ALD518, a humanized monoclonal antibody that binds circulating IL-6 cytokine rather than the IL-6 receptor, blocking both classic signaling and trans-signaling (Weinblatt, Michael E., et al. "The Efficacy and Safety of Subcutaneous Clazakizumab in Patients With Moderate-to-Severe Rheumatoid Arthritis and an Inadequate Response to Methotrexate: Results From a Multinational, Phase IIb, Randomized, Double-Blind, Placebo/Active-Controlled, Dose-Ranging Study." Arthritis & Rheumatology 67.10 (2015): 2591-2600)); sarilumab (REGN88 or SAR153191; Huizinga et al., *Ann. Rheum. Dis.* 73(9):1626-1634, 2014; Sieper et al., *Ann. Rheum. Dis.* 74(6):1051-1057, 2014; Cooper, *Immunotherapy* 8(3): 249-250, 2016); MR-16 (Hartman et al., *PLosOne* 11(12): e0167195, 2016; Fujita et al., *Biochim. Biophys. Acta.* 10:3170-80, 2014; Okazaki et al., *Immunol. Lett.* 84(3):231-40, 2002; Noguchi-Sasaki et al., *BMC Cancer* 16:270, 2016; Ueda et al., *Sci. Rep.* 3:1196, 2013); rhPM-1 (MRA; Nishimoto et al., *Blood* 95: 56-61, 2000; Nishimoto et al., *Blood* 106: 2627-2632, 2005; Nakahara et al., *Arthritis Rheum.* 48(6): 1521-1529, 2003); NI-1201 (Lacroix et al., *J. Biol. Chem.* 290(45):26943-26953, 2015); EBI-029 (Schmidt et al., Eleven Biotherapeutics Poster #B0200, 2014). In some embodiments, the antibody is a nanobody (e.g., ALX-0061 (Van Roy et al., *Arthritis Res. Ther.* 17: 135, 2015; Kim et al., *Arch. Pharm. Res.* 38(5):575-584, 2015)). In some embodiments, the antibody is NRI or a variant thereof (Adachi et al., *Mol. Ther.* 11(1):S262-263, 2005; Hoshino et al., *Can. Res.* 67(3): 871-875, 2007). In some embodiments, the antibody is PF-04236921 (Pfizer) (Wallace et al., *Ann. Rheum. Dis.* 76(3):534-542, 2017).

In some embodiments, the IL-6 receptor inhibitor is olokizumab (CDP-6038).

IL-6 Inhibitor Fusion Proteins

In some embodiments, the IL-6 receptor inhibitor is a fusion protein, a soluble receptor, or a peptide (see e.g., U.S. Pat. No. 5,591,827). In some embodiments, the IL-6 receptor fusion protein comprises or consists of soluble gp130 (Jostock et al., *Eur. J. Biochem.* 268(1):160-167, 2001; Richards et al., *Arthritis Rheum.* 54(5):1662-1672, 2006; Rose-John et al., *Exp. Opin. Ther. Targets* 11(5):613-624, 2007).

In some embodiments, the IL-6 receptor fusion protein comprises or consists of FE999301 (Jostock et al., *Eur. J. Biochem.* 268(1):160-167, 2001) or sgp130Fc protein (Jones et al., *J. Clin. Invest.* 121(9):3375-3383, 2011). In some embodiments, the IL-6 receptor inhibitor is a peptide (e.g., S7 (Su et al., *Cancer Res.* 65(11):4827-4835, 2005). In some embodiments, the IL-6 receptor inhibitor is a triterpenoid saponin (e.g., chikusetsuaponin IVa butyl ester (CS-Iva-Be) (Yang et al., *Mol. Cancer. Ther.* 15(6):1190-200, 2016).

IL-6 Inhibitor Small Molecules

In some embodiments, the IL-6 receptor inhibitor is a small molecule (see, e.g., U.S. Pat. No. 9,409,990). In some embodiments, the small molecule is LMT-28 (Hong et al., *J. Immunol.* 195(1): 237-245, 2015); ERBA (Enomoto et al., *Biochem. Biophys. Res. Commun.* 323:1096-1102, 2004; Boos et al., *J. Nat. Prod.* 75(4):661-668, 2012), ERBF (TB-2-081) (Hayashi et al., *J. Pharmacol. Exp. Ther.* 303: 104-109, 2002; Vardanyan et al., *Pain* 151(2):257-265, 2010; Kino et al., *J. Allergy Clin. Immunol.* 120(2):437-444, 2007), or a variant thereof.

In some embodiments, the IL-6 receptor inhibitor is YSIL6.

IL-10 Receptor Agonists

In some embodiments, the therapeutic suitable for use with the devices and methods described herein is an IL-10 receptor agonist. The term "IL-10 receptor agonist" is any molecule that binds to and activates a receptor for IL-10 expressed on a mammalian cell or a nucleic acid that encodes any such molecule. A receptor for IL-10 can include, e.g., a complex of two IL-10 receptor-1 (IL-10R1) proteins and two IL-10 receptor 2 (IL-10R2) proteins. In some examples, an IL-10 receptor agonist is an antibody or an antigen-binding antibody fragment that specifically binds to and activates a receptor for IL-10 (e.g., a human receptor for IL-10). In some examples, an IL-10 receptor agonist is a recombinant IL-10 (e.g., human recombinant IL-10). In some examples, an IL-10 receptor agonist is a pegylated recombinant IL-10 (e.g., pegylated recombinant human IL-10). In some examples, an IL-10 receptor agonist is a fusion protein. In some examples, an IL-10 receptor agonist is an IL-10 peptide mimetic.

Nucleic Acids and Vectors that Encode an IL-10 Receptor Agonist

In some examples, an IL-10 receptor agonist can be a nucleic acid (e.g., a vector) that includes a sequence encoding an IL-10 receptor agonist (e.g., any of the IL-10 proteins described herein). A non-limiting example of a composition including a nucleic acid that encodes an IL-10 receptor agonist is XT-150 (Xalud Therapeutics).

IL-10 Inhibitor Antibodies and Antigen-Binding Fragments

In some embodiments, the IL-10 receptor agonist is an antibody or an antigen-binding antibody fragment that binds to and activates an IL-10 receptor (e.g., a human IL- receptor). In some embodiments, the antibody or antigen-binding antibody fragment that specifically binds to an epitope on IL-10R-1 protein (e.g., human IL-10R-1 protein). In some embodiments, the antibody or antigen-binding antibody fragment that specifically binds to an epitope on IL-10R-2 protein (e.g., a human IL-10R-2 protein). In some embodiments, the antibody or the antigen-binding antibody fragment that specifically binds to an epitope on IL-10R-1 and IL-10R-2 proteins (e.g., human IL-10R-1 and human IL-10R-2 proteins).

In some embodiments, the IL-10 receptor agonist is an antibody, e.g., F8-IL10 (also known as DEKAVIL) or a variant thereof (see, e.g., Schwager et al., *Arthritis Res. Ther.* 11(5):R142, 2009; Franz et al., *Int. J. Cardiol.* 195:311-322, 2015; Galeazzi et al., *Isr. Med. Assoc. J.* 16(10):666, 2014).

IL-10 Inhibitor Fusion Proteins

In some embodiments, the IL-10 receptor agonist is a fusion protein. In some embodiments, the fusion protein comprises the amino acid sequence of an IL-10 protein (or a functional fragment thereof) and a fusion partner (e.g., an Fc region (e.g., human IgG Fc) or human serum albumin). In some embodiments the fusion partner can be an antibody or an antigen-binding antibody fragment (e.g., an scFv) that targets IL-10 receptor agonist to an inflamed tissue. In some embodiments, the antibody or antigen-binding fragment that is a fusion partner can bind specifically, or preferentially, to inflamed gastrointestinal cells by, e.g., CD69. In some embodiments, an IL-10 receptor agonist that is a fusion protein can be, e.g., F8-IL-10, such as Dekavil (Philogen).

In some embodiments, the fusion protein is a L19-IL-10 fusion protein, a HyHEL10-IL-10 fusion protein, or a variant thereof. See, e.g., Trachsel et al., *Arthritis Res. Ther.* 9(1):R9, 2007, and Walmsley et al., *Arthritis Rheum.* 39: 495-503, 1996.

In some embodiments, the IL-10 receptor agonist is RG-7880.

IL-10 Peptide Mimetic

In some embodiments, the IL-10 receptor agonist is an IL-10 peptide mimetic. A non-limiting example of an IL-10 peptide mimetic is IT 9302 or a variant thereof (Osman et al., *Surgery* 124(3):584-92, 1998; Lopez et al., *Immunobiology* 216(10):1117-1126, 2011). Additional examples of IL-10 peptide mimetics are described in DeWitt, *Nature Biotech.* 17:214, 1999, and Reineke et al., *Nature Biotech.* 17:271-275, 1999.

Recombinant IL-10

In some examples, an IL-10 receptor agonist is a recombinant IL-10 protein. In some examples, a recombinant human IL-10 protein can be Tenovil™ (Schering Corporation). In some examples, a recombinant IL-10 protein is a functional fragment of human IL-10 protein.

In some embodiments, the IL-10 receptor agonist is rhuIL-10 (Tenovil) or a variant thereof. See, e.g., McHutchison et al., *J. Interferon Cytokine Res.* 1:1265-1270, 1999; Rosenblum et al., *Regul. Toxicol. Pharmacol.* 35:56-71, 2002; Schreiber et al., *Gastroenterology* 119(6):1461-1472, 2000; Maini et al., *Arthritis Rheum.* 40(Suppl):224, 1997.

Exemplary methods of making a recombinant human IL-10 are described in Pajkrt et al., *J. Immunol.* 158:3971-3977, 1997). Additional exemplary methods of making recombinant IL-10 are described herein and are known in the art.

In some embodiments, a recombinant IL-10 is a pegylated recombinant IL-10 (e.g., pegylated recombinant human IL-10) (e.g., a 5 kDa N-terminally PEGylated form of IL-10; AM0010) (Infante et al., *ASCO Meeting Abstracts* 33(15_suppl):3017, 2015; Chan et al., *PLoS One* 11(6): e0156229, 2016; Mumm et al., *Cancer Cell* 20(6):781-796, 2011; Teng et al., *Cancer Cell* 20(6):691-693, 2011; U.S. Pat. Nos. 8,691,205; 8,865,652; 9,259,478; and 9,364,517; and U.S. Patent Application Publication Nos. 2008/0081031; 2009/0214471; 2011/0250163; 2011/0091419; 2014/0227223; 2015/0079031; 2015/0086505; 2016/031402; 2016/0367689; 2016/0375101; and 2016/0166647).

In some embodiments, a recombinant IL-10 is a stabilized isoform of a recombinant IL-10. In some embodiments, the stabilized isoform of a recombinant IL-10 is a viral IL-10 protein (e.g., a human cytomegalovirus IL10 (e.g., cmv-IL10, LA-cmv-IL-10 (e.g., Lin et al., *Virus Res.* 131(2):213-223, 2008; Jenkins et al., *J. Virol.* 78(3):1440-1447, 2004; Kotenko et al., *Proc. Natl. Acad. Sci. U.S.A.* 97(4):1695-1700, 2000; Jones et al., *Proc. Natl. Acad. Sci. U.S.A.* 99(14):9404-9409, 2002) or a latency-associated viral IL-10 protein (e.g., Poole et al., *J. Virol.* 88(24):13947-13955, 2014).

In some embodiments, the recombinant IL-10 is a mammalian IL-10 homolog (see, e.g., WO 00/073457). In some embodiments, a mammalian IL-10 homolog is BCRF1, an EBV homolog of human IL-10, also known as viral IL-10, or a variant thereof (Liu et al., *J. Immunol.* 158(2):604-613, 1997).

Cells Producing a Recombinant IL-10

In some embodiments, any of the devices or compositions described herein can include a recombinant cell (e.g., a recombinant mammalian cell) that secretes a recombinant IL-10 (e.g., any of the recombinant IL-10 proteins described herein). In some embodiments, any of the devices or compositions described herein can include a cell (e.g., a mammalian cell) that secretes IL-10 (e.g., human IL-10). In some embodiments, the mammalian cell can be a mammalian cell obtained from the subject, and after introduction of a nucleic acid encoding the recombinant IL-10 (e.g., any of the recombinant IL-10 proteins described herein) into the cell obtained from the subject, the cell is incorporated into any of the compositions or devices described herein.

Non-limiting examples of methods that can be used to introduce a vector or a nucleic acid into a cell (e.g., a mammalian cell) include lipofection, transfection, electroporation, microinjection, calcium phosphate transfection, dendrimer-based transfection, cationic polymer transfection, cell squeezing, sonoporation, optical transfection, impalection, hydrodynamic delivery, magnetofection, viral transduction (e.g., adenoviral and lentiviral transduction), and nanoparticle transfection. These and other methods of introducing a vector or a nucleic acid into a cell are well known in the art.

In some examples, the recombinant mammalian cell can be a Chinese Hamster Ovary (CHO) cell, a B cell, a CD8+ T cell, a dendritic cell, a keratinocyte or an epithelial cell. See, e.g., Mosser et al., *Immunol. Rev.* 226:205-218, 2009; Fillatreau et al., *Nat. Rev. Immunol.* 8:391-397, 2008; Ryan et al., *Crit. Rev. Immunol.* 27:15-32, 2007; Moore et al., *Annu. Rev. Immunol.* 19:683-765, 2001. In some embodiments, the recombinant mammalian cell can be a mesenchymal stem cell (e.g., Gupte et al., *Biomed. J.* 40(1):49-54, 2017).

Additional Examples of IL-10 Inhibitors

In some embodiments, the recombinant cell is a recombinant Gram-positive bacterial cell (e.g., a genetically modified *Lactococcus lactis* (LL-Thy12) (see, e.g., Steidler et al., *Science* 289:1352-1355, 2000; Braat et al., *Clin. Gastroenterol. Heptal.* 4:754-759, 2006). In some embodiments, the recombinant cell is a recombinant Gram-negative bacterial cell (e.g., a *Shigella flexneri* cell) that secretes an IL-10 receptor agonist (e.g., a recombinant IL-10 protein) (Chamekh et al., *J. Immunol.* 180(6): 4292-4298, 2008).

In some embodiments, the IL-10 receptor agonist is a cell (e.g., a *Clostridium butyricum* cell) that induces IL-10 production and secretion by a different cell (e.g., a macrophage) (e.g., Hayashi et al., *Cell Host Microbe* 13:711-722, 2013). In some embodiments, the IL-10 receptor agonist is a recombinant bacterial cell (e.g., a *Lactobacillus acidophilus* cell) that is deficient in lipoteichoic acid and induces IL-10 production and secretion by a different cell (e.g., a dendritic cell) (e.g., Mohamadzadeh et al., *Proc. Natl. Acad. Sci. U.S.A.* 108(suppl 1):4623-4630, 2011; Konstantinov et al., *Proc. Natl. Acad. Sci. U.S.A.* 105(49):19474-9, 2008). In some embodiments, the IL-10 receptor agonist is a bacterial cell or a fragment of a bacterial cell that is maintained in the supernatant that induces IL-10 secretion in a different cell (e.g., an immune cell) (e.g., a *Faecalibacterium prausnitzii* cell or a *Faecalibacterium prausnitzii* supernatant) (see, e.g., Sokol et al., *Proc. Natl. Acad. Sci. U.S.A.* 105(43):16731-16736, 2008).

Additional examples of other IL-10 receptor agonists are described in, e.g., U.S. Pat. No. 6,936,586; WO 96/01318; WO 91/00349; and WO 13/130913; each of which is incorporated by reference in its entirety herein.

IL-12/IL-23 Inhibitors

In some embodiments, the therapeutic suitable for use with the devices and methods described herein is an IL-12/IL-23 inhibitor. The term "IL-12/IL-23 inhibitor" refers to an agent which decreases IL-12 or IL-23 expression and/or the ability of IL-12 to bind to an IL-12 receptor or the ability of IL-23 to bind to an IL-23 receptor. In some embodiments, the IL-12/IL-23 inhibitory agent targets IL-12B (p40) subunit. In some embodiments, the IL-12/IL-23 inhibitory agent targets IL-12A (p35). In some embodiments, the IL-12/IL-23 inhibitory agent targets IL-23 (p19). In some embodiments, the IL-12/IL-23 inhibitory agent targets the receptor for IL-12 (one or both of IL-12R β1 or IL-12R β2). In some embodiments, the IL-12/IL-23 inhibitory agent targets the receptor for IL-23 (one or both of IL-12R β1 and IL-23R).

In some embodiments, an IL-12/IL-23 inhibitor can be an inhibitory nucleic acid. In some embodiments, the inhibitory nucleic acid can be an antisense nucleic acid, a ribozyme, and a small interfering RNA (siRNA).

Non-limiting examples of siRNAs targeting IL-12A (p35), IL-12B (p40), IL-23 (p19), IL-12R β1, IL-12R β2, or IL-23R are described in Tan et al., *J. Alzheimers Dis.* 38(3): 633-646, 2014; Niimi et al., *J. Neuroimmunol.* 254(1-2):39-45, 2013. Non-limiting examples of short hairpin RNA (shRNA) targeting IL-12A (p35), IL-12B (p40), IL-23 (p19), IL-12R β1, IL-12R β2, or IL-23R are described in Bak et al., *BMC Dermatol.* 11:5, 2011.

Non-limiting examples of inhibitory nucleic acids are microRNAs (e.g., microRNA-29 (Brain et al., *Immunity* 39(3):521-536, 2013), miR-10a (Xue et al., *J. Immunol.* 187(11):5879-5886, 2011), microRNA-155 (Podsiad et al., *Am. J. Physiol. Lung Cell Mol. Physiol.* 310(5):L465-75, 2016).

IL-12/IL-23 Inhibitor Antibodies

In some embodiments, the IL-12/IL-23 inhibitor is an antibody or an antigen-binding fragment thereof (e.g., a Fab or a scFv). In some embodiments, an antibody or antigen-binding fragment described herein binds specifically to any one of IL-12A (p35), IL-12B (p40), IL-23 (p19), IL-12R β1, IL-12R β2, or IL-23R, or a combination thereof.

In some embodiments, the antibody is ustekinumab (CNTO 1275, Stelara®) or a variant thereof (Krueger et al., *N. Engl. J. Med.* 356(6):580-592, 2007; Kauffman et al., *J. Invest. Dermatol.* 123(6):1037-1044, 2004; Gottlieb et al., *Curr. Med. Res. Opin.* 23(5):1081-1092, 2007; Leonardi et al., *Lancet* 371(9625):1665-1674, 2008; Papp et al., *Lancet* 371(9625):1675-1684, 2008). In some embodiments, the antibody is briakinumab (ABT-874, J-695) or a variant thereof (Gordon et al., *J. Invest. Dermatol.* 132(2):304-314, 2012; Kimball et al., *Arch Dermatol.* 144(2): 200-207, 2008).

In some embodiments, the antibody is guselkumab (CNTO-1959) (Callis-Duffin et al., *J. Am. Acad. Dermatol.* 70(5 Suppl 1), 2014); AB162 (Sofen et al., *J. Allergy Clin. Immunol.* 133: 1032-40, 2014); tildrakizumab (MK-3222, SCH900222) (Papp et al. (2015) *Br. J. Dermatol.* 2015); Langley et al., Oral Presentation at: American Academy of Dermatology, March 21-25, Denver Colo., 2014); AMG 139 (MEDI2070, brazikumab) (Gomollon, *Gastroenterol. Hepatol.* 38(Suppl. 1):13-19, 2015; Kock et al., *Br. J. Pharmacol.* 172(1):159-172, 2015); FM-202 (Tang et al., *Immunology* 135(2):112-124, 2012); FM-303 (Tang et al., *Immunology* 135(2):112-124, 2012); ADC-1012 (Tang et al., *Immunology* 135(2):112-124, 2012); LY-2525623 (Gaffen et al., *Nat. Rev. Immunol.* 14:585-600, 2014; Sands, *Gastroenterol. Hepatol.* 12(12):784-786, 2016), LY-3074828 (Coskun et al., *Trends Pharmacol. Sci.* 38(2):127-142, 2017), BI-655066 (risankizumab) (Singh et al., *MAbs* 7(4):778-791, 2015; Krueger et al., *J. Allergy Clin. Immunol.* 136(1):116-124, 2015) or a variant thereof.

Further teachings of IL-12/IL-23 antibodies and antigen-binding fragments thereof are described in U.S. Pat. Nos. 6,902,734; 7,247,711; 7,252,971; and 7,491,391; US 2012/0288494; and US 2013/0302343, each of which is incorporated by reference in its entirety.

In some embodiments, the IL-12/IL-23 inhibitor is PTG-200, an IL-23R inhibitor currently in preclinical development by Protagonist Therapeutics.

In some embodiments, the IL-12/IL-23 inhibitor is Mirikizumab (LY 3074828), an IL-23R inhibitor currently in clinical development (Phase II) by Eli Lilly.

In some embodiments, the IL-12/IL-23 inhibitor is AK-101.

In some embodiments, the IL-12/IL-23 inhibitor is a bispecific antibody, e.g., IL-23/CGRP currently in clinical development (Phase EL) by Eli Lilly.

IL-12/IL-23 Inhibitor Fusion Proteins

In some embodiments, the IL-12/IL-23 inhibitor is a fusion protein, a soluble antagonist, or an antimicrobial peptide. In some embodiments, the fusion protein comprises a soluble fragment of a receptor of IL-12 or a soluble fragment of a receptor of IL-23. In some embodiments, the fusion protein comprises an extracellular domain of a receptor of IL-12 or an extracellular domain of a receptor of IL-23.

In some embodiments, the fusion protein is adnectin or a variant thereof (Tang et al., *Immunology* 135(2):112-124, 2012). In some embodiments, the soluble antagonist is a human IL-23Ra-chain mRNA transcript (Raymond et al., *J. Immunol.* 185(12):7302-7308, 2010). In some embodiments, the IL-12/IL-23 is an antimicrobial peptide (e.g., MP-196 (Wenzel et al., *PNAS* 111(14):E1409-E1418, 2014)).

IL-12/IL-23 Inhibitor Small Molecules

In some embodiments, the IL-12/IL-23 inhibitor is a small molecule. In some embodiments, the small molecule is STA-5326 (apilimod) or a variant thereof (Keino et al., *Arthritis Res. Ther.* 10: R122, 2008; Wada et al., *Blood* 109(3):1156-1164, 2007; Sands et al., *Inflamm. Bowel Dis.* 16(7):1209-1218, 2010).

IL-13 Inhibitors

In some embodiments, the therapeutic suitable for use with the devices and methods described herein is an IL-13 inhibitor. The term "IL-13 inhibitor" refers to an agent which decreases IL-13 expression and/or decreases the binding of IL-13 to an IL-13 receptor. In some embodiments, the IL-13 inhibitor decreases the ability of IL-13 to bind an IL-13 receptor (e.g., a complex including IL-4Rα and IL-13Rα1, or a complex including IL-13Rα1 and IL-13Rα2).

In some embodiments, an IL-13 inhibitor is an inhibitory nucleic acid, an antibody or an antigen-binding fragment thereof, or a fusion protein. In some embodiments, the inhibitory nucleic acid can be an antisense nucleic acid, a ribozyme, a small interfering RNA, a small hairpin RNA, or a microRNA. Examples of aspects of these different inhibitory nucleic acids are described below. Any of the examples of inhibitory nucleic acids that can decrease expression of an IL-13, IL-13Rα1, IL-13Rα2, or IL-4Rα mRNA in a mammalian cell can be synthesized in vitro.

Non-limiting examples of short interfering RNA (siRNA) that are IL-13 inhibitors are described in Lively et al., *J. Allergy Clin. Immunol.* 121(1):88-94, 2008). Non-limiting examples of short hairpin RNA (shRNA) that are IL-13 inhibitors are described in Lee et al., *Hum Gene Ther.* 22(5):577-586, 2011, and Shilovskiy et al., *Eur. Resp. J.* 42:P523, 2013).

In some embodiments, an inhibitory nucleic acid can be a microRNA. Non-limiting examples of microRNAs that are IL-13 inhibitors are let-7 (Kumar et al., *J. Allergy Clin. Immunol.* 128(5):1077-1085, 2011).

IL-13 Inhibitor Antibodies

In some embodiments, the IL-13 inhibitor is an antibody or an antigen-binding fragment thereof (e.g., a Fab or a scFv). In some embodiments, an antibody or antigen-binding fragment described herein binds specifically to any one of IL-13, IL-13Rα1, IL-13Rα2, or IL-4Rα, or a combination thereof. In some embodiments, an antibody or antigen-binding fragment of an antibody described herein can bind specifically to IL-13. In some embodiments, an antibody or antigen-binding fragment of an antibody described herein can bind specifically to an IL-13 receptor (e.g., a complex including IL-4Rα and IL-13Rα1, or a complex including IL-13Rα1 and IL-13Rα2).

In some embodiments, the IL-13 inhibitor is a monoclonal antibody (Bagnasco et al., *Int. Arch. Allergy Immunol.* 170:122-131, 2016). In some embodiments, the IL-13 inhibitor is QAX576 (Novartis) or an antigen-binding fragment thereof (see, e.g., Kariyawasam et al., *B92 New Treatment Approaches for Asthma and Allergy San Diego*, 2009; Rothenberg et al., *J. Allergy Clin. Immunol.* 135:500-507, 2015). In some embodiments, the IL-13 inhibitor is ABT-308 (Abbott) or an antigen-binding fragment thereof (see, e.g., Ying et al., American Thoracic Society 2010 International Conference, May 14-19, 2010, New Orleans; Abstract A6644). In some embodiments, the IL-13 inhibitor is CNTO-5825 (Centrocore) or an antigen-binding fragment thereof (see, e.g., van Hartingsveldt et al., *British J. Clin. Pharmacol.* 75:1289-1298, 2013). In some embodiments, the IL-13 inhibitor is dupilumab (REGN668/SAR231893) or an antigen-binding fragment thereof (see, e.g., Simpson et al., *N. Eng. J. Med.* 375:2335-2348, 2016; Thaci et al., *Lancet* 387:40-52, 2016). In some embodiments, the IL-13 inhibitor is AMG317 (Amgen) or an antigen-binding fragment thereof (Polosa et al., *Drug Discovery Today* 17:591-599, 2012; Holgate, British J. Clinical Pharmacol. 76:277-291, 2013). In some embodiments, the IL-13 inhibitor is an antibody that specifically binds to IL-13Rα1 (see, e.g., U.S. Pat. No. 7,807,158; WO 96/29417; WO 97/15663; and WO 03/080675).

In some embodiments, the IL-13 inhibitor is a humanized monoclonal antibody (e.g., lebrikizumab (TNX-650) (Thomson et al., *Biologics* 6:329-335, 2012; and Hanania et al., *Thorax* 70(8):748-756, 2015). In some embodiments, the IL-13 inhibitor is an anti-IL-13 antibody, e.g., GSK679586 or a variant thereof (Hodsman et al., *Br. J. Clin. Pharmacol.* 75(1):118-128, 2013; and De Boever et al., *J. Allergy Clin. Immunol.* 133(4):989-996, 2014). In some embodiments, the IL-13 inhibitor is tralokinumab (CAT-354) or a variant thereof (Brightling et al., *Lancet* 3(9): 692-701, 2015; Walsh et al. (2010) *Curr. Opin. Investig. Drugs* 11(11):1305-1312, 2010; Piper et al., *Euro. Resp. J.* 41:330-338, 2013; May et al., *Br. J. Pharmacol.* 166(1): 177-193, 2012; Singh et al., *BMC Pulm Med.* 10:3, 2010; Blanchard et al., *Clin. Exp. Allergy* 35(8): 1096-1103, 2005). In some embodiments, the Il-13 inhibitor is anrukinzumab (IMA-638) (Hua et al., *Br. J. Clin. Pharmacol.* 80: 101-109, 2015; Reinisch et al., Gut 64(6): 894-900, 2015; Gauvreau et al., *Am. J. Respir. Crit. Care Med.* 183(8):1007-1014, 2011; Bree et al., *J. Allergy Clin. Immunol.* 119(5):1251-1257, 2007). Further teachings of IL-13 inhibitors that are antibodies or antigen-binding fragments thereof are described in U.S. Pat. Nos. 8,067,199; 7,910,708; 8,221,752; 8,388,965; 8,399,630; and 8,734,801; US 2014/0341913; US 2015/0259411; US 2016/0075777; US 2016/0130339, US 2011/0243928, and US 2014/0105897 each of which is incorporated by reference in its entirety.

IL-13 Inhibitor Fusion Proteins

In some embodiments, the IL-13 inhibitor is a fusion protein or a soluble antagonist. In some embodiments, the fusion protein comprises a soluble fragment of a receptor of IL-13 (e.g., a soluble fragment of a complex including IL-13Rα1 and IL-4Rα, a soluble fragment of a complex including IL-13Rα1 and IL-13Rα2, a soluble fragment of IL-13Rα1, a soluble fragment of IL-13Rα2, or soluble fragment of IL-4Rα). In some embodiments, the fusion protein comprises an extracellular domain of a receptor of IL-13 (e.g., a fusion protein including an extracellular domain of both IL-13Rα1 and IL-4Rα, a fusion protein including an extracellular domain of both IL-13Rα1 and IL-13Rα2, a fusion protein including an extracellular domain of IL-13Rα1, a fusion protein including an extracellular domain of IL-13Rα2, or a fusion protein including an extracellular domain of IL-4Rα).

In some embodiments, the fusion protein comprises or consists of sIL-13Rα2-Fc (see, e.g., Chiaramonte et al., *J. Clin. Invest.* 104(6):777-785, 1999; Kasaian et al., *Am. J. Respir. Cell. Mol. Biol.* 36(3):368-376, 2007; Miyahara et al., *J. Allergy Clin. Immunol.* 118(5):1110-1116, 2006; Rahaman et al., *Cancer Res.* 62(4):1103-1109, 2002; incorporated by reference herein). In some embodiments, the fusion protein comprises or consists of an IL-13 fusion cytotoxin (e.g., IL-13/diphtheria toxin fusion protein (Li et al., *Protein Eng.* 15(5):419-427, 2002), IL-13-PE38QQR (IL-13-PE) (Blease et al. (2001) *J. Immunol.* 167(11):6583-6592, 2001; and Husain et al., *J. Neuro-Oncol.* 65(1):37-48, 2003)).

CD3 Inhibitors

In some embodiments, the therapeutic suitable for use with the devices and methods described herein is a CD3 inhibitor. The term "CD3 inhibitor" refers to an agent which decreases the ability of one or more of CD3γ, CD3δ, CD3ε, and CD3ζ to associate with one or more of TCR-α, TCR-β, TCR-δ, and TCR-γ. In some embodiments, the CD3 inhibitor can decrease the association between one or more of CD3γ, CD3δ, CD3ε, and CD3ζ and one or more of TCR-α, TCR-β, TCR-δ, and TCR-γ by blocking the ability of one or more of CD3γ, CD3δ, CD3ε, and CD3ζ to interact with one or more of TCR-α, TCR-β, TCR-δ, and TCR-γ.

In some embodiments, the CD3 inhibitor is an antibody or an antigen-binding fragment thereof, a fusion protein, or a small molecule. Exemplary CD3 inhibitors are described herein. Additional examples of CD3 inhibitors are known in the art.

CD3 Inhibitor Antibodies

In some embodiments, the CD3 inhibitor is an antibody or an antigen-binding fragment thereof (e.g., a Fab or a scFv). In some embodiments, the CD3 inhibitor is an antibody or antigen-binding fragment that binds specifically to CD3γ. In some embodiments, the CD3 inhibitor is an antibody or antigen-binding fragment that binds specifically to CD3δ. In some embodiments, the CD3 inhibitor is an antibody or antigen-binding fragment that binds specifically to CD3ε. In some embodiments, the CD3 inhibitor is an antibody or antigen-binding fragment that binds specifically to CD3. In some embodiments, the CD3 inhibitor is an antibody or an antigen-binding fragment that can bind to two or more (e.g., two, three, or four) of CD3γ, CD3δ, CD3ε, and CD3ζ.

In certain embodiments, the antibody comprises or consists of an antigen-binding fragment or portion of visiluzumab (Nuvion; HuM-291; M291; SMART anti-CD3 antibody) (Carpenter et al., *Biol. Blood Marrow Transplant* 11(6): 465-471, 2005; Trajkovic *Curr. Opin. Investig. Drugs* 3(3): 411-414, 2002; Malviya et al., *J. Nucl. Med.* 50(10): 1683-1691, 2009); muromonab-CD3 (orthoclone OKT3) (Hori et al., *Surg. Today* 41(4): 585-590, 2011; Norman *Ther. Drug Monit.* 17(6): 615-620, 1995; and Gramatzki et al., *Leukemia* 9(3): 382-390, 19); otelixizumab (TRX4) (Vossenkamper et al., *Gastroenterology* 147(1): 172-183, 2014; and Wiczling et al., *J. Clin. Pharmacol.* 50(5): 494-506, 2010); foralumab (NI-0401) (Ogura et al., *Clin. Immunol.* 183: 240-246; and van der Woude et al., *Inflamm. Bowel Dis.* 16: 1708-1716, 2010); ChAgly CD3; teplizumab (MGA031) (Waldron-Lynch et al., *Sci. Transl. Med.* 4(118): 118ra12, 2012; and Skelley et al., *Ann. Pharmacother.* 46(10): 1405-1412, 2012); or catumaxomab (Removab®) (Linke et al., *Mabs* 2(2): 129-136, 2010; and Bokemeyer et al., *Gastric Cancer* 18(4): 833-842, 2015).

Additional examples of CD3 inhibitors that are antibodies or antibody fragments are described in, e.g., U.S. Patent Application Publication Nos. 2017/0204194, 2017/0137519, 2016/0368988, 2016/0333095, 2016/0194399, 2016/0168247, 2015/0166661, 2015/0118252, 2014/0193399, 2014/0099318, 2014/0088295, 2014/0080147, 2013/0115213, 2013/0078238, 2012/0269826, 2011/0217790, 2010/0209437, 2010/0183554, 2008/0025975, 2007/0190045, 2007/0190052, 2007/0154477, 2007/0134241, 2007/0065437, 2006/0275292, 2006/0269547, 2006/0233787, 2006/0177896, 2006/0165693, 2006/0088526, 2004/0253237, 2004/0202657, 2004/0052783, 2003/0216551, and 2002/0142000, each of which is herein incorporated by reference in its entirety (e.g., the sections describing the CD3 inhibitors). Additional CD3 inhibitors that are antibodies or antigen-binding antibody fragments are described in, e.g., Smith et al., *J. Exp. Med.* 185(8):1413-1422, 1997; Chatenaud et al., *Nature* 7:622-632, 2007.

In some embodiments, the CD3 inhibitor comprises or consists of a bispecific antibody (e.g., JNJ-63709178) (Gaudet et al., *Blood* 128(22): 2824, 2016); JNJ-64007957 (Girgis et al., *Blood* 128: 5668, 2016); MGD009 (Tolcher et al., *J. Clin. Oncol.* 34:15, 2016); ERY974 (Ishiguro et al., *Sci. Transl. Med.* 9(410): pii.eaa14291, 2017); AMV564 (Hoseini and Cheung *Blood Cancer J.* 7:e522, 2017); AFM11 (Reusch et al., *MAbs* 7(3): 584-604, 2015); duvortuxizumab (JNJ 64052781); R06958688; blinatumomab (Blincyto®; AMG103) (Ribera *Expert Rev. Hematol.* 1:1-11, 2017; PF-06671008; IMC-C103C; RG-6160; XmAb-14045; and Mori et al., *N Engl. J. Med.* 376(23):e49, 2017); XmAb13676; or REGN1979 (Bannerji et al., *Blood* 128: 621, 2016; and Smith et al., *Sci. Rep.* 5:17943, 2015)).

In some embodiments, the CD3 inhibitor comprises or consists of a trispecific antibody (e.g., ertumaxomab (Kiewe and Thiel, *Expert Opin. Investig. Drugs* 17(10): 1553-1558, 2008; and Haense et al., *BMC Cancer* 16:420, 2016); or FBTA05 (Bi20; Lymphomun) (Buhmann et al., *J. Transl. Med.* 11:160, 2013; and Schuster et al., *Br. J. Haematol.* 169(1): 90-102, 2015)).

CD3 Inhibitor Fusion and Truncated Proteins and Peptides

In some embodiments, the CD3 inhibitor is a fusion protein, a truncated protein (e.g., a soluble receptor), or a peptide. In some embodiments, the CD3 inhibitor can be a fusion protein (see, e.g., Lee et al., *Oncol. Rep.* 15(5): 1211-1216, 2006).

CD3 Inhibitor Small Molecules

In some embodiments, the CD3 inhibitor comprises or consists of a bispecific small molecule-antibody conjugate (see, e.g., Kim et al., *PNAS* 110(44): 17796-17801, 2013; Viola et al., *Eur. J. Immunol.* 27(11):3080-3083, 1997).

CD14 Inhibitors

In some embodiments, the therapeutic suitable for use with the devices and methods described herein is a CD14 inhibitor. The term "CD14 inhibitors" refers to an agent which decreases the ability of CD14 to bind to lipopolysaccharide (LPS). CD14 acts as a co-receptor with Toll-like receptor 4 (TLR4) that binds LPS in the presence of lipopolysaccharide-binding protein (LBP).

In some embodiments, the CD14 inhibitor can decrease the binding between CD14 and LPS by blocking the ability of CD14 to interact with LPS.

In some embodiments, the CD14 inhibitor is an antibody or an antigen-binding fragment thereof. In some embodiments, the CD14 inhibitor is a small molecule. Exemplary CD14 inhibitors are described herein. Additional examples of CD14 inhibitors are known in the art.

CD14 Inhibitor Antibodies

In some embodiments, the CD14 inhibitor is an antibody or an antigen-binding fragment thereof (e.g., a Fab or a scFv). In some embodiments, the CD14 inhibitor is an antibody or antigen-binding fragment that binds specifically to CD14.

In certain embodiments, the antibody comprises or consists of an antigen-binding fragment or portion of IC14 (Axtelle and Pribble, *J. Endotoxin Res.* 7(4): 310-314, 2001; Reinhart et al., *Crit. Care Med.* 32(5): 1100-1108, 2004; Spek et al., *J. Clin. Immunol.* 23(2): 132-140, 2003). Additional examples of anti-CD14 antibodies and CD14 inhibitors can be found, e.g., in WO 2015/140591 and WO 2014/122660, incorporated in its entirety herein.

Additional examples of CD14 inhibitors that are antibodies or antibody fragments are described in, e.g., U.S. Patent Application Serial No. 2017/0107294, 2014/0050727, 2012/0227412, 2009/0203052, 2009/0029396, 2008/0286290, 2007/0106067, 2006/0257411, 2006/0073145, 2006/0068445, 2004/0092712, 2004/0091478, and 2002/

0150882, each of which is herein incorporated by reference (e.g., the sections that describe CD14 inhibitors).

CD14 Inhibitor Small Molecules

In some embodiments, the CD14 inhibitor is a small molecule. Non-limiting examples of CD14 inhibitors that are small molecules are described in, e.g., methyl 6-deoxy-6-N-dimethyl-N-cyclopentylammonium-2,3-di-O-tetradecyl-α-D-glucopyranoside iodide (IAXO-101); methyl 6-Deoxy-6-amino-2,3-di-O-tetradecyl-α-D-glucopyranoside (IAXO-102); N-(3,4-bi s-tetradecyloxy-benzyl)-N-cyclopentyl-N,N-dimethylammonium iodide (IAXO-103); and IMO-9200.

CD20 Inhibitors

In some embodiments, the therapeutic suitable for use with the devices and methods described herein is a CD20 inhibitor. The term "CD20 inhibitors" refers to an agent that binds specifically to CD20 expressed on the surface of a mammalian cell.

In some embodiments, the CD20 inhibitor is an antibody or an antigen-binding fragment thereof, or a fusion protein or peptide. Exemplary CD20 inhibitors are described herein. Additional examples of CD20 inhibitors are known in the art.

CD20 Inhibitor Antibodies

In some embodiments, the CD20 inhibitor is an antibody or an antigen-binding fragment thereof (e.g., a Fab or a scFv).

In certain embodiments, the antibody comprises or consists of an antigen-binding fragment or portion of rituximab (Rituxan®, MabThera®, MK-8808) (Ji et al., *Indian J. Hematol. Blood Transfus.* 33 (4): 525-533, 2017; and Calderon-Gomez and Panes *Gastroenterology* 142(1): 1741-76, 2012); ocrelizumab (Ocrevus™) (Sharp *N. Engl. J. Med.* 376(17):1692, 2017); ofatumumab (Arzerra®; HuMax-CD20) (AlDallal *Ther. Clin. Risk Manag.* 13:905-907, 2017; and Furman et al., *Lancet Haematol.* 4(1):e24-e34, 2017); PF-05280586 (Williams et al., *Br. J. Clin. Pharmacol.* 82(6):1568-1579, 2016; and Cohen et al., *Br. J. Clin. Pharmacol.* 82(1):129-138, 2016); obinutuzumab (Gazyva®) (Reddy et al., *Rheumatology* 56(7):1227-1237, 2017; and Marcus et al., *N. Engl. J. Med.* 377(14): 1331-1344, 2017); ocaratuzumab (AME-133v; LY2469298) (Cheney et al., *Mabs* 6(3):749-755, 2014; and Tobinai et al., *Cancer Sci.* 102(2):432-8, 2011); GP2013 (Jurczak et al., *Lancet Haematol.* 4(8): e350-e361, 2017); IBI301; HLX01; veltuzumab (hA20) (Kalaycio et al., *Leuk. Lymphoma* 57(4):803-811, 2016; and Ellebrecht et al., *JAMA Dermatol.* 150(12):1331-1335, 2014); SCT400 (Gui et al., *Chin. J. Cancer Res.* 28(2):197-208); ibritumomab tiuxetan (Zevalin®) (Philippe et al., *Bone Marrow Transplant* 51(8):1140-1142, 2016; and Lossos et al., *Leuk. Lymphoma* 56(6):1750-1755, 2015); ublituximab (TG1101) (Sharman et al., *Blood* 124:4679, 2014; and Sawas et al., *Br. Haematol.* 177(2):243-253, 2017); LFB-R603 (Esteves et al., *Blood* 118:1660, 2011; and Baritaki et al., *Int. J. Oncol.* 38(6):1683-1694, 2011); or HSK-III-001 from Haisco Pharmaceutical Group, or tositumomab (Bexxar) (Buchegger et al., *J Nucl. Med.* 52(6):896-900, 2011; and William and Bierman *Expert Opin. Biol. Ther.* 10(8):1271-1278, 2010). Additional examples of CD20 antibodies are known in the art (see, e.g., WO 2008/156713).

In certain embodiments, the antibody comprises or consists of an antigen-binding fragment or portion of a bispecific antibody (e.g., XmAb13676; REGN1979 (Bannerji et al., *Blood* 128:621, 2016; and Smith et al., *Sci. Rep.* 5:17943, 2015); PRO131921 (Casulo et al., *Clin. Immnol.* 154(1):37-46, 2014; and Robak and Robak *BioDrugs* 25(1):13-25, 2011); or Acellbia).

In some embodiments, the CD20 inhibitor comprises or consists of a trispecific antibody (e.g., FBTA05 (Bi20; Lymphomun) (Buhmann et al., *J Transl. Med.* 11:160, 2013; and Schuster et al., *Br. J. Haematol.* 169(1):90-102, 2015)).

Additional examples of CD20 inhibitors that are antibodies or antigen-binding fragments are described in, e.g., U.S. Patent Application Publication Nos. 2017/0304441, 2017/0128587, 2017/0088625, 2017/0037139, 2017/0002084, 2016/0362472, 2016/0347852, 2016/0333106, 2016/0271249, 2016/0243226, 2016/0115238, 2016/0108126, 2016/0017050, 2016/0017047, 2016/0000912, 2016/0000911, 2015/0344585, 2015/0290317, 2015/0274834, 2015/0265703, 2015/0259428, 2015/0218280, 2015/0125446, 2015/0093376, 2015/0079073, 2015/0071911, 2015/0056186, 2015/0010540, 2014/0363424, 2014/0356352, 2014/0328843, 2014/0322200, 2014/0294807, 2014/0248262, 2014/0234298, 2014/0093454, 2014/0065134, 2014/0044705, 2014/0004104, 2014/0004037, 2013/0280243, 2013/0273041, 2013/0251706, 2013/0195846, 2013/0183290, 2013/0089540, 2013/0004480, 2012/0315268, 2012/0301459, 2012/0276085, 2012/0263713, 2012/0258102, 2012/0258101, 2012/0251534, 2012/0219549, 2012/0183545, 2012/0100133, 2012/0034185, 2011/0287006, 2011/0263825, 2011/0243931, 2011/0217298, 2011/0200598, 2011/0195022, 2011/0195021, 2011/0177067, 2011/0165159, 2011/0165152, 2011/0165151, 2011/0129412, 2011/0086025, 2011/0081681, 2011/0020322, 2010/0330089, 2010/0310581, 2010/0303808, 2010/0183601, 2010/0080769, 2009/0285795, 2009/0203886, 2009/0197330, 2009/0196879, 2009/021165, 2009/0175854, 2009/0155253, 2009/0136516, 2009/0130089, 2009/0110688, 2009/0098118, 2009/0074760, 2009/0060913, 2009/0035322, 2008/0260641, 2008/0213273, 2008/0089885, 2008/0044421, 2008/0038261, 2007/0280882, 2007/0231324, 2007/0224189, 2007/0059306, 2007/0020259, 2007/0014785, 2007/0014720, 2006/0121032, 2005/0180972, 2005/0112060, 2005/0069545, 2005/0025764, 2004/0213784, 2004/0167319, 2004/0093621, 2003/0219433, 2003/0206903, 2003/0180292, 2003/0026804, 2002/0039557, 2002/0012665, and 2001/0018041, each herein incorporated by reference in their entirety (e.g., sections describing CD20 inhibitors).

CD20 Inhibitor Peptides and Fusion Proteins

In some embodiments, the CD20 inhibitor is an immunotoxin (e.g., MT-3724 (Hamlin *Blood* 128: 4200, 2016).

In some embodiments, the CD20 inhibitor is a fusion protein (e.g., TRU-015 (Rubbert-Roth *Curr. Opin. Mol. Ther.* 12(1): 115-123, 2010). Additional examples of CD20 inhibitors that are fusion proteins are described in, e.g., U.S. Patent Application Publication Nos. 2012/0195895, 2012/0034185, 2009/0155253, 2007/0020259, and 2003/0219433, each of which are herein incorporated by reference in their entirety (e.g., sections describing CD20 inhibitors).

CD25 Inhibitors

In some embodiments, the therapeutic suitable for use with the devices and methods described herein is a CD25 inhibitor. The term "CD25 inhibitors" refers to an agent which decreases the ability of CD25 (also called interleukin-2 receptor alpha chain) to bind to interleukin-2. CD25 forms a complex with interleukin-2 receptor beta chain and interleukin-2 common gamma chain.

In some embodiments, the CD25 inhibitor is an antibody or an antigen-binding fragment thereof, or a fusion protein.

Exemplary CD25 inhibitors are described herein. Additional examples of CD25 inhibitors are known in the art.

CD25 Inhibitor Antibodies

In some embodiments, the CD25 inhibitor is an antibody or an antigen-binding fragment thereof (e.g., a Fab or a scFv). In some embodiments, a CD25 inhibitor is an antibody or an antigen-binding fragment thereof that specifically binds to CD25. In some embodiments, a CD25 inhibitor is an antibody that specifically binds to IL-2.

In certain embodiments, the antibody comprises or consists of an antigen-binding fragment or portion of basiliximab (Simulect™) (Wang et al., *Clin. Exp. Immunol.* 155(3): 496-503, 2009; and Kircher et al., *Clin. Exp. Immunol.* 134(3): 426-430, 2003); daclizumab (Zenapax; Zinbryta®) (Berkowitz et al., *Clin. Immunol.* 155(2): 176-187, 2014; and Bielekova et al., *Arch Neurol.* 66(4): 483-489, 2009); or IMTOX-25.

In some embodiments, the CD25 inhibitor is an antibody-drug-conjugate (e.g., ADCT-301 (Flynn et al., *Blood* 124: 4491, 2014)).

In some embodiments, the CD25 inhibitor is a PEG IL-2 conjugate (e.g., NKTR-358).

Additional examples of CD25 inhibitors that are antibodies are known in the art (see, e.g., WO 2004/045512). Additional examples of CD25 inhibitors that are antibodies or antigen-binding fragments are described in, e.g., U.S. Patent Application Publication Nos. 2017/0240640, 2017/0233481, 2015/0259424, 2015/0010539, 2015/0010538, 2012/0244069, 2009/0081219, 2009/0041775, 2008/0286281, 2008/0171017, 2004/0170626, 2001/0041179, and 2010/0055098, each of which is incorporated herein by reference (e.g., sections that describe CD25 inhibitors).

CD25 Inhibitor Fusion Proteins

In some embodiments, the CD25 inhibitor is a fusion protein. See, e.g., Zhang et al., *PNAS* 100(4): 1891-1895, 2003.

CD28 Inhibitors

In some embodiments, the therapeutic suitable for use with the devices and methods described herein is a CD28 inhibitor. The term "CD28 inhibitors" refers to an agent which decreases the ability of CD28 to bind to one or both of CD80 and CD86. CD28 is a receptor that binds to its ligands, CD80 (also called B7.1) and CD86 (called B7.2).

In some embodiments, the CD28 inhibitor can decrease the binding between CD28 and CD80 by blocking the ability of CD28 to interact with CD80. In some embodiments, the CD28 inhibitor can decrease the binding between CD28 and CD86 by blocking the ability of CD28 to interact with CD86. In some embodiments, the CD28 inhibitor can decrease the binding of CD28 to each of CD80 and CD86.

In some embodiments, the CD28 inhibitor is an antibody or an antigen-binding fragment thereof, a fusion protein, or peptide. Exemplary CD28 inhibitors are described herein. Additional examples of CD28 inhibitors are known in the art.

CD28 Inhibitor Antibodies

In some embodiments, the CD28 inhibitor is an antibody or an antigen-binding fragment thereof (e.g., a Fab or a scFv).

In some embodiments, the CD28 inhibitor is a monovalent Fab' antibody (e.g., CFR104) (Poirier et al., *Am. J. Transplant* 15(1): 88-100, 2015).

Additional examples of CD28 inhibitors that are antibodies or antigen-binding fragments are described in, e.g., U.S. Patent Application Publication Nos. 2017/0240636, 2017/0114136, 2016/0017039, 2015/0376278, 2015/0299321, 2015/0232558, 2015/0150968, 2015/0071916, 2013/0266577, 2013/0230540, 2013/0109846, 2013/0078257, 2013/0078236, 2013/0058933, 2012/0201814, 2011/0097339, 2011/0059071, 2011/0009602, 2010/0266605, 2010/0028354, 2009/0246204, 2009/0117135, 2009/0117108, 2008/0095774, 2008/0038273, 2007/0154468, 2007/0134240, 2007/0122410, 2006/0188493, 2006/0165690, 2006/0039909, 2006/0009382, 2006/0008457, 2004/0116675, 2004/0092718, 2003/0170232, 2003/0086932, 2002/0006403, 2013/0197202, 2007/0065436, 2003/0180290, 2017/0015747, 2012/0100139, and 2007/0148162, each of which is incorporated by reference in its entirety (e.g., sections that described CD28 inhibitors).

CD28 Inhibitor Fusion Proteins and Peptides

In some embodiments, the CD28 inhibitor is a fusion protein (see, e.g., U.S. Pat. No. 5,521,288; and US 2002/0018783). In some embodiments, the CD28 inhibitor is abatacept (Orencia®) (Herrero-Beaumont et al., *Rheumatol. Clin.* 8:78-83, 2012; and Korhonen and Moilanen *Basic Clin. Pharmacol. Toxicol.* 104(4):276-284, 2009).

In some embodiments, the CD28 inhibitor is a peptide mimetic (e.g., AB103) (see, e.g., Bulger et al., *JAMA Surg.* 149(6):528-536, 2014), or a synthetic peptoid (see, e.g., Li et al., *Cell Mol. Immunol.* 7(2):133-142, 2010).

CD40/CD40L Inhibitors

In some embodiments, the therapeutic suitable for use with the devices and methods described herein is a CD40/CD40L inhibitor. The term "CD40/CD40L inhibitors" refers to an agent which decreases CD40 or CD40L (CD154) expression and/or the ability of CD40 to bind to CD40L (CD154). CD40 is a costimulatory receptor that binds to its ligand, CD40L (CD154).

In some embodiments, the CD40/CD40L inhibitor can decrease the binding between CD40 and CD40L by blocking the ability of CD40 to interact with CD40L. In some embodiments, the CD40/CD40L inhibitor can decrease the binding between CD40 and CD40L by blocking the ability of CD40L to interact with CD40. In some embodiments, the CD40/CD40L inhibitor decreases the expression of CD40 or CD40L. In some embodiments, the CD40/CD40L inhibitor decreases the expression of CD40. In some embodiments, the CD40/CD40L inhibitor decreases the expression of CD40L.

In some embodiments, the CD40/CD40L inhibitor is an inhibitory nucleic acid, an antibody or an antigen-binding fragment thereof, a fusion protein, or a small molecule. In some embodiments, the inhibitory nucleic acid is a small interfering RNA, an antisense nucleic acid, an aptamer, or a microRNA. Exemplary CD40/CD40L inhibitors are described herein. Additional examples of CD40/CD40L inhibitors are known in the art.

Inhibitory Nucleic Acids of CD40/CD40L

Some exemplary antisense nucleic acids that are CD40 or CD40L inhibitors are described, e.g., in U.S. Pat. Nos. 6,197,584 and 7,745,609; Gao et al., *Gut* 54(1):70-77, 2005; Arranz et al., *J. Control Release* 165(3):163-172, 2012; Donner et al., *Mol. Ther. Nucleic Acids* 4:e265, 2015.

Non-limiting examples of short interfering RNA (siRNA) that are CD40/CD40L inhibitors are described in, e.g., Pluvinet et al., *Blood* 104:3642-3646, 2004; Karimi et al., *Cell Immunol.* 259(1):74-81, 2009; and Zheng et al., *Arthritis Res. Ther.* 12(1):R13, 2010. Non-limiting examples of short hairpin RNA (shRNA) targeting CD40/CD40L are described in Zhang et al., *Gene Therapy* 21:709-714, 2014. Non-limiting examples of microRNAs that are CD40/CD40L inhibitors include, for example, miR146a (Chen et al., *FEBS Letters* 585(3):567-573, 2011), miR-424, and miR-503 (Lee et al., *Sci. Rep.* 7:2528, 2017).

Non-limiting examples of aptamers that are CD40/CD40L inhibitors are described in Soldevilla et al., *Biomaterials* 67:274-285, 2015.

CD40/CD40L Inhibitor Antibodies

In certain embodiments, the antibody comprises or consists of an antigen-binding fragment or portion of PG102 (Pangenetics) (Bankert et al., *J. Immunol.* 194(9):4319-4327, 2015); 2C10 (Lowe et al., *Am. J. Transplant* 12(8): 2079-2087, 2012); ASKP1240 (Bleselumab) (Watanabe et al., *Am. J. Transplant* 13(8):1976-1988, 2013); 4D11 (Imai et al., *Transplantation* 84(8):1020-1028, 2007); BI 655064 (Boehringer Ingelheim) (Visvanathan et al., 2016 American College of Rheumatology Annual Meeting, Abstract 1588, Sep. 28, 2016); 5D12 (Kasran et al., *Aliment. Pharmacol. Ther.*, 22(2):111-122, 2005; Boon et al., *Toxicology* 174(1): 53-65, 2002); ruplizumab (hu5c8) (Kirk et al., *Nat. Med.* 5(6):686-693, 1999); CHIR12.12 (HCD122) (Weng et al., *Blood* 104(11):3279, 2004; Tai et al., *Cancer Res.* 65(13): 5898-5906, 2005); CDP7657 (Shock et al., *Arthritis Res. Ther.* 17(1):234, 2015); BMS-986004 domain antibody (dAb) (Kim et al., *Am. J. Transplant.* 17(5):1182-1192, 2017); 5c8 (Xie et al., *J. Immunol.* 192(9):4083-4092, 2014); dacetuzumab (SGN-40) (Lewis et al., *Leukemia* 25(6):1007-1016, 2011; and Khubchandani et al., *Curr. Opin. Investig. Drugs* 10(6):579-587, 2009); lucatumumab (HCD122) (Bensinger et al., *Br. J. Haematol.* 159: 58-66, 2012; and Byrd et al., *Leuk. Lymphoma* 53(11): 10.3109/10428194.2012.681655, 2012); PG102 (FFP104) (Bankert et al., *J. Immunol.* 194(9):4319-4327, 2015); mitazalimab (JNJ-64457107); Chi Lob 7/4 (Johnson et al., *J. Clin. Oncol.* 28:2507, 2019); dapirolizumab pegol (CDP-7657) and ASKP1240 (Okimura et al., *Am. J. Transplant.* 14(6): 1290-1299, 2014; or Ma et al., *Transplantation* 97(4): 397-404, 2014).

Further teachings of CD40/CD40L antibodies and antigen-binding fragments thereof are described in, for example, U.S. Pat. Nos. 5,874,082; 7,169,389; 7,271,152; 7,288,252; 7,445,780; 7,537,763; 8,277,810; 8,293,237; 8,551,485; 8,591,900; 8,647,625; 8,784,823; 8,852,597; 8,961,976; 9,023,360, 9,028,826; 9,090,696, 9,221,913; US2014/0093497; and US2015/0017155 each of which is incorporated by reference in its entirety.

CD40/CD40L Inhibitor Fusion and Truncated Proteins and Peptides

In some embodiments, the CD40/CD40L inhibitor is a fusion protein, a truncated protein (e.g., a soluble receptor) or a peptide. In some embodiments, the CD40/CD40L inhibitor is a truncated protein as disclosed in, for example, WO 01/096397. In some embodiments, the CD40/CD40L inhibitor is a peptide, such as a cyclic peptide (see, e.g., U.S. Pat. No. 8,802,634; Bianco et al., *Org. Biomol. Chem.* 4:1461-1463, 2006; Deambrosis et al., *J. Mol. Med.* 87(2): 181-197, 2009; Vaitaitis et al., *Diabetologia* 57(11):2366-2373, 2014). In some embodiments, the CD40/CD40L inhibitor is a CD40 ligand binder, for example, a Tumor Necrosis Factor Receptor-associated Factor (TRAF): TRAF2, TRAF3, TRAF6, TRAFS and TTRAP, or E3 ubiquitin-protein ligase RNF128.

CD40/CD40L Inhibitor Small Molecules

In some embodiments, the CD40/CD40L inhibitor is a small molecule (see, e.g., U.S. Pat. No. 7,173,046, U.S. Patent Application No. 2011/0065675). In some embodiments, the small molecule is Bio8898 (Silvian et al., *ACS Chem. Biol.* 6(6):636-647, 2011); Suramin (Margolles-Clark et al., *Biochem. Pharmacol.* 77(7):1236-1245, 2009); a small-molecule organic dye (Margolles-Clark et al., *J. Mol. Med.* 87(11):1133-1143, 2009; Buchwald et al., *J. Mol. Recognit.* 23(1):65-73, 2010), a naphthalenesulfonic acid derivative (Margolles-Clark et al., *Chem. Biol. Drug Des.* 76(4):305-313, 2010), or a variant thereof.

CD49 Inhibitors

In some embodiments, the therapeutic suitable for use with the devices and methods described herein is a CD49 inhibitor. The term "CD49 inhibitors" refers to an agent which decreases the ability of CD49 to bind to one of its ligands (e.g., MMP1). In some embodiments, the CD49 inhibitor is an antibody or an antigen-binding fragment thereof. Exemplary CD49 inhibitors are described herein. Additional examples of CD49 inhibitors are known in the art.

CD49 Inhibitor Antibodies

In some embodiments, the CD49 inhibitor is an antibody or an antigen-binding fragment thereof (e.g., a Fab or a scFv).

In certain embodiments, the antibody comprises or consists of an antigen-binding fragment or portion of natalizumab (Tysabri®; Antegren®) (see, e.g., Pagnini et al., *Expert Opin. Biol. Ther.* 17(11): 1433-1438, 2017; and Chataway and Miller *Neurotherapeutics* 10(1): 19-28, 2013; or vatelizumab (ELND-004)).

CD89 Inhibitors

In some embodiments, the therapeutic suitable for use with the devices and methods described herein is a CD89 inhibitor. The term "CD89 inhibitors" refers to an agent which decreases the ability of CD89 to bind to IgA. CD89 is a transmembrane glycoprotein that binds to the heavy-chain constant region of IgA. In some embodiments, the CD89 inhibitor can decrease the binding between CD89 and IgA by blocking the ability of CD89 to interact with IgA. In some embodiments, the CD89 inhibitor is an antibody or an antigen-binding fragment thereof. Exemplary CD89 inhibitors are described herein. Additional examples of CD89 inhibitors are known in the art.

CD89 Inhibitor Antibodies

In some embodiments, the CD89 inhibitor is an antibody or an antigen-binding fragment thereof (e.g., a Fab or a scFv).

In certain embodiments, the antibody comprises or consists of an antigen-binding fragment or portion of HF-1020. Additional examples of CD89 antibodies are known in the art (see, e.g., WO 2002/064634).

Integrin Inhibitors

In some embodiments, the therapeutic suitable for use with the devices and methods described herein is an integrin inhibitor. The term "integrin inhibitor" refers to an agent which decreases the expression of one or more integrins and/or decreases the binding of an integrin ligand to one or more integrins that play a role in the recruitment, extravasation, and/or activation of a leukocyte. In some embodiments, the integrin inhibitor specifically binds to at least a portion of a ligand binding site on a target integrin. In some embodiments, the integrin inhibitor specifically binds to a target integrin at the same site as an endogenous ligand. In some embodiments, the integrin inhibitor decreases the level of expression of the target integrin in a mammalian cell. In some embodiments, the integrin inhibitor specifically binds to an integrin ligand.

Non-limiting examples of integrins that can be targeted by any of the integrin inhibitors described herein include: $\alpha 2\beta 1$ integrin, $\alpha 1\beta 1$ integrin, $\alpha 4\beta 7$ integrin, integrin $\alpha 4\beta 1$ (VLA-4), E-selectin, ICAM-1, $\alpha 5\beta 1$ integrin, $\alpha 4\beta 1$ integrin, VLA-4, $\alpha 2\beta 1$ integrin, $\alpha 5\beta 3$ integrin, $\alpha 5\beta 5$ integrin, $\alpha IIb\beta 3$ integrin, and MAdCAM-1. A non-limiting example of integrin inhibitor that can decrease the expression and/or activity of α4β7 integrin is FTY720. A non-limiting example of an integrin inhibitor that specifically targets MAdCAM is PF-547659 (Pfizer). Non-limiting examples of an integrin inhibitor that specifically targets α4β7 is AJM300 (Ajinomoto), etrolizumab (Genentech), and vedolizumab (Millenium/Takeda).

In some embodiments, the integrin inhibitor is an αIIbβ3 integrin inhibitor. In some embodiments, the αIIbβ3 integrin inhibitor is abciximab (ReoPro®, c7E3; Kononczuk et al., Curr. Drug Targets 16(13):1429-1437, 2015; Jiang et al., Appl. Microbiol. Biotechnol. 98(1):105-114, 2014), eptifibatide (Integrilin®; Scarborough et al., J. Biol. Chem. 268: 1066-1073, 1993; Tcheng et al., Circulation 91:2151-2157, 1995) or tirofiban (Aggrastat®; Hartman et al., J. Med. Chem. 35:4640-4642, 1992; Pierro et al., Eur. J. Ophthalmol. 26(4):e74-76, 2016; Guan et al., Eur. J. Pharmacol 761:144-152, 2015). In some embodiments, the integrin inhibitor is an αL-selective integrin inhibitor. In some embodiments, the integrin inhibitor is a β2 integrin inhibitor.

In some embodiments, the integrin inhibitor is an α4 integrin (e.g., an α4β1 integrin (e.g., Very Late Antigen-4 (VLA-4), CD49d, or CD29)) inhibitor, an α4β7 integrin inhibitor. In some embodiments, the integrin inhibitor targets endothelial VCAM1, fibronectin, mucosal addressin cellular adhesion molecule-1 (MAdCAM-1), vitronectin, tenascin-C, osteopontin (OPN), nephronectin, agiostatin, tissue-type transglutaminase, factor XIII, Von Willebrand factor (VWF), an ADAM protein, an ICAM protein, collagen, e-cadherin, laminin, fibulin-5, or TGFβ. In some embodiments, the α4 integrin inhibitor is natalizumab (Tysabri®; Targan et al., Gastroenterology 132(5):1672-1683, 2007; Sandborn et al., N. Engl. J. Med. 353(18):1912-1925, 2005; Nakamura et al., Intern. Med. 56(2):211-214, 2017; and Singh et al., J. Pediatr. Gastroenterol. Nutr. 62(6):863-866, 2016). In some embodiments, the integrin inhibitor is an endogenous integrin inhibitor (e.g., SHARPIN (Rantala et al., Nat. Cell. Biol. 13(11):1315-1324, 2011).

In some embodiments, the integrin inhibitor is an αv integrin (e.g., an α5β1 integrin, an α5β3 integrin, an α5β5 integrin inhibitor, and/or an α5β6 integrin) inhibitor.

In some embodiments, the integrin inhibitor is an α5β1 integrin inhibitor.

In some embodiments, an integrin inhibitor is an inhibitory nucleic acid, an antibody or antigen-binding fragment thereof, a fusion protein, an integrin antagonist, a cyclic peptide, a disintegrin, a peptidomimetic, or a small molecule. In some embodiments, the inhibitory nucleic acid is a small hairpin RNA, a small interfering RNA, an antisense, an aptamer, or a microRNA.

Inhibitory Nucleic Acids of Integrins

In some embodiments, the inhibitory nucleic acid can be an antisense nucleic acid, a ribozyme, a small interfering RNA, a small hairpin RNA, or a microRNA. Examples of aspects of these different inhibitory nucleic acids are described below.

Exemplary integrin inhibitors that are antisense nucleic acids include ATL1102 (e.g., Limmroth et al., Neurology 83(20):1780-1788, 2014; Li et al., Dig. Liver Dis. 39(6): 557-565, 2007; Goto et al., Inflamm. Bowel Dis. 12(8):758-765, 2006).

Non-limiting examples of integrin inhibitors that are short interfering RNAs (siRNAs) are described in Wang et al., Cancer Cell Int. 16:90, 2016). In some embodiments, the integrin inhibitor is a short hairpin RNA (shRNA).

Non-limiting examples of integrin inhibitors that are microRNA include miR-124 (Cai et al., Sci. Rep. 7:40733, 2017), miR-134 (Qin et al., Oncol. Rep. 37(2):823-830, 2017), miR-92b (Ma et al., Oncotarget 8(4):6681-6690, 2007), miR-17 (Gong et al., Oncol. Rep. 36(4), 2016), miR-338 (Chen et al., Oncol. Rep. 36(3):1467-74, 2016), and miR-30a-5p (Li et al., Int. J. Oncol. 48(3):1155-1164, 2016).

In some embodiments, the integrin inhibitor can include modified bases/locked nucleic acids (LNAs). In some embodiments, the integrin inhibitor is an aptamer (e.g., Berg et al., Mol. Ther. Nucl. Acids 5:e294, 2016; and Hussain et al., Nucleic Acid Ther. 23(3):203-212, 2013). Additional examples of integrin inhibitors that are inhibitory nucleic acids are described in Juliano et al., Theranostics 1:211-219, 2011; Millard et al., Theranostics 1:154-188, 2011; and Teoh et al., Curr. Mol. Med. 15:714-734, 2015. In some embodiments, the integrin inhibitor is an antisense nucleic acid, e.g., alicaforsen (Yacyshyn et al., Clin. Gastroenterol. Hepatol. 5(2):215-220, 2007).

Integrin Inhibitor Antibodies

In some embodiments, the antibody is a pan-β1 antibody (e.g., OS2966 (Carbonell et al., Cancer Res. 73(10):3145-3154, 2013). In some embodiments, the integrin antibody is a monoclonal antibody (e.g., 17E6 (Castel et al., Eur. J. Cell. Biol. 79(7):502-512, 2000); Mitjans et al., Int. J. Cancer 87(5):716-723, 2000)). In some embodiments, the monoclonal antibody is vedolizumab (e.g., Entyvio®) or a variant thereof (Feagan et al., N. Engl. J. Med 369:699-710, 2013; Sandborn et al., N. Engl. J. Med. 369:711-721, 2013; Sands et al., Gastroenterology 147:618-627, 2014; and Milch et al., Neuroimmunol. 264:123-126, 2013; Wyant et al., J. Crohns Colitis 10(12):1437-1444, 2016; and Feagan et al., Gastroenterology 142(5): S160-S161, 2012). In some embodiments, the monoclonal antibody is VPI-2690B or a variant thereof.

In some embodiments, the antibody can be a Fab fragment of a monoclonal chimeric mouse-human antibody (e.g., abciximab (ReoPro, c7E3), Kononczuk et al., Curr. Drug Targets 16(13):1429-1437, 2015; Jiang et al., Appl. Microbiol. Biotechnol. 98(1):105-114, 2014), or a variant thereof. In some embodiments, the integrin antibody is a humanized monoclonal antibody. In some embodiments, the humanized monoclonal antibody is natalizumab (Tysabri®) (Targan et al., Gastroenterology 132(5):1672-1683, 2007; Sandborn et al., N. Engl. J. Med. 353(18):1912-1925, 2005; Nakamura et al., Intern Med. 56(2):211-214, 2017; Singh et al., J. Pediatr. Gastroenterol. Nutr. 62(6):863-866, 2016). In some embodiments, the humanized monoclonal antibody is vitaxin (MEDI-523) or a variant thereof (Huveneers et al., Int. J. Radiat. Biol. 81(11-12):743-751, 2007; Coleman et al., Circ. Res. 84(11):1268-1276, 1999). In some embodiments, the humanized monoclonal antibody is etaracizumab (Abegrin®, MEDI-522, LM609) or a variant thereof (Hersey et al., Cancer 116(6):1526-1534, 2010; Delbaldo et al., Invest New Drugs 26(1):35-43, 2008). In some embodiments, the humanized monoclonal antibody is CNTO95 (Intetumumab®) or a variant thereof (Jia et al., Anticancer Drugs 24(3):237-250, 2013; Heidenreich et al., Ann. Oncol. 24(2): 329-336, 2013; Wu et al., J. Neurooncol. 110(1):27-36, 2012). In some embodiments, the humanized monoclonal antibody is efalizumab (Raptiva®) or a variant thereof (Krueger et al., J. Invest. Dermatol. 128(11):2615-2624, 2008; Li et al., PNAS 106(11):4349-4354, 2009; Woolacott et al., Health Technol. Assess 10:1-233, 2006). In some embodiments, the humanized monoclonal antibody is STX-100 (Stromedix®) or a variant thereof (van Aarsen et al., Cancer Res. 68:561-570, 2008; Lo et al., Am. J. Transplant. 13(12):3085-3093, 2013). In some embodiments, the humanized monoclonal antibody is 264RAD or a variant thereof (Eberlein et al., *Oncogene* 32(37):4406-4417, 2013).

In some embodiments, the humanized monoclonal antibody is rovelizumab or a variant thereof (Goodman et al., *Trends Pharmacol. Sci* 33:405-412, 2012). In some embodiments, the humanized monoclonal antibody is Cytolin® or a variant thereof (Rychert et al., *Virology* J. 10:120, 2013). In some embodiments, the humanized monoclonal antibody is etrolizumab or a variant thereof (Vermeire et al., *Lancet* 384:309-318, 2014; Rutgeerts et al., *Gut* 62:1122-1130, 2013; Lin et al., *Gastroenterology* 146:307-309, 2014; Ludviksson et al., *J. Immunol.* 162(8):4975-4982, 1999; Stefanich et al., *Br. J. Pharmacol.* 162(8):1855-1870, 2011). In some embodiments, the humanized monoclonal antibody is abrilumab (AMG 181; MEDI-7183) or a variant thereof (Pan et al., *Br. J. Pharmacol.* 169(1): 51-68, 2013; Pan et al., *Br. J. Clin. Pharmacol.* 78(6): 1315-1333, 2014). In some embodiments, the humanized monoclonal antibody is PF-00547659 (SHP647) or a variant thereof (Vermeire et al., *Gut* 60(8):1068-1075, 2011; Sandborn et al., *Gastroenterology* 1448(4):S-162, 2015). In some embodiments, the humanized monoclonal antibody is SAN-300 (hAQC2) or a variant thereof (Karpusas et al., *J Mol. Biol.* 327:1031-1041, 2003). In some embodiments, the humanized monoclonal antibody is DI176E6 (EMD 5257) or a variant thereof (Goodman et al., *Trends Pharmacol. Sci* 33:405-412, 2012; and Sheridan et al., *Nat. Biotech.* 32:205-207, 2014).

In some embodiments, the integrin antibody is a chimeric monoclonal antibody. In some embodiments, the chimeric monoclonal antibody is volociximab or a variant thereof (Kuwada et al., *Curr. Opin. Mol. Ther.* 9(1):92-98, 2007; Ricart et al., *Clin. Cancer Res.* 14(23):7924-7929, 2008; Ramakrishnan et al., *J Exp. Ther. Oncol.* 5(4):273-86, 2006; Bell-McGuinn et al., *Gynecol. Oncol.* 121:273-279, 2011; Almokadem et al., *Exp. Opin. Biol. Ther.* 12:251-7, 2012).

In some embodiments, the antibody specifically binds one or more (e.g., 1, 2, 3, 4, or 5) integrin. In some embodiments, the antibody specifically binds an integrin dimer (e.g., MLN-00002, MLN02 (Feagan et al., *Clin. Gastroenterol. Hepatol.* 6(12):1370-1377, 2008; Feagan et al., *N. Engl. J. Med.* 352(24):2499-2507, 2005). In certain embodiments, the antibody comprises or consists of an antigen-binding fragment of abciximab (Reopro™) (Straub et al., *Eur. J. Cardiothorac Surg.* 27(4):617-621, 2005; Kim et al., *Korean J. Intern. Med.* 19(4):220-229, 2004). In some embodiments, the integrin inhibitor is an antibody-drug conjugate (e.g., IMGN388 (Bendell et al., *EJC Suppl* 8(7):152, 2010).

Further examples of antibodies and antigen-binding fragments thereof are described in U.S. Pat. Nos. 5,919,792; 6,214,834; 7,074,408; 6,833,373; 7,655,624; 7,465,449; 9,558,899; 7,659,374; 8,562,986; 8,398,975; and 8,853,149; US 2007/0117849; US 2009/0180951; US 2014/0349944; US 2004/0018192; WO 11/137418; and WO 01/068586; each of which is incorporated by reference in its entirety.

Integrin Inhibitor Fusion Proteins

In some embodiments, the integrin inhibitor is a fusion protein (e.g., an Fc fusion protein of an extracellular domain of an integrin or an integrin receptor), a soluble receptor (e.g., the extracellular domain of an integrin or an integrin receptor), or a recombinant integrin binding protein (e.g., an integrin ligand). See, e.g., Lode et al., *PNAS* 96(4):1591-1596, 1999; Stephens et al., *Cell Adhesion Comm.* 7:377-390, 2000; and US 2008/0739003; incorporated by reference herein). Non-limiting examples of fusion proteins that are integrin inhibitors include Ag25426 (Proteintech).

Integrin Inhibitor Small Molecule Antagonists

In some embodiments, the integrin inhibitor is a small molecule. In some embodiments, the small molecule is a non-peptide small molecule. In some embodiments, the non-peptide small molecule is a RGD (ArgGlyAsp)-mimetic antagonist (e.g., tirofiban (Aggrastat®); Pierro et al., *Eur. J. Ophthalmol.* 26(4):e74-76, 2016; Guan et al., *Eur. J. Pharmacol* 761:144-152, 2015. In some embodiments, the small molecule is a4 antagonist (e.g., firategrast (Miller et al., *Lancet Neurol.* 11(2):131-139, 2012) AJM300 (Yoshimura et al., *Gastroenterology* 149(7):1775-1783, 2015; Takazoe et al., *Gastroenterology* 136(5):A-181, 2009; Sugiura et al., *J. Crohns Colitis* 7(11):e533-542, 2013)). In some embodiments, the small molecule is α4β1 antagonist (e.g., IVL745 (Norris et al., *J. Allergy Clin. Immunol.* 116(4):761-767, 2005; Cox et al., *Nat. Rev. Drug Discov.* 9(10):804-820, 2010)), BIO-1211 (Abraham et al., *Am. J. Respir. Crit. Care Med.* 162:603-611, 2000; Ramroodi et al., *Immunol. Invest.* 44(7):694-712, 2015; Lin et al., *J. Med. Chem.* 42(5):920-934, 1999), HMR 1031 (Diamant et al., *Clin. Exp. Allergy* 35(8):1080-1087, 2005); valategrast (R411) (Cox et al., *Nat. Rev. Drug Discov.* 9(10):804-820, 2010), GW559090X (Ravensberg et al., *Allergy* 61(9):1097-1103, 2006), TR14035 (Sircar et al., *Bioorg. Med. Chem.* 10(6):2051-2066, 2002; Cortijo et al., *Br J. Pharmacol.* 147(6):661-670, 2006)). In some embodiments, the small molecule is αvβ3 antagonist (e.g., L0000845704, SB273005). In some embodiments, the small molecule is α5β1 antagonist (e.g., JSM6427). In some embodiments, the small molecule is GLPG0974 (Vermeire et al., *J. Crohns Colitis* Suppl. 1:S39, 2015). In some embodiments, the small molecule is MK-0429 (Pickarksi et al., *Oncol. Rep.* 33(6):2737-45, 2015; Rosenthal et al., *Asia Pad Clin. Oncol.* 6:42-8, 2010). In some embodiments, the small molecule is JSM-6427 or a variant thereof (Zahn et al., *Arch. Ophthalmol.* 127(10):1329-1335, 2009; Stragies et al., *J. Med. Chem.* 50:3786-94, 2007).

In some embodiments, the small molecule integrin inhibitor can be PTG-100, which is described in, e.g., Shames et al., "Pharmakokinetics and Pharmacodynamics of the Novel Oral Peptide Therapeutic PTG-100 (α4β7 Integrin Antagonist) in Normal Healthy Volunteers," 24th *United European Gastroentrology Week*, October 15-19, Vienna, Austria, 2016.

In some embodiments, the small molecule targets a β2 integrin. In some embodiments, the small molecule is SAR-118 (SAR1118) or a variant thereof (Zhong et al., *ACS Med. Chem. Lett.* 3(3):203-206, 2012; Suchard et al., *J. Immunol.* 184:3917-3926, 2010; Yandrapu et al., *J. Ocul. Pharmacol. Ther.* 29(2):236-248, 2013; Semba et al., *Am. J. Ophthalmol.* 153:1050-60, 2012). In some embodiments, the small molecule is BMS-587101 or a variant thereof (Suchard et al., *J. Immunol.* 184(7):3917-3926, 2010; Potin et al., *J. Med. Chem.* 49:6946-6949, 2006). See e.g., Shimaoka et al., *Immunity* 19(3):391-402, 2003; U.S. Pat. Nos. 7,138,417; 7,928,113; 7,943,660; and 9,216,174; US 2008/0242710; and US 2008/0300237.

Other exemplary integrin inhibitors include the following: SMART anti-L-selectin Mab from PDL BioPharma Inc., which is L-Selectin antagonist, and described in WO-09706822, and Co M S, et al. "Properties and pharmacokinetics of two humanized antibodies specific for L-selectin"; Immunotechnology; 1999 4 253-266; both of which are hereby incorporated by reference; SEL-K2, an anti-PSGL-1 antibody, from Tetherex Pharmaceuticals Inc, which is described in Barbara Muz, et al. "Inhibition of P-Selectin and PSGL-1 Using Humanized Monoclonal Antibodies Increases the Sensitivity of Multiple Myeloma Cells to Proteasome Inhibitors" American Society of Hematology Annual Meeting and Exposition; 2014 56th (December 8) Abs 4758, which is hereby incorporated by reference; Vatelizumab described in I. A. Antonijevic, et al. "Safety, tolerability and pharmacodynamic characterization of vatelizumab, a monoclonal antibody targeting very-late-antigen (VLA)-2: a randomized, double-blind, placebo-controlled phase 1 study" Abstract release date: Sep. 23, 2015) ECTRIMS Online Library. Oct. 9, 2015; and WO-2010095031; WO-2011104604; WO-2010052556, which are all hereby incorporated by reference; and anti-VCAM mAb, which is described in Soriano, Antonio, et al. "VCAM-1, but not ICAM-1 or MAdCAM-1, immunoblockade ameliorates DSS-induced colitis in mice." Laboratory investigation 80.10 (2000): 1541; and Gerritsen M E, et al. (1995). Activation-dependent isolation and culture of murine pulmonary microvascular endothelium. Microcirculation 2:151-163.

Integrin Inhibitor Cyclic Peptides

In some embodiments, the integrin inhibitor is a cyclic peptide. In some embodiments, the synthetic cyclic peptide is eptifabitide (Integrilin™), or a variant thereof. In some embodiments, the cyclic peptide comprises a heterocyclic nucleic (e.g., a benzodiazepinone, a piperazine, a benzoazepinone, a nitroaryl, an isoxazoline, an indazole, or a phenol; Spalluto et al., Curr. Med. Chem. 12:51-70, 2005). In some embodiments, the cyclic peptide is a macrocycle (see, e.g., Halland et al., ACS Med. Chem. Lett. 5(2):193-198, 2014). In some embodiments, the peptide is ALG-1001 or a variant thereof (Mathis et al., Retin. Phys. 9:70, 2012). In some embodiments, the cyclic peptide is an imidazolone-phenylalanine derivative, a heteroaryl, heterocycle, and aryl derivative, a bicyclic-aromatic amino acid derivative, a cyclohexane-carboxylic acid derivative, a di-aryl substituted urea derivative, a multimeric L-alanine derivative, a L-alanine derivative, or a pyrimidyl-sulfonamide derivative (see, e.g., U.S. Pat. Nos. 6,630,492; 6,794,506; 7,049,306; 7,371,854; 7,759,387; 8,030,328; 8,129,366; 7,820,687; 8,350,010; and 9,345,793).

Integrin Inhibitor Peptidomimetics

In some embodiments, the integrin inhibitor is a peptidomimetic. In some embodiments, the peptidomimetic has an integrin-ligand recognition motif (e.g., RGD, KTS, or MLD). See, e.g., Carron et al., Cancer Research 58:1930-1935, 1998; Fanelli et al., Vascular Cell 6:11, 2014; and De Marco et al., Curr. Top. Med. Chem. 16(3):343-359, 2016.

In some embodiments, the peptidomimetic is an RGD (ArgGlyAsp)-based peptide (U.S. Pat. No. 8,809,338, incorporated by reference in its entirety herein). In some embodiments, the RGD-based peptide can be cilengitide or a variant thereof (EMD 12974) (Mas-Moruno et al., Anticancer Agents Med. Chem. 10:753-768, 2010; Reardon et al., Future Oncol. 7(3):339-354, 2011; Beekman et al., Clin. Genitourin Cancer 4(4):299-302, 2006; SC56631 (e.g., Engleman et al., Am Soc. Clin. Invest. 99(9):2284-2292, 1997; Peng et al., Nature Chem Biol. 2:381-389, 2006). In some embodiments, the peptidomimetic can be a Lys-Gly-Asp (KGD)-based peptide. In some embodiments, the peptidomimetic can be vipegitide or a variant thereof (Momic et al., Drug Design Devel. Therapy 9:291-304, 2015). In some embodiments, the peptidomimetic can be a peptide conjugated with an antimicrobial synthetic peptide. (e.g., ACDCRGDCFC conjugated with (KLAKLAK)$_2$ (Ellerby et al., Nat. Med. 5(9):1032-1038, 1999). See, e.g., U.S. Pat. No. 8,636,977.

Disintegrins

In some embodiments, the integrin inhibitor can be a disintegrin. The term "disintegrin" as used herein refers to a low molecular weight peptide integrin inhibitor derived from a snake venom (e.g., pit viper venom). In some embodiments, the disintegrin is a RGD(ArgGlyAsp)-, a KTS- or an MLD-based disintegrin.

Non-limiting examples of disintegrins include accutin, accurhagin-C, albolabrin, alternagin-c, barbourin, basilicin, bitisgabonin-1, bitisgabonin-2, bitistatin, cerastin, cereberin, cumanastatin 1, contortrostatin, cotiarin, crotatroxin, dendroaspin, disba-01, durissin, echistatin, EC3, elegantin, eristicophin, eristostatin, EMS11, E04, E05, flavoridin, flavostatin, insularin, jarastatin, jerdonin, jerdostatin, lachesin, lebein (e.g., lebein-1, lebein-2), leberagin-C, lebestatin, lutosin, molossin, obtustatin, ocellatusin, rhodocetin, rhodostomin, R-mojastin 1, salmosin, saxatilin, schistatin, tablysin-15, tergeminin, triflavin, trigramin, trimestatin, VA6, vicrostatin, viridin, viperstatin, VB7, VLO4, and VLO5, or a variant thereof. See, e.g., Arruda Macedo et al., Curr. Protein. Pept. Sci. 16(6):532-548, 2015; Hsu et al., Sci. Rep. 6:23387, 2016; Kele et al. Curr. Protein Pept. Sci. 6:532-548, 2015; Koh et al., Toxicon 59(4):497-506, 2012; Scarborough et al., J. Biol. Chem. 268:1058-1065, 1993; Kisiel et al., FEBS Lett. 577:478-482, 2004; Souza et al., Arch. Biochem. Biophys. 384:341-350, 2000; Eble et al., J Biol. Chem. 278:26488-26496, 2003; Marcinkiewicz et al., J Biol. Chem. 274:12468-12473, 1999; Calvete et al., J Proteome Res. 6:326-336, 2007; Scibelli et al., FEMS Microbiol. Lett. 247:51-57, 2005; Oliva et al., Toxicon 50:1053-1063, 2007; Minea et al., Toxicon 59:472-486, 2012; Smith et al., FEBS Lett. 512:111-115, 2002; Tselepis et al., J Biol. Chem. 272:21341-21348, 1997; Da Silva et al., Tromb. Res. 123:731-739, 2009; Thibault et al., Mol. Pharmacol. 58:1137-1145, 2000; Lu et al., Biochem. J. 304:818-825, 1994; Yeh et al., Biochim. Biophys. Acta. 1425:493-504, 1998; Huang et al., Exp. Hematol. 36:1704-1713, 2008; Shih et al., Matrix Biol. 32:152-159, 2013; Wang et al., Br. J. Pharmacol. 160:1338-1351, 2010; Della-Casa et al., Toxicon 57:125-133, 2011; Sheu et al., Biochim. Biophys. Acta. 1336:445-454, 1997; Fujii et al., J. Mol. Biol. 332: 115-122, 2003; Bilgrami et al., J. Mol. Biol. 341:829-837, 2004; Zhou et al., Toxicon 43:69-75, 2004; Scarborough et al., J Biol. Chem. 268:1066-1073, 1993; Shebuski et al., J Biol. Chem. 264:21550-21556, 1989; Lu et al., Biochem. J. 304:929-936, 1994; McLane et al., Biochem. J. 301:429-436, 1994; Juarez et al., Toxicon 56:1052-1058, 2010; Olfa et al., Lab. Invest. 85:1507-1516, 2005; Elbe et al., Matrix Biol. 21:547-558, 2002; Bazan-Socha et al., Biochemistry 43:1639-1647, 2004; Danen et al., Exp. Cell. Res. 238:188-196, 1998; Marcinkiewicz et al., Biochemistry 38(40): 13302-13309, 1999; Calvete et al., Biochem. J. 372:725-734, 2003; Swenson et al., Pathophysiol. Haemost. Thromb. 34:169-176, 2005; Kwon et al., PLoS One 8; e81165, 2013; Yang et al., Toxicon 45:661-669, 2005; Limam et al., Matrix Biol. 29:117-126, 2010; Gan et al., J Biol. Chem. 263:19827-19832, 1988; Ma et al., Thromb. Haemost. 105(6):1032-1045, 2011; and U.S. Pat. No. 7,074,408, each of which are incorporated in their entirety herein.

CXCL10 (IP-10) Inhibitors

In some embodiments, the therapeutic suitable for use with the devices and methods described herein is a CXCL10 (IP-10) inhibitor. As used herein, "CXCL10," "interferon gamma-induced protein 10" and "IP-10" can be used interchangeably. CXCL10 binds to the CXCR3 receptor (e.g., CXCR3-A or CXCR3-B). The term "CXCL10 inhibitor" refers to an agent which decreases the ability of CXCL10 to bind to a CXCR3 receptor (e.g., CXCR3-A and/or CXCR3-B).

CXCL10 (IP-10) Inhibitor Antibodies

In some embodiments, the CXCL10 inhibitor is an antibody or an antigen-binding fragment thereof (e.g., a Fab or a scFv). In some embodiments, an antibody or antigen-binding fragment described herein binds specifically to CXCL10 or a CXCR3 receptor (e.g., CXCR3-A and/or CXCR3-B), or both a CXCL10 and a CXCR3 receptor (e.g., CXCR3-A and/or CXCR3-B). In some embodiments, a CXCL10 inhibitor can bind to both CXCR3-A and CXCR3-B.

In some instances, the CXCL10 inhibitor is a monoclonal antibody (mAb) (see, e.g., WO 05/58815). For example, the CXCL10 inhibitor can be Eldelumab® (MDX-1100 or BMS-936557), BMS-986184 (Bristol-Meyers Squibb), or NI-0801 (NovImmune). See, e.g., Kuhne et al., *J. Immunol.* 178(1):S241, 2007; Sandborn et al., *J. Crohns Colitis* 11(7):811-819, 2017; and Danese et al., *Gastroenterology* 147(5):981-989, 2014. Additional examples of CXCL10 inhibitors that are antibodies are described in U.S. Patent Application Publication Nos. 2017/0158757, 2017/0081413, 2016/0009808, 2015/0266951, 2015/0104866, 2014/0127229, 2014/0065164, 2013/0216549, 2010/0330094, 2010/0322941, 2010/0077497, 2010/0021463, 2009/0285835, 2009/0169561, 2008/0063646, 2005/0191293, 2005/0112119, 2003/0158392, 2003/0031645, and 2002/0018776; and WO 98/11218, each of which is incorporated by reference in its entirety (e.g., the description of CXCL10 inhibitors).

CXCL10 (IP-10) Inhibitor Small Molecules and Peptides

In some instances, the CXCL10 inhibitor is a small molecule. For example, the CXCL10 inhibitor can be ganodermycin (see, e.g., Jung et al., *J. Antibiotics* 64:683-686, 2011). Additional exemplary small molecule CXCL10 inhibitors are described in: U.S. Patent Application Publication No. 2005/0075333; U.S. Patent Application Publication No. 2004/0242498; U.S. Patent Application Publication No. 2003/0069234; U.S. Patent Application Publication No. 2003/0055054; U.S. Patent Application Publication No. 2002/0169159; WO 97/24325; WO 98/38167; WO 97/44329; WO 98/04554; WO 98/27815; WO 98/25604; WO 98/25605; WO 98/25617; WO 98/31364; Hesselgesser et al., *J. Biol. Chem.* 273(25):15687-15692 (1998); and Howard et al., *J. Med. Chem.* 41(13):2184-2193 (1998).

In some examples, the CXCL10 inhibitor is a peptide antagonist of a CXCR3 receptor (e.g., as described in U.S. Patent Application Publication No. 2007/0116669, 2006/0204498, and WO 98/09642). In some examples, the CXCL10 inhibitor is a chemokine mutant or analogue, e.g., those described in U.S. Pat. No. 5,739,103, WO 96/38559, and WO 98/06751. Additional examples of CXCL10 inhibitors that are small molecules or peptides are known in the art.

CCL11 Inhibitors

In some embodiments, the therapeutic suitable for use with the devices and methods described herein is a CCL11 inhibitor. The term "CCL11 inhibitor" refers to an agent which decreases the ability of CCL11 to bind to one or more of CCR2, CCR3, and CCR5. In some embodiments, a CCL11 inhibitor is an antibody or an antigen-binding fragment thereof.

CCL11 Inhibitor Antibodies

In some embodiments, the CCL11 inhibitor is an antibody or an antigen-binding fragment thereof (e.g., a Fab or a scFv). In some embodiments, an antibody or antigen-binding fragment described herein binds specifically to CCL11, CCR2, CCR3, or CCR5, or can specifically bind to two or more of CCL11, CCR2, CCR3, and CCR5. In some embodiments, a CCL11 inhibitor can bind to two or more of CCR2, CCR3, and CCR5.

In some examples the chemokine/chemokine receptor inhibitor is bertilimumab (Immune Pharmaceuticals), an anti-eotaxin-1 monoclonal antibody that targets CCL11, and is currently in a Phase II clinical study for ulcerative colitis. Additional examples of CCL11 inhibitors are described in U.S. Patent Application Publication Nos. 2016/0289329, 2015/0086546, 2014/0342450, 2014/0178367, 2013/0344070, 2013/0071381, 2011/0274696, 2011/0038871, 2010/0074886, 2009/0297502, 2009/021162, 2009/0169541, 2009/0142339, 2008/0268536, 2008/0241923, 2008/0241136, 2005/0260139, 2005/0048052, 2004/0265303, 2004/0132980, 2004/0126851, 2003/0165494, 2002/0150576, 2002/0150570, 2002/0051782, 2002/0051781, 2002/0037285, 2002/0028436, 2002/0015700, 2002/0012664, 2017/0131282, 2016/0368979, 2016/0208011, 2011/0268723, 2009/0123375, 2007/0190055, 2017/0049884, 2011/0165182, 2009/0226434, 2009/0110686, 2009/0047735, 2009/0028881, 2008/0107647, 2008/0107595, 2008/0015348, 2007/0274986, 2007/0231327, 2007/0036796, 2007/0031408, 2006/0229336, 2003/0228306, 2003/0166870, 2003/0003440, 2002/0019345, and 2001/0000241, each of which is incorporated by reference in its entirety (e.g., the description of CCL11 inhibitors).

CCR2 Inhibitors

In some embodiments, the therapeutic suitable for use with the devices and methods described herein is a CCR2 inhibitor. As used herein, "CCR2," "CC chemokine receptor 2," or "MCP-1" can be used interchangeably. CCL2, CCL8, and CCL16 each individually bind to CCR2. The term "CCR2 inhibitor" refers to an agent which decreases the ability of CCR2 to bind to one or more (e.g., two, or three) of CCL2, CCL8, and CCL16.

In some instances, the CCR2 inhibitor is a small molecule. In some instances, the CCR2 inhibitor is an antibody or an antigen-binding antibody fragment. In some instances, the CCR2 inhibitor is a peptide.

CCR2 Inhibitor Antibodies

In some embodiments, the CCR2 inhibitor is an antibody or an antigen-binding fragment thereof (e.g., a Fab or a scFv). In some embodiments, an antibody or antigen-binding fragment described herein binds specifically to CCR2. In some embodiments, an antibody or antigen-binding fragment described herein binds specifically to CCL2. In some embodiments, an antibody or antigen-binding fragment described herein binds specifically to CCL8. In some embodiments, an antibody or antigen-binding fragment described herein binds specifically to CCL16. In some embodiments, an antibody or antigen-binding fragment described herein binds specifically to CCR2 and one or more of (e.g., one, two, or three) of CCL2, CCL8, and CCL16.

In some embodiments, the CCR2 inhibitor is a monoclonal antibody. For example, the CCR2 inhibitor can be MLN1202 (Millennium Pharmaceuticals), C775, STI-B0201, STI-B0211, STI-B0221, STI-B0232, carlumab (CNTO 888; Centocor, Inc.), or STI-B0234, or an antigen-binding fragment thereof. See also, e.g., Vergunst et al., *Arthritis Rheum.* 58(7):1931-1939, 2008. Additional examples of CCR2 inhibitors that are antibodies or antigen-binding antibody fragments are described in, e.g., U.S. Patent Application Publication Nos. 2015/0086546, 2016/0272702, 2016/0289329, 2016/0083482, 2015/0361167; 2014/0342450, 2014/0178367, 2013/0344070, 2013/0071381, 2011/0274696, 2011/0059107, 2011/0038871, 2009/0068109, 2009/0297502, 2009/0142339, 2008/0268536, 2008/0241923, 2008/0241136, 2007/0128112, 2007/0116708, 2007/0111259, 2006/0246069, 2006/0039913, 2005/0232923, 2005/0260139, 2005/0058639, 2004/0265303, 2004/0132980, 2004/0126851, 2004/0219644, 2004/0047860, 2003/0165494, 2003/0211105, 2002/0150576, 2002/0051782, 2002/0042370, and 2002/0015700; and U.S. Pat. Nos. 6,312,689, 6,084,075, 6,406,694, 6,406,865, 6,696,550, 6,727,349, 7,442,775, 7,858,318, 5,859,205, 5,693,762, and 6,075,181, each of which is incorporated by reference (e.g., the description of the CCR2 inhibitors). Additional examples of CCR2 inhibitors are described in, e.g., WO 00/05265. Additional examples of CCR2 inhibitors that are antibodies or antigen-binding antibodies fragments are described in, e.g., Loberg et al., *Cancer Res.* 67(19):9417, 2007.

CCR2 Inhibitor Small Molecules and Peptides

In some examples, the CCR2 inhibitor is a small molecule. For example, the CCR2 inhibitor can be elubrixin, PF-04634817, BMS-741672, or CCX872. See, e.g., U.S. Pat. No. 9,434,766; U.S. Patent Application Publication No. 20070021466; Deerberg et al., *Org. Process Rev. Dev.* 20(11):1949-1966, 2016; and Morganti et al., *J. Neurosci.* 35(2):748-760, 2015.

Additional non-limiting examples of CCR2 inhibitors that are small molecules include, e.g., the phenylamino substituted quaternary salt compounds described in U.S. Patent Application Publication No. 2009/0112004; the biaryl derivatives described in U.S. Patent Application Publication No. 2009/0048238; the pyrazol derivatives described in U.S. Patent Application Publication No. 2009/0029963; the heterocyclic compounds described in U.S. Patent Application Publication No. 2009/0023713; the imidazole derivatives described in U.S. Patent Application Publication No. 2009/0012063; the aminopyrrolidines described in U.S. Patent Application Publication No. 2008/0176883; the heterocyclic cyclopentyl tetrahydroisoquinolones and tetrahydropyridopyridines described in U.S. Patent Application Publication No. 2008/0081803; the heteroaryl sulfonamides described in U.S. Patent Application Publication No. 2010/0056509; the triazolyl pyridyl benzenesulfonamides described in U.S. Patent Application Publication No. 2010/0152186; the bicyclic and bridged nitrogen heterocycles described in U.S. Patent Application Publication No. 2006/0074121; the fused heteroaryl pyridyl and phenyl benzenesulfonamides described in WO 09/009740; and the 3-aminopyrrolidene derivatives described in WO 04/050024.

Additional non-limiting examples of CCR2 inhibitors include: N-((1R,3S)-3-isopropyl-3-{[3-(trifluoromethyl)-7,8-dihydro-1,6-naph-thyri-din-6(5H)-yl]carbonyl}cyclopentyl)-N-[(3 S,4S)-3-methoxytetrahydro-2H-pyran-4-yl]amine; 3 [(3 S,4R)-1-((1R,3S)-3-isopropyl-2-oxo-3-{[6-(trifluoromethyl)-2H-1,3-ben-z-oxazin-3 (4H)-yl]methyl}cyclopentyl)-3-methylpiperidin-4-yl]benzoic acid; (3 S,48)-N-((1R,3S)-3-isopropyl-3-{[7-(trifluoromethyl)-3,4-dihydroisoquin-olin-2(1B)-yl]carbonyl}cyclopentyl)-3-methyltetrahydro-2H-p-yran-4-aminium; 3-[(3 S,4R)-1-((1R,3S)-3-isopropyl-3-{[6-(trifluoromethyl)-2H-1,3-benzoxazin-3-(4H)-yl]carbonyl}cyclopentyl)-3-methylpiperidin-4-yl]benzoic acid; (3R,4S)-1-((1R,3S)-3-isopropyl-3-{[6-(trifluoromethyl)-2H-1,3-benzoxazin-3-(4H)-yl]carbonyl}cyclopentyl)-3-methylpiperidin-4-yl]benzoic acid; INCB3284; Eotaxin-3; PF-04178903 (Pfizer), and pharmaceutically acceptable salts thereof.

Additional non-limiting examples of CCR2 inhibitors include: bindarit (2-(((1-benzyl-1H-indazol-3-yl)methoxy)-2-methylpropionic acid); AZD2423 (AstraZeneca); the indole describes described in U.S. Pat. Nos. 7,297,696, 6,962,926, 6,737,435, and 6,569,888; the bicyclic pyrrole derivatives described in U.S. Pat. Nos. 6,441,004 and 6,479,527; the CCR2 inhibitors described in U.S. Patent Application Publications Nos. 2005/0054668, 2005/0026975, 2004/0198719, and 2004/0047860, and Howard et al., *Expert Opin. Ther. Patents* 11(7):1147-1151 (2001).

Additional non-limiting examples of CCR2 inhibitors that are small molecules are described in, e.g., WO 97/24325; WO 98/38167; WO 97/44329; WO 98/04554; WO 98/27815; WO 98/25604; WO 98/25605; WO 98/25617; WO 98/31364; Hesselgesser et al., *J. Biol. Chem.* 273(25): 15687-15692, 1998; and Howard et al., *J. Med. Chem.* 41(13):2184-2193, 1998.

In some embodiments, the CCR2 inhibitor is a small nucleic acid, e.g., NOX-E36 (a 40-nucleotide L-RNA oligonucleotide that is linked to a 40-kDa PEG; NOXXON Pharma AG).

In some embodiments, the CCR2 inhibitor is a peptide, e.g., a dominant negative peptide described in, e.g., Kiyota et al., *Mol. Ther.* 17(5):803-809, 2009, and U.S. Patent Application Publication No. 20070004906, or an antagonistic peptide, e.g., the antagonistic peptides described in WO 05/037305 and Jiang-Hong Gong, et al., *J. Exp. Med.* 186:131, 1997. Additional examples of CCR2 inhibitors that are peptides are described in, e.g., U.S. Pat. No. 5,739,103; WO 96/38559; WO 98/06751; and WO 98/09642. In some embodiments, a CCR2 inhibitor is a CCR2 mutein (e.g., U.S. Patent Application Publication No. 2004/0185450).

Additional examples of CCR2 inhibitors that are small molecules and peptides are known in the art.

CCR9 Inhibitors

In some embodiments, the therapeutic suitable for use with the devices and methods described herein is a CCR9 inhibitor. As used herein "CCR9" or "CC chemokine receptor 9" can be used interchangeably. CCR9 specifically binds to CCL25. The term "CCR9 inhibitor" refers to an agent which decreases the ability of CCR9 to bind to CCL25.

CCR9 Inhibitor Antibodies

In some embodiments, the CCR9 inhibitor is an antibody or an antigen-binding fragment thereof (e.g., a Fab or a scFv). In some embodiments, an antibody or antigen-binding fragment described herein binds specifically to CCR9. In some embodiments, an antibody or antigen-binding fragment described herein binds specifically to CCL25. In some embodiments, an antibody or antigen-binding fragment described herein binds specifically to both CCR9 and CCL25.

In other instances, the CCR9 inhibitor is a monoclonal antibody. For example, the CCR9 antibody can be 91R, see, e.g., Chamorro et al., MAbs 6(4): 1000-1012, 2014. Additional non-limiting examples of CCR9 inhibitors are described in, e.g., U.S. Patent Application Publication Nos. 2012/0100554, 2012/0100154, 2011/0123603, 2009/0028866, and 2005/0181501.

CCR9 Inhibitor Small Molecules

In some instances, the CCR9 inhibitor is a small molecule. For example, the CCR9 inhibitor can be Traficet-EN® (also called Vercirnon, CCX282, and GSK1605786) or Tu1652 CCX507. See, e.g., Eksteen et al., *IDrugs* 13(7): 472-481, 2010; and Walters et al., *Gastroenterology* 144(5): S-815, 2013. Additional examples of CCR9 inhibitors that are small molecules are known in the art.

ELR Chemokine Inhibitors

In some embodiments, the therapeutic suitable for use with the devices and methods described herein is an ELR chemokine inhibitor. ELR chemokines are CXC chemokines that have a glutamic acid-leucine-arginine (ELR) motif. See, e.g., Strieter et al., *J. Biol. Chem.* 270:27348-27357, 1995. The term "ELR chemokine inhibitor" refers to an agent which decreases the ability of CXCR1 and/or CXCR2 to bind to one or more (e.g., two, three, four, five, six, seven, or eight) of CXCL1, CXCL2, CXCL3, CXCL4, CXCL5, CXCL6, CXCL7, and CXCL8.

In some instances, the ELR chemokine inhibitor is a small molecule. In some instances, the ELR chemokine inhibitor is an antibody or an antigen-binding antibody fragment.

ELR Chemokine Inhibitor Antibodies

In some embodiments, the ELR chemokine inhibitor is an antibody or an antigen-binding fragment thereof (e.g., a Fab or a scFv). In some embodiments, an antibody or antigen-binding fragment binds specifically to CXCR1 and/or CXCR2. In some embodiments, an antibody or antigen-binding fragment described herein binds specifically to one or more (e.g., two, three, four, five, six, seven, or eight) of: CXCL1, CXCL2, CXCL3, CXCL4, CXCL5, CXCL6, CXCL7, and CXCL8 (IL-8).

An ELR chemokine inhibitor can be, e.g., a monoclonal antibody. A non-limiting example of an ELR inhibitor is TAB-099MZ. Additional examples of ELR chemokine inhibitors that are antibodies or antigen-binding antibody fragments are described in, e.g., U.S. Pat. No. 9,290,570; and U.S. Patent Application Publication Nos. 2004/0170628, 2010/0136031, 2015/0160227, 2015/0224190, 2016/0060347, 2016/0152699, 2016/0108117, 2017/0131282, 2016/0060347, 2014/0271647, 2014/0170156, 2012/0164143, 2010/0254941, 2009/0130110, 2008/0118517, 2004/0208873, 2003/0021790, 2002/0082396, and 2001/0006637, each of which is herein incorporated by reference (e.g., the portions describing ELR chemokine inhibitors).

ELR Chemokine Inhibitor Small Molecules

In some instances, the ELR chemokine inhibitor is, e.g., a small molecule. For example, the ELR chemokine inhibitor can be, e.g., LY-3041658 or repertaxin (Reparixin; DF 1681Y). Additional non-limiting examples of ELR chemokine inhibitors that are small molecules are described in, e.g., U.S. Patent Application Publication Nos. 2007/0248594, 2006/0014794, 2004/0063709, 2004/0034229, 2003/0204085, 2003/0097004, 2004/0186142, 2004/0235908, 2006/0025453, 2017/0224679, 2017/0190681, 2017/0144996, and 2017/0128474, each of which are incorporated by reference (e.g., the portions describing the ELR chemokine inhibitors).

In some embodiments, the ELR chemokine inhibitor is a peptide, e.g., any of the peptides described in U.S. Patent Application Publication Nos. 2009/0270318, 2009/0118469, and 2007/0160574, 2007/0021593, 2003/0077705, and 2007/0181987, each of which is incorporated by reference (e.g., the portions describing the ELR chemokine inhibitors).

Phosphodiesterase 4 (PDE4) Inhibitors

In some embodiments, the therapeutic suitable for use with the devices and methods described herein is a PDE4 inhibitor. The term "PDE4 inhibitor" refers to an agent which decreases PDE4 activity in vitro or in a mammalian cell, e.g., as compared to the level of PDE4 activity in the absence of the agent; and/or decreases the level of a PDE4 protein in a mammalian cell contacted with the agent, e.g., as compared to the same mammalian cell not contacted with the agent. A non-limiting example of PDE4 activity is the degradation of cAMP.

In some embodiments, a PDE4 inhibitor can be a small molecule (e.g., an organic, an inorganic, or bioinorganic molecule) having a molecule weight of less than 900 Daltons (e.g., less than 500 Daltons). In some embodiments, a PDE4 inhibitor can be an inhibitory nucleic acid.

Inhibitory Nucleic Acids of PDE4

In some embodiments, a PDE4 inhibitor can be an inhibitory nucleic acid. In some embodiments, the inhibitory nucleic acid can be an antisense nucleic acid, a ribozyme, and a small interfering RNA (siRNA).

Examples of modified nucleotides which can be used to generate an antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an anti sense orientation (i.e., RNA transcribed from the inserted nucleic acid will be of an antisense orientation to a target nucleic acid of interest).

Another example of an inhibitory nucleic acid is a ribozyme that has specificity for a nucleic acid encoding a PDE4 protein (e.g., specificity for a PDE4 mRNA). Ribozymes are catalytic RNA molecules with ribonuclease activity that are capable of cleaving a single-stranded nucleic acid, such as an mRNA, to which they have a complementary region. Thus, ribozymes (e.g., hammerhead ribozymes (described in Haselhoff and Gerlach, *Nature* 334:585-591, 1988)) can be used to catalytically cleave mRNA transcripts to thereby inhibit translation of the protein encoded by the mRNA. A ribozyme having specificity for a PDE4 mRNA can be designed based upon the nucleotide sequence of any of the PDE4 mRNA sequences disclosed herein. For example, a derivative of a Tetrahymena L-19 IVS RNA can be constructed in which the nucleotide sequence of the active site is complementary to the nucleotide sequence to be cleaved in a PDE4 mRNA (see, e.g., U.S. Pat. Nos. 4,987,071 and 5,116,742). Alternatively, a PDE4 mRNA can be used to select a catalytic RNA having a specific ribonuclease activity from a pool of RNA molecules. See, e.g., Bartel et al., *Science* 261:1411-1418, 1993.

An inhibitor nucleic acid can also be a nucleic acid molecule that forms triple helical structures. For example, expression of a PDE4 polypeptide can be inhibited by targeting nucleotide sequences complementary to the regulatory region of the gene encoding the PDE4 polypeptide (e.g., the promoter and/or enhancer, e.g., a sequence that is at least 1 kb, 2 kb, 3 kb, 4 kb, or 5 kb upstream of the transcription initiation start state) to form triple helical structures that prevent transcription of the gene in target cells. See generally Helene, *Anticancer Drug Des.* 6(6):569-84, 1991; Helene, *Ann. N.Y. Acad. Sci.* 660:27-36, 1992; and Maher, Bioassays 14(12):807-15, 1992.

Non-limiting examples of siRNAs targeting PDE4 are described in Takakura et al., *PLosOne* 10(12):e0142981, 2015; Watanabe et al., *Cell Signal* 27(7):1517-1524, 2015; Suzuki et al., *PLos One* 11(7):e0158967, 2016; Kai et al., *Mol. Ther. Nucl. Acids* 6:163-172, 2017. See, e.g., Cheng et al., *Exp Ther Med* 12(4):2257-2264, 2016; Peter et al., *J. Immunol.* 178(8):4820-4831, 2007; and Lynch et al., *J Biol. Chem.* 280:33178-33189, 2005. Additional examples of PDE4 inhibitory nucleic acids are described in U.S. Patent Application Publication Nos. 2010/0216703 and 2014/0171487, which are incorporated by reference in its entirety.

PDE4 Inhibitor Small Molecules

In some embodiments, a PDE4 inhibitor is a small molecule. Non-limiting examples of small molecules that are PDE4 inhibitors include: Apremilast (CC-10004; CC-110004; CDC-104; Otezla®; lead selCID (2); selCID); CC-1088 (CC-1088; CC-5048; CC-801; CDC-801; lead SelCID (1)); Tetomilast (OPC-6535); KF-19514; PF-06266047; SKF-107806; PDB-093; Tolafentrine (BY-4070); TAK-648; CH-928; CH-673; CH-422; ABI-4 (18F-PF-06445974; Fluorine-18-PF-06445974); roflumilast; Roflumilast N-oxide (APTA-2217; B9302-107; BY-217; BYK-20860; Daliresp®; Dalveza; Daxas®; Libertek; Xevex; roflumist); NVP-ABE-171; BYK-321084; WAY-127093B; NCS-613; SDZ-ISQ-844; GS-5759; Ro-20-1724; Hemay-005; KCA-1490; TVX-2706; Nitraquazone; Filaminast (PDA-641; WAY-PDA-641); LASSBio-596; ASP-3258; TAS-203; AN-2889; AN-5322; AN-6414; AN-6415; Lotamilast (E-6005; RVT-501); GPD-1116; Cipamfylline (BRL-61063; HEP-688); MNP-001; MS-23; MSP-001; K-34; KF-66490; AL-38583 (cilomast); ZL-N-91; Almirall; CDP-840; GSK-356728; Cilomilast (Ariflo; SB-207499); OCID-2987; AN-2898; CBS-3595; ASP-9831 (ASP9831); E-4021 (4-Piperidinecarboxylic acid, 1-[4-[(1,3-benzodioxol-5-ylmethyl)amino]-6-chloro-2-quinazolinyl]); Piclamilast (RP-73401; RPR-73401); CD-160130; GSK-256066 (256066); 4AZA-PDE4; YM-393059; Revamilast (GRC-4039); AN-2728 (PF-06930164; crisaborole (Eucrisa™)); MK-0952 (MK-952); Ibudilast (AV-411; MN-166; KC-404); GP-0203; ELB-526; Theophylline (Teonova); CHF-6001 (CHF-5480); Elbimilast (AWD-12-353; ELB-353; ronomilast); AWD-12-281 (842470); OS-0217; Oglemilast (GRC-3886); R-1627; ND-1510; ND-1251; WAY-122331; GRC-3566; Tofimilast (CP-325366); BAY-61-9987; Rolipram (ME-3167; ZK-62711); MEM-1414 (R-1533); Adenosine A3 antagonists (CGH-2466); RPL-554 (RPL-565; VMX-554; VMX-565; VRP-554; trequinsin analog); CT-5357; Etazolate (EHT-0202; SQ-20009; etazolate hydrochloride); Z-15370 (Z-15370A); Org-30029; Org-20241; Arofylline (LAS-31025); Arofylline derivatives; KW-4490; HT-0712 (IPL-455903); HT-0712; IPL-455903; CT-2450; CT-2820; CT-3883; CT-5210; L-454560; L-787258; L-791943; L-826141; L-869298; MK-0359; OX-914 (BLX-028914; BLX-914; IPL-4088; IPL-4182; IPL-4722); SDZ-PDI-747; AP-0679; Sch-351591 (D-4396; Sch-365351); TA-7906 (T-2585; TA-7906); HMR-1571; Lirimilast (BAY-19-8004); Daxalipram (Mesopram; SH-636; ZK-117137); SelCIs (CC-10036; CC-10083; CC-110007; CC-110036; CC-110037; CC-110038; CC-110049; CC-110052; CC-110083; CC-11069; CC-111050; CC-13039; CC-14046; CC-17034; CC-17035; CC-17075; CC-17085; CC-18062; CC-7075); RPR-117658; AWD-12-281 (842470; AWD-12-343; GW842470X); 256066 (GSK-256066; SB-207499); RPR-132294 (RPR-132703); CI-1018; CI-1044; PD-168787; PD-189659; PD-190036; PD-190749; YM-976; XT-611; Losartan derivatives; DWP-205 derivatives (DWP-205297); WAY-126120; YM-58997; CP-293321; V-11294A; CH-3697; CP-353164; Atizoram (CP-80633); D-4418; RPR-114597; IC-197; IC-246; IC-247; IC-485; IC-86518; IC-86518/IC-86521; IC-86521; CP-220629; ZL-n-91; D-22888 (AWD-12-232); GW-3600; GSK356278; TPI 1100; BPN14770; and MK-0873. See, e.g., Schafter et al. (2014) *Cellular Signaling* 26(9): 2016-2029); Gurney et al. (2011) *Handb Exp Pharmacol* 204: 167-192; Spadaccini et al. (2017) *Intl J Mol Sciences* 18: 1276; Bickston et al. (2012) *Expert Opinion Invest Drugs* 21:12, 1845-1849; Keshavarzian et al. (2007) *Expert Opinion Invest Drugs* 16:9, 1489-1506.

Additional examples of small molecules that are PDE4 inhibitors are described in, e.g., U.S. Patent Application Publication Nos. 2017/0348311, 20176/0319558, 2016/0213642, 2015/0328187, 2015/0306079, 2015/0272949, 2015/0272936, 2015/0080359, 2015/0051254, 2014/0350035, 2014/0148420, 2014/0121221, 2013/0252928, 2013/0237527, 2013/0225609, 2012/0309726, 2012/0196867, 2012/0088743, 2012/0059031, 2012/0035143, 2012/0028932, 2011/0021478, 2011/0021476, 2010/0234382, 2010/0129363, 2010/0069392, 2010/0056604, 2010/0048616, 2010/0048615, 2009/0099148, 2009/0093503, 2008/0287522, 2008/0255209, 2008/0255186, 2008/0221111, 2007/0232637, 2007/0208181, 2007/0167489, 2006/0269600, 2006/0183764, 2006/0154934, 2006/0094723, 2006/0079540, 2005/0267135, 2005/0234238, 2005/0033521, 2003/0229134, 2003/0220352, 2003/0212112, 2003/0158189, 2003/0069260, 2003/0050329, 2002/0058687, and 2002/0028842. Additional examples of small molecules that are PDE4 inhibitors are known in the art.

Additional Inhibitors

In some embodiments, the therapeutic agent suitable for use with the devices and methods described herein is selected from a non-oral small molecule therapeutic, a heparin, a JAK inhibitor (e.g., PF-06700841, PF-06651600, abrocitinib); live biotherapeutics (e.g., Neuregulin 4, NN8555, darvadstrocel), an immune modulator (e.g., KHK-4083, GSK2618960, Toralizumab), a chemokine (e.g., GSK3050002 (previously known as KANAb071), E-6011, HGS-1025), a CHST15 inhibitor (e.g., SB-012), a TLR agonist (e.g., BL-7040; EN-101; Monarsen), and combinations thereof.

Non-Oral Small Molecule Therapeutics

In some embodiments, the therapeutic suitable for use with the devices and methods described herein is a non-oral small molecule.

In some embodiments, the therapeutic suitable for use with the devices and methods described herein is a non-oral antibiotic. Antibiotics which are not given orally include: amikacin, ampicillin sulbactam, azlocillin, aztreonam, cefazolin, cefeprime, cefoperazone, cefotaxime, cefotetan, cefoxitin, ceftaroline, ceftazidime, ceftizoxime, ceftobiprole, ceftriaxone, cephalothin, colistin, daptomycin, doripenem, ertapenem, gentamicin, imipenem, kanamycin, meropenem, mezlocillin, mupirocin, nafcillin, ofloxicin, oritovacin, piperacillin, piperacillin tazobactam, polymyxin B, quinupristin dalfopristin, spectinomycin, streptomycin, teicoplanin, telavancin, ticarcillin, ticarcillin clavulanic acid, tigecycline and tobramycin.

Other exemplary non-oral small molecules for delivery using any of the devices or methods described herein include, but are not limited to, those listed in Table 11.

TABLE 11

Non-oral small molecule therapeutics adaptable for delivery via ingestible device for the treatment of the listed diseases and conditions

| Drug Name | Existing Formulation Technologies and Methods of Administration | Exemplary Patent Literature | Therapeutic Area (Exemplary Indications) [Target-based Action] |
|---|---|---|---|
| Enoxaparin sodium | Intravenous; Subcutaneous | EP-00040144; US-04486420; WO-08102737 | Hematologic; Cardiovascular (Myocardial infarction; Thromboembolism) [Low molecular weight heparin] |
| Hydroxyprogesterone caproate | Intramuscular; Solution; Subcutaneous; Sustained release | WO-00009186 | Genitourinary/sexual function (Premature labor; long-acting, preterm birth prevention) [Progesterone receptor agonist] |
| Plerixafor | Infusion; Intravenous; Solution; Subcutaneous | EP-00434385 | Cancer; Cardiovascular; Dermatologic; Hematologic; Immune; Infection (Bone marrow transplantation; Sickle cell anemia) [CXCR4 chemokine antagonist; Neuroplastin inhibitor] |
| Ferumoxytol | Drug coating; Infusion; Intravenous; Nanoparticle formulation injectable; | WO-00061191 | Cancer; Hematologic; Cardiovascular (Iron deficiency anemia) |
| Bortezomib | Formulation powder; Freeze drying; Infusion; Intravenous; Subcutaneous | WO-02059130; WO-09613266 | Hematologic; Endocrine/Metabolic; Immune; Neurology/Psychiatric; Cancer (Acute lymphoblastic leukemia; Acute myelogenous leukemia; Chronic lymphocytic leukemia; Graft versus host disease; Lymphoplasmacytic lymphoma; Macroglobulinemia; Mantle cell lymphoma; Multiple myeloma; Myelodysplastic syndrome; Non-Hodgkin lymphoma; Non-small-cell lung cancer) [26S proteasome complex inhibitor; Proteasome inhibitor] |
| Pemetrexed disodium | Formulation powder; Freeze drying; Infusion; Intravenous | EP-00432677; HU-00211941 | Cancer (Mesothelioma; Metastatic bladder cancer; Metastatic non-small cell lung cancer) [DHFR inhibitor; GAR transformylase inhibitor; Thymidylate synthase inhibitor; Transferase inhibitor] |
| Fulvestrant | Intramuscular; Sustained release | EP-00138504 | Cancer; Inflammatory; Genitourinary/Sexual Function; Endocrine/Metabolic (Fallopian tube cancer; Metastatic breast cancer; Metastatic ovary cancer; Peritoneal tumor; Precocious puberty) [Estrogen receptor antagonist] |
| Carfilzomib | Formulation powder; Freeze drying; Infusion; Intravenous | WO-2005105827 | Cancer; Hematologic (Acute lymphoblastic leukemia; Cutaneous T-cell lymphoma; Hormone refractory prostate cancer; Mantle cell lymphoma; Multiple myeloma; Neuroendocrine tumor; Non-Hodgkin lymphoma; Peripheral T-cell lymphoma; Renal cell carcinoma; Small-cell lung cancer; Solid tumor) [Proteasome inhibitor; Ubiquitin inhibitor] |
| Azacitidine | Formulation powder; Freeze drying; Intravenous; Subcutaneous | US-04965251 | Cancer; Hematologic (Acute myelogenous leukemia; Chronic myelomonocytic leukemia; Myelodysplastic syndrome) [DNA methyltransferase inhibitor] |
| Bendamustine | Formulation powder; Freeze drying; Infusion; Intravenous; Solution | WO-2005034944 | Endocrine/Metabolic; Cancer (Amyloidosis; B-cell lymphoma; Chronic lymphocytic leukemia; Diffuse large B-cell lymphoma; Follicle center lymphoma; Lymphoma; Mantle cell lymphoma; Multiple myeloma; Non-Hodgkin lymphoma) [PARP modulator] |
| Cabazitaxel | Infusion; Intravenous; Intravesical; Solution | WO-09630356 | Cancer (Hormone refractory prostate cancer; Liposarcoma; Metastatic breast cancer; Metastatic prostate cancer; Transitional cell carcinoma) |
| Oxaliplatin | Infusion; Intravenous Solution | CN-101289468; US-04169846 | Cancer (Colon tumor; Colorectal tumor; Hepatocellular carcinoma; Metastatic colorectal cancer; Metastatic pancreas cancer; Metastatic stomach cancer; Pancreas tumor; Small intestine cancer; Stomach tumor) |
| Eribulin mesylate | Infusion; Intravenous; Solution | WO-09965894 | Cancer (Angiosarcoma; Ewing sarcoma; Liposarcoma; Metastatic bladder cancer; Metastatic breast cancer; Rhabdomyosarcoma; Soft tissue sarcoma) |
| Docetaxel | Infusion; Intravenous; Solution | EP-00253738 | Cancer (Breast tumor; Cancer; Endometrioid carcinoma; Esophagus tumor; Head and neck tumor; Hormone refractory prostate cancer; Metastatic breast cancer; Metastatic non-small cell lung cancer; Metastatic stomach cancer; Ovary tumor; Prostate tumor; Squamous cell carcinoma) |

TABLE 11-continued

Non-oral small molecule therapeutics adaptable for delivery via ingestible device for the treatment of the listed diseases and conditions

| Drug Name | Existing Formulation Technologies and Methods of Administration | Exemplary Patent Literature | Therapeutic Area (Exemplary Indications) [Target-based Action] |
|---|---|---|---|
| Sugammadex | Intravenous; Solution | WO-00140316; WO-2008065142 | Neurology/Psychiatric (general anesthesia) |
| Cefoperazone sodium + sulbactam sodium | Intramuscular; Intravenous | US-04234579 | Genitourinary/Sexual Function; Gastrointestinal; Infection (Bacterial infection; Bacterial meningitis; Bacterial respiratory tract infection; Bacterial urinary tract infection; Bone and joint infection; Cholangitis; Cholecystitis; Complicated skin and skin structure infection; Endometriosis; Neisseria gonorrhoeae infection; Peritonitis; Sepsis) [Beta lactamase inhibitor] |
| Rotigotine | Drug coating; Patch; Transdermal | WO-02089777; WO-09949852 | Musculoskeletal; Neurology/Psychiatric (Parkinsons disease; Restless legs syndrome) [5-HT receptor agonist; adrenergic receptor agonist; Dopamine D1, D2, D3, D4, D5 receptor agonist] |
| Caspofungin | Formulation powder; Freeze drying; Infusion; Intravenous; Solution | US-05792746; WO-09421677 | Gastrointestinal; Infection (Abdominal abscess; Aspergillus infection; Candida infection; Fungal infection; Peritonitis) [1,3 beta glucan synthase inhibitor] |
| Iron sucrose injection, | Intravenous | WO-2004019032 | Neurology/Psychiatric; Other/Miscellaneous; Hematologic (Anemia; Iron deficiency anemia) |
| Piperacillin + tazobactam (injectable) | Antibiotic; Formulation powder; Freeze drying; Infusion; Intravenous; Solution | EP-00097446 | Gastrointestinal; Genitourinary/Sexual Function; Hematologic; Dermatologic; Cardiovascular; Infection (Abdominal abscess; Abscess; Acinetobacter infection; Appendicitis; Bacterial infection; Bacterial pneumonia; Bacterial skin infection; Bacterial urinary tract infection; *Bacteroides fragilis* infection; *Bacteroides* infection; Cellulitis; Cholangitis; Cholecystitis; Cystitis; Diabetic foot ulcer; *Escherichia coli* infection; Febrile neutropenia; *Haemophilus influenzae* infection; *Klebsiella pneumoniae* infection; Lower respiratory tract infection; Pelvic inflammatory disease; Peritonitis; *Pseudomonas aeruginosa* infection; Pyelonephritis; Sepsis; *Staphylococcus aureus* infection) [Beta lactamase inhibitor] |
| Dexmedetomidine | Infusion; Intravenous; Solution | EP-00300652 | Neurology/Psychiatric (Anesthesia; Delirium) [Alpha 2 adrenoceptor agonist] |
| Dalteparin sodium | Subcutaneous | WO-08001383 | Hematologic; Dermatologic; Cardiovascular (coronary thrombosis; deep vein thrombosis; lung embolism; thromboembolism) [Factor IIa antagonist; Factor Xa antagonist; Low molecular weight heparin] |
| Bupivacaine | Liposome ; Subcutaneous; Suspension; Sustained/extended release; depot foam | EP-00280503 | Neurology/Psychiatric (pain; topical anesthesia, post-operative pain) [Sodium channel inhibitor] |
| Imipenem + cilastatin | Antibiotic; Infusion; Intramuscular; Intravenous | EP-00048025 | Dermatologic; Gastrointestinal; Genitourinary/Sexual Function; Cardiovascular; Infection; Respiratory; Inflammatory; Musculoskeletal; Ocular (Abscess; Acinetobacter infection; Acute bronchitis; Appendicitis; Bacterial infection; Bacterial pneumonia; Bacterial respiratory tract infection; Bacterial skin infection; Bacterial urinary tract infection; *Bacteroides fragilis* infection; *Bacteroides* infection; Bartholinitis; *Bifidobacterium* infection; Bone and joint infection; Cellulitis; Cholangitis; Cholecystitis; *Citrobacter* infection; *Clostridium* infection; Complicated urinary tract infection; Corneal ulcer; Cystitis; Empyema; Endocarditis; Endophthalmitis; Enterobacter infection; *Enterococcus faecalis* infection; *Escherichia coli* infection; Female genital tract infection; Gram negative bacterium infection; Gram positive bacterium infection; *Haemophilus* infection; *Haemophilus influenzae* infection; Infectious arthritis; Keratitis; *Klebsiella* infection; *Klebsiella pneumoniae* infection; *Morganella* infection; Osteomyelitis; Panophthalmitis; Pelvic inflammatory disease; Peritonitis; Prostatitis; Proteus infection; Providencia infection; *Pseudomonas* |

TABLE 11-continued

Non-oral small molecule therapeutics adaptable for delivery via ingestible device for the treatment of the listed diseases and conditions

| Drug Name | Existing Formulation Technologies and Methods of Administration | Exemplary Patent Literature | Therapeutic Area (Exemplary Indications) [Target-based Action] |
|---|---|---|---|
| | | | aeruginosa infection; Pyelonephritis; Sepsis; Serratia infection; Skin ulcer; Staphylococcus aureus infection; Staphylococcus infection; Streptococcus agalactiae infection; Streptococcus infection; Streptococcus pneumoniae infection; Streptococcus pyogenes infection) [Dehydropeptidase-1 inhibitor] |
| Tigecycline | Antibiotic; Infusion; Intravenous | EP-00536515 | Dermatologic; Infection (Acinetobacter infection; Bacterial infection; Bacterial pneumonia; Bacterial skin infection; Bacteroides fragilis infection; Bacteroides infection; Citrobacter infection; Clostridiaceae infection; Clostridium infection; Enterobacter infection; Enterococcus faecalis infection; Escherichia coli infection; Haemophilus influenzae infection; Klebsiella infection; Klebsiella pneumoniae infection; Legionella pneumophila infection; MRSA infection; Staphylococcus aureus infection; Streptococcus agalactiae infection; Streptococcus infection; Streptococcus pneumoniae infection; Streptococcus pyogenes infection) |
| Meropenem | Antibiotic; Infusion; Intravenous | EP-00126587 | Gastrointestinal; Infection; Respiratory (Appendicitis; Bacterial infection; Bacterial meningitis; Bacterial pneumonia; Bacterial respiratory tract infection; Bacterial skin infection; Bacterial urinary tract infection; Bacteroides fragilis infection; Bacteroides infection; Bacteroides thetaiotaomicron infection; Complicated skin and skin structure infection; Complicated urinary tract infection; Cystic fibrosis; Enterococcus faecalis infection; Escherichia coli infection; Haemophilus influenzae infection; Klebsiella pneumoniae infection; Neisseria meningitidis meningitis; Peptostreptococcus infection; Peritonitis; Pneumonia; Proteus mirabilis infection; Pseudomonas aemginosa infection; Staphylococcus aureus infection; Streptococcus agalactiae infection; Streptococcus infection; Streptococcus pneumoniae infection; Streptococcus pyogenes infection; viridans group Streptococcus infection) [Penicillin binding protein inhibitor] |
| Ceftaroline fosamil | Antibiotic; Formulation powder; Infusion; Intravenous; Prodrug Solution | WO-09932497 | Bacterial pneumonia; Bacterial skin infection; Complicated skin and skin structure infection; Escherichia coli infection; Haemophilus influenzae infection; Klebsiella infection; Klebsiella pneumoniae infection; MRSA infection; Osteomyelitis; Staphylococcus aureus infection; Streptococcus agalactiae infection; Streptococcus pneumoniae infection; Streptococcus pyogenes infection [Penicillin binding protein 2X inhibitor] |
| Gemcitabine | Formulation powder; Freeze drying; Infusion; Intravenous | CN-104650169; EP-00122707; KR-00858842 | Cancer (Bladder tumor; Hepatobiliary system tumor; Lymphoma; Metastatic bladder cancer; Metastatic breast cancer; Metastatic non-small cell lung cancer; Metastatic ovary cancer; Metastatic pancreas cancer; Ovary tumor) |
| Leuprorelin acetate | Lyophilized powder reconstituted as suspension; extended-release formulation; intramuscular; subcutaneous; | | Cancer (prostate, breast); endometriosis; uterine fibroids; central precocious puberty; in vitro fertilization techniques. [Gonadotropin-releasing hormone receptor (GnRHR) agonist to decrease testosterone and estradiol] |
| Aztreonam + Avibactam | Intravenous | | Antibiotic [Beta lactamase inhibitor] |
| Prexasertib | Intravenous | | Cancer [Checkpoint kinase inhibitor] |
| Avibactam sodium + Ceftaroline | Intravenous | | Antibiotic [Beta lactamase inhibitor] |
| LY-3451838 | Intravenous; subcutaneous | | Unidentified indication |

TABLE 11-continued

Non-oral small molecule therapeutics adaptable for delivery via ingestible device for the treatment of the listed diseases and conditions

| Drug Name | Existing Formulation Technologies and Methods of Administration | Exemplary Patent Literature | Therapeutic Area (Exemplary Indications) [Target-based Action] |
|---|---|---|---|
| Gedatolisib | Intravenous | | Cancer [Phosphoinositide 3-kinase inhibitor; mTOR inhibitor] |
| LY-3463251 | Subcutaneous | | Unidentified indication |
| PF-06763809 | Topical | | Psoriasis [Transcription factor inhibitor] |
| LY-3437943 | Subcutaneous | | Unidentified indication |
| Pevonedistat | Intravenous; | | Cancer [Amyloid protein binding protein-1 inhibitor; Ubiquitin ligase modulator] |
| LY-3454738 | Intravenous; subcutaneous | | Atopic dermatitis |
| TD-8954 | Intravenous; | | Diabetic gastroparesis; Gastrointestinal function disorder; Gastrointestinal motility disorder; Gastroparesis [5-HT 4 receptor agonist] |
| Oxytocin | Dry powder inhalant | | Postpartum hemorrhage [hormone, neurotransmitter] |
| JNJ-64232025 | Intravenous; Subcutaneous | | Unidentified indication |
| LY-3462817 | Intravenous; subcutaneous | | Unidentified indication |
| JNJ-64304500 | Subcutaneous formulation | | Crohns disease |
| TAK-981 | Intravenous; | | Cancer [Small ubiquitin related modifier inhibitor] |
| LY-3361237 | Intravenous; subcutaneous | | Unidentified indication |
| Ixazomib citrate | Intravenous; | | Cancer [Proteasome inhibitor] |
| LY-3316531 | Intravenous; subcutaneous | | Psoriasis |
| Rilpivirine | Intramuscular; subcutaneous; sustained-release | | HIV-1 infection [Non-nucleoside reverse transcriptase inhibitor] |
| Pazopanib + pembrolizumab | Intravenous | | Metastatic renal cell carcinoma [PDGF receptor alpha and beta antagonist; Programmed cell death protein 1 inhibitor; VEGF-1/VEGF-2/VEGF-3 receptor antagonist] |
| QBW-276 | Inhalant | | Cystic fibrosis [CFTR modulator] |
| CLL-442 | Dermatological emulsion | | Bowen disease [Phosphoinositide 3-kinase inhibitor; mTOR inhibitor] |
| MGV-354 | Ophthalmic suspension | | Glaucoma; Ocular hypertension [Guanylate cyclase stimulator] |
| Patupilone | Intravenous | | Colorectal tumor |
| S-64315 | Intravenous | | Cancer [Mcl-1 differentiation protein inhibitor] |
| MIW-815 | Intratumoral | | Advanced solid tumor; Breast tumor; Head and neck tumor; Lymphoma; Melanoma; Renal cell carcinoma [Stimulator of interferon genes protein stimulator] |
| LRX-712 | Intra-articular | | Osteoarthritis |

Heparins

In some embodiments, the therapeutic suitable for use with the devices and methods described herein is a heparin. In some embodiments, the heparin is a low molecular weight heparin.

An exemplary heparin is dalteparin. Dalteparin is a low molecular weight heparin. Like other low molecular weight heparins, dalteparin is used for prophylaxis or treatment of deep vein thrombosis, pulmonary embolism, venous thromboembolism, unstable angina, and non-Q-wave myocardial infarction.

Dalteparin is delivered as an SC injection of 2500-18000 units once or twice daily, depending on the reason for treatment. It is available in single-dose vials, multi-dose vials, and pre-filled syringes for self-administration by the patient. The maximum concentration in currently available formulations is 25,000 units/mL, and many formulations contain only water and HCl/NaOH for pH adjustment. The bioavailability is approximately 87% by SC injection, the half-life is approximately 3-5 hours, and it is primarily eliminated by the kidneys. Dalteparin is stable at room temperature and studies have demonstrated 30 days stability in commercial off-the-shelf syringes.

The primary risk of dalteparin overdose is uncontrolled hemorrhage at the site of injection. There are few cases of dalteparin overdose in the literature but, in most cases, the patients were discharged after observation without any intervention. One case describes self-administration of 360,000 units of dalteparin that was successfully managed with medical observation followed by discharge from the hospital with no notable sequelae. In the case of overdose, the action of dalteparin may be partially reversed by the administration of protamine sulfate.

Dalteparin is a suitable therapeutic for delivery via ingestible device as described herein. It is currently available as a liquid, administered by self-injection, and, because adverse injection site reactions are not uncommon, patients may readily adopt an alternative dosage form. The primary method of elimination is renal, so first-pass through the liver should not present an obstacle to using the drug delivery system. Lastly, the probability of acute reactions to overdose is low which, theoretically, could allow an increase in dose to compensate for lower bioavailability than SC injection. Dalteparin dose is normally specified as a single value based on the condition being treated and the weight range of the patient. Each weight range can span 10-15 kg, suggesting that precise dosing is not critical to achieving therapeutic effect.

Immune Modulators

In some embodiments, the therapeutic suitable for use with the devices and methods described herein is an immune modulator. As used herein, an "immune modulator" or "immune modulatory agent" is an agent that stimulates or suppresses the immune system and can help the body fight cancer, infection, or other diseases. The immune modulator can be a therapeutic agent that decreases the activation of an immune cell (e.g., a T cell, e.g., memory T cell), decreases the secretion or expression of a pro-inflammatory cytokine, decreases the recruitment or migration of T-lymphocytes (e.g., memory T lymphocytes), and/or increases the secretion or expression of an anti-inflammatory cytokine.

In some embodiments, an immune modulator is an antibody or antigen-binding fragment, a nucleic acid (e.g., inhibitory nucleic acid), a small molecule, a cancer vaccine, or a live biotherapeutic, such as a probiotic. In some embodiments, the immune modulator is a therapeutic agent used for the treatment of inflammatory bowel disease (IBD), for example, Crohn's Disease or Ulcerative Colitis (UC). Non-limiting immune modulators that are useful for treating or preventing inflammatory bowel disease include substances that suppress cytokine production, down-regulate or suppress self-antigen expression, or mask MHC antigens.

Examples of immune modulators include, without limitation: CHST15 inhibitors (e.g., STNM01); IL-6 receptor inhibitors (e.g., tocilizumab); IL-12/IL-23 inhibitors (e.g., PTG-200, ustekinumab and brazikumab); integrin inhibitors (e.g., vedolizumab and natalizumab); JAK inhibitors (e.g., tofacitinib); SMAD7 inhibitors (e.g., Mongersen); IL-13 inhibitors; IL-1 receptor inhibitors; TLR agonists (e.g., Kappaproct); stem cells (e.g., Cx601); 2-amino-6-aryl-5-substituted pyrimidines (see U.S. Pat. No. 4,665,077); non-steroidal anti-inflammatory drugs (NSAIDs); ganciclovir; tacrolimus; glucocorticoids such as Cortisol or aldosterone; anti-inflammatory agents such as a cyclooxygenase inhibitor; a 5-lipoxygenase inhibitor; or a leukotriene receptor antagonist; purine antagonists such as azathioprine or mycophenolate mofetil (MMF); NN-9499; alkylating agents such as cyclophosphamide; bromocryptine; danazol; dapsone; glutaraldehyde (which masks the MHC antigens, as described in U.S. Pat. No. 4,120,649); anti-idiotypic antibodies for MHC antigens and MHC fragments; cyclosporine; 6-mercaptopurine; steroids such as corticosteroids or glucocorticosteroids or glucocorticoid analogs, e.g., prednisone, methylprednisolone, including SOLU-MEDROL®, methylprednisolone sodium succinate, and dexamethasone; dihydrofolate reductase inhibitors such as methotrexate (oral or subcutaneous); anti-malarial agents such as chloroquine and hydroxychloroquine; sulfasalazine; leflunomide; cytokine or cytokine receptor antibodies or antagonists including anti-interferon-alpha, -beta, or -gamma antibodies, anti-tumor necrosis factor (TNF)-alpha antibodies (infliximab (REMICADE®) or adalimumab), anti-TNF-alpha immunoadhesin (etanercept), anti-TNF-beta antibodies, anti-interleukin-2 (IL-2) antibodies and anti-IL-2 receptor antibodies, and anti-interleukin-6 (IL-6) receptor antibodies and antagonists; anti-LFA-1 antibodies, including anti-CD11a and anti-CD18 antibodies; anti-L3T4 antibodies; heterologous anti-lymphocyte globulin; pan-T antibodies, anti-CD3 or anti-CD4/CD4a antibodies; soluble peptide containing a LFA-3 binding domain (WO 90/08187 published Jul. 26, 1990); streptokinase; transforming growth factor-beta (TGF-beta); streptodomase; RNA or DNA from the host; FK506; RS-61443; chlorambucil; deoxyspergualin; rapamycin; T-cell receptor (Cohen et al., U.S. Pat. No. 5,114,721); T-cell receptor fragments (Offner et al., *Science*, 251:430-432 (1991); WO 90/11294; Ianeway, *Nature*, 341: 482 (1989); and WO 91/01133); BAFF antagonists such as BAFF or BR3 antibodies or immunoadhesins and zTNF4 antagonists (for review, see Mackay and Mackay, *Trends Immunol.*, 23:113-5 (2002)); biologic agents that interfere with T cell helper signals, such as anti-CD40 receptor or anti-CD40 ligand (CD 154), including blocking antibodies to CD40-CD40 ligand (e.g., Durie et al., *Science*, 261:1328-30 (1993); Mohan et al., *J. Immunol.*, 154:1470-80 (1995)) and CTLA4-Ig (Finck et al., *Science*, 265:1225-7 (1994)); CD40/CD40L inhibitors; CD3 inhibitors; CD14 inhibitors; CD20 inhibitors; CD25 inhibitors; CD28 inhibitors; CD49 inhibitors; CD89 inhibitors; and T-cell receptor antibodies (EP 340,109) such as T10B9. Non-limiting examples of agents also include the following: budesonide; epidermal growth factor; aminosalicylates; metronidazole; mesalamine; olsalazine; balsalazide; antioxidants; thromboxane inhibitors; IL-1 receptor antagonists; anti-IL-1 monoclonal antibodies; growth factors; elastase inhibitors; pyridinylimidazole compounds; TNF antagonists; IL-4, IL-10, IL-13 and/or TGFβ cytokines or agonists thereof (e.g., agonist antibodies); IL-11; glucuronide- or dextran-conjugated prodrugs of prednisolone, dexamethasone or budesonide; ICAM-I antisense phosphorothioate oligodeoxynucleotides (ISIS 2302; Isis Pharmaceuticals, Inc.); soluble complement receptor 1 (TP10; T Cell Sciences, Inc.); slow-release mesalazine; cancer vaccines; antagonists of platelet activating factor (PAF); ciprofloxacin; and lignocaine.

Non-limiting examples of immune modulators that are useful for treating ulcerative colitis include sulfasalazine and related salicylate-containing drugs for mild cases and corticosteroid drugs for severe cases. Non-limiting examples of immune modulators that are useful for treating a liver disease or disorder (e.g., liver fibrosis or NASH) include: elafibranor (GFT 505; Genfit Corp.), obeticholic acid (OCA; Intercept Pharmaceuticals, Inc.), cenicriviroc (CVC; Allergan plc), selonsertib (formerly GS-4997; Gilead Sciences, Inc.), an anti-LOXL2 antibody (simtuzumab (formerly GS 6624; Gilead Sciences, Inc.)), GS-9450 (Gilead Sciences, Inc.), GS-9674 (Gilead Sciences, Inc.), GS-0976 (formerly NDI-010976; Gilead Sciences, Inc.), Emricasan (Conatus Pharmaceuticals, Inc.), Arachidyl-amido cholanoic acid (Aramchol™; Galmed Pharmaceuticals Ltd.), AKN-083 (Allergan plc (Akarna Therapeutics Ltd.)), TGFTX4 (Genfit Corp.), TGFTX5 (Genfit Corp.), TGFTX1 (Genfit Corp.), a RoRy agonist (e.g., LYC-55716; Lycera Corp.), an ileal bile acid transporter (iBAT) inhibitor (e.g., elobixibat, Albireo Pharma, Inc.; GSK2330672, GlaxoSmithKline plc; and A4250; Albireo Pharma, Inc.), stem cells, a CCR2 inhibitor, bardoxolone methyl (Reata Pharmaceuticals, Inc.), a bone morphogenetic protein-7 (BMP-7) mimetic (e.g., THR-123 (see, e.g., Sugimoto et al. (2012) *Nature Medicine* 18: 396-404)), an anti-TGF-β antibody (e.g., fresolimumab; see also U.S. Pat. Nos. 7,527,791 and 8,383,780, incorporated herein by reference; NIS-793 (Novartis)), pirfenidone (Esbriet®, Genentech USA Inc.), an anti-integrin αvβ6 antibody, an anti-connective tissue growth factor (CTGF) antibody (e.g., pamrevlumab; FibroGen Inc.), pentoxifylline, vascular endothelial growth factor (VEGF), a renin angiotensin aldosterone system (RAAS) inhibitor (e.g., a rennin inhibitor (e.g. pepstatin, CGP2928, aliskiren), or an ACE inhibitor (e.g., captopril, zofenopril, enalapril, ramipril, quinapril, perindopril, lisinopril, benazepril, imidapril, fosinopril, and trandolapril)), thrombospondin, a statin, bardoxolone, a PDE5 inhibitor (e.g., sidenafil, vardenafil, and tadalafil), a NADPH oxidase-1 (NOX1) inhibitor (see, e.g., U.S. Publication No. 2011/0178082, incorporated herein by reference), a NADPH oxidase-4 (NOX4) inhibitor (see, e.g., U.S. Publication No. 2014/0323500, incorporated herein by reference), an ETA antagonist (e.g., sitaxentan, ambrisentan, atrasentan, BQ-123, and zibotentan), nintedanib (Boehringer Ingelheim), INT-767 (Intercept Pharmaceuticals, Inc.), VBY-376 (Virobay Inc.), PF-04634817 (Pfizer), EXC 001 (Pfizer), GM-CT-01 (Galectin Therapeutics), GCS-100 (La Jolla Pharmaceuticals), hepatocyte growth factor mimetic (Refanalin®; Angion Biomedica), SAR156597 (Sanofi), tralokinumab (AstraZeneca), pomalidomide (Celgene), STX-100 (Biogen IDEC), CC-930 (Celgene), anti-miR-21 (Regulus Therapeutics), PRM-151 (Promedior), BOT191 (BiOrion), Palomid 529 (Paloma Pharamaceuticals), IMD1041 (IMMD, Japan), serelaxin (Novartis), PEG-relaxin (Ambrx and Bristol-Myers Squibb), ANG-4011 (Angion Biomedica), FT011 (Fibrotech Therapeutics), pirfenidone (InterMune), F351 (pirfenidone derivative (GNI Pharma), vitamin E (e.g., tocotrienol (alpha, beta, gamma, and delta) and tocopherol (alpha, beta, gamma, and delta)), pentoxifylline, an insulin sensitizer (e.g., rosiglitazone and pioglitazone), cathepsin B inhibitor R-3020, etanercept and biosimilars thereof, peptides that block the activation of Fas (see, e.g., International Publication No. WO 2005/117940, incorporated herein by reference), caspase inhibitor VX-166, caspase inhibitor Z-VAD-fmk, fasudil, belnacasan (VX-765), and pralnacasan (VX-740).

In some embodiments, the immune modulator is an anti-inflammatory agent. Examples of anti-inflammatory agents include, but are not limited to, IL-12/IL-23 inhibitors, TNFα inhibitors, IL-6 receptor inhibitors, immune modulatory agents (e.g., CD40/CD40L inhibitors), IL-1 inhibitors, IL-13 inhibitors, IL-10 receptor agonists, chemokine/chemokine receptor inhibitors, integrin inhibitors, and S1P modulators.

In some embodiments, the immune modulator is an integrin inhibitor. Examples of integrin inhibitors include, but are not limited to, β7 (beta-7) integrin inhibitors, such as α4β7 (alpha4beta7) integrin inhibitors.

In some embodiments, the immune modulator is a PDE4 inhibitor.

In some embodiments, the immune modulator is a cancer vaccine. In some embodiments, the cancer vaccine is an adenoviral cancer vaccine. In some embodiments, the cancer vaccine is an mRNA-based cancer vaccine. In some embodiments, the cancer vaccine is a vaccine for prostate cancer. Examples of cancer vaccines include, but are not limited to, PF-06936308, PF-06753512, and RG-6180.

In some embodiments of any of the devices or methods described herein, the therapeutic is an immune modulator. In some embodiments of any of the devices or methods described herein, the immune modulator is an IL-12/IL-23 inhibitor, a TNFα inhibitor, a CD40/CD40L inhibitor, an anti-integrin, or an IL-1 inhibitor. In some embodiments, the therapeutic is an immune modulator for use in a method of treating an inflammatory disease or condition that arises in a tissue originating from the endoderm in a subject, where the method includes orally administering to the subject an ingestible device loaded with the immune modulator, wherein the immune modulator is released by the device into the submucosa and/or the mucosa (e.g., into the lamina propria) of the gastrointestinal tract of the subject.

Advanced Therapeutic Medicinal Products (ATMPs) and Regenerative Medicine

In some embodiments of any of the devices or methods described herein, the therapeutic is a glycoprotein, enzyme, gene therapy, nude DNA, mRNA, viral vector, a somatic/stem cell therapy, an allogeneic or autologous stem cell therapeutic, or a medium conditioned by stem cells. In some embodiments, the therapeutic comprises a DNA or mRNA vaccine alone or with adjuvant therapy and may employ replication incompetent viruses for insertion.

In some embodiments, the therapeutic includes regulatory T cells (Treg cells). For example, from about 106 to about 109 (e.g., 106, 107, 108, or 109) autologous Treg cells (e.g., ova-specific T cells) can be delivered using the devices and methods described herein. Autologous Treg cells can be prepared by isolating peripheral blood mononuclear cells (PBMCs) from the subject's blood and then expanding ova-specific T cells by culturing the PBMCs in the presence of ovalbumin using *Drosophila* derived artificial antigen presenting cells transfected with specific stimulatory molecules. See, e.g., Brun, et al., *Int Immunopharmacol.*, 2009, 9(5): 609-13. T cells can be cloned and Ova-Treg clones can be selected based on an ovalbumin-specific IL-10 production. A phase 1/2a study in 20 patients showed that a single injection of antigen-specific (ovalbumin) Treg cells was safe in CD and about 40% of the patients show a clinical response after treatment. See, e.g., Neurath, 2014, supra; and Desreumaux, et al., *Gastroenterology*, 2012, 143:1207-1217.

In some embodiments, stem cells are delivered using the devise and methods described herein. The delivery of stem cells can offer measurable therapeutic benefit as the stem cells have the ability to differentiate into numerous different cell types, and rejuvenate the surrounding area. In some embodiments, a population of cells is delivered that includes at least about 50% stem cells (at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99% stem cells). The term "stem cell" is used herein to refer to a cell that is capable of differentiating into a two or more different cell types. As used herein, the term "a stem cell" may refer to one or more stem cells.

In some embodiments, the stem cells can be hematopoietic stem cells (HSC) capable of differentiating into different types of blood cells, including myeloid and lymphoid lineages of blood cells. HSC can be obtained from bone marrow, cord blood, or peripheral blood, and are commonly used for bone marrow transfusions in combination with chemotherapy to restart the immune system. HSC are CD34+ cells. Cell-surface markers can be identified by any suitable conventional technique, including, for example, positive selection using monoclonal antibodies against cell-surface markers.

The HSC used in the methods described herein can be, with respect to the subject, autologous or allogenic. HSC may have a high immunogenicity. As a result, if autologous HSC are not used, the HLA receptors of the donor and receiver must be matched. HSC can be harvested by mobilizing stem cells from the subject (autologous) or an HLA-matched donor (allogeneic) using granulocyte colony stimulating factor (GCSF) to promote the creation of HSC and their migration into the bloodstream. CD34+ cells can be collected from the peripheral blood or BM of the subject or donor, and then the cells can be cryopreserved until infusion or can be placed in a medium such as an alginate hydrogel. When stored for five days in an alginate-hydrogel in ambient temperature in an air-tight environment, stem cells showed a survival rate of 74-80%. For IBD, HSC therapy is preceded by chemotherapy, which removes the majority of the T-cells causing the inflammation, followed by administration of the HSC in the ingestible device.

In some embodiments, the stem cells used in the methods described herein are capable of differentiating into two or more different cell types other than blood cells. In some embodiments, the stem cells are capable of differentiating into cells of each of the three embryonic germ layers (i.e., endoderm, ectoderm, and mesoderm). As used herein, "capable of differentiating" means that a given cell, or its progeny, can proceed to a differentiated phenotype under the appropriate culture conditions. The capacity of the cells to differentiate into at least two cell types can be assayed by methods known in the art.

Non-limiting examples of stem cells include embryonic stem cells or adult stem cells such as mesenchymal stem cells (MSC) (also can be referred to as mesenchymal stromal cells) or other multipotent stem cells; endothelial progenitor cells; stem cells from a particular tissue or organ such as intestinal stem cells, adipose stem cells, or testes stem cells; or induced pluripotent stem cells (iPSC). In some embodiments, stem cells from a particular tissue also can be classified as MSC.

In some embodiments, the stem cells are MSC, which can differentiate into bone, muscle, cartilage, or adipose type cells. MSC can down-regulate inflammation and have a strong immunoregulatory potential. MSC can be obtained from various tissues, including from, for example, bone marrow, placenta, amniotic fluid, Wharton's jelly, amniotic membrane, chorionic villi, umbilical cord, umbilical cord blood, adipose tissue, dental pulp, synovial membrane, or peripheral blood. Depending on the source of MSC and the stemness (i.e., multipotency), the MSC can express a variety of different markers, including, for example, one or more of CD105, CD73, CD90, CD13, CD29, CD44, CD10, Stro-1, CD271, SSEA-4, CD146, CD49f, CD349, GD2, 3G5, SSEA-3, SISD2, Stro-4, MSCA-1, CD56, CD200, PODX1, Sox11, or TM4SF1 (e.g., 2 or more, 3 or more, 4 or more, 5 or more, 6 or more, 7 or more, 8 or more, 9 or more, or 10 or more of such markers), and lack expression of one or more of CD45, CD34, CD14, CD19, and HLA-DR (e.g., lack expression of two or more, three or more, four or more, or five or more such markers). In some embodiments, MSC can express CD105, CD73, and CD90. In some embodiments, MSC can express CD105, CD73, CD90, CD13, CD29, CD44, and CD10. In some embodiments, MSC can express CD105, CD73, and CD90 and one or more stemness markers such as Stro-1, CD271, SSEA-4, CD146, CD49f, CD349, GD2, 3G5, SSEA-3, SISD2, Stro-4, MSCA-1, CD56, CD200, PODX1, Sox11, or TM4SF1. In some embodiments, MSC can express CD105, CD73, CD90, CD13, CD29, CD44, and CD10 and one or more stemness markers such as Stro-1, CD271, SSEA-4, CD146, CD49f, CD349, GD2, 3G5, SSEA-3, SISD2, Stro-4, MSCA-1, CD56, CD200, PODX1, Sox11, or TM4SF1. See, e.g., Lv, et al., Stem Cells, 2014, 32:1408-1419.

The MSC used in the methods described herein can be, with respect to the subject, autologous or allogenic. MSC have low immunogenicity due to a dearth of HLA receptors on their surface. As a result, allogenic MSC therapy is a far more viable option for patients. Furthermore, MSC are able to downregulate the immune system, which can modulate the inflammation caused in many autoimmune disorders.

In some embodiments, MSC are commercially available. See, e.g. Prochymal® from Osiris Therapeutics.

In some embodiments, MSC can be harvested from bone marrow by ex vivo culture of the adherent cell fraction of bone marrow aspirates. The solid surface to which the MSC adhere can be a plastic material such as a polystyrene plate, optionally coated with poly-D-Lysine, laminin, or other reagent.

In some embodiments, the stem cells can be PF-05285401 cells (Multistem® cells), which are human stem cells obtained from adult bone marrow or other nonembryonic tissue sources. Multistem® cells are commercially available from Athersys Inc.

In some embodiments, MSC can be harvested from adipose tissue such as brown or white adipose tissue from subcutaneous, omental/visceral, mammary, gonadal, or other adipose tissue site. For example, the MSC can be harvested from subcutaneous white adipose tissue such as that isolated from liposuction. The cells can be harvested by mincing the adipose tissue and washing to remove blood. If the adipose tissue is obtained from a liposuction procedure, mincing is not required. The adipose tissue can be incubated with an enzyme such as Type I collagenase, and the stromal vascular fraction (SVF), which contains a variety of cell types including MSC, can be recovered and the MSC selected from the mixed cell population by adherence to a solid surface such as plastic cell culture surface optionally coated as described above. Yield of MSC from adipose tissue is up to 300-fold higher than the yield of MSC from bone marrow. See, e.g., Fellows, et al., Front Genet. 2016, 7:213; Lechanteur, et al., J Transl Med. 2016; 14: 145. In some embodiments, the stem cells can be autologous adipose derived stem cells such as Cx401 cells.

In some embodiments, the MSC can be expanded in cultured, e.g., passaged at least two times, at least three times, at least four times, at least five times, at least six times, at least seven times, at least eight times, at least nine times, or at least ten times. In some embodiments, cells can be passaged more than three times to improve the homogeneity of the cell phenotype in the cell population. In some embodiments, the cells can be expanded in culture until needed, so long as the homogeneity of the cell phenotype is improved and differential capacity is maintained. See Martin, et al., Cytotherapy, 2016, 18(5): 613-620 for methods of culturing MSCs.

The MSC can be cryopreserved until formulated for the ingestible device or can be placed in a medium such as an alginate hydrogel. The viability of MSC cells stored in alginate hydrogels after 50 days at ambient temperature is 80%.

In some embodiments, the MSC can be coated with antibodies, e.g., anti-vascular cell adhesion molecule-1 (e.g., VCAM-1) antibodies or anti-addressin antibodies, to improve, for example, their ability to target and hone into inflamed lesions in the GI tract. See, e.g., Ko, et al., Mol Ther. 2010, 18(7): 1365-1372.

In some embodiments, human iPSCs can be generated from adult somatic cells (e.g., fibroblasts, keratinocytes, dental pulp cells, cord blood, or peripheral blood mononuclear cells) or MSC. iPSCs can be generated using retroviral or non-retroviral methods. See, for example, Loh, et al., *Blood* 2009, 113:5476-5479, Okita, et al., *Nat Methods.* 2011, 8(5):409-12, or Okita, et al., *Stem Cells,* 2013, 31(3): 458-466. In some embodiments, p53 suppression and non-transforming L-Myc can be used to generate human induced pluripotent stem cells (iPSCs) with episomal plasmid vectors encoding OCT3/4, SOX2, KLF4, and LIN28. In some embodiments, adult somatic cells can be transduced with retroviruses encoding four pluripotency factors (SOX2, KLF4, c-MYC, and OCT4). Fully reprogrammed iPSCs have similar properties to embryonic stem cells (ESCs). Patient's cells can be used to derive iPSCs, which can then be induced to undergo differentiation into various types of somatic cells, all with the same genetic information as the patient. See, Azizeh-Mitra, et al., *Stem Cells Int.* 2016; 6180487. In other embodiments, allogenic cells are used to derive iPSCs.

In some embodiments, the stem cells can be intestinal stem cells (ISC), which can differentiate into intestinal cell subtypes such as globet cells, Paneth cells, and enterocytes. ISC are located at the crypt base within the intestine and can be positive for one or more markers such as Musashi-1 (Msi-1), Ascl2, Bmi-1, Doublecortin and Ca2+/calmodulin-dependent kinase-like 1 (DCAMKL1), and Leucin-rich repeat-containing G-protein-coupled receptor 5 (Lgr5). See, e.g., Mohamed, et al., *Cytotechnology,* 2015 67(2): 177-189. In addition, ISC or crypts can be used to produce intestinal organoids using a biodegradable scaffold (e.g., poly-glycolic acid), growth factors such as epidermal growth factor (EGF), R-spondin, Jagged-1 peptide, or Noggin, and extracellular matrix. In some embodiments, mesenchymal cells are included in the culture to support the growth. The intestinal organoid can include a central lumen lined by a villus-like epithelium. See, e.g., US20160287670A1 and WO2015183920A2. Pre-clinical studies have demonstrated the intestinal organoid efficacy in differentiating into all GI cell lineages and regrowing parts of the intestine, muscle layer included. See, Agopian, et al., *J Gastrointest Surg.,* 2009, 13(5):971-82; Kuratnik and Giardina, *Biochem Pharmacol.,* 2013, 85:1721-1726; and Belchior et al., *Semin Pediatr Surg.,* 2014, 23:141-149.

In some embodiments, the stem cells can be allogeneic adipose-derived stem cells (ASC) such as ALLO-ASC cells or expanded ASC (eASC) (e.g., Cx601 cells). See, for example, Panes et al., *Lancet;* 2016, 388: 1281-90; and U.S. Patent Publication No. 20120020930. Cx601 cells are commercially available from TiGenix. Cx601 cells have been used for treating complex perianal fistulas in Crohn's disease patients. For example, Cx601 cells can be used for treating complex perianal fistulas with non-active/mildly active luminal Crohn's disease. ALLO-ASC cells are commercially available from Anterogen Co., Ltd., and have been used for treating Crohn's disease.

In some embodiments of any of the devices or methods described herein, the therapeutic is a live yeast, bacteriophage or prophage (i.e., the genetic material of a bacteriophage incorporated into the genome of a bacterium or existing as an extrachromosomal plasmid of the bacterium, and able to produce phages if specifically activated). The bacteriophage can be lytic or lysogenic. In some embodiments, the bacteriophage can infect bacteria commonly found in the GI tract. For example, the bacteriophage can infect one or more, two or more, three or more, four or more, five or more, six or more, seven or more, eight or more, nine or more, or ten or more species of bacteria within the GI tract. See, for example, Wang, et al., *Inflamm Bowel Dis.* 2015; 21(6): 1419-1427. In some embodiments, the bacteriophage can be lytic bacteriophage and infect one or more detrimental bacterial species in the GI tract to reduce the detrimental species in the GI tract. For example, the bacteriophage can infect two or more, three or more, four or more, five or more, six or more, or seven or more detrimental bacterial species. In some embodiments, bacteriophage can be a member of the families from the order Caudovirales such as Siphoviridae, Myroviridae, Podoviridae, or Microviridae. See, e.g., Babickova and Gardlik, *World J. Gastroentrol.* 2015; 21(40): 11321-11330. In some embodiments, the bacteriophage can include one or more of bacteriophage K (such as ATCC strain 19685-B 1), bacteriophage 17 (such as ATCC strain 23361-B 1), and Stab8. See, e.g., WO2016172380A1. In some embodiments, one or more bacteriophages, and one or more probiotics or prebiotics, optionally in combination with an antibiotic, are used to reduce detrimental bacterial species.

For therapeutics containing stem cells, the cells can be formulated to include one or more additional compounds such as a growth factor, a plurality of different growth factors, an anti-inflammatory agent, an immunosuppressive agent, a biological agent, an antibiotic, an anti-diarrheal agent, an adhesive, or other compounds that affect cell differentiation and/or proliferation. For example, the live biotherapeutic can be formulated to include one or more of the following: granulocyte colony-stimulating factor (G-CSF); an anti-inflammatory agent such as an agent comprising mesalamine; an immunosuppressive agent such as 6-mercaptopurine or azathioprine; a biological agent such as infliximab (Remicade®); an antibiotic, an antidiarrheal agent such as diphenoxylate, loperamide, and codeine; or an adhesive such as fibrin.

In some embodiments, the therapeutic can include glycoproteins, for example, a granulocyte-macrophage colony-stimulating factor (GM-CSF). Pharmaceutical analogs of naturally occurring GM-CSF include sargramostim and molgramostim Nartograstim, myelopoietins, circularly permuted G-CSF sequences, and SB247464 are among the known mimetics of G-CSF.

In some embodiments, the therapeutic can include bacteriophage or prophage that are genetically modified to produce one or more products that are anti-inflammatory and/or that can enhance intestinal barrier function.

In some embodiments, the ingestible device includes a targeted antimicrobial in which RNA-guided nucleases (RGNs) targeting specific DNA sequences within a target bacteria can be efficiently delivered to microbial populations using bacteriophage or bacteria carrying plasmids. For example, a targeted antimicrobial can couple a phage vector with the CRISPR (clustered regularly interspaced short palindromic repeats)/Cas system (e.g., the biological nanobots from Eligo Bioscience (Eligobiotics)). The biological nanobots can be composed of a capsid from a bacteriophage virus (modified to not multiply) that can deliver the CRISPR/Cas9 system into the targeted bacteria, resulting in the targeted bacteria being killed by cleavage of the bacterial genome by Cas9 enzyme within a predetermined pathogenic sequence. See, for example, WO2017009399A1 and Citorik, et al., *Nat Biotechnol.,* 2014, 32(11): 1141-1145.

For therapeutics containing bacteriophage or prophage, the bacteriophage or prophage can be lyophilized, or can be in saline or other pharmaceutical carrier. Lyophilized phage can be incorporated into a solid or semi-solid formulation without materially reducing efficiency, and can be temperature stable up to 55° C. with a shelf life of 14 months. Liquid formulations of phage can be stored at 4° C.

Oral Vaccines

In some embodiments, the therapeutic suitable for use with the devices and methods described herein is an oral vaccine. As used herein, an "oral vaccine" is one or more antigens administered orally which can induce an immune response against one or more diseases caused by pathogens in the mucosal sites within the GI tract. The antigen in an oral vaccine can induce an immune response associated with the production of immunoglobulins both systemically (IgG) and locally at the mucosa (secretory IgA (sIgA)) (for review, see Brandtzaeg, Curr. Top. Microbiol. Immunol., 146:13-25 (1989)). Oral administration of vaccine antigens can induce immune responses both at the induction sites and other effector sites within the mucosal immune compartments through the dissemination of sensitized lymphoid cells from the induction sites. In some embodiments, the use of needle-free injection of an oral vaccine as compared to a parenteral vaccine improves patient compliance and safety. In some embodiments, the intact and active antigen is delivered to the intestine. In some embodiments, successful delivery of an oral vaccine includes protecting the antigens against the harsh stomach environment (e.g., low pH) and the hydrolytic enzymes present in the GI tract that can degrade the antigens. As such, in some embodiments, encapsulation of an oral vaccine within the ingestible device obviates the need for higher doses of the antigens that can result in immunological tolerance to the vaccine. Encapsulation of an oral vaccine within the ingestible device can further prevent antigen dilution over the large surface area of the GI tract. The oral vaccine can be released from the ingestible device at desired locations within the GI tract, for example, in the small intestine where the majority of absorption processes occur, thereby solving the temporal limitation challenge for absorption of the vaccine formulations.

In some embodiments, the oral vaccine comprises one or more antigens in a mixture selected from a live-attenuated pathogen, an inactivated pathogen, a live pathogen, a protein subunit of a pathogen, a carbohydrate subunit of a pathogen, and a carbohydrate-polysaccharide conjugate of a pathogen. In some embodiments, the oral vaccine antigen is a live-attenuated pathogen. In some embodiments, the antigen is an inactivated pathogen. In some embodiments, the antigen is a live pathogen. In some embodiments, the antigen is a protein subunit of a pathogen. In some embodiments, the antigen is a carbohydrate subunit of a pathogen. In some embodiments, the antigen is a carbohydrate-polysaccharide conjugate of a pathogen. In some embodiments, the oral vaccine formulation comprises one or more adjuvants. As used herein, an "adjuvant" is a substance added to a vaccine to enhance the immunogenicity of an antigen. Suitable adjuvants for use in the oral vaccine formulations of the present disclosure include any adjuvant known by one of skill in the art that can be used to enhance the immunogenicity of an antigen. In some embodiments, the adjuvants are particulates of aluminum salts. In some embodiments, the adjuvants are oil-in-water emulsions. In some embodiments, the adjuvants are toll-like receptor (TLR) ligands. In some embodiments, the adjuvants are immuno-stimulating complexes (ISCOMs). In some embodiments, the adjuvants are QS-21. In some embodiments, the adjuvants are AS03. In some embodiments, the adjuvants are AS04. In some embodiments, the adjuvants are virosomes. In some embodiments, the adjuvants are MF59® (for review, see Di Pasquale et al., Vaccines, 3; 320-343 (2015)).

In some embodiments, the oral vaccine is used to induce an immune response against a viral pathogen. Non-limiting examples of viral pathogens include strains of adenovirus, Chikungunya virus, coronavirus, dengue virus, Ebola virus, enterovirus D68 (EV-D68), enterovirus 71 (EV-71), hepatitis virus, herpes simplex virus, human immunodeficiency virus (HIV), human papilloma virus (HPV), influenza virus, Japanese encephalitis virus, measles virus, mumps virus, Nipah virus, norovirus (Norwalk virus), poliomyelitis virus, rabies virus, respiratory syncytial virus (RSV), rotavirus, rubella virus, tick-borne encephalitis virus, varicella zoster virus, yellow fever virus and Zika virus. In some embodiments, the oral vaccine is used to induce an immune response against a bacterial pathogen. Non-limiting examples of bacterial pathogens include *Bordetella pertussis, Campylobacter jejuni, Clostridium difficile, Clostridium tetani, Corynebacterium diphtherias*, enterotoxigenic *Escherichia coli*, Group B *Streptococcus* (GBS), *Haemophilus influenzae* type b (Hib), *Helicobacter pylori, Mycobacterium tuberculosis* (TB), *Neisseria meningitidis, Salmonella typhi, Salmonella enterica*, nontyphoidal *Salmonella* species, *Shigella, Vibrio cholerae, Staphylococccus aureus, Streptococcus pneumoniae, Streptococcus pyrogenes*. In some embodiments, the oral vaccine is used to induce an immune response against a parasitic pathogen. Non-limiting examples of parasitic pathogens include human hookworm, leishmania, plasmodium, schistosomes and *Trypanosoma cruzi*.

In some embodiments, the oral vaccine is selected from oral vaccines including Sabin Live OPV (for polio); Vivotif® (for typhoid fever); Dukoral® (for cholera); Vaxchora® (for cholera); Rotarix® (for gastroenteritis); RotaTeq® (for gastroenteritis), live Adenovirus oral vaccine (for acute respiratory disease), BNT162 from Pfizer, BioNTech (for SARS-CoV-2), mRNA-1273 from Moderna (for SARS-CoV-2), AZD1222 from AstraZeneca (for SARS-CoV-2), CoronaVac from Sinovac (for SARS-CoV-2), and JNJ-78436735 from Johnson & Johnson (for SARS-CoV-2). In some embodiments, the oral vaccine is selected from vaccines currently under clinical development including PF-06425090 (for *C. difficile*); PF-06482077 (for *S. pneumoniae*); PF-06760805 (for GBS); PF-06842433 (for *S. pneumoniae*); PF-06928316 (for RSV); PF-06886992 (for *N. meningitidis*); Ad26.ZEBOV+MVA-BN Filo regimen (for Ebola); JNJ-1623 (for HPV); JNJ-63682931 (for HPV); JNJ-63682918 (for HPV); Ad26.Mod.HIV+MVA mosaic vaccine+gp140 (for HIV); JNJ-9220 (for HIV); JNJ-64400141 (for RSV); JNJ-860 (for *E. coli*); JNJ-64213175 (for RSV); JNJ-64152348 (for poliovirus); Ad26-RSV-FA2 (for RSV); JNJ-66684657 (for Zika virus); JNJ-64300535 (for hepatitis B virus); Ad26.Filo+MVA-BN-Filo (for Filovirus) Vi-CRM197 (for *S. typhi*); VLA-84 (for *C. difficile*); monomeric gp120 HIV-1 subtype C (for HIV); TAK-003 (for dengue virus); TAK-214 (for Norwarlk virus); TAK-021 (for enterovirus 71); TAK-195 (for polio virus); TAK-426 (for Zika virus); VLP norovirus (for Norwalk virus).

Nucleic Acid Therapies

In some embodiments, the therapeutic suitable for use with the devices and methods described herein is a nucleic acid therapy. Exemplary "nucleic acid therapies" include nucleic acids complementary to target sequence, such as plasmid DNA, CRISPR-Cas, and other gene-editing tools, antisense nucleic acids such as antisense oligonucleotides (ASOs), ribozymes, deoxyribozymes, small interfering RNAs (siRNAs), microRNA (miRNA) analogs, and inhibitors; and nucleic acids that are not complementary to the target sequence, such as mRNAs, aptamers, CpG, and decoy nucleic acids. Exemplary nucleic acids for delivery using any of the devices or methods described herein are provided in the Table below:

| Brand Name (Drug Name) | Company | Type | Traditional Route of Administration & Dosing | Target: Indication (target organ) |
|---|---|---|---|---|
| Kynamro (mipomersen) | Ionis/ Genzyme | Antisense oligo | SQ | APOB: homozygous familial hypercholesterolaemia (Liver) |
| Defitelio (Defibrotide) | Jazz | Oligo | 6.25 mg/kg/dose IV q6h for at least 21 days | NA: hepatic veno-occlusive disease (liver) |
| Exondys 51 (Eteplirsen) | Sarepta Tx | Antisense oligo | 30 mg/kg/dose IV qwk | DMD exon 51: Duchenne muscular dystrophy (skeletal muscle |
| Tegsedi (Inotersen) | Ionis | Antisense oligo | 284 mg (1.5 ml) SC qwk | TTR: hereditary transthyretin amyloidosis, polyneuropathy (Liver) |
| Onpattro (Patisiran) | Alynlam | siRNA | Up to 30 mg IV q3wk | TTR: hereditary transthyretin amyloidosis, polyneuropathy (Liver) |
| Givlaari (Givosiran) | Alynlam | siRNA | 2.5 mg/kg/dose SC qmo | ALAS1: acute hepatic porphyria (Liver) |
| Vyondys 53 (Golodiersen) | Sarepta Tx | Antisense oligo | 30 mg/kg/dose IV qwk | DMD exon 53 (Duchenne muscular dystrophy) |

Antibody-Drug Conjugates

In some embodiments, the therapeutic agent is delivered to target cells or tissues as a conjugate covalently linked to a monoclonal antibody (mAb), a fragment of an antibody, or biosimilars thereof. In some embodiments, the therapeutic agent is linked to an antibody. The resulting pharmaceutical entity, commonly known as an antibody-drug conjugate (ADC), can enable the delivery of a therapeutic agent to target cells expressing an antigen recognized by the antibody. In some embodiments, undesirable off-target toxicity is reduced. In some embodiments, the therapeutic index of the therapeutic agent is improved. In some embodiments, the antibody of an ADC binds to one antigen. In some embodiments, the antibody of an ADC binds to two different antigens (i.e., bispecific). In some embodiments, the antibody of an ADC binds to more than two different antigens (i.e., multi-specific). In some embodiments, the therapeutic agent of an ADC is a small molecule drug. In some embodiments, the therapeutic agent of an ADC is a peptide drug. In some embodiments, the therapeutic agent of an ADC is an imaging agent. In some embodiments, the therapeutic agent of an ADC is a radiolabeled drug. In some embodiments, the ADC is used as a treatment for cancer. In some embodiments, the ADC is used as an immune modulator. In some embodiments, the ADC is used as a treatment for an infectious disease (see for example, Liu et al., Expert Opin. Biol. Ther., 16:591-593 (2016)). Examples of ADC drugs include, but are not limited to, gemtuzumab ozogamicin (Mylotarg®), brentuximab vedotin (Adcetris®), trastuzumab emtansine (Kadcyla®), inotuzumab ozogamicin (Besponsa®), polatuzumab vedotin-piiq (Polivy®), enfortumab vedotin (Padcev®), trastuzumab deruxtecan (Enhertu®), and sacituzumab govitecan (Trodelvy®).

In some embodiments, the therapeutic agent is linked to an antibody or an antibody fragment via a chemical linker. In some embodiments, the chemical linker is stable during systemic circulation, but releases the therapeutic agent in or near target cells. In some embodiments, the linker is cleavable. In some embodiments, the cleavable linker is cleaved by enzymes. In some embodiments, the cleavable linker is cleaved by changes in pH. In some embodiments, the cleavable linker is cleaved by changes in redox potential. In some embodiments, the linker is non-cleavable. In some embodiments, the drug-linker is linked to an antibody or an antibody fragment via a surface-exposed native amino acid residue of an antibody. In some embodiments, the native amino acid is lysine. In some embodiments, the native amino acid is cysteine. In some embodiments, the the native amino acid is tyrosine. In some embodiments, the native amino acid is glutamine. In some embodiments, the drug-linker is linked to an antibody or an antibody fragment via a non-native amino acid residue engineered into specific locations of the antibody. In some embodiments, the non-native amino acid isp-azido-L-phenylalanine (pAzF). In some embodiments, the non-native amino acid is p-azidomethyl-L-phenylalanine (pAMF). In some embodiments, the non-native amino acid is selenocysteine (Sec). In some embodiments, the non-native amino acid is azido-lysine. In some embodiments, the non-native amino acid is a cyclopropene derivative of lysine (CypK).

In some embodiments, the conjugation site is non-specific, wherein the ADC molecules comprise drugs conjugated to different locations on the antibody molecules. In some embodiments, the conjugation sites are specific, wherein the ADC molecules comprise drugs conjugated to the same locations of each antibody molecule. Since not every possible conjugation site of each antibody molecule or antibody fragment are conjugated to drug molecules, the average drug-to-antibody ratio (DAR) is commonly used to describe the amount of drug molecules relative to the amount of antibody molecules present in an ADC mixture on a molar basis. In some embodiments, the average DAR in an ADC mixture is about 1:1. In some embodiments, the average DAR in an ADC mixture is about 2:1. In some embodiments, the average DAR in an ADC mixture is about 3:1. In some embodiments, the average DAR in an ADC mixture is about 4:1. In some embodiments, the average DAR in an ADC mixture is about 5:1. In some embodiments, the average DAR in an ADC mixture is about 6:1. In some embodiments, the average DAR in an ADC mixture is between about 1:1 and about 2:1. In some embodiments, the average DAR in an ADC mixture is between about 2:1 and about 3:1. In some embodiments, the average DAR in an ADC mixture is between about 3:1 and about 4:1. In some embodiments, the average DAR in an ADC mixture is between about 4:1 and about 5:1. In some embodiments, the average DAR in an ADC mixture is between about 5:1 and about 6:1.

In some embodiments, the therapeutic agent is linked to an antibody fragment. The relatively large size of an intact antibody scaffold (e.g., approximately 150,000 daltons) can present several issues for an ADC based on intact antibodies, including poor tumor penetration, high systemic accumulation, and slow clearance profiles. The use of other scaffolds such as antibody fragments or antibody mimics for targeted delivery of therapeutic agents has been explored (see, e.g., Richards, *Drug Discov. Today Technol.*, 30:35-46 (2018)). In some embodiments, the antibody fragment is a fragment antigen binding (Fab) domain. In some embodiments, the antibody fragment is a F(ab')$_2$ domain. In some embodiments, the F(ab')$_2$ domain is obtained by treating an immunoglobulin monomer with the enzyme papain. In some embodiments, the antibody fragment is a Fab' fragment. In some embodiments, the Fab' fragment is obtained by mild reduction of a F(ab')$_2$ domain. In some embodiments, the antibody fragment is a single chain fragment variable (scFv) domain. In some embodiments, the scFv domain comprises fused variable regions of the heavy and light chains of an antibody. In some embodiments, the antibody fragment is a diabody. In some embodiments, the diabody is comprised of two scFv fragments bivalent complex. In some embodiments, the diabody is a bivalent homodimer complex. In some embodiments, the diabody is a bivalent heterodimer, bispecific complex. In some embodiments, the antibody fragment is an antibody fragment crystalizable (Fc) domain. The Fc domain of an antibody is about 50,000 daltons in molecular weight, and is the base portion of an antibody that binds to a corresponding Fc receptor on the surface of certain types of immune cells (e.g., macrophages, neutrophils, eosinophils, dendritic cells, B cells, natural killer cells, and mast cells) and some proteins in the complement system. Conjugation of the therapeutic agent to an Fc domain can significantly increase its serum half-life and thereby prolonging its therapeutic activity due to the increase in the overall molecular weight of the conjugate and engagement in the neonatal Fc receptor (FcRn)-mediated recycling process. The Fc domain can also slow down renal clearance of the therapeutic agent, and may help improve its solubility and stability (see, e.g., Pechtner et al. Prim. Health Care, 7:1-5 (2017)). Attachment of an Fc domain to a therapeutic agent can also direct the therapeutic agent to target immune cells via interactions with the corresponding Fc receptors. In some embodiments, the Fc-conjugated therapeutic agent is etanercept (Enbrel®). In some embodiments, the Fc-conjugated therapeutic agent is belatacept (Nulojix®). In some embodiments, the Fc-conjugated therapeutic agent is aflibercept (Eylea®). In some embodiments, the Fc-conjugated therapeutic agent is dulaglutide (Trulicity®).

In some embodiments, targeted delivery of a therapeutic agent can be achieved via conjugation to small immunoproteins (SIPS). In some embodiments, the SIPS comprises scFv fragments fused to an immunoglobulin-derived constant region. In some embodiments, targeted delivery of a therapeutic agent can be achieved via conjugation to synthetic antibody scaffolds. Examples of synthetic antibody scaffolds include, but are not limited to, affibodies, which are small (~7,000 daltons) 3-helix proteins derived from the Z-domain of *Staphylococcus* protein-A; monobodies, which are small (~10,000 daltons) cysteine-free scaffolds based on the 10$^{th}$ type-III fibronectin; centyrins, which are structurally similar to monobodies but are based on the Fn3 domain of Tenascin C instead of fibronectin; DARPins, which are designed scaffolds based on Akyrin repeats; and knottins, which are designed knotted peptides with 30-50 amino acid residue and three or more disulfide bridges.

Pharmaceutical Formulations

Agents such as antibodies and other therapeutic proteins and the other therapeutic agents disclosed herein can be delivered using the devices and methods described herein, including an ingestible device as disclosed herein. The therapeutic agents can be incorporated into pharmaceutical formulations, which can be loaded into a device for release and delivery to a subject, or more particularly, for delivery of the formulation and/or antibody or therapeutic protein or agent to the gastrointestinal tract of a subject. In some embodiments, the formulation is delivered to the tissue of the GI tract. In some embodiments, the formulation is delivered onto or into tissue of the GI tract, e.g., the mucus, mucosa or submucosa of the GI tract. In some embodiments, the formulations are fluid. In some embodiments, the fluid is a solution or a suspension. In some embodiments, the formulation is a liquid, but can be semi-solid, or solid formulations that are later converted to a liquid formulation. The formulations can comprise the agent and a physiologically acceptable carrier. Some formulations, which may be commercially or otherwise available for IV or subcutaneous delivery, and which may be available in pre-loaded syringes or pens, may alternatively be incorporated or loaded into a device, such as an ingestible device, as disclosed herein, for release and topical delivery of the formulation and/or antibody or therapeutic protein to the gastrointestinal tract of a subject.

In some embodiments, the therapeutic agent is formulated as a solution (e.g., an aqueous solution formulation) or a suspension or dispersion. In some embodiments, the formulation contains an antibody. Formulations can be prepared, for example, by incorporating an antibody in the required amount in an appropriate solvent with at least one, or a combination of, ingredients described herein. Generally, dispersions can be prepared by incorporating an antibody into a vehicle that contains a basic dispersion medium and/or other ingredients. In some embodiments, proper fluidity of a formulation is maintained using an appropriate coating, by the maintenance of the required particle size in the case of dispersion, and/or by the use of surfactants. Prolonged absorption of compositions can be brought about by including in the composition an agent that delays absorption. In some embodiments, formulations further comprise one or more additional excipients to enhance performance, such as tissue or mucosa permeation enhancement, disruption of tight epithelial junctions, absorption and/or stability. Excipients that can be incorporated to enhance absorption by the GI tract and/or at the disease site within the GI tract include, for example, bile salts, chelators, surfactants, anti-oxidants, fatty acids and derivatives thereof, cationic polymers, anionic polymers, and acylcarnitines.

In some embodiments, the formulation contains a concentration of the therapeutic agent of, e.g., about 50 mg/mL, about 100 mg/mL, about 150 mg/mL or about 400 mg/mL or greater. In some embodiments, the therapeutic agent is formulated in a solution. In some embodiments, the therapeutic agent is formulated as a suspension or dispersion.

In some embodiments, a formulation comprising a peptide or a protein therapeutic agent is mixed with a pharmaceutically acceptable preservative, one or more surfactants and optionally a pharmaceutically acceptable tonicity modifier. In some embodiments, the formulation is subjected to heat treatment at a predetermined pH. In some embodiments, the heat treatment improves the physical stability of the formulation. In some embodiments, the formulation comprises a pharmaceutically acceptable preservative. In some embodiments, the pharmaceutically-acceptable preservative is selected from the group consisting of phenol, m-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thimerosal. In some embodiments, the formulation comprises one or more surfactants. Examples of surfactants include, but are not limited to, poloxamer 188, poloxamer 407, poloxamer 124, poloxamer 181, poloxamer 182, poloxamer 237, poloxamer 331, poloxamer 338, and polysorbate 20. In some embodiments, the formulation comprises a pharmaceutically acceptable tonicity modifier. In some embodiments, the pharmaceutically acceptable tonicity modifier is selected from glycerol, propylene glycol, and mannitol.

In some embodiments, the formulation is subjected to heat treatment at a predetermined pH. In some embodiments, the heat treatment improves the physical stability of the formulation. In some embodiments, the formulation is subjected to heat treatment at about 50° C. In some embodiments, the formulation is subjected to heat treatment at about 60° C. In some embodiments, the formulation is subjected to heat treatment at about 70° C. In some embodiments, the formulation is subjected to heat treatment at about 80° C. In some embodiments, the formulation is subjected to heat treatment at about pH 6. In some embodiments, the formulation is subjected to heat treatment at about pH 7. In some embodiments, the formulation is subjected to heat treatment at about pH 8. In some embodiments, the formulation is subjected to heat treatment at about pH 9. In some embodiments, the formulation is subjected to heat treatment at about pH 10. In some embodiments, the formulation is subjected to heat treatment for about 1 minute to about 10 minutes. In some embodiments, the formulation is subjected to heat treatment for about 10 minutes to about 20 minutes. In some embodiments, the formulation is subjected to heat treatment for about 20 minutes to about 60 minutes. In some embodiments, the formulation is subjected to heat treatment for about 60 minutes to about 120 minutes. In some embodiments, the formulation is subjected to heat treatment for about 120 minutes to about 240 minutes. In some embodiments, the conditions for heat treatment is about 3 minutes to about 20 minutes at about pH 9-10.5 and at a temperature between about 70° C. and about 85° C. In some embodiments, the conditions for heat treatment is heating at a temperature between about 50° C. and about 80° C. and at about pH 8.0-10.5 for a period between about 3 minutes and about 180 minutes. In some embodiments, the conditions for heat treatment is heating at a temperature between about 50° C. and about 80° C. and at about pH 8.0-10.0 for a period between about 3 minutes and about 180 minutes. In some embodiments, the conditions for heat treatment is heating at a temperature between about 50° C. and about 80° C. and at about pH 8.0-10.0 for a period between about 3 minutes and about 120 minutes. In some embodiments, the conditions for heat treatment is heating at a temperature between about 60° C. and about 80° C. for a period between about 5 minutes and about 15 minutes. In some embodiments, the conditions for heat treatment is heating at a temperature between about 60° C. and about 80° C. for a period between about 1 minute and about 15 minutes. In some embodiments, the conditions for heat treatment is heating at a temperature between about 60° C. and about 80° C. for a period between about 3 minutes and about 30 minutes. In some embodiments, the conditions for heat treatment is heating at a temperature between about 60° C. and about 80° C. for a period between about 5 minutes and about 30 minutes. In some embodiments, the conditions for heat treatment is heating at a temperature between about 50° C. and about 80° C. and at about pH 8.0-10.0 for a period between about 3 minutes and about 120 minutes. In some embodiments, the conditions for heat treatment is heating at a temperature between about 50° C. and about 80° C. and at about pH 8.0-10.0 for a period between about 3 minutes and about 180 minutes.

In some embodiments, the formulation suitable for use with the devices and methods described herein optionally includes a topical anesthetic agent. Thus, in some embodiments, the formulation includes an additional agent, for example, an anesthetic agent in an amount effective to mitigate pain experienced on delivery of the drug. Examples of anesthetic agents include, but are not limited to, ambucaine, amolanone, amylocaine, benoxinate, benzocaine, betoxycaine, biphenamine, bupivacaine, butacaine, butamben, butanilicaine, butethamine, butoxycaine, carticaine, chloroprocaine, cocaethylene, cocaine, cyclomethycaine, dibucaine, dimethisoquin, dimethocaine, diperodon, dicyclomine, ecgonidine, ecgonine, ethyl chloride, etidocaine, beta-eucaine, euprocin, fenalcomine, formocaine, hexylcaine, hydroxytetracaine, isobutyl p-aminobenzoate, leucinocaine mesylate, levoxadrol, lidocaine, mepivacaine, meprylcaine, metabutoxycaine, methyl chloride, myrtecaine, naepaine, octocaine, orthocaine, oxethazaine, parethoxycaine, phenacaine, phenol, piperocaine, piridocaine, polidocanol, pramoxine, prilocaine, procaine, propanocaine, proparacaine, propipocaine propoxycaine, pseudococaine, pyrrocaine, ropivacaine, salicyl alcohol, tetracaine, tolycaine, trimecaine, and zolamine; and pharmaceutically acceptable salts thereof.

Formulations Containing Insulin

In some embodiments, the pharmaceutical preparation or formulation that can be used in the described methods and device contains insulin. As used herein, the term "insulin" includes animal-derived insulin (such as a bovine, pig, or bovine-pig insulin, for example, as obtained from a bovine or pig pancreas), native human insulin, and recombinant human insulin. The formulation can be a liquid, semi-solid, or solid. In some embodiments, the formulation contains the insulin and a physiologically acceptable carrier.

In some embodiments, the insulin preparation is provided at a concentration of about 40 units/mL to about 500 units/mL (U-40 to U-500). In some embodiments, the insulin is provided at a concentration of about 100 units/mL (U-100). In other embodiments, the insulin is provided at a concentration of about 300 units/mL (U-300). In yet other embodiments, the insulin is provided at a concentration of about 500 units/mL (U-500). In yet another embodiment, there is provided an insulin preparation containing about 40 units/mL (U-40).

In some embodiments, the insulin preparation is an excipient-free insulin.

In other embodiments, the insulin preparation contains one or more excipients. In some embodiments, the insulin preparation is an aqueous formulation comprising the insulin, an aqueous medium, and one or more excipients. In some embodiments, the aqueous medium is water, such as water for injection (WFI), a buffer or a pH-adjusted water. In some embodiments, the buffer is a phosphate buffer. In some embodiments, the water (e.g., the WFI) or the final formulation pH is adjusted to a neutral pH, for example, a pH of about 6.5 to about 8, about pH 6.8 to about 7.8, about pH 7 to about pH 7.8, about pH 7, or more particularly, about pH 7.3 or about 7.4. A mineral acid or base can be used to adjust the pH. In some embodiments, the mineral acid or base is selected from hydrochloric acid (e.g., about 1N to about 2N) and sodium hydroxide (e.g., about 1N to about 2N).

In some embodiments, the one or more excipients is a preservative. In some embodiments, the preservative is a phenolic excipient, such as phenol, m-cresol or a combination thereof.

In some embodiments, the one or more excipients is a salt or buffering agent. In some embodiments, the salt or buffering agent is tromethamine (tris(hydroxymethyl)aminomethane), sodium chloride, or a combination thereof. In some embodiments, the salt is zinc chloride.

In some embodiments, the one or more excipients is a surfactant. In some embodiments, the surfactant is a non-ionic surfactant. In some embodiments, the non-ionic surfactant is a polysorbate, such as polysorbate 20, 40, 60 or 80. In some embodiments, the surfactant is a poloxamer, such as 101, 105, 108, 122, 123, 124, 181, 182, 183, 184, 185, 188, 212, 215, 217, 231, 234, 235, 237, 238, 282, 284, 288, 331, 333, 334, 335, 338, 401, 402, 403, and/or 407.

In some embodiments, the one or more excipients is at least one stabilizing agent. In some embodiments, the stabilizing agent is a tonicity stabilizer. In some embodiments, the stabilizing agent inhibits insulin aggregation. In some embodiments, an excipient provides one or more functions in the formulation, for example, to provide both sterility and stabilization from aggregation. In some embodiments, the stabilizing agent is albumin, serum (e.g., a patient's serum), or blood (e.g., a patient's blood). In some embodiments, the one or more stabilizing agents is glycerol (glycerin), a phenolic excipient, and/or a source of zinc ions, such as zinc chloride and/or zinc oxide.

In some embodiments, the formulation is a zinc-free or low zinc formulation, for example, as described in U.S. Pat. No. 7,205,276B2, the entire content of which is hereby incorporated by reference in its entirety.

In some embodiments, the at least one stabilizing agent is a phenolic excipient. In some embodiments, the phenolic excipient is incorporated into the formulation in order to stabilize the insulin molecule, for example, in a hexameric form to avoid aggregation, and/or to maintain sterility of the solution. In some embodiments, the phenolic excipient is phenol, meta-cresol, or a combination thereof. In some embodiments, the phenolic excipient is present at a concentration of about 25-35 millimolar, or more particularly, about 29-32 millimolar, or about 2.5 to 3.5 mg/mL, or more particularly, about 2.7 to 3.2 mg/mL. (See Toxicology Reports, V2:194-202 (2015)).

In some embodiments, the formulation does not contain a phenolic excipient.

In some embodiments, the insulin formulation is an aqueous solution comprising the insulin, an aqueous medium, glycerol, and one or more agents selected from a phenolic excipient a source of zinc ions, and/or a surfactant.

In some embodiments, the formulation is an aqueous solution comprising an insulin, an aqueous medium, glycerol, a phenolic excipient and a source of zinc ions. In some embodiments, the phenolic excipient is phenol or m-cresol. In a further embodiment, the phenolic excipient is m-cresol. In some embodiments, the source of zinc ions is zinc chloride. In some embodiments the aqueous medium is water for injection (WFI). In other embodiments, the aqueous medium is a buffer or pH-adjusted water. In some embodiments, the formulation pH is adjusted to a neutral pH 7, or more particularly, to 7.4. In some embodiments, the formulation is an aqueous solution containing insulin, glycerol, metacresol, zinc chloride and water for injection, which may be pH adjusted. In some particular embodiments, the formulation is an aqueous solution containing insulin (e.g., 100 units/mL), glycerol (16 mg/mL), metacresol (3 mg/mL), zinc chloride (approximately 7 mcg/mL) and water for injection, and the pH is adjusted to 7.4 (for example, using hydrochloric acid 2N or sodium hydroxide 2N). In a more particular embodiment, the insulin is recombinant human insulin. In an even more particular embodiment, the formulation is Novolin® R or a generic equivalent thereof, which may be commercially or otherwise available, for example, for IV or subcutaneous delivery.

In some embodiments, the formulation is an aqueous solution containing an insulin (e.g., insulin glulisine), an aqueous medium, a phenolic excipient, a surfactant, and one or more salts and/or buffering agents. In some embodiments, the phenolic excipient is phenol or m-cresol. In a further embodiment, the phenolic excipient is m-cresol. In some embodiments, the surfactant is polysorbate 20 or polysorbate 80. In some embodiments, the surfactant is polysorbate 20. In some embodiments the aqueous medium is water for injection (WFI). In other embodiments, the aqueous medium is a buffer or pH-adjusted water. In some embodiments, the formulation pH is adjusted to a neutral pH 7, or more particularly, to 7.3. In some embodiments, the aqueous medium further comprises sodium chloride and/or trimethylamine. In some particular embodiments, the formulation is an aqueous solution containing insulin glulisine, metacresol, tromethamine, sodium chloride, polysorbate 20, and water for injection, which may be pH adjusted. In some particular embodiments, the formulation is an aqueous solution containing insulin glulisine (e.g., 100 units/mL), metacresol (3.15 mg/mL), tromethamine (6 mg/mL), 5 mg sodium chloride (5 mg/mL), polysorbate 20 (0.01 mg/mL), and water for injection, wherein the pH is adjusted by addition of aqueous solutions of hydrochloric acid and/or sodium hydroxide. In an even more particular embodiment, the formulation is APIDRA or a generic equivalent thereof, which may be commercially or otherwise available, for example, for IV or subcutaneous delivery.

In some embodiments, the formulation is an aqueous solution containing insulin, an aqueous medium, glycerol, a phenolic excipient, a surfactant, a source of zinc ions, and one or more salts and/or buffering agents. In some embodiments, the surfactant is a polysorbate or a poloxamer. In a further embodiment, the surfactant is poloxamer 171. In some embodiments, the phenolic excipient is phenol or m-cresol. In a further embodiment, the phenolic excipient is phenol. In some embodiments, the source of zinc ions is zinc chloride. In some embodiments, the salt or buffering agent is trometamol or a combination thereof. In some embodiments, the aqueous medium is pH-adjusted water for injections. In some embodiments, the formulation is an aqueous solution containing insulin (e.g., 100 units/mL), phenol, zinc chloride, trometamol, poloxamer 171, glycerol, hydrochloric acid (for pH adjustment), and water for injections. In a more particular embodiment, the formulation is Insuman Infusat or a generic equivalent thereof, which may be commercially or otherwise available, for example, for IV or subcutaneous delivery.

In some embodiments, the formulation is an aqueous solution containing an insulin (e.g., insulin lispro), an aqueous medium, glycerin, a phenolic excipient, a source of zinc ions, and one or more salts and/or buffering agents. In some embodiments, the phenolic excipient is phenol or m-cresol. In a further embodiment, the phenolic excipient is m-cresol, which may contain trace amounts of phenol. In some embodiments, the source of zinc ions is zinc oxide. In some embodiments, the salt or buffering agent is a phosphate buffer, such has dibasic sodium phosphate. In some embodiments, the aqueous medium is an aqueous buffer containing the dibasic sodium phosphate and water for injections. In some embodiments, the formulation is an aqueous solution containing insulin or insulin lispro (e.g., 100 units/mL), glycerin, m-cresol (which may contain trace phenol), zinc oxide, sodium phosphate dibasic and WFI, which may be pH adjusted, for example, to a pH of between about pH 7.0 and 7.8. In a more particular embodiment, the formulation contains insulin lispro (100 units/mL), glycerin (16 mg/mL), dibasic sodium phosphate (1.88 mg/mL), 3.15 mg metacresol (3.15 mg/mL), zinc oxide content adjusted to provide 0.0197 mg/mL zinc ion, trace amounts of phenol, and Water for Injection, such that the final formulation solution has a pH of 7.0 to 7.8, which can be achieved by addition of aqueous solutions of hydrochloric acid 10% and/or sodium hydroxide 10%. In an even more particular embodiment, the formulation is HUMALOG or a generic equivalent thereof, which may be commercially or otherwise available, for example, for IV or subcutaneous delivery.

In some embodiments, the formulation is an aqueous solution containing an insulin, an aqueous medium, glycerol, a phenolic excipient, a source of zinc ions, and one or more salts and/or buffering agents. In some embodiments, the phenolic excipient is phenol, m-cresol, or a combination thereof. In a further embodiment, the phenolic excipient is phenol and m-cresol. In some embodiments, the source of zinc ions is zinc chloride. In some embodiments, the salt and/or buffering agent is sodium chloride and a phosphate buffer, such has disodium phosphate dihydrate. In some embodiments, the aqueous medium is an aqueous buffer containing the sodium chloride, the disodium phosphate dihydrate and water for injections. In some embodiments, the formulation is an aqueous solution containing insulin (e.g., 100 units/mL), glycerol, phenol, m-cresol, zinc chloride, sodium chloride, disodium phosphate dihydrate, water for injections, and hydrochloric acid and/or sodium hydroxide (for pH adjustment). In a more particular embodiment, the formulation is NovoRapid or a generic equivalent thereof, which may be commercially or otherwise available, for example, for IV or subcutaneous delivery.

In some embodiments, the formulation is an aqueous solution containing an insulin, an aqueous medium, glycerin, a phenolic excipient, and a source of zinc ions. In some embodiments, the phenolic excipient is phenol or m-cresol. In a further embodiment, the phenolic excipient is m-cresol. In some embodiments, the source of zinc ions is zinc oxide. In some embodiments, the aqueous medium is pH-adjusted water for injections. In some embodiments, the formulation is an aqueous solution containing insulin (e.g., 500 units/mL), glycerin, m-cresol, zinc oxide, water for injections, and hydrochloric acid and/or sodium hydroxide (for pH adjustment). In a more particular embodiment, the formulation is an aqueous solution containing insulin (500 units/mL), glycerin (16 mg/mL), m-cresol (2.5 mg/mL), zinc oxide (to supplement endogenous zinc to obtain a total zinc content of 0.017 mg/100 units), water for injections, and hydrochloric acid and/or sodium hydroxide (for pH adjustment). In an even more particular embodiment, the formulation is HUMULIN R U-500 or a generic equivalent thereof, which may be commercially or otherwise available, for example, for IV or subcutaneous delivery.

In some embodiments, the insulin is a commercially available insulin or generic formulation thereof (see Donner T. Insulin—Pharmacology, Therapeutic Regimens And Principles Of Intensive Insulin Therapy. [Updated 2015 Oct. 12]. In: De Groot L J, Chrousos G, Dungan K, et al., editors. Endotext [Internet]. South Dartmouth (MA): MDText.com, Inc.; 2000. Available from: https://www.ncbi.nlm.nih.gov/books/NBK278938/), the entire content of which is hereby incorporated by reference in its entirety). Examples of commercially available insulins include, but are not limited to, rapid-acting insulins such as insulin lispro (Humalog®, Lilly), insulin aspart (NovoLog®, Novo Nordisk), insulin glulisine (Apidra®, Sanofi-Aventis), and technosphere insulin (Afrezza®); short-acting insulins such as regular human insulin (Humulin® R, Lilly; Novolin® R, Novo Nordisk); intermediate-acting insulins such as NPH (isophane) human insulin (Humulin® N, Lilly; Novolin® N, Novo Nordisk); long-acting insulins such as insulin detemir (Levemir®, Novo Nordisk) and insulin glargine (Lantus®, Sanofi-Aventis); and insulin mixtures, for example, NPH/regular mixtures, such as 70% NPH/30% regular (Humulin® 70/30, Lilly; Novolin® 70/30, Novo Nordisk), protamine/lispro mixtures, such as 50% protamine/50% lispro (Humalog® Mix 50/50, Lilly) and 75% protamine/25%; ispro (Humalog® Mix 75/25, Lilly), and protamine/aspart mixtures, such as 70% protamine/30% aspart (Novolog® Mix 70/30, Novo Norkisk); and generic versions thereof. Commercially available insulin preparations, and generics thereof, are available in vials, cartridges, disposable pens, and/or inhalers.

Some insulin preparations disclosed herein, which may be commercially or otherwise available in pre-loaded vials, cartridges, syringes, inhalers or pens, may alternatively be incorporated or loaded into a device as disclosed herein, for release and topical delivery of the insulin formulation to the gastrointestinal tract of a subject.

In some embodiments, an insulin preparation as described herein can be further diluted prior to administration, for example, with 0.9% sodium chloride, 5% dextrose, or 10% dextrose with 40 mmol/L potassium chloride.

Dosages

In some embodiments of the devices and methods described herein, the amount of the therapeutic that is administered is about 0.01 mg to about 500 mg. In some embodiments, the therapeutic is a therapeutic agent as disclosed herein. In some embodiments of any of the methods described herein, the therapeutic is an antibody or an antigen-binding antibody fragment. In some embodiments of any of the methods described herein, the antibody is a humanized antibody.

In some embodiments, a formulation can include a dose of about 0.01-1.0 mg, about 0.1-1.0 mg, about 0.5-5.0 mg, about 1.0-5 mg, about 2.0-10 mg, about 5.0-20 mg, about 5.0-30 mg, about 30-90 mg, about 70-90 mg, about 30-110 mg, about 70-110 mg, about 150-450 mg, or about 300-1200 mg of a therapeutic agent. In some embodiments, the therapeutic agent is an antibody, an antigen-binding portion or a biosimilar thereof, or other therapeutic protein. In some embodiments, an effective dose of the therapeutic agent in a formulation is about 30 mg, about 40 mg, about 50 mg, about 60 mg, about 70 mg, about 80 mg, about 90 mg, about 100 mg, about 125 mg, about 150 mg, about 160 mg, about 175 mg, about 200 mg, about 300 mg, about 400 mg, about 450 mg, about 500 mg, about 600 mg, about 750 mg, about 1000 mg, or about 1200 mg. In some embodiments, the dose is an induction dose. In other embodiments, the dose is a maintenance dose.

In some embodiments, the subject is administered the dose of the therapeutic once a day. In some embodiments, the subject is administered the dose of the therapeutic once every two days. In some embodiments, the subject is administered the dose of the therapeutic once every three days. In some embodiments, the subject is administered the dose of the therapeutic once every four days. In some embodiments, the subject is administered the dose of the therapeutic once every five days. In some embodiments, the subject is administered the dose of the therapeutic once every six days. In some embodiments, the subject is administered the dose of the therapeutic once every seven days. In some embodiments, the subject is administered the dose of the therapeutic once every eight days. In some embodiments, the subject is administered the dose of the therapeutic once every nine days. In some embodiments, the subject is administered the dose of the therapeutic once every ten days. In some embodiments, the subject is administered the dose of the therapeutic once every two weeks. In some embodiments, the subject is administered the dose of the therapeutic once every three weeks. In some embodiments, the subject is administered the dose of the therapeutic once every month.

In some embodiments, the amount of therapeutic agent absorbed by the body, as measured in blood or plasma over time and expressed as AUC (µg·day/mL), when delivered using any of the devices or methods described herein, is between about 10% and about 95% of the amount when the therapeutic agent is administered subcutaneously or intramuscularly (IM), such as about 10% to about 90%, about 10% to about 80%, about 10% to about 70%, about 10% to about 60%, about 10% to about 50%, about 10% to about 40%, about 10% to about 30%, about 10% to about 20%, about 20% to about 95%, about 20% to about 90%, about 20% to about 80%, about 20% to about 70%, about 20% to about 60%, about 20% to about 50%, about 20% to about 40%, about 20% to about 30%, about 30% to about 95%, about 30% to about 90%, about 30% to about 80%, about 30% to about 70%, about 30% to about 60%, about 30% to about 50%, about 30% to about 40%, about 40% to about 95%, about 40% to about 90%, about 40% to about 80%, about 40% to about 70%, about 40% to about 60%, about 40% to about 50%, about 50% to about 95%, about 50% to about 90%, about 50% to about 80%, about 50% to about 70%, about 50% to about 60%, about 60% to about 95%, about 60% to about 90%, about 60% to about 80%, about 60% to about 70%, about 70% to about 95%, about 70% to about 90%, about 70% to about 80%, about 80% to about 95%, about 80% to about 90%, about 90% to about 95%, or about 10%, about 15%, about 20%, about 25%, about 30%, about 35%, about 40%, about 45%, about 50%, about 55%, about 60%, about 65%, about 70%, about 75%, about 80%, about 85%, about 90%, or about 95% of the amount when the therapeutic agent is administered subcutaneously or intramuscularly (IM).

In some embodiments, the amount of therapeutic agent absorbed by the body, as measured in blood or plasma over time and expressed as AUC (µg·day/mL), when delivered using any of the devices or methods described herein, is between about 10% and about 95% of the amount when the therapeutic agent is administered intravenously, such as about 10% to about 90%, about 10% to about 80%, about 10% to about 70%, about 10% to about 60%, about 10% to about 50%, about 10% to about 40%, about 10% to about 30%, about 10% to about 20%, about 20% to about 95%, about 20% to about 90%, about 20% to about 80%, about 20% to about 70%, about 20% to about 60%, about 20% to about 50%, about 20% to about 40%, about 20% to about 30%, about 30% to about 95%, about 30% to about 90%, about 30% to about 80%, about 30% to about 70%, about 30% to about 60%, about 30% to about 50%, about 30% to about 40%, about 40% to about 95%, about 40% to about 90%, about 40% to about 80%, about 40% to about 70%, about 40% to about 60%, about 40% to about 50%, about 50% to about 95%, about 50% to about 90%, about 50% to about 80%, about 50% to about 70%, about 50% to about 60%, about 60% to about 95%, about 60% to about 90%, about 60% to about 80%, about 60% to about 70%, about 70% to about 95%, about 70% to about 90%, about 70% to about 80%, about 80% to about 95%, about 80% to about 90%, about 90% to about 95%, or about 10%, about 15%, about 20%, about 25%, about 30%, about 35%, about 40%, about 45%, about 50%, about 55%, about 60%, about 65%, about 70%, about 75%, about 80%, about 85%, about 90%, or about 95% of the amount when the therapeutic agent is administered intravenously.

Bioavailability (AUC) and other measures can be used to assess the pharmacokinetic (PK) characteristics of administration of therapeutics administered according to the devices and methods of the disclosure and compare with other routes of administration. Example PK parameters include plasma half-life ($t_{1/2}$ (min)), maximum plasma concentration ($C_{max}$ (pg/mL)), time to maximum plasma concentration ($T_{max}$ (min)), and clearance rate (CL). For individual drugs, pharmacodynamic (PD) characteristics can be measured and compared with other routes of administration. PD characteristics can be specific to the drug being administered. For example, where insulin is the drug being administered, PD characteristics can include dextrose infusion rate (mg/kg/min) and total amount of glucose (mg/kg) infused (from 20% dextrose infusion) required to maintain the target blood glucose concentration, as well as plasma glucose levels at select time points. Tables 12-14 show the number of capsules needed for a given relative bioavailability % for several exemplary drugs. The asterisk (*) indicates that dosing frequency can be increased to reduce number of capsules per dose, particularly for Humira and Interferon alpha-2b.

TABLE 12

Relative bioavailability for 0.5 mL ingestible device capsules of various drugs

| Drug | Potential Dose | Dosing Frequency (IFU) | Selected Dose | Commercially Available Drug Concentration | \multicolumn{9}{c}{Number of Capsules Needed (for a given Relative Bioavailability %)} | Dosing Freq.* |
|---|---|---|---|---|---|---|---|---|---|---|---|---|---|---|
| | | | | | 100% | 90% | 80% | 70% | 60% | 50% | 40% | 30% | 20% | |
| Humira (adalimumab) | 40, 80, 160 mg | q 2wk | 80 mg | 0.4 mL ~40 mg | 1.6 | 1.8 | 2.0 | 2.3 | 2.7 | 3.2 | 4.0 | 5.3 | 8.0 | q 2wk |
| Victoza (liraglutide) | 1.2 mg | qd | 1.2 mg | 1 mL ~6 mg | 0.4 | 0.4 | 0.5 | 0.6 | 0.7 | 0.8 | 1.0 | 1.3 | 2.0 | qd |
| Trulicity (dulaglutide) | 0.75 mg | q wk | 0.75 mg | 1.5 mg ~0.5 mL | 0.5 | 0.6 | 0.6 | 0.7 | 0.8 | 1.0 | 1.3 | 1.7 | 2.5 | q wk |
| Avonex (interferon beta-1a) | 30 μg | q wk | 30 μg | 0.5 mL ~30 μg | 1.0 | 1.1 | 1.3 | 1.4 | 1.7 | 2.0 | 2.5 | 3.3 | 5.0 | q wk |
| Interferon alfa-2b | 3-30 million IU | 3 times a week | 15 million IU | 1 mL ~50 million IU | 0.6 | 0.7 | 0.8 | 0.9 | 1.0 | 1.2 | 1.5 | 2.0 | 3.0 | 3 times a week |
| Natpara (parathyroid hormone; PTH) | 50-100 μg | qd | 75 μg | 1 mL ~1 mg | 0.2 | 0.2 | 0.2 | 0.2 | 0.3 | 0.3 | 0.4 | 0.5 | 0.8 | qd |

TABLE 13

Relative bioavailability for 0.4 mL ingestible device capsules of various drugs

| Drug | Potential Dose | Dosing Frequency (IFU) | Selected Dose | Commercially Available Drug Concentration | \multicolumn{9}{c}{Number of Capsules Needed (for a given Relative Bioavailability %)} | Dosing Freq.* |
|---|---|---|---|---|---|---|---|---|---|---|---|---|---|---|
| | | | | | 100% | 90% | 80% | 70% | 60% | 50% | 40% | 30% | 20% | |
| Humira (adalimumab) | 40, 80, 160 mg | q 2wk | 80 mg | 0.4 mL ~40 mg | 2.0 | 2.2 | 2.5 | 2.9 | 3.3 | 4.0 | 5.0 | 6.7 | 10.0 | q 2wk |
| Victoza (liraglutide) | 1.2 mg | qd | 1.2 mg | 1 mL ~6 mg | 0.5 | 0.6 | 0.6 | 0.7 | 0.8 | 1.0 | 1.3 | 1.7 | 2.5 | qd |
| Trulicity (dulaglutide) | 0.75 mg | q wk | 0.75 mg | 1.5 mg ~0.5 mL | 0.6 | 0.7 | 0.8 | 0.9 | 1.0 | 1.3 | 1.6 | 2.1 | 3.1 | q wk |
| Avonex (interferon beta-1a) | 30 μg | q wk | 30 μg | 0.5 mL ~30 μg | 1.3 | 1.4 | 1.6 | 1.8 | 2.1 | 2.5 | 3.1 | 4.2 | 6.3 | q wk |
| Interferon alfa-2b | 3-30 million IU | 3 times a week | 15 million IU | 1 mL ~50 million IU | 0.8 | 0.8 | 0.9 | 1.1 | 1.3 | 1.5 | 1.9 | 2.5 | 3.8 | 3 times a week |
| Natpara (parathyroid hormone; PTH) | 50-100 μg | qd | 75 μg | 1 mL ~1 mg | 0.2 | 0.2 | 0.2 | 0.3 | 0.3 | 0.4 | 0.5 | 0.6 | 0.9 | qd |

TABLE 14

Relative bioavailability for 0.3 mL ingestible device capsules of various drugs

| Drug | Potential Dose | Dosing Frequency (IFU) | Selected Dose | Commercially Available Drug Concentration | \multicolumn{9}{c}{Number of Capsules Needed (for a given Relative Bioavailability %)} | Dosing Freq.* |
|---|---|---|---|---|---|---|---|---|---|---|---|---|---|---|
| | | | | | 100% | 90% | 80% | 70% | 60% | 50% | 40% | 30% | 20% | |
| Humira (adalimumab) | 40, 80, 160 mg | q 2wk | 80 mg | 0.4 mL ~40 mg | 2.7 | 3.0 | 3.3 | 3.8 | 4.4 | 5.3 | 6.7 | 8.9 | 13.3 | q 2wk |
| Victoza (liraglutide) | 1.2 mg | qd | 1.2 mg | 1 mL ~6 mg | 0.7 | 0.7 | 0.8 | 1.0 | 1.1 | 1.3 | 1.7 | 2.2 | 3.3 | qd |
| Trulicity (dulaglutide) | 0.75 mg | q wk | 0.75 mg | 1.5 mg ~0.5 mL | 0.8 | 0.9 | 1.0 | 1.2 | 1.4 | 1.7 | 2.1 | 2.8 | 4.2 | q wk |

TABLE 14-continued

Relative bioavailability for 0.3 mL ingestible device capsules of various drugs

| Drug | Potential Dose | Dosing Frequency (IFU) | Selected Dose | Commercially Available Drug Concentration | \multicolumn{9}{c}{Number of Capsules Needed (for a given Relative Bioavailability %)} | Dosing Freq.* |
|---|---|---|---|---|---|---|---|---|---|---|---|---|---|---|
| | | | | | 100% | 90% | 80% | 70% | 60% | 50% | 40% | 30% | 20% | |
| Avonex (interferon beta-1a) | 30 μg | q wk | 30 μg | 0.5 mL ~30 μg | 1.7 | 1.9 | 2.1 | 2.4 | 2.8 | 3.3 | 4.2 | 5.6 | 8.3 | q wk |
| Interferon alfa-2b | 3-30 million IU | 3 times a week | 15 million IU | 1 mL ~50 million IU | 1.0 | 1.1 | 1.3 | 1.4 | 1.7 | 2.0 | 2.5 | 3.3 | 5.0 | 3 times a week |
| Natpara (parathyroid hormone; PTH) | 50-100 μg | qd | 75 μg | 1 mL ~1 mg | 0.3 | 0.3 | 0.3 | 0.4 | 0.4 | 0.5 | 0.6 | 0.8 | 1.3 | qd |

TABLE 15

Additional drugs for consideration for delivery via ingestible device

| Drug | Potential Dose | Dosing Frequency |
|---|---|---|
| Remicade ® (infliximab) | 400 mg* | q 0, 2, 6, 8 wk |
| Cimzia ® (certolizumab pegol) | 400 mg | q 4 wk |
| Enbrel ® (etanercept) | 50 mg | q 2 wk |
| Lantus ® (insulin) | sq | qd |
| NovoLog ® (insulin) | sq | qd |
| Bydureon ® (exenatide) | 2 mg | q wk |
| Tanzeum ® (albiglutide) | 30 mg | q wk |
| Growth hormone-inhibiting hormone (GHIH; somatostatin) | 0.48-2 mg* | qd |
| Sandostatin ® (octreotide) | 100-500 μg | qd; bid; tid |
| Avastin ® (bevacizumab) | 5 mg | q 2 wk; 3 wk |
| Entyvio ® (vedolizumab) | 300 mg | |
| Fragmin ® (dalteparin) | 2500-18000 IU | qd |
| Rocephin ® (ceftriaxone) (or other antimicrobials) | 1 g | qd |
| Genotropin ® (human growth hormone; HGH) | 0.2-2 mg | qd |

Tables 16 and 17 show illustrative dosing regimens for different therapeutics agents delivered with ingestible devices described herein. For the purposes of the tables, the ingestible devices have two different payload sizes: 200 μL in 00-sized device and 400 μL in 000-sized device. The dosing regimens were generated using a model that accounts for different therapeutic agent characteristics (e.g., approved dose, approved dosing frequency, and bioavailability via intravenous (IV), subcutaneous (SC) or intramuscular (IM) administration). The model assumes each drug can be formulated for the device to a maximum concentration of 175 mg/mL. Given the payload size, therapeutic agent characteristics, and a 175 mg/mL drug concentration, bioavailability benchmarks ("Required Bioavailability") for different dosing regimens ("PGN Regimen") are shown in the table. For example, as shown in Table 16 for adalimumab, an approved 40 mg subcutaneous injection provides an effective dose of 25.6 mg given adalimumab's subcutaneous bioavailability of 64%. This dose is approved in the U.S. for subcutaneous administration every two weeks. Administration of adalimumab at a concentration of 175 mg/mL using a 000-sized ingestible device with a payload of 400 μL achieves the same effective dose when administered weekly (qwk) given a bioavailability of 18.3%. Likewise, using a 00-sized ingestible device with a payload of 200 μL achieves the same effective dose when administered daily (qd) given a bioavailability of 5.2%. If, for example, the bioavailability for the ingestible device is fixed at 25% for a therapeutic agent, similar calculations can be used to calculate the required drug concentration to achieve a desired effective dose.

Table 17 provides the same information for a different set of therapeutic agents. For non-approved therapeutic agents, dose information was sourced from publicly available clinical trial information. Also, for dose based on patient weight, the assumed weight is 70 kg.

TABLE 16

| | \multicolumn{5}{c}{Approved Dosing Info} | \multicolumn{2}{c}{000 Capsule Dosing Profile} | \multicolumn{2}{c}{00 Capsule Dosing Profile} | |
|---|---|---|---|---|---|---|---|---|---|---|
| Drug Name | Dose (mg) | Bio Avail | Eff Dose (mg) | Freq | Admin | PGN Regimen | Req. Bioav. | PGN Regimen | Req. Bioav. | Class |
| adalimumab | 40 | 64% | 25.6 | q2wk | SC | qwk | 18.3% | qd | 5.2% | TNF |
| etanercept | 50 | 58% | 29.0 | qwk | SC | qwk | 41.4% | qd | 11.8% | TNF |
| semaglutide | 0.5 | 89% | 0.45 | qwk | SC | qwk | 0.6% | qwk | 1.3% | GLP-1 |
| dulaglutide | 0.75 | 65% | 0.49 | qwk | SC | qwk | 0.7% | qwk | 1.4% | GLP-1 |
| interferon beta-1a | 0.03 | 40% | 0.01 | qwk | IM | qwk | 0.02% | qwk | 0.03% | Interferon beta |
| alirocumab | 75 | 85% | 63.8 | q2wk | SC | qwk | 45.5% | qd | 13.0% | PCSK9 |
| evolocumab | 140 | 82% | 114.8 | q2wk | SC | qwk | 82.0% | qd | 23.4% | PCSK9 |
| emicizumab | 105 | 85% | 89.3 | qwk | SC | qd | 18.2% | qd | 36.4% | ACP |
| ustekinumab | 45 | 78% | 35.1 | q12wk | SC | q8wk | 33.4% | q4wk | 33.4% | IL-12/23 |
| pegfilgrastim | 6 | 70% | 4.2 | x1 | SC | qd | 6.0% | qd | 12.0% | GCSF |
| denosumab | 60 | 61% | 36.6 | qmo | SC | q8wk | 16.1% | q8wk | 32.2% | Osteoclast |

TABLE 16-continued

| | Approved Dosing Info | | | | 000 Capsule Dosing Profile | | 00 Capsule Dosing Profile | | |
|---|---|---|---|---|---|---|---|---|---|
| Drug Name | Dose (mg) | Bio Avail | Eff Dose (mg) | Freq | Admin | PGN Regimen | Req. Bioav. | PGN Regimen | Req. Bioav. | Class |
| golimumab | 50 | 51% | 25.5 | qmo | SC | q4wk | 36.4% | q2wk | 36.4% | TNF |
| certolizumab pegol | 200 | 80% | 160 | q2wk | SC | qd | 16.3% | qd | 32.7% | TNF |
| vedolizumab | 300 | 100% | 300 | q8wk | IV | qwk | 53.6% | qd | 15.3% | Intergrin |
| secukinumab | 150 | 73% | 109.5 | q4wk | SC | qwk | 39.1% | qd | 11.2% | IL-17 |
| abatacept | 125 | 79% | 98.8 | qwk | SC | qd | 20.2% | qd | 40.3% | CD28 inhibitor |
| natalizumab | 300 | 100% | 300 | q4wk | IV | qd | 15.3% | qd | 30.6% | Intergrin |
| tocilizumab | 162 | 80% | 129.6 | qwk | SC | qd | 26.4% | qd | 52.9% | IL-6 |
| teriparatide | 0.02 | 95% | 0.02 | qd | SC | qd | 0.03% | qd | 0.05% | Parathyroid |
| sargramostim | 0.25 | 100% | 0.025 | qd | IV | qd | 0.66% | qd | 1.32% | GM-CSF |

TABLE 17

| Drug | Target-based Actions | Baseline dose Dose (mg) | Bioavail. | Eff. Dose (mg) | Freq. | Admin. | PGN Regimen | Notes |
|---|---|---|---|---|---|---|---|---|
| Hemophilia A + B | | | | | | | | |
| concizumab | Tissue factor pathway inhibitor inhibitor | 17.5 | 93.0% | 16.3 | qd | SC | qd | Feasible; min. bioavailability of 32.6% (0.35 mg/kg) or 23.3% (0.25 mg/kg) required for 000 capsule |
| Growth disorders | | | | | | | | |
| somatropin | Growth hormone ligand; Skeletal muscle MLCK stimulator | 1.0 | 80.5% | 0.8 | qd | SC | qd | Feasible; min. bioavailability of 2.3% required for 00 capsule |
| somapacitan | Growth hormone ligand; Insulin like GF1 ligand modulator | 11.2 | 100.0% | 11.20 | qwk | sc | qwk | Feasible; min. bioavailability of 32% required for 00 capsule |
| Obesity | | | | | | | | |
| AM-833 | Amylin receptor agonist | 2.4 | 100.0% | 2.4 | qwk | sc | qwk | Feasible; min. bioavailability of 6.9% required for 00 capsule |
| NN-9277 | Glucagon receptor agonist; GLP-1 agonist | 6 | 100.0% | 6.0 | qwk | sc | qwk | Feasible; min. bioavailability of 17.1% required for 00 capsule |
| NN-9775 | Peptide YY ligand | 2.4 | 100.0% | 2.4 | x1 | sc | qd | Feasible; min. bioavailability of 6.9% required for 00 capsule |
| Diabetes | | | | | | | | |
| glucagon (SC) | | 2 | 100.0% | 2.0 | qd | sc | qd | Feasible; min. bioavailability of 5.7% required for 00 capsule |

In some embodiments of any of the devices or methods described herein, the effective amount of the therapeutic administered is generally less than an amount that is effective when the therapeutic is administered subcutaneously, intramuscularly, or intravenously. In some embodiments of any of the methods described herein, the methods include administering (i) an amount of the therapeutic that is a maintenance dose. In some embodiments of any of the methods described herein, the methods include administering (i) an amount of the therapeutic that is an induction dose. Some embodiments of any of the methods described herein further include (ii) administering an amount of the therapeutic that is a maintenance dose following the administration of the induction dose. In some embodiments of any of the methods described herein, the induction dose is administered by another delivery means, for example, topically, subcutaneously, intramuscularly, or intravenously. In some embodiments of any of the methods described herein, step (ii) is repeated one or more times. In some embodiments of any of the methods described herein, step (ii) is repeated once a day, once every two days, once every three days, once every four days, once every five days, once a week over a period of about 6-8 weeks.

In some embodiments of any of the methods described herein, the induction dose is equal to the maintenance dose. In some embodiments of any of the methods described herein, the induction dose is greater than the maintenance dose. In some embodiments of any of the methods described herein, the induction dose is 5 times greater than the maintenance dose. In some embodiments of any of the methods described herein, the induction dose is 2 times greater than the maintenance dose.

In some embodiments, the release mechanism is an actuation system. In some embodiments, the release mechanism is an enteric actuation system. In some embodiments, the release mechanism is a mechanical actuation system. In some embodiments, the release mechanism is an electrical actuation system. In some embodiments, the actuation system comprises an enteric actuation system coupled to a mechanical actuation system. In some embodiments, the actuation system comprises a pre-pressurized air reservoir that drives a piston.

In some embodiments, the formulation comprises a therapeutically effective amount of the therapeutic agent as disclosed herein. In some embodiments, the formulation comprises a human equivalent dose (HED) of the therapeutic agent as disclosed herein.

Methods of Treatment

In some embodiments, provided herein is a method of treating a disease as disclosed herein, the method comprising: administering to the subject a pharmaceutical formulation that comprises a therapeutic agent as disclosed herein, wherein the pharmaceutical formulation is released at a location in the gastrointestinal tract of the subject. In some embodiments, the pharmaceutical formulation is released from the device with sufficient power, pressure and/or force for trans-epithelial delivery of the therapeutic agent to the gastrointestinal tract. In some embodiments, the pharmaceutical formulation is released from the device with sufficient power, pressure and/or force for epithelial delivery of the therapeutic agent to the gastrointestinal tract. In some embodiments, the pharmaceutical formulation is released from the device with sufficient power, pressure and/or force for topical delivery of the therapeutic agent to the gastrointestinal tract.

Trans-Epithelial Administration

In some embodiments, the method comprises trans-epithelial administration of a therapeutic agent to the GI tract of the subject. In some embodiments, the method provides systemic uptake of the therapeutic agent of about 10% to about 99%, for example, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, or at least about 90%, relative to intravenous or subcutaneous administration of the same amount of the therapeutic agent. In some embodiments, the same amount of therapeutic agent is an approved or commercially-available dose. In some more particular embodiments, the systemic uptake is at least about 10% relative to intravenous or subcutaneous administration of the same amount of the therapeutic agent. In other embodiments, the systemic uptake is at least about 15% relative to intravenous or subcutaneous administration of the same amount of the therapeutic agent. In yet other embodiments, the systemic uptake is at least about 20% relative to intravenous or subcutaneous administration of the same amount of the therapeutic agent. In yet other embodiments, the systemic uptake is at least about 25% relative to intravenous or subcutaneous administration of the same amount of the therapeutic agent. In yet other embodiments, the systemic uptake is at least about 30% relative to intravenous or subcutaneous administration of the same amount of the therapeutic agent. In yet other embodiments, the systemic uptake is at least about 35% relative to intravenous or subcutaneous administration of the same amount of the therapeutic agent. In yet other embodiments, the systemic uptake is at least about 40%, or even higher, relative to intravenous or subcutaneous administration of the same amount of the therapeutic agent.

In some embodiments, the trans-epithelial administration provides an area under a curve ($AUC_{TE}$) of the therapeutic agent in systemic circulation versus time of about 10% to about 99%, for example, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, or at least about 90% as the AUC obtained when the same amount of the therapeutic agent is delivered intravenously (to the same subject, or to a population of subjects) ($AUC_{IV}$). In some embodiments, the same amount of therapeutic agent is an approved or commercially-available dose. In some more particular embodiments, the area under a curve ($AUC_{TE}$) of the therapeutic agent in systemic circulation versus time is at least about 15% of the AUC obtained when the same amount of the therapeutic agent is delivered intravenously ($AUC_{IV}$). In some other embodiments, the area under a curve ($AUC_{TE}$) of the therapeutic agent in systemic circulation versus time is at least about 20% of the AUC obtained when the same amount of the therapeutic agent is delivered intravenously ($AUC_{IV}$). In some other embodiments, the area under a curve ($AUC_{TE}$) of the therapeutic agent in systemic circulation versus time is at least about 25% of the AUC obtained when the same amount of the therapeutic agent is delivered intravenously ($AUC_{IV}$). In some other embodiments, the area under a curve ($AUC_{TE}$) of the therapeutic agent in systemic circulation versus time is at least about 30% of the AUC obtained when the same amount of the therapeutic agent is delivered intravenously ($AUC_{IV}$). In some other embodiments, the area under a curve ($AUC_{TE}$) of the therapeutic agent in systemic circulation versus time is at least about 35% of the AUC obtained when the same amount of the therapeutic agent is delivered intravenously ($AUC_{IV}$). In some other embodiments, the area under a curve ($AUC_{TE}$) of the therapeutic agent in systemic circulation versus time is at least about 40% of the AUC obtained when the same amount of the therapeutic agent is delivered intravenously ($AUC_{IV}$). In some other embodiments, the area under a curve ($AUC_{TE}$) of the therapeutic agent in systemic circulation versus time is at least about 45% of the AUC obtained when the same amount of the therapeutic agent is administered intravenously ($AUC_{IV}$). In some embodiments, particularly when an AUC is determined from a plurality of subjects, the AUC is a mean AUC obtained from the plurality of subjects. Thus, in some further embodiments, $AUC_{TE}$ or $AUC_{IV}$ may refer to a mean $AUC_{TE}$ or mean $AUC_{IV}$, respectively. In some other embodiments, an individual AUC value obtained for a single subject may be compared to a mean AUC obtained from a plurality of subjects.

In some embodiments, the trans-epithelial administration provides an area under a curve ($AUC_{TE}$) of the therapeutic agent in systemic circulation versus time of about 10% to about 99%, for example, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, or at least about 90% as the AUC obtained when the same amount of the therapeutic agent is delivered subcutaneously (to the same subject, or to a population of subjects) ($AUC_{SC}$). In some embodiments, the same amount of therapeutic agent is an approved or commercially-available dose. In some more particular embodiments, the area under a curve ($AUC_{TE}$) of the therapeutic agent in systemic circulation versus time is at least about 15% of the AUC obtained when the same amount of the therapeutic agent is delivered subcutaneously ($AUC_{SC}$). In some other embodiments, the area under a curve ($AUC_{TE}$) of the therapeutic agent in systemic circulation versus time is at least about 20% of the AUC obtained when the same amount of the therapeutic agent is delivered subcutaneously ($AUC_{SC}$). In some other embodiments, the area under a curve ($AUC_{TE}$) of the therapeutic agent in systemic circulation versus time is at least about 25% of the AUC obtained when the same amount of the therapeutic agent is delivered subcutaneously ($AUC_{SC}$). In some other embodiments, the area under a curve ($AUC_{TE}$) of the therapeutic agent in systemic circulation versus time is at least about 30% of the AUC obtained when the same amount of the therapeutic agent is delivered subcutaneously ($AUC_{SC}$). In some other embodiments, the area under a curve ($AUC_{TE}$) of the therapeutic agent in systemic circulation versus time is at least about 35% of the AUC obtained when the same amount of the therapeutic agent is delivered subcutaneously ($AUC_{SC}$). In some other embodiments, the area under a curve ($AUC_{TE}$) of the therapeutic agent in systemic circulation versus time is at least about 40% of the AUC obtained when the same amount of the therapeutic agent is delivered subcutaneously ($AUC_{SC}$). In some other embodiments, the area under a curve ($AUC_{TE}$) of the therapeutic agent in systemic circulation versus time is at least about 45% of the AUC obtained when the same amount of the therapeutic agent is administered subcutaneously ($AUC_{SC}$). In some embodiments, particularly when an AUC is determined from a plurality of subjects, the AUC is a mean AUC obtained from the plurality of subjects. Thus, in some further embodiments, $AUC_{TE}$ or $AUC_{SC}$ may refer to a mean $AUC_{TE}$ or mean $AUC_{SC}$, respectively. In some other embodiments, an individual AUC value obtained for a single subject may be compared to a mean AUC obtained from a plurality of subjects.

In some embodiments, the trans-epithelial administration provides an area under a curve ($AUC_{TE}$) of the therapeutic agent in systemic circulation versus time that is at least about 100%, at least about 150%, at least about 200%, at least about 250%, at least about 300%, at least about 400%, at least about 500%, at least about 600%, at least about 700%, at least about 800%, at least about 900%, at least about 1000%, at least about 1100%, at least about 1200%, at least about 1300%, at least about 1400%, at least about 1500%, at least about 1600%, at least about 1700%, at least about 1800%, at least about 1900%, at least about 2000%, at least about 2200%, at least about 2300%, at least about 2400%, at least about 2500%, at least about 2600%, at least about 2700%, at least about 2800%, at least about 2900%, at least about 3000%, at least about 3100%, at least about 3200%, at least about 3300%, at least about 3400%, at least about 3500%, at least about 3600%, at least about 3700%, at least about 3800%, at least about 3900%, at least about 4000%, at least about 4100%, at least about 4200%, at least about 4300%, at least about 4400%, at least about 4500%, at least about 4600%, at least about 4700%, at least about 4800%, at least about 4900%, at least about 5000%, at least about 5100%, at least about 5200%, at least about 5300%, at least about 5400%, at least about 5500%, at least about 5600%, at least about 5700%, at least about 5800%, at least about 5900%, at least about 6000%, at least about 6100%, at least about 6200%, at least about 6300%, at least about 6400%, at least about 6500%, at least about 6600%, at least about 6700%, at least about 6800%, at least about 6900%, at least about 7000%, at least about 7100%, at least about 7200%, at least about 7300%, at least about 7400%, at least about 7500%, at least about 7600%, at least about 7700%, at least about 7800%, at least about 7900%, at least about 8000%, at least about 8100%, at least about 8200%, at least about 8300%, at least about 8400%, at least about 8500%, at least about 8600%, at least about 8700%, at least about 8800%, at least about 8900%, at least about 9000%, at least about 9100%, at least about 9200%, at least about 9300%, at least about 9400%, at least about 9500%, at least about 9600%, at least about 9700%, at least about 9800%, at least about 9900%, or at least about 10,000% as that obtained when the same amount of the therapeutic agent is administered orally (to the same subject, or to a population of subjects). In some embodiments, the same amount of therapeutic agent is an approved or commercially-available dose. In some embodiments, the AUC is the mean AUC.

In some embodiments, the trans-epithelial administration provides a maximum plasma concentration (($C_{max})_{TE}$) of the therapeutic agent in systemic circulation versus time of about 10% to about 99%, for example, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, or at least about 90% as the AUC obtained when the same amount of the therapeutic agent is delivered intravenously (to the same subject, or to a population of subjects) (($C_{max})_{IV}$). In some embodiments, the same amount of therapeutic agent is an approved or commercially-available dose. In some more particular embodiments, the maximum plasma concentration (($C_{max})_{TE}$) of the therapeutic agent in systemic circulation versus time is at least about 15% of the AUC obtained when the same amount of the therapeutic agent is delivered intravenously (($C_{max})_{IV}$). In some other embodiments, the maximum plasma concentration (($C_{max})_{TE}$) of the therapeutic agent in systemic circulation versus time is at least about 20% of the AUC obtained when the same amount of the therapeutic agent is delivered intravenously (($C_{max})_{IV}$). In some other embodiments, the maximum plasma concentration (($C_{max})_{TE}$) of the therapeutic agent in systemic circulation versus time is at least about 25% of the AUC obtained when the same amount of the therapeutic agent is delivered intravenously (($C_{max})_{IV}$). In some other embodiments, the maximum plasma concentration (($C_{max})_{TE}$) of the therapeutic agent in systemic circulation versus time is at least about 30% of the AUC obtained when the same amount of the therapeutic agent is delivered intravenously (($C_{max})_{IV}$). In some other embodiments, the maximum plasma concentration (($C_{max})_{TE}$) of the therapeutic agent in systemic circulation versus time is at least about 35% of the AUC obtained when the same amount of the therapeutic agent is delivered intravenously (($C_{max})_{IV}$). In some other embodiments, the maximum plasma concentration (($C_{max})_{TE}$) of the therapeutic agent in systemic circulation versus time is at least about 40% of the AUC obtained when the same amount of the therapeutic agent is delivered intravenously (($C_{max})_{IV}$). In some other embodiments, the maximum plasma concentration (($C_{max})_{TE}$) of the therapeutic agent in systemic circulation versus time is at least about 45% of the AUC obtained when the same amount of the therapeutic agent is delivered intravenously ($(C_{max})_{IV}$). In some embodiments, particularly when the $C_{max}$ is determined from a plurality of subjects, the $C_{max}$ is a mean $C_{max}$ obtained from the plurality of subjects. Thus, in some further embodiments, $(C_{max})_{TE}$ or $(C)_{IV}$ may refer to a mean $(C_{max})_{TE}$ or mean $(C_{max})_{IV}$, respectively. In some other embodiments, an individual $C_{max}$ value obtained for a single subject may be compared to a mean $C_{max}$ obtained from a plurality of subjects.

In some embodiments, the trans-epithelial administration provides a maximum plasma concentration ($(C_{max})_{TE}$) of the therapeutic agent in systemic circulation versus time of about 10% to about 99%, for example, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, or at least about 90% as the AUC obtained when the same amount of the therapeutic agent is delivered subcutaneously (to the same subject, or to a population of subjects) ($(C_{max})_{SC}$). In some embodiments, the same amount of therapeutic agent is an approved or commercially-available dose. In some more particular embodiments, the maximum plasma concentration ($(C_{max})_{TE}$) of the therapeutic agent in systemic circulation versus time is at least about 15% of the AUC obtained when the same amount of the therapeutic agent is delivered subcutaneously ($(C_{max})_{SC}$). In some other embodiments, the maximum plasma concentration ($(C_{max})_{TE}$) of the therapeutic agent in systemic circulation versus time is at least about 20% of the AUC obtained when the same amount of the therapeutic agent is delivered subcutaneously ($(C_{max})_{SC}$). In some other embodiments, the maximum plasma concentration ($(C_{max})_{TE}$) of the therapeutic agent in systemic circulation versus time is at least about 25% of the AUC obtained when the same amount of the therapeutic agent is delivered subcutaneously ($(C_{max})_{SC}$). In some other embodiments, the maximum plasma concentration ($(C_{max})_{TE}$) of the therapeutic agent in systemic circulation versus time is at least about 30% of the AUC obtained when the same amount of the therapeutic agent is delivered subcutaneously ($(C_{max})_{SC}$). In some other embodiments, the maximum plasma concentration ($(C_{max})_{TE}$) of the therapeutic agent in systemic circulation versus time is at least about 35% of the AUC obtained when the same amount of the therapeutic agent is delivered subcutaneously ($(C_{max})_{SC}$). In some other embodiments, the maximum plasma concentration ($(C_{max})_{TE}$) of the therapeutic agent in systemic circulation versus time is at least about 40% of the AUC obtained when the same amount of the therapeutic agent is delivered subcutaneously ($(C_{max})_{SC}$). In some other embodiments, the maximum plasma concentration ($(C_{max})_{TE}$) of the therapeutic agent in systemic circulation versus time is at least about 45% of the AUC obtained when the same amount of the therapeutic agent is delivered subcutaneously ($(C_{max})_{SC}$). In some embodiments, particularly when the $C_{max}$ is determined from a plurality of subjects, the $C_{max}$ is a mean $C_{max}$ obtained from the plurality of subjects. Thus, in some further embodiments, $(C_{max})_{TE}$ or $(C_{max})_{SC}$ may refer to a mean $(C_{max})_{TE}$ or mean $(C_{max})_{SC}$, respectively. In some other embodiments, an individual $C_{max}$ value obtained for a single subject may be compared to a mean $C_{max}$ obtained from a plurality of subjects.

Epithelial Administration

In some embodiments, the method comprises epithelial administration of a therapeutic agent to the GI tract of the subject. In some embodiments, the method provides systemic uptake of the therapeutic agent of about 10% to about 99%, for example, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, or at least about 90%, relative to topical delivery or a non-device oral delivery. In some embodiments, the same amount of therapeutic agent is an approved or commercially-available dose. In some more particular embodiments, the systemic uptake is at least about 10% relative to topical delivery or non-device oral delivery of the same amount of the therapeutic agent. In other embodiments, the systemic uptake is at least about 15% relative to topical delivery or non-device oral delivery of the same amount of the therapeutic agent. In yet other embodiments, the systemic uptake is at least about 20% relative to topical delivery or non-device oral delivery of the same amount of the therapeutic agent. In yet other embodiments, the systemic uptake is at least about 25% relative to topical delivery or non-device oral delivery of the same amount of the therapeutic agent. In yet other embodiments, the systemic uptake is at least about 30% relative to topical delivery or non-device oral delivery of the same amount of the therapeutic agent. In yet other embodiments, the systemic uptake is at least about 35% relative to topical delivery or non-device oral delivery of the same amount of the therapeutic agent. In yet other embodiments, the systemic uptake is at least about 40%, or even higher, relative to topical delivery or non-device oral delivery of the same amount of the therapeutic agent.

In some embodiments, the epithelial administration provides systemic uptake of the therapeutic agent of about 0.5% to about 10% or more, for example, about 0.5%, about 1%, about 2%, about 3%, about 4%, about 5%, about 6%, about 7%, about 8%, about 9%, about 10%, or more, relative to intravenous or subcutaneous administration of the same amount of the therapeutic agent. In some embodiments, the same amount of therapeutic agent is an approved or commercially-available dose. In some more particular embodiments, the systemic uptake is at least about 0.5% relative to intravenous or subcutaneous administration of the same amount of the therapeutic agent. In other embodiments, the systemic uptake is at least about 2% relative to intravenous or subcutaneous administration of the same amount of the therapeutic agent. In yet other embodiments, the systemic uptake is at least about 3% relative to intravenous or subcutaneous administration of the same amount of the therapeutic agent. In yet other embodiments, the systemic uptake is at least about 4% relative to intravenous or subcutaneous administration of the same amount of the therapeutic agent. In yet other embodiments, the systemic uptake is at least about 5% relative to intravenous or subcutaneous administration of the same amount of the therapeutic agent. In yet other embodiments, the systemic uptake is at least about 6% relative to intravenous or subcutaneous administration of the same amount of the therapeutic agent. In yet other embodiments, the systemic uptake is at least about 7% relative to intravenous or subcutaneous administration of the same amount of the therapeutic agent. In yet other embodiments, the systemic uptake is at least about 8% relative to intravenous or subcutaneous administration of the same amount of the therapeutic agent. In yet other embodiments, the systemic uptake is at least about 9% relative to intravenous or subcutaneous administration of the same amount of the therapeutic agent. In yet other embodiments, the systemic uptake is at least about 10%, or even higher, relative to intravenous or subcutaneous administration of the same amount of the therapeutic agent.

In some embodiments, the systemic uptake of the therapeutic agent is greater than the systemic uptake provided by topical administration of the same amount of the therapeutic agent, but less than the systemic uptake provided by trans-epithelial administration of the same amount of the therapeutic agent. In some embodiments, epithelial administration provides systemic uptake of the therapeutic agent of about 10%, about 15%, about 20%, about about 25%, about 30%, about 35%, about 40%, about 45%, about 50%, about 55%, about 60%, about 65%, about 70%, about 75%, about 80%, about 85%, about 90%, about 100%, about 125%, about 150%, about 175%, about 200%, about 225%, about 250%, about 275%, about 300%, about 325%, about 350%, about 375%, about 400%, about 425%, about 450%, about 475%, or about 500% greater than the systemic uptake of the same amount of the therapeutic agent provided by topical administration. In some embodiments, the same amount of therapeutic agent is an approved or commercially-available dose.

In some embodiments, the epithelial administration provides an area under a curve ($AUC_E$) of the therapeutic agent in systemic circulation versus time of about 10% to about 99%, for example, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, or at least about 90% as the AUC obtained when the same amount of the therapeutic agent is delivered intravenously (to the same subject, or to a population of subjects) ($AUC_{IV}$). In some embodiments, the same amount of therapeutic agent is an approved or commercially-available dose. In some more particular embodiments, the area under a curve ($AUC_E$) of the therapeutic agent in systemic circulation versus time is at least about 15% of the AUC obtained when the same amount of the therapeutic agent is delivered intravenously ($AUC_{IV}$). In some other embodiments, the area under a curve ($AUC_E$) of the therapeutic agent in systemic circulation versus time is at least about 20% of the AUC obtained when the same amount of the therapeutic agent is delivered intravenously ($AUC_{IV}$). In some other embodiments, the area under a curve ($AUC_E$) of the therapeutic agent in systemic circulation versus time is at least about 25% of the AUC obtained when the same amount of the therapeutic agent is delivered intravenously ($AUC_{IV}$). In some other embodiments, the area under a curve ($AUC_E$) of the therapeutic agent in systemic circulation versus time is at least about 30% of the AUC obtained when the same amount of the therapeutic agent is delivered intravenously ($AUC_{IV}$). In some other embodiments, the area under a curve (AUCT) of the therapeutic agent in systemic circulation versus time is at least about 35% of the AUC obtained when the same amount of the therapeutic agent is delivered intravenously ($AUC_{IV}$). In some other embodiments, the area under a curve ($AUC_E$) of the therapeutic agent in systemic circulation versus time is at least about 40% of the AUC obtained when the same amount of the therapeutic agent is delivered intravenously ($AUC_{IV}$). In some other embodiments, the area under a curve ($AUC_E$) of the therapeutic agent in systemic circulation versus time is at least about 45% of the AUC obtained when the same amount of the therapeutic agent is administered intravenously ($AUC_{IV}$). In some embodiments, particularly when an AUC is determined from a plurality of subjects, the AUC is a mean AUC obtained from the plurality of subjects. Thus, in some further embodiments, $AUC_E$ or $AUC_{IV}$ may refer to a mean $AUC_E$ or mean $AUC_{IV}$, respectively. In some other embodiments, an individual AUC value obtained for a single subject may be compared to a mean AUC obtained from a plurality of subjects.

In some embodiments, the epithelial administration provides an area under a curve ($AUC_E$) of the therapeutic agent in systemic circulation versus time of about 10% to about 99%, for example, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, or at least about 90% as the AUC obtained when the same amount of the therapeutic agent is delivered subcutaneously (to the same subject, or to a population of subjects) ($AUC_{SC}$). In some embodiments, the same amount of therapeutic agent is an approved or commercially-available dose. In some more particular embodiments, the area under a curve ($AUC_E$) of the therapeutic agent in systemic circulation versus time is at least about 15% of the AUC obtained when the same amount of the therapeutic agent is delivered subcutaneously ($AUC_{SC}$). In some other embodiments, the area under a curve ($AUC_E$) of the therapeutic agent in systemic circulation versus time is at least about 20% of the AUC obtained when the same amount of the therapeutic agent is delivered subcutaneously ($AUC_{SC}$). In some other embodiments, the area under a curve ($AUC_E$) of the therapeutic agent in systemic circulation versus time is at least about 25% of the AUC obtained when the same amount of the therapeutic agent is delivered subcutaneously ($AUC_{SC}$). In some other embodiments, the area under a curve ($AUC_E$) of the therapeutic agent in systemic circulation versus time is at least about 30% of the AUC obtained when the same amount of the therapeutic agent is delivered subcutaneously ($AUC_{SC}$). In some other embodiments, the area under a curve ($AUC_E$) of the therapeutic agent in systemic circulation versus time is at least about 35% of the AUC obtained when the same amount of the therapeutic agent is delivered subcutaneously ($AUC_{SC}$). In some other embodiments, the area under a curve ($AUC_E$) of the therapeutic agent in systemic circulation versus time is at least about 40% of the AUC obtained when the same amount of the therapeutic agent is delivered subcutaneously ($AUC_{SC}$). In some other embodiments, the area under a curve ($AUC_E$) of the therapeutic agent in systemic circulation versus time is at least about 45% of the AUC obtained when the same amount of the therapeutic agent is administered subcutaneously ($AUC_{SC}$). In some embodiments, particularly when an AUC is determined from a plurality of subjects, the AUC is a mean AUC obtained from the plurality of subjects. Thus, in some further embodiments, $AUC_E$ or $AUC_{SC}$ may refer to a mean $AUC_E$ or mean $AUC_{SC}$, respectively. In some other embodiments, an individual AUC value obtained for a single subject may be compared to a mean AUC obtained from a plurality of subjects.

In some embodiments, the epithelial administration provides an area under a curve ($AUC_E$) of the therapeutic agent in systemic circulation versus time that is at least about 100%, at least about 150%, at least about 200%, at least about 250%, at least about 300%, at least about 400%, at least about 500%, at least about 600%, at least about 700%, at least about 800%, at least about 900%, at least about 1000%, at least about 1100%, at least about 1200%, at least about 1300%, at least about 1400%, at least about 1500%, at least about 1600%, at least about 1700%, at least about 1800%, at least about 1900%, at least about 2000%, at least about 2200%, at least about 2300%, at least about 2400%, at least about 2500%, at least about 2600%, at least about 2700%, at least about 2800%, at least about 2900%, at least about 3000%, at least about 3100%, at least about 3200%, at least about 3300%, at least about 3400%, at least about 3500%, at least about 3600%, at least about 3700%, at least about 3800%, at least about 3900%, at least about 4000%, at least about 4100%, at least about 4200%, at least about 4300%, at least about 4400%, at least about 4500%, at least about 4600%, at least about 4700%, at least about 4800%, at least about 4900%, at least about 5000%, at least about 5100%, at least about 5200%, at least about 5300%, at least about 5400%, at least about 5500%, at least about 5600%, at least about 5700%, at least about 5800%, at least about 5900%, at least about 6000%, at least about 6100%, at least about 6200%, at least about 6300%, at least about 6400%, at least about 6500%, at least about 6600%, at least about 6700%, at least about 6800%, at least about 6900%, at least about 7000%, at least about 7100%, at least about 7200%, at least about 7300%, at least about 7400%, at least about 7500%, at least about 7600%, at least about 7700%, at least about 7800%, at least about 7900%, at least about 8000%, at least about 8100%, at least about 8200%, at least about 8300%, at least about 8400%, at least about 8500%, at least about 8600%, at least about 8700%, at least about 8800%, at least about 8900%, at least about 9000%, at least about 9100%, at least about 9200%, at least about 9300%, at least about 9400%, at least about 9500%, at least about 9600%, at least about 9700%, at least about 9800%, at least about 9900%, or at least about 10,000% as that obtained when the same amount of the therapeutic agent is administered orally (to the same subject, or to a population of subjects). In some embodiments, the same amount of therapeutic agent is an approved or commercially-available dose. In some embodiments, the AUC is the mean AUC.

In some embodiments, the epithelial administration provides a maximum plasma concentration $((C_{max})_E)$ of the therapeutic agent in systemic circulation versus time of about 10% to about 99%, for example, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, or at least about 90% as the AUC obtained when the same amount of the therapeutic agent is delivered intravenously (to the same subject, or to a population of subjects) $((C_{max})_{IV})$. In some embodiments, the same amount of therapeutic agent is an approved or commercially-available dose. In some more particular embodiments, the maximum plasma concentration $((C_{max})_E)$ of the therapeutic agent in systemic circulation versus time is at least about 15% of the AUC obtained when the same amount of the therapeutic agent is delivered intravenously $((C_{max})_{IV})$. In some other embodiments, the maximum plasma concentration $((C_{max})_E)$ of the therapeutic agent in systemic circulation versus time is at least about 20% of the AUC obtained when the same amount of the therapeutic agent is delivered intravenously $((C_{max})_{IV})$. In some other embodiments, the maximum plasma concentration $((C_{max})_E)$ of the therapeutic agent in systemic circulation versus time is at least about 25% of the AUC obtained when the same amount of the therapeutic agent is delivered intravenously $((C_{max})_{IV})$. In some other embodiments, the maximum plasma concentration $((C_{max})_E)$ of the therapeutic agent in systemic circulation versus time is at least about 30% of the AUC obtained when the same amount of the therapeutic agent is delivered intravenously $((C_{max})_{IV})$. In some other embodiments, the maximum plasma concentration $((C_{max})_E)$ of the therapeutic agent in systemic circulation versus time is at least about 35% of the AUC obtained when the same amount of the therapeutic agent is delivered intravenously $((C_{max})_{IV})$. In some other embodiments, the maximum plasma concentration $((C_{max})_E)$ of the therapeutic agent in systemic circulation versus time is at least about 40% of the AUC obtained when the same amount of the therapeutic agent is delivered intravenously $((C_{max})_{IV})$. In some other embodiments, the maximum plasma concentration $((C_{max})_E)$ of the therapeutic agent in systemic circulation versus time is at least about 45% of the AUC obtained when the same amount of the therapeutic agent is delivered intravenously $((C_{max})_{IV})$. In some embodiments, particularly when the $C_{max}$ is determined from a plurality of subjects, the $C_{max}$ is a mean $C_{max}$ obtained from the plurality of subjects. Thus, in some further embodiments, $(C_{max})_E$ or $(C)_{IV}$ may refer to a mean $(C_{max})_E$ or mean $(C_{max})_{IV}$, respectively. In some other embodiments, an individual $C_{max}$ value obtained for a single subject may be compared to a mean $C_{max}$ obtained from a plurality of subjects.

In some embodiments, the epithelial administration provides a maximum plasma concentration $((C_{max})_E)$ of the therapeutic agent in systemic circulation versus time of about 10% to about 99%, for example, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, or at least about 90% as the AUC obtained when the same amount of the therapeutic agent is delivered subcutaneously (to the same subject, or to a population of subjects) $((C_{max})_{SC})$. In some embodiments, the same amount of therapeutic agent is an approved or commercially-available dose. In some more particular embodiments, the maximum plasma concentration $((C_{max})_E)$ of the therapeutic agent in systemic circulation versus time is at least about 15% of the AUC obtained when the same amount of the therapeutic agent is delivered subcutaneously $((C_{max})_{SC})$. In some other embodiments, the maximum plasma concentration $((C_{max})_E)$ of the therapeutic agent in systemic circulation versus time is at least about 20% of the AUC obtained when the same amount of the therapeutic agent is delivered subcutaneously $((C_{max})_{SC})$. In some other embodiments, the maximum plasma concentration $((C_{max})_E)$ of the therapeutic agent in systemic circulation versus time is at least about 25% of the AUC obtained when the same amount of the therapeutic agent is delivered subcutaneously $((C_{max})_{SC})$. In some other embodiments, the maximum plasma concentration $((C_{max})_E)$ of the therapeutic agent in systemic circulation versus time is at least about 30% of the AUC obtained when the same amount of the therapeutic agent is delivered subcutaneously $((C_{max})_{SC})$. In some other embodiments, the maximum plasma concentration $((C_{max})_E)$ of the therapeutic agent in systemic circulation versus time is at least about 35% of the AUC obtained when the same amount of the therapeutic agent is delivered subcutaneously $((C_{max})_{SC})$. In some other embodiments, the maximum plasma concentration $((C_{max})_E)$ of the therapeutic agent in systemic circulation versus time is at least about 40% of the AUC obtained when the same amount of the therapeutic agent is delivered subcutaneously $((C_{max})_{SC})$. In some other embodiments, the maximum plasma concentration $((C_{max})_E)$ of the therapeutic agent in systemic circulation versus time is at least about 45% of the AUC obtained when the same amount of the therapeutic agent is delivered subcutaneously (($C_{max}$)$_{SC}$). In some embodiments, particularly when the $C_{max}$ is determined from a plurality of subjects, the $C_{max}$ is a mean $C_{max}$ obtained from the plurality of subjects. Thus, in some further embodiments, ($C_{max}$)$_E$ or ($C_{max}$)$_{SC}$ may refer to a mean ($C_{max}$)$_E$ or mean ($C_{max}$)$_{SC}$, respectively. In some other embodiments, an individual $C_{max}$ value obtained for a single subject may be compared to a mean $C_{max}$ obtained from a plurality of subjects.

Topical Administration

In some embodiments, the method comprises topical administration of a therapeutic agent to the GI tract of the subject. In some embodiments, the method provides systemic uptake of the therapeutic agent of about 0.1% to about 20%, for example, at most about 1%, at most about 3%, at most about 5%, at most about 10%, at most about 15%, or at most about 20%, relative to intravenous or subcutaneous administration of the same amount of the therapeutic agent. In some embodiments, the same amount of therapeutic agent is an approved or commercially-available dose. In some more particular embodiments, the systemic uptake is at most about 1% relative to intravenous or subcutaneous administration of the same amount of the therapeutic agent. In some more particular embodiments, the systemic uptake is at most about 3% relative to intravenous or subcutaneous administration of the same amount of the therapeutic agent. In other embodiments, the systemic uptake is at most about 5% relative to intravenous or subcutaneous administration of the same amount of the therapeutic agent. In yet other embodiments, the systemic uptake is at most about 10% relative to intravenous or subcutaneous administration of the same amount of the therapeutic agent. In yet other embodiments, the systemic uptake is at most about 15% relative to intravenous or subcutaneous administration of the same amount of the therapeutic agent. In yet other embodiments, the systemic uptake is at most about 20% relative to intravenous or subcutaneous administration of the same amount of the therapeutic agent.

In some embodiments, the topical administration provides an area under a curve ($AUC_{TOP}$) of the therapeutic agent in systemic circulation versus time of about 0.1% to about 20%, for example, at most about 1%, at most about 3%, at most about 5%, at most about 10%, at most about 15%, or at most about 20%, as the AUC obtained when the same amount of the therapeutic agent is delivered intravenously (to the same subject, or to a population of subjects) ($AUC_{IV}$). In some embodiments, the same amount of therapeutic agent is an approved or commercially-available dose. In some more particular embodiments, the area under a curve ($AUC_{TOP}$) of the therapeutic agent in systemic circulation versus time is at most about 1% of the AUC obtained when the same amount of the therapeutic agent is delivered intravenously ($AUC_{IV}$). In some other embodiments, the area under a curve ($AUC_{TOP}$) of the therapeutic agent in systemic circulation versus time is at most about 3% of the AUC obtained when the same amount of the therapeutic agent is delivered intravenously ($AUC_{IV}$). In some other embodiments, the area under a curve ($AUC_{TOP}$) of the therapeutic agent in systemic circulation versus time is at most about 5% of the AUC obtained when the same amount of the therapeutic agent is delivered intravenously ($AUC_{IV}$). In some other embodiments, the area under a curve ($AUC_{TOP}$) of the therapeutic agent in systemic circulation versus time is at most about 10% of the AUC obtained when the same amount of the therapeutic agent is delivered intravenously ($AUC_{IV}$). In some other embodiments, the area under a curve ($AUC_{TOP}$) of the therapeutic agent in systemic circulation versus time is at most about 15% of the AUC obtained when the same amount of the therapeutic agent is delivered intravenously ($AUC_{IV}$). In some other embodiments, the area under a curve ($AUC_{TOP}$) of the therapeutic agent in systemic circulation versus time is at most about 20% of the AUC obtained when the same amount of the therapeutic agent is delivered intravenously ($AUC_{IV}$). In some embodiments, particularly when an AUC is determined from a plurality of subjects, the AUC is a mean AUC obtained from the plurality of subjects. Thus, in some further embodiments, $AUC_{TOP}$ or $AUC_{IV}$ may refer to a mean $AUC_{TOP}$ or mean $AUC_{IV}$, respectively. In some other embodiments, an individual AUC value obtained for a single subject may be compared to a mean AUC obtained from a plurality of subjects.

In some embodiments, the topical administration provides an area under a curve ($AUC_{TOP}$) of the therapeutic agent in systemic circulation versus time of about 0.1% to about 20%, for example, at most about 1%, at most about 3%, at most about 5%, at most about 10%, at most about 15%, or at most about 20%, as that obtained when the same amount of the therapeutic agent is delivered subcutaneously (to the same subject, or to a population of subjects) ($AUC_{SC}$). In some embodiments, the same amount of therapeutic agent is an approved or commercially-available dose. In some more particular embodiments, the area under a curve ($AUC_{TOP}$) of the therapeutic agent in systemic circulation versus time is at most about 1% of the AUC obtained when the same amount of the therapeutic agent is delivered subcutaneously ($AUC_{SC}$). In some other embodiments, the area under a curve ($AUC_{TOP}$) of the therapeutic agent in systemic circulation versus time is at most about 3% of the AUC obtained when the same amount of the therapeutic agent is delivered subcutaneously ($AUC_{SC}$). In some other embodiments, the area under a curve ($AUC_{TOP}$) of the therapeutic agent in systemic circulation versus time is at most about 5% of the AUC obtained when the same amount of the therapeutic agent is delivered subcutaneously ($AUC_{SC}$). In some other embodiments, the area under a curve ($AUC_{TOP}$) of the therapeutic agent in systemic circulation versus time is at most about 10% of the AUC obtained when the same amount of the therapeutic agent is delivered subcutaneously ($AUC_{SC}$). In some other embodiments, the area under a curve ($AUC_{TOP}$) of the therapeutic agent in systemic circulation versus time is at most about 15% of the AUC obtained when the same amount of the therapeutic agent is delivered subcutaneously ($AUC_{SC}$). In some other embodiments, the area under a curve ($AUC_{TOP}$) of the therapeutic agent in systemic circulation versus time is at most about 20% of the AUC obtained when the same amount of the therapeutic agent is delivered subcutaneously ($AUC_{SC}$). In some embodiments, particularly when an AUC is determined from a plurality of subjects, the AUC is a mean AUC obtained from the plurality of subjects. Thus, in some further embodiments, $AUC_{TOP}$ or $AUC_{SC}$ may refer to a mean $AUC_{TOP}$ or mean $AUC_{SC}$, respectively. In some other embodiments, an individual AUC value obtained for a single subject may be compared to a mean AUC obtained from a plurality of subjects.

In some embodiments, the topical administration provides a maximum plasma concentration (($C_{max}$)$_{TOP}$) of the therapeutic agent in systemic circulation versus time of about 0.1% to about 20%, for example, at most about 1%, at most about 3%, at most about 5%, at most about 10%, at most about 15%, or at most about 20%, as that obtained when the same amount of the therapeutic agent is delivered intravenously (to the same subject, or to a population of subjects) $((C_{max})_{IV})$ In some embodiments, the same amount of therapeutic agent is an approved or commercially-available dose. In some more particular embodiments, the maximum plasma concentration $((C_{max})_{TOP})$ of the therapeutic agent in systemic circulation versus time is at most about 1% of the AUC obtained when the same amount of the therapeutic agent is delivered intravenously $((C_{max})_{IV})$. In some other embodiments, the maximum plasma concentration $((C_{max})_{TOP})$ of the therapeutic agent in systemic circulation versus time is at most about 3% of the AUC obtained when the same amount of the therapeutic agent is delivered intravenously $((C_{max})_{IV})$ In some other embodiments, the maximum plasma concentration $((C_{max})_{TOP})$ of the therapeutic agent in systemic circulation versus time is at most about 5% of the AUC obtained when the same amount of the therapeutic agent is delivered intravenously $((C_{max})_{IV})$. In some other embodiments, the maximum plasma concentration $((C_{max})_{TOP})$ of the therapeutic agent in systemic circulation versus time is at most about 10% of the AUC obtained when the same amount of the therapeutic agent is delivered intravenously $((C_{max})_{IV})$. In some other embodiments, the maximum plasma concentration $((C_{max})_{TOP})$ of the therapeutic agent in systemic circulation versus time is at most about 15% of the AUC obtained when the same amount of the therapeutic agent is delivered intravenously $((C_{max})_{IV})$. In some other embodiments, the maximum plasma concentration $((C_{max})_{TOP})$ of the therapeutic agent in systemic circulation versus time is at most about 20% of the AUC obtained when the same amount of the therapeutic agent is delivered intravenously $((C_{max})_{IV})$. In some embodiments, particularly when the $C_{max}$ is determined from a plurality of subjects, the $C_{max}$ is a mean $C_{max}$ obtained from the plurality of subjects. Thus, in some further embodiments, $(C_{max})_{TOP}$ or $(C_{max})_{IV}$ may refer to a mean $(C_{max})_{TOP}$ or mean $(C_{max})_{IV}$, respectively. In some other embodiments, an individual $C_{max}$ value obtained for a single subject may be compared to a mean $C_{max}$ obtained from a plurality of subjects.

In some embodiments, the topical administration provides a maximum plasma concentration $((C_{max})_{TOP})$ of the therapeutic agent in systemic circulation versus time of about 0.1% to about 20%, for example, at most about 1%, at most about 3%, at most about 5%, at most about 10%, at most about 15%, or at most about 20%, as that obtained when the same amount of the therapeutic agent is delivered subcutaneously (to the same subject, or to a population of subjects) $((C_{max})_{SC})$. In some embodiments, the same amount of therapeutic agent is an approved or commercially-available dose. In some more particular embodiments, the maximum plasma concentration $((C_{max})_{TOP})$ of the therapeutic agent in systemic circulation versus time is at most about 1% of the AUC obtained when the same amount of the therapeutic agent is delivered subcutaneously $((C_{max})_{SC})$. In some other embodiments, the maximum plasma concentration $((C_{max})_{TOP})$ of the therapeutic agent in systemic circulation versus time is at most about 3% of the AUC obtained when the same amount of the therapeutic agent is delivered subcutaneously $((C_{max})_{SC})$. In some other embodiments, the maximum plasma concentration $((C_{max})_{TOP})$ of the therapeutic agent in systemic circulation versus time is at most about 5% of the AUC obtained when the same amount of the therapeutic agent is delivered subcutaneously $((C_{max})_{SC})$. In some other embodiments, the maximum plasma concentration $((C_{max})_{TOP})$ of the therapeutic agent in systemic circulation versus time is at most about 10% of the AUC obtained when the same amount of the therapeutic agent is delivered subcutaneously $((C_{max})_{SC})$. In some other embodiments, the maximum plasma concentration $((C_{max})_{TOP})$ of the therapeutic agent in systemic circulation versus time is at most about 15% of the AUC obtained when the same amount of the therapeutic agent is delivered subcutaneously $((C_{max})_{SC})$. In some other embodiments, the maximum plasma concentration $((C_{max})_{TOP})$ of the therapeutic agent in systemic circulation versus time is at most about 20% of the AUC obtained when the same amount of the therapeutic agent is delivered subcutaneously $((C_{max})_{SC})$. In some embodiments, particularly when the $C_{max}$ is determined from a plurality of subjects, the $C_{max}$ is a mean $C_{max}$ obtained from the plurality of subjects. Thus, in some further embodiments, $(C_{max})_{TOP}$ or $(C_{max})_{SC}$ may refer to a mean $(C_{max})_{TOP}$ or mean $(C_{max})_{SC}$, respectively. In some other embodiments, an individual $C_{max}$ value obtained for a single subject may be compared to a mean $C_{max}$ obtained from a plurality of subjects.

Diseases of the Endoderm

Also provided herein is a method of treating a disease or condition that arises in a tissue originating from the endoderm of a subject. In some embodiments, the method comprises: releasing a pharmaceutical formulation containing a therapeutically effective amount of a therapeutic agent from an ingestible device as disclosed herein to the gastrointestinal tract of a subject. In some embodiments, the pharmaceutical formulation is released with sufficient power, pressure and/or force for trans-epithelial delivery of the therapeutic agent to the gastrointestinal tract. In some embodiments, the pharmaceutical formulation is released with sufficient power, pressure and/or force for epithelial delivery of the therapeutic agent to the gastrointestinal tract. In some embodiments, the pharmaceutical formulation is released with sufficient power, pressure and/or force for topical delivery of the therapeutic agent to the gastrointestinal tract.

In some embodiments of the methods described herein, the tissue originating from the endoderm is selected from the group of: the stomach, the colon, the liver, the pancreas, the urinary bladder, the epithelial parts of the trachea, the lungs, the pharynx, the thyroid, the parathyroid, the intestines, and the gallbladder. In some embodiments of any of the methods described herein, the disease or condition that arises in a tissue originating from the endoderm is selected from the group of: gastritis, Celiac disease, hepatitis, alcoholic lever disease, fatty liver disease (hepatic steatosis), non-alcoholic fatty liver disease (NASH), cirrhosis, primary schlerosing cholangitis, pancreatitis, insterstitial cystitits, asthma, chronic obstructic pulmonary disease, pulmonary fibrosis, pharyngitis, thyroiditis, hyperthyroidism, parathyroiditis, nephritis, Hashimoto's disease, Addison's disease, Graves' disease, Sjögren syndrome, type 1 diabetes, pelvic inflammatory disease, auditory canal inflammation, tinnitus, vestibular neuritis, otitis media, auditory canal inflammation, tracheitis, cholestatic liver disease, primary biliary sclerosis, liver parenchyma, an inherited metabolic disorder of the liver, Byler syndrome, cerebrotendinous, xanthomatosis, Zellweger's syndrome, neonatal hepatitis, cystic fibrosis, ALGS (Alagilles syndrome), PFIC (progressive familial intrahepatic cholestasis), autoimmune hepatitis, primary biliary cirrhosis (PBC), liver fibrosis, NAFLD, portal hypertension, general cholestasis, such as in jaundice due to drugs or during pregnancy, intra- and extrahepatic cholestasis, such as hereditary forms of cholestasis, such as PFIC1, gall stones and choledocholithiasis, malignancy causing obstruction of the biliary tree, symptoms (scratching, pruritus) due to cholestasis/jaundice, chronic autoimmune liver disease leading to progressive cholestasis, and pruritus of cholestatic liver disease, duodenal ulcers, enteritis (radiation-, chemotherapy-, or infection-induced enteritis), diverticulitis, pouchitis, cholecystitis, and cholangitis. In some embodiments of any of the methods described herein, the inflammatory disease or condition that arises in a tissue originating from the endoderm is inflammation of the liver.

In some embodiments, the disease or condition that arises in a tissue originating from the endoderm is a disease or condition related to the gut-brain axis. In some embodiments, the disease or condition is selected from the group consisting of multiple sclerosis, Parkinson's disease, mild cognitive impairment, Alzheimer's, disease, encephalitis, and hepatic encephalopathy.

Administration of Additional Therapeutic Agents

Some embodiments of the methods described herein further include administering one or more additional therapeutic agents. In some embodiments, the additional therapeutic agent is administered orally, intravenously or subcutaneously, where the additional therapeutic agent is the same therapeutic agent; a different therapeutic agent; or an agent having the same or a different biological target from the therapeutic agent. In some embodiments of the methods described herein, the therapeutic agent is administered prior to the additional therapeutic agent. In some embodiments of the methods described herein, the therapeutic agent is administered after the additional therapeutic agent. In some embodiments of the methods described herein, the therapeutic agent and the additional therapeutic agent are administered substantially at the same time. In some embodiments of the methods described herein, the additional therapeutic agent is administered orally. In some embodiments of the methods described herein, the additional therapeutic agent is administered intravenously. In some embodiments of the methods described herein, the additional therapeutic agent is administered subcutaneously. In some embodiments of the methods described herein, the amount of the additional therapeutic agent when administered alone is less than the amount of the additional therapeutic agent when the therapeutic agent and the additional therapeutic agent are both administered systemically. In some embodiments of the methods described herein, the method does not include administering an additional therapeutic agent.

Thus, the therapeutic agents for the treatment of the diseases or conditions disclosed herein can optionally be used with one or more additional agents. In some embodiments, the therapeutic agents can be used with one or more additional agents for the treatment of metabolic and/or endocrine diseases or conditions. In some embodiments, the therapeutic agent for treating a metabolic or endocrine disease or condition as described herein is administered with one or more of: insulin or insulin analogs; glucagon receptor agonists or glucagon-like peptide-1 (GLP-1) receptor agonists, DGAT2 inhibitors, (DPP-4) inhibitors, PCSK9 inhibitors, SGLT-2 inhibitors, sulfonylureas, biguanides, α-glucosidase inhibitors, thiazolidinediones, meglitinides, bile-acid sequestrants, peptide YY ligands, amylin analogs, statins, FXR agonists, PPAR agonists, ACC inhibitors, FGFR modulators, FGF analogs, caspase pathway inhibitors, TNF-α inhibitors, and lipase inhibitors.

Nonlimiting examples of such agents that can be used in combination therapy with the therapeutic agents disclosed herein for the treatment of one or more metabolic and/or endocrine diseases include, but are not limited to, an insulin or insulin analog (e.g., uman insulin, insulin aspart, ultra-fast acting insulin aspart, insulin degludec, insulin detemir, isophane insulin, insulin glargine, insulin glulisine, insulin lispro, insulin tregopil, FSI-965, hinsbet, and LAI-287); a glucagon receptor agonist or a glucagon-like peptide-1 (GLP-1) receptor agonist (e.g., albiglutide, benaglutide, cotadutide, dulaglutide, ebenatide, efpeglenatide, exenatide, glutazumab, glucagon, liraglutide, lixisenatide, NN-9277, NN-9423, NNC-0090-2746, PF-06882961, PEG-loxenatide, pegapamodutide, semaglutide, and tirzepatide); a dipeptidyl peptidase-4 (DPP-4) inhibitor (e.g., anagliptin, alogliptin, berberine, dutogliptin, ebenatide, evogliptin, gemigliptin, gosogliptin, linagliptin, omarigliptin, saxagliptin, sitagliptin, teneligliptin, trelagliptin, and vildagliptin); biguanides (e.g., metformin), a sodium-glucose cotransporter-2 (SGLT-2) inhibitor (e.g., canagliflozin, dapagliflozin, empagliflozin, ertugliflozin, licogliflozin bis(prolinate), and remogliflozin); a sulfonylurea (e.g., acetohexamide, carbutamide, chlorpropamide, glibornuride, glyburide, gliclazide, glipizide, glimepiride, gliquidone, glisoxepide, glyclopyramide, metahexamide, tolazamide, tolbutamide, and tolcyclamide); an α-glucosidase inhibitor (e.g., acarbose, miglitol, and volglibose); meglitinides (e.g., repaglinide and nateglinide); a thiazolidinedione (e.g., rosiglitazone and pioglitazone); a dopamine-2-agonist (e.g., bromocriptine), a bile-acid sequestrant (e.g., colesevelam, cholestyramine, and colestipol); a peptide YY ligand (e.g., NN-9775, NN-9747, and NN-9748); an amylin analog (e.g., pramlintide acetate, and AM-833); a statin (e.g., atorvastatin, fluvastatin, lovastatin, pravastatin, rosuvastatin, simvastatin, and pitavastatin); a PCSK9 inhibitor (e.g., alirocumab, evolocumab, bococizumab, frovocimab, 1D05-IgG2, evinacumab, SHR-1209, lodelcizumab, IBI-306, LIB-003, JS-002, AK-102, ATH-06, C-8304, and NNC-0385-0434); FXR agonists (e.g. tropifexor, cilofexor (GS-9674), obeticholic acid (ocaliva), EDP-305, and nidufexor (LMB-763); a peroxisome proliferator-activated receptor (PPAR) agonist (e.g., elafibranor, lanifibranor, lipaglyn, and seladelpar); an acetyl-CoA carboxylase (ACC) inhibitor (e.g., firsocostat (GS-976), PF-05221304, PF-07055341, and MK-4074); an alpha-1-antitrypsin (e.g., prolastin); an FGFR modulator or an FGF analog (e.g., aldafermin (NGM282), RG7992, NGM313, ARX618, and BMS-986036); a caspase pathway inhibitor (e.g., selonsertib and emricasan); a lipase inhibitor (e.g., cetilistat and orlistat); a DGAT2 inhibitor (e.g., IONIS-DGAT2Rx and PF-06865571); a TNF-α inhibitor (e.g., OPRX-106 and golimumab); cenicriviroc, aramchol, BI 1467335, DS 102, gemcabene, belapectin, GRI-0621, IMM-124E, resmetirom, tipelukast, MSDC-0602K, NC101, NS-0200, PF-06835919, volixibat, TVB-2640, VK2809, butanoic acid, CER209, DUR928, OPRX-106, PXS-5382A, RG-125, RYI-018, SGM-1019, abatacept, aldesleukin, bermekimab, bimagrumab, cibinetide, diabecell, diamyd, iscalimab, mecasermin, osilodrostat, otelixizumab, protrans, rexmyelocel-t, somatostatin, teplizumab, bortezomib, fulvestrant, bendamustine, itolizumab, canakinumab, trichuris suis ova, DACRA-089, and remestemcel-L.

In some embodiments, the therapeutic agent for treating a metabolic or endocrine disease or condition is a GLP-1 receptor agonist. In some embodiments, the GLP-1 receptor agonist is administered with one or more additional therapeutic agents for treating diabetes.

In some embodiments, the one or more additional therapeutic agents for treating diabetes are selected from insulin or insulin analogs, DPP-4 inhibitors, SGLT2 inhibitors, biguanides, sulfonylureas, α-glucosidase inhibitors, thiazolidinediones, dopamine-2 agonists, meglitinides, bile acid sequestrants, and amylin analogs.

In some embodiments, the therapeutic agent for treating a metabolic or endocrine disease or condition is a GLP-1 receptor agonist. In some embodiments, the GLP-1 receptor agonist is administered with an insulin or an insulin analog.

In some embodiments, the therapeutic agent for treating a metabolic or endocrine disease or condition is a GLP-1 receptor agonist. In some embodiments, the GLP-1 receptor agonist is administered with an amylin analog.

In some embodiments, the therapeutic agent for treating a metabolic or endocrine disease or condition is a GLP-1 receptor agonist. In some embodiments, the GLP-1 receptor agonist can be administered with an α-glucosidase inhibitor, or a pharmaceutically acceptable salt thereof.

In some embodiments, the therapeutic agent for treating a metabolic or endocrine disease or condition is a GLP-1 receptor agonist. In some embodiments, the GLP-1 receptor agonist is administered with a biguanide. In some embodiments, the biguanide is metformin or a pharmaceutically acceptable salt thereof.

In some embodiments, the therapeutic agent for treating a metabolic or endocrine disease or condition is a GLP-1 receptor agonist. In some embodiments, the GLP-1 receptor agonist is administered with a bile acid sequestrant.

In some embodiments, the therapeutic agent for treating a metabolic or endocrine disease or condition is a GLP-1 receptor agonist. In some embodiments, the GLP-1 receptor agonist is administered with a DPP-4 inhibitor or a pharmaceutically acceptable salt thereof.

In some embodiments, the therapeutic agent for treating a metabolic or endocrine disease or condition is a GLP-1 receptor agonist. In some embodiments, the GLP-1 receptor agonist is administered with a dopamine-2 agonist or a pharmaceutically acceptable salt thereof.

In some embodiments, the therapeutic agent for treating a metabolic or endocrine disease or condition is a GLP-1 receptor agonist. In some embodiments, the GLP-1 receptor agonist is administered with a meglitinide or a pharmaceutically acceptable salt thereof.

In some embodiments, the therapeutic agent for treating a metabolic or endocrine disease or condition is a GLP-1 receptor agonist. In some embodiments, the GLP-1 receptor agonist is administered with an SGLT2 inhibitor or a pharmaceutically acceptable salt thereof.

In some embodiments, the therapeutic agent for treating a metabolic or endocrine disease or condition is a GLP-1 receptor agonist. In some embodiments, the GLP-1 receptor agonist is administered with a sulfonylurea or a pharmaceutically acceptable salt thereof.

In some embodiments, the therapeutic agent for treating a metabolic or endocrine disease or condition is a GLP-1 receptor agonist. In some embodiments, the GLP-1 receptor agonist is administered with a thiazolidinedione inhibitor or a pharmaceutically acceptable salt thereof.

In some embodiments, the therapeutic agent for treating a metabolic or endocrine disease or condition is a GLP-1 receptor agonist. In some embodiments, the GLP-1 receptor agonist is administered with an anti-fibrotic drug for the treatment of NASH/NAFLD. In some embodiments, the anti-fibrotic drug is selected from rituximab, abatacept, tocilizumab, rilonacept, BB-3, ensifentrine, pirfenidone, GSK-3008348, PLN-74809, AVID-200, and RES-529. In some embodiments, the anti-fibrotic drug is a monoclonal antibody or a fragment or biosimilar thereof. In some embodiments, the monoclonal antibody is selected from rituximab, abatacept, tocilizumab, rilonacept, or a fragment or biosimilar thereof. In some embodiments, the anti-fibrotic drug is a small molecule or a pharmaceutically acceptable salt thereof. In some embodiments, the small molecule drug is selected from BB-3, ensifentrine, pirfenidone, GSK-3008348, PLN-74809, AVID-200, and RES-529, or pharmaceutically acceptable salts thereof.

In some embodiments, the therapeutic agent for treating a metabolic or endocrine disease or condition is a GLP-1 receptor agonist. In some embodiments, the GLP-1 receptor agonist is administered with an FXR agonist. In some embodiments, the FXR agonist is a small molecule drug.

In some embodiments, the therapeutic agent for treating a metabolic or endocrine disease or condition is a GLP-1 receptor agonist. In some embodiments, the GLP-1 receptor agonist is administered with an ACC inhibitor. In some embodiments, the ACC inhibitor is a small molecule drug.

In some embodiments, the therapeutic agent for treating a metabolic or endocrine disease or condition is a GLP-1 receptor agonist. In some embodiments, the GLP-1 receptor agonist is administered with an FXR agonist and an ACC inhibitor.

In some embodiments, the therapeutic agent for treating a metabolic or endocrine disease or condition is a GLP-1 receptor agonist. In some embodiments, the GLP-1 receptor agonist is administered with an anti-IL-21 monoclonal antibody or a fragment or biosimilar thereof.

In some embodiments, the therapeutic agent for treating a metabolic or endocrine disease or condition is a PCSK9 inhibitor. In some embodiments, the PCSK9 inhibitor is administered with one or more additional therapeutic agents for the reduction of LDL cholesterol (LDL-C) levels and protection of the subject from cardiovascular diseases. In some embodiments, the PCSK9 inhibitor is selected from alirocumab, evolocumab, bococizumab, frovocimab, 1D05-IgG2, evinacumab, SHR-1209, lodelcizumab, IBI-306, LIB-003, JS-002, AK-102, ATH-06, C-8304, and NNC-0385-0434; or a fragment or biosimilar thereof. In some more particular embodiments, the PCSK9 inhibitor is alirocumab or evolocumab, or a fragment or biosimilar thereof. In some embodiments, the one or more additional therapeutic agents administered with the PCSK9 inhibitor for the reduction of LDL cholesterol (LDL-C) levels and protection of the subject from cardiovascular diseases is a statin. In some embodiments, the statin is selected from atorvastatin, fluvastatin, lovastatin, pravastatin, rosuvastatin, simvastatin, and pitavastatin; or a pharmaceutically acceptable salt thereof.

Examples of particular combinations include the following. Unless otherwise specified, the first component (component (1)) is administered in an ingestible device, such as the ingestible device of the present disclosure, while the second component (component (2)) is administered either topically, for example, via an ingestible device, which may be the same or different ingestible device as the first component, or by another form of administration. Each listed small molecule, peptide or nucleic acid agent optionally includes a pharmaceutically acceptable salt thereof, whether or not such a form is expressly indicated. Each listed antibody agent optionally includes a biosimilar thereof, whether or not such a biosimilar is expressly indicated. Examples of the first component and the second component recited in combinations disclosed below are optionally provided in a formulation as disclosed herein.

(1) GLP-1 receptor agonist; (2) an FXR agonist, an ACC inhibitor, an amylin analog, or an anti-IL-21 monoclonal antibody. In some embodiments, the GLP-1 receptor agonist is selected from albiglutide, benaglutide, cotadutide, dulaglutide, ebenatide, efpeglenatide, exenatide, glutazumab, glucagon, liraglutide, lixisenatide, NN-9277, NN-9423, NNC-0090-2746, PF-06882961, PEG-loxenatide, pegapamodutide, semaglutide, and tirzepatide. In some more particular embodiments, the GLP-1 receptor agonist is selected from exenatide, liraglutide, lixisenatide, albiglutide, dulaglutide, and semaglutide.

(1) GLP-1 receptor agonist; (2) an FXR agonist. In some embodiments, the GLP-1 receptor agonist is selected from albiglutide, benaglutide, cotadutide, dulaglutide, ebenatide, efpeglenatide, exenatide, glutazumab, glucagon, liraglutide, lixisenatide, NN-9277, NN-9423, NNC-0090-2746, PF-06882961, PEG-loxenatide, pegapamodutide, semaglutide, and tirzepatide. In some more particular embodiments, the GLP-1 receptor agonist is selected from exenatide, liraglutide, lixisenatide, albiglutide, dulaglutide, and semaglutide. In some embodiments, the FXR agonist is selected from tropifexor, cilofexor (GS-9674), obeticholic acid (ocaliva), EDP-305, and nidufexor (LMB-763); or a pharmaceutically acceptable salt thereof.

(1) GLP-1 receptor agonist; (2) FXR agonist administered topically, for example, via an ingestible device. In some embodiments, the GLP-1 receptor agonist is selected from albiglutide, benaglutide, cotadutide, dulaglutide, ebenatide, efpeglenatide, exenatide, glutazumab, glucagon, liraglutide, lixisenatide, NN-9277, NN-9423, NNC-0090-2746, PF-06882961, PEG-loxenatide, pegapamodutide, semaglutide, and tirzepatide. In some more particular embodiments, the GLP-1 receptor agonist is selected from exenatide, liraglutide, lixisenatide, albiglutide, dulaglutide, and semaglutide. In some embodiments, the FXR agonist is selected from tropifexor, cilofexor (GS-9674), obeticholic acid (ocaliva), EDP-305, and nidufexor (LMB-763); or a pharmaceutically acceptable salt thereof.

(1) GLP-1 receptor agonist; (2) FXR agonist administered orally. In some embodiments, the GLP-1 receptor agonist is selected from albiglutide, benaglutide, cotadutide, dulaglutide, ebenatide, efpeglenatide, exenatide, glutazumab, glucagon, liraglutide, lixisenatide, NN-9277, NN-9423, NNC-0090-2746, PF-06882961, PEG-loxenatide, pegapamodutide, semaglutide, and tirzepatide. In some more particular embodiments, the GLP-1 receptor agonist is selected from exenatide, liraglutide, lixisenatide, albiglutide, dulaglutide, and semaglutide. In some embodiments, the FXR agonist is selected from tropifexor, cilofexor (GS-9674), obeticholic acid (ocaliva), EDP-305, and nidufexor (LMB-763); or a pharmaceutically acceptable salt thereof. In some embodiments, the FXR agonist is administered orally as a tablet. In some embodiments, the FXR agonist is administered orally as a capsule. In some embodiments, the FXR agonist is administered orally as an oral suspension. In some embodiments, the FXR agonist is administered orally as an oral solution.

(1) GLP-1 receptor agonist; (2) FXR agonist administered systemically. In some embodiments, the GLP-1 receptor agonist is selected from albiglutide, benaglutide, cotadutide, dulaglutide, ebenatide, efpeglenatide, exenatide, glutazumab, glucagon, liraglutide, lixisenatide, NN-9277, NN-9423, NNC-0090-2746, PF-06882961, PEG-loxenatide, pegapamodutide, semaglutide, and tirzepatide. In some more particular embodiments, the GLP-1 receptor agonist is selected from exenatide, liraglutide, lixisenatide, albiglutide, dulaglutide, and semaglutide. In some embodiments, the FXR agonist is selected from tropifexor, cilofexor (GS-9674), obeticholic acid (ocaliva), EDP-305, and nidufexor (LMB-763); or a pharmaceutically acceptable salt thereof. In some embodiments, the FXR agonist is administered systemically via subcutaneous administration. In some embodiments, the FXR agonist is administered systemically via intravenous administration.

(1) FXR agonist; (2) GLP-1 receptor agonist. In some embodiments, the FXR agonist is selected from tropifexor, cilofexor (GS-9674), obeticholic acid (ocaliva), EDP-305, and nidufexor (LMB-763); or a pharmaceutically acceptable salt thereof. In some embodiments, the GLP-1 receptor agonist is selected from albiglutide, benaglutide, cotadutide, dulaglutide, ebenatide, efpeglenatide, exenatide, glutazumab, glucagon, liraglutide, lixisenatide, NN-9277, NN-9423, NNC-0090-2746, PF-06882961, PEG-loxenatide, pegapamodutide, semaglutide, and tirzepatide. In some more particular embodiments, the GLP-1 receptor agonist is selected from exenatide, liraglutide, lixisenatide, albiglutide, dulaglutide, and semaglutide.

(1) FXR agonist; (2) GLP-1 receptor agonist administered topically, for example, via an ingestible device. In some embodiments, the FXR agonist is selected from tropifexor, cilofexor (GS-9674), obeticholic acid (ocaliva), EDP-305, and nidufexor (LMB-763); or a pharmaceutically acceptable salt thereof. In some embodiments, the GLP-1 receptor agonist is selected from albiglutide, benaglutide, cotadutide, dulaglutide, ebenatide, efpeglenatide, exenatide, glutazumab, glucagon, liraglutide, lixisenatide, NN-9277, NN-9423, NNC-0090-2746, PF-06882961, PEG-loxenatide, pegapamodutide, semaglutide, and tirzepatide. In some more particular embodiments, the GLP-1 receptor agonist is selected from exenatide, liraglutide, lixisenatide, albiglutide, dulaglutide, and semaglutide.

(1) FXR agonist; (2) GLP-1 receptor agonist administered systemically. In some embodiments, the FXR agonist is selected from tropifexor, cilofexor (GS-9674), obeticholic acid (ocaliva), EDP-305, and nidufexor (LMB-763); or a pharmaceutically acceptable salt thereof. In some embodiments, the GLP-1 receptor agonist is selected from albiglutide, benaglutide, cotadutide, dulaglutide, ebenatide, efpeglenatide, exenatide, glutazumab, glucagon, liraglutide, lixisenatide, NN-9277, NN-9423, NNC-0090-2746, PF-06882961, PEG-loxenatide, pegapamodutide, semaglutide, and tirzepatide. In some more particular embodiments, the GLP-1 receptor agonist is selected from exenatide, liraglutide, lixisenatide, albiglutide, dulaglutide, and semaglutide. In some embodiments, the GLP-1 receptor agonist is administered systemically via subcutaneous administration. In some embodiments, the GLP-1 receptor agonist is administered systemically via intravenous administration.

(1) GLP-1 receptor agonist; (2) ACC inhibitor. In some embodiments, the GLP-1 receptor agonist is selected from albiglutide, benaglutide, cotadutide, dulaglutide, ebenatide, efpeglenatide, exenatide, glutazumab, glucagon, liraglutide, lixisenatide, NN-9277, NN-9423, NNC-0090-2746, PF-06882961, PEG-loxenatide, pegapamodutide, semaglutide, and tirzepatide. In some more particular embodiments, the GLP-1 receptor agonist is selected from exenatide, liraglutide, lixisenatide, albiglutide, dulaglutide, and semaglutide. In some embodiments, the ACC inhibitor is selected from firsocostat (GS-976), PF-05221304, PF-07055341, and MK-4074; or a pharmaceutically acceptable salt thereof.

(1) GLP-1 receptor agonist; (2) ACC inhibitor administered topically, for example, via an ingestible device. In some embodiments, the GLP-1 receptor agonist is selected from albiglutide, benaglutide, cotadutide, dulaglutide, ebenatide, efpeglenatide, exenatide, glutazumab, glucagon, liraglutide, lixisenatide, NN-9277, NN-9423, NNC-0090-2746, PF-06882961, PEG-loxenatide, pegapamodutide, semaglutide, and tirzepatide. In some more particular embodiments, the GLP-1 receptor agonist is selected from exenatide, liraglutide, lixisenatide, albiglutide, dulaglutide, and semaglutide. In some embodiments, the ACC inhibitor is selected from firsocostat (GS-976), PF-05221304, PF-07055341, and MK-4074; or a pharmaceutically acceptable salt thereof.

(1) GLP-1 receptor agonist; (2) ACC inhibitor administered orally. In some embodiments, the GLP-1 receptor agonist is selected from albiglutide, benaglutide, cotadutide, dulaglutide, ebenatide, efpeglenatide, exenatide, glutazumab, glucagon, liraglutide, lixisenatide, NN-9277, NN-9423, NNC-0090-2746, PF-06882961, PEG-loxenatide, pegapamodutide, semaglutide, and tirzepatide. In some more particular embodiments, the GLP-1 receptor agonist is selected from exenatide, liraglutide, lixisenatide, albiglutide, dulaglutide, and semaglutide. In some embodiments, the ACC inhibitor is selected from firsocostat (GS-976), PF-05221304, PF-07055341, and MK-4074; or a pharmaceutically acceptable salt thereof. In some embodiments, the ACC inhibitor is administered orally as a tablet. In some embodiments, the ACC inhibitor is administered orally as a capsule. In some embodiments, the ACC inhibitor is administered orally as an oral suspension. In some embodiments, the ACC inhibitor is administered orally as an oral solution.

(1) GLP-1 receptor agonist; (2) ACC inhibitor administered sysmtemically. In some embodiments, the GLP-1 receptor agonist is selected from albiglutide, benaglutide, cotadutide, dulaglutide, ebenatide, efpeglenatide, exenatide, glutazumab, glucagon, liraglutide, lixisenatide, NN-9277, NN-9423, NNC-0090-2746, PF-06882961, PEG-loxenatide, pegapamodutide, semaglutide, and tirzepatide. In some more particular embodiments, the GLP-1 receptor agonist is selected from exenatide, liraglutide, lixisenatide, albiglutide, dulaglutide, and semaglutide. In some embodiments, the ACC inhibitor is selected from firsocostat (GS-976), PF-05221304, PF-07055341, and MK-4074; or a pharmaceutically acceptable salt thereof. In some embodiments, the ACC inhibitor is administered systemically via subcutaneous administration. In some embodiments, the ACC inhibitor is administered systemically via intravenous administration.

(1) ACC inhibitor; (2) GLP-1 receptor agonist. In some embodiments, the ACC inhibitor is selected from firsocostat (GS-976), PF-05221304, PF-07055341, and MK-4074; or a pharmaceutically acceptable salt thereof. In some embodiments, the GLP-1 receptor agonist is selected from albiglutide, benaglutide, cotadutide, dulaglutide, ebenatide, efpeglenatide, exenatide, glutazumab, glucagon, liraglutide, lixisenatide, NN-9277, NN-9423, NNC-0090-2746, PF-06882961, PEG-loxenatide, pegapamodutide, semaglutide, and tirzepatide. In some more particular embodiments, the GLP-1 receptor agonist is selected from exenatide, liraglutide, lixisenatide, albiglutide, dulaglutide, and semaglutide.

(1) ACC inhibitor; (2) GLP-1 receptor agonist administered topically, for example, via an ingestible device. In some embodiments, the ACC inhibitor is selected from firsocostat (GS-976), PF-05221304, PF-07055341, and MK-4074; or a pharmaceutically acceptable salt thereof. In some embodiments, the GLP-1 receptor agonist is selected from albiglutide, benaglutide, cotadutide, dulaglutide, ebenatide, efpeglenatide, exenatide, glutazumab, glucagon, liraglutide, lixisenatide, NN-9277, NN-9423, NNC-0090-2746, PF-06882961, PEG-loxenatide, pegapamodutide, semaglutide, and tirzepatide. In some more particular embodiments, the GLP-1 receptor agonist is selected from exenatide, liraglutide, lixisenatide, albiglutide, dulaglutide, and semaglutide.

(1) ACC inhibitor; (2) GLP-1 receptor agonist administered systemically. In some embodiments, the the ACC inhibitor is selected from firsocostat (GS-976), PF-05221304, PF-07055341, and MK-4074; or a pharmaceutically acceptable salt thereof. In some embodiments, the GLP-1 receptor agonist is selected from albiglutide, benaglutide, cotadutide, dulaglutide, ebenatide, efpeglenatide, exenatide, glutazumab, glucagon, liraglutide, lixisenatide, NN-9277, NN-9423, NNC-0090-2746, PF-06882961, PEG-loxenatide, pegapamodutide, semaglutide, and tirzepatide. In some more particular embodiments, the GLP-1 receptor agonist is selected from exenatide, liraglutide, lixisenatide, albiglutide, dulaglutide and semaglutide. In some embodiments, the GLP-1 receptor agonist is administered systemically via subcutaneous administration. In some embodiments, the GLP-1 receptor agonist is administered systemically via intravenous administration.

(1) GLP-1 receptor agonist; (2) FXR agonist; (3) ACC inhibitor. In some embodiments, the GLP-1 receptor agonist is selected from albiglutide, benaglutide, cotadutide, dulaglutide, ebenatide, efpeglenatide, exenatide, glutazumab, glucagon, liraglutide, lixisenatide, NN-9277, NN-9423, NNC-0090-2746, PF-06882961, PEG-loxenatide, pegapamodutide, semaglutide, and tirzepatide. In some more particular embodiments, the GLP-1 receptor agonist is selected from exenatide, liraglutide, lixisenatide, albiglutide, dulaglutide, and semaglutide. In some embodiments, the FXR agonist is selected from tropifexor, cilofexor (GS-9674), obeticholic acid (ocaliva), EDP-305, and nidufexor (LMB-763); or a pharmaceutically acceptable salt thereof. In some embodiments, the ACC inhibitor is selected from firsocostat (GS-976), PF-05221304, PF-07055341, and MK-4074; or a pharmaceutically acceptable salt thereof.

(1) GLP-1 receptor agonist; (2) FXR agonist administered orally; (3) ACC inhibitor administered orally. In some embodiments, the GLP-1 receptor agonist is selected from albiglutide, benaglutide, cotadutide, dulaglutide, ebenatide, efpeglenatide, exenatide, glutazumab, glucagon, liraglutide, lixisenatide, NN-9277, NN-9423, NNC-0090-2746, PF-06882961, PEG-loxenatide, pegapamodutide, semaglutide, and tirzepatide. In some more particular embodiments, the GLP-1 receptor agonist is selected from exenatide, liraglutide, lixisenatide, albiglutide, dulaglutide and semaglutide. In some embodiments, the FXR agonist is selected from tropifexor, cilofexor (GS-9674), obeticholic acid (ocaliva), EDP-305, and nidufexor (LMB-763); or a pharmaceutically acceptable salt thereof. In some embodiments, the FXR agonist is administered orally as a tablet. In some embodiments, the FXR agonist is administered orally as a capsule. In some embodiments, the FXR agonist is administered orally as an oral suspension. In some embodiments, the FXR agonist is administered orally as an oral solution. In some embodiments, the ACC inhibitor is selected from firsocostat (GS-976), PF-05221304, PF-07055341, and MK-4074; or a pharmaceutically acceptable salt thereof. In some embodiments, the ACC inhibitor is administered orally as a tablet. In some embodiments, the ACC inhibitor is administered orally as a capsule. In some embodiments, the ACC inhibitor is administered orally as an oral suspension. In some embodiments, the ACC inhibitor is administered orally as an oral solution.

(1) GLP-1 receptor agonist; (2) FXR agonist administered topically, for example, via an ingestible device; (3) ACC inhibitor administered topically, for example, via an ingestible device. In some embodiments, the GLP-1 receptor agonist is selected from albiglutide, benaglutide, cotadutide, dulaglutide, ebenatide, efpeglenatide, exenatide, glutazumab, glucagon, liraglutide, lixisenatide, NN-9277, NN-9423, NNC-0090-2746, PF-06882961, PEG-loxenatide, pegapamodutide, semaglutide, and tirzepatide. In some more particular embodiments, the GLP-1 receptor agonist is selected from exenatide, liraglutide, lixisenatide, albiglutide, dulaglutide, and semaglutide. In some embodiments, the FXR agonist is selected from tropifexor, cilofexor (GS-9674), obeticholic acid (ocaliva), EDP-305, and nidufexor (LMB-763); or a pharmaceutically acceptable salt thereof. In some embodiments, the ACC inhibitor is selected from firsocostat (GS-976), PF-05221304, PF-07055341, and MK-4074; or a pharmaceutically acceptable salt thereof.

(1) GLP-1 receptor agonist; (2) FXR agonist administered systemically; (3) ACC inhibitor administered systemically. In some embodiments, the GLP-1 receptor agonist is selected from albiglutide, benaglutide, cotadutide, dulaglutide, ebenatide, efpeglenatide, exenatide, glutazumab, glucagon, liraglutide, lixisenatide, NN-9277, NN-9423, NNC-0090-2746, PF-06882961, PEG-loxenatide, pegapamodutide, semaglutide, and tirzepatide. In some more particular embodiments, the GLP-1 receptor agonist is selected from exenatide, liraglutide, lixisenatide, albiglutide, dulaglutide, and semaglutide. In some embodiments, the FXR agonist is selected from tropifexor, cilofexor (GS-9674), obeticholic acid (ocaliva), EDP-305, and nidufexor (LMB-763); or a pharmaceutically acceptable salt thereof. In some embodiments, the FXR agonist is administered systemically via subcutaneous administration. In some embodiments, the FXR agonist is administered systemically via intravenous administration. In some embodiments, the ACC inhibitor is selected from firsocostat (GS-976), PF-05221304, PF-07055341, and MK-4074; or a pharmaceutically acceptable salt thereof. In some embodiments, the ACC inhibitor is administered systemically via subcutaneous administration. In some embodiments, the ACC inhibitor is administered systemically via subcutaneous administration.

(1) GLP-1 receptor agonist; (2) anti-IL-21 monoclonal antibody. In some embodiments, the GLP-1 receptor agonist is selected from albiglutide, benaglutide, cotadutide, dulaglutide, ebenatide, efpeglenatide, exenatide, glutazumab, glucagon, liraglutide, lixisenatide, NN-9277, NN-9423, NNC-0090-2746, PF-06882961, PEG-loxenatide, pegapamodutide, semaglutide, and tirzepatide. In some more particular embodiments, the GLP-1 receptor agonist is selected from exenatide, liraglutide, lixisenatide, albiglutide, dulaglutide, and semaglutide. In some embodiments, the anti-IL-12 antibody is an antibody described in WO 2010/055366 and WO 2012/098113, each of which is incorporated by reference in its entirety.

(1) GLP-1 receptor agonist; (2) anti-IL-21 monoclonal antibody administered topically, for example, via an ingestible device. In some embodiments, the GLP-1 receptor agonist is selected from albiglutide, benaglutide, cotadutide, dulaglutide, ebenatide, efpeglenatide, exenatide, glutazumab, glucagon, liraglutide, lixisenatide, NN-9277, NN-9423, NNC-0090-2746, PF-06882961, PEG-loxenatide, pegapamodutide, semaglutide, and tirzepatide. In some more particular embodiments, the GLP-1 receptor agonist is selected from exenatide, liraglutide, lixisenatide, albiglutide, dulaglutide, and semaglutide. In some embodiments, the anti-IL-12 antibody is an antibody described in WO 2010/055366 and WO 2012/098113, each of which is incorporated by reference in its entirety.

(1) GLP-1 receptor agonist; (2) anti-IL-21 monoclonal antibody administered systemically. In some embodiments, the GLP-1 receptor agonist is selected from albiglutide, benaglutide, cotadutide, dulaglutide, ebenatide, efpeglenatide, exenatide, glutazumab, glucagon, liraglutide, lixisenatide, NN-9277, NN-9423, NNC-0090-2746, PF-06882961, PEG-loxenatide, pegapamodutide, semaglutide, and tirzepatide. In some more particular embodiments, the GLP-1 receptor agonist is selected from exenatide, liraglutide, lixisenatide, albiglutide, dulaglutide, and semaglutide. In some embodiments, the anti-IL-12 antibody is an antibody described in WO 2010/055366 and WO 2012/098113, each of which is incorporated by reference in its entirety. In some embodiments, the anti-IL-21 antibody is administered systemically via subcutaneous administration. In some embodiments, the anti-IL-21 antibody is administered systemically via intravenous administration.

(1) Anti-IL-21 monoclonal antibody; (2) GLP-1 receptor agonist administered systemically. In some embodiments, the anti-IL-12 antibody is an antibody described in WO 2010/055366 and WO 2012/098113, each of which is incorporated by reference in its entirety. In some embodiments, the GLP-1 receptor agonist is selected from albiglutide, benaglutide, cotadutide, dulaglutide, ebenatide, efpeglenatide, exenatide, glutazumab, glucagon, liraglutide, lixisenatide, NN-9277, NN-9423, NNC-0090-2746, PF-06882961, PEG-loxenatide, pegapamodutide, semaglutide, and tirzepatide. In some more particular embodiments, the GLP-1 receptor agonist is selected from exenatide, liraglutide, lixisenatide, albiglutide, dulaglutide, and semaglutide. In some embodiments, GLP-1 receptor agonist is administered systemically via subcutaneous administration. In some embodiments, the GLP-1 receptor agonist is administered systemically via intravenous administration.

(1) GLP-1 receptor agonist; (2) amylin analog. In some embodiments, the GLP-1 receptor agonist is selected from albiglutide, benaglutide, cotadutide, dulaglutide, ebenatide, efpeglenatide, exenatide, glutazumab, glucagon, liraglutide, lixisenatide, NN-9277, NN-9423, NNC-0090-2746, PF-06882961, PEG-loxenatide, pegapamodutide, semaglutide, and tirzepatide. In some more particular embodiments, the GLP-1 receptor agonist is selected from exenatide, liraglutide, lixisenatide, albiglutide, dulaglutide, and semaglutide. In some embodiments, the amylin analog is pramlintide acetate or AM-833.

(1) GLP-1 receptor agonist; (2) amylin analog administered topically, for example, via an ingestible device. In some embodiments, the GLP-1 receptor agonist is selected from albiglutide, benaglutide, cotadutide, dulaglutide, ebenatide, efpeglenatide, exenatide, glutazumab, glucagon, liraglutide, lixisenatide, NN-9277, NN-9423, NNC-0090-2746, PF-06882961, PEG-loxenatide, pegapamodutide, semaglutide, and tirzepatide. In some more particular embodiments, the GLP-1 receptor agonist is selected from exenatide, liraglutide, lixisenatide, albiglutide, dulaglutide, and semaglutide. In some embodiments, the amylin analog is pramlintide acetate or AM-833.

(1) GLP-1 receptor agonist; (2) amylin analog administered systemically. In some embodiments, the GLP-1 receptor agonist is selected from albiglutide, benaglutide, cotadutide, dulaglutide, ebenatide, efpeglenatide, exenatide, glutazumab, glucagon, liraglutide, lixisenatide, NN-9277, NN-9423, NNC-0090-2746, PF-06882961, PEG-loxenatide, pegapamodutide, semaglutide, and tirzepatide. In some more particular embodiments, the GLP-1 receptor agonist is selected from exenatide, liraglutide, lixisenatide, albiglutide, dulaglutide, and semaglutide. In some embodiments, the amylin analog is pramlintide acetate or AM-833. In some embodiments, the amylin analog is administered systemically via subcutaneous administration. In some embodiments, the amylin analog is administered systemically via intravenous administration.

(1) Amylin analog; (2) GLP-1 receptor agonist administered systemically. In some embodiments, the amylin analog is pramlintide acetate or AM-833. In some embodiments, the GLP-1 receptor agonist is selected from albiglutide, benaglutide, cotadutide, dulaglutide, ebenatide, efpeglenatide, exenatide, glutazumab, glucagon, liraglutide, lixisenatide, NN-9277, NN-9423, NNC-0090-2746, PF-06882961, PEG-loxenatide, pegapamodutide, semaglutide, and tirzepatide. In some more particular embodiments, the GLP-1 receptor agonist is selected from exenatide, liraglutide, lixisenatide, albiglutide, dulaglutide, and semaglutide. In some embodiments, GLP-1 receptor agonist is administered systemically via subcutaneous administration. In some embodiments, the GLP-1 receptor agonist is administered systemically via intravenous administration.

(1) GLP-1 receptor agonist; (2) anti-fibrotic drug. In some embodiments, the GLP-1 receptor agonist is selected from albiglutide, benaglutide, cotadutide, dulaglutide, ebenatide, efpeglenatide, exenatide, glutazumab, glucagon, liraglutide, lixisenatide, NN-9277, NN-9423, NNC-0090-2746, PF-06882961, PEG-loxenatide, pegapamodutide, semaglutide, and tirzepatide. In some more particular embodiments, the GLP-1 receptor agonist is selected from exenatide, liraglutide, lixisenatide, albiglutide, dulaglutide, and semaglutide. In some embodiments, the anti-fibrotic drug is selected from rituximab, abatacept, tocilizumab, and rilonacept, or a fragment or biosimilar thereof; BB-3, ensifentrine, pirfenidone, GSK-3008348, PLN-74809, AVID-200, and RES-529, or a pharmaceutically acceptable salt thereof.

(1) GLP-1 receptor agonist; (2) anti-fibrotic drug administered topically, for example, via an ingestible device. In some embodiments, the GLP-1 receptor agonist is selected from albiglutide, benaglutide, cotadutide, dulaglutide, ebenatide, efpeglenatide, exenatide, glutazumab, glucagon, liraglutide, lixisenatide, NN-9277, NN-9423, NNC-0090-2746, PF-06882961, PEG-loxenatide, pegapamodutide, semaglutide, and tirzepatide. In some more particular embodiments, the GLP-1 receptor agonist is selected from exenatide, liraglutide, lixisenatide, albiglutide, dulaglutide, and semaglutide. In some embodiments, the anti-fibrotic drug is selected from rituximab, abatacept, tocilizumab, and rilonacept, or a fragment or biosimilar thereof; BB-3, ensifentrine, pirfenidone, GSK-3008348, PLN-74809, AVID-200, and RES-529, or a pharmaceutically acceptable salt thereof.

(1) GLP-1 receptor agonist; (2) anti-fibrotic drug administered systemically. In some embodiments, the GLP-1 receptor agonist is selected from albiglutide, benaglutide, cotadutide, dulaglutide, ebenatide, efpeglenatide, exenatide, glutazumab, glucagon, liraglutide, lixisenatide, NN-9277, NN-9423, NNC-0090-2746, PF-06882961, PEG-loxenatide, pegapamodutide, semaglutide, and tirzepatide. In some more particular embodiments, the GLP-1 receptor agonist is selected from exenatide, liraglutide, lixisenatide, albiglutide, dulaglutide, and semaglutide. In some embodiments, the anti-fibrotic drug is selected from rituximab, abatacept, tocilizumab, and rilonacept, or a fragment or biosimilar thereof; BB-3, ensifentrine, pirfenidone, GSK-3008348, PLN-74809, AVID-200, and RES-529, or a pharmaceutically acceptable salt thereof. In some embodiments, the anti-fibrotic drug is administered systemically via subcutaneous administration. In some embodiments, the anti-fibrotic drug is administered systemically via intravenous administration.

(1) GLP-1 receptor agonist; (2) anti-fibrotic drug administered orally. In some embodiments, the GLP-1 receptor agonist is selected from albiglutide, benaglutide, cotadutide, dulaglutide, ebenatide, efpeglenatide, exenatide, glutazumab, glucagon, liraglutide, lixisenatide, NN-9277, NN-9423, NNC-0090-2746, PF-06882961, PEG-loxenatide, pegapamodutide, semaglutide, and tirzepatide. In some more particular embodiments, the GLP-1 receptor agonist is selected from exenatide, liraglutide, lixisenatide, albiglutide, dulaglutide, and semaglutide. In some embodiments, the anti-fibrotic drug is selected from BB-3, ensifentrine, pirfenidone, GSK-3008348, PLN-74809, AVID-200, and RES-529, or a pharmaceutically acceptable salt thereof. In some embodiments, the anti-fibrotic drug is administered orally as a tablet. In some embodiments, the anti-fibrotic drug is administered orally as a capsule. In some embodiments, the anti-fibrotic drug is administered orally as an oral suspension. In some embodiments, the anti-fibrotic drug is administered orally as an oral solution.

(1) Anti-fibrotic drug; (2) GLP-1 receptor agonist administered systemically. In some embodiments, the anti-fibrotic drug is selected from rituximab, abatacept, tocilizumab, and rilonacept, or a fragment or biosimilar thereof; BB-3, ensifentrine, pirfenidone, GSK-3008348, PLN-74809, AVID-200, and RES-529, or a pharmaceutically acceptable salt thereof. In some embodiments, the GLP-1 receptor agonist is selected from albiglutide, benaglutide, cotadutide, dulaglutide, ebenatide, efpeglenatide, exenatide, glutazumab, glucagon, liraglutide, lixisenatide, NN-9277, NN-9423, NNC-0090-2746, PF-06882961, PEG-loxenatide, pegapamodutide, semaglutide, and tirzepatide. In some more particular embodiments, the GLP-1 receptor agonist is selected from exenatide, liraglutide, lixisenatide, albiglutide, dulaglutide, and semaglutide. In some embodiments, the GLP-1 receptor agonist is administered systemically via subcutaneous administration. In some embodiments, the GLP-1 receptor agonist is administered systemically via intravenous administration.

(1) PCSK9 inhibitor; (2) statin. In some embodiments, the PCSK9 inhibitor is selected from alirocumab, evolocumab, bococizumab, frovocimab, 1D05-IgG2, evinacumab, SHR-1209, lodelcizumab, IBI-306, LIB-003, JS-002, AK-102, ATH-06, C-8304, and NNC-0385-0434, or a fragment or biosimilar thereof. In some more particular embodiments, the PCSK9 inhibitor is alirocumab or evolocumab, or a fragment or biosimilar thereof. In some embodiments, the statin is selected from atorvastatin, fluvastatin, lovastatin, pravastatin, rosuvastatin, simvastatin, and pitavastatin, or a pharmaceutically acceptable salt thereof.

(1) PCSK9 inhibitor; (2) statin administered orally. In some embodiments, the PCSK9 inhibitor is selected from alirocumab, evolocumab, bococizumab, frovocimab, 1D05-IgG2, evinacumab, SHR-1209, lodelcizumab, IBI-306, LIB-003, JS-002, AK-102, ATH-06, C-8304, and NNC-0385-0434, or a fragment or biosimilar thereof. In some more particular embodiments, the PCSK9 inhibitor is alirocumab or evolocumab, or a fragment or biosimilar thereof. In some embodiments, the statin is selected from atorvastatin, fluvastatin, lovastatin, pravastatin, rosuvastatin, simvastatin, and pitavastatin, or a pharmaceutically acceptable salt thereof. In some embodiments, the statin is administered orally as a tablet. In some embodiments, the statin is administered orally as a capsule. In some embodiments, the statin is administered orally as an oral suspension. In some embodiments, the statin is administered orally as an oral solution.

(1) PCSK9 inhibitor; (2) statin administered systemically. In some embodiments, the PCSK9 inhibitor is selected from alirocumab, evolocumab, bococizumab, frovocimab, 1D05-IgG2, evinacumab, SHR-1209, lodelcizumab, IBI-306, LIB-003, JS-002, AK-102, ATH-06, C-8304, and NNC-0385-0434, or a fragment or biosimilar thereof. In some more particular embodiments, the PCSK9 inhibitor is alirocumab or evolocumab, or a fragment or biosimilar thereof. In some embodiments, the statin is selected from atorvastatin, fluvastatin, lovastatin, pravastatin, rosuvastatin, simvastatin, and pitavastatin, or a pharmaceutically acceptable salt thereof. In some embodiments, the statin is administered systemically via subcutaneous administration. In some embodiments, the statin is administered systemically via intravenous administration.

(1) Statin; (2) PCSK9 inhibitor administered systemically. In some embodiments, the statin is selected from atorvastatin, fluvastatin, lovastatin, pravastatin, rosuvastatin, simvastatin, and pitavastatin, or a pharmaceutically acceptable salt thereof. In some embodiments, the PCSK9 inhibitor is selected from alirocumab, evolocumab, bococizumab, frovocimab, 1D05-IgG2, evinacumab, SHR-1209, lodelcizumab, IBI-306, LIB-003, JS-002, AK-102, ATH-06, C-8304, and NNC-0385-0434, or a fragment or biosimilar thereof. In some more particular embodiments, the PCSK9 inhibitor is alirocumab or evolocumab, or a fragment or biosimilar thereof. In some embodiments, the PCSK9 inhibitor is administered systemically via subcutaneous administration. In some embodiments, the PCSK9 inhibitor is administered systemically via intravenous administration.

Exemplary Conditions or Diseases

The presently described devices and methods can be used to treat numerous conditions and diseases. In some embodiments, the conditions and diseases are inflammatory and immune conditions and diseases. Exemplary inflammatory and immune conditions and diseases include, but are not limited to allergy, asthma, autoimmune diseases, coeliac disease, glomerulonephritis, chronic peptic ulcer, tuberculosis, rheumatoid arthritis, juvenile rheumatoid arthritis, spondylarthritis, psoriasis, psoriatic arthritis, hidradenitis suppurativa, pyoderma gangrenosum, ankylosing spondylitis, periodontitis, ulcerative colitis and Crohn's disease, sinusitis, active hepatitis, non-alcoholic fatty liver disease (NAFLD), non-alcoholic steatohepatitis (NASH), liver fibrosis, liver cirrhosis, alcoholic fatty liver disease, alcoholic hepatitis, alcoholic liver disease, systemic lupus erythematosus (SLE, Lupus), preperfusion injury, multiple sclerosis (MS), transplant rejection, graft versus host disease, dermatomyositis, interstitial lung disease, lupus nephritis, motor neurone disease, osteoarthritis, myasthenia gravis, polymyositis, cholecystitis, scleroderma, Sjoegrens syndrome, and Wegener granulomatosis. In some embodiments, the inflammatory and immune conditions and disease is selected from the group consisting of rheumatoid arthritis, psoriasis, psoriatic arthritis, ankylosing spondylitis, ulcerative colitis and Crohn's disease, non-alcoholic fatty liver disease (NAFLD), non-alcoholic steatohepatitis (NASH), liver fibrosis, liver cirrhosis.

In some embodiments, the conditions and diseases are metabolic, endocrine and cardiovascular conditions and diseases. Exemplary metabolic, endocrine and cardiovascular conditions and diseases include, but are not limited to diabetes mellitus, insulin dependent diabetes, obesity, obstructive sleep apnea, NAFLD, NASH, liver fibrosis, liver cirrhosis, hypertension, pulmonary artery hypertension, primary sclerosing cholangitis, hyperlipidemia, hyperlipoproteinemia type I, lipodystrophy, acromegaly, myocardial infarction, and thromboembolism. In some embodiments, the metabolic, endocrine and cardiovascular conditions and diseases are selected from the group consisting of diabetes mellitus, obesity, NAFLD, NASH, liver fibrosis, liver cirrhosis, and acromegaly.

In some embodiments, the conditions and diseases are hematologic conditions and diseases. Exemplary hematologic conditions and diseases include, but are not limited to hemophilia, Factor VIII deficiency, Factor IX deficiency, Von Willebrands disease, Sickle cell anemia, Iron deficiency anemia, Neurology/Psychiatric, and Parkinsons disease. In some embodiments, the hematologic condition is hemophilia.

In some embodiments, the conditions and diseases are musculoskeletal conditions and diseases. Exemplary musculoskeletal conditions and diseases include, but are not limited to bone resorption; joint injury; male osteoporosis; osteogenesis imperfecta; osteoporosis; and postmenopausal osteoporosis.

In some embodiments, the conditions and diseases are infections. Exemplary infections include, but are not limited to, bacterial infection, bacterial meningitis, bacterial respiratory tract infection, bacterial urinary tract infection, bone and joint infection, cholangitis, complicated skin and skin structure infection, *Neisseria gonorrhoeae* infection, peritonitis, sepsis, abdominal abscess, *Aspergillus* infection, *Candida* infection, fungal infection, *Acinetobacter* infection, appendicitis, *Escherichia coli* infection, febrile neutropenia, *Haemophilus influenzae* infection; *Klebsiella pneumoniae* infection; lower respiratory tract infection; and pelvic inflammatory disease. In some embodiments, the conditions and diseases are infections selected from the group consisting of bacterial infections and sepsis.

In some embodiments, the conditions and diseases are respiratory conditions and diseases. Exemplary respiratory conditions and diseases include, but are not limited to, idiopathic pulmonary fibrosis.

In some embodiments, the conditions and diseases are cancers. Exemplary cancers include, but are not limited to acute myelogenous leukemia; anal tumor; niliary cancer; bladder cancer; bone tumor; breast tumor; central nervous system tumor; chronic lymphocytic leukemia; chronic myelocytic leukemia; diffuse large B-cell lymphoma; endometrioid carcinoma; esophagus tumor; fallopian tube cancer; follicle center lymphoma; germ cell and embryonic cancer; glioblastoma; gonad tumor; head and neck tumor; hematological neoplasm; hepatitis C virus infection; hepatocellular carcinoma; Hodgkins disease; hormone dependent prostate cancer; Kaposis sarcoma; leukoplakia; liver tumor; melanoma; Merkel cell carcinoma; mesothelioma; metastatic bladder cancer; metastatic breast cancer; metastatic esophageal cancer; metastatic head and neck cancer; metastatic liver cancer; metastatic non-small cell lung cancer; metastatic ovary cancer; metastatic pancreas cancer; metastatic prostate cancer; metastatic renal cancer; metastatic renal cell carcinoma; metastatic stomach cancer; mouth tumor; multiple myeloma; myelodysplastic syndrome; neoplastic meningitis; non-Hodgkin lymphoma; non-small-cell lung cancer; ocular melanoma; osteosarcoma; ovary tumor; pancreas tumor; pancreatic ductal adenocarcinoma; peritoneal tumor; prostate tumor; rectal tumor; renal cell carcinoma; salivary gland cancer; sepsis; small-cell lung cancer; soft tissue sarcoma; solid tumor; squamous cell carcinoma; stage III melanoma; stage IV melanoma; stomach tumor; gestis tumor; uterine cervix tumor; uterus tumor; uveal melanoma. In some embodiments, the cancer is selected from the group consisting of leukemia, lymphoma, hepatocellular carcinoma and metastatic cancer.

Inflammatory Conditions or Diseases

In some embodiments, the condition or disease that can be treated with the methods and devices disclosed herein is an inflammatory condition or disease. The presently described devices and methods are based, in part, on the unexpected discovery that administration of an immune modulator into the tissue of a subject's gastrointestinal tract can result in the observation of pharmacodynamics effects in tissues beyond the site of deposition. For example, an immune modulator administered into the tissue (e.g., mucosa or submucosa) of a subject's gastrointestinal tract can result in one or more of the following: changes in anatomical features, including suppressed or reduced development, aggregation, or accumulation of one or more of intestinal lymphoid tissues, isolated lymphoid follicles (ILFs), or intestinal lymphoid aggregates; suppressed immune response, including fewer T cells measured in lymph nodes or lymph tissues (which results in greater T cells forced into circulation, i.e., blood); decreased differentiation of immune cells (e.g., as measured using histology or through the use of a sampling device, or using a sampling device); a decreased level of inflammatory cytokine levels (e.g., as measured using biopsy or through the use of a sampling device); decreased endoscopic scoring; and improved efficacy of treatment for IBD (e.g., using any of the clinical assessments of a treatment for IBD described herein) or other inflammatory conditions of the GI tract or endoderm (e.g., in the liver).

In some embodiments, the presently described devices provide for a higher concentration of α4β7 expressing cells in the periphery (e.g., blood) when an immune modulator is delivered into the GI tissue (e.g., mucosa or submucosa) of one or more parts of the GI tract distal to the stomach (e.g., the small or large intestine) as compared to when the same dose of the immune modulator is orally (without a device), intravenously, or subcutaneously administered. The presently described devices can, e.g., result in trafficked cells being forced out of the local gastrointestinal tissue (including the mucosa) and lymph system, and back into systemic circulation of a subject.

Accordingly, also provided herein are methods of treating a disease or condition that arises in a tissue originating from the endoderm. The endoderm forms the gastrointestinal tract, respiratory tract, endocrine glands, and organs, the auditory system and urinary system. Thus, the present disclosure includes compositions and devices for treating diseases and conditions found in the following tissues that originate from the endoderm (e.g., the stomach, the colon, the liver, the pancreas, the urinary bladder, the epithelial parts of the trachea, the lungs, the pharynx, the thyroid, the parathyroid, the intestines, and the gallbladder). Also provided herein are methods of treating a disease or a condition that arises in a tissue originating from the endoderm (e.g., any of the exemplary diseases or conditions that arise in a tissue originating from the endoderm described herein) that include depositing one or more immune modulators into the tissue of the small intestine using any of the devices or compositions described herein. In a preferred embodiment, the compositions, devices and methods are for treating inflammatory diseases and conditions found in the liver (e.g., NAFLD, NASH, or cirrhosis).

Non-limiting examples of an inflammatory disease or condition that arises in a tissue originating from the endoderm includes gastritis, celiac disease, hepatitis, alcoholic lever disease, fatty liver disease (hepatic steatosis), non-alcoholic fatty liver disease (NASH), cirrhosis, primary schlerosing cholangitis, pancreatitis, insterstitial cystitits, asthma, chronic obstructive pulmonary disease, pulmonary fibrosis, pharyngitis, thyroiditis, hyperthyroidism, parathyroiditis, nephritis, Hashimoto's disease, Addison's disease, Graves' disease, Sjögren syndrome, type 1 diabetes, pelvic inflammatory disease, auditory canal inflammation, tinnitus, vestibular neuritis, otitis media, auditory canal inflammation, tracheitis, cholestatic liver disease, primary biliary schlerosis, liver parenchyma, an inherited metabolic disorder of the liver, Byler syndrome, cerebrotendinous, xanthomatosis, Zellweger's syndrome, neonatal hepatitis, cystic fibrosis, ALGS (Alagilles syndrome), PFIC (progressive familial intrahepatic cholestasis), autoimmune hepatitis, primary biliary cirrhosis (PBC), liver fibrosis, NAFLD, portal hypertension, general cholestasis, such as in jaundice due to drugs or during pregnancy, intra- and extrahepatic cholestasis, such as hereditary forms of cholestasis, such as PFIC1, gall stones and choledocholithiasis, malignancy causing obstruction of the biliary tree, symptoms (scratching, pruritus) due to cholestasis/jaundice, chronic autoimmune liver disease leading to progressive cholestasis, and pruritus of cholestatic liver disease, duodenal ulcers, enteritis (radiation-, chemotherapy-, or infection-induced enteritis), diverticulitis, pouchitis, cholecystitis, and cholangitis. Additional examples of diseases and conditions that arise in a tissue originating from the endoderm are known in the art.

In some embodiments of any of the devices or methods described herein, the methods result in the introduction of the immune modulator to one or more of the following, or the PD effects of the immune modulator (e.g., any of the PD effects of immune modulators described herein) are detectable in one or more of the following: throughout or in part of the paraaortic lymph nodes, throughout or in part of the MALT, throughout or in part of the GALT, throughout or in part of the inferior and superior mesenteric lymph nodes, and in one or more sections or subsections of the subject's gastrointestinal tract that is different than the section or subsection of the subject's gastrointestinal tract where the immune modulator is released. In some embodiments of any of the devices or methods described herein, the devices or methods result in the presence or accumulation of the immune modulator in tissues or organs of the endoderm (e.g., the liver) at higher doses as compared to administration of the immune modulator orally (without a device), intravenously, or subcutaneously.

In some embodiments of any of the methods described herein, the methods do not result in (or do not result in a significant effect in) pharmacodynamics effect(s) (e.g., any of the clinical effects or measurements of an immune modulator described herein) outside of the paraaortic lymph nodes.

In some embodiments of any of the methods described herein, the methods do not result in (or do not result in a significant effect in) pharmacodynamics effect(s) (e.g., any of the clinical effects or measurements of an immune modulator described herein) outside of the MALT.

In some embodiments of any of the methods described herein, the methods do not result in (or do not result in a significant effect in) pharmacodynamics effect(s) (e.g., any of the clinical effects or measurements of an immune modulator described herein) outside of the GALT.

In any of the methods described herein, the subject can be any mammal (e.g., an animal model of any of the diseases described herein).

In some embodiments of any of the methods described herein, the method results in the suppression of the subject's immune response in one or more of the paraaortic lymph nodes.

In some embodiments of any of the methods described herein, the method results in the suppression of the subject's immune response in mucosa-associated lymphoid tissue (MALT).

In some embodiments of any of the methods described herein, the method results in the suppression of the subject's immune response throughout or in part of the gut-associated lymphoid tissue (GALT). For example, in some embodiments of any of the methods described herein, the method results in a reduction of T cells (e.g., any of the T cells described herein, e.g., memory T cells) in Peyer's patches and/or mesenteric lymph nodes found in the GALT. In some embodiments of any of the methods described herein, the method results in a decreased level of T cells (e.g., any of the types of T cells described herein or known in the art) in a section or subsection of the subject's gastrointestinal tract that is different than the section or subsection of the subject's gastrointestinal tract where the immune modulator is released.

In some embodiments of any of the methods described herein, the method results in the suppression or reduction in the development, the aggregation, or accumulation of one or more of intestinal lymphoid tissues, isolated lymphoid follicles (ILFs), or intestinal lymphoid aggregates in mucosa-associated lymphoid tissue (MALT). In some embodiments of any of the methods described herein, the method results in the suppression of the development of one or more of intestinal lymphoid tissues, isolated lymphoid follicles, or intestinal lymphoid aggregates in gut-associated lymphoid tissue (GALT). In some embodiments of any of the methods described herein, the method results in the suppression of the immune response in one or more sections or subsections of the subject's gastrointestinal tract that is different than the section or subsection of the subject's gastrointestinal tract where the drug is released.

In some embodiments of any of the methods described herein, the methods result in pharmacodynamics effects proximal ("upstream") to the site of disease in the subject. For example, in some embodiments of any of the methods described herein, the immune modulator is deposited in the tissue of the small intestine (e.g., duodenum or jejunum), but pharmacodynamics effects of the immune modulator are observed in the liver. In some embodiments of any of the methods described herein, the immune modulator is deposited in the tissue of the small intestine (e.g., the duodenum or jejunum) and immune suppression is observed throughout the mesenteric lymph system and other systems of the paraaortic lymph nodes, including the hepatic lymph nodes of the celiac group of the preaortic lymph nodes (preaortic lymph nodes are part of the paraaortic lymph nodes). In some embodiments of any of the methods described herein, the immune modulator is deposited in the small intestine (e.g., duodenum, jejunum, or ileum) or colon (e.g., ascending colon, transverse colon, descending colon, rectum, or cecum), but pharmacodynamics effects of the immune modulator are throughout or in part of the MALT, GALT, Peyer's patches, mesenteric lymph nodes, paraaortic lymph nodes, or any of the other tissues originating from the endoderm described herein or known in the art, in the mammal.

In some embodiments of any of the methods described herein, the method results in a decreased level or a decreased level of activation of one or more of the following immune cells that participate in mucosal immune response in a mammal: microfold cells (M cells), antigen-presenting cells (e.g., B-lymphocytes, dendritic cells, and macrophages), and effector cells (e.g., T-lymphocytes).

Microfold cells (M cells) are found in the gut-associated lymphoid tissue (GALT) of the Peyer's patches in the small intestine. M cells allow for the transport of microbes and particles across the epithelial cell layer from the gut lumen to the lamina propria where interactions with immune cells can take place. M cells provide for the initiation of mucosal immunity responses on the apical membrane by delivering antigens to antigen-presenting cells.

Antigen-presenting cells (APCs) include B-lymphocytes, dendritic cells, and macrophages. B-lymphocytes, also called B-cells, can internalize antigen that binds to their B-cell receptor. Dendritic cells have the broadest range of antigen presentation and are necessary for activation of naïve T cells. Dendritic cells present antigen to both helper and cytotoxic T cells. Macrophages can be stimulated by T-cell secretion of interferon gamma. After this activation, macrophages are able to express major histocompatibility complex (MHC) class II and co-stimulatory molecules, and can present phagocytosed peptide fragments to helper T cells. The activation of macrophages can assist pathogen-infected macrophages in clearing the infection.

MHCs bind antigens derived from pathogens and display them on the cell surface for recognition by appropriate T-cells. MHC class I presents antigens from intracellular pathogens, such as viruses and bacteria. MHC class II presents antigens from phagocytosed/pinocytosed pathogens.

Effector cells, as used herein, include T-lymphocytes, including $CD4^+$ (also called helper T cells), $CD8^+$ (also called cytotoxic T cells), $CD45Rb^-$ (more IL-10 and less $TNF\alpha$ in IBD) as compared with $CD4^+CD45Rb^+$, and $CD44^+$ T cells. CD44 participates in lymphocytes activation, recirculation, and homing, and is an indicative marker for effector memory T cells.

In some embodiments of any of the devices or methods described herein, the therapeutic is an anti-Siglec-8 antibody. Anti-Siglec-8 antibodies deplete eosinophils and inhibit mast cells and may be useful for the treatment of eosinophilic gastritis and duodenitis. In some embodiments, the anti-Siglec-8 antibody is AK002 (lirentelimab). AK002 is a humanized, nonfucosylated IgG1 anti-Siglec-8 monoclonal antibody that depletes eosinophils through natural killer cell—mediated antibody-dependent cellular cytotoxicity (in the blood) and apoptosis (in tissues). See Dellon, Evan S., et al. "Anti-Siglec-8 Antibody for Eosinophilic Gastritis and Duodenitis." *New England Journal of Medicine* 383.17 (2020): 1624-1634.

Exemplary Methods

Provided herein are methods of treating a disease or condition in a subject in need thereof. In some embodiments, the method includes administering a dispensable substance to the gastrointestinal (GI) tract of the subject, where the administration includes orally administering an ingestible device containing the dispensable substance to the subject, where the dispensable substance contains a pharmaceutical formulation including a therapeutically effective amount of a therapeutic agent, and releasing the dispensable substance from the ingestible device as a jet to a desired location of the GI tract of the subject, thereby directly delivering the dispensable substance to the GI tract of the subject. In some embodiments, the administration is trans-epithelial. In some embodiments, the administration is epithelial. In some embodiments, the administration is topical.

In some embodiments, the direct delivery of the dispensable substance to the submucosa and/or the mucosa (e.g., into the lamina propria) of the subject provides systemic uptake of the therapeutic agent.

In some embodiments, the desired location of the GI tract is the small intestine. In some embodiments, the desired location of the GI tract is one or more of the duodenum, the jejunum, and the ileum. In some embodiments, a portion of the dispensable substance is delivered to the mucosa of the GI tract of the subject.

The disease or condition treatable by the methods provided herein can be any disease or condition described herein. In some embodiments, the disease or condition is selected from an autoimmune disease or condition, fibrosis, rheumatoid arthritis, non-alcoholic steatohepatitis (NASH), non-alcoholic fatty liver disease (NAFLD), an inflammatory disease or disorder (e.g., inflammatory bowel disease (IBD)), hepatocellular carcinoma, a growth disorder (e.g., a growth hormone deficiency or disorder (GHD)), an endocrine or metabolic disease or condition (e.g., diabetes, insulin resistance, hyperglycemia, hyperlipidemia, obesity, hepatic steatosis, hyperinsulinemia, obstructive sleep apnea, liver fibrosis, liver cirrhosis, hypertension, pulmonary artery hypertension, primary sclerosing cholangitis, hyperlipoproteinemia type I, hypercholesterolemia, lipodystrophy, acromegaly, myocardial infarction, and thromboembolism), hemophilia (e.g., hemophilia A, hemophilia B, Von Willebrand disease), and combinations thereof.

In some embodiments, the disease or condition is diabetes, for example, type I or type II diabetes. In some embodiments, the diabetes is selected from diabetes with Alzheimer's disease, diabetes with dementia, diabetes with Alzheimer's disease and dementia, diabetes with obesity, diabetes with NAFLD, diabetes with NASH, diabetes with NAFLD and NASH, and diabetes with a cardiovascular disease.

The therapeutic agent suitable for use in the methods described herein can be any therapeutic agent disclosed herein. In some embodiments, the therapeutic agent is a glucagon receptor agonist or a glucagon-like peptide-1 (GLP-1) receptor agonist. In some embodiments, the therapeutic agent is a growth hormone. In some embodiments, the therapeutic agent is an insulin. In some embodiments, the therapeutic agent is a TNF-alpha inhibitor. In some embodiments, the therapeutic agent is a peptide YY ligand. In some embodiments, the therapeutic agent is an amylin analog. In some embodiments, the therapeutic agent is an alternative coagulation promotor (ACP).

In some embodiments of the methods provided herein, the pharmaceutical formulation is a fluid. In some embodiments, the pharmaceutical formulation is a solution or suspension. In some embodiments, the pharmaceutical formulation has a viscosity of less than or equal to about 100 cP (e.g., less than or equal to about 10 cP). In some embodiments, the pharmaceutical formulation has a viscosity of at least about 0.5 cP (e.g., at least about 0.8 cP).

Particular Medical Approaches

Some embodiments of the invention relate to particular medical approaches, which use the ingestible device to deliver a particular therapeutic agent, or class of agent, by a particular delivery mode to treat a particular disease, or class of disease. Particular medical approaches are disclosed in Table 18. All therapeutic agents disclosed in Table 18 optionally include the pharmaceutically acceptable salts and solvates thereof in the case of small molecules, peptides, and nucleic acids, and the biosimilars thereof, and/or glycosylation variants thereof, in the case of biologics such as antibodies, unless expressly indicated otherwise.

TABLE 18

Particular medical approaches

| Approach | Therapeutic agent | Disease | Delivery mode |
|---|---|---|---|
| 1 | GLP-1 receptor agonist | A disease or condition responsive to treatment with a GLP-1 receptor agonist | Trans-epithelial |
| 2 | GLP-1 receptor agonist | Metabolic or endocrine disorder | Trans-epithelial |
| 3 | GLP-1 receptor agonist | Diabetes | Trans-epithelial |
| 4 | GLP-1 receptor agonist | Diabetes with Alzheimer's disease, diabetes with dementia, diabetes with Alzheimer's disease and dementia, diabetes with obesity, diabetes with non-alcoholic fatty liver disease (NAFLD), diabetes with non-alcoholic steatohepatitis (NASH), diabetes with NAFLD and NASH, or diabetes with a cardiovascular disease | Trans-epithelial |
| 5 | GLP-1 receptor agonist | A liver disease or disorder | Trans-epithelial |
| 6 | GLP-1 receptor agonist | Compensated liver cirrhosis | Trans-epithelial |
| 7 | GLP-1 receptor agonist | Non-alcoholic steatohepatitis (NASH) or non-alcoholic fatty liver disease (NAFLD) | Trans-epithelial |
| 8 | GLP-1 receptor agonist | A binge eating disorder | Trans-epithelial |
| 9 | GLP-1 receptor agonist | Hyperglycemia | Trans-epithelial |
| 10 | GLP-1 receptor agonist | Postprandial hyperglycemia | Trans-epithelial |
| 11 | GLP-1 receptor agonist | Nicotine dependence | Trans-epithelial |
| 12 | GLP-1 receptor agonist | A central nervous system (CNS) disorder | Trans-epithelial |

TABLE 18-continued

Particular medical approaches

| Approach | Therapeutic agent | Disease | Delivery mode |
|---|---|---|---|
| 13 | GLP-1 receptor agonist | Alzheimer's disease or Parkinson's disease | Trans-epithelial |
| 14 | semaglutide | A disease or condition responsive to treatment with a GLP-1 receptor agonist | Trans-epithelial |
| 15 | semaglutide | Metabolic or endocrine disorder | Trans-epithelial |
| 16 | semaglutide | Diabetes | Trans-epithelial |
| 17 | semaglutide | Diabetes with Alzheimer's disease, diabetes with dementia, diabetes with Alzheimer's disease and dementia, diabetes with obesity, diabetes with non-alcoholic fatty liver disease (NAFLD), diabetes with non-alcoholic steatohepatitis (NASH), diabetes with NAFLD and NASH, or diabetes with a cardiovascular disease | Trans-epithelial |
| 18 | semaglutide | A liver disease or disorder | Trans-epithelial |
| 19 | semaglutide | Compensated liver cirrhosis | Trans-epithelial |
| 20 | semaglutide | Non-alcoholic steatohepatitis (NASH) or non-alcoholic fatty liver disease (NAFLD) | Trans-epithelial |
| 21 | semaglutide | A binge eating disorder | Trans-epithelial |
| 22 | semaglutide | Hyperglycemia | Trans-epithelial |
| 23 | semaglutide | Postprandial hyperglycemia | Trans-epithelial |
| 24 | semaglutide | Nicotine dependence | Trans-epithelial |
| 25 | semaglutide | A central nervous system (CNS) disorder | Trans-epithelial |
| 26 | semaglutide | Alzheimer's disease or Parkinson's disease | Trans-epithelial |
| 27 | dulaglutide | A disease or condition responsive to treatment with a GLP-1 receptor agonist | Trans-epithelial |
| 28 | dulaglutide | Metabolic or endocrine disorder | Trans-epithelial |
| 29 | dulaglutide | Diabetes | Trans-epithelial |
| 30 | dulaglutide | Diabetes with Alzheimer's disease, diabetes with dementia, diabetes with Alzheimer's disease and dementia, diabetes with obesity, diabetes with non-alcoholic fatty liver disease (NAFLD), diabetes with non-alcoholic steatohepatitis (NASH), diabetes with NAFLD and NASH, or diabetes with a cardiovascular disease | Trans-epithelial |
| 31 | dulaglutide | A liver disease or disorder | Trans-epithelial |
| 32 | dulaglutide | Compensated liver cirrhosis | Trans-epithelial |
| 33 | dulaglutide | Non-alcoholic steatohepatitis (NASH) or non-alcoholic fatty liver disease (NAFLD) | Trans-epithelial |
| 34 | dulaglutide | A binge eating disorder | Trans-epithelial |
| 35 | dulaglutide | Hyperglycemia | Trans-epithelial |
| 36 | dulaglutide | Postprandial hyperglycemia | Trans-epithelial |
| 37 | dulaglutide | Nicotine dependence | Trans-epithelial |
| 38 | dulaglutide | A central nervous system (CNS) disorder | Trans-epithelial |
| 39 | dulaglutide | Alzheimer's disease or Parkinson's disease | Trans-epithelial |
| 40 | albiglutide | A disease or condition responsive to treatment with a GLP-1 receptor agonist | Trans-epithelial |
| 41 | albiglutide | Metabolic or endocrine disorder | Trans-epithelial |
| 42 | albiglutide | Diabetes | Trans-epithelial |
| 43 | albiglutide | Diabetes with Alzheimer's disease, diabetes with dementia, diabetes with Alzheimer's disease and dementia, diabetes with obesity, diabetes with non-alcoholic fatty liver disease (NAFLD), diabetes with non-alcoholic steatohepatitis (NASH), diabetes with NAFLD and NASH, or diabetes with a cardiovascular disease | Trans-epithelial |
| 44 | albiglutide | A liver disease or disorder | Trans-epithelial |
| 45 | albiglutide | Compensated liver cirrhosis | Trans-epithelial |
| 46 | albiglutide | Non-alcoholic steatohepatitis (NASH) or non-alcoholic fatty liver disease (NAFLD) | Trans-epithelial |
| 47 | albiglutide | A binge eating disorder | Trans-epithelial |

TABLE 18-continued

| Particular medical approaches | | | |
|---|---|---|---|
| Approach | Therapeutic agent | Disease | Delivery mode |
| 48 | albiglutide | Hyperglycemia | Trans-epithelial |
| 49 | albiglutide | Postprandial hyperglycemia | Trans-epithelial |
| 50 | albiglutide | Nicotine dependence | Trans-epithelial |
| 51 | albiglutide | A central nervous system (CNS) disorder | Trans-epithelial |
| 52 | albiglutide | Alzheimer's disease or Parkinson's disease | Trans-epithelial |
| 53 | exenatide | A disease or condition responsive to treatment with a GLP-1 receptor agonist | Trans-epithelial |
| 54 | exenatide | Metabolic or endocrine disorder | Trans-epithelial |
| 55 | exenatide | Diabetes | Trans-epithelial |
| 56 | exenatide | Diabetes with Alzheimer's disease, diabetes with dementia, diabetes with Alzheimer's disease and dementia, diabetes with obesity, diabetes with non-alcoholic fatty liver disease (NAFLD), diabetes with non-alcoholic steatohepatitis (NASH), diabetes with NAFLD and NASH, or diabetes with a cardiovascular disease | Trans-epithelial |
| 57 | exenatide | A liver disease or disorder | Trans-epithelial |
| 58 | exenatide | Compensated liver cirrhosis | Trans-epithelial |
| 59 | exenatide | Non-alcoholic steatohepatitis (NASH) or non-alcoholic fatty liver disease (NAFLD) | Trans-epithelial |
| 60 | exenatide | A binge eating disorder | Trans-epithelial |
| 61 | exenatide | Hyperglycemia | Trans-epithelial |
| 62 | exenatide | Postprandial hyperglycemia | Trans-epithelial |
| 63 | exenatide | Nicotine dependence | Trans-epithelial |
| 64 | exenatide | A central nervous system (CNS) disorder | Trans-epithelial |
| 65 | exenatide | Alzheimer's disease or Parkinson's disease | Trans-epithelial |
| 66 | liraglutide | A disease or condition responsive to treatment with a GLP-1 receptor agonist | Trans-epithelial |
| 67 | liraglutide | Metabolic or endocrine disorder | Trans-epithelial |
| 68 | liraglutide | Diabetes | Trans-epithelial |
| 69 | liraglutide | Diabetes with Alzheimer's disease, diabetes with dementia, diabetes with Alzheimer's disease and dementia, diabetes with obesity, diabetes with non-alcoholic fatty liver disease (NAFLD), diabetes with non-alcoholic steatohepatitis (NASH), diabetes with NAFLD and NASH, or diabetes with a cardiovascular disease | Trans-epithelial |
| 70 | liraglutide | A liver disease or disorder | Trans-epithelial |
| 71 | liraglutide | Compensated liver cirrhosis | Trans-epithelial |
| 72 | liraglutide | Non-alcoholic steatohepatitis (NASH) or non-alcoholic fatty liver disease (NAFLD) | Trans-epithelial |
| 73 | liraglutide | A binge eating disorder | Trans-epithelial |
| 74 | liraglutide | Hyperglycemia | Trans-epithelial |
| 75 | liraglutide | Postprandial hyperglycemia | Trans-epithelial |
| 76 | liraglutide | Nicotine dependence | Trans-epithelial |
| 77 | liraglutide | A central nervous system (CNS) disorder | Trans-epithelial |
| 78 | liraglutide | Alzheimer's disease or Parkinson's disease | Trans-epithelial |
| 79 | lixisenatide | A disease or condition responsive to treatment with a GLP-1 receptor agonist | Trans-epithelial |
| 80 | lixisenatide | Metabolic or endocrine disorder | Trans-epithelial |
| 81 | lixisenatide | Diabetes | Trans-epithelial |
| 82 | lixisenatide | Diabetes with Alzheimer's disease, diabetes with dementia, diabetes with Alzheimer's disease and dementia, diabetes with obesity, diabetes with non-alcoholic fatty liver disease (NAFLD), diabetes with non-alcoholic steatohepatitis (NASH), diabetes with NAFLD and NASH, or diabetes with a cardiovascular disease | Trans-epithelial |
| 83 | lixisenatide | A liver disease or disorder | Trans-epithelial |

TABLE 18-continued

Particular medical approaches

| Approach | Therapeutic agent | Disease | Delivery mode |
|---|---|---|---|
| 84 | lixisenatide | Compensated liver cirrhosis | Trans-epithelial |
| 85 | lixisenatide | Non-alcoholic steatohepatitis (NASH) or non-alcoholic fatty liver disease (NAFLD) | Trans-epithelial |
| 86 | lixisenatide | A binge eating disorder | Trans-epithelial |
| 87 | lixisenatide | Hyperglycemia | Trans-epithelial |
| 88 | lixisenatide | Postprandial hyperglycemia | Trans-epithelial |
| 89 | lixisenatide | Nicotine dependence | Trans-epithelial |
| 90 | lixisenatide | A central nervous system (CNS) disorder | Trans-epithelial |
| 91 | lixisenatide | Alzheimer's disease or Parkinson's disease | Trans-epithelial |
| 92 | NNC-0090-2746 | A disease or condition responsive to treatment with a GLP-1 receptor agonist | Trans-epithelial |
| 93 | NNC-0090-2746 | Metabolic or endocrine disorder | Trans-epithelial |
| 94 | NNC-0090-2746 | Diabetes | Trans-epithelial |
| 95 | NNC-0090-2746 | Diabetes with Alzheimer's disease, diabetes with dementia, diabetes with Alzheimer's disease and dementia, diabetes with obesity, diabetes with non-alcoholic fatty liver disease (NAFLD), diabetes with non-alcoholic steatohepatitis (NASH), diabetes with NAFLD and NASH, or diabetes with a cardiovascular disease | Trans-epithelial |
| 96 | NNC-0090-2746 | A liver disease or disorder | Trans-epithelial |
| 97 | NNC-0090-2746 | Compensated liver cirrhosis | Trans-epithelial |
| 98 | NNC-0090-2746 | Non-alcoholic steatohepatitis (NASH) or non-alcoholic fatty liver disease (NAFLD) | Trans-epithelial |
| 99 | NNC-0090-2746 | A binge eating disorder | Trans-epithelial |
| 100 | NNC-0090-2746 | Hyperglycemia | Trans-epithelial |
| 101 | NNC-0090-2746 | Postprandial hyperglycemia | Trans-epithelial |
| 102 | NNC-0090-2746 | Nicotine dependence | Trans-epithelial |
| 103 | NNC-0090-2746 | A central nervous system (CNS) disorder | Trans-epithelial |
| 104 | NNC-0090-2746 | Alzheimer's disease or Parkinson's disease | Trans-epithelial |
| 105 | glucagon | A disease or condition responsive to treatment with a GLP-1 receptor agonist | Trans-epithelial |
| 106 | glucagon | Metabolic or endocrine disorder | Trans-epithelial |
| 107 | glucagon | Diabetes | Trans-epithelial |
| 108 | glucagon | Diabetes with Alzheimer's disease, diabetes with dementia, diabetes with Alzheimer's disease and dementia, diabetes with obesity, diabetes with non-alcoholic fatty liver disease (NAFLD), diabetes with non-alcoholic steatohepatitis (NASH), diabetes with NAFLD and NASH, or diabetes with a cardiovascular disease | Trans-epithelial |
| 109 | glucagon | A liver disease or disorder | Trans-epithelial |
| 110 | glucagon | Compensated liver cirrhosis | Trans-epithelial |
| 111 | glucagon | Non-alcoholic steatohepatitis (NASH) or non-alcoholic fatty liver disease (NAFLD) | Trans-epithelial |
| 112 | glucagon | A binge eating disorder | Trans-epithelial |
| 113 | glucagon | Hyperglycemia | Trans-epithelial |
| 114 | glucagon | Postprandial hyperglycemia | Trans-epithelial |
| 115 | glucagon | Nicotine dependence | Trans-epithelial |
| 116 | glucagon | A central nervous system (CNS) disorder | Trans-epithelial |
| 117 | glucagon | Alzheimer's disease or Parkinson's disease | Trans-epithelial |
| 118 | NN-9277 | A disease or condition responsive to treatment with a GLP-1 receptor agonist | Trans-epithelial |
| 119 | NN-9277 | Metabolic or endocrine disorder | Trans-epithelial |
| 120 | NN-9277 | Diabetes | Trans-epithelial |
| 121 | NN-9277 | Diabetes with Alzheimer's disease, diabetes with dementia, diabetes with Alzheimer's disease and dementia, diabetes with obesity, diabetes with non-alcoholic fatty liver disease | Trans-epithelial |

TABLE 18-continued

Particular medical approaches

| Approach | Therapeutic agent | Disease | Delivery mode |
|---|---|---|---|
| | | (NAFLD), diabetes with non-alcoholic steatohepatitis (NASH), diabetes with NAFLD and NASH, or diabetes with a cardiovascular disease | |
| 122 | NN-9277 | A liver disease or disorder | Trans-epithelial |
| 123 | NN-9277 | Compensated liver cirrhosis | Trans-epithelial |
| 124 | NN-9277 | Non-alcoholic steatohepatitis (NASH) or non-alcoholic fatty liver disease (NAFLD) | Trans-epithelial |
| 125 | NN-9277 | A binge eating disorder | Trans-epithelial |
| 126 | NN-9277 | Hyperglycemia | Trans-epithelial |
| 127 | NN-9277 | Postprandial hyperglycemia | Trans-epithelial |
| 128 | NN-9277 | Nicotine dependence | Trans-epithelial |
| 129 | NN-9277 | A central nervous system (CNS) disorder | Trans-epithelial |
| 130 | NN-9277 | Alzheimer's disease or Parkinson's disease | Trans-epithelial |
| 131 | NN-9423 | A disease or condition responsive to treatment with a GLP-1 receptor agonist | Trans-epithelial |
| 132 | NN-9423 | Metabolic or endocrine disorder | Trans-epithelial |
| 133 | NN-9423 | Diabetes | Trans-epithelial |
| 134 | NN-9423 | Diabetes with Alzheimer's disease, diabetes with dementia, diabetes with Alzheimer's disease and dementia, diabetes with obesity, diabetes with non-alcoholic fatty liver disease (NAFLD), diabetes with non-alcoholic steatohepatitis (NASH), diabetes with NAFLD and NASH, or diabetes with a cardiovascular disease | Trans-epithelial |
| 135 | NN-9423 | A liver disease or disorder | Trans-epithelial |
| 136 | NN-9423 | Compensated liver cirrhosis | Trans-epithelial |
| 137 | NN-9423 | Non-alcoholic steatohepatitis (NASH) or non-alcoholic fatty liver disease (NAFLD) | Trans-epithelial |
| 138 | NN-9423 | A binge eating disorder | Trans-epithelial |
| 139 | NN-9423 | Hyperglycemia | Trans-epithelial |
| 140 | NN-9423 | Postprandial hyperglycemia | Trans-epithelial |
| 141 | NN-9423 | Nicotine dependence | Trans-epithelial |
| 142 | NN-9423 | A central nervous system (CNS) disorder | Trans-epithelial |
| 143 | NN-9423 | Alzheimer's disease or Parkinson's disease | Trans-epithelial |
| 144 | GLP-1 receptor agonist | A disease or condition responsive to treatment with a GLP-1 receptor agonist | Epithelial |
| 145 | GLP-1 receptor agonist | Metabolic or endocrine disorder | Epithelial |
| 146 | GLP-1 receptor agonist | Diabetes | Epithelial |
| 147 | GLP-1 receptor agonist | Diabetes with Alzheimer's disease, diabetes with dementia, diabetes with Alzheimer's disease and dementia, diabetes with obesity, diabetes with non-alcoholic fatty liver disease (NAFLD), diabetes with non-alcoholic steatohepatitis (NASH), diabetes with NAFLD and NASH, or diabetes with a cardiovascular disease | Epithelial |
| 148 | GLP-1 receptor agonist | A liver disease or disorder | Epithelial |
| 149 | GLP-1 receptor agonist | Compensated liver cirrhosis | Epithelial |
| 150 | GLP-1 receptor agonist | Non-alcoholic steatohepatitis (NASH) or non-alcoholic fatty liver disease (NAFLD) | Epithelial |
| 151 | GLP-1 receptor agonist | A binge eating disorder | Epithelial |
| 152 | GLP-1 receptor agonist | Hyperglycemia | Epithelial |
| 153 | GLP-1 receptor agonist | Postprandial hyperglycemia | Epithelial |
| 154 | GLP-1 receptor agonist | Nicotine dependence | Epithelial |

TABLE 18-continued

Particular medical approaches

| Approach | Therapeutic agent | Disease | Delivery mode |
|---|---|---|---|
| 155 | GLP-1 receptor agonist | A central nervous system (CNS) disorder | Epithelial |
| 156 | GLP-1 receptor agonist | Alzheimer's disease or Parkinson's disease | Epithelial |
| 157 | semaglutide | A disease or condition responsive to treatment with a GLP-1 receptor agonist | Epithelial |
| 158 | semaglutide | Metabolic or endocrine disorder | Epithelial |
| 159 | semaglutide | Diabetes | Epithelial |
| 160 | semaglutide | Diabetes with Alzheimer's disease, diabetes with dementia, diabetes with Alzheimer's disease and dementia, diabetes with obesity, diabetes with non-alcoholic fatty liver disease (NAFLD), diabetes with non-alcoholic steatohepatitis (NASH), diabetes with NAFLD and NASH, or diabetes with a cardiovascular disease | Epithelial |
| 161 | semaglutide | A liver disease or disorder | Epithelial |
| 162 | semaglutide | Compensated liver cirrhosis | Epithelial |
| 163 | semaglutide | Non-alcoholic steatohepatitis (NASH) or non-alcoholic fatty liver disease (NAFLD) | Epithelial |
| 164 | semaglutide | A binge eating disorder | Epithelial |
| 165 | semaglutide | Hyperglycemia | Epithelial |
| 166 | semaglutide | Postprandial hyperglycemia | Epithelial |
| 167 | semaglutide | Nicotine dependence | Epithelial |
| 168 | semaglutide | A central nervous system (CNS) disorder | Epithelial |
| 169 | semaglutide | Alzheimer's disease or Parkinson's disease | Epithelial |
| 170 | dulaglutide | A disease or condition responsive to treatment with a GLP-1 receptor agonist | Epithelial |
| 171 | dulaglutide | Metabolic or endocrine disorder | Epithelial |
| 172 | dulaglutide | Diabetes | Epithelial |
| 173 | dulaglutide | Diabetes with Alzheimer's disease, diabetes with dementia, diabetes with Alzheimer's disease and dementia, diabetes with obesity, diabetes with non-alcoholic fatty liver disease (NAFLD), diabetes with non-alcoholic steatohepatitis (NASH), diabetes with NAFLD and NASH, or diabetes with a cardiovascular disease | Epithelial |
| 174 | dulaglutide | A liver disease or disorder | Epithelial |
| 175 | dulaglutide | Compensated liver cirrhosis | Epithelial |
| 176 | dulaglutide | Non-alcoholic steatohepatitis (NASH) or non-alcoholic fatty liver disease (NAFLD) | Epithelial |
| 177 | dulaglutide | A binge eating disorder | Epithelial |
| 178 | dulaglutide | Hyperglycemia | Epithelial |
| 179 | dulaglutide | Postprandial hyperglycemia | Epithelial |
| 180 | dulaglutide | Nicotine dependence | Epithelial |
| 181 | dulaglutide | A central nervous system (CNS) disorder | Epithelial |
| 182 | dulaglutide | Alzheimer's disease or Parkinson's disease | Epithelial |
| 183 | albiglutide | A disease or condition responsive to treatment with a GLP-1 receptor agonist | Epithelial |
| 184 | albiglutide | Metabolic or endocrine disorder | Epithelial |
| 185 | albiglutide | Diabetes | Epithelial |
| 186 | albiglutide | Diabetes with Alzheimer's disease, diabetes with dementia, diabetes with Alzheimer's disease and dementia, diabetes with obesity, diabetes with non-alcoholic fatty liver disease (NAFLD), diabetes with non-alcoholic steatohepatitis (NASH), diabetes with NAFLD and NASH, or diabetes with a cardiovascular disease | Epithelial |

TABLE 18-continued

| | | Particular medical approaches | |
|---|---|---|---|
| Approach | Therapeutic agent | Disease | Delivery mode |
| 187 | albiglutide | A liver disease or disorder | Epithelial |
| 188 | albiglutide | Compensated liver cirrhosis | Epithelial |
| 189 | albiglutide | Non-alcoholic steatohepatitis (NASH) or non-alcoholic fatty liver disease (NAFLD) | Epithelial |
| 190 | albiglutide | A binge eating disorder | Epithelial |
| 191 | albiglutide | Hyperglycemia | Epithelial |
| 192 | albiglutide | Postprandial hyperglycemia | Epithelial |
| 193 | albiglutide | Nicotine dependence | Epithelial |
| 194 | albiglutide | A central nervous system (CNS) disorder | Epithelial |
| 195 | albiglutide | Alzheimer's disease or Parkinson's disease | Epithelial |
| 196 | exenatide | A disease or condition responsive to treatment with a GLP-1 receptor agonist | Epithelial |
| 197 | exenatide | Metabolic or endocrine disorder | Epithelial |
| 198 | exenatide | Diabetes | Epithelial |
| 199 | exenatide | Diabetes with Alzheimer's disease, diabetes with dementia, diabetes with Alzheimer's disease and dementia, diabetes with obesity, diabetes with non-alcoholic fatty liver disease (NAFLD), diabetes with non-alcoholic steatohepatitis (NASH), diabetes with NAFLD and NASH, or diabetes with a cardiovascular disease | Epithelial |
| 200 | exenatide | A liver disease or disorder | Epithelial |
| 201 | exenatide | Compensated liver cirrhosis | Epithelial |
| 202 | exenatide | Non-alcoholic steatohepatitis (NASH) or non-alcoholic fatty liver disease (NAFLD) | Epithelial |
| 203 | exenatide | A binge eating disorder | Epithelial |
| 204 | exenatide | Hyperglycemia | Epithelial |
| 205 | exenatide | Postprandial hyperglycemia | Epithelial |
| 206 | exenatide | Nicotine dependence | Epithelial |
| 207 | exenatide | A central nervous system (CNS) disorder | Epithelial |
| 208 | exenatide | Alzheimer's disease or Parkinson's disease | Epithelial |
| 209 | liraglutide | A disease or condition responsive to treatment with a GLP-1 receptor agonist | Epithelial |
| 210 | liraglutide | Metabolic or endocrine disorder | Epithelial |
| 211 | liraglutide | Diabetes | Epithelial |
| 212 | liraglutide | Diabetes with Alzheimer's disease, diabetes with dementia, diabetes with Alzheimer's disease and dementia, diabetes with obesity, diabetes with non-alcoholic fatty liver disease (NAFLD), diabetes with non-alcoholic steatohepatitis (NASH), diabetes with NAFLD and NASH, or diabetes with a cardiovascular disease | Epithelial |
| 213 | liraglutide | A liver disease or disorder | Epithelial |
| 214 | liraglutide | Compensated liver cirrhosis | Epithelial |
| 215 | liraglutide | Non-alcoholic steatohepatitis (NASH) or non-alcoholic fatty liver disease (NAFLD) | Epithelial |
| 216 | liraglutide | A binge eating disorder | Epithelial |
| 217 | liraglutide | Hyperglycemia | Epithelial |
| 218 | liraglutide | Postprandial hyperglycemia | Epithelial |
| 219 | liraglutide | Nicotine dependence | Epithelial |
| 220 | liraglutide | A central nervous system (CNS) disorder | Epithelial |
| 221 | liraglutide | Alzheimer's disease or Parkinson's disease | Epithelial |
| 222 | lixisenatide | A disease or condition responsive to treatment with a GLP-1 receptor agonist | Epithelial |

TABLE 18-continued

Particular medical approaches

| Approach | Therapeutic agent | Disease | Delivery mode |
|---|---|---|---|
| 223 | lixisenatide | Metabolic or endocrine disorder | Epithelial |
| 224 | lixisenatide | Diabetes | Epithelial |
| 225 | lixisenatide | Diabetes with Alzheimer's disease, diabetes with dementia, diabetes with Alzheimer's disease and dementia, diabetes with obesity, diabetes with non-alcoholic fatty liver disease (NAFLD), diabetes with non-alcoholic steatohepatitis (NASH), diabetes with NAFLD and NASH, or diabetes with a cardiovascular disease | Epithelial |
| 226 | lixisenatide | A liver disease or disorder | Epithelial |
| 227 | lixisenatide | Compensated liver cirrhosis | Epithelial |
| 228 | lixisenatide | Non-alcoholic steatohepatitis (NASH) or non-alcoholic fatty liver disease (NAFLD) | Epithelial |
| 229 | lixisenatide | A binge eating disorder | Epithelial |
| 230 | lixisenatide | Hyperglycemia | Epithelial |
| 231 | lixisenatide | Postprandial hyperglycemia | Epithelial |
| 232 | lixisenatide | Nicotine dependence | Epithelial |
| 233 | lixisenatide | A central nervous system (CNS) disorder | Epithelial |
| 234 | lixisenatide | Alzheimer's disease or Parkinson's disease | Epithelial |
| 235 | NNC-0090-2746 | A disease or condition responsive to treatment with a GLP-1 receptor agonist | Epithelial |
| 236 | NNC-0090-2746 | Metabolic or endocrine disorder | Epithelial |
| 237 | NNC-0090-2746 | Diabetes | Epithelial |
| 238 | NNC-0090-2746 | Diabetes with Alzheimer's disease, diabetes with dementia, diabetes with Alzheimer's disease and dementia, diabetes with obesity, diabetes with non-alcoholic fatty liver disease (NAFLD), diabetes with non-alcoholic steatohepatitis (NASH), diabetes with NAFLD and NASH, or diabetes with a cardiovascular disease | Epithelial |
| 239 | NNC-0090-2746 | A liver disease or disorder | Epithelial |
| 240 | NNC-0090-2746 | Compensated liver cirrhosis | Epithelial |
| 241 | NNC-0090-2746 | Non-alcoholic steatohepatitis (NASH) or non-alcoholic fatty liver disease (NAFLD) | Epithelial |
| 242 | NNC-0090-2746 | A binge eating disorder | Epithelial |
| 243 | NNC-0090-2746 | Hyperglycemia | Epithelial |
| 244 | NNC-0090-2746 | Postprandial hyperglycemia | Epithelial |
| 245 | NNC-0090-2746 | Nicotine dependence | Epithelial |
| 246 | NNC-0090-2746 | A central nervous system (CNS) disorder | Epithelial |
| 247 | NNC-0090-2746 | Alzheimer's disease or Parkinson's disease | Epithelial |
| 248 | glucagon | A disease or condition responsive to treatment with a GLP-1 receptor agonist | Epithelial |
| 249 | glucagon | Metabolic or endocrine disorder | Epithelial |
| 250 | glucagon | Diabetes | Epithelial |
| 251 | glucagon | Diabetes with Alzheimer's disease, diabetes with dementia, diabetes with Alzheimer's disease and dementia, diabetes with obesity, diabetes with non-alcoholic fatty liver disease (NAFLD), diabetes with non-alcoholic steatohepatitis (NASH), diabetes with NAFLD and NASH, or diabetes with a cardiovascular disease | Epithelial |
| 252 | glucagon | A liver disease or disorder | Epithelial |
| 253 | glucagon | Compensated liver cirrhosis | Epithelial |
| 254 | glucagon | Non-alcoholic steatohepatitis (NASH) or non-alcoholic fatty liver disease (NAFLD) | Epithelial |
| 255 | glucagon | A binge eating disorder | Epithelial |
| 256 | glucagon | Hyperglycemia | Epithelial |
| 257 | glucagon | Postprandial hyperglycemia | Epithelial |
| 258 | glucagon | Nicotine dependence | Epithelial |
| 259 | glucagon | A central nervous system (CNS) disorder | Epithelial |

TABLE 18-continued

Particular medical approaches

| Approach | Therapeutic agent | Disease | Delivery mode |
|---|---|---|---|
| 260 | glucagon | Alzheimer's disease or Parkinson's disease | Epithelial |
| 261 | NN-9277 | A disease or condition responsive to treatment with a GLP-1 receptor agonist | Epithelial |
| 262 | NN-9277 | Metabolic or endocrine disorder | Epithelial |
| 263 | NN-9277 | Diabetes | Epithelial |
| 264 | NN-9277 | Diabetes with Alzheimer's disease, diabetes with dementia, diabetes with Alzheimer's disease and dementia, diabetes with obesity, diabetes with non-alcoholic fatty liver disease (NAFLD), diabetes with non-alcoholic steatohepatitis (NASH), diabetes with NAFLD and NASH, or diabetes with a cardiovascular disease | Epithelial |
| 265 | NN-9277 | A liver disease or disorder | Epithelial |
| 266 | NN-9277 | Compensated liver cirrhosis | Epithelial |
| 267 | NN-9277 | Non-alcoholic steatohepatitis (NASH) or non-alcoholic fatty liver disease (NAFLD) | Epithelial |
| 268 | NN-9277 | A binge eating disorder | Epithelial |
| 269 | NN-9277 | Hyperglycemia | Epithelial |
| 270 | NN-9277 | Postprandial hyperglycemia | Epithelial |
| 271 | NN-9277 | Nicotine dependence | Epithelial |
| 272 | NN-9277 | A central nervous system (CNS) disorder | Epithelial |
| 273 | NN-9277 | Alzheimer's disease or Parkinson's disease | Epithelial |
| 274 | NN-9423 | A disease or condition responsive to treatment with a GLP-1 receptor agonist | Epithelial |
| 275 | NN-9423 | Metabolic or endocrine disorder | Epithelial |
| 276 | NN-9423 | Diabetes | Epithelial |
| 277 | NN-9423 | Diabetes with Alzheimer's disease, diabetes with dementia, diabetes with Alzheimer's disease and dementia, diabetes with obesity, diabetes with non-alcoholic fatty liver disease (NAFLD), diabetes with non-alcoholic steatohepatitis (NASH), diabetes with NAFLD and NASH, or diabetes with a cardiovascular disease | Epithelial |
| 278 | NN-9423 | A liver disease or disorder | Epithelial |
| 279 | NN-9423 | Compensated liver cirrhosis | Epithelial |
| 280 | NN-9423 | Non-alcoholic steatohepatitis (NASH) or non-alcoholic fatty liver disease (NAFLD) | Epithelial |
| 281 | NN-9423 | A binge eating disorder | Epithelial |
| 282 | NN-9423 | Hyperglycemia | Epithelial |
| 283 | NN-9423 | Postprandial hyperglycemia | Epithelial |
| 284 | NN-9423 | Nicotine dependence | Epithelial |
| 285 | NN-9423 | A central nervous system (CNS) disorder | Epithelial |
| 286 | NN-9423 | Alzheimer's disease or Parkinson's disease | Epithelial |
| 287 | GLP-1 receptor agonist | A disease or condition responsive to treatment with a GLP-1 receptor agonist | Topical |
| 288 | GLP-1 receptor agonist | Metabolic or endocrine disorder | Topical |
| 289 | GLP-1 receptor agonist | Diabetes | Topical |
| 290 | GLP-1 receptor agonist | Diabetes with Alzheimer's disease, diabetes with dementia, diabetes with Alzheimer's disease and dementia, diabetes with obesity, diabetes with non-alcoholic fatty liver disease (NAFLD), diabetes with non-alcoholic steatohepatitis (NASH), diabetes with NAFLD and NASH, or diabetes with a cardiovascular disease | Topical |
| 291 | GLP-1 receptor agonist | A liver disease or disorder | Topical |
| 292 | GLP-1 receptor agonist | Compensated liver cirrhosis | Topical |

TABLE 18-continued

Particular medical approaches

| Approach | Therapeutic agent | Disease | Delivery mode |
|---|---|---|---|
| 293 | GLP-1 receptor agonist | Non-alcoholic steatohepatitis (NASH) or non-alcoholic fatty liver disease (NAFLD) | Topical |
| 294 | GLP-1 receptor agonist | A binge eating disorder | Topical |
| 295 | GLP-1 receptor agonist | Hyperglycemia | Topical |
| 296 | GLP-1 receptor agonist | Postprandial hyperglycemia | Topical |
| 297 | GLP-1 receptor agonist | Nicotine dependence | Topical |
| 298 | GLP-1 receptor agonist | A central nervous system (CNS) disorder | Topical |
| 299 | GLP-1 receptor agonist | Alzheimer's disease or Parkinson's disease | Topical |
| 300 | semaglutide | A disease or condition responsive to treatment with a GLP-1 receptor agonist | Topical |
| 301 | semaglutide | Metabolic or endocrine disorder | Topical |
| 302 | semaglutide | Diabetes | Topical |
| 303 | semaglutide | Diabetes with Alzheimer's disease, diabetes with dementia, diabetes with Alzheimer's disease and dementia, diabetes with obesity, diabetes with non-alcoholic fatty liver disease (NAFLD), diabetes with non-alcoholic steatohepatitis (NASH), diabetes with NAFLD and NASH, or diabetes with a cardiovascular disease | Topical |
| 304 | semaglutide | A liver disease or disorder | Topical |
| 305 | semaglutide | Compensated liver cirrhosis | Topical |
| 306 | semaglutide | Non-alcoholic steatohepatitis (NASH) or non-alcoholic fatty liver disease (NAFLD) | Topical |
| 307 | semaglutide | A binge eating disorder | Topical |
| 308 | semaglutide | Hyperglycemia | Topical |
| 309 | semaglutide | Postprandial hyperglycemia | Topical |
| 310 | semaglutide | Nicotine dependence | Topical |
| 311 | semaglutide | A central nervous system (CNS) disorder | Topical |
| 312 | semaglutide | Alzheimer's disease or Parkinson's disease | Topical |
| 313 | dulaglutide | A disease or condition responsive to treatment with a GLP-1 receptor agonist | Topical |
| 314 | dulaglutide | Metabolic or endocrine disorder | Topical |
| 315 | dulaglutide | Diabetes | Topical |
| 316 | dulaglutide | Diabetes with Alzheimer's disease, diabetes with dementia, diabetes with Alzheimer's disease and dementia, diabetes with obesity, diabetes with non-alcoholic fatty liver disease (NAFLD), diabetes with non-alcoholic steatohepatitis (NASH), diabetes with NAFLD and NASH, or diabetes with a cardiovascular disease | Topical |
| 317 | dulaglutide | A liver disease or disorder | Topical |
| 318 | dulaglutide | Compensated liver cirrhosis | Topical |
| 319 | dulaglutide | Non-alcoholic steatohepatitis (NASH) or non-alcoholic fatty liver disease (NAFLD) | Topical |
| 320 | dulaglutide | A binge eating disorder | Topical |
| 321 | dulaglutide | Hyperglycemia | Topical |
| 322 | dulaglutide | Postprandial hyperglycemia | Topical |
| 323 | dulaglutide | Nicotine dependence | Topical |
| 324 | dulaglutide | A central nervous system (CNS) disorder | Topical |
| 325 | dulaglutide | Alzheimer's disease or Parkinson's disease | Topical |
| 326 | albiglutide | A disease or condition responsive to treatment with a GLP-1 receptor agonist | Topical |
| 327 | albiglutide | Metabolic or endocrine disorder | Topical |
| 328 | albiglutide | Diabetes | Topical |

TABLE 18-continued

Particular medical approaches

| Approach | Therapeutic agent | Disease | Delivery mode |
|---|---|---|---|
| 329 | albiglutide | Diabetes with Alzheimer's disease, diabetes with dementia, diabetes with Alzheimer's disease and dementia, diabetes with obesity, diabetes with non-alcoholic fatty liver disease (NAFLD), diabetes with non-alcoholic steatohepatitis (NASH), diabetes with NAFLD and NASH, or diabetes with a cardiovascular disease | Topical |
| 330 | albiglutide | A liver disease or disorder | Topical |
| 331 | albiglutide | Compensated liver cirrhosis | Topical |
| 332 | albiglutide | Non-alcoholic steatohepatitis (NASH) or non-alcoholic fatty liver disease (NAFLD) | Topical |
| 333 | albiglutide | A binge eating disorder | Topical |
| 334 | albiglutide | Hyperglycemia | Topical |
| 335 | albiglutide | Postprandial hyperglycemia | Topical |
| 336 | albiglutide | Nicotine dependence | Topical |
| 337 | albiglutide | A central nervous system (CNS) disorder | Topical |
| 338 | albiglutide | Alzheimer's disease or Parkinson's disease | Topical |
| 339 | exenatide | A disease or condition responsive to treatment with a GLP-1 receptor agonist | Topical |
| 340 | exenatide | Metabolic or endocrine disorder | Topical |
| 341 | exenatide | Diabetes | Topical |
| 342 | exenatide | Diabetes with Alzheimer's disease, diabetes with dementia, diabetes with Alzheimer's disease and dementia, diabetes with obesity, diabetes with non-alcoholic fatty liver disease (NAFLD), diabetes with non-alcoholic steatohepatitis (NASH), diabetes with NAFLD and NASH, or diabetes with a cardiovascular disease | Topical |
| 343 | exenatide | A liver disease or disorder | Topical |
| 344 | exenatide | Compensated liver cirrhosis | Topical |
| 345 | exenatide | Non-alcoholic steatohepatitis (NASH) or non-alcoholic fatty liver disease (NAFLD) | Topical |
| 346 | exenatide | A binge eating disorder | Topical |
| 347 | exenatide | Hyperglycemia | Topical |
| 348 | exenatide | Postprandial hyperglycemia | Topical |
| 349 | exenatide | Nicotine dependence | Topical |
| 350 | exenatide | A central nervous system (CNS) disorder | Topical |
| 351 | exenatide | Alzheimer's disease or Parkinson's disease | Topical |
| 352 | liraglutide | A disease or condition responsive to treatment with a GLP-1 receptor agonist | Topical |
| 353 | liraglutide | Metabolic or endocrine disorder | Topical |
| 354 | liraglutide | Diabetes | Topical |
| 355 | liraglutide | Diabetes with Alzheimer's disease, diabetes with dementia, diabetes with Alzheimer's disease and dementia, diabetes with obesity, diabetes with non-alcoholic fatty liver disease (NAFLD), diabetes with non-alcoholic steatohepatitis (NASH), diabetes with NAFLD and NASH, or diabetes with a cardiovascular disease | Topical |
| 356 | liraglutide | A liver disease or disorder | Topical |
| 357 | liraglutide | Compensated liver cirrhosis | Topical |
| 358 | liraglutide | Non-alcoholic steatohepatitis (NASH) or non-alcoholic fatty liver disease (NAFLD) | Topical |
| 359 | liraglutide | A binge eating disorder | Topical |
| 360 | liraglutide | Hyperglycemia | Topical |
| 361 | liraglutide | Postprandial hyperglycemia | Topical |
| 362 | liraglutide | Nicotine dependence | Topical |
| 363 | liraglutide | A central nervous system (CNS) disorder | Topical |
| 364 | liraglutide | Alzheimer's disease or Parkinson's disease | Topical |

TABLE 18-continued

Particular medical approaches

| Approach | Therapeutic agent | Disease | Delivery mode |
|---|---|---|---|
| 365 | lixisenatide | A disease or condition responsive to treatment with a GLP-1 receptor agonist | Topical |
| 366 | lixisenatide | Metabolic or endocrine disorder | Topical |
| 367 | lixisenatide | Diabetes | Topical |
| 368 | lixisenatide | Diabetes with Alzheimer's disease, diabetes with dementia, diabetes with Alzheimer's disease and dementia, diabetes with obesity, diabetes with non-alcoholic fatty liver disease (NAFLD), diabetes with non-alcoholic steatohepatitis (NASH), diabetes with NAFLD and NASH, or diabetes with a cardiovascular disease | Topical |
| 369 | lixisenatide | A liver disease or disorder | Topical |
| 370 | lixisenatide | Compensated liver cirrhosis | Topical |
| 371 | lixisenatide | Non-alcoholic steatohepatitis (NASH) or non-alcoholic fatty liver disease (NAFLD) | Topical |
| 372 | lixisenatide | A binge eating disorder | Topical |
| 373 | lixisenatide | Hyperglycemia | Topical |
| 374 | lixisenatide | Postprandial hyperglycemia | Topical |
| 375 | lixisenatide | Nicotine dependence | Topical |
| 376 | lixisenatide | A central nervous system (CNS) disorder | Topical |
| 377 | lixisenatide | Alzheimer's disease or Parkinson's disease | Topical |
| 378 | NNC-0090-2746 | A disease or condition responsive to treatment with a GLP-1 receptor agonist | Topical |
| 379 | NNC-0090-2746 | Metabolic or endocrine disorder | Topical |
| 380 | NNC-0090-2746 | Diabetes | Topical |
| 381 | NNC-0090-2746 | Diabetes with Alzheimer's disease, diabetes with dementia, diabetes with Alzheimer's disease and dementia, diabetes with obesity, diabetes with non-alcoholic fatty liver disease (NAFLD), diabetes with non-alcoholic steatohepatitis (NASH), diabetes with NAFLD and NASH, or diabetes with a cardiovascular disease | Topical |
| 382 | NNC-0090-2746 | A liver disease or disorder | Topical |
| 383 | NNC-0090-2746 | Compensated liver cirrhosis | Topical |
| 384 | NNC-0090-2746 | Non-alcoholic steatohepatitis (NASH) or non-alcoholic fatty liver disease (NAFLD) | Topical |
| 385 | NNC-0090-2746 | A binge eating disorder | Topical |
| 386 | NNC-0090-2746 | Hyperglycemia | Topical |
| 387 | NNC-0090-2746 | Postprandial hyperglycemia | Topical |
| 388 | NNC-0090-2746 | Nicotine dependence | Topical |
| 389 | NNC-0090-2746 | A central nervous system (CNS) disorder | Topical |
| 390 | NNC-0090-2746 | Alzheimer's disease or Parkinson's disease | Topical |
| 391 | glucagon | A disease or condition responsive to treatment with a GLP-1 receptor agonist | Topical |
| 392 | glucagon | Metabolic or endocrine disorder | Topical |
| 393 | glucagon | Diabetes | Topical |
| 394 | glucagon | Diabetes with Alzheimer's disease, diabetes with dementia, diabetes with Alzheimer's disease and dementia, diabetes with obesity, diabetes with non-alcoholic fatty liver disease (NAFLD), diabetes with non-alcoholic steatohepatitis (NASH), diabetes with NAFLD and NASH, or diabetes with a cardiovascular disease | Topical |
| 395 | glucagon | A liver disease or disorder | Topical |
| 396 | glucagon | Compensated liver cirrhosis | Topical |
| 397 | glucagon | Non-alcoholic steatohepatitis (NASH) or non-alcoholic fatty liver disease (NAFLD) | Topical |
| 398 | glucagon | A binge eating disorder | Topical |
| 399 | glucagon | Hyperglycemia | Topical |
| 400 | glucagon | Postprandial hyperglycemia | Topical |

TABLE 18-continued

Particular medical approaches

| Approach | Therapeutic agent | Disease | Delivery mode |
|---|---|---|---|
| 401 | glucagon | Nicotine dependence | Topical |
| 402 | glucagon | A central nervous system (CNS) disorder | Topical |
| 403 | glucagon | Alzheimer's disease or Parkinson's disease | Topical |
| 404 | NN-9277 | A disease or condition responsive to treatment with a GLP-1 receptor agonist | Topical |
| 405 | NN-9277 | Metabolic or endocrine disorder | Topical |
| 406 | NN-9277 | Diabetes | Topical |
| 407 | NN-9277 | Diabetes with Alzheimer's disease, diabetes with dementia, diabetes with Alzheimer's disease and dementia, diabetes with obesity, diabetes with non-alcoholic fatty liver disease (NAFLD), diabetes with non-alcoholic steatohepatitis (NASH), diabetes with NAFLD and NASH, or diabetes with a cardiovascular disease | Topical |
| 408 | NN-9277 | A liver disease or disorder | Topical |
| 409 | NN-9277 | Compensated liver cirrhosis | Topical |
| 410 | NN-9277 | Non-alcoholic steatohepatitis (NASH) or non-alcoholic fatty liver disease (NAFLD) | Topical |
| 411 | NN-9277 | A binge eating disorder | Topical |
| 412 | NN-9277 | Hyperglycemia | Topical |
| 413 | NN-9277 | Postprandial hyperglycemia | Topical |
| 414 | NN-9277 | Nicotine dependence | Topical |
| 415 | NN-9277 | A central nervous system (CNS) disorder | Topical |
| 416 | NN-9277 | Alzheimer's disease or Parkinson's disease | Topical |
| 417 | NN-9423 | A disease or condition responsive to treatment with a GLP-1 receptor agonist | Topical |
| 418 | NN-9423 | Metabolic or endocrine disorder | Topical |
| 419 | NN-9423 | Diabetes | Topical |
| 420 | NN-9423 | Diabetes with Alzheimer's disease, diabetes with dementia, diabetes with Alzheimer's disease and dementia, diabetes with obesity, diabetes with non-alcoholic fatty liver disease (NAFLD), diabetes with non-alcoholic steatohepatitis (NASH), diabetes with NAFLD and NASH, or diabetes with a cardiovascular disease | Topical |
| 421 | NN-9423 | A liver disease or disorder | Topical |
| 422 | NN-9423 | Compensated liver cirrhosis | Topical |
| 423 | NN-9423 | Non-alcoholic steatohepatitis (NASH) or non-alcoholic fatty liver disease (NAFLD) | Topical |
| 424 | NN-9423 | A binge eating disorder | Topical |
| 425 | NN-9423 | Hyperglycemia | Topical |
| 426 | NN-9423 | Postprandial hyperglycemia | Topical |
| 427 | NN-9423 | Nicotine dependence | Topical |
| 428 | NN-9423 | A central nervous system (CNS) disorder | Topical |
| 429 | NN-9423 | Alzheimer's disease or Parkinson's disease | Topical |
| 430 | Growth hormone | Growth disorder | Trans-epithelial |
| 431 | Growth hormone | Growth hormone deficiency or disorder (GHD) | Trans-epithelial |
| 432 | Growth hormone | Acquired, congenital, or idiopathic GHD; or combination thereof | Trans-epithelial |
| 433 | Growth hormone | GHD as a result of trauma, infection, radiation therapy, or tumor growth | Trans-epithelial |
| 434 | Growth hormone | Adult-onset GHD | Trans-epithelial |
| 435 | Recombinant growth hormone (rHGH) | Growth disorder | Trans-epithelial |
| 436 | Recombinant growth hormone (rHGH) | Growth hormone deficiency or disorder (GHD) | Trans-epithelial |
| 437 | Recombinant growth hormone (rHGH) | Acquired, congenital, or idiopathic GHD; or combination thereof | Trans-epithelial |

TABLE 18-continued

Particular medical approaches

| Approach | Therapeutic agent | Disease | Delivery mode |
|---|---|---|---|
| 438 | Recombinant growth hormone (rHGH) | GHD as a result of trauma, infection, radiation therapy, or tumor growth | Trans-epithelial |
| 439 | Recombinant growth hormone (rHGH) | Adult-onset GHD | Trans-epithelial |
| 440 | Somatropin | Growth disorder | Trans-epithelial |
| 441 | Somatropin | Growth hormone deficiency or disorder (GHD) | Trans-epithelial |
| 442 | Somatropin | Acquired, congenital, or idiopathic GHD; or combination thereof | Trans-epithelial |
| 443 | Somatropin | GHD as a result of trauma, infection, radiation therapy, or tumor growth | Trans-epithelial |
| 444 | Somatropin | Adult-onset GHD | Trans-epithelial |
| 445 | Somapacitan | Growth disorder | Trans-epithelial |
| 446 | Somapacitan | Growth hormone deficiency or disorder (GHD) | Trans-epithelial |
| 447 | Somapacitan | Acquired, congenital, or idiopathic GHD; or combination thereof | Trans-epithelial |
| 448 | Somapacitan | GHD as a result of trauma, infection, radiation therapy, or tumor growth | Trans-epithelial |
| 449 | Somapacitan | Adult-onset GHD | Trans-epithelial |
| 450 | Lonapegsomatropin | Growth disorder | Trans-epithelial |
| 451 | Lonapegsomatropin | Growth hormone deficiency or disorder (GHD) | Trans-epithelial |
| 452 | Lonapegsomatropin | Acquired, congenital, or idiopathic GHD; or combination thereof | Trans-epithelial |
| 453 | Lonapegsomatropin | GHD as a result of trauma, infection, radiation therapy, or tumor growth | Trans-epithelial |
| 454 | Lonapegsomatropin | Adult-onset GHD | Trans-epithelial |
| 455 | YPEG-somatropin | Growth disorder | Trans-epithelial |
| 456 | YPEG-somatropin | Growth hormone deficiency or disorder (GHD) | Trans-epithelial |
| 457 | YPEG-somatropin | Acquired, congenital, or idiopathic GHD; or combination thereof | Trans-epithelial |
| 458 | YPEG-somatropin | GHD as a result of trauma, infection, radiation therapy, or tumor growth | Trans-epithelial |
| 459 | YPEG-somatropin | Adult-onset GHD | Trans-epithelial |
| 460 | Efpegsomatropin | Growth disorder | Trans-epithelial |
| 461 | Efpegsomatropin | Growth hormone deficiency or disorder (GHD) | Trans-epithelial |
| 462 | Efpegsomatropin | Acquired, congenital, or idiopathic GHD; or combination thereof | Trans-epithelial |
| 463 | Efpegsomatropin | GHD as a result of trauma, infection, radiation therapy, or tumor growth | Trans-epithelial |
| 464 | Efpegsomatropin | Adult-onset GHD | Trans-epithelial |
| 465 | Somatrogon | Growth disorder | Trans-epithelial |
| 466 | Somatrogon | Growth hormone deficiency or disorder (GHD) | Trans-epithelial |
| 467 | Somatrogon | Acquired, congenital, or idiopathic GHD; or combination thereof | Trans-epithelial |
| 468 | Somatrogon | GHD as a result of trauma, infection, radiation therapy, or tumor growth | Trans-epithelial |
| 469 | Somatrogon | Adult-onset GHD | Trans-epithelial |
| 470 | TJ-101 | Growth disorder | Trans-epithelial |
| 471 | TJ-101 | Growth hormone deficiency or disorder (GHD) | Trans-epithelial |
| 472 | TJ-101 | Acquired, congenital, or idiopathic GHD; or combination thereof | Trans-epithelial |
| 473 | TJ-101 | GHD as a result of trauma, infection, radiation therapy, or tumor growth | Trans-epithelial |
| 474 | TJ-101 | Adult-onset GHD | Trans-epithelial |
| 475 | ALT-P1 | Growth disorder | Trans-epithelial |
| 476 | ALT-P1 | Growth hormone deficiency or disorder (GHD) | Trans-epithelial |
| 477 | ALT-P1 | Acquired, congenital, or idiopathic GHD; or combination thereof | Trans-epithelial |
| 478 | ALT-P1 | GHD as a result of trauma, infection, radiation therapy, or tumor growth | Trans-epithelial |
| 479 | ALT-P1 | Adult-onset GHD | Trans-epithelial |
| 480 | JR-142 | Growth disorder | Trans-epithelial |
| 481 | JR-142 | Growth hormone deficiency or disorder (GHD) | Trans-epithelial |
| 482 | JR-142 | Acquired, congenital, or idiopathic GHD; or combination thereof | Trans-epithelial |
| 483 | JR-142 | GHD as a result of trauma, infection, radiation therapy, or tumor growth | Trans-epithelial |
| 484 | JR-142 | Adult-onset GHD | Trans-epithelial |

TABLE 18-continued

Particular medical approaches

| Approach | Therapeutic agent | Disease | Delivery mode |
|---|---|---|---|
| 485 | Growth hormone | Growth disorder | Epithelial |
| 486 | Growth hormone | Growth hormone deficiency or disorder (GHD) | Epithelial |
| 487 | Growth hormone | Acquired, congenital, or idiopathic GHD; or combination thereof | Epithelial |
| 488 | Growth hormone | GHD as a result of trauma, infection, radiation therapy, or tumor growth | Epithelial |
| 489 | Growth hormone | Adult-onset GHD | Epithelial |
| 490 | Recombinant growth hormone (rHGH) | Growth disorder | Epithelial |
| 491 | Recombinant growth hormone (rHGH) | Growth hormone deficiency or disorder (GHD) | Epithelial |
| 492 | Recombinant growth hormone (rHGH) | Acquired, congenital, or idiopathic GHD; or combination thereof | Epithelial |
| 493 | Recombinant growth hormone (rHGH) | GHD as a result of trauma, infection, radiation therapy, or tumor growth | Epithelial |
| 494 | Recombinant growth hormone (rHGH) | Adult-onset GHD | Epithelial |
| 495 | Somatropin | Growth disorder | Epithelial |
| 496 | Somatropin | Growth hormone deficiency or disorder (GHD) | Epithelial |
| 497 | Somatropin | Acquired, congenital, or idiopathic GHD; or combination thereof | Epithelial |
| 498 | Somatropin | GHD as a result of trauma, infection, radiation therapy, or tumor growth | Epithelial |
| 499 | Somatropin | Adult-onset GHD | Epithelial |
| 500 | Somapacitan | Growth disorder | Epithelial |
| 501 | Somapacitan | Growth hormone deficiency or disorder (GHD) | Epithelial |
| 502 | Somapacitan | Acquired, congenital, or idiopathic GHD; or combination thereof | Epithelial |
| 503 | Somapacitan | GHD as a result of trauma, infection, radiation therapy, or tumor growth | Epithelial |
| 504 | Somapacitan | Adult-onset GHD | Epithelial |
| 505 | Lonapegsomatropin | Growth disorder | Epithelial |
| 506 | Lonapegsomatropin | Growth hormone deficiency or disorder (GHD) | Epithelial |
| 507 | Lonapegsomatropin | Acquired, congenital, or idiopathic GHD; or combination thereof | Epithelial |
| 508 | Lonapegsomatropin | GHD as a result of trauma, infection, radiation therapy, or tumor growth | Epithelial |
| 509 | Lonapegsomatropin | Adult-onset GHD | Epithelial |
| 510 | YPEG-somatropin | Growth disorder | Epithelial |
| 511 | YPEG-somatropin | Growth hormone deficiency or disorder (GHD) | Epithelial |
| 512 | YPEG-somatropin | Acquired, congenital, or idiopathic GHD; or combination thereof | Epithelial |
| 513 | YPEG-somatropin | GHD as a result of trauma, infection, radiation therapy, or tumor growth | Epithelial |
| 514 | YPEG-somatropin | Adult-onset GHD | Epithelial |
| 515 | Efpegsomatropin | Growth disorder | Epithelial |
| 516 | Efpegsomatropin | Growth hormone deficiency or disorder (GHD) | Epithelial |
| 517 | Efpegsomatropin | Acquired, congenital, or idiopathic GHD; or combination thereof | Epithelial |
| 518 | Efpegsomatropin | GHD as a result of trauma, infection, radiation therapy, or tumor growth | Epithelial |
| 519 | Efpegsomatropin | Adult-onset GHD | Epithelial |
| 520 | Somatrogon | Growth disorder | Epithelial |
| 521 | Somatrogon | Growth hormone deficiency or disorder (GHD) | Epithelial |
| 522 | Somatrogon | Acquired, congenital, or idiopathic GHD; or combination thereof | Epithelial |
| 523 | Somatrogon | GHD as a result of trauma, infection, radiation therapy, or tumor growth | Epithelial |
| 524 | Somatrogon | Adult-onset GHD | Epithelial |
| 525 | TJ-101 | Growth disorder | Epithelial |
| 526 | TJ-101 | Growth hormone deficiency or disorder (GHD) | Epithelial |
| 527 | TJ-101 | Acquired, congenital, or idiopathic GHD; or combination thereof | Epithelial |
| 528 | TJ-101 | GHD as a result of trauma, infection, radiation therapy, or tumor growth | Epithelial |
| 529 | TJ-101 | Adult-onset GHD | Epithelial |
| 530 | ALT-P1 | Growth disorder | Epithelial |

TABLE 18-continued

Particular medical approaches

| Approach | Therapeutic agent | Disease | Delivery mode |
|---|---|---|---|
| 531 | ALT-P1 | Growth hormone deficiency or disorder (GHD) | Epithelial |
| 532 | ALT-P1 | Acquired, congenital, or idiopathic GHD; or combination thereof | Epithelial |
| 533 | ALT-P1 | GHD as a result of trauma, infection, radiation therapy, or tumor growth | Epithelial |
| 534 | ALT-P1 | Adult-onset GHD | Epithelial |
| 535 | JR-142 | Growth disorder | Epithelial |
| 536 | JR-142 | Growth hormone deficiency or disorder (GHD) | Epithelial |
| 537 | JR-142 | Acquired, congenital, or idiopathic GHD; or combination thereof | Epithelial |
| 538 | JR-142 | GHD as a result of trauma, infection, radiation therapy, or tumor growth | Epithelial |
| 539 | JR-142 | Adult-onset GHD | Epithelial |
| 540 | Growth hormone | Growth disorder | Topical |
| 541 | Growth hormone | Growth hormone deficiency or disorder (GHD) | Topical |
| 542 | Growth hormone | Acquired, congenital, or idiopathic GHD; or combination thereof | Topical |
| 543 | Growth hormone | GHD as a result of trauma, infection, radiation therapy, or tumor growth | Topical |
| 544 | Growth hormone | Adult-onset GHD | Topical |
| 545 | Recombinant growth hormone (rHGH) | Growth disorder | Topical |
| 546 | Recombinant growth hormone (rHGH) | Growth hormone deficiency or disorder (GHD) | Topical |
| 547 | Recombinant growth hormone (rHGH) | Acquired, congenital, or idiopathic GHD; or combination thereof | Topical |
| 548 | Recombinant growth hormone (rHGH) | GHD as a result of trauma, infection, radiation therapy, or tumor growth | Topical |
| 549 | Recombinant growth hormone (rHGH) | Adult-onset GHD | Topical |
| 550 | Somatropin | Growth disorder | Topical |
| 551 | Somatropin | Growth hormone deficiency or disorder (GHD) | Topical |
| 552 | Somatropin | Acquired, congenital, or idiopathic GHD; or combination thereof | Topical |
| 553 | Somatropin | GHD as a result of trauma, infection, radiation therapy, or tumor growth | Topical |
| 554 | Somatropin | Adult-onset GHD | Topical |
| 555 | Somapacitan | Growth disorder | Topical |
| 556 | Somapacitan | Growth hormone deficiency or disorder (GHD) | Topical |
| 557 | Somapacitan | Acquired, congenital, or idiopathic GHD; or combination thereof | Topical |
| 558 | Somapacitan | GHD as a result of trauma, infection, radiation therapy, or tumor growth | Topical |
| 559 | Somapacitan | Adult-onset GHD | Topical |
| 560 | Lonapegsomatropin | Growth disorder | Topical |
| 561 | Lonapegsomatropin | Growth hormone deficiency or disorder (GHD) | Topical |
| 562 | Lonapegsomatropin | Acquired, congenital, or idiopathic GHD; or combination thereof | Topical |
| 563 | Lonapegsomatropin | GHD as a result of trauma, infection, radiation therapy, or tumor growth | Topical |
| 564 | Lonapegsomatropin | Adult-onset GHD | Topical |
| 565 | YPEG-somatropin | Growth disorder | Topical |
| 566 | YPEG-somatropin | Growth hormone deficiency or disorder (GHD) | Topical |
| 567 | YPEG-somatropin | Acquired, congenital, or idiopathic GHD; or combination thereof | Topical |
| 568 | YPEG-somatropin | GHD as a result of trauma, infection, radiation therapy, or tumor growth | Topical |
| 569 | YPEG-somatropin | Adult-onset GHD | Topical |
| 570 | Efpegsomatropin | Growth disorder | Topical |
| 571 | Efpegsomatropin | Growth hormone deficiency or disorder (GHD) | Topical |
| 572 | Efpegsomatropin | Acquired, congenital, or idiopathic GHD; or combination thereof | Topical |
| 573 | Efpegsomatropin | GHD as a result of trauma, infection, radiation therapy, or tumor growth | Topical |
| 574 | Efpegsomatropin | Adult-onset GHD | Topical |
| 575 | Somatrogon | Growth disorder | Topical |
| 576 | Somatrogon | Growth hormone deficiency or disorder (GHD) | Topical |

TABLE 18-continued

Particular medical approaches

| Approach | Therapeutic agent | Disease | Delivery mode |
|---|---|---|---|
| 577 | Somatrogon | Acquired, congenital, or idiopathic GHD; or combination thereof | Topical |
| 578 | Somatrogon | GHD as a result of trauma, infection, radiation therapy, or tumor growth | Topical |
| 579 | Somatrogon | Adult-onset GHD | Topical |
| 580 | TJ-101 | Growth disorder | Topical |
| 581 | TJ-101 | Growth hormone deficiency or disorder (GHD) | Topical |
| 582 | TJ-101 | Acquired, congenital, or idiopathic GHD; or combination thereof | Topical |
| 583 | TJ-101 | GHD as a result of trauma, infection, radiation therapy, or tumor growth | Topical |
| 584 | TJ-101 | Adult-onset GHD | Topical |
| 585 | ALT-P1 | Growth disorder | Topical |
| 586 | ALT-P1 | Growth hormone deficiency or disorder (GHD) | Topical |
| 587 | ALT-P1 | Acquired, congenital, or idiopathic GHD; or combination thereof | Topical |
| 588 | ALT-P1 | GHD as a result of trauma, infection, radiation therapy, or tumor growth | Topical |
| 589 | ALT-P1 | Adult-onset GHD | Topical |
| 590 | JR-142 | Growth disorder | Topical |
| 591 | JR-142 | Growth hormone deficiency or disorder (GHD) | Topical |
| 592 | JR-142 | Acquired, congenital, or idiopathic GHD; or combination thereof | Topical |
| 593 | JR-142 | GHD as a result of trauma, infection, radiation therapy, or tumor growth | Topical |
| 594 | JR-142 | Adult-onset GHD | Topical |
| 595 | TNF-alpha inhibitor | A disease or condition responsive to treatment with a TNF-alpha inhibitor | Trans-epithelial |
| 596 | TNF-alpha inhibitor | Inflammatory disease or disorder | Trans-epithelial |
| 597 | TNF-alpha inhibitor | Inflammatory bowel disease | Trans-epithelial |
| 598 | TNF-alpha inhibitor | Ulcerative colitis | Trans-epithelial |
| 599 | TNF-alpha inhibitor | Crohn's disease | Trans-epithelial |
| 600 | TNF-alpha inhibitor | Ileal Crohn's disease | Trans-epithelial |
| 601 | TNF-alpha inhibitor | Ankylosing spondylitis, asthma, Behcet's disease, hidradenitis suppurativa, an inflammatory disease, an inflammatory bowel disease, insulin-dependent (type 1) diabetes, type 2 diabetes, juvenile rheumatoid arthritis, Kawasaki disease, lower back pain, osteoarthritis, pouchitis, psoriasis, psoriatic arthritis, pyoderma gangrenosum, rheumatoid arthritis, spondylarthritis, uveitis, or combinations thereof | Trans-epithelial |
| 602 | Adalimumab | A disease or condition responsive to treatment with a TNF-alpha inhibitor | Trans-epithelial |
| 603 | Adalimumab | Inflammatory disease or disorder | Trans-epithelial |
| 604 | Adalimumab | Inflammatory bowel disease | Trans-epithelial |
| 605 | Adalimumab | Ulcerative colitis | Trans-epithelial |
| 606 | Adalimumab | Crohn's disease | Trans-epithelial |
| 607 | Adalimumab | Ileal Crohn's disease | Trans-epithelial |
| 608 | Adalimumab | Ankylosing spondylitis, asthma, Behcet's disease, hidradenitis suppurativa, an inflammatory disease, an inflammatory bowel disease, insulin-dependent (type 1) diabetes, type 2 diabetes, juvenile rheumatoid arthritis, Kawasaki disease, lower back pain, osteoarthritis, pouchitis, psoriasis, psoriatic arthritis, pyoderma gangrenosum, rheumatoid arthritis, spondylarthritis, uveitis, or combinations thereof | Trans-epithelial |
| 609 | Certolizumab pegol | A disease or condition responsive to treatment with a TNF-alpha inhibitor | Trans-epithelial |
| 610 | Certolizumab pegol | Inflammatory disease or disorder | Trans-epithelial |
| 611 | Certolizumab pegol | Inflammatory bowel disease | Trans-epithelial |
| 612 | Certolizumab pegol | Ulcerative colitis | Trans-epithelial |
| 613 | Certolizumab pegol | Crohn's disease | Trans-epithelial |
| 614 | Certolizumab pegol | Ileal Crohn's disease | Trans-epithelial |

TABLE 18-continued

Particular medical approaches

| Approach | Therapeutic agent | Disease | Delivery mode |
|---|---|---|---|
| 615 | Certolizumab pegol | Ankylosing spondylitis, asthma, Behcet's disease, hidradenitis suppurativa, an inflammatory disease, an inflammatory bowel disease, insulin-dependent (type 1) diabetes, type 2 diabetes, juvenile rheumatoid arthritis, Kawasaki disease, lower back pain, osteoarthritis, pouchitis, psoriasis, psoriatic arthritis, pyoderma gangrenosum, rheumatoid arthritis, spondylarthritis, uveitis, or combinations thereof | Trans-epithelial |
| 616 | Etanercept | A disease or condition responsive to treatment with a TNF-alpha inhibitor | Trans-epithelial |
| 617 | Etanercept | Inflammatory disease or disorder | Trans-epithelial |
| 618 | Etanercept | Inflammatory bowel disease | Trans-epithelial |
| 619 | Etanercept | Ulcerative colitis | Trans-epithelial |
| 620 | Etanercept | Crohn's disease | Trans-epithelial |
| 621 | Etanercept | Ileal Crohn's disease | Trans-epithelial |
| 622 | Etanercept | Ankylosing spondylitis, asthma, Behcet's disease, hidradenitis suppurativa, an inflammatory disease, an inflammatory bowel disease, insulin-dependent (type 1) diabetes, type 2 diabetes, juvenile rheumatoid arthritis, Kawasaki disease, lower back pain, osteoarthritis, pouchitis, psoriasis, psoriatic arthritis, pyoderma gangrenosum, rheumatoid arthritis, spondylarthritis, uveitis, or combinations thereof | Trans-epithelial |
| 623 | Golimumab | A disease or condition responsive to treatment with a TNF-alpha inhibitor | Trans-epithelial |
| 624 | Golimumab | Inflammatory disease or disorder | Trans-epithelial |
| 625 | Golimumab | Inflammatory bowel disease | Trans-epithelial |
| 626 | Golimumab | Ulcerative colitis | Trans-epithelial |
| 627 | Golimumab | Crohn's disease | Trans-epithelial |
| 628 | Golimumab | Ileal Crohn's disease | Trans-epithelial |
| 629 | Golimumab | Ankylosing spondylitis, asthma, Behcet's disease, hidradenitis suppurativa, an inflammatory disease, an inflammatory bowel disease, insulin-dependent (type 1) diabetes, type 2 diabetes, juvenile rheumatoid arthritis, Kawasaki disease, lower back pain, osteoarthritis, pouchitis, psoriasis, psoriatic arthritis, pyoderma gangrenosum, rheumatoid arthritis, spondylarthritis, uveitis, or combinations thereof | Trans-epithelial |
| 630 | Ustekinumab | Inflammatory disease or disorder | Trans-epithelial |
| 631 | Ustekinumab | Inflammatory bowel disease | Trans-epithelial |
| 632 | Vedolizumab | Inflammatory disease or disorder | Trans-epithelial |
| 633 | Vedolizumab | Inflammatory bowel disease | Trans-epithelial |
| 634 | Natalizumab | Inflammatory disease or disorder | Trans-epithelial |
| 635 | Natalizumab | Inflammatory bowel disease | Trans-epithelial |
| 636 | TNF-alpha inhibitor | A disease or condition responsive to treatment with a TNF-alpha inhibitor | Epithelial |
| 637 | TNF-alpha inhibitor | Inflammatory disease or disorder | Epithelial |
| 638 | TNF-alpha inhibitor | Inflammatory bowel disease | Epithelial |
| 639 | TNF-alpha inhibitor | Ulcerative colitis | Epithelial |
| 640 | TNF-alpha inhibitor | Crohn's disease | Epithelial |
| 641 | TNF-alpha inhibitor | Ileal Crohn's disease | Epithelial |
| 642 | TNF-alpha inhibitor | Ankylosing spondylitis, asthma, Behcet's disease, hidradenitis suppurativa, an inflammatory disease, an inflammatory bowel disease, insulin-dependent (type 1) diabetes, type 2 diabetes, juvenile rheumatoid arthritis, Kawasaki disease, lower back pain, osteoarthritis, pouchitis, psoriasis, psoriatic arthritis, pyoderma gangrenosum, rheumatoid arthritis, spondylarthritis, uveitis, or combinations thereof | Epithelial |

TABLE 18-continued

Particular medical approaches

| Approach | Therapeutic agent | Disease | Delivery mode |
|---|---|---|---|
| 643 | Adalimumab | A disease or condition responsive to treatment with a TNF-alpha inhibitor | Epithelial |
| 644 | Adalimumab | Inflammatory disease or disorder | Epithelial |
| 645 | Adalimumab | Inflammatory bowel disease | Epithelial |
| 646 | Adalimumab | Ulcerative colitis | Epithelial |
| 647 | Adalimumab | Crohn's disease | Epithelial |
| 648 | Adalimumab | Ileal Crohn's disease | Epithelial |
| 649 | Adalimumab | Ankylosing spondylitis, asthma, Behcet's disease, hidradenitis suppurativa, an inflammatory disease, an inflammatory bowel disease, insulin-dependent (type 1) diabetes, type 2 diabetes, juvenile rheumatoid arthritis, Kawasaki disease, lower back pain, osteoarthritis, pouchitis, psoriasis, psoriatic arthritis, pyoderma gangrenosum, rheumatoid arthritis, spondylarthritis, uveitis, or combinations thereof | Epithelial |
| 650 | Certolizumab pegol | A disease or condition responsive to treatment with a TNF-alpha inhibitor | Epithelial |
| 651 | Certolizumab pegol | Inflammatory disease or disorder | Epithelial |
| 652 | Certolizumab pegol | Inflammatory bowel disease | Epithelial |
| 653 | Certolizumab pegol | Ulcerative colitis | Epithelial |
| 654 | Certolizumab pegol | Crohn's disease | Epithelial |
| 655 | Certolizumab pegol | Ileal Crohn's disease | Epithelial |
| 656 | Certolizumab pegol | Ankylosing spondylitis, asthma, Behcet's disease, hidradenitis suppurativa, an inflammatory disease, an inflammatory bowel disease, insulin-dependent (type 1) diabetes, type 2 diabetes, juvenile rheumatoid arthritis, Kawasaki disease, lower back pain, osteoarthritis, pouchitis, psoriasis, psoriatic arthritis, pyoderma gangrenosum, rheumatoid arthritis, spondylarthritis, uveitis, or combinations thereof | Epithelial |
| 657 | Etanercept | A disease or condition responsive to treatment with a TNF-alpha inhibitor | Epithelial |
| 658 | Etanercept | Inflammatory disease or disorder | Epithelial |
| 659 | Etanercept | Inflammatory bowel disease | Epithelial |
| 660 | Etanercept | Ulcerative colitis | Epithelial |
| 661 | Etanercept | Crohn's disease | Epithelial |
| 662 | Etanercept | Ileal Crohn's disease | Epithelial |
| 663 | Etanercept | Ankylosing spondylitis, asthma, Behcet's disease, hidradenitis suppurativa, an inflammatory disease, an inflammatory bowel disease, insulin-dependent (type 1) diabetes, type 2 diabetes, juvenile rheumatoid arthritis, Kawasaki disease, lower back pain, osteoarthritis, pouchitis, psoriasis, psoriatic arthritis, pyoderma gangrenosum, rheumatoid arthritis, spondylarthritis, uveitis, or combinations thereof | Epithelial |
| 664 | Golimumab | A disease or condition responsive to treatment with a TNF-alpha inhibitor | Epithelial |
| 665 | Golimumab | Inflammatory disease or disorder | Epithelial |
| 666 | Golimumab | Inflammatory bowel disease | Epithelial |
| 667 | Golimumab | Ulcerative colitis | Epithelial |
| 668 | Golimumab | Crohn's disease | Epithelial |
| 669 | Golimumab | Ileal Crohn's disease | Epithelial |
| 670 | Golimumab | Ankylosing spondylitis, asthma, Behcet's disease, hidradenitis suppurativa, an inflammatory disease, an inflammatory bowel disease, insulin-dependent (type 1) diabetes, type 2 diabetes, juvenile rheumatoid arthritis, Kawasaki disease, lower back pain, osteoarthritis, pouchitis, psoriasis, psoriatic arthritis, pyoderma gangrenosum, rheumatoid arthritis, spondylarthritis, uveitis, or combinations thereof | Epithelial |

TABLE 18-continued

Particular medical approaches

| Approach | Therapeutic agent | Disease | Delivery mode |
|---|---|---|---|
| 671 | Ustekinumab | Inflammatory disease or disorder | Epithelial |
| 672 | Ustekinumab | Inflammatory bowel disease | Epithelial |
| 673 | Vedolizumab | Inflammatory disease or disorder | Epithelial |
| 674 | Vedolizumab | Inflammatory bowel disease | Epithelial |
| 675 | Natalizumab | Inflammatory disease or disorder | Epithelial |
| 676 | Natalizumab | Inflammatory bowel disease | Epithelial |
| 677 | TNF-alpha inhibitor | A disease or condition responsive to treatment with a TNF-alpha inhibitor | Topical |
| 678 | TNF-alpha inhibitor | Inflammatory disease or disorder | Topical |
| 679 | TNF-alpha inhibitor | Inflammatory bowel disease | Topical |
| 680 | TNF-alpha inhibitor | Ulcerative colitis | Topical |
| 681 | TNF-alpha inhibitor | Crohn's disease | Topical |
| 682 | TNF-alpha inhibitor | Ileal Crohn's disease | Topical |
| 683 | TNF-alpha inhibitor | Ankylosing spondylitis, asthma, Behcet's disease, hidradenitis suppurativa, an inflammatory disease, an inflammatory bowel disease, insulin-dependent (type 1) diabetes, type 2 diabetes, juvenile rheumatoid arthritis, Kawasaki disease, lower back pain, osteoarthritis, pouchitis, psoriasis, psoriatic arthritis, pyoderma gangrenosum, rheumatoid arthritis, spondylarthritis, uveitis, or combinations thereof | Topical |
| 684 | Adalimumab | A disease or condition responsive to treatment with a TNF-alpha inhibitor | Topical |
| 685 | Adalimumab | Inflammatory disease or disorder | Topical |
| 686 | Adalimumab | Inflammatory bowel disease | Topical |
| 687 | Adalimumab | Ulcerative colitis | Topical |
| 688 | Adalimumab | Crohn's disease | Topical |
| 689 | Adalimumab | Ileal Crohn's disease | Topical |
| 690 | Adalimumab | Ankylosing spondylitis, asthma, Behcet's disease, hidradenitis suppurativa, an inflammatory disease, an inflammatory bowel disease, insulin-dependent (type 1) diabetes, type 2 diabetes, juvenile rheumatoid arthritis, Kawasaki disease, lower back pain, osteoarthritis, pouchitis, psoriasis, psoriatic arthritis, pyoderma gangrenosum, rheumatoid arthritis, spondylarthritis, uveitis, or combinations thereof | Topical |
| 691 | Certolizumab pegol | A disease or condition responsive to treatment with a TNF-alpha inhibitor | Topical |
| 692 | Certolizumab pegol | Inflammatory disease or disorder | Topical |
| 693 | Certolizumab pegol | Inflammatory bowel disease | Topical |
| 694 | Certolizumab pegol | Ulcerative colitis | Topical |
| 695 | Certolizumab pegol | Crohn's disease | Topical |
| 696 | Certolizumab pegol | Ileal Crohn's disease | Topical |
| 697 | Certolizumab pegol | Ankylosing spondylitis, asthma, Behcet's disease, hidradenitis suppurativa, an inflammatory disease, an inflammatory bowel disease, insulin-dependent (type 1) diabetes, type 2 diabetes, juvenile rheumatoid arthritis, Kawasaki disease, lower back pain, osteoarthritis, pouchitis, psoriasis, psoriatic arthritis, pyoderma gangrenosum, rheumatoid arthritis, spondylarthritis, uveitis, or combinations thereof | Topical |
| 698 | Etanercept | A disease or condition responsive to treatment with a TNF-alpha inhibitor | Topical |
| 699 | Etanercept | Inflammatory disease or disorder | Topical |
| 700 | Etanercept | Inflammatory bowel disease | Topical |
| 701 | Etanercept | Ulcerative colitis | Topical |
| 702 | Etanercept | Crohn's disease | Topical |
| 703 | Etanercept | Ileal Crohn's disease | Topical |
| 704 | Etanercept | Ankylosing spondylitis, asthma, Behcet's disease, hidradenitis suppurativa, an inflammatory disease, an inflammatory bowel disease, insulin-dependent (type 1) diabetes, type 2 diabetes, juvenile rheumatoid | |

TABLE 18-continued

Particular medical approaches

| Approach | Therapeutic agent | Disease | Delivery mode |
|---|---|---|---|
| | | arthritis, Kawasaki disease, lower back pain, osteoarthritis, pouchitis, psoriasis, psoriatic arthritis, pyoderma gangrenosum, rheumatoid arthritis, spondylarthritis, uveitis, or combinations thereof | |
| 705 | Golimumab | A disease or condition responsive to treatment with a TNF-alpha inhibitor | Topical |
| 706 | Golimumab | Inflammatory disease or disorder | Topical |
| 707 | Golimumab | Inflammatory bowel disease | Topical |
| 708 | Golimumab | Ulcerative colitis | Topical |
| 709 | Golimumab | Crohn's disease | Topical |
| 710 | Golimumab | Ileal Crohn's disease | Topical |
| 711 | Golimumab | Ankylosing spondylitis, asthma, Behcet's disease, hidradenitis suppurativa, an inflammatory disease, an inflammatory bowel disease, insulin-dependent (type 1) diabetes, type 2 diabetes, juvenile rheumatoid arthritis, Kawasaki disease, lower back pain, osteoarthritis, pouchitis, psoriasis, psoriatic arthritis, pyoderma gangrenosum, rheumatoid arthritis, spondylarthritis, uveitis, or combinations thereof | Topical |
| 712 | Ustekinumab | Inflammatory disease or disorder | Topical |
| 713 | Ustekinumab | Inflammatory bowel disease | Topical |
| 714 | Vedolizumab | Inflammatory disease or disorder | Topical |
| 715 | Vedolizumab | Inflammatory bowel disease | Topical |
| 716 | Natalizumab | Inflammatory disease or disorder | Topical |
| 717 | Natalizumab | Inflammatory bowel disease | Topical |
| 718 | An alternative coagulation promotor (ACP) | Hemophilia | Trans-epithelial |
| 719 | An alternative coagulation promotor (ACP) | Hemophilia A | Trans-epithelial |
| 720 | An alternative coagulation promotor (ACP) | Hemophilia B | Trans-epithelial |
| 721 | An alternative coagulation promotor (ACP) | Von Willebrand disease | Trans-epithelial |
| 722 | An anti-tissue factor pathway inhibitor (anti-TFPI) | Hemophilia | Trans-epithelial |
| 723 | An anti-tissue factor pathway inhibitor (anti-TFPI) | Hemophilia A | Trans-epithelial |
| 724 | An anti-tissue factor pathway inhibitor (anti-TFPI) | Hemophilia B | Trans-epithelial |
| 725 | An anti-tissue factor pathway inhibitor (anti-TFPI) | Von Willebrand disease | Trans-epithelial |
| 726 | Concizumab | Hemophilia | Trans-epithelial |
| 727 | Concizumab | Hemophilia A | Trans-epithelial |
| 728 | Concizumab | Hemophilia B | Trans-epithelial |
| 729 | Concizumab | Von Willebrand disease | Trans-epithelial |
| 730 | Factor VII mimetic | Hemophilia | Trans-epithelial |
| 731 | Factor VII mimetic | Hemophilia A | Trans-epithelial |
| 732 | Factor VII mimetic | Hemophilia B | Trans-epithelial |
| 733 | Factor VII mimetic | Von Willebrand disease | Trans-epithelial |
| 734 | Emicizumab | Hemophilia | Trans-epithelial |
| 735 | Emicizumab | Hemophilia A | Trans-epithelial |
| 736 | Emicizumab | Hemophilia B | Trans-epithelial |
| 737 | Emicizumab | Von Willebrand disease | Trans-epithelial |
| 738 | An alternative coagulation promotor (ACP) | Hemophilia | Epithelial |
| 739 | An alternative coagulation promotor (ACP) | Hemophilia A | Epithelial |
| 740 | An alternative coagulation promotor (ACP) | Hemophilia B | Epithelial |

TABLE 18-continued

Particular medical approaches

| Approach | Therapeutic agent | Disease | Delivery mode |
|---|---|---|---|
| 741 | An alternative coagulation promotor (ACP) | Von Willebrand disease | Epithelial |
| 742 | An anti-tissue factor pathway inhibitor (anti-TFPI) | Hemophilia | Epithelial |
| 743 | An anti-tissue factor pathway inhibitor (anti-TFPI) | Hemophilia A | Epithelial |
| 744 | An anti-tissue factor pathway inhibitor (anti-TFPI) | Hemophilia B | Epithelial |
| 745 | An anti-tissue factor pathway inhibitor (anti-TFPI) | Von Willebrand disease | Epithelial |
| 746 | Concizumab | Hemophilia | Epithelial |
| 747 | Concizumab | Hemophilia A | Epithelial |
| 748 | Concizumab | Hemophilia B | Epithelial |
| 749 | Concizumab | Von Willebrand disease | Epithelial |
| 750 | Factor VII mimetic | Hemophilia | Epithelial |
| 751 | Factor VII mimetic | Hemophilia A | Epithelial |
| 752 | Factor VII mimetic | Hemophilia B | Epithelial |
| 753 | Factor VII mimetic | Von Willebrand disease | Epithelial |
| 754 | Emicizumab | Hemophilia | Epithelial |
| 755 | Emicizumab | Hemophilia A | Epithelial |
| 756 | Emicizumab | Hemophilia B | Epithelial |
| 757 | Emicizumab | Von Willebrand disease | Epithelial |
| 758 | An alternative coagulation promotor (ACP) | Hemophilia | Topical |
| 759 | An alternative coagulation promotor (ACP) | Hemophilia A | Topical |
| 760 | An alternative coagulation promotor (ACP) | Hemophilia B | Topical |
| 761 | An alternative coagulation promotor (ACP) | Von Willebrand disease | Topical |
| 762 | An anti-tissue factor pathway inhibitor (anti-TFPI) | Hemophilia | Topical |
| 763 | An anti-tissue factor pathway inhibitor (anti-TFPI) | Hemophilia A | Topical |
| 764 | An anti-tissue factor pathway inhibitor (anti-TFPI) | Hemophilia B | Topical |
| 765 | An anti-tissue factor pathway inhibitor (anti-TFPI) | Von Willebrand disease | Topical |
| 766 | Concizumab | Hemophilia | Topical |
| 767 | Concizumab | Hemophilia A | Topical |
| 768 | Concizumab | Hemophilia B | Topical |
| 769 | Concizumab | Von Willebrand disease | Topical |
| 770 | Factor VII mimetic | Hemophilia | Topical |
| 771 | Factor VII mimetic | Hemophilia A | Topical |
| 772 | Factor VII mimetic | Hemophilia B | Topical |
| 773 | Factor VII mimetic | Von Willebrand disease | Topical |
| 774 | Emicizumab | Hemophilia | Topical |
| 775 | Emicizumab | Hemophilia A | Topical |
| 776 | Emicizumab | Hemophilia B | Topical |
| 777 | Emicizumab | Von Willebrand disease | Topical |
| 778 | Abatacept | Autoimmune disease or condition | Trans-epithelial |
| 779 | Abatacept | Rheumatoid arthritis | Trans-epithelial |
| 780 | Abatacept | Fibrosis | Trans-epithelial |
| 781 | Teriparatide | Autoimmune disease or condition | Trans-epithelial |
| 782 | Teriparatide | Rheumatoid arthritis | Trans-epithelial |
| 783 | Teriparatide | Fibrosis | Trans-epithelial |
| 784 | Pegfilgrastim | Autoimmune disease or condition | Trans-epithelial |
| 785 | Pegfilgrastim | Rheumatoid arthritis | Trans-epithelial |
| 786 | Pegfilgrastim | Fibrosis | Trans-epithelial |
| 787 | Sargramostim | Autoimmune disease or condition | Trans-epithelial |
| 788 | Sargramostim | Rheumatoid arthritis | Trans-epithelial |
| 789 | Sargramostim | Fibrosis | Trans-epithelial |
| 790 | Tocilizumab | Autoimmune disease or condition | Trans-epithelial |

TABLE 18-continued

Particular medical approaches

| Approach | Therapeutic agent | Disease | Delivery mode |
|---|---|---|---|
| 791 | Tocilizumab | Rheumatoid arthritis | Trans-epithelial |
| 792 | Tocilizumab | Fibrosis | Trans-epithelial |
| 793 | Interferon beta-1a | Autoimmune disease or condition | Trans-epithelial |
| 794 | Interferon beta-1a | Rheumatoid arthritis | Trans-epithelial |
| 795 | Interferon beta-1a | Fibrosis | Trans-epithelial |
| 796 | Abatacept | Autoimmune disease or condition | Epithelial |
| 797 | Abatacept | Rheumatoid arthritis | Epithelial |
| 798 | Abatacept | Fibrosis | Epithelial |
| 799 | Teriparatide | Autoimmune disease or condition | Epithelial |
| 800 | Teriparatide | Rheumatoid arthritis | Epithelial |
| 801 | Teriparatide | Fibrosis | Epithelial |
| 802 | Pegfilgrastim | Autoimmune disease or condition | Epithelial |
| 803 | Pegfilgrastim | Rheumatoid arthritis | Epithelial |
| 804 | Pegfilgrastim | Fibrosis | Epithelial |
| 805 | Sargramostim | Autoimmune disease or condition | Epithelial |
| 806 | Sargramostim | Rheumatoid arthritis | Epithelial |
| 807 | Sargramostim | Fibrosis | Epithelial |
| 808 | Tocilizumab | Autoimmune disease or condition | Epithelial |
| 809 | Tocilizumab | Rheumatoid arthritis | Epithelial |
| 810 | Tocilizumab | Fibrosis | Epithelial |
| 811 | Interferon beta-1a | Autoimmune disease or condition | Epithelial |
| 812 | Interferon beta-1a | Rheumatoid arthritis | Epithelial |
| 813 | Interferon beta-1a | Fibrosis | Epithelial |
| 814 | Abatacept | Autoimmune disease or condition | Topical |
| 815 | Abatacept | Rheumatoid arthritis | Topical |
| 816 | Abatacept | Fibrosis | Topical |
| 817 | Teriparatide | Autoimmune disease or condition | Topical |
| 818 | Teriparatide | Rheumatoid arthritis | Topical |
| 819 | Teriparatide | Fibrosis | Topical |
| 820 | Pegfilgrastim | Autoimmune disease or condition | Topical |
| 821 | Pegfilgrastim | Rheumatoid arthritis | Topical |
| 822 | Pegfilgrastim | Fibrosis | Topical |
| 823 | Sargramostim | Autoimmune disease or condition | Topical |
| 824 | Sargramostim | Rheumatoid arthritis | Topical |
| 825 | Sargramostim | Fibrosis | Topical |
| 826 | Tocilizumab | Autoimmune disease or condition | Topical |
| 827 | Tocilizumab | Rheumatoid arthritis | Topical |
| 828 | Tocilizumab | Fibrosis | Topical |
| 829 | Interferon beta-1a | Autoimmune disease or condition | Topical |
| 830 | Interferon beta-1a | Rheumatoid arthritis | Topical |
| 831 | Interferon beta-1a | Fibrosis | Topical |
| 832 | Natalizumab | Autoimmune disease or condition | Trans-epithelial |
| 833 | Vedolizumab | Autoimmune disease or condition | Trans-epithelial |
| 834 | Ustekinumab | Autoimmune disease or condition | Trans-epithelial |
| 835 | Denosumab | Autoimmune disease or condition | Trans-epithelial |
| 836 | Secukinumab | Metabolic or endocrine disorder | Trans-epithelial |
| 837 | Natalizumab | Autoimmune disease or condition | Epithelial |
| 838 | Vedolizumab | Autoimmune disease or condition | Epithelial |
| 839 | Ustekinumab | Autoimmune disease or condition | Epithelial |
| 840 | Denosumab | Autoimmune disease or condition | Epithelial |
| 841 | Secukinumab | Metabolic or endocrine disorder | Epithelial |
| 842 | Natalizumab | Autoimmune disease or condition | Topical |
| 843 | Vedolizumab | Autoimmune disease or condition | Topical |
| 844 | Ustekinumab | Autoimmune disease or condition | Topical |
| 845 | Denosumab | Autoimmune disease or condition | Topical |
| 846 | Secukinumab | Metabolic or endocrine disorder | Topical |
| 847 | Insulin | Metabolic or endocrine disease or condition | Trans-epithelial |
| 848 | Insulin | Diabetes | Trans-epithelial |
| 849 | Insulin | Obesity | Trans-epithelial |
| 850 | Insulin | Hypercholesterolemia | Trans-epithelial |
| 851 | Insulin | A lipid metabolism disorder | Trans-epithelial |
| 852 | Insulin | Hyperlipidemia | Trans-epithelial |
| 853 | Insulin | Atherosclerosis | Trans-epithelial |
| 854 | TNF-alpha inhibitor | Metabolic or endocrine disease or condition | Trans-epithelial |
| 855 | TNF-alpha inhibitor | Diabetes | Trans-epithelial |
| 856 | TNF-alpha inhibitor | Obesity | Trans-epithelial |
| 857 | TNF-alpha inhibitor | Hypercholesterolemia | Trans-epithelial |
| 858 | TNF-alpha inhibitor | A lipid metabolism disorder | Trans-epithelial |
| 859 | TNF-alpha inhibitor | Hyperlipidemia | Trans-epithelial |
| 860 | TNF-alpha inhibitor | Atherosclerosis | Trans-epithelial |
| 861 | Adalimumab | Metabolic or endocrine disease or condition | Trans-epithelial |
| 862 | Adalimumab | Diabetes | Trans-epithelial |
| 863 | Adalimumab | Obesity | Trans-epithelial |

TABLE 18-continued

Particular medical approaches

| Approach | Therapeutic agent | Disease | Delivery mode |
|---|---|---|---|
| 864 | Adalimumab | Hypercholesterolemia | Trans-epithelial |
| 865 | Adalimumab | A lipid metabolism disorder | Trans-epithelial |
| 866 | Adalimumab | Hyperlipidemia | Trans-epithelial |
| 867 | Adalimumab | Atherosclerosis | Trans-epithelial |
| 868 | A proprotein convertase PC9 (PCSK9) inhibitor | Metabolic or endocrine disease or condition | Trans-epithelial |
| 869 | A proprotein convertase PC9 (PCSK9) inhibitor | Diabetes | Trans-epithelial |
| 870 | A proprotein convertase PC9 (PCSK9) inhibitor | Obesity | Trans-epithelial |
| 871 | A proprotein convertase PC9 (PCSK9) inhibitor | Hypercholesterolemia | Trans-epithelial |
| 872 | A proprotein convertase PC9 (PCSK9) inhibitor | A lipid metabolism disorder | Trans-epithelial |
| 873 | A proprotein convertase PC9 (PCSK9) inhibitor | Hyperlipidemia | Trans-epithelial |
| 874 | A proprotein convertase PC9 (PCSK9) inhibitor | Atherosclerosis | Trans-epithelial |
| 875 | Alirocumab | Metabolic or endocrine disease or condition | Trans-epithelial |
| 876 | Alirocumab | Diabetes | Trans-epithelial |
| 877 | Alirocumab | Obesity | Trans-epithelial |
| 878 | Alirocumab | Hypercholesterolemia | Trans-epithelial |
| 879 | Alirocumab | A lipid metabolism disorder | Trans-epithelial |
| 880 | Alirocumab | Hyperlipidemia | Trans-epithelial |
| 881 | Alirocumab | Atherosclerosis | Trans-epithelial |
| 882 | Evolocumab | Metabolic or endocrine disease or condition | Trans-epithelial |
| 883 | Evolocumab | Diabetes | Trans-epithelial |
| 884 | Evolocumab | Obesity | Trans-epithelial |
| 885 | Evolocumab | Hypercholesterolemia | Trans-epithelial |
| 886 | Evolocumab | A lipid metabolism disorder | Trans-epithelial |
| 887 | Evolocumab | Hyperlipidemia | Trans-epithelial |
| 888 | Evolocumab | Atherosclerosis | Trans-epithelial |
| 889 | Peptide YY ligand | Metabolic or endocrine disease or condition | Trans-epithelial |
| 890 | Peptide YY ligand | Diabetes | Trans-epithelial |
| 891 | Peptide YY ligand | Obesity | Trans-epithelial |
| 892 | Peptide YY ligand | Hypercholesterolemia | Trans-epithelial |
| 893 | Peptide YY ligand | A lipid metabolism disorder | Trans-epithelial |
| 894 | Peptide YY ligand | Hyperlipidemia | Trans-epithelial |
| 895 | Peptide YY ligand | Atherosclerosis | Trans-epithelial |
| 896 | NN-9747 | Metabolic or endocrine disease or condition | Trans-epithelial |
| 897 | NN-9747 | Diabetes | Trans-epithelial |
| 898 | NN-9747 | Obesity | Trans-epithelial |
| 899 | NN-9747 | Hypercholesterolemia | Trans-epithelial |
| 900 | NN-9747 | A lipid metabolism disorder | Trans-epithelial |
| 901 | NN-9747 | Hyperlipidemia | Trans-epithelial |
| 902 | NN-9747 | Atherosclerosis | Trans-epithelial |
| 903 | NN-9748 | Metabolic or endocrine disease or condition | Trans-epithelial |
| 904 | NN-9748 | Diabetes | Trans-epithelial |
| 905 | NN-9748 | Obesity | Trans-epithelial |
| 906 | NN-9748 | Hypercholesterolemia | Trans-epithelial |
| 907 | NN-9748 | A lipid metabolism disorder | Trans-epithelial |
| 908 | NN-9748 | Hyperlipidemia | Trans-epithelial |
| 909 | NN-9748 | Atherosclerosis | Trans-epithelial |
| 910 | NN-9775 | Metabolic or endocrine disease or condition | Trans-epithelial |
| 911 | NN-9775 | Diabetes | Trans-epithelial |
| 912 | NN-9775 | Obesity | Trans-epithelial |
| 913 | NN-9775 | Hypercholesterolemia | Trans-epithelial |
| 914 | NN-9775 | A lipid metabolism disorder | Trans-epithelial |
| 915 | NN-9775 | Hyperlipidemia | Trans-epithelial |
| 916 | NN-9775 | Atherosclerosis | Trans-epithelial |
| 917 | FSI-965 | Metabolic or endocrine disease or condition | Trans-epithelial |
| 918 | FSI-965 | Diabetes | Trans-epithelial |

TABLE 18-continued

Particular medical approaches

| Approach | Therapeutic agent | Disease | Delivery mode |
|---|---|---|---|
| 919 | FSI-965 | Obesity | Trans-epithelial |
| 920 | FSI-965 | Hypercholesterolemia | Trans-epithelial |
| 921 | FSI-965 | A lipid metabolism disorder | Trans-epithelial |
| 922 | FSI-965 | Hyperlipidemia | Trans-epithelial |
| 923 | FSI-965 | Atherosclerosis | Trans-epithelial |
| 924 | NN-0385-0434 | Metabolic or endocrine disease or condition | Trans-epithelial |
| 925 | NN-0385-0434 | Diabetes | Trans-epithelial |
| 926 | NN-0385-0434 | Obesity | Trans-epithelial |
| 927 | NN-0385-0434 | Hypercholesterolemia | Trans-epithelial |
| 928 | NN-0385-0434 | A lipid metabolism disorder | Trans-epithelial |
| 929 | NN-0385-0434 | Hyperlipidemia | Trans-epithelial |
| 930 | NN-0385-0434 | Atherosclerosis | Trans-epithelial |
| 931 | Amylin analog | Metabolic or endocrine disease or condition | Trans-epithelial |
| 932 | Amylin analog | Diabetes | Trans-epithelial |
| 933 | Amylin analog | Obesity | Trans-epithelial |
| 934 | Amylin analog | Hypercholesterolemia | Trans-epithelial |
| 935 | Amylin analog | A lipid metabolism disorder | Trans-epithelial |
| 936 | Amylin analog | Hyperlipidemia | Trans-epithelial |
| 937 | Amylin analog | Atherosclerosis | Trans-epithelial |
| 938 | AM-833 | Metabolic or endocrine disease or condition | Trans-epithelial |
| 939 | AM-833 | Diabetes | Trans-epithelial |
| 940 | AM-833 | Obesity | Trans-epithelial |
| 941 | AM-833 | Hypercholesterolemia | Trans-epithelial |
| 942 | AM-833 | A lipid metabolism disorder | Trans-epithelial |
| 943 | AM-833 | Hyperlipidemia | Trans-epithelial |
| 944 | AM-833 | Atherosclerosis | Trans-epithelial |
| 945 | Insulin | Metabolic or endocrine disease or condition | Epithelial |
| 946 | Insulin | Diabetes | Epithelial |
| 947 | Insulin | Obesity | Epithelial |
| 948 | Insulin | Hypercholesterolemia | Epithelial |
| 949 | Insulin | A lipid metabolism disorder | Epithelial |
| 950 | Insulin | Hyperlipidemia | Epithelial |
| 951 | Insulin | Atherosclerosis | Epithelial |
| 952 | TNF-alpha inhibitor | Metabolic or endocrine disease or condition | Epithelial |
| 953 | TNF-alpha inhibitor | Diabetes | Epithelial |
| 954 | TNF-alpha inhibitor | Obesity | Epithelial |
| 955 | TNF-alpha inhibitor | Hypercholesterolemia | Epithelial |
| 956 | TNF-alpha inhibitor | A lipid metabolism disorder | Epithelial |
| 957 | TNF-alpha inhibitor | Hyperlipidemia | Epithelial |
| 958 | TNF-alpha inhibitor | Atherosclerosis | Epithelial |
| 959 | Adalimumab | Metabolic or endocrine disease or condition | Epithelial |
| 960 | Adalimumab | Diabetes | Epithelial |
| 961 | Adalimumab | Obesity | Epithelial |
| 962 | Adalimumab | Hypercholesterolemia | Epithelial |
| 963 | Adalimumab | A lipid metabolism disorder | Epithelial |
| 964 | Adalimumab | Hyperlipidemia | Epithelial |
| 965 | Adalimumab | Atherosclerosis | Epithelial |
| 966 | A proprotein convertase PC9 (PCSK9) inhibitor | Metabolic or endocrine disease or condition | Epithelial |
| 967 | A proprotein convertase PC9 (PCSK9) inhibitor | Diabetes | Epithelial |
| 968 | A proprotein convertase PC9 (PCSK9) inhibitor | Obesity | Epithelial |
| 969 | A proprotein convertase PC9 (PCSK9) inhibitor | Hypercholesterolemia | Epithelial |
| 970 | A proprotein convertase PC9 (PCSK9) inhibitor | A lipid metabolism disorder | Epithelial |
| 971 | A proprotein convertase PC9 (PCSK9) inhibitor | Hyperlipidemia | Epithelial |
| 972 | A proprotein convertase PC9 (PCSK9) inhibitor | Atherosclerosis | Epithelial |
| 973 | Alirocumab | Metabolic or endocrine disease or condition | Epithelial |

TABLE 18-continued

Particular medical approaches

| Approach | Therapeutic agent | Disease | Delivery mode |
|---|---|---|---|
| 974 | Alirocumab | Diabetes | Epithelial |
| 975 | Alirocumab | Obesity | Epithelial |
| 976 | Alirocumab | Hypercholesterolemia | Epithelial |
| 977 | Alirocumab | A lipid metabolism disorder | Epithelial |
| 978 | Alirocumab | Hyperlipidemia | Epithelial |
| 979 | Alirocumab | Atherosclerosis | Epithelial |
| 980 | Evolocumab | Metabolic or endocrine disease or condition | Epithelial |
| 981 | Evolocumab | Diabetes | Epithelial |
| 982 | Evolocumab | Obesity | Epithelial |
| 983 | Evolocumab | Hypercholesterolemia | Epithelial |
| 984 | Evolocumab | A lipid metabolism disorder | Epithelial |
| 985 | Evolocumab | Hyperlipidemia | Epithelial |
| 986 | Evolocumab | Atherosclerosis | Epithelial |
| 987 | Peptide YY ligand | Metabolic or endocrine disease or condition | Epithelial |
| 988 | Peptide YY ligand | Diabetes | Epithelial |
| 989 | Peptide YY ligand | Obesity | Epithelial |
| 990 | Peptide YY ligand | Hypercholesterolemia | Epithelial |
| 991 | Peptide YY ligand | A lipid metabolism disorder | Epithelial |
| 992 | Peptide YY ligand | Hyperlipidemia | Epithelial |
| 993 | Peptide YY ligand | Atherosclerosis | Epithelial |
| 994 | NN-9747 | Metabolic or endocrine disease or condition | Epithelial |
| 995 | NN-9747 | Diabetes | Epithelial |
| 996 | NN-9747 | Obesity | Epithelial |
| 997 | NN-9747 | Hypercholesterolemia | Epithelial |
| 998 | NN-9747 | A lipid metabolism disorder | Epithelial |
| 999 | NN-9747 | Hyperlipidemia | Epithelial |
| 1000 | NN-9747 | Atherosclerosis | Epithelial |
| 1001 | NN-9748 | Metabolic or endocrine disease or condition | Epithelial |
| 1002 | NN-9748 | Diabetes | Epithelial |
| 1003 | NN-9748 | Obesity | Epithelial |
| 1004 | NN-9748 | Hypercholesterolemia | Epithelial |
| 1005 | NN-9748 | A lipid metabolism disorder | Epithelial |
| 1006 | NN-9748 | Hyperlipidemia | Epithelial |
| 1007 | NN-9748 | Atherosclerosis | Epithelial |
| 1008 | NN-9775 | Metabolic or endocrine disease or condition | Epithelial |
| 1009 | NN-9775 | Diabetes | Epithelial |
| 1010 | NN-9775 | Obesity | Epithelial |
| 1011 | NN-9775 | Hypercholesterolemia | Epithelial |
| 1012 | NN-9775 | A lipid metabolism disorder | Epithelial |
| 1013 | NN-9775 | Hyperlipidemia | Epithelial |
| 1014 | NN-9775 | Atherosclerosis | Epithelial |
| 1015 | FSI-965 | Metabolic or endocrine disease or condition | Epithelial |
| 1016 | FSI-965 | Diabetes | Epithelial |
| 1017 | FSI-965 | Obesity | Epithelial |
| 1018 | FSI-965 | Hypercholesterolemia | Epithelial |
| 1019 | FSI-965 | A lipid metabolism disorder | Epithelial |
| 1020 | FSI-965 | Hyperlipidemia | Epithelial |
| 1021 | FSI-965 | Atherosclerosis | Epithelial |
| 1022 | NN-0385-0434 | Metabolic or endocrine disease or condition | Epithelial |
| 1023 | NN-0385-0434 | Diabetes | Epithelial |
| 1024 | NN-0385-0434 | Obesity | Epithelial |
| 1025 | NN-0385-0434 | Hypercholesterolemia | Epithelial |
| 1026 | NN-0385-0434 | A lipid metabolism disorder | Epithelial |
| 1027 | NN-0385-0434 | Hyperlipidemia | Epithelial |
| 1028 | NN-0385-0434 | Atherosclerosis | Epithelial |
| 1029 | Amylin analog | Metabolic or endocrine disease or condition | Epithelial |
| 1030 | Amylin analog | Diabetes | Epithelial |
| 1031 | Amylin analog | Obesity | Epithelial |
| 1032 | Amylin analog | Hypercholesterolemia | Epithelial |
| 1033 | Amylin analog | A lipid metabolism disorder | Epithelial |
| 1034 | Amylin analog | Hyperlipidemia | Epithelial |
| 1035 | Amylin analog | Atherosclerosis | Epithelial |
| 1036 | AM-833 | Metabolic or endocrine disease or condition | Epithelial |
| 1037 | AM-833 | Diabetes | Epithelial |
| 1038 | AM-833 | Obesity | Epithelial |
| 1039 | AM-833 | Hypercholesterolemia | Epithelial |
| 1040 | AM-833 | A lipid metabolism disorder | Epithelial |

TABLE 18-continued

Particular medical approaches

| Approach | Therapeutic agent | Disease | Delivery mode |
|---|---|---|---|
| 1041 | AM-833 | Hyperlipidemia | Epithelial |
| 1042 | AM-833 | Atherosclerosis | Epithelial |
| 1043 | Insulin | Metabolic or endocrine disease or condition | Topical |
| 1044 | Insulin | Diabetes | Topical |
| 1045 | Insulin | Obesity | Topical |
| 1046 | Insulin | Hypercholesterolemia | Topical |
| 1047 | Insulin | A lipid metabolism disorder | Topical |
| 1048 | Insulin | Hyperlipidemia | Topical |
| 1049 | Insulin | Atherosclerosis | Topical |
| 1050 | TNF-alpha inhibitor | Metabolic or endocrine disease or condition | Topical |
| 1051 | TNF-alpha inhibitor | Diabetes | Topical |
| 1052 | TNF-alpha inhibitor | Obesity | Topical |
| 1053 | TNF-alpha inhibitor | Hypercholesterolemia | Topical |
| 1054 | TNF-alpha inhibitor | A lipid metabolism disorder | Topical |
| 1055 | TNF-alpha inhibitor | Hyperlipidemia | Topical |
| 1056 | TNF-alpha inhibitor | Atherosclerosis | Topical |
| 1057 | Adalimumab | Metabolic or endocrine disease or condition | Topical |
| 1058 | Adalimumab | Diabetes | Topical |
| 1059 | Adalimumab | Obesity | Topical |
| 1060 | Adalimumab | Hypercholesterolemia | Topical |
| 1061 | Adalimumab | A lipid metabolism disorder | Topical |
| 1062 | Adalimumab | Hyperlipidemia | Topical |
| 1063 | Adalimumab | Atherosclerosis | Topical |
| 1064 | A proprotein convertase PC9 (PCSK9) inhibitor | Metabolic or endocrine disease or condition | Topical |
| 1065 | A proprotein convertase PC9 (PCSK9) inhibitor | Diabetes | Topical |
| 1066 | A proprotein convertase PC9 (PCSK9) inhibitor | Obesity | Topical |
| 1067 | A proprotein convertase PC9 (PCSK9) inhibitor | Hypercholesterolemia | Topical |
| 1068 | A proprotein convertase PC9 (PCSK9) inhibitor | A lipid metabolism disorder | Topical |
| 1069 | A proprotein convertase PC9 (PCSK9) inhibitor | Hyperlipidemia | Topical |
| 1070 | A proprotein convertase PC9 (PCSK9) inhibitor | Atherosclerosis | Topical |
| 1071 | Alirocumab | Metabolic or endocrine disease or condition | Topical |
| 1072 | Alirocumab | Diabetes | Topical |
| 1073 | Alirocumab | Obesity | Topical |
| 1074 | Alirocumab | Hypercholesterolemia | Topical |
| 1075 | Alirocumab | A lipid metabolism disorder | Topical |
| 1076 | Alirocumab | Hyperlipidemia | Topical |
| 1077 | Alirocumab | Atherosclerosis | Topical |
| 1078 | Evolocumab | Metabolic or endocrine disease or condition | Topical |
| 1079 | Evolocumab | Diabetes | Topical |
| 1080 | Evolocumab | Obesity | Topical |
| 1081 | Evolocumab | Hypercholesterolemia | Topical |
| 1082 | Evolocumab | A lipid metabolism disorder | Topical |
| 1083 | Evolocumab | Hyperlipidemia | Topical |
| 1084 | Evolocumab | Atherosclerosis | Topical |
| 1085 | Peptide YY ligand | Metabolic or endocrine disease or condition | Topical |
| 1086 | Peptide YY ligand | Diabetes | Topical |
| 1087 | Peptide YY ligand | Obesity | Topical |
| 1088 | Peptide YY ligand | Hypercholesterolemia | Topical |
| 1089 | Peptide YY ligand | A lipid metabolism disorder | Topical |
| 1090 | Peptide YY ligand | Hyperlipidemia | Topical |
| 1091 | Peptide YY ligand | Atherosclerosis | Topical |
| 1092 | NN-9747 | Metabolic or endocrine disease or condition | Topical |
| 1093 | NN-9747 | Diabetes | Topical |
| 1094 | NN-9747 | Obesity | Topical |
| 1095 | NN-9747 | Hypercholesterolemia | Topical |

TABLE 18-continued

Particular medical approaches

| Approach | Therapeutic agent | Disease | Delivery mode |
|---|---|---|---|
| 1096 | NN-9747 | A lipid metabolism disorder | Topical |
| 1097 | NN-9747 | Hyperlipidemia | Topical |
| 1098 | NN-9747 | Atherosclerosis | Topical |
| 1099 | NN-9748 | Metabolic or endocrine disease or condition | Topical |
| 1100 | NN-9748 | Diabetes | Topical |
| 1101 | NN-9748 | Obesity | Topical |
| 1102 | NN-9748 | Hypercholesterolemia | Topical |
| 1103 | NN-9748 | A lipid metabolism disorder | Topical |
| 1104 | NN-9748 | Hyperlipidemia | Topical |
| 1105 | NN-9748 | Atherosclerosis | Topical |
| 1106 | NN-9775 | Metabolic or endocrine disease or condition | Topical |
| 1107 | NN-9775 | Diabetes | Topical |
| 1108 | NN-9775 | Obesity | Topical |
| 1109 | NN-9775 | Hypercholesterolemia | Topical |
| 1110 | NN-9775 | A lipid metabolism disorder | Topical |
| 1111 | NN-9775 | Hyperlipidemia | Topical |
| 1112 | NN-9775 | Atherosclerosis | Topical |
| 1113 | FSI-965 | Metabolic or endocrine disease or condition | Topical |
| 1114 | FSI-965 | Diabetes | Topical |
| 1115 | FSI-965 | Obesity | Topical |
| 1116 | FSI-965 | Hypercholesterolemia | Topical |
| 1117 | FSI-965 | A lipid metabolism disorder | Topical |
| 1118 | FSI-965 | Hyperlipidemia | Topical |
| 1119 | FSI-965 | Atherosclerosis | Topical |
| 1120 | NN-0385-0434 | Metabolic or endocrine disease or condition | Topical |
| 1121 | NN-0385-0434 | Diabetes | Topical |
| 1122 | NN-0385-0434 | Obesity | Topical |
| 1123 | NN-0385-0434 | Hypercholesterolemia | Topical |
| 1124 | NN-0385-0434 | A lipid metabolism disorder | Topical |
| 1125 | NN-0385-0434 | Hyperlipidemia | Topical |
| 1126 | NN-0385-0434 | Atherosclerosis | Topical |
| 1127 | Amylin analog | Metabolic or endocrine disease or condition | Topical |
| 1128 | Amylin analog | Diabetes | Topical |
| 1129 | Amylin analog | Obesity | Topical |
| 1130 | Amylin analog | Hypercholesterolemia | Topical |
| 1131 | Amylin analog | A lipid metabolism disorder | Topical |
| 1132 | Amylin analog | Hyperlipidemia | Topical |
| 1133 | Amylin analog | Atherosclerosis | Topical |
| 1134 | AM-833 | Metabolic or endocrine disease or condition | Topical |
| 1135 | AM-833 | Diabetes | Topical |
| 1136 | AM-833 | Obesity | Topical |
| 1137 | AM-833 | Hypercholesterolemia | Topical |
| 1138 | AM-833 | A lipid metabolism disorder | Topical |
| 1139 | AM-833 | Hyperlipidemia | Topical |
| 1140 | AM-833 | Atherosclerosis | Topical |

The ingestible device disclosed herein can be used to implement any of medical approaches 1-1140.

OTHER EMBODIMENTS

While certain embodiments have been provided, other embodiments are possible.

As an example, some embodiments have been described in which an ingestible device includes one or more pins. However, the disclosure is not limited in this sense. Rather, in such embodiments, any element having the appropriate shape and size, as well as being made of the appropriate material(s), may be used instead of (or, in some cases, in addition to) one or more of the pins.

As another example, while embodiments have been described in which the dispensable substance is released in a single stage. Other embodiments are possible. In some embodiments, multi-stage (e.g., two stage, three stage, four stage) release of the dispensable substance is used. Multi-staged release can be achieved, for example, via multiple elements (e.g., pins, plugs or the like) formed of different materials (e.g., different enteric materials) that degrade/dissolve erode under different conditions (e.g., different pH, temperature, enzyme concentration) present in different locations in the GI tract of a subject.

As an additional example, while embodiments have been described in which an ingestible device includes a seal or a coating, the disclosure is not limited in this sense. For example, in some embodiments, an ingestible device housing may be covered in one or more coverings, e.g., to seal the ingestible device and/or to hold two modules of the device together. In certain embodiments, an ingestible device may be sealed to prevent contaminants from entering the ingestible device prior to administration to a subject (e.g., during storage of the device) or after administration to a subject (e.g., during transit through the stomach), or to prevent the contents of the ingestible device (e.g., a dispensable substance) from exiting the ingestible device before desired (e.g., prior to triggering). In certain embodiments, an ingestible device is assembled from two modules: one module contains the dispensable substance ("drug module"), while the other module contains the drive force generator and the drive coupling ("drive module"). One or more coverings can be used to partially or wholly join and/or seal the two modules after they are assembled together to form an ingestible device. In some embodiments, one or more coverings cover the entirety of the housing of the ingestible device, while in other embodiments one or more coverings cover only a portion of the housing the ingestible device (e.g., parts of the housing with an opening, parts of the housing that comprise enteric materials, or parts of the housing assembled from two or more different modules after the modules are joined together to form an ingestible device). Examples of covering materials include foils, films, and other materials that degrade or erode in the GI tract, and/or that are made of a relatively low mechanical strength material (e.g., so that a dispensable substance can pass through the covering and exit in the form of a jet after triggering). In some embodiments, one or more coverings are made of a gelatin material, for example, using a gel-enrobed technology such as PressFit® or XPressFit® gelcap from Lonza (see, e.g., U.S. Pat. Nos. 5,317,849, 5,460,824, 5,464,631, 5,511,361, 5,795,588, 5,609,010, 6,080,426, and 6,245,350). In some embodiments, the one or more coverings are applied to the device housing using a cold-shrink process. In some embodiments, the one or more coverings degrade or erode in the stomach or in the proximal small intestine (e.g., in the duodenum).

As a further example, while certain embodiments of an ingestible device have been described in relation to certain forms of delivery (trans-epithelial, epithelial, topical), the disclosure is not limited in this sense. As an example, in some embodiments, a device described for use in trans-epithelial delivery or for use in epithelial delivery can be used in topical delivery. Generally, such embodiments involve modifying the relevant parameters (e.g., internal pressure, fluid pressure) accordingly. As another example, in some embodiments, a device described for use in epithelial delivery or for use in epithelial delivery can be used in topical delivery. Generally, such embodiments involve modifying the relevant parameters (e.g., internal pressure, fluid pressure) accordingly.

As another example, in some embodiments, one or more of the components of an ingestible device that contact the dispensable substance (e.g., a reservoir, a housing) include a cyclic olefin copolymer ("COC"). In some embodiments, one or more portions of the housing are formed of a COC, and/or the drive coupling (e.g., piston) is formed of a COC. COCs can be advantageous because they are relatively inert to certain therapeutic agents, such as monoclonal antibodies. Examples of COCs include those which are commercially available, such as those found at http://polymerdatabase.com/Polymer%20Brands/COC.html, which is incorporated by reference herein. Examples of commercially available COCs include Topas (5013/6013/6015/8007), Zeon (Zeonex) and Mitsui (Apel). In some embodiments, one or more of an ingestible device that contact the dispensable substance (e.g., a reservoir, a housing) include one or more cyclic olefin polymers (COPS), silicon dioxide, Resin CZ (Daikyo), polyetheretherketones (PEEKS) (e.g., Solvay (Ketaspire) or Invibio (Peek Optima)), polysulfones (PSs) (e.g., Solvay), one or more ethylene tetrafluoroethylene (ETFEs) Chemours or St. Gobain). In general, such materials are compatible with a wide range of drugs and drug formulations. In some embodiments, a reservoir and/or a housing is made of a different material, and the interior surface of the reservoir (which contacts the dispensable substance) is coated with said material. As an example, a reservoir and/or a housing can be made of polycarbonate coated with one of the noted materials.

As yet a further example, in some embodiments the surface of an ingestible device is very smooth. However, in certain embodiments, the outer surface of an ingestible device has a non-zero degree of roughness. In such embodiments, having a non-zero degree of roughness for the outer surface of an ingestible device may result in a relatively desirable navigation of the ingestible device navigate through the GI tract of a subject. As an example, an ingestible device having an outer surface with a non-zero rugosity may pass through one or more regions of the GI tract in a relatively slow manner. In some embodiments, an ingestible device can have an outer surface with a non-zero rugosity can include, for example, one or more regions that are grooved. An outer surface with a non-zero rugosity can, for example, allow for more time and opportunity to deliver one or more dispensable substances when the ingestible device is disposed within an appropriate region of the GI tract. Such a device can be used for delivery as desired, including, for example, trans-epithelial delivery, epithelial delivery or topical delivery. Generally, the parameters for such delivery are similar to those described elsewhere herein.

As still a further example, while various embodiments of ingestible devices having one or more nozzles have been described in which the exit(s) of the nozzle(s) is flush with an exterior surface of the ingestible devices, the disclosure is not limited to such embodiments. For example, an ingestible device having one or more nozzles may be configured so that the nozzle exit(s) extend outwardly from one or more regions of the outer surface of the ingestible device. In some embodiments in which an ingestible device includes one or more nozzles that extend outwardly from one or more regions of the outer surface of the device, the nozzle(s) are disposed on a longer axis of the device. In another embodiments in which an ingestible device includes one or more nozzles that extend outwardly from one or more regions of the outer surface of the device, the nozzle(s) are disposed on the radial axis of the device. Such an arrangement can allow for enhanced alignment with the surface of the GI tract, e.g., the one or more nozzles are in closer proximity to the mucosal tissue of the GI tract. More generally, any ingestible device described herein having one or more nozzles can be configured such one or more of the nozzles extend outwardly from one or more regions of the outer surface of the ingestible device.

As an additional example, while certain capsule shapes have been disclosed, the disclosure is not limited to such shapes. For example, in some embodiments, the diameter of the capsule adjacent one end that is substantially different (e.g., substantially smaller) from the diameter of the capsule adjacent to the opposite end of the capsule. An example of such a capsule is a droplet-shaped capsule. In certain embodiments, a capsule have a shape described in the present paragraph may allow for the capsule to get relatively close to the mucus (and, as a result, relatively close to the epithelial layer) of the GI tract.

As another example, in some embodiments, an ingestible device is less dense than the fluid present in one or more (e.g., all) regions of the GI tract that are of interest in using the ingestible device to delivery one or more dispensable substances. Such an ingestible device can pass through one or more regions of the GI tract in a relatively predictable fashion, which can enhance the ability to deliver the one or more dispensable substances to one or more desired locations in a relatively controlled and/or predictable fashion. In some situations, an ingestible device is less dense than the fluid present in one or more (e.g., all) regions of the GI tract that are of interest in using the ingestible device to delivery one or more dispensable substances can be referred to as not being buoyant.

As another example, while certain examples of embodiments of a seal (e.g., a foil seal) for a nozzle exit have been described, the disclosure is not limited to such seals. More generally, a seal for a nozzle exit can have any shape and be formed of any material such that it resists breakage until breakage is desired. In addition, a seal for a nozzle exit can be in the interior of the device (e.g., on the surface of the drug reservoir) whereby the entrance to the nozzle is sealed. In some embodiments, a seal for a nozzle exit can be formed of ethyl cellulose (e.g., EthoCel) or polyvinyl acetate (e.g., Kollicoat). In certain embodiments, a seal can in the form of a film, such as, for example, a film having a thickness of from about 10 µm to about 50 µm (e.g., from about 20 µm to about 40 such as about 30 µm). In some embodiments, a seal for a nozzle exit can be formed of a coating that covers some or all of the exterior surface of the capsule material, including the nozzle exit(s) to be sealed. Such coatings can be a monolayer coating or a multilayer coating. Materials that can be used in a monolayer coating include cyclic olefin copolymer (COC), polytetrafluoroethylene (PTFE), thermopolymers, and cellulose acetate. The thickness of such a monolayer can be, for example, from about 25 µm to about 200 µm (e.g., about 35 about 75 about 140 about 200 µm). In some embodiments, the coating is a 140 µm COC monolayer. COC is commercially available from, for example, TekniPlex. In certain embodiments, the coating is a 75 µm PTFE monolayer. In some embodiments, the coating is a 200 µm PTFE monolayer. In certain embodiments, the coating is a 35 µm cellulose acetate monolayer. In some embodiments, the coating is a 75 µm cellulose acetate monolayer. Cellulose acetate is commercially available from, for example, Agar Scientific. A multilayer coating can be formed of, for example, a layer of COC and a polymer layer (e.g., polychlorotrifluoroethylene (PCTFE)) with a tie layer therebetween. Such a multilayer coating can have a thickness of from about 25 µm to about 75 µm (e.g., about 50 µm). For example, a multilayer coating be formed of a layer of COC (e.g., 20 µm), a tie layer (e.g., 16 µm) and a layer of polychlorotrifluoroethylene (e.g., 15 µm). An example of such a commercially available multilayer material is Tekniflex CTA160 (TekniPlex). As noted above, in some embodiments, the seal for a nozzle can be a polyolefin material, for example, having a thickness of from about 40 µm to about 60 µm (e.g., about 50 µm). An example, a commercially available polyolefin Trans-Pharma TRA-150 (Tanscendia). In certain embodiments, a seal can be composed of LDPE, for example, having a thickness of from about 10 µm to about 100 µm (e.g., from about 20 µm to about 80 µm, about 25 µm, about 50 µm, about 100 µm). An example of a commercial supplier of such LDPE is Goodfellows. In some embodiments, the seal for a nozzle can be composed of polyethylene terephthalate (PET), for example having a thickness of from about 5 µm to about 15 µm (e.g., about 13 µm), such as can be acquired from Nordsen Medical. As disclosed above, in certain embodiments, the seal for a nozzle can be composed of PTFE, for example having a thickness of from about 50 µm to about 250 µm (e.g., about 75 µm, about 75 µm), such as can be acquired from RS Components. In certain embodiments, the seal for a nozzle can be composed of fluorinated ethylene propylene (FEP) or nylon (e.g., nylon 12). In some embodiments, the seal for a nozzle can be formed of a metal (e.g., a metal foil). An example of such a metal is aluminum, such as household aluminum foil. In some embodiments, a film containing a metal may have a multilayer construction.

As an additional example, while various examples of general categories and specific examples of materials have been described above, the disclosure is not limited to such materials. In general, according to the disclosure, any appropriate material can be used for any component of an ingestible device. A non-limiting list of general types of materials includes water soluble materials, water insoluble materials, biodegradable materials, non-biodegradable materials and pH dependent soluble materials. In some cases, a given material may fall within more than one such type.

In some embodiments, one or more components of an ingestible device can include one or more thermoplastic materials, e.g., which may facilitate efficient absorption and access to the blood stream in the gastrointestinal tract. Additionally or alternatively, one or more components of an ingestible device can be formed of one or more water soluble polymers, water insoluble polymers, biodegradable polymers and/or a pH-dependent polymers. In some embodiments, suitable polymers may be selected and adapted to have a desired degradation rate and/or dissolution rate. Alternatively, or additionally, a degradation rate and/or dissolution rate may be fine-tuned by associating or mixing other materials as described herein. In some embodiments, a thermoplastic material may for example be polymers that may be formed by heat and may be used to create desired shapes of the material. In one embodiment, thermoplastic materials may be manufactured to the desired shape by injection molding, for example, 3D-printing or hot melt extrusion. In some embodiments, an ingestible device can include one or more components that include one or more starch based polymers, cellulose based polymers, synthetic polymers, and/or biodegradable polymers. In some embodiments, a thermoplastic polymer may be made up of long, unlinked polymer molecules, generally with a high molecular weight. Because the molecular chains may be unlinked, they rely on other interactions, such as dipole-dipole interactions, aromatic ring stacking, or Van der Waals forces. Thermoplastics generally form a crystalline structure when cooled below a certain temperature, resulting in a smooth surface finish and significant structural strength. Above this temperature, thermoplastics may be elastic. As the temperature increases, thermoplastics gradually soften, eventually melting.

In some embodiments, one or more components of an ingestible device can include one or more starch based polymers, such as one or more thermoplastic starch polymers. In some embodiments, the starch based polymer may be starch as such or a polymer having a high starch content selected from more than 70% starch, more than 80% starch, or more than 90% starch. Examples of molecules in starch include amylose and amylopectin. In some embodiments, a starch-based polymer can be general fully biodegradable. In some embodiments, a starch based polymer may be maize starch, such as, for example, Cornpack. A starch based polymers may be decomposable. In some cases, a starch based polymer can be relatively stable and relatively inert in solid dosage forms.

In some embodiments, one or more of the components of an ingestible device can include one or more cellulose based polymers. A cellulose based polymer may be cellulose, wherein one or more of the free —OH groups have been substituted with an R-group to form a —O—R group. R may in this context, for example, be linear or branched lower alkyl, linear or branched lower alkyl-OH, linear or branched lower alkyl-COOH, —CO-(linear or branched lower alkyl), nitrate, aromatic rings or combinations of the aforementioned. Lower alkyl is preferably a $C_{1-10}$ alkyl, more preferably $C_{1-6}$ alkyl. A cellulose based polymer may, for example, be one or more selected from ethyl cellulose, cellulose acetate, cellulose propionate, cellulose nitrate, methylcellulose, carboxymethylcellulose and salts thereof, cellulose acetate phthalate, include hydroxypropyl methylcellulose phthalate (HPMC-P), ethylhydroxyethylcellulose, ethylmethylcellulose, hydroxyethylcellulose, hydroxyethylmethylcellulose, hydroxypropylcellulose, hydroxypropyl methylcellulose, hydroxymethylcellulose and hydroxymethylpropylcellulose and cellulose acetate. Cellulose based polymers also include cellulose acetate, cellulose propionate, silicified microcrystalline cellulose, cellulose nitrate, methylcellulose, carboxymethylcellulose and salts thereof, cellulose acetate phthalate, microcrystalline cellulose, ethylhydroxyethylcellulose, ethylmethylcellulose, hydroxyethylcellulose, hydroxyethylmethylcellulose, hydroxypropylcellulose, hydroxypropylmethylcellulose, hydroxymethylcellulose phthalate, hydroxymethylcellulose and hydroxymethylpropylcellulose, cellulose acetate, and ceratonia.

In some embodiments, one or more components of an ingestible device can include one or more synthetic polymers. Examples include polyamide, polyethylene, polyethylene terephthalate, polypropylene, polyurethane, polyvinyl acetate, polyvinyl alcohol, polyvinyl butural, polyvinyl chloride), Eudragit L methyl ester, Eudragit RL, Eudragit RS, Eudragit S and Eudragit E, silicone rubber, latex, resin, shellac, Polytetrafluoroethylene (teflon), copolymers such as ethylene vinyl acetate (EVA), styrene-butadienestyrene (SBS) and styrene-isoprene-styrene (SIS), Polyethylene glycols, polyvinylpyrrolidone, polyethylene oxide, carboxymethylene (Carbomer) and sugars thereof (for example, allylsucrose) and co-polymers of ethylene and propylene oxide (Poloxamers), polyvinylchloride (PVC), polytetrafluoroethylene (PTFE), Polyethersulfone (PES), polyethylene (PE), polyetheretherketone (PEEK), polysulfone (PS), polypropylene (PP), hydroxypropyl methylcellulose acetate succinate (HPMCAS), polydioxanone (PDS), Poly(methyl acrylate), Poly(methyl methacrylate), Polyhydroxyethylmethacrylate, poly(monosteroyl glyceryl-co-succinate), copolymers of vinylpyrrolidone, polydimethylene-siloxane, poly(N-isopropyl acrylamide), Poly(amidoamine) dendrimers, polyacrylic acid, polyacrylamide, poly (2-(dimethylamino)ethyl acrylate (PDEAEMA), poly(2-(dimethylamino)ethyl methacrylate (PDMAEMA), Poly (methyl methacrylate), Polyhydroxyethylmethacrylate, polyorthoesters, polyacrylic acid, polyalkyl cyanoacrylates, poly(n-butylcyanoacrylate) (PBCA), and Polyhydroxycarboxylic Acid (PHCA).

In some embodiments, one or more components of an ingestible device include one or more biodegradable polymers. In certain embodiments, a biodegradable polymer can be a starch based polymer and/or a cellulose based polymer. Examples of biodegradable polymers include polyhydroxybutyrate (PHB), polyhydroxyvalerate (PHV), polyhydroxyvalerate-co-hydroxyvalerate (PHV/VH), Polyhydroxyalkanoates (PHA), poly-3-hydroxy-5-phenylvalerate (PHPV), aliphatic polyesters, polycaprolactone (PCL), polylactic acid (PLA), polyglycolic acid (PGA), copolymers or block copolymers of polycaprolactone (PCL), polylactic acid (PLA) and/or polyglycolic acid (PGA), polypropylene carbonate (PPC), polyester amide (PEA), polybutylene succinate adipate (PBSA), polybutylene adipate co-terephtalate (PBAT) and polybutylene succinate-adipate (PESA), terephthalic acid (PTA), Polyhydroxybutyrate (PHB), polysebatic acid, polyphosphazenes, polyphosphonate, polycyanoacrylates, polyurethenes, polyorthoesters, and Polydioxanone (PDS). Additional examples include copolymers or block copolymers of polycaprolactone (PCL), polylactic acid (PLA) and/or polyglycolic acid (PGA) may, for example, be selected from poly(lactic-co-glycolic acid) (PLGA), polylactic acid and epsilon-caprolactone copolymer (PLA/CL) and polylactic acid/glycolic acid polymers)(PLA/GA). Further examples include polylactic acid (PLA), polycaprolactone (PCL) and polyhydroxy butyrate (PHB), preferably the delivery device, body delivery part and/or the payload may comprise both polylactic acid (PLA), polycaprolactone (PCL) and polyhydroxybutyrate (PHB).

In some embodiments, one or more components of an ingestible device can include one or more different polymers and/or co-polymers, such as, for example, one or more different polymers selected from starch based polymers, cellulose based polymers, synthetic polymers and biodegradable polymers.

In some embodiments, one or more components of an ingestible device can include one or more polyglycols. Examples include polyethylene glycols and polyethylene oxides.

In some embodiments, one or more components of an ingestible device can include one or more plasticizers. Examples include poloxamer, mono- and di-acetylated monoglycerides, diacetylated monoglycerides, acetylated hydrogenated cottonseed glyceride, glyceryl cocoate, polyethylene glycols, polyethylene oxides, dipropylene glycol salicylate glycerin, fatty acids and esters, phthalate esters, phosphate esters, amides, diocyl phthalate, diethyl phthalate, phthalyl glycolate, mineral oils, hydrogenated vegetable oils, vegetable oils, acetylated hydrogenated soybean oil glycerides, castor oil, acetyl tributyl citrate, acetyl triethyl citrate, methyl abietate, nitrobenzene, carbon disulfide, beta-naphtyl salicylate, citric acid, tromethamine, xylitol, maltitol, chitosan, sorbitol, sorbitol sorbitan solution, sorbitol glyceryl tricitrate, fatty alcohols, cetostearyl alcohol, cetyl alcohol, stearyl alcohol, oleyl alcohol, myristyl alcohol, sucrose octaacetate, alfatocopheryl polyethylene glycol succinate (TPGS), tocopheryl derivative, diacetylated monoglycerides, diethylene glycol monostearate, ethylene glycol monostearate, glyceryl monooleate, glyceryl monostearate, propylene glycol monostearate, macrogol esters, macrogol stearate 400, macrogol stearate 2,000, polyoxyethylene 50 stearate, macrogol ethers, cetomacrogol 1000, lauromacrogols, nonoxinols, octocinols, tyloxapol, polyvinyl alcohols, polysorbate 20, polysorbate 40, polysorbate 60, polysorbate 65, polysorbate 80, polysorbate 85, sorbitan monolaurate, sorbitan monooleate, sorbitan monopalmitate, sorbitan monostearate, sorbitan sesquioleate, sorbitan trioleate, sorbitan tristearate and sucrose esters, amyl oleate, butyl oleate, butyl stearate, diethylene glycol monolaurate, glycerol tributyrate, Cumar W-1, Cumar MH-1, Cumar V-1, Flexol B-400, monomeric polyethylene ester, Piccolastic A-5, Piccalastic A-25, Beckolin, Clorafin 40, acetyl tributyl citrate, acetyl triethyl citrate, benzyl benzoate, butoxyethyl stearate, butyl and glycol esters of fatty acids, butyl diglycol carbonate, butyl ricinoleate, butyl phthalyl butyl glycolate, camphor, dibutyl sebacate, dibutyl tartrate, diphenyl oxide, glycerine, HB-40, hydrogenated methyl ester of rosin, methoxyethyl oleate, monoamylphthalate, Nevillac 10, Paracril 26, technical hydroabietyl alcohol, methylene glycol dipelargonate, and solid aliphatic alcohols.

In some embodiments, one or more components of an ingestible device can include one or more excipients. Examples of excipients include diluents such as dicalcium phosphate, calcium sulfate, lactose or sucrose or other disaccharides, cellulose, cellulose derivatives, kaolin, mannitol, dry starch, glucose or other monosaccharides, dextrin or other polysaccharides, sorbitol, inositol or mixtures thereof; binders such as alginic acid, calcium alginate, sodium alginate, starch, gelatin, saccharides (including glucose, sucrose, dextrose and lactose), carboxymethylcellulose, methylcellulose, veegum, larch arabolactan, polyethylene glycols, ethylcellulose, water, alcohols, waxes, polyvinylpyrrolidone such as PVP K90 or mixtures thereof; lubricants such as talc, silicium dioxide, magnesium stearate, calcium stearate, stearic acid, hydrogenated vegetable oils, sodium benzoate, sodium chloride, leucine, carbowax 4000, magnesium lauryl sulfate, Sodium lauryl sulfate, Stearyl alcohol, Polysorbate 20, Polysorbate 60, Polysorbate 80, Macrogol stearate, Macrogol lauryl ether, Stearoyl macrogolglycerides, Sorbitan stearate, Sorbitan laurate, Macrogol glycerol hydroxystearat, colloidal silicon dioxide and mixtures thereof, disintegrants such as starches, clays, cellulose derivatives including crosscarmellose, gums, aligns, various combinations of hydrogencarbonates with weak acids (for example, sodium hydrogencarbonate/tartaric acid or citric acid) crosprovidone, sodium starch glycolate, agar, cation exchange resins, citrus pulp, glycollate, natural sponge, bentonite, sucralfate, and calcium hydroxyl-apatite. In some cases, an excipient can be selected from polymers, such as polyglycols selected from substantially water soluble, thermoplastic, crystalline, semi-crystalline or amorphous or a mixture of substantially water soluble, crystalline, semi-crystalline or amorphous polymers. In some embodiments, the delivery device, body, delivery part, payload and/or the pharmaceutical composition may include a pharmaceutically acceptable excipient selected from suitable polyglycols for example derivatives of polyethylene glycol, such as mono or dimethoxypolyethylene glycols (mPEGs), polyethylene oxides and/or block copolymers of ethylene oxide and propylene oxide. In some embodiments, an excipient can be selected from polymers, such as, for example, modified or unmodified water soluble natural polymers such as glucomannan, galactan, glucan, polygalacturonic acid, polyxylane, polygalactomannans, rhanogalacturonan, polyxyloglycan, arabinogalactan, and starch, cellulose, chitosan, alginate, fibrin, collagen, gelatin, hyaluronic acid, amylopectin, pectin including low methylated or methoxylated pectins, dextran and fatty acids and alcohols; synthetic polymers such as Carbopol, carbomer, carbomer homopolymer, carboxyvinyl polymer, polyvinylpyrrolidone (PVP), PVA, PVB, Eudragit L methyl ester, Eudragit L, Eudragit RL, Eudragit RS, Eudragit E, Eudragit S, PHPV, PHA, PCL, PLGA and PLA; and hydrogels made from the polymers or combined polymers mentioned above and or from polymers originated from HEMA, HEEMA, MEMA, MEEMA, EDGMA, NVP, VAc, AA, acrylamide, MAA, HPMA, PEGA, PEGMA, PEGDMA, PEGDA, and PEGDMA. In some embodiments, an excipient can be a gelling agents. Examples may be polymers, such as modified or unmodified water soluble natural polymers such as glucomannan, galactan, glucan, polygalacturonic acid, polyxylane, polygalactomannans, polyxyloglycan, arabinogalactan, starch, cellulose, chitosan, alginate, fibrin, collagen, gelatin, amylopectin, pectin including low methylated or methoxylated pectins, dextran; synthetic polymers such as PVA and PVB; and hydrogels made from the polymers or combined polymers mentioned above and or from polymers originated from: HEMA, HEEMA, MEMA, MEEMA, EDGMA, NVP, VAc, AA, acrylamide, MAA, HPMA, PEGA, PEGMA, PEGDMA, PEGDA, and/or PEGDMA, hydroxypropyl methylcellulose, hydroxypropyl cellulose, methylcellulose, hydroxyethyl cellulose, ethylcellulose, hydroxypropyl methylcellulose phthalate, hydroxypropyl methylcellulose acetate succinate or other cellulose derivates, carboxymethylcellulose sodium, carboxymethylcellulose calcium, carrageenans, guar gum, gellan gum, xanthan gum, tragacanth and arabic gum. In some embodiments, an excipient can be an effervescent agent. Examples include citric acid, ascorbic acid, glutaric acid, malic acid, malonic acid, adipic acid, clavulanic acid, oxalic acid, tartaric acid, fumaric acid, succinic acid, sodium acid pyrophosphate, sorbic acid, sodium citrate dehydrate, lactic acid, hexamic acid, benzoic acid, etianic acids, disphosphonoic acids and acidic salts and acid anhydrides thereof, and mixtures thereof. Examples of useful acid anhydrides may include citraconic anhydride, glucono-D-lactone, sulphuric acid, hyaluronic acid and succinic anhydride. Examples of useful acid salts may include potassium bitartrate, acid citrate salts, sodium dihydrogen phosphate, disodium dihydrogen phosphate, and combinations thereof. The base preferably is capable of generating carbon dioxide. Examples of useful bases may include water soluble carbonates and bicarbonates. Further specific examples of suitable bases may include sodium bicarbonate such as "Effer-Soda," sodium carbonate, sodium sesqui-carbonate, potassium carbonate, potassium bicarbonate, ammonium bicarbonate, calcium carbonate, magnesium carbonate, sodium glycine carbonate, L-lysine carbonate, arginine carbonate, zinc carbonate, and mixtures thereof.

In some embodiments, one or more components of an ingestible device can include one or more disintegrants. Examples include sodium starch glycolate, povidone, sodium alginate, alginic acid, calcium alginate, carboxymethylcellulose calcium, carboxymethylcellulose sodium, powdered cellulose, chitosan, croscarmellose sodium (croscarmellose Na), crospovidone, cross-linked polyvinylpyrrolidone, hydroxypropyl starch, hydroxypropyl cellulose low-substituted, magnesium aluminium silicate, methylcellulose, microcrystalline cellulose, pregelatinized starch, docusae sodium, guar gum, and polacrilin potassium.

In some embodiments, one or more components of an ingestible device can include one or more stabilizers. Examples include TPG, for example, in the form of TPGS (Vitamin E Polyehtylene glycol succinate) and BHT, BHA, t-butyl hydroquinone, butylhydroxy toluene, calcium ascorbate, gallic acid, hydroquinone, maltol, octyl gallate, sodium bisulfite, sodium metabisulfite, tocopherol and derivates thereof, citric acid, tartaric acid, and ascorbic acid. Other stabilizers may include trivalent phosphorous, such as, for example, phosphite, phenolic antioxidants, hydroxylamines, lactones such as substituted benzofuranones, hindered phenols, thiosynergists and/or hindered amines, acids (ascorbic acid, erythorbic acid, etidronic acid, hypophosphorous acid, nordihydroguaiaretic acid, propionic acid etc.), phenols, dodecyl gallate, octyl gallate, 1,3,5-trihydroxybenzene, organic and inorganic salts (calcium ascorbate, sodium ascorbate, sodium bisulphite, sodium metabisulfite, sodium sulfite, potassium bisulphite, potassium metabisulphite), esters (calcium ascorbate, dilauryl thiodipropionate, dimyristyl thiodipropionate, distearyl thiodipropionate), pyranon (maltol), and vitamin E (tocopherol, D-[alpha]-tocopherol, DL-[alpha]-tocopherol, tocopheryl acetate, d-[alpha]-tocopheryl acetate, and dL-[alpha]-tocopheryl acetate.

In some embodiments, one or more components of an ingestible device can include one or more surfactants. Examples include Gelucire such as, for example Gelucire 50/13, Gelucire 44/14, Gelucire 50/10, Gelucire 62/05, Sucro-ester 7, Sucro-ester 11, Sucro-ester 15, Polyethoxylated fatty acids such as, for example fatty acid mono- or diesters of polyethylene glycol or mixtures thereof such as, for example mono- or diesters of polyethylene glycol with lauric acid, oleic acid, stearic acid, myristic add, ricinoleic acid, polyethylene glycol such as for example PEG 4, PEG 5, PEG 6, PEG 7, PEG 8, PEG 9, PEG 10, PEG 12, PEG 15, PEG 20, PEG 25, PEG 30, PEG 32, PEG 40, PEG 45, PEG 50, PEG 55, PEG 100, PEG 200, PEG 400, PEG 600, PEG 800, PEG 1000, PEG 2000, PEG 3000, PEG 4000, PEG 5000, PEG 6000, PEG 7000, PEG 8000, PEG 9000, PEG 1000, PEG 10,000, PEG 15,000, PEG 20,000, PEG 35,000, polyethylene glycol glycerol fatty acid esters, i.e. esters like the above-mentioned but in the form of glyceryl esters of the individual fatty acids; glycerol, propylene glycol, ethylene glycol, PEG or sorbitol esters with for example vegetable oils like for example hydrogenated castor oil, almond oil, palm kernel oil, castor oil, apricot kernel oil, olive oil, peanut oil, hydrogenated palm kernel oil and the like, polyglycerized fatty acids like for example polyglycerol stearate, polyglycerol oleate, polyglycerol ricinoleate, polyglycerol linoleate, propylene glycol fatty acid esters such as, for example propylene glycol monolaurate, propylene glycol ricinoleate and the like, mono- and diglycerides like for example glyceryl monooleate, glyceryl dioleae, glyceryl mono- and/or dioleate, glyceryl caprylate, glyceryl caprate etc. sterol and sterol derivatives, polyethylene glycol sorbitan fatty acid esters (PEG-sorbitan fatty acid esters) such as esters of PEG with the various molecular weights indicated above, and the various Tween® series; polyethylene glycol alkyl ethers such as, for example PEG oleyl ether and PEG lauryl ether, sugar esters like for example sucrose monopalmitate and sucrose monolaurate; polyethylene glycol alkyl phenols like for example the Triton® X or N series: polyoxyethylene-polyoxypropylene block copolymers such as, for example, the Pluronic® series, the Synperonic® series, Emkalyx®, Lutrol®, and Supronic®.

In some embodiments, one or more components of an ingestible device can include one or more organic acids. Examples include acetic acid/ethanoic acid, adipic acid, angelic acid, ascorbic acid/vitamin C, carbamic acid, cinnamic acid, citramalic acid, formic acid, fumaric acid, gallic acid, gentisic acid, glutaconic acid, glutaric acid, glyceric acid, glycolic acid, glyoxylic acid, lactic acid, levulinic acid, malonic acid, mandelic acid, oxalic acid, oxamic acid, pimelic acid, citric acid, tartaric acid and pyruvic acid.

In some embodiments, one or more components of an ingestible device can include one or more inorganic acids. Examples include pyrophosphoric, glycerophosphoric, phosphoric such as ortho and meta phosphoric, boric acid, hydrochloric acid, or sulfuric acid. Examples of suitable inorganic compounds include, for example, aluminum, calcium or kalium.

In some embodiments, one or more components of an ingestible device can include one or more organic bases. Examples include p-nitrophenol, tromethamine, succinimide, benzenesulfonamide, 2-hydroxy-2cyclohexenone, imidazole, pyrrole, diethanolamine, ethyleneamine tris (hydroxymethyl) aminomethane, hydroxylamine and derivates of amines, sodium citrate, aniline and hydrazine.

In some embodiments, one or more components of an ingestible device can include one or more inorganic bases. Examples include aluminium oxide such as, for example, aluminium oxide trihydrate, alumina, sodium hydroxide, potassium hydroxide, calcium carbonate, ammonium carbonate, and ammonium hydroxide.

In some embodiments, one or more components of an ingestible device can include one or more pharmaceutically acceptable salts of an organic acid. Examples include an alkali metal salt or an alkaline earth metal salt such as, for example, sodium phosphate, sodium dihydrogenphosphate, disodium hydrogenphosphate etc., potassium phosphate, potassium dihydrogenphosphate, potassium hydrogenphosphate etc., calcium phosphate, dicalcium phosphate etc., sodium sulfate, potassium sulfate, calcium sulfate, sodium carbonate, sodium hydrogencarbonate, potassium carbonate, potassium hydrogencarbonate, calcium carbonate, magnesium carbonate etc., sodium acetate, potassium acetate, calcium acetate, sodium succinate, potassium succinate, calcium succinate, sodium citrate, potassium citrate, calcium citrate, sodium tartrate, potassium tartrate and calcium tartrate.

In some embodiments, one or more components of an ingestible device can include one or more inorganic salts. Examples include sodium chloride, potassium chloride, calcium chloride and magnesium chloride.

In some embodiments, one or more components of an ingestible device can include one or more release modifiers. Examples include fatty acids and esters, fatty alcohols, cetyl alcohol, stearyl alcohol, mineral oils, hydrogenated vegetable oils, vegetable oils, acetylated hydrogenated soybean oil glycerides, Castor oil, phosphate esters, amides, phthalate esters, glyceryl cocoate oleyl alcohol, myristyl alcohol, sucrose octaacetate, diacetylated monoglycerides, diethylene glycol monostearate, ethylene glycol monostearate, glyceryl monooleate, glyceryl monostearate, propylene glycol monostearate, macrogol esters, macrogol stearate 400, macrogol stearate 2000, polyoxyethylene 50 stearate, macrogol ethers, cetomacrogol 1000, lauromacrogols, poloxamers, polyvinyl alcohols, sorbitan monolaurate, sorbitan monooleate, sorbitan monopalmitate, sorbitan monostearate, sorbitan sesquioleate, sorbitan trioleate, sorbitan tristearate, ethylcellulose, cellulose acetate, cellulose propionate, cellulose nitrate, cellulose derivative selected from the group consisting of methylcellulose, carboxymethylcellulose and salts thereof, cellulose acetate phthalate, microcrystalline cellulose, ethylhydroxyethylcellulose, ethyl methylcellulose, hydroxyethylcellulose, hydroxyethylmethylcellulose, hydroxypropylcellulose, hydroxymethylcellulose and hydroxymethylpropylcellulose, cellulose acetate, polylactic acid or polyglycolic acid and copolymers thereof, methacrylates, a co-polymer of methacrylate-galactomannan etc., polyvinyl alcohols, glycerinated gelatine and cocoa butter. Other suitable release modifiers may be selected from inorganic acids, inorganic bases, inorganic salts, organic acids or bases and pharmaceutically acceptable salts thereof, saccharides, oligosaccharides, polysaccharides, polyethylene glycol derivatives and cellulose and cellulose derivatives.

In some embodiments, one or more components of an ingestible device can include one or more saccharides. Examples include glucose, ribose, arabinose, xylose, lyxose, xylol, allose, altrose, inosito, glucose, sorbitol, mannose, gulose, glycerol, idose, galactose, talose, mannitol, erythritol, ribitol, xylitol, maltitol, isomalt, lactitol, sucrose, fructose, lactose, dextrin, dextran, amylase or xylan.

As a further example, in some embodiments, the formulation is deposited in the submucosa and/or the mucosa (e.g., into the lamina propria) of the small intestine of the subject. In some embodiments, the formulation is deposited in the submucosa and/or the mucosa (e.g., into the lamina propria) of the duodenum of the subject. In some embodiments, the formulation is deposited in the submucosa and/or the mucosa (e.g., into the lamina propria) of the jejunum of the subject. In some embodiments, the formulation is deposited in the submucosa and/or the mucosa (e.g., into the lamina propria) of the ileum of the subject.

As yet another example, in some embodiments, a first portion of the pharmaceutical formulation released from the device is deposited in the submucosa and a second portion is deposited in the mucosa (such as the lamina propria), and/or is released into the lumen, and may subsequently adhere to the mucus of the gastrointestinal tract. In some embodiments, the first portion of the pharmaceutical formulation deposited into the submucosa contains at least about 99% of the total pharmaceutical formulation released from the device, wherein the % is a w/w %, a w/v %, or a v/v % of the pharmaceutical formulation. In other embodiments, the first portion of the pharmaceutical formulation deposited into the submucosa contains at least about 95%, about 90%, about 85%, about 80%, about 75%, about 70%, about 75%, about 70%, about 65%, about 60%, about 55% or about 50% of the pharmaceutical formulation, wherein the % is a w/w %, a w/v %, or a v/v % of the pharmaceutical formulation. In yet other embodiments, the first portion of the pharmaceutical formulation deposited into the submucosa contains at least about 45%, at least about 40%, at least about 35%, at least about 30%, at least about 25%, at least about 20%, at least about 15%, at least about 10%, or at least about 5% of the pharmaceutical formulation, wherein the % is a w/w %, a w/v %, or a v/v % of the pharmaceutical formulation.

As an additional example, in some embodiments, the formulation is topically delivered to the small intestine of the subject. In some embodiments, the formulation is topically delivered to the duodenum of the subject. In some embodiments, the formulation is topically delivered to the jejunum of the subject. In some embodiments, the formulation is topically delivered to the ileum of the subject. In some embodiments, the topical delivery of the formulation to the small intestine of the subject is for use in treating ileal Crohn's disease.

As another example, in some embodiments, the formulation is topically delivered to the large intestine of the subject. In some embodiments, the formulation is topically delivered to the cecum of the subject. In some embodiments, the formulation is topically delivered to the colon of the subject. In some embodiments, the formulation is topically delivered to the rectum of the subject. In some embodiments, the topical delivery of the formulation to the large intestine of the subject is for use in treating an inflammatory bowel disease (IBD), where the IBD is Crohn's disease or ulcerative colitis.

As a further example, in some embodiments of any of the devices or methods described herein, the releasing of the therapeutic is triggered by one or more of: a pH in the jejunum of about 6.1 to about 7.2, a pH in the mid small bowel of about 7.0 to about 7.8, a pH in the ileum of about 7.0 to about 8.0, a pH in the right colon of about 5.7 to about 7.0, a pH in the mid colon of about 5.7 to about 7.4, or a pH in the left colon of about 6.3 to about 7.7, such as about 7.0.

As another example, in some embodiments of any of the devices or methods described herein, the releasing of the therapeutic is triggered by degradation of a release component located in the device. In some embodiments of any of the devices or methods described herein, the releasing of the therapeutic is dependent on enzymatic activity at or in the vicinity of the location. In some embodiments of any of the devices or methods described herein, the composition includes a plurality of electrodes including a coating, and releasing the therapeutic is triggered by an electric signal by the electrodes resulting from the interaction of the coating with an intended site of release of the therapeutic. In some embodiments of any of the devices or methods described herein, the release of the therapeutic is triggered by a remote electromagnetic signal. In some embodiments of any of the devices or methods described herein, the release of the therapeutic is triggered by generation in the composition of a gas in an amount sufficient to expel the therapeutic. In some embodiments of any of the devices or methods described herein, the release of the therapeutic is triggered by an electromagnetic signal generated within the device according to a pre-determined drug release profile.

As a further example, in some embodiments, an ingestible device includes one or more safety mechanisms, e.g., to reduce/eliminate the possibility of an undesirably high pressure building within the ingestible device. Such a safety mechanism can be configured, for example, as a disc that opens (e.g., bursts) when the pressure within the ingestible device reaches or exceeds a certain value. Optionally, a safety mechanism can be configured as a valve that opens when the pressure within the ingestible device reaches or exceeds a certain value. In some embodiments, a safety mechanism can be configured as one or more recess channels, e.g., in the interior wall of the device.

A number of embodiments have been described. Nevertheless, various modifications may be made without departing from the spirit and scope of the disclosure. Accordingly, other embodiments are within the scope of the following claims.

What is claimed is:

1. An ingestible device comprising:
a housing comprising an interior and an opening;
a gas cylinder in the interior of the housing, the gas cylinder having a breakable seal;
a spring in the interior of the housing;
a piston in the interior of the housing;
a piercer in the interior of the housing;
a retainer; and
a trigger exposed to an environment external to the housing, wherein, in a first state of the ingestible device:
the trigger holds the retainer in a first position; the retainer holds the piercer in a first position in which the piercer does not break the breakable seal of the gas cylinder; and the interior of the ingestible device is configured to contain a dispensable substance without the dispensable substance being delivered from the ingestible device via the opening in the housing, and
wherein, in a second state of the ingestible device:
the trigger is at least partially dissolved, degraded and/or eroded so that the trigger is unable to hold the retainer in its first position; the retainer is unable to hold the piercer in its first position; the spring applies a force to the piercer to move the piercer so that the piercer breaks the breakable seal of the gas cylinder; a gas is released from the gas cylinder; the gas applies a force to the piston so that the piston applies a force to the dispensable substance; and the dispensable substance is delivered out of the ingestible device via the opening in the housing.

2. The ingestible device of claim 1, further comprising a seal between the piston and the housing.

3. The ingestible device of claim 1, further comprising a seal between the piercer and the housing.

4. The ingestible device of claim 1, wherein the ingestible device is a 00 sized device.

5. The ingestible device of claim 1, wherein the trigger comprises an enteric material.

6. The ingestible device of claim 1, wherein:
the housing comprises first and second housing parts;
the piston and the dispensable substance are inside the first housing part; and
the spring and the retainer are inside the second housing part.

7. The ingestible device of claim 1, wherein the opening is a nozzle having a diameter of from about 325 μm to 375 μm.

8. The ingestible device of claim 1, wherein at least one of the following holds: the ingestible device is configured for trans-epithelial delivery of a dispensable subject to the GI tract of a subject;
the ingestible device is configured for epithelial delivery of the dispensable subject to the GI tract of a subject; and
the ingestible device is configured for topical delivery of the dispensable subject to the GI tract of a subject.

9. The ingestible device of claim 1, wherein the dispensable substance comprises a solution or a suspension.

10. The ingestible device of claim 1, wherein at least one of the following holds: the ingestible device is configured to deliver the dispensable substance to tissue of the GI tract of a subject as a jet with a peak jet power of from about one Watt to about three Watts;
the ingestible device is configured to deliver the dispensable substance at a peak jet velocity of from about 25 meters per second to about 45 meters per second;
the ingestible device is configured to deliver the dispensable substance to tissue of the GI tract of a subject at a peak jet pressure of from about 100 psig to about 250 psig;
the ingestible device is configured to deliver the dispensable substance to tissue of the GI tract of a subject at a peak jet force of from about 0.09 N to about 0.15 N;
the ingestible device is configured to deliver the dispensable substance as a jet having jet stable length of at least about 0.5 millimeter;
the ingestible device is configured to provide an internal pressure of from about 225 psig to about 425 psig; and
the ingestible device is configured to contain the dispensable substance at a peak fluid pressure of from about 200 psig to about 400 psig.

11. The ingestible device of claim 1, further comprising an element having a first state in which the element at least partially covers the opening in the housing and a second state in which the element does not cover the opening in the housing, wherein the ingestible device is configured so that, when the piston moves, the element moves from its first state to its second state.

12. The ingestible device of claim 1, further comprising a covering over the opening in the housing.

13. The ingestible device of claim 12, wherein the covering is configured to be removed from the housing due to pressure applied by the dispensable substance.

14. The ingestible device of claim 12, wherein the covering comprises an enteric material.

15. The ingestible device of claim 12, wherein the covering comprises a member selected from the group consisting of a film, a foil, a band, a plug, and a patch.

16. The ingestible device of claim 12, wherein the covering has a burst pressure of at most 420 psig.

17. The ingestible device of claim 1, further comprising a second piston configured so that, when the first piston applies the force on the dispensable substance, the dispensable substance applies a force on the second piston to slide the second piston to expose the openings and the dispensable substance is forced out of the ingestible device via the openings.

18. The ingestible device of claim 1, further comprising a removable cap affixed to the ingestible device and configured so that, when the piston moves to apply the force on the dispensable substance, the dispensable substance applies a force on the cap to slide the cap to expose the opening in the housing.

19. The ingestible device of claim 1, further comprising an inflated membrane volume covering the opening and configured so that, when the piston moves to apply force on the dispensable substance, the dispensable substance applies force on the inflated membrane volume and the inflated membrane volume is compressed to expose the opening in the housing.

* * * * *